(12) United States Patent
Kiuchi et al.

(10) Patent No.: US 8,129,361 B2
(45) Date of Patent: Mar. 6, 2012

(54) AMINE COMPOUND AND PHARMACEUTICAL USE THEREOF

(75) Inventors: Masatoshi Kiuchi, Osaka (JP); Kaoru Tashiro, Osaka (JP); Maiko Hamada, Osaka (JP); Kunio Sugahara, Osaka (JP)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 0 days.

(21) Appl. No.: 12/664,366

(22) PCT Filed: Jun. 13, 2008

(86) PCT No.: PCT/JP2008/060915
§ 371 (c)(1),
(2), (4) Date: Dec. 11, 2009

(87) PCT Pub. No.: WO2008/153159
PCT Pub. Date: Dec. 18, 2008

(65) Prior Publication Data
US 2010/0179216 A1    Jul. 15, 2010

(30) Foreign Application Priority Data
Jun. 14, 2007   (JP) ................................ 2007-157128

(51) Int. Cl.
*A61K 31/045* (2006.01)
*A61K 31/137* (2006.01)
*C07C 215/20* (2006.01)
*C07C 215/28* (2006.01)

(52) U.S. Cl. .......................... 514/109; 514/576; 564/355

(58) Field of Classification Search .................... 564/355
See application file for complete search history.

(56) References Cited

U.S. PATENT DOCUMENTS

| | | | |
|---|---|---|---|
| 5,948,820 A | 9/1999 | Fujita et al. | |
| 2006/0211658 A1 | 9/2006 | Hinterding et al. | |
| 2007/0010494 A1 | 1/2007 | Ehrhardt et al. | |
| 2009/0137530 A1 | 5/2009 | Kiuchi et al. | |

FOREIGN PATENT DOCUMENTS

| EP | 0 627 406 A1 | 12/1994 |
|---|---|---|
| EP | 0 778 263 A1 | 6/1997 |
| EP | 1 002 792 A1 | 5/2000 |
| EP | 1431275 A1 | 6/2004 |
| EP | 1431284 A1 | 6/2004 |
| JP | 2006-524660 A | 11/2006 |
| JP | 2006-527231 A | 11/2006 |
| JP | 2007-8957 A | 1/2007 |
| WO | WO 94/08943 | 4/1994 |
| WO | WO 96/06068 A1 | 2/1996 |
| WO | WO 98/45249 | 10/1998 |
| WO | WO 02/076995 A2 | 10/2002 |
| WO | WO 2004/096752 A1 | 11/2004 |
| WO | WO 2004/110979 A2 | 12/2004 |
| WO | WO-2007/069712 A1 | 6/2007 |

OTHER PUBLICATIONS

Vippagunta, et al. Advanced Drug Delivery Reviews 48 (2001) 3-26.*
Lupus erythematosus [online] retrieved from the internet on Aug. 10, 2011. (<URL:http://www.ncbi.nlm.nih.gov/pubmedhealth/PMH0001471/>).*
Type 1 diabetes [online] retrieved from the internet on Aug. 10, 2011. (<URL:http://www.mayoclinic.com/health/type-1-diabetes/DS00329/DSECTION=prevention).*
Mandala et al., "Alteration of Lymphocyte Trafficking by Sphingosine-1-Phosphate Receptor Agonists", Science, vol. 296, pp. 346-349. Apr. 12, 2002.
Matloubian et al., "Lymphocyte Egress From Thymus and Peripheral Lymphoid Organs is Dependent on S1P Receptor 1", Nature, vol. 427, pp. 355-360, Jan. 22, 2004.
Extended European Search Report, Nov. 2, 2011, Application No. EP08777226.5-2103.

* cited by examiner

*Primary Examiner* — Shawquia Young
(74) *Attorney, Agent, or Firm* — Birch, Stewart, Kolasch & Birch, LLP

(57) ABSTRACT

Provided is a novel amine compound represented by the following formula (I) having a superior peripheral blood lymphocyte decreasing action and superior in the immunosuppressive action, rejection suppressive action and the like, which shows decreased side effects of, for example, bradycardia and the like, or a pharmaceutically acceptable acid addition salt thereof, or a hydrate thereof, or a solvate thereof.

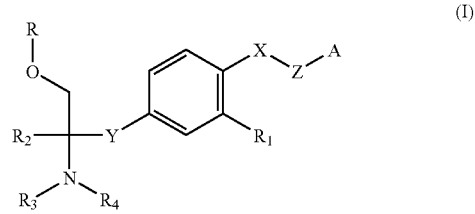

(I)

wherein each symbol is as defined in the specification.

12 Claims, No Drawings

AMINE COMPOUND AND PHARMACEUTICAL USE THEREOF

TECHNICAL FIELD

The present invention relates to an amine compound and use thereof as a medicament.

BACKGROUND ART

In recent years, a calcineurin inhibitor such as cyclosporine and FK506 is used to decrease rejections in patients who received organ transplants. However, a certain kind of calcineurin inhibitor such as cyclosporine sometimes causes toxic side effects such as nephrotoxicity, hepatotoxicity, neurotoxicity and the like. Thus, the development of a safer and highly effective medicament is ongoing to decrease rejections in patients after transplantation.

Patent documents 1-3 disclose 2-aminopropane-1,3-diol compounds useful as an (acute or chronic) rejection suppressant in organ or bone marrow transplantation, or as a therapeutic drug for various autoimmune diseases such as psoriasis, Behcet's disease and the like, or rheumatological diseases.

One of these compounds, 2-amino-2-[2-(4-octylphenyl) ethyl]propane-1,3-diol hydrochloride (hereinafter sometimes to be referred to as FTY720) is a compound currently under clinical development as a rejection suppressant in kidney transplantation or a therapeutic drug for multiple sclerosis. FTY720 is rapidly converted to phosphorylated FTY720 [hereinafter sometimes to be referred to as FTY720-P, for example, 2-amino-2-phosphoryloxymethyl-4-(4-octylphenyl)butanol] by sphingosine kinase in the body. FTY720-P acts as an agonist on 4 kinds of SlP receptors (except S1P2) out of 5 kinds of sphingosine-1-phosphate (hereinafter sometimes to be referred to as S1P) receptors (hereinafter sometimes to be referred to as S1P1-S1P5) (non-patent document 1).

It has been recently reported that S1P1 in the SlP receptors is essential for emigration of mature lymphocytes from the thymus and secondary lymphoid tissues. FTY720-P downregulates S1P1 on lymphocytes by acting as an S1P1 agonist. As a result, it has been suggested, the emigration of mature lymphocytes from the thymus and secondary lymphoid tissues is inhibited, and circulating mature lymphocytes in the blood are isolated in the secondary lymphoid tissues, whereby an immunosuppressive action is exhibited (non-patent document 2).

On the other hand, conventional 2-aminopropane-1,3-diol compounds are feared to cause transient bradycardia expression as a side effect, and to solve this problem, many novel compounds obtained by modifying the chemical structure of 2-aminopropane-1,3-diol compound have been reported. From such compounds, as a compound with a substituent added to a benzene ring of FTY720, patent document 4 discloses an aminopropanol derivative as an SlP receptor modulator having a phosphate group, and patent documents 5 and 6 both disclose aminopropanol derivatives as S1P receptor modulators. However, a trihaloalkyl group, for example, a trifluoromethyl group, is not disclosed as a substituent on the benzene ring in these documents. In any event, none of them have reached a satisfactory level as regards the safety of a pharmaceutical product, as the situation now stands.

patent document 1: WO 94/08943
patent document 2: WO 96/06068
patent document 3: WO 98/45249
patent document 4: WO 02/076995
patent document 5: WO 2004/096752
patent document 6: WO 2004/110979
non-patent document 1: Science, 2002, Vol. 296, pages 346-349
non-patent document 2: Nature, 2004, Vol. 427, pages 355-360

DISCLOSURE OF THE INVENTION

Problems to be Solved by the Invention

An object of the present invention is to provide a novel amine compound superior in the immunosuppressive action, rejection suppressive action and the like, which shows decreased side effects of, for example, bradycardia and the like.

Means of Solving the Problems

The present inventors have conducted intensive studies in consideration of the above-mentioned situations, and found that an amine compound having a particular structural formula as shown below can achieve the desired object, which resulted in the completion of the present invention. Accordingly, the gist of the present invention is as follows.

(1) An amine compound represented by the following formula (I)

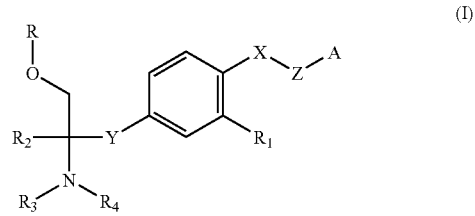

wherein R is a hydrogen atom or $P(=O)(OH)_2$, X is an oxygen atom or a sulfur atom, Y is $-CH_2CH_2-$ or $-CH=CH-$, Z is alkylene having 1 to 5 carbon atoms, alkenylene having 2 to 5 carbon atoms or alkynylene having 2 to 5 carbon atoms, $R_1$ is cyano or alkyl having 1 to 4 carbon atoms, which is substituted by a halogen atom, $R_2$ is alkyl having 1 to 4 carbon atoms, which is optionally substituted by a hydroxyl group or halogen atom, $R_3$ and $R_4$ are optionally the same or different and each is a hydrogen atom or alkyl having 1 to 4 carbon atoms, and A is optionally substituted aryl having 6 to 10 carbon atoms, optionally substituted heteroaryl having 5 to 10 ring-constituting atoms, which contains, as ring-constituting atom(s), 1 or 2 atoms from nitrogen atom, oxygen atom and sulfur atom, optionally substituted cycloalkyl having 3 to 7 carbon atoms, which is optionally condensed with optionally substituted benzene, or heterocycloalkyl having 5 to 7 ring-constituting atoms, which contains, as ring-constituting atom(s), optionally substituted 1 or 2 atoms from nitrogen atom and oxygen atom, or a pharmaceutically acceptable acid addition salt thereof, or a hydrate thereof, or a solvate thereof.

(2) The amine compound of (1), wherein X is an oxygen atom, $R_3$ is a hydrogen atom and $R_4$ is a hydrogen atom, or a pharmaceutically acceptable acid addition salt thereof, or a hydrate thereof, or a solvate thereof.

(3) The amine compound of (1) or (2), wherein A is optionally substituted aryl having 6 to 10 carbon atoms, or optionally substituted heteroaryl having 5 to 9 ring-constituting atoms, which contains, as ring-constituting atom(s), 1 or 2 atoms from sulfur atom and oxygen atom, or a pharmaceutically acceptable acid addition salt thereof, or a hydrate thereof, or a solvate thereof.

(4) The amine compound of any of (1) to (3), wherein A is unsubstituted or when it has substituents, the number of the substituents is 1 to 3, the substituents are the same or different and each is alkyl having 1 to 4 carbon atoms, which is optionally substituted by a halogen atom; alkoxy having 1 to 4 carbon atoms, which is optionally substituted by a halogen atom; alkylthio having 1 to 4 carbon atoms; alkylsulfinyl having 1 to 4 carbon atoms; alkylsulfonyl having 1 to 4 carbon atoms; alkylcarbonyl having 2 to 5 carbon atoms; a halogen atom; cyano; nitro; cycloalkyl having 3 to 7 carbon atoms; aryl having 6 to 10 carbon atoms; aralkyloxy having 7 to 14 carbon atoms; or aryloxy having 6 to 10 carbon atoms; or alkylene having 3 or 4 carbon atoms, which is optionally substituted by oxo or a halogen atom, alkyleneoxy having 2 or 3 carbon atoms, which is optionally substituted by oxo or a halogen atom, or alkylenedioxy having 1 or 2 carbon atoms, which is optionally substituted by oxo or a halogen atom, each of which is formed by two substituents from the above in combination, or a pharmaceutically acceptable acid addition salt thereof, or a hydrate thereof, or a solvate thereof.

(5) The amine compound of any of (1) to (4), wherein A is represented by

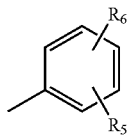

wherein $R_5$ and $R_6$ may be the same or different and each is a hydrogen atom, alkyl having 1 to 4 carbon atoms, which is optionally substituted by a halogen atom, alkoxy having 1 to 4 carbon atoms, which is optionally substituted by a halogen atom or a halogen atom, or a pharmaceutically acceptable acid addition salt thereof, or a hydrate thereof, or a solvate thereof.

(6) The amine compound of any of (1) to (5), wherein Z is trimethylene, or a pharmaceutically acceptable acid addition salt thereof, or a hydrate thereof, or a solvate thereof.

(7) The amine compound of any of (1) to (6), wherein $R_1$ is trifluoromethyl, or a pharmaceutically acceptable acid addition salt thereof, or a hydrate thereof, or a solvate thereof.

(8) The amine compound of any of (1) to (7), wherein $R_2$ is hydroxymethyl, or a pharmaceutically acceptable acid addition salt thereof, or a hydrate thereof, or a solvate thereof.

(9) The amine compound of any of (1) to (8), wherein R is a hydrogen atom, or a pharmaceutically acceptable acid addition salt thereof, or a hydrate thereof, or a solvate thereof.

(10) The amine compound of any of (1) to (8), wherein the compound of the formula (I) is any of the following a-z and aa-ff, or a pharmaceutically acceptable acid addition salt thereof, or a hydrate thereof, or a solvate thereof:

a. 2-amino-2-(2-{3-trifluoromethyl-4-[3-(4-trifluoromethylphenyl)propoxy]phenyl}ethyl)propane-1,3-diol, or a pharmaceutically acceptable acid addition salt thereof, or a hydrate thereof, or a solvate thereof b. 2-amino-2-(phosphoryloxymethyl)-4-{3-trifluoromethyl-4-[3-(4-trifluoromethylphenyl)propoxy]phenyl}butanol, or a pharmaceutically acceptable acid addition salt thereof, or a hydrate thereof, or a solvate thereof c. 2-amino-2-(2-{3-trifluoromethyl-4-[3-(3-trifluoromethylphenyl)propoxy]phenyl}ethyl)propane-1,3-diol, or a pharmaceutically acceptable acid addition salt thereof, or a hydrate thereof, or a solvate thereof d. 2-amino-2-(phosphoryloxymethyl)-4-{3-trifluoromethyl-4-[3-(3-trifluoromethylphenyl)propoxy]phenyl}butanol, or a pharmaceutically acceptable acid addition salt thereof, or a hydrate thereof, or a solvate thereof e. 2-amino-2-(2-{4-[3-(3-methylphenyl)propoxy]-3-trifluoromethylphenyl}ethyl)propane-1,3-diol or a pharmaceutically acceptable acid addition salt thereof, or a hydrate thereof, or a solvate thereof f. 2-amino-4-{4-[3-(3-methylphenyl)propoxy]-3-trifluoromethylphenyl}-2-(phosphoryloxymethyl)butanol or a pharmaceutically acceptable acid addition salt thereof, or a hydrate thereof, or a solvate thereof g. 2-amino-2-(2-{4-[3-(3,4-dichlorophenyl)propoxy]-3-trifluoromethylphenyl}ethyl)propane-1,3-diol, or a pharmaceutically acceptable acid addition salt thereof, or a hydrate thereof, or a solvate thereof h. 2-amino-4-{4-[3-(3,4-dichlorophenyl)propoxy]-3-trifluoromethylphenyl}-2-(phosphoryloxymethyl)butanol, or a pharmaceutically acceptable acid addition salt thereof, or a hydrate thereof, or a solvate thereof i. 2-amino-2-(2-{4-[3-(4-trifluoromethoxyphenyl)propoxy-3-trifluoromethyl]phenyl}ethyl)propane-1,3-diol, or a pharmaceutically acceptable acid addition salt thereof, or a hydrate thereof, or a solvate thereof j. 2-amino-2-(phosphoryloxymethyl)-4-{4-[3-(4-trifluoromethoxyphenyl)propoxy]-3-trifluoromethylphenyl}butanol, or a pharmaceutically acceptable acid addition salt thereof, or a hydrate thereof, or a solvate thereof k. 2-amino-2-(2-{4-[3-(3-trifluoromethoxyphenyl)propoxy-3-trifluoromethyl]phenyl}ethyl)propane-1,3-diol, or a pharmaceutically acceptable acid addition salt thereof, or a hydrate thereof, or a solvate thereof l. 2-amino-2-(phosphoryloxymethyl)-4-{4-[3-(3-trifluoromethoxyphenyl)propoxy]-3-trifluoromethylphenyl}butanol, or a pharmaceutically acceptable acid addition salt thereof, or a hydrate thereof, or a solvate thereof m. 2-amino-2-(2-{4-[3-(3-fluoro-4-trifluoromethylphenyl)propoxy]-3-trifluoromethylphenyl}ethyl)propane-1,3-diol, or a pharmaceutically acceptable acid addition salt thereof, or a hydrate thereof, or a solvate thereof n. 2-amino-4-{4-[3-(3-fluoro-4-trifluoromethylphenyl)propoxy]-3-trifluoromethylphenyl}-2-(phosphoryloxymethyl)butanol, or a pharmaceutically acceptable acid addition salt thereof, or a hydrate thereof, or a solvate thereof o. (R)-2-amino-2-methyl-4-{3-trifluoromethyl-4-[3-(4-trifluoromethylphenyl)propoxy]phenyl}butanol, or a pharmaceutically acceptable acid addition salt thereof, or a hydrate thereof, or a solvate thereof p. (R)-phosphoric acid mono(2-amino-2-methyl-4-{3-trifluoromethyl-4-[3-(4-trifluoromethylphenyl)propoxy]phenyl}butyl)ester, or a pharmaceutically acceptable acid addition salt thereof, or a hydrate thereof, or a solvate thereof q. (R)-2-amino-2-ethyl-4-{3-trifluoromethyl-4-[3-(4-trifluoromethylphenyl)propoxy]phenyl}butanol, or a pharmaceutically acceptable acid addition salt thereof, or a hydrate thereof, or a solvate thereof r. (R)-phosphoric acid mono(2-amino-2-ethyl-4-{3-trifluoromethyl-4-[3-(4-trifluoromethylphenyl)propoxy]phenyl}butyl)ester, or a pharmaceutically acceptable acid addition salt thereof, or a hydrate thereof, or a solvate thereof s. 2-amino-2-(2-{4-[3-(3-chlorophenyl)allyloxy]-3-trifluoromethylphenyl}ethyl)propane-1,3-diol, or a pharmaceutically acceptable acid addition salt thereof, or a hydrate thereof, or a solvate thereof t. 2-amino-4-{4-[3-(3-chlorophenyl)allyloxy]-3-trifluoromethylphenyl}-2-(phosphoryloxymethyl)butanol, or a pharmaceutically acceptable acid addition salt thereof, or a hydrate thereof, or a solvate thereof u. (E)-2-amino-2-{2-[4-(3-phenylpropoxy)-3-trifluoromethylphenyl]vinyl}propane-1,3-diol, or a pharmaceutically acceptable acid addition salt thereof, or a hydrate thereof, or a solvate thereof v. (E)-2-amino-4-[4-(3-phenylpropoxy)-3-trifluoromethylphenyl]-2-(phosphoryloxymethyl)-3-butenol, or a pharmaceutically acceptable acid addition salt thereof, or a hydrate thereof, or a solvate thereof w. (E)-2-amino-2-(2-{4-[3-(2-fluorophenyl)propoxy]-3-trifluoromethylphenyl}vinyl)propane-1,3-diol, or a pharmaceutically acceptable acid addition salt thereof, or a hydrate thereof, or a solvate thereof x. (E)-2-amino-4-{4-[3-(2-fluorophenyl)propoxy]-3-trifluoromethylphenyl}-2-(phosphoryloxymethyl)-3-butenol, or a pharmaceutically acceptable acid addition salt thereof, or a hydrate thereof, or a solvate thereof y. (R)-2-amino-4-{4-[3-(3,4-dichlorophenyl)propoxy]-3-trifluoromethylphenyl}-2-methylbutanol, or a pharmaceutically acceptable acid addition salt thereof, or a hydrate thereof, or a solvate thereof z. phosphoric acid mono(2-amino-4-{4-[3-(3,4-dichlorophenyl)propoxy]-3-trifluoromethylphenyl}-2-methylbutyl)ester, or a pharmaceutically acceptable acid addition salt thereof, or a hydrate thereof, or a solvate thereof aa. (R)-2-amino-4-{4-[3-(3,4-dichlorophenyl)propoxy]-3-trifluoromethylphenyl}-2-ethylbutanol, or a pharmaceutically acceptable acid addition salt thereof, or a hydrate thereof, or a solvate thereof bb. (R)-phosphoric acid mono(2-amino-4-{4-[3-(3,4-dichlorophenyl)propoxy]-3-trifluoromethylphenyl}-2-ethylbutyl)ester, or a pharmaceutically acceptable acid addition salt thereof, or a hydrate thereof, or a solvate thereof cc. (R)-2-amino-2-ethyl-4-{4-[3-(4-trifluoromethoxyphenyl)propoxy]-3-trifluoromethylphenyl}butanol, or a pharmaceutically acceptable acid addition salt thereof, or a hydrate thereof, or a solvate thereof dd. (R)-phosphoric acid mono(2-amino-2-ethyl-4-{4-[3-(4-trifluoromethoxyphenyl)propoxy]-3-trifluoromethylphenyl}butyl)ester, or a pharmaceutically acceptable acid addition salt thereof, or a hydrate thereof, or a solvate thereof ee. (R)-2-amino-2-ethyl-4-{4-[3-(3-trifluoromethoxyphenyl)propoxy]-3-trifluoromethylphenyl}butanol, or a pharmaceutically acceptable acid addition salt thereof, or a hydrate thereof, or a solvate thereof ff. (R)-phosphoric acid mono(2-amino-2-ethyl-4-{4-[3-(3-trifluoromethoxyphenyl)propoxy]-3-trifluoromethylphenyl}butyl)ester, or a pharmaceutically acceptable acid addition salt thereof, or a hydrate thereof, or a solvate thereof

(11) 2-Amino-2-(2-{3-trifluoromethyl-4-[3-(4-trifluoromethylphenyl)propoxy]phenyl}ethyl)propane-1,3-diol, or a hydrochloride thereof.

(12) 2-Amino-2-(2-{3-trifluoromethyl-4-[3-(3-trifluoromethylphenyl)propoxy]phenyl}ethyl)propane-1,3-diol, or a hydrochloride thereof.

(13) 2-Amino-2-(2-{4-[3-(3-methylphenyl)propoxy]-3-trifluoromethylphenyl}ethyl)propane-1,3-diol, or a hydrochloride thereof.

(14) 2-Amino-2-(2-{4-[3-(3,4-dichlorophenyl)propoxy]-3-trifluoromethylphenyl}ethyl)propane-1,3-diol, or a hydrochloride thereof.

(15) 2-Amino-2-(2-{4-[3-(4-trifluoromethoxyphenyl)propoxy-3-trifluoromethyl]phenyl}ethyl)propane-1,3-diol, or a hydrochloride thereof.

(16) 2-Amino-2-(2-{4-[3-(3-trifluoromethoxyphenyl)propoxy-3-trifluoromethyl]phenyl}ethyl)propane-1,3-diol, or a hydrochloride thereof.

(17) 2-Amino-2-(2-{4-[3-(3-fluoro-4-trifluoromethylphenyl)propoxy]-3-trifluoromethylphenyl}ethyl)propane-1,3-diol, or a hydrochloride thereof.

(18) (R)-2-Amino-2-methyl-4-{3-trifluoromethyl-4-[3-(4-trifluoromethylphenyl)propoxy]phenyl}butanol, or a hydrochloride thereof.

(19) (R)-2-Amino-2-ethyl-4-{3-trifluoromethyl-4-[3-(4-trifluoromethylphenyl)propoxy]phenyl}butanol, or a hydrochloride thereof.

(20) 2-Amino-2-(2-{4-[3-(3-chlorophenyl)allyloxy]-3-trifluoromethylphenyl}ethyl)propane-1,3-diol, or a hydrochloride thereof.

(21) (E)-2-Amino-2-{2-[4-(3-phenylpropoxy)-3-trifluoromethylphenyl]vinyl}propane-1,3-diol, or a hydrochloride thereof.

(22) (E)-2-Amino-2-(2-{4-[3-(2-fluorophenyl)propoxy]-3-trifluoromethylphenyl}vinyl)propane-1,3-diol, or a hydrochloride thereof.

(23) (R)-2-Amino-4-{4-[3-(3,4-dichlorophenyl)propoxy]-3-trifluoromethylphenyl}-2-methylbutanol, or a hydrochloride thereof.

(24) (R)-2-Amino-4-{4-[3-(3,4-dichlorophenyl)propoxy]-3-trifluoromethylphenyl}-2-ethylbutanol, or a hydrochloride thereof.

(25) (R)-2-Amino-2-ethyl-4-{4-[3-(4-trifluoromethoxyphenyl)propoxy]-3-trifluoromethylphenyl}butanol, or a hydrochloride thereof.

(26) (R)-2-Amino-2-ethyl-4-{4-[3-(3-trifluoromethoxyphenyl)propoxy]-3-trifluoromethylphenyl}butanol, or a hydrochloride thereof.

(27) A pharmaceutical composition comprising a compound of any of (1) to (10) or a pharmaceutically acceptable acid addition salt thereof, or a hydrate thereof, or a solvate thereof, or a compound of any of (11) to (26) or a hydrochloride thereof, and a pharmaceutically acceptable carrier.

(28) The pharmaceutical composition of (27), which is used for the treatment or prophylaxis of an autoimmune disease; prophylaxis or suppression of resistance or acute rejection or chronic rejection in transplantation of an organ or tissue; treatment or prophylaxis of graft vs host (GvH) disease caused by bone marrow transplantation; or treatment or prophylaxis of an allergic disease.

(29) The pharmaceutical composition of (28), wherein the autoimmune disease is rheumatoid arthritis, multiple sclerosis, encephalomyelitis, systemic lupus erythematosus, lupus nephritis, nephrosis syndrome, psoriasis or Type I diabetes mellitus.

(30) The pharmaceutical composition of (28), wherein the allergic disease is atopic dermatitis, allergic rhinitis or asthma.

(31) Use of a compound of any of (1) to (10), or a pharmaceutically acceptable acid addition salt thereof, or a hydrate thereof, or a solvate thereof, or a compound of any of (11) to (26) or a hydrochloride thereof for the production of an agent for the treatment or prophylaxis of an autoimmune lo disease; an agent for the prophylaxis or suppression of resistance or acute rejection or chronic rejection in transplantation of an organ or tissue; an agent for the treatment or prophylaxis of graft vs host (GvH) disease caused by bone marrow transplantation; or an agent for the treatment or prophylaxis of an allergic disease.

(32) The use of (31), wherein the autoimmune disease is rheumatoid arthritis, multiple sclerosis, encephalomyelitis, systemic lupus erythematosus, lupus nephritis, nephrosis syndrome, psoriasis or Type I diabetes mellitus.

(33) The use of (31), wherein the allergic disease is atopic dermatitis, allergic rhinitis or asthma.

(34) A method for the treatment or prophylaxis of an autoimmune disease; prophylaxis or suppression of resistance or acute rejection or chronic rejection in transplantation of an organ or tissue; treatment or prophylaxis of graft vs host (GvH) disease caused by bone marrow transplantation; or treatment or prophylaxis of an allergic disease, comprising administering an effective amount of a compound of any of (1) to (10) or a pharmaceutically acceptable acid addition salt thereof, or a hydrate thereof, or a solvate thereof, or a compound of any of (11) to (26) or a hydrochloride thereof to a subject.

(35) The method of (34), wherein the autoimmune disease is rheumatoid arthritis, multiple sclerosis, encephalomyelitis, systemic lupus erythematosus, lupus nephritis, nephrosis syndrome, psoriasis or Type I diabetes mellitus.

(36) The method of (34), wherein the allergic disease is atopic dermatitis, allergic rhinitis or asthma.

EFFECT OF THE INVENTION

According to the present invention, a novel compound having superior peripheral blood lymphocyte decreasing action, which shows decreased side effects of, for example, bradycardia and the like can be provided.

BEST MODE FOR CARRYING OUT THE INVENTION

The present invention is explained in detail in the following.

The compound of the present invention is an amine compound represented by the following formula (I)

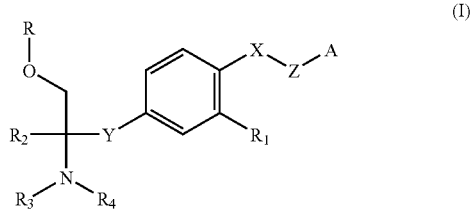

(I)

wherein R is a hydrogen atom or $P(=O)(OH)_2$, X is an oxygen atom or a sulfur atom, Y is $—CH_2CH_2—$ or $—CH=CH—$, Z is alkylene having 1 to 5 carbon atoms, alkenylene having 2 to 5 carbon atoms or alkynylene having 2 to 5 carbon atoms, $R_1$ is cyano or alkyl having 1 to 4 carbon atoms, which is substituted by a halogen atom, $R_2$ is alkyl having 1 to 4 carbon atoms, which is optionally substituted by a hydroxyl group or halogen atom, $R_3$ and $R_4$ are optionally the same or different and each is a hydrogen atom or alkyl having 1 to 4 carbon atoms, and A is optionally substituted aryl having 6 to 10 carbon atoms, optionally substituted heteroaryl having 5 to 10 ring-constituting atoms, which contains, as ring-constituting atom(s), 1 or 2 atoms from nitrogen atom, oxygen atom and sulfur atom, optionally substituted cycloalkyl having 3 to 7 carbon atoms, which is optionally condensed with optionally substituted benzene, or optionally substituted heterocycloalkyl having 5 to 7 ring-constituting atoms, which contains, as ring-constituting atom(s), 1 or 2 atoms from nitrogen atom and oxygen atom, or a pharmaceutically acceptable acid addition salt thereof, or a hydrate thereof, or a solvate thereof.

In the present invention, the halogen atom is a fluorine atom, a chlorine atom, a bromine atom or an iodine atom, and preferable examples include a fluorine atom, a chlorine atom and a bromine atom.

The alkyl having 1 to 4 carbon atoms means straight chain or branched chain alkyl having 1 to 4 carbon atoms, such as methyl, ethyl, n-propyl, isopropyl, n-butyl, isobutyl, secondary butyl, tertiary butyl (hereinafter "tertiary" is sometimes indicated as t- or tert-) and the like.

The alkyl having 1 to 4 carbon atoms, which is substituted by a halogen atom, and the alkyl having 1 to 4 carbon atoms, which is substituted by a halogen atom, mean the aforementioned alkyl having 1 to 4 carbon atoms, which is substituted by 1 to 5 halogen atoms, such as fluoromethyl, difluoromethyl, trifluoromethyl, fluoroethyl, difluoroethyl, trifluoroethyl, pentafluoroethyl, fluoro-n-propyl, trifluoro-n-propyl, pentafluoro-n-propyl, fluoroisopropyl, difluoroisopropyl, fluoro-n-butyl, trifluoro-n-butyl, pentafluoro-n-butyl and the like, as well as those wherein the fluorine atom exemplified as the substituent here is partially or entirely substituted by other halogen atom and the like.

The alkyl having 1 to 4 carbon atoms, which is substituted by a hydroxyl group, means the aforementioned alkyl having 1 to 4 carbon atoms, which is substituted by a hydroxyl group, such as hydroxymethyl, 1-hydroxyethyl, 2-hydroxyethyl, dihydroxyethyl, 1-hydroxy-n-propyl, 2-hydroxy-n-propyl, 3-hydroxy-n-propyl, hydroxyisopropyl, dihydroxyisopropyl, hydroxybutyl, dihydroxybutyl and the like.

Examples of the aryl having 6 to 10 carbon atoms include phenyl, 1-naphthyl, 2-naphthyl and the like.

Examples of the heteroaryl having 5 to 10 ring-constituting atoms, which contains, as ring-constituting atom(s), 1 or 2 atoms from nitrogen atom, oxygen atom and sulfur atom, include pyrrolyl, imidazolyl, pyrazolyl, pyridyl, pyridazinyl, pyrimidinyl, pyrazinyl, furyl, thienyl, oxazolyl, isoxazolyl, thiazolyl, isothiazolyl, indolyl, isoindolyl, indolizinyl, indazolyl, benzofuryl, benzothienyl, quinolyl, isoquinolyl and the like.

Examples of the cycloalkyl having 3 to 7 carbon atoms include cyclopropyl, cyclobutyl, cyclopentyl, cyclohexyl and the like.

Examples of the cycloalkyl having 3 to 7 carbon atoms, which is optionally condensed with benzene, include 1,2,3,4-tetrahydronaphthyl, indanyl, 6,7,8,9-tetrahydro-5H-benzocycloheptyl and the like.

Examples of the heterocycloalkyl having 5 to 7 ring-constituting atoms, which contains, as ring-constituting atom(s), 1 or 2 atoms from nitrogen atom and oxygen atom, include piperidyl, piperazinyl, morpholyl, tetrahydrofuryl, tetrahydropyranyl and the like.

Examples of the alkylene having 1 to 5 carbon atoms include methylene, ethylene, trimethylene, tetramethylene, pentamethylene, propylene, ethylethylene, methyltrimethylene, dimethyltrimethylene, cyclopropylidene, cyclopropylene, (cyclopropylidene)ethylene, cyclopropylene-methylene and the like.

Examples of the alkenylene having 2 to 5 carbon atoms include vinylene, propenylene, butenylene, pentenylene, methylvinylene, dimethylvinylene, ethylvinylene, methylpropenylene, dimethylpropenylene and the like.

Examples of the alkynylene having 2 to 5 carbon atoms include ethynylene, propynylene, butynylene, pentynylene, methylpropynylene, dimethylpropynylene and the like.

The number of substituents that the "aryl having 6 to 10 carbon atoms", "heteroaryl having 5 to 10 ring-constituting atoms, which contains, as ring-constituting atom(s), 1 or 2 atoms from nitrogen atom, oxygen atom and sulfur atom", "cycloalkyl having 3 to 7 carbon atoms" and "heterocycloalkyl having 5 to 7 ring-constituting atoms, which contains, as ring-constituting atom(s), 1 or 2 atoms from nitrogen atom and oxygen atom" may have is 1 to 5, preferably 1 to 3, more preferably 1 or 2. In addition, the "benzene" of the "optionally substituted cycloalkyl having 3 to 7 carbon atoms, which is optionally condensed with optionally substituted benzene" is preferably unsubstituted. When the "benzene" has a substituent, the number thereof is 1 to 5, preferably 1 to 3, more preferably 1 or 2. Examples of the substituent include alkyl having 1 to 4 carbon atoms, which is optionally substituted by the above-mentioned halogen atom; alkoxy having 1 to 4 carbon atoms, which is optionally substituted by the above-mentioned halogen atom; alkylthio having 1 to 4 carbon atoms; alkylsulfinyl having 1 to 4 carbon atoms; alkylsulfonyl having 1 to 4 carbon atoms; alkylcarbonyl having 2 to 5 carbon atoms; the above-mentioned halogen atom; cyano; nitro; the above-mentioned cycloalkyl having 3 to 7 carbon atoms; the above-mentioned aryl having 6 to 10 carbon atoms; aralkyloxy having 7 to 14 carbon atoms; and aryloxy having 6 to 10 carbon atoms; and alkylene having 3 or 4 carbon atoms, which is optionally substituted by oxo or a halogen atom, alkyleneoxy having 2 or 3 carbon atoms, which is optionally substituted by oxo or a halogen atom, or alkylenedioxy having 1 or 2 carbon atoms, which is optionally substituted by oxo or a halogen atom, each of which is formed by two substituents from the above in combination.

The alkoxy having 1 to 4 carbon atoms means straight chain or branched chain alkoxy having 1 to 4 carbon atoms, such as methoxy, ethoxy, n-propoxy, isopropoxy, n-butoxy, isobutoxy, secondary butoxy, t-butoxy and the like. The alkoxy having 1 to 4 carbon atoms, which is substituted by a halogen atom, means the aforementioned alkoxy having 1 to 4 carbon atoms, which is substituted by 1-5 halogen atoms, such as fluoromethoxy, difluoromethoxy, trifluoromethoxy, difluoroethoxy, trifluoroethoxy, pentafluoroethoxy, difluoro-n-propoxy, trifluoro-n-propoxy, fluoroisopropoxy, trifluoroisopropoxy, difluoro-n-butoxy, trifluoro-n-butoxy and the like, as well as those wherein the fluorine atom exemplified as the substituent here is partially or entirely substituted by other halogen atom and the like.

The alkylthio having 1 to 4 carbon atoms, alkylsulfinyl having 1 to 4 carbon atoms and alkylsulfonyl having 1 to 4 carbon atoms each have an alkyl moiety constituted by the above-mentioned alkyl having 1 to 4 carbon atoms, such as methylthio, ethylthio, propylthio, methanesulfinyl, methanesulfonyl and the like.

The alkylcarbonyl having 2 to 5 carbon atoms is that wherein the alkyl moiety comprises the above-mentioned alkyl having 1 to 4 carbon atoms and carbonyl bonded thereto, such as methylcarbonyl, ethylcarbonyl and the like.

The aralkyloxy having 7 to 14 carbon atoms is the above-mentioned alkoxy having 1 to 4 carbon atoms, which is substituted by the above-mentioned aryl having 6 to 10 carbon atoms, such as benzyloxy, phenethyloxy, naphthylmethoxy, naphthylethoxy and the like.

The aryloxy having 6 to 10 carbon atoms is that wherein an oxygen atom is bonded to the above-mentioned aryl having 6 to 10 carbon atoms, such as phenoxy, 1-naphthoxy, 2-naphthoxy and the like.

Examples of the alkylene having 3 or 4 carbon atoms include trimethylene, tetramethylene, methyltrimethylene and the like. Examples of the alkylene having 3 or 4 carbon atoms, which is substituted by oxo, include —C(=O)—CH$_2$—CH$_2$—, —CH$_2$—C(=O)—CH$_2$—, —C(=O)—CH$_2$—CH$_2$—CH$_2$—, —CH$_2$—C(=O)—CH$_2$—CH$_2$— and the like. The alkylene having 3 or 4 carbon atoms, which is substituted by a halogen atom, is the above-mentioned alkylene having 3 or 4 carbon atoms, wherein hydrogen atom is partially or entirely substituted by a halogen atom.

Examples of the alkyleneoxy having 2 or 3 carbon atoms include ethyleneoxy, trimethylenoxy, propyleneoxy and the like. Examples of the alkyleneoxy having 2 or 3 carbon atoms, which is substituted by oxo, include —O—C(=O)—CH$_2$—, —C(=O)—CH$_2$—O—, —O—C(=O)—CH$_2$—CH$_2$—, —C(=O)—CH$_2$—CH$_2$—O—, —O—CH$_2$—C(=O)—CH$_2$—, —CH$_2$—C(=O)—CH$_2$—O— and the like. The alkyleneoxy having 2 or 3 carbon atoms, which is substituted by a halogen atom, is the above-mentioned alkyleneoxy having 2 or 3 carbon atoms, wherein hydrogen atom is partially or entirely substituted by a halogen atom.

Examples of the alkylenedioxy having 1 or 2 carbon atoms include methylenedioxy, ethylenedioxy and the like. Examples of the alkylenedioxy having 1 or 2 carbon atoms, which is substituted by oxo, include —O—C(=O)—O—, —O—CH$_2$—C(=O)—O— and the like. The alkylenedioxy having 1 or 2 carbon atoms, which is substituted by a halogen atom, is the above-mentioned alkylenedioxy having 1 or 2 carbon atoms, wherein hydrogen atom is partially or entirely substituted by a halogen atom, such as —O—CF$_2$—O— and the like.

A preferable example of R in the above-mentioned formula (I) is a hydrogen atom.

A preferable example of X is an oxygen atom.

A preferable example of Y is —CH$_2$CH$_2$—.

Preferable examples of Z include trimethylene, methyltrimethylene, propenylene and propynylene. More preferable examples thereof are trimethylene, methyltrimethylene bonded to X and A in the formula (I) as shown by X—CH$_2$—CH$_2$—CH(CH$_3$)-A, propenylene bonded as shown by X—CH$_2$—CH=CH-A and propynylene bonded as shown by X—CH$_2$—C≡C-A, and further preferable example is trimethylene.

Preferable examples of R$_1$ include difluoromethyl, trifluoromethyl, 2,2,2-trifluoroethyl and cyano, more preferable examples include trifluoromethyl and cyano, and further preferable example is trifluoromethyl.

Preferable examples of R$_2$ include methyl, ethyl, hydroxymethyl, hydroxyethyl, fluoromethyl, fluoroethyl, 2,2-difluoroethyl and 2,2,2-trifluoroethyl, more preferable examples include methyl, ethyl and hydroxymethyl, and further preferable example is hydroxymethyl.

Preferable examples of R$_3$ and R$_4$ are the same or different and include a hydrogen atom, methyl and ethyl, and more preferable example is a hydrogen atom.

Preferable examples of A include optionally substituted aryl having 6 to 10 carbon atoms or optionally substituted heteroaryl having a ring-constituting atom number of 5-9, which contains, as ring-constituting atom(s), 1 or 2 atoms from sulfur atom and oxygen atom can be mentioned. In addition, from the other aspects, preferable examples of A include optionally substituted phenyl, optionally substituted naphthyl, optionally substituted thienyl, optionally substituted benzothienyl, cyclohexyl optionally condensed with substituted optionally substituted benzene, optionally substituted morpholinyl, optionally substituted piperidyl, more preferably optionally substituted phenyl. Preferable examples of the substituent, which A has a substituent include methyl, ethyl, trifluoromethyl, methoxy, trifluoromethoxy, methylthio, methanesulfinyl, methanesulfonyl, methylcarbonyl, fluorine atom, chlorine atom, bromine atom, cyano, nitro, cyclopropyl, phenyl, benzyloxy, phenoxy, trimethylene, —C(=O)—CH$_2$—CH$_2$—, ethyleneoxy, methylenedioxy, difluoromethylenedioxy, more preferably methyl, ethyl, trifluoromethyl, methoxy, trifluoromethoxy, a fluorine atom, a chlorine atom, a bromine atom, cyclopropyl, phenyl, trimethylene, ethyleneoxy, methylenedioxy, difluoromethylenedioxy, further more preferably methyl, trifluoromethyl, trifluoromethoxy, a fluorine atom, a chlorine atom.

Specific preferable examples of A include methylphenyl, (trifluoromethyl)phenyl, (trifluoromethoxy)phenyl, chlorophenyl, dichlorophenyl and fluoro(trifluoromethyl)phenyl.

Examples of the pharmaceutically acceptable acid addition salt in the compound of the present invention include inorganic acid salt (e.g., hydrochloride etc.), or organic acid salt and the like. In addition, the compound of the present invention is encompassed in, besides the above-mentioned compound of the formula (I) and a pharmaceutically acceptable acid addition salt thereof, a hydrate thereof and a solvate.

When the compound of the present invention has isomer such as optical isomer, cis-trans isomer and the like, any isomer and a mixture are also encompassed in the above-mentioned compound of the formula (I) and the like.

As the synthesis methods of the compound of the present invention, the following methods can be exemplified.

1) Of the compounds of the present invention, a compound (I-1), which is a compound of the formula (I) wherein R, R$_3$ and R$_4$ are hydrogen atoms, X is an oxygen atom, and Y is —CH$_2$CH$_2$—, is synthesized according to the following scheme (II).

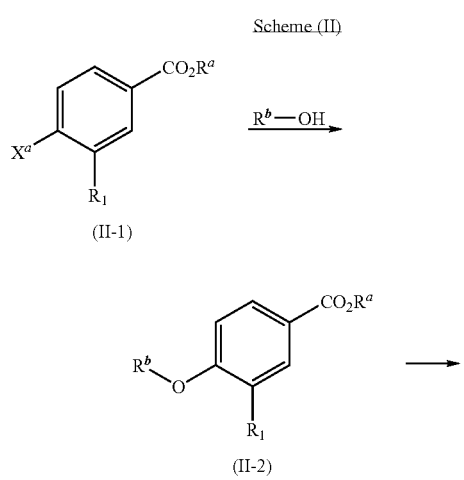

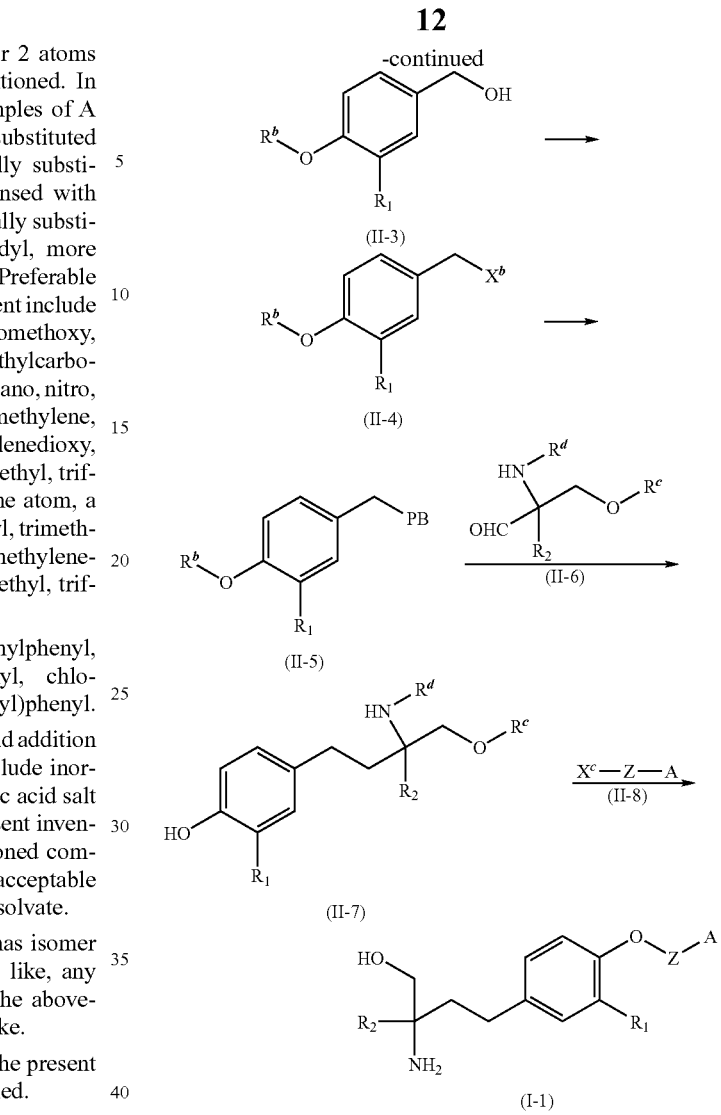

wherein, Z, R$_1$, R$_2$ and A are as defined for these symbols in the formula (I), R$^a$ is a hydrogen atom or a protecting group, R$^b$, R$^c$ and R$^d$ are protecting groups, X$^a$ and X$^b$ are leaving groups, X$^c$ is a leaving group or a hydroxyl group, and PB is a leaving group containing phosphorus.

R$^a$ in the formula is not particularly limited as long as it is a hydrogen atom, or a carboxyl-protecting group, such as alkyl (specifically methyl, ethyl etc.), aralkyl (benzyl etc.), the same substituents as R$^b$ and the like. R$^b$ in the formula is not particularly limited as long as it protects a phenolic hydroxyl group, such as alkyl (specifically methyl, ethyl etc.), aralkyl (benzyl etc.) and the like. When a partial structure —Z'-A wherein Z' is alkylene having 1 to 5 carbon atoms of the compound (I-1) of the present invention is used as R$^b$, the compound (I-1) of the present invention can be obtained without deprotecting R$^b$. R$^c$ in the formula is not particularly limited as long as it protects a hydroxyl group.

For example, acyl (preferably that having about 2 to 4 carbon atoms, specifically acetyl etc.), trialkylsilyl (specifically trimethylsilyl etc.), benzyl and a substituent forming an acetal compound (specifically, methoxymethyl, tetrahydropyranyl etc.) can be mentioned. When R$_2$ has a hydroxyl group, the hydroxyl group may be protected by a suitable protecting group, and specific examples of the hydroxyl-protecting group R$^e$ include those similar to R$^c$. In addition, R$^c$ and R$^e$ may be bonded to form cyclic acetal to (hereinafter $R^e$ in the present specification means as defined here). The protecting group for $R^d$ in the formula is not particularly limited as long as it protects an amino group. For example, acyl (preferably those having about 2 to 4 carbon atoms, specifically acetyl etc.), carbamate (specifically t-butyloxycarbonyl, benzyloxycarbonyl etc.) and the like can be mentioned. In addition, the leaving group for $X^a$ is not particularly limited as long as it is dissociated during a substitution reaction with alkoxide ion ($R^b$—$O^-$). For example, a halogen atom (specifically fluorine atom etc.), toluenesulfonyloxy and the like can be mentioned. The leaving group for $X^b$ is not particularly limited as long as it is dissociated during reaction of intermediate (II-4) with a phosphorus compound and does not inhibit the next reaction with aldehyde (II-6). For example, a halogen atom (specifically iodine atom, bromine atom, chlorine atom etc.), methanesulfonyloxy, toluenesulfonyloxy and the like can be mentioned. Examples of the leaving group containing phosphorus for PB include triarylphosphonium (specifically $P(C_6H_5)_3$) and $P(O)(OR^f)_2$ ($R^f$ is alkyl having 1 to 4 carbon atoms, hereinafter the same). When $X^c$ is a leaving group, the leaving group is not particularly limited as long as it is dissociated during alkylation of a phenolic hydroxyl group and does not inhibit the reaction. For example, a halogen atom (specifically iodine atom, bromine atom, chlorine atom etc.) and the like can be mentioned.

In the first step, an oxygen functional group having a protecting group $R^b$ is introduced into the 4-position by condensing benzoic acid derivative (II-1) having a leaving group $X^a$ at the 4-position and alcohol $R^b$—OH, whereby intermediate (II-2) is obtained. This step can be performed in a polar solvent such as N,N-dimethylformamide, dimethyl sulfoxide and the like, and an ether solvent such as tetrahydrofuran and the like in the presence of a base. As the base, an inorganic base such as sodium hydride, potassium hydroxide, potassium carbonate and the like, alkoxide such as potassium t-butoxide and the like, an organic base such as 1,8-diazabicyclo[5.4.0]undec-7-ene and the like can be used. The reaction conditions are, for example, ice-cooling—about 100° C. for about 10 min-10 hr. After the reaction, purification and the like are performed according to conventional methods to give the object product.

In the second step, a carboxyl group of intermediate (II-2) is reduced to give intermediate (II-3) having a hydroxyl group. The reagent to be used for the reduction is not particularly limited as long as it is generally used, and an alkali metal (e.g., sodium and the like), an alkaline earth metal, a metal hydride (e.g., diisobutylaluminum hydride and the like), a metal hydride complex compound (e.g., lithium aluminum hydride, sodium borohydride and the like), a boron compound (e.g., diborane and the like), catalytic hydrogenation using a homogeneous or heterogeneous catalyst and the like can be mentioned. For reaction conditions, temperature and time appropriate for the reducing reagent to be used are selected. Specific examples include reduction with diborane, lithium aluminum hydride or lithium borohydride in an ether solvent such as tetrahydrofuran and the like at −30° C.—under refluxing for about 10 min-12 hr, reduction with sodium borohydride or calcium borohydride in an alcohol solvent such as ethanol and the like or a mixed solvent of an alcohol solvent and an ether solvent such as tetrahydrofuran and the like under ice-cooling—refluxing for about 30 min-24 hr, and the like. After the reaction, purification and the like are performed according to conventional methods to give the object product.

In the third step, a hydroxyl group of intermediate (II-3) is converted to a leaving group $X^b$. The reagent is not particularly limited as long as it can convert an alcoholic hydroxyl group to $X^b$. Examples of the reagent to be used when $X^b$ is a halogen atom include N-chlorosuccinimide, N-bromosuccinimide, carbon tetrachloride, a combination thereof with a reaction aid such as triphenylphosphine, base and the like, an inorganic acid such as hydrochloric acid, hydrobromic acid and hydroiodic acid, phosphorus tribromide, phosphorus pentabromide, phosphorus trichloride, phosphorus pentachloride, iodine, bromine, chlorine, thionyl halide, α-haloenamine and the like. The reaction conditions are, for example, an organic solvent such as halogen solvents (e.g., methylene chloride etc.), ether solvents (e.g., tetrahydrofuran etc.), and the like at −30° C.-130° C. for about 10 min-6 hr. When the inorganic acid is used, the reaction can also be performed in an aqueous solution or a two-layer system of an organic solvent such as toluene and the like and water. As the reagent to be used when $X^b$ is sulfonyloxy, a combination with sulfonyl chloride such as methanesulfonyl chloride, toluenesulfonyl chloride and the like, and organic base such as triethylamine, pyridine and the like can be used. Examples of the reaction conditions include an organic solvent such as halogen solvents (e.g., methylene chloride etc.), ether solvents (e.g., tetrahydrofuran etc.), and the like at −30° C.-50° C. for about 5 min-3 hr. After the reaction, purification and the like are performed according to conventional methods to give the object product.

In the fourth step, intermediate (II-4) having a leaving group $X^b$ and a phosphorus compound are reacted to give intermediate (II-5) having a leaving group PB containing phosphorus. When PB is triarylphosphonium, intermediate (II-5) can be obtained by reacting intermediate (II-4) with triarylphosphine. The reaction conditions are, for example, an inert solvent such as diethyl ether, benzene, toluene and the like at room temperature—under refluxing for about 30 min-12 hr. After the reaction, the solvent is evaporated, cooled, and a poorly soluble solvent such as diisopropyl ether, hexane and the like is added, as necessary, and the precipitated solid is collected by filtration to give the object product. When PB is $P(O)(OR^f)_2$, intermediate (II-5) can be obtained by Arbuzov reaction of intermediate (II-4) with phosphorous acid triester. The reaction conditions are, for example, no solvent or an inert solvent such as xylene and the like at 50° C.-170° C. for about 30 min-12 hr. After the reaction, excess phosphorous acid triester is evaporated or distilled away to give the object product. In addition, when PB is $P(O)(OR^f)_2$, intermediate (II-5) can also be obtained by reacting phosphonic acid diester with intermediate (II-4) in the presence of an additive such as tetraalkylammonium, cesium carbonate and the like. The reaction conditions are, for example, an inert solvent such as tetrahydrofuran, xylene and the like or a polar solvent such as N,N-dimethylformamide and the like under ice-cooling at −50° C. for about 30 min-6 hr. After the reaction, purification and the like are performed according to conventional methods to give the object product.

In the fifth step, intermediate (II-5) containing phosphorus is condensed with aldehyde (II-6) synthesized by according to a known method (e.g., Tetrahedron vol. 57 (2001), pages 6531-6538, Journal of Organic Chemistry vol. 69 (2004) pages 7765-7768), and then the obtained olefin compound is reduced, and the protecting group $R^b$ is deprotected to give phenolic intermediate (I1-7). When PB is triarylphosphonium, the conditions of conventional Wittig reaction are used. The conditions are, for example, an ether solvent such as tetrahydrofuran and the like, a base such as sodium hydride, potassium t-butoxide and the like at −30° C. —under refluxing for about 30 min-12 hr. A Z-configuration may be preferentially obtained by reaction in an aprotic polar solvent under conditions free of salts, or an E-configuration may be preferentially obtained by a Schlosser modification method. After the reaction, purification and the like are performed according to conventional methods to give the object product. When PB is $P(O)(OR^f)_2$, the conditions of conventional Horner-Wadsworth-Emmons reaction are used. The conditions are, for example, a hydrocarbon solvent such as benzene and the like or an ether solvent such as tetrahydrofuran and the like, a base such as sodium hydride, potassium t-butoxide, lithium hexamethyldisilasane and the like at −20° C.—under refluxing for about 30 min-12 hr. An E-configuration of olefin can be preferentially obtained. After the reaction, purification and the like can be performed according to conventional methods to give the object product. The reagent to be used for the reduction of double bond to be performed successively is not limited as long as it is a reagent to be used for conventional olefin reduction. For example, catalytic hydrogenation using a heterogeneous catalyst such as palladium carbon, Raney-nickel and the like, or a homogeneous catalyst such as rhodium complex (chlorotris(triphenylphosphine)rhodium (I) etc.) and the like can be mentioned. The reaction conditions are, for example, a solvent such as alcohol solvents (e.g., ethanol etc.), ether solvents (e.g., dioxane etc.), or hydrocarbon solvents (e.g., toluene etc.) under a hydrogen pressure of 1-20 atm under ice-cooling—refluxing for 30 min-1 week. Depending on the reaction rate, stability of the compound and the like, an acid such as acetic acid and the like, or a base such as triethylamine and the like can also be added to the reaction mixture. After the reaction, purification and the like are performed to give the object product. The conditions of removal of protecting group $R^b$ are not particularly limited as long as they are used for conventional deprotection of protecting groups. For example, when $R^b$ is methyl, a method using Lewis acid such as tribromide boron and the like in a methylene chloride solvent, when $R^b$ is acyl such as acetyl and the like, a method using inorganic base such as sodium hydroxide and the like in a mixed solvent of alcohol solvent and water, when $R^b$ is an ether protecting group such as methoxymethyl, tetrahydropyranyl, t-butyl and the like, a method using an acid such as hydrochloric acid, trifluoroacetic acid etc., and the like. When a protecting group that can be removed by hydrogenolysis, catalytic hydrogenation conditions, such as benzyl, substituted benzyl, benzyloxymethyl and the like is used as $R^b$, $R^b$ can also be removed simultaneously with the reduction of the aforementioned double bond. When a partial structure —Z'-A of the compound (I-1) of the present invention is used as $R^b$, removal of $R^b$ is not necessary and alkylation of phenol in the next step can also be omitted.

In the sixth step, a phenolic hydroxyl group of intermediate (II-7) is alkylated with intermediate (II-8) $X^c$—Z-A obtained by reduction of the corresponding optionally substituted cinnamic acid and the like or condensation of A and Z by a generally-known synthesis method, and then, $R^c$, $R^d$ and $R^e$ ($R^e$ is a hydroxyl-protecting group when $R_2$ has a hydroxyl group, and $R^e$ is sometimes absent) are removed to give the compound (I-1) of the present invention. When $X^c$ is a leaving group, the reagent to be used for alkylation of a phenolic hydroxyl group that intermediate (II-7) has is, for example, a combination of intermediate (II-8) and an inorganic base such as potassium carbonate, sodium hydride and the like. The reaction conditions are, for example, a polar solvent such as N,N-dimethylformamide and the like or an ether solvent such as tetrahydrofuran and the like under ice-cooling–80° C. for about 30 min-12 hr. When $X^c$ is a hydroxyl group, Mitsunobu reaction using a phosphine compound such as a triphenylphosphine and the like and an azodicarboxylic acid derivative such as azodicarboxylic acid diisopropyl ester and the like can also be used for alkylation of a phenolic hydroxyl group that intermediate (II-7) has. The reaction to conditions therefor are, for example, an ether solvent such as tetrahydrofuran and the like under ice-cooling–50° C. for about 10 min-6 hr. After the reaction, purification and the like are performed according to conventional methods to give the object product. For deprotection to be successively performed, those generally used for removal of protecting groups can be used without particular limitation, and all protecting groups can be removed at once or in a step-wise manner. For example, when $R^c$ and $R^e$ are bonded to form a cyclic acetal and $R^d$ is t-butyloxycarbonyl, they can be simultaneously removed with an acid. Examples of the acid include an inorganic acid such as hydrochloric acid and the like, trifluoroacetic acid and the like. The reaction conditions are, for example, an alcohol solvent such as ethanol and the like, an ether solvent such as tetrahydrofuran and the like, water, or a mixed solvent thereof under ice-cooling–80° C. for about 10 min-12 hr. After the reaction, purification and the like are performed according to conventional methods to give the object product.

2) Of the compounds of the present invention, a compound (I-1), which is a compound of the formula (I) wherein R, $R_3$ and $R_4$ are hydrogen atoms, X is an oxygen atom, and Y is —$CH_2CH_2$—, is also synthesized using intermediate (III-1) synthesized from intermediate (II-2', $R^a$ is H) contained in scheme (II) or a compound represented by the formula (III-2) according to the following scheme (III).

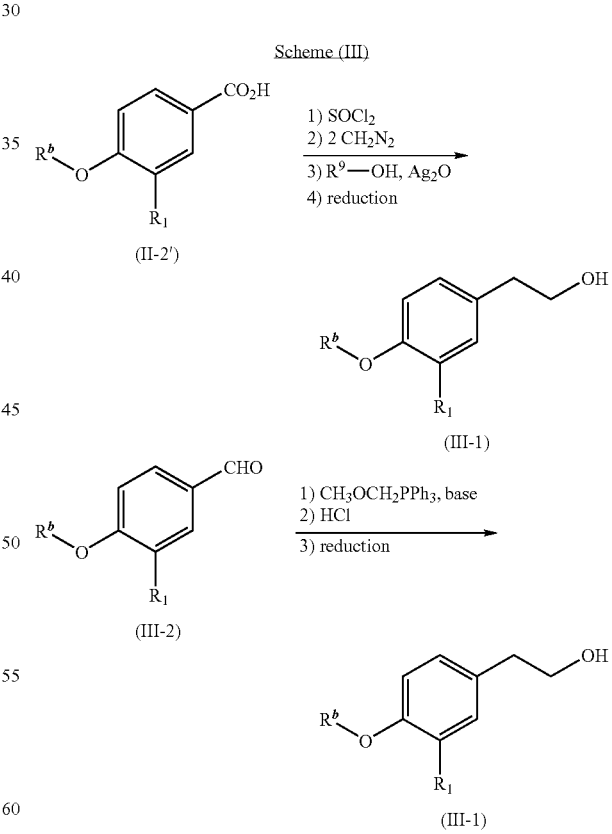

wherein $R_1$ is as defined for the formula (I), $R^b$ is a protecting group, and $R^g$—OH is alcohol used for solvolysis reaction.

$R^b$ in the formula is as defined for scheme (II). As $R^g$, methyl, ethyl, benzyl and the like can be mentioned. In the scheme, general reaction conditions for Arndt-Eistert reaction are used for the synthesis from compound (II-2'). For the reduction of the ester group obtained thereby, the reagent and conditions used for the second step of scheme (II) can be employed. In the scheme, the conditions for general Wittig reaction are used for the synthesis from compound (III-2). For the acid treatment thereafter, an inorganic acid such as hydrochloric acid and the like is used in water or a mixed solvent of an organic solvent such as tetrahydrofuran and the like and water. For the reduction thereafter, a catalytic hydrogenation using a metal hydride complex compound such as lithium aluminum hydride, sodium borohydride and the like, a heterogeneous catalyst such as palladium carbon, Raney-nickel and the like or a homogeneous catalyst such as a rhodium complex (chlorotris(triphenylphosphine)rhodium(I) and the like), and the like, or continuous and successive operation thereof can be mentioned. The alcoholic intermediate (III-1) obtained by this scheme can be led to the compound of the present invention by a known method (for example, Journal of Medicinal Chemistry, vol. 43 (2000) pages 2946-2961).

3) Of the compounds of the present invention, a compound (I-3), which is a compound of the formula (I) wherein R, $R_3$ and $R_4$ are hydrogen atoms, and $R_2$ is an ω-fluoroalkyl is also synthesized according to the following scheme (IV).

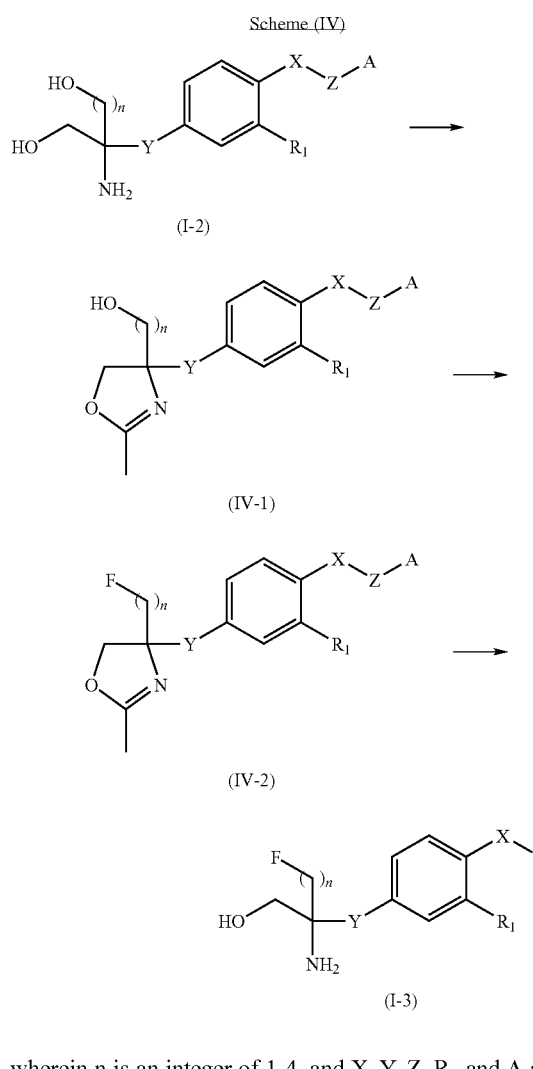

In the first step, compound (I-2) of the formula (I) wherein R is a hydrogen atom, and $R_2$ is ω-hydroxyalkyl is protected, whereby oxazoline compound (IV-1) is synthesized. In this step, a reaction can be performed in a polar solvent such as acetonitrile, N,N-dimethylformamide and the like, a halogen solvent such as methylene chloride and the like, or a hydrocarbon solvent such as toluene and the like and using orthoacetic acid ester as a reagent. In addition, a base such as N,N-diisopropylethylamine and the like, or an acid such as p-toluenesulfonic acid and the like can be added to promote the reaction. The reaction conditions are, for example, at room temperature—under refluxing for about 30 min-12 hr. After the reaction, purification and the like are performed according to conventional methods to give the object product.

In the second step, the hydroxyl group of compound (IV-1) is fluorinated, whereby fluoride (IV-2) is synthesized. As a fluorinating agent, diethylaminosulfur trifluoride (DAST), 2,2-difluoro-1,3-dimethylimidazolidine (DFI) and the like can be mentioned. In this step, the reaction can be performed in a halogen solvent such as methylene chloride and the like, or a hydrocarbon solvent such as hexane and the like. The reaction conditions are, for example, at −78° C.—at room temperature for about 30 min-12 hr. After the reaction, purification and the like are performed according to conventional methods to give the object product. This step can also be performed by a method including converting the hydroxyl group of compound (IV-1) to the corresponding sulfonate, and reacting the compound with fluoride ion. For example, when p-toluenesulfonyl fluoride and tetrabutylammonium fluoride (TBAF) are used, the reaction is performed in an ether solvent such as tetrahydrofuran and the like at room temperature–80° C. for about 1 hr-24 hr. A dehydrating agent such as molecular sieves and the like can be added to this reaction. After the reaction, purification and the like are performed according to conventional methods to give the object product.

In the third step, compound (IV-2) is deprotected to give the compound (I-3) of the present invention. This step can be performed by general deprotection. To be specific, an acid such as hydrochloric acid, trifluoroacetic acid and the like can be used. The reaction conditions are, for example, alcohol solvents such as ethanol and the like, or a mixed solvent thereof with water at room temperature—100° C. for about 30 min-12 hr. The reaction mixture is subjected to purification and the like according to a conventional method to give the object product.

4) A compound (I-4), which is a compound of the formula (I) wherein R, $R_3$ and $R_4$ are hydrogen atoms, Z is alkylene having 1 to 5 carbon atoms or alkenylene having 2 to 5 carbon atoms, and $R_1$ is trifluoromethyl or cyano is synthesized according to the following scheme (V).

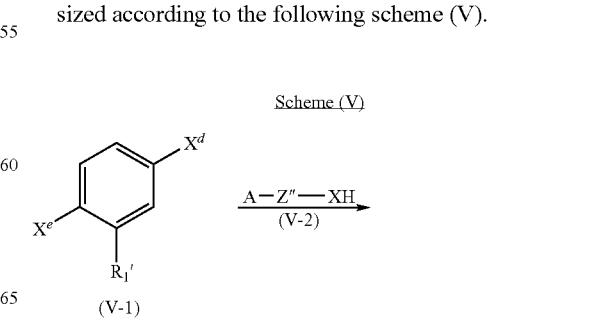

wherein n is an integer of 1-4, and X, Y, Z, $R_1$ and A are as defined for each symbol in the formula (I).

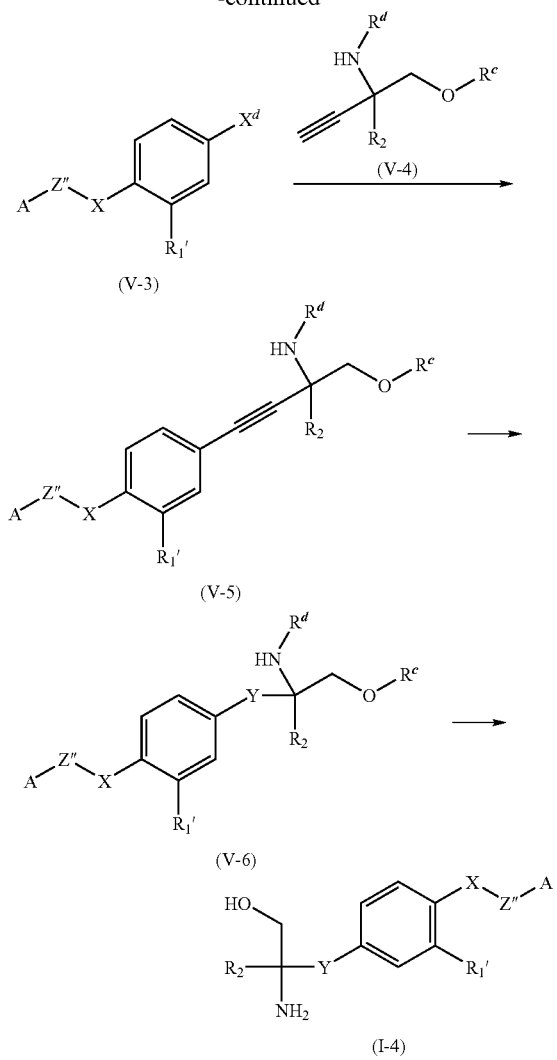

wherein $R_1'$ is trifluoromethyl or cyano, $Z''$ is alkylene having 1 to 5 carbon atoms or alkenylene having 2 to 5 carbon atoms, $R^c$ and $R^d$ are protecting groups, $X^d$ and $X^e$ are leaving groups, and $R_2$, X, Y and A are as defined for each symbol in the formula (I).

$R^c$ and $R^d$ in the formula are as defined above. The leaving group for $X^d$ is not particularly limited as long as it can be activated and released by a catalyst during Sonogashira reaction. For example, halogen atom (preferably iodine atom, bromine atom and the like), trifluoromethanesulfonyloxy and the like can be mentioned. The leaving group for $X^e$ is not particularly limited as long as it can be released during substitution reaction with alkoxide or thiol anion. For example, halogen atom (specifically fluorine atom and the like), toluenesulfonyloxy and the like can be mentioned.

In the first step, compound (V-1) having a leaving group $X^e$ is condensed with compound (V-2), whereby intermediate (V-3) is obtained. This step can be performed in a polar solvent such as N,N-dimethylformamide, dimethyl sulfoxide and the like, and an ether solvent such as tetrahydrofuran and the like in the presence of a base. As the base, an inorganic base such as sodium hydride, potassium hydroxide, potassium carbonate and the like, alkoxide such as potassium t-butoxide and the like, an organic base such as 1,8-diazabicyclo[5.4.0]undec-7-ene and the like can be used. The reaction conditions are, for example, ice-cooling—about 100° C. for about 10 min-10 hr. After the reaction, purification and the like are performed according to conventional methods to give the object product.

In the second step, intermediate (V-4) synthesized from intermediate (V-3) and intermediate (II-6) by a known method (for example, Tetrahedron vol. 57 (2001) pages 6531-6538, Chemical and Pharmaceutical Bulletin vol. 53 (2005) pages 100-102) is condensed by Sonogashira reaction to give intermediate (V-5) containing a triple bond. As the catalyst to be used, palladium compounds such as tetrakis(triphenylphosphine)palladium(0), tris(dibenzylideneacetone)dipalladium(0), dichlorobis(acetonitrile)palladium(II) and the like can be mentioned. To promote the reaction, an additive, for example, an organic base such as triethylamine and the like, an inorganic base such as ammonia and the like, a copper compound such as copper iodide, copper bromide and the like, a phosphine compound such as 2-dicyclohexylphosphino-2',4',6'-triisopropylbiphenyl and the like, and the like can also be added. The reaction conditions are, for example, a solvent such as ether solvents (e.g., tetrahydrofuran, dioxane etc.), polar solvents (e.g., acetonitrile, dimethylformamide etc.), or hydrocarbon (e.g., benzene etc.) under ice-cooling—refluxing for about 30 min-24 hr. After the reaction, purification and the like are performed according to conventional methods to give the object product.

In the third step, a triple bond of intermediate (V-5) is reduced to give intermediate (V-6). The reagent to be used when Y is —$CH_2CH_2$— and $Z''$ is alkenylene having 1 to 5 carbon atoms is not limited as long as it is a reagent to be used for conventional reduction of unsaturated carbon bond. For example, catalytic hydrogenation using a heterogeneous catalyst such as palladium carbon, Raney-nickel, a palladium carbon ethylene diamine complex and the like, or a homogeneous catalyst such as rhodium complex (chlorotris(triphenylphosphine)rhodium(I) etc.) and the like can be mentioned. The reaction conditions are, for example, a solvent such as alcohol solvents (e.g., ethanol etc.), ether solvents (e.g., dioxane etc.), or hydrocarbon solvents (e.g., toluene etc.) under a hydrogen pressure of 1-20 atm under ice-cooling—refluxing for 30 min-1 week. Depending on the reaction rate, stability of the compound and the like, an acid such as acetic acid and the like, or a base such as triethylamine and the like can also be added to the reaction mixture. After the reaction, purification and the like are performed according to conventional methods to give the object product. The reaction used when Y is —CH═CH— or $Z''$ is alkenylene having 2 to 5 carbon atoms includes catalytic hydrogenation performed in the presence of a catalyst having controlled activity such as Lindlar catalyst, nickel-graphite-ethylenediamine complex, various complexes of diene compound, phosphine compound and rhodium, and the like. In addition, reduction reaction using metal hydride such as diisobutylaluminum hydride and the like can also be employed. After the reaction, purification and the like are performed according to conventional methods to give the object product.

In the fourth step, intermediate (V-6) is deprotected to give the compound (I-4) of the present invention. For removal of $R^c$, $R^d$ and $R^e$ ($R^e$ is a hydroxyl-protecting group when $R_2$ has a hydroxyl group, and $R^e$ is sometimes absent), those generally used for removal of protecting groups can be used without particular limitation, and all protecting groups can be removed at once or in a step-wise manner. For example, when $R^c$ and $R^e$ are bonded to form a cyclic acetal and $R^d$ is t-butyloxycarbonyl, cyclic acetal is deprotected with a catalytic amount of an acid, and stronger acidic conditions are employed for deprotection of $R^d$. The conditions for acetal deprotection are, for example, an alcohol solvent such as methanol and the like or a mixed solution of alcohol solvent and other organic solvent, a catalytic amount of hydrochloric acid or toluenesulfonic acid under ice-cooling–80° C. for about 30 min-12 hr. The reaction conditions for deprotection of $R^d$ following the acetal deprotection are, for example, an inorganic acid such as hydrochloric acid and the like, trifluoroacetic acid and the like in an equivalent amount or above, an alcohol solvent such as ethanol and the like, an ether solvent such as tetrahydrofuran and the like, water, or a mixed solvent thereof under ice-cooling–80° C. for about 10 min-12 hr. After the reaction, purification and the like are performed according to conventional methods to give the object product.

5) A compound (I-5), which is a compound of the formula (I) wherein R, $R_3$ and $R_4$ are hydrogen atoms, X is a sulfur atom, Y is —$CH_2CH_2$—, Z is alkylene having 1 to 5 carbon atoms is synthesized according to the following scheme (VI).

Scheme (VI)

(VI-1) → (VI-3) → (VI-4) → (VI-5) → (VI-6) → (VI-7) → (I-5)

wherein $R^a$ is a hydrogen atom or a protecting group, $R^c$ and $R^d$ are each a protecting group, $X^b$ and $X^f$ are leaving groups, m is an integer of 1-5, PB is a leaving group containing phosphorus, and $R_1$, $R_2$ and A are as defined for each symbol in the formula (I).

$R^a$, $R^c$, $R^d$, $X^b$, PB in the formula are as defined above. The leaving group for $X^f$ is not particularly limited as long as it is dissociated during a substitution reaction with alkylthio ion $A(CH_2)_mS^-$. For example, a halogen atom (specifically fluorine atom etc.), toluenesulfonyloxy and the like can be mentioned.

In the first step, an alkylthio group is introduced into the 4-position by condensing benzoic acid derivative (VI-1) having a leaving group $X^f$ at the 4-position and thiol (VI-2), whereby intermediate (VI-3) is obtained. This step can be performed in a polar solvent such as N,N-dimethylformamide, dimethyl sulfoxide and the like, and an ether solvent such as tetrahydrofuran and the like in the presence of a base. As the base, an inorganic base such as potassium carbonate, sodium hydride and the like, an organic base such as triethylamine, 1,8-diazabicyclo[5.4.0]undec-7-ene and the like can be used. The reaction conditions are, for example, about –30-80° C. for about 10 min-10 hr. After the reaction, purification and the like are performed according to conventional methods to give the object product.

In the second step, a carboxyl group of intermediate (VI-3) is reduced to give intermediate (VI-4) having a hydroxyl group. The reagent to be used for the reduction is not particularly limited as long as it is generally used, and an alkali metal (e.g., sodium and the like), an alkaline earth metal, a metal hydride (e.g., diisobutylaluminum hydride and the like), a metal hydride complex compound (e.g., lithium aluminum hydride, sodium borohydride and the like), a boron compound (e.g., diborane and the like), catalytic hydrogenation using a homogeneous or heterogeneous catalyst and the like can be mentioned. For reaction conditions, temperature and time appropriate for the reducing reagent to be used are selected. Specific examples include reduction with diborane, lithium aluminum hydride or lithium borohydride in an ether solvent such as tetrahydrofuran and the like at –30° C.—under refluxing for about 10 min-12 hr, reduction with sodium borohydride or calcium borohydride in an alcohol solvent such as ethanol and the like or a mixed solvent of an alcohol solvent and an ether solvent such as tetrahydrofuran and the like under ice-cooling—refluxing for about 30 min-24 hr, and the like. After the reaction, purification and the like are performed according to conventional methods to give the object product.

In the third step, a hydroxyl group of intermediate (VI-4) is converted to a leaving group $X^b$. The reagent is not particularly limited as long as it can convert an alcoholic hydroxyl group to $X^b$. Examples of the reagent to be used when $X^b$ is halogen include N-chlorosuccinimide, N-bromosuccinimide, carbon tetrachloride, a combination thereof with a reaction aid such as triphenylphosphine, base and the like, an inorganic acid such as hydrochloric acid, hydrobromic acid and hydroiodic acid, phosphorus tribromide, phosphorus pentabromide, phosphorus trichloride, phosphorus pentachloride, iodine, bromine, chlorine, thionyl halide, a-haloenamine and the like. The reaction conditions are, for example, an organic solvent such as halogen solvents (e.g., methylene chloride etc.), ether solvents (e.g., tetrahydrofuran etc.), and the like at −30° C.-130° C. for about 10 min-6 hr. When the inorganic acid is used, the reaction can also be performed in an aqueous solution or a two-layer system of an organic solvent such as toluene and the like and water. As the reagent to be used when $X^b$ is a sulfonyloxy group, a combination with sulfonyl chloride such as methanesulfonyl chloride, toluenesulfonyl chloride and the like, and organic base such as triethylamine, pyridine and the like can be used. Examples of the reaction conditions include an organic solvent such as halogen solvents (e.g., methylene chloride etc.), ether solvents (e.g., tetrahydrofuran etc.), and the like at −30° C.-50° C. for about 5 min-3 hr. After the reaction, purification and the like are performed according to conventional methods to give the object product.

In the fourth step, intermediate (VI-5) having a leaving group $X^b$ and a phosphorus compound are reacted to give intermediate (VI-6) having a leaving group PB containing phosphorus. When PB is triarylphosphonium, intermediate (VI-6) can be obtained by reacting intermediate (VI-5) with triarylphosphine. The reaction conditions are, for example, an inert solvent such as diethyl ether, benzene, toluene and the like at room temperature—under refluxing for about 30 min-12 hr. After the reaction, the solvent is evaporated, cooled, and a poorly soluble solvent such as diisopropyl ether, hexane and the like is added, as necessary, and the precipitated solid is collected by filtration to give the object product. When PB is $P(O)(OR^f)_2$, intermediate (VI-6) can be obtained by Arbuzov reaction of intermediate (VI-5) with phosphorous acid triester. The reaction conditions are, for example, no solvent or an inert solvent such as xylene and the like at 50° C.-170° C. for about 30 min-12 hr. After the reaction, excess phosphorous acid triester is evaporated or distilled away to give the object product. In addition, when PB is $P(O)(OR^f)_2$, intermediate (VI-6) can also be obtained by reacting phosphonic acid diester with intermediate (VI-5) in the presence of an additive such as tetraalkylammonium, cesium carbonate and the like. The reaction conditions are, for example, an inert solvent such as tetrahydrofuran, xylene and the like or a polar solvent such as N,N-dimethylformamide and the like under ice-cooling–50° C. for about 30 min-6 hr. After the reaction, purification and the like are performed according to conventional methods to give the object product.

In the fifth step, intermediate (VI-6) containing phosphorus is condensed with aldehyde (II-6) synthesized separately, and then the obtained olefin compound is reduced to give intermediate (II-7). When PB is triarylphosphonium, the conditions of conventional Wittig reaction are used. The conditions are, for example, an ether solvent such as tetrahydrofuran and the like, a base such as sodium hydride, potassium t-butoxide and the like at −30° C.—under refluxing for about 30 min-12 hr. A Z-configuration may be preferentially obtained by reaction in an aprotic polar solvent under conditions free of salts, or an E-configuration may be preferentially obtained by a Schlosser modification method. After the reaction, purification and the like are performed according to conventional methods to give the object product. When PB is $P(O)(OR^f)_2$, the conditions of conventional Horner-Wadsworth-Emmons reaction are used. The conditions are, for example, a hydrocarbon solvent such as benzene and the like or an ether solvent such as tetrahydrofuran and the like, a base such as sodium hydride, potassium t-butoxide, lithiumhexamethyldisilasane and the like at −20° C.—under refluxing for about 30 min-12 hr. An E-configuration of olefin can be preferentially obtained. After the reaction, purification and the like can be performed according to conventional methods to give the object product. The reagent to be used for the reduction of double bond to be performed successively is not limited as long as it is a reagent to be used for conventional olefin reduction. For example, catalytic hydrogenation using a heterogeneous catalyst such as palladium carbon, Raney-nickel and the like, or a homogeneous catalyst such as rhodium complex (chlorotris(triphenylphosphine)rhodium (I) etc.) and the like can be mentioned. The reaction conditions are, for example, a solvent such as alcohol solvents (e.g., ethanol etc.), ether solvents (e.g., dioxane etc.), or hydrocarbon solvents (e.g., toluene etc.) under a hydrogen pressure of 1-20 atm under ice-cooling—refluxing for 30 min-1 week. Depending on the reaction rate, stability of the compound and the like, an acid such as acetic acid and the like, or a base such as triethylamine and the like can also be added to the reaction mixture. After the reaction, purification and the like are performed according to conventional methods to give the object product.

In the sixth step, $R^c$, $R^d$ and $R^e$ of intermediate (VI-7) ($R^e$ is a hydroxyl-protecting group when $R_2$ has a hydroxyl group, and $R^e$ is sometimes absent) are removed to give the compound (I-5) of the present invention. For deprotection of intermediate (VI-7), those generally used for removal of protecting groups can be used without particular limitation, and all protecting groups can be removed at once or in a step-wise manner. For example, when $R^c$ and $R^e$ are bonded to form a cyclic acetal and $R^d$ is t-butyloxycarbonyl, they can be simultaneously removed with an acid. Examples of the acid include an inorganic acid such as hydrochloric acid and the like, trifluoroacetic acid and the like. The reaction conditions are, for example, an alcohol solvent such as ethanol and the like, an ether solvent such as tetrahydrofuran and the like, water, or a mixed solvent thereof under ice-cooling—80° C. for about 10 min-12 hr. After the reaction, purification and the like are performed according to conventional methods to give the object product.

6) A compound (I-6), which is a compound of the formula (I) wherein R, $R_3$ and $R_4$ are hydrogen atoms, and X is a sulfur atom is synthesized according to the following scheme (VII).

Scheme (VII)

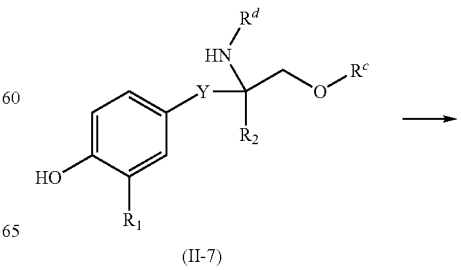

(II-7)

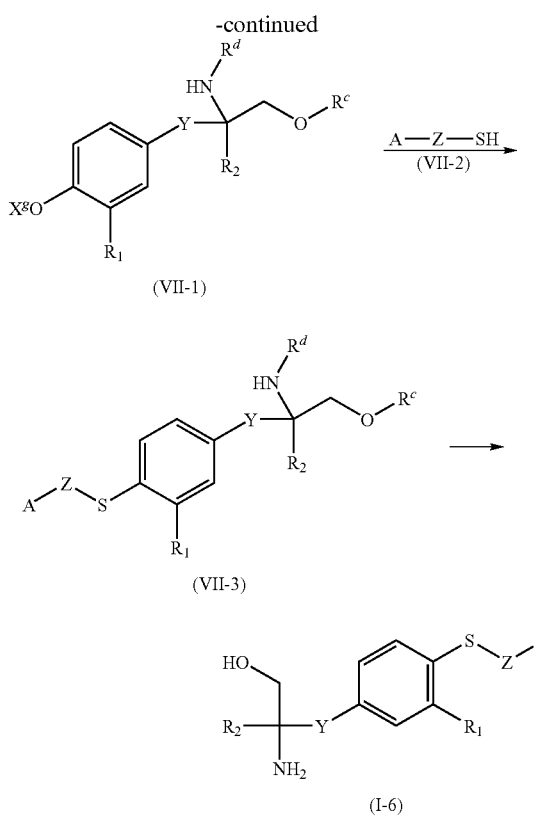

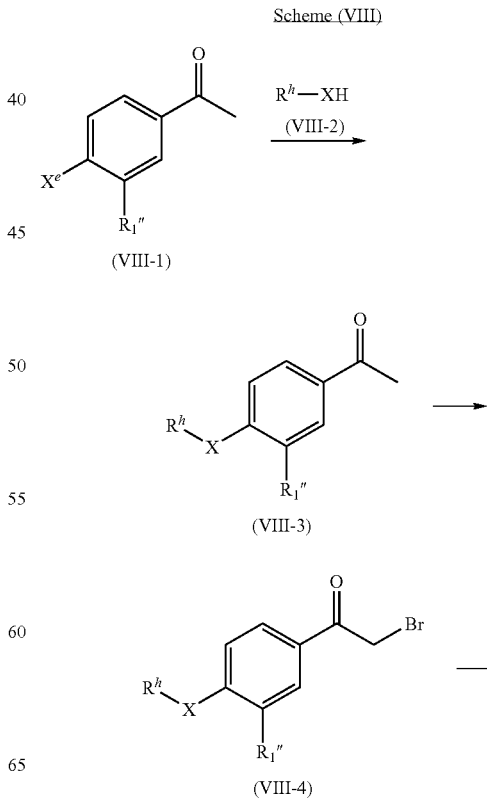

wherein $R^c$, $R^d$ are protecting groups, $X^g$ is a hydroxyl-activating group, and Y, Z, $R_1$, $R_2$ and A are as defined for each symbol in the formula (I).

$R^c$, $R^d$ in the formula are as defined above. The hydroxyl-activating group for $X^g$ is, for example, sulfonyl such as trifluoromethanesulfonyl, toluenesulfonyl and the like.

In the first step, an activating group is introduced into the phenolic hydroxyl group of intermediate (II-7) to give intermediate (VII-1). This step can be performed in a halogen solvent such as methylene chloride and chloroform, an ether solvent such as tetrahydrofuran and the like, in the presence of a base. As the reagent to be used for this reaction, activated sulfone acid derivatives such as trifluoromethanesulfonic acid anhydride, 1-(trifluoromethanesulfonyl)imidazole and toluenesulfonyl chloride are used. This reaction can also be performed using sulfonic acid and a condensing agent in combination. As the base, an organic base such as triethylamine, pyridine, lutidine and the like can be used. The reaction conditions are, for example, about −50-50° C. for about 5 min-3 hr. After the reaction, purification and the like are performed according to conventional methods to give the object product.

In the second step, intermediate (VII-1) is condensed with thiol (VII-2) A-Z—SH, which is obtained by condensing A and Z by a generally known synthesis method and introducing a thiol group, to give intermediate (VII-3). This step can be performed in an ether solvent such as dioxane and the like or a hydrocarbon solvent such as toluene and the like in the presence of a palladium catalyst. As the palladium catalyst, palladium acetate (II), tris(dibenzylideneacetone)dipalladium(O) and the like can be mentioned. In this reaction, a phosphine compound or a base can be added as a reaction aid. As the phosphine compound, triphenylphosphine, 4,5-bis (diphenylphosphino)-9,9-dimethylxanthene and the like can be mentioned. As the base, an inorganic base such as cesium carbonate and the like, and an organic base such as N,N-diisopropylethylamine and the like can be mentioned. The reaction conditions are, for example, room temperature—under refluxing for about 30 min-24 hr. After the reaction, purification and the like are performed according to conventional methods to give the object product.

In the third step, $R^c$, $R^d$ and $R^e$ ($R^e$ is a hydroxyl-protecting group when $R_2$ has a hydroxyl group, and $R^e$ is sometimes absent) of intermediate (VII-3) are deprotected to give the compound (I-6) of the present invention. For deprotection of intermediate (VII-3), those generally used for removal of protecting groups can be used without particular limitation, and all protecting groups can be removed at once or in a step-wise manner. For example, when $R^c$ is a protecting group that can be removed by an acid such as methoxymethyl and the like and $R^d$ is t-butyloxycarbonyl, they can be simultaneously removed with an acid. Examples of the acid include an inorganic acid such as hydrochloric acid and the like, trifluoroacetic acid and the like. The reaction conditions are, for example, an alcohol solvent such as ethanol and the like, an ether solvent such as tetrahydrofuran and the like, water, or a mixed solvent thereof under ice-cooling—80° C. for about 10 min-12 hr. After the reaction, purification and the like are performed according to conventional methods to give the object product.

7) Of the compounds of the present invention, a compound (I-7), which is a compound of the formula (I) wherein R, $R_3$ and $R_4$ are hydrogen atoms, Y is —$CH_2CH_2$—, Z is alkylene having 1 to 5 carbon atoms, and $R_1$ is alkyl having 1 to 4 carbon atoms, which is substituted by a halogen atom, is also synthesized according to the following scheme (VIII).

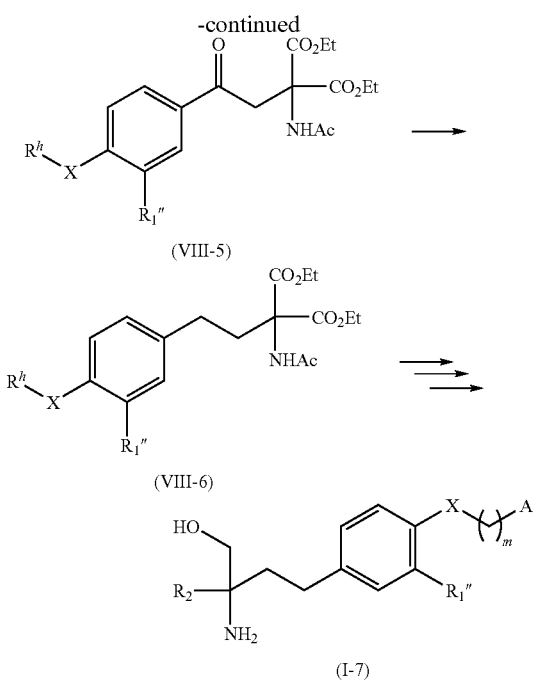

(VIII-5)

(VIII-6)

(I-7)

wherein $R_1''$ is a alkyl having 1 to 4 carbon atoms, which is substituted by a halogen atom, $X^e$ is a leaving group, $R^h$ is a protecting group or —$(CH_2)_m$-A, m is an integer of 1-5, and X, $R_2$ and A are as defined for each symbol in the formula (I).

$X^e$ in the formula is as defined above. When $R^h$ in the formula is a protecting group, $R^h$ is not particularly limited as long as it protects phenol group or thiol group. Examples of $R^h$ when X is an oxygen atom include alkyl (methyl and the like), aralkyl (benzyl and the like), protecting group forming acetal (methoxymethyl, ethoxyethyl and the like) and the like. When X is a sulfur atom, alkyl (methyl and the like), aralkyl (benzyl and the like) and the like can be mentioned.

In the first step, acetophenone (VIII-1) having a leaving group $X^e$ at the 4-position and alcohol or thiol (VIII-2) are condensed, whereby intermediate (VIII-3) is obtained. This step can be performed in a polar solvent such as N,N-dimethylformamide, dimethyl sulfoxide and the like, and an ether solvent such as tetrahydrofuran and the like in the presence of a base. As the base, an inorganic base such as sodium hydride, potassium hydroxide and the like, an organic base such as 1,8-diazabicyclo[5.4.0]undec-7-ene and the like can be used. The reaction conditions are, for example, ice-cooling—about 100° C. for about 10 min-10 hr. After the reaction, purification and the like are performed according to conventional methods to give the object product.

In the second step, acetyl group of intermediate (VIII-3) is brominated to give phenacyl bromide compound (VIII-4). This step can be performed in a solvent, for example, a halogen solvent such as chloroform and the like, an ether solvent such as dioxane and the like, an alcohol solvent such as methanol and the like or acetic acid and the like. As a reagent for bromination, bromine, pyridinium tribromide, phenyltrimethylammoniumtribromide and the like can be mentioned. In this reaction, a base such as pyridine, triethylamine and the like can be added as necessary. The reaction conditions are, for example, under ice-cooling—about 60° C. for about 30 min-10 hr. After the reaction, purification and the like are performed according to conventional methods to give the object product.

In the third step, intermediate (VIII-4) and diethyl acetamidemalonate are condensed to give intermediate (VIII-5). This step can be performed in a polar solvent such as N,N-dimethylformamide, dimethylsulfoxide and the like, an ether solvent such as tetrahydrofuran and the like, in the presence of a base. As the base, sodium hydride, potassium hydroxide, potassium t-butoxide and the like can be mentioned. The reaction conditions are, for example, under ice-cooling— about 50° C. for about 10 min-5 hr. After the reaction, purification and the like are performed according to conventional methods to give the object product.

In the fourth step, carbonyl group of intermediate (VIII-5) is reduced to methylene to give intermediate (VIII-6). As the reducing agent, a combination of trialkylsilane and trifluoroacetic acid or Lewis acid such as titanium tetrachloride and the like, and the like can be used. The reaction can be performed in a halogen solvent such as 1,2-dichloroethane and the like or without solvent. The reaction conditions are, for example, under ice-cooling—refluxing for about 1-48 hr. After the reaction, purification and the like are performed according to conventional methods to give the object product.

The obtained intermediate can be led to the compound (I-7) of the present invention by a known method (for example, Journal of Medicinal Chemistry vol. 43 (2000) pages 2946-2961).

8) Of the compounds of the present invention, a compound (I-8), which is a compound of the formula (I) wherein one or both of $R_3$ and $R_4$ are alkyl having 1 to 4 carbon atoms is synthesized according to the following scheme (IX).

Scheme (IX)

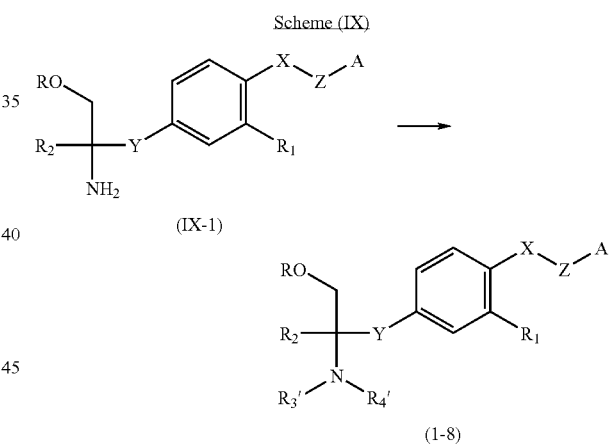

(IX-1)

(1-8)

wherein, one or both of $R_3'$ and $R_4'$ is(are) alkyl having 1 to 4 carbon atoms, and R, X, Y, Z, $R_1$, $R_2$ and A are as defined for each symbol in the formula (I).

In this step, amino group of compound (IX-1) having a primary amino group from among the compounds of the present invention is alkylated to give the compound (1-8) of the present invention. For this synthesis, reductive amination reaction, alkylation reaction of amine using alkyl halide and a base can be used. When a reductive amination reaction is used, aldehyde having the same carbon number as the carbon number of $R_3$ or $R_4$ is reacted with compound (IX-1) in an alcohol solvent such as methanol and the like or halogen solvent such as dichloroethane and the like, using a reducing agent such as sodium borohydride, sodium cyanoborohydride, sodium triacetoxyborohydride and the like to give an object product. For the reduction, hydrogen and a catalyst such as Raney-nickel, platinum oxide and the like can also be used. In this reaction, production of a Schiff base and reduction reaction can also be performed successively. In this reductive amination reaction, an acid such as acetic acid and the like can also be added as a reaction promoter. The reaction conditions are, for example, under ice-cooling—about 50° C. for about 30 min-10 hr. After the reaction, purification and the like are performed according to conventional methods to give the object product. When $R_3$ and $R_4$ are methyl, methylation reaction of Eschweiler-Clarke may also be employed using a reducing agent such as formic acid and formaldehyde, or formaldehyde and sodium cyanoborohydride and the like.

9) Of the compounds of the present invention, a compound (I-9), which is a compound of the formula (I) wherein R, $R_3$ and $R_4$ are hydrogen atoms, and Y is —CH=CH— is synthesized according to the following scheme (X).

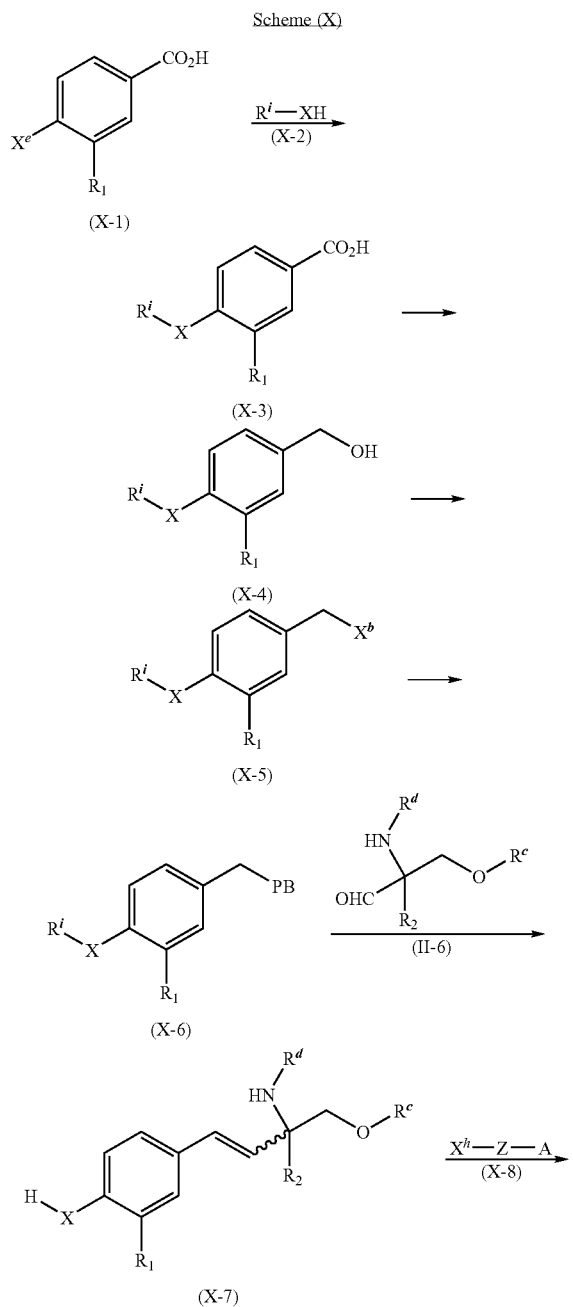

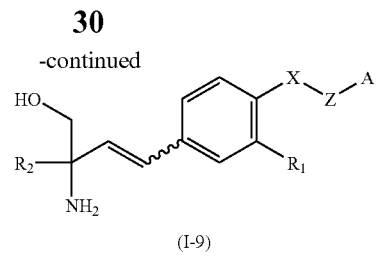

wherein $R^c$ and $R^d$ are protecting groups, $R^i$ is a protecting group or —Z-A, $X^b$ and $X^e$ are leaving groups, $X^h$ is a leaving group or hydroxyl group, PB is a leaving group containing phosphorus, and X, Z, $R_1$, $R_2$ and A are as defined for each symbol in the formula (I).

$R^c$, $R^d$, $X^b$, $X^e$, PB in the formula are as defined above. When $X^h$ is a leaving group, the leaving group is not particularly limited as long as it is dissociated during alkylation of a phenolic hydroxyl group or a thiol group and does not inhibit the reaction. For example, a halogen atom (specifically iodine atom, bromine atom, chlorine atom etc.) and the like can be mentioned. When $R^i$ in the formula is a protecting group, $R^i$ is not particularly limited as long as it protects a phenol group or a thiol group. Examples of $R^i$ when X is an oxygen atom include alkyl (methyl and the like), aralkyl (4-methoxybenzyl and the like), a protecting group forming acetal (methoxymethyl, ethoxyethyl and the like) and the like. When X is a sulfur atom, alkyl (methyl and the like), aralkyl (4-methoxybenzyl and the like), a protecting group forming thioacetal (methoxymethyl, phenylthiomethyl, acetamidemethyl and the like) and the like can be mentioned.

In the first step, benzoic acid (II-1) having a leaving group $X^e$ at the 4-position and alcohol or thiol (X-2) are condensed, whereby intermediate (X-3) is obtained. This step can be performed in a polar solvent such as N,N-dimethylformamide, dimethyl sulfoxide and the like, and an ether solvent such as tetrahydrofuran and the like in the presence of a base. As the base, an inorganic base such as sodium hydride, potassium hydroxide, potassium carbonate and the like, alkoxide such as potassium t-butoxide and the like, an organic base such as 1,8-diazabicyclo[5.4.0]undec-7-ene and the like can be used. The reaction conditions are, for example, ice-cooling—about 80° C. for about 30 min-24 hr. After the reaction, purification and the like are performed according to conventional methods to give the object product.

In the second step, a carboxyl group of intermediate (X-3) is reduced to give intermediate (X-4) having a hydroxyl group. The reagent to be used for the reduction is not particularly limited as long as it is generally used, and an alkali metal (e.g., sodium and the like), an alkaline earth metal, a metal hydride (e.g., diisobutylaluminum hydride and the like), a metal hydride complex compound (e.g., lithium aluminum hydride, sodium bis(2-methoxyethoxy)aluminum sodium and the like), a boron compound (e.g., diborane and the like), catalytic hydrogenation using a homogeneous or heterogeneous catalyst and the like can be mentioned. For reaction conditions, temperature and time appropriate for the reducing reagent to be used are selected. Specific examples include reduction with diborane, lithium aluminum hydride or lithium borohydride in an ether solvent such as tetrahydrofuran and the like at −30° C.—under refluxing for about 10 min-12 hr, reduction with bis(2-methoxyethoxy)aluminum-sodium hydride in an inert solvent such as toluene and the like under ice-cooling—50° C. for about 30 min-24 hr, and the like. After the reaction, purification and the like are performed according to conventional methods to give the object product.

In the third step, a hydroxyl group of intermediate (X-4) is converted to a leaving group $X^b$. The reagent is not particularly limited as long as it can convert an alcoholic hydroxyl group to $X^b$. Examples of the reagent to be used when $X^b$ is a halogen atom include N-chlorosuccinimide, N-bromosuccinimide, carbon tetrachloride, a combination thereof with a reaction aid such as triphenylphosphine, base and the like, an inorganic acid such as hydrochloric acid, hydrobromic acid and hydroiodic acid, phosphorus tribromide, phosphorus pentabromide, phosphorus trichloride, phosphorus pentachloride, iodine, bromine, chlorine, thionyl halide, α-haloenamine and the like. The reaction conditions are, for example, an organic solvent such as halogen solvents (e.g., methylene chloride etc.), ether solvents (e.g., tetrahydrofuran etc.), and the like at −30° C.-130° C. for about 10 min-6 hr. When the inorganic acid is used, the reaction can also be performed in an aqueous solution or a two-layer system of an organic solvent such as toluene and the like and water. As the reagent to be used when $X^b$ is sulfonyloxy, a combination with sulfonyl chloride such as methanesulfonyl chloride, toluenesulfonyl chloride and the like, and organic base such as triethylamine, pyridine and the like can be used. Examples of the reaction conditions include an organic solvent such as halogen solvents (e.g., methylene chloride etc.), ether solvents (e.g., tetrahydrofuran etc.), and the like at −30° C.-50° C. for about 5 min-3 hr. After the reaction, purification and the like are performed according to conventional methods to give the object product.

In the fourth step, intermediate (X-5) having a leaving group $X^b$ and a phosphorus compound are reacted to give intermediate (X-6) having a leaving group PB containing phosphorus. When PB is triarylphosphonium, intermediate (X-6) can be obtained by reacting intermediate (X-5) with triarylphosphine in the presence of an additive such as tetraalkylammonium, cesium carbonate and the like. The reaction conditions are, for example, an inert solvent such as diethyl ether, benzene, toluene and the like at room temperature—under refluxing for about 30 min-12 hr. After the reaction, the solvent is evaporated, cooled, and a poorly soluble solvent such as diisopropyl ether, hexane and the like is added, as necessary, and the precipitated solid is collected by filtration to give the object product. When PB is $P(O)(OR^f)_2$, intermediate (X-6) can be obtained by Arbuzov reaction of intermediate (X-5) with phosphorous acid triester. The reaction conditions are, for example, no solvent or an inert solvent such as xylene and the like at 50° C.-170° C. for about 30 min-12 hr. After the reaction, excess phosphorous acid triester is evaporated or distilled away to give the object product. In addition, when PB is $P(O)(OR^f)_2$. intermediate (X-6) can also be obtained by reacting phosphonic acid diester with intermediate (X-5). The reaction conditions are, for example, an inert solvent such as tetrahydrofuran, xylene and the like or a polar solvent such as N,N-dimethylformamide and the like under ice-cooling at −50° C. for about 30 min-6 hr. After the reaction, purification and the like are performed according to conventional methods to give the object product.

In the fifth step, intermediate (X-6) containing phosphorus is condensed with aldehyde (II-6) synthesized separately, and the protecting group $R^i$ of the obtained olefin compound is deprotected to give phenolic intermediate or thiolic intermediate (X-7). When PB is triarylphosphonium, the conditions of conventional Wittig reaction are used. The conditions are, for example, an ether solvent such as tetrahydrofuran and the like, a base such as sodium hydride, potassium t-butoxide and the like at −30° C.—under refluxing for about 30 min-12 hr. A Z-configuration may be preferentially obtained by reaction in an aprotic polar solvent under conditions free of salts, or an E-configuration may be preferentially obtained by a Schlosser modification method. After the reaction, purification and the like are performed according to conventional methods to give the object product. When PB is $P(O)(OR^f)_2$, the conditions of conventional Horner-Wadsworth-Emmons reaction are used. The conditions are, for example, a hydrocarbon solvent such as benzene and the like or an ether solvent such as tetrahydrofuran and the like, a base such as sodium hydride, potassium t-butoxide, lithiumhexamethyldisilasane and the like at −20° C.—under refluxing for about 30 min-12 hr. An E-configuration of olefin can be preferentially obtained. After the reaction, purification and the like can be performed according to conventional methods to give the object product. The conditions for removal of protecting group $R^i$ to follow are not particularly limited as long as alkenylene is not damaged. For example, when $R^i$ is 4-methoxybenzyl, oxidization reaction with 2,3-dichloro-5,6-dicyano-1,4-benzoquinone (DDQ) and the like, when $R^i$ is silyl such as trialkylsilyl and the like, deprotection with an inorganic acid such as hydrochloric acid and the like or a fluorine compound such as tetrabutylammonium fluoride and the like can be mentioned. When a partial structure —Z'-A of the compound (I-9) of the present invention is used as $R^i$, removal of $R^i$ is not necessary and alkylation of phenol or thiol in the next step can also be omitted.

In the sixth step, a phenolic hydroxyl group or thiol group of intermediate (X-7) is alkylated, and then, $R^c$, $R^d$ and $R^e$ ($R^e$ is a hydroxyl-protecting group when $R_2$ has a hydroxyl group, and $R^e$ is sometimes absent) are removed to give the compound (I-9) of the present invention. When $X^h$ is a leaving group, the reagent to be used for alkylation of a phenolic hydroxyl group or thiol that intermediate (X-7) has is, for example, a combination of intermediate (X-8) and an inorganic base such as potassium carbonate, sodium hydride and the like. The reaction conditions are, for example, a polar solvent such as N,N-dimethylformamide and the like or an ether solvent such as tetrahydrofuran and the like under ice-cooling to −80° C. for about 30 min-12 hr. When $X^h$ is a hydroxyl group, and intermediate (X-7) has a phenolic hydroxyl group, Mitsunobu reaction using a phosphine compound such as a triphenylphosphine and the like and an azodicarboxylic acid derivative such as azodicarboxylic acid diisopropyl ester and the like can also be used for alkylation. The reaction conditions therefor are, for example, an ether solvent such as tetrahydrofuran and the like under ice-cooling−50° C. for about 10 min-6 hr. After the reaction, purification and the like are performed according to conventional methods to give the object product. For deprotection to be successively performed, those generally used for removal of protecting groups can be used without particular limitation, and all protecting groups can be removed at once or in a step-wise manner. For example, when $R^c$ and $R^e$ are bonded to form a cyclic acetal and $R^d$ is t-butyloxycarbonyl, they can be simultaneously removed with an acid. Examples of the acid include an inorganic acid such as hydrochloric acid and the like, trifluoroacetic acid and the like. The reaction conditions are, for example, an alcohol solvent such as ethanol and the like, an ether solvent such as tetrahydrofuran and the like, water, or a mixed solvent thereof under ice-cooling−80° C. for about 10 min-12 hr. After the reaction, purification and the like are performed according to conventional methods to give the object product.

10) A compound (I-10), which is a compound of the formula (I) wherein R, $R_3$ and $R_4$ are hydrogen atoms, and $R_1$ is difluoromethyl is also synthesized according to the following scheme (XI).

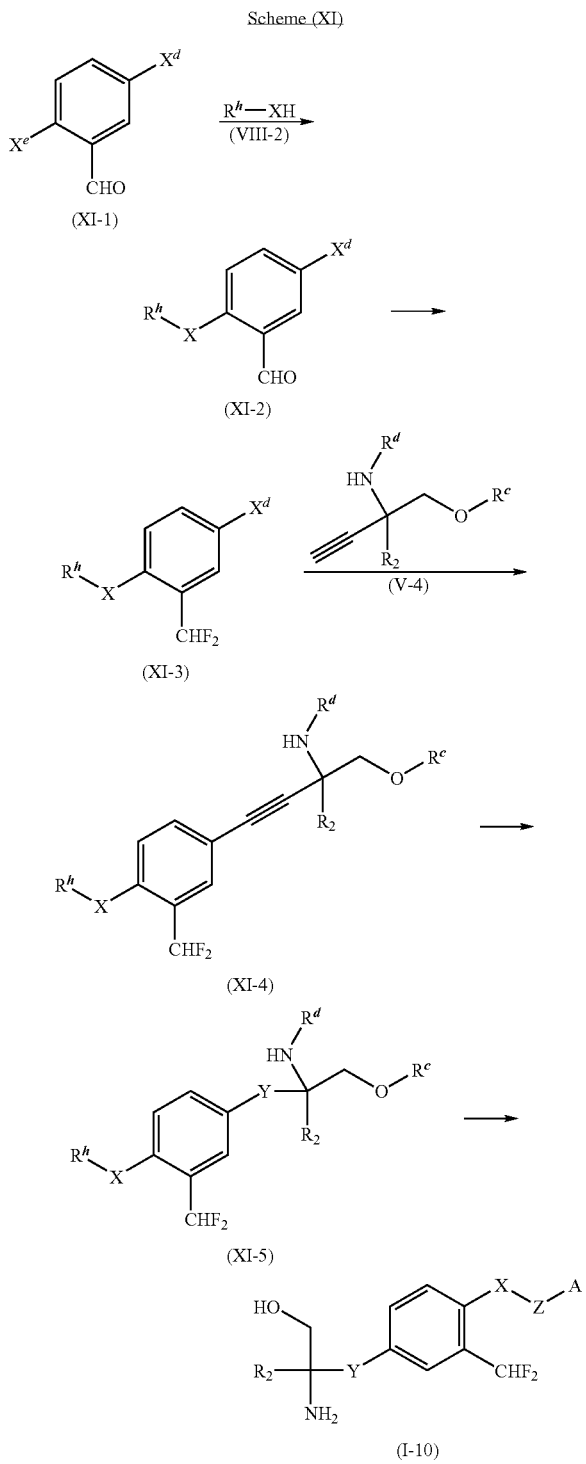

wherein $R^c$ and $R^d$ are protecting groups, $R^h$ is a protecting group or —$(CH_2)_m$-A, m is an integer of 1-5, $X^d$ and $X^e$ are leaving groups, and X, Y, $R_2$, A are as defined for each symbol in the formula (I).

Specific examples of $R^c$, $R^d$, $R^h$, $X^d$ and $X^e$ in the formula are as defined above.

In the first step, starting material (XI-1) having a leaving group $X^e$ at the 4-position and alcohol or thiol (VIII-2) are condensed, whereby intermediate (XI-2) is obtained.

This step can be performed in a polar solvent such as N,N-dimethylformamide, dimethyl sulfoxide and the like, and an ether solvent such as tetrahydrofuran and the like in the presence of a base. As the base, an inorganic base such as sodium hydride, potassium hydroxide, potassium carbonate and the like, alkoxide such as potassium t-butoxide and the like, an organic base such as 1,8-diazabicyclo[5.4.0]undec-7-ene and the like can be used. The reaction conditions are, for example, ice-cooling—about 80° C. for about 30 min-24 hr. After the reaction, purification and the like are performed according to conventional methods to give the object product. In addition, compound (XI-1) wherein leaving group $X^e$ is a phenolic hydroxyl group or thiol can also be used as a starting material, in which case the first step is alkylation of phenolic hydroxyl group or thiol. As the reagent to be used for the alkylation, a combination of an alkylating agent such as alkyl halide and the like and an inorganic base such as potassium carbonate, sodium hydride and the like can be mentioned. The reaction conditions are, for example, a polar solvent such as N,N-dimethylformamide and the like or an ether solvent such as tetrahydrofuran and the like under ice-cooling–80° C. for about 10 min-12 hr. In addition, Mitsunobu reaction can also be used for alkylation of a phenolic hydroxyl group.

In the second step, the formyl group of intermediate (XI-2) is fluorinated to give intermediate (XI-3) having difluoromethyl. This step can be performed in a halogen solvent such as methylene chloride and the like using a fluorinating agent such as diethylaminosulfur trifluoride (DAST), xenon difluoride and the like. This fluorination reaction can also be performed by reacting an oxidant such as N-iodosuccinimide and the like in the presence of fluoride ion such as tetrabutylammonium fluoride and the like, instead of a single fluorinating agent. The reaction conditions are, for example, under ice-cooling–50° C. for about 1-24 hr. After the reaction, purification and the like are performed according to conventional methods to give the object product.

In the third step, inteLmediate (XI-3) and intermediate (V-4) are condensed by Sonogashira reaction to give intermediate (XI-4) containing a triple bond. As the catalyst to be used, palladium compounds such as tetrakis(triphenylphosphine)palladium(0), tris(dibenzylideneacetone)dipalladium(0), dichlorobis(acetonitrile)palladium(II) and the like can be mentioned. To promote the reaction, an additive, for example, an organic base such as triethylamine and the like, an inorganic base such as ammonia and the like, a copper compound such as copper iodide, copper bromide and the like, a phosphine compound such as 2-dicyclohexylphosphino-2',4',6'-triisopropylbiphenyl and the like and the like can also be added. The reaction conditions are, for example, a solvent such as ether solvents (e.g., tetrahydrofuran, dioxane etc.), polar solvents (e.g., acetonitrile, dimethylformamide etc.), or hydrocarbon (e.g., benzene etc.) under ice-cooling—refluxing for about 30 min-24 hr. After the reaction, purification and the like are performed according to conventional methods to give the object product.

In the fourth step, a triple bond of intermediate (XI-4) is reduced to give intermediate (XI-5). The reagent to be used when Y is —$CH_2CH_2$— is not limited as long as it is a reagent to be used for conventional reduction of unsaturated carbon bond. For example, catalytic hydrogenation using a heterogeneous catalyst such as palladium carbon, Raney-nickel, a palladium carbonethylenediamine complex and the like, or a homogeneous catalyst such as rhodium complex (chlorotris (triphenylphosphine)rhodium(I) etc.) and the like can be mentioned. The reaction conditions are, for example, a solvent such as alcohol solvents (e.g., ethanol etc.), ether solvents (e.g., dioxane etc.), or hydrocarbon solvents (e.g., toluene etc.) under a hydrogen pressure of 1-20 atm under ice-cooling—refluxing for 30 min-1 week. Depending on the reaction rate, stability of the compound and the like, an acid such as acetic acid and the like, or a base such as triethylamine and the like can also be added to the reaction mixture. After the reaction, purification and the like are performed according to conventional methods to give the object product. The reaction used when Y is —CH=CH— includes catalytic hydrogenation performed in the presence of a catalyst having controlled activity such as Lindlar catalyst, nickel-graphite-ethylenediamine complex, various complexes of diene compound, phosphine compound and rhodium, and the like. In addition, reduction reaction using metal hydride such as diisobutylaluminum hydride and the like can also be employed. After the reaction, purification and the like are performed according to conventional methods to give the object product.

In the fifth step, intermediate (XII-5) is deprotected to give the compound (I-10) of the present invention. For removal of $R^c$, $R^d$ and $R^e$ ($R^e$ is a hydroxyl-protecting group when $R_2$ has a hydroxyl group, and $R^e$ is sometimes absent), those generally used for removal of protecting groups can be used without particular limitation, and all protecting groups can be removed at once or in a step-wise manner. For example, when $R^e$ and $R^e$ are bonded to form a cyclic acetal and $R^d$ is t-butyloxycarbonyl, cyclic acetal is deprotected with a catalytic amount of an acid, and stronger acidic conditions are employed for deprotection of $R^d$. The conditions for acetal deprotection are, for example, an alcohol solvent such as ethanol and the like or a mixed solution of alcohol solvent and other organic solvent using a catalytic amount of hydrochloric acid or toluenesulfonic acid under ice-cooling—80° C. for about 30 min-12 hr. The reaction conditions for deprotection of $R^d$ following the acetal deprotection are, for example, an inorganic acid such as hydrochloric acid and the like, trifluoroacetic acid and the like in an equivalent amount or above, an alcohol solvent such as ethanol and the like, an ether solvent such as tetrahydrofuran and the like, water, or a mixed solvent thereof under ice-cooling–80° C. for about 10 min-12 hr. After the reaction, purification and the like are performed according to conventional methods to give the object product. When $R^h$ is a protecting group, $R^h$ can be removed prior to the removal of the protecting groups $R^c$ and $R^d$, and then the resulting phenolic hydroxyl group or thiol group can be alkylated. The reaction conditions for removal of $R^h$ are not particularly limited as long as they are generally used for the removal of protecting groups. For example, when $R^h$ is benzyl, hydrogenolysis using a homogeneous catalyst such as palladium carbon, Raney-nickel and the like can be mentioned; when it is 4-methoxybenzyl, an oxidization reaction with 2,3ˉdichloro-5,6-dicyano-1,4-benzoquinone(DDQ) and the like can be mentioned; and when it is a silyl group such as trialkylsilyl and the like, deprotection with an inorganic acid such as hydrochloric acid and the like or a fluorine compound such as tetrabutylammonium fluoride and the like can be mentioned. As the reagent to be used for alkylation of the phenolic hydroxyl group or thiol group that the obtained compound has, a combination of an alkylating agent such as alkyl halide and the like and an inorganic base such as potassium carbonate, sodium hydride and the like can be mentioned. The reaction conditions are, for example, a polar solvent such as N,N-dimethylformamide and the like or an ether solvent such as tetrahydrofuran and the like, under ice-cooling—80° C. for about 10 min-12 hr. In addition, Mitsunobu reaction can also be used for alkylation of a phenolic hydroxyl group.

11) A compound (I-11), which is a compound of the formula (I) wherein R, $R_3$ and $R_4$ are hydrogen atoms, and $R_1$ is fluoromethyl is also synthesized according to the following scheme (XII).

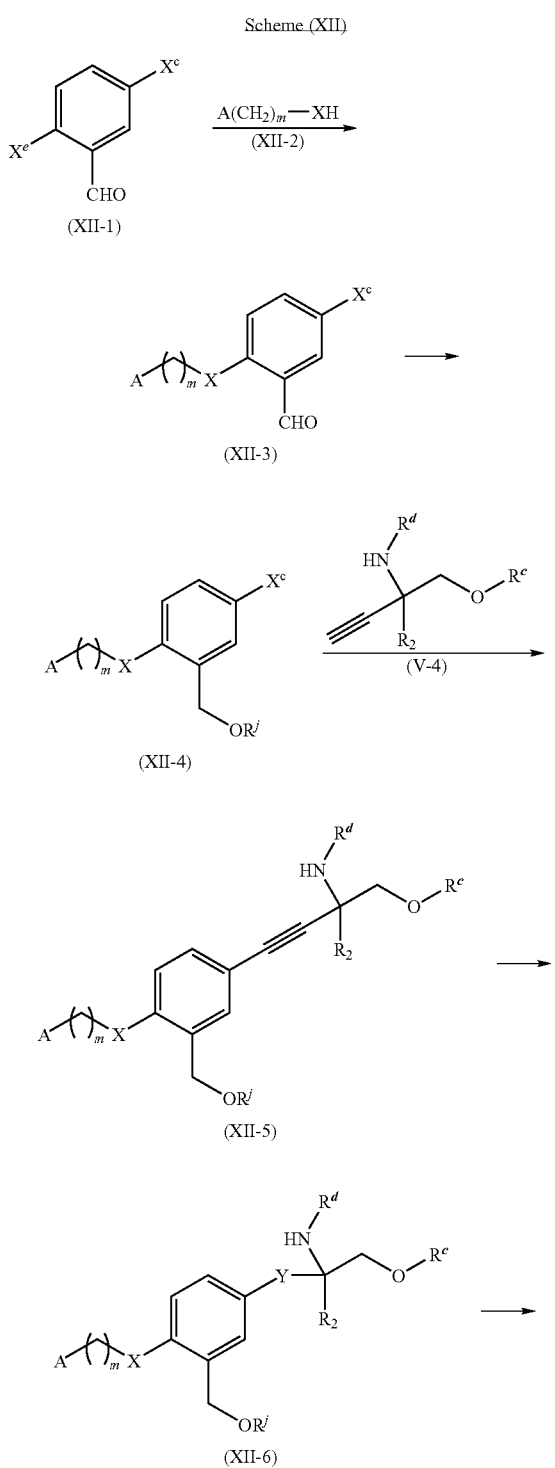

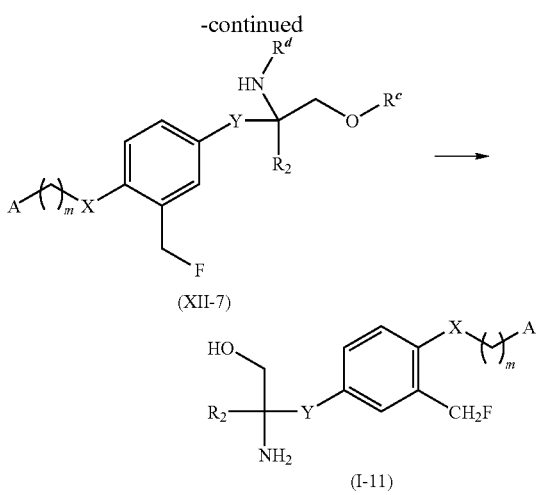

wherein $R^c$, $R^d$ and $R^j$ are protecting groups, $X^c$ and $X^e$ are leaving groups, m is an integer of 1-5, and X, Y, and A are as defined for each symbol in the formula (I).

Specific examples of $R^c$, $R^d$, $X^c$ and $X^e$ in the formula are as defined above. The protecting group for $R^j$ in the formula is not particularly limited as long as it protects hydroxyl group. For example, trialkylsilyl (specifically t-butyldimethylsilyl and the like) can be mentioned.

In the first step, starting material (XII-1) having a leaving group $X^e$ and alcohol or thiol (XII-2) are condensed, whereby intermediate (XII-3) is obtained. This step can be performed in a polar solvent such as N,N-dimethylformamide, dimethyl sulfoxide and the like, and an ether solvent such as tetrahydrofuran and the like in the presence of a base. As the base, an inorganic base such as sodium hydride, potassium hydroxide, potassium carbonate and the like, alkoxide such as potassium t-butoxide and the like, an organic base such as 1,8-diazabicyclo[5.4.0]undec-7-ene and the like can be used. The reaction conditions are, for example, ice-cooling—about 80° C. for about 30 min-24 hr. After the reaction, purification and the like are performed according to conventional methods to give the object product. In addition, compound (XII-1) wherein leaving group $X^e$ is a phenolic hydroxyl group or thiol can also be used as a starting material, in which case the first step is alkylation of phenolic hydroxyl group or thiol. As the reagent to be used for the alkylation, a combination of an alkylating agent such as alkyl halide and the like and an inorganic base such as potassium carbonate, sodium hydride and the like can be mentioned. The reaction conditions are, for example, a polar solvent such as N,N-dimethylformamide and the like or an ether solvent such as tetrahydrofuran and the like under ice-cooling—80° C. for about 10 min-12 hr. In addition, Mitsunobu reaction can also be used for alkylation of a phenolic hydroxyl group.

In the second step, a formyl group of intermediate (XII-3) is reduced to give hydroxymethyl and then protecting group $R^j$ is introduced. The reagent to be used for the reduction of formyl group is not particularly limited as long as it is generally used, and a metal hydride (e.g., diisobutylaluminum hydride and the like), a metal hydride complex compound (e.g., lithium aluminum hydride, sodium borohydride and the like), catalytic hydrogenation using a homogeneous or heterogeneous catalyst and the like can be mentioned. For reaction conditions, temperature and time appropriate for the reducing reagent to be used are selected. Specific examples include reduction with diborane, lithium aluminum hydride or lithium borohydride in an ether solvent such as tetrahydrofuran and the like at −30° C.—room temperature for about 10 min-3 hr, reduction with sodium borohydride or calcium borohydride in an alcohol solvent such as ethanol and the like or a mixed solvent of an alcohol solvent and an ether solvent such as tetrahydrofuran and the like under ice-cooling—room temperature for about 10 min-3 hr, and the like. After the reaction, purification and the like are performed according to conventional methods to give the object product. A general introduction reaction of protecting group is employed for introduction of protecting group $R^j$. When a trialkylsilyl group is used as $R^j$, a silylating agent such as t-butyldimethylchlorosilane and the like is used as the reagent, and a base such as imidazole, triethylamine and the like can be added as a reaction promoter. After the reaction, purification and the like are performed according to conventional methods to give the object product.

In the third step, intermediate (XII-4) and intermediate (V-4) are condensed by Sonogashira reaction to give intermediate (XII-5) containing a triple bond. As the catalyst to be used, palladium compounds such as tetrakis(triphenylphosphine)palladium(0), tris(dibenzylideneacetone)dipalladium (0), dichlorobis(acetonitrile)palladium(II) and the like can be mentioned. To promote the reaction, an additive, for example, an organic base such as triethylamine and the like, an inorganic base such as ammonia and the like, a copper compound such as copper iodide, copper bromide and the like, a phosphine compound such as 2-dicyclohexylphosphino-2',4',6'-triisopropylbiphenyl and the like, and the like can also be added. The reaction conditions are, for example, a solvent such as ether solvents (e.g., tetrahydrofuran, dioxane etc.), polar solvents (e.g., acetonitrile, dimethylformamide etc.), or hydrocarbon (e.g., benzene etc.) under ice-cooling—refluxing for about 30 min-24 hr. After the reaction, purification and the like are performed according to conventional methods to give the object product.

In the fourth step, a triple bond of intermediate (XII-5) is reduced to give intermediate (XII-6). The reagent to be used when Y is —$CH_2CH_2$— is not limited as long as it is a reagent to be used for conventional reduction of unsaturated carbon bond. For example, catalytic hydrogenation using a heterogeneous catalyst such as palladium carbon, Raney-nickel, a palladium carbonethylenediamine complex and the like, or a homogeneous catalyst such as rhodium complex (chlorotris(triphenylphosphine)rhodium(I) etc.) and the like can be mentioned. The reaction conditions are, for example, a solvent such as alcohol solvents (e.g., ethanol etc.), ether solvents (e.g., dioxane etc.), or hydrocarbon solvents (e.g., toluene etc.) under a hydrogen pressure of 1-20 atm under ice-cooling—refluxing for 30 min-1 week. Depending on the reaction rate, stability of the compound and the like, an acid such as acetic acid and the like, or a base such as triethylamine and the like can also be added to the reaction mixture. After the reaction, purification and the like are performed according to conventional methods to give the object product. The reaction used when Y is —CH=CH— includes catalytic hydrogenation performed in the presence of a catalyst having controlled activity such as Lindlar catalyst, nickel-graphite-ethylenediamine complex, various complexes of diene, phosphine and rhodium, and the like. In addition, reduction reaction using metal hydride such as diisobutylaluminum hydride and the like can also be employed. After the reaction, purification and the like are performed according to conventional methods to give the object product.

In the fifth step, R of compound (XII-6) is removed, and the hydroxyl group of the obtained compound is fluorinated to give fluoride compound (XII-7). The protecting group $R^j$ can be removed by general deprotection. As the reagent to be used when $R^j$ is trialkylsilyl, a fluorine compound such as tetrabutylammonium fluoride and the like can be used. The reaction conditions are, for example, an ether solvent such as tetrahydrofuran and the like, under ice-cooling to refluxing for about 30 min-24 hr can be mentioned. After the reaction, purification and the like are performed according to conventional methods to give the object product. As a reagent to be used for the fluorination to be performed successively, diethylaminosulfur trifluoride (DAST), 2,2-difluoro-1,3-dimethylimidazolidine (DFI) and the like can be mentioned. In this step, the reaction can be performed in a halogen solvent such as methylene chloride and the like, or a hydrocarbon solvent such as hexane and the like. The reaction conditions are, for example, −78° C.—room temperature for about 30 min-12 hr. After the reaction, purification and the like are performed according to conventional methods to give the object product. This step can also be performed by a method including converting the hydroxyl group to the corresponding sulfonate, and reacting the compound with fluoride ion. For example, when p-toluenesulfonyl fluoride and tetrabutylammonium fluoride (TBAF) are used, the reaction is performed in an ether solvent such as tetrahydrofuran and the like at room temperature −80° C. for about 1 hr-24 hr. A dehydrating agent such as molecular sieves and the like can be added to this reaction. After the reaction, purification and the like are performed according to conventional methods to give the object product. When $R^j$ is trialkylsilyl, fluorination can also be performed without removing R.

In the sixth step, intermediate (XII-7) is deprotected to give the compound (I-11) of the present invention. For removal of $R^c$, $R^d$ and $R^e$ ($R^e$ is a hydroxyl-protecting group when $R_2$ has a hydroxyl group, and $R^e$ is sometimes absent), those generally used for removal of protecting groups can be used without particular limitation, and all protecting groups can be removed at once or in a step-wise manner. For example, when $R^c$ and $R^e$ are bonded to form a cyclic acetal and $R^d$ is t-butyloxycarbonyl, cyclic acetal is deprotected with a catalytic amount of an acid, and stronger acidic conditions are employed for deprotection of $R^d$. The conditions for acetal deprotection are, for example, an alcohol solvent such as ethanol and the like or a mixed solution of alcohol solvent and other organic solvent using a catalytic amount of hydrochloric acid or toluenesulfonic acid under ice-cooling—80° C. for about 30 min-12 hr. The reaction conditions for deprotection of $R^d$ following the acetal deprotection are, for example, an inorganic acid such as hydrochloric acid and the like, trifluoroacetic acid and the like in an equivalent amount or above, an alcohol solvent such as ethanol and the like, an ether solvent such as tetrahydrofuran and the like, water, or a mixed solvent thereof under ice-cooling—room temperature for about 10 min-5 hr. After the reaction, purification and the like are performed according to conventional methods to give the object product. In addition, a solvent having low dissolution property such as diisopropyl ether and the like may be added to the reaction solution and the precipitated object can be collected by filtration.

12) Of the compounds of the present invention, a compound (I-12), which is a compound of the formula (I) wherein R is $P(=O)(OH)_2$, and $R_3$ and $R_4$ are hydrogen atoms, is synthesized according to the following scheme (XIII).

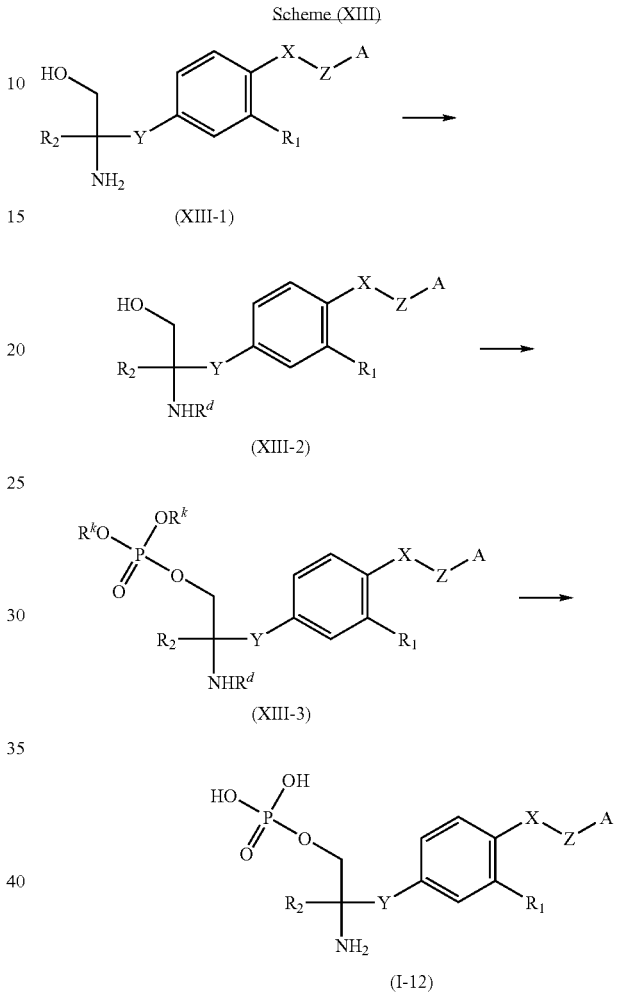

wherein $R^d$ and $R^k$ are protecting groups, and X, Y, Z, $R_1$, $R_2$ and A are as defined for each symbol in the formula (I).

$R^d$ in the formula is as defined above. When $R_2$ of compound (XIII-2) contains a hydroxyl group, the hydroxyl group may be protected by a protecting group $R^e$ ($R^e$ is as defined above). When $R_2$ is protected hydroxymethyl or hydroxyethyl, the protecting group $R^e$ is bonded to a nitrogen atom bonded to $R^d$ or $R^d$ to form the following cyclic compound (XIII-2', XIII-2")

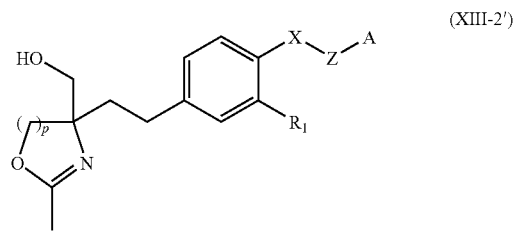

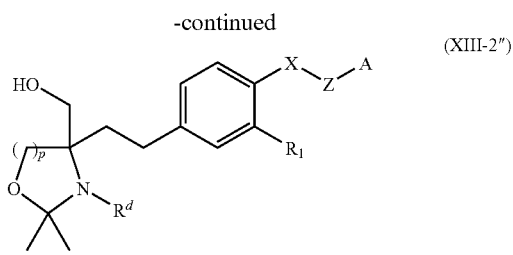

(XIII-2″)

wherein p is 1 or 2, and other symbols are as defined for scheme (XIII), whereby the amino group and hydroxyl group can also be protected. The protecting group for $R^k$ in the formula is not particularly limited as long as it protects a phosphate group. For example, alkyl (preferably having about 1 to 6 carbon atoms, specifically t-butyl and the like), benzyl, phenyl and the like can be mentioned.

In the first step, the amino group of compound (XIII-1) wherein R is a hydrogen atom, from among the compounds of the present invention, is protected to give amino group-protected compound (XIII-2). This step can be performed by a general amino protection reaction. Specifically, when acyl, alkyloxycarbonyl or benzyloxycarbonyl and the like is used as protecting group $R^d$, this step can be performed in alcohol such as methanol and the like, or a two-layer system or a mixture of an organic solvent such as ethyl acetate, chloroform and the like and water. As the reagent to be used, acid chloride such as acetyl chloride, benzyloxycarbonyl chloride and the like, and acid anhydride such as acetic anhydride, di-t-butyl-dicarbonate and the like can be mentioned. In this reaction, an organic base such as triethylamine and the like or an inorganic base such as sodium bicarbonate and the like can be added as a reaction promoter. The reaction conditions are, for example, under ice-cooling–50° C. for about 30 min-24 hr can be mentioned. After the reaction, purification and the like are performed according to conventional methods to give the object product. When an amino group as oxazoline shown in the formula (XIII-2') and a hydroxyl group contained in $R_2$ are to be simultaneously protected, the reaction can be performed in a polar solvent such as acetonitrile, N,N-dimethylformamide and the like, a halogen solvent such as methylene chloride and the like, or a hydrocarbon solvent such as toluene and the like and using orthoacetic acid ester as a reagent. In addition, a base such as N,N-diisopropylethylamine and the like, or an acid such as p-toluenesulfonic acid and the like can be added to promote the reaction. The reaction conditions are, for example, room temperature—under refluxing for about 30 min-12 hr. After the reaction, purification and the like are performed according to conventional methods to give the object product.

In the second step, an amino group-protected compound (XIII-2) and a phosphorylating reagent (e.g., phosphoryl chloride, phosphoramidite and oxidant, pyrophosphoric acid tetrabenzyl ester and the like) are reacted to give phosphorylated compound (XIII-3). When pyrophosphoric acid tetrabenzyl ester is used as a phosphorylating reagent, this step can be performed using an additive (e.g., silver oxide, tetra-n-hexylammonium iodide and the like) under non-aqueous conditions, preferably in an organic solvent such as toluene, dichloromethane, a mixed solvent thereof and the like. The reaction conditions are, for example, under ice-cooling–50° C. for about 5-24 hr. After the reaction, purification and the like are performed according to conventional methods to give the object product. For this reaction, moreover, a general phosphorylating reagent (phosphoryl chloride and base, phosphoramidite and oxidant and the like) may be reacted according to a known method for the synthesis. For example, when phosphoramidite and an oxidant are used, they are reacted using phosphoramidite such as di-t-butyldiisopropylphosphoramidite and the like in a halogen solvent such as dichloromethane and the like, an ether solvent such as tetrahydrofuran and the like, a polar solvent such as acetonitrile and the like or a mixed solvent thereof, under ice-cooling–50° C. for about 10 min-5 hr. For this reaction, a reaction promoter such as 1H-tetrazole and the like can be added. For the oxidization reaction of phosphorus following this phosphorylation, organic peroxide such as m-chloroperbenzoic acid, t-butyl hydroperoxide and the like or inorganic peroxide such as hydrogen peroxide and the like can be used. The reaction is performed under ice-cooling–50° C. for about 3 min-1 hr. After the reaction, purification and the like are performed according to conventional methods to give the object product.

In the third step, the compound (I-12) of the present invention is prepared from phosphorylated compound (XIII-3). This step can be performed by general deprotection. Specifically, hydrogenolysis, acid such as hydrochloric acid, trifluoroacetic acid and the like, Lewis acid such as trimethylsilyl bromide and the like can be used. When hydrogenolysis is performed for this reaction, this step can be performed, for example, in an alcohol solvent such as methanol and the like using a catalyst such as palladium carbon and the like under a hydrogen atmosphere. The reaction conditions are, for example, room temperature–60° C. for about 1-24 hr. The reaction mixture is subjected to purification and the like according to conventional methods to give the object product. The reaction conditions when an acid is used for this reaction are, for example, an alcohol solvent such as ethanol and the like or a mixed solvent thereof with water at room temperature–100° C. for about 30 min-12 hr. After the reaction, purification and the like are performed according to conventional methods to give the object product. When one of $R_3$ and $R_4$ is a hydrogen atom, and the other is alkyl having 1 to 4 carbon atoms, a similar method can be used for the synthesis.

13) Of the compounds of the present invention, a compound of the formula (I) wherein R is $P(=O)(OH)_2$, and $R_3$ and $R_4$ are alkyl having 1 to 4 carbon atoms can be synthesized using, instead of (XIII-1),

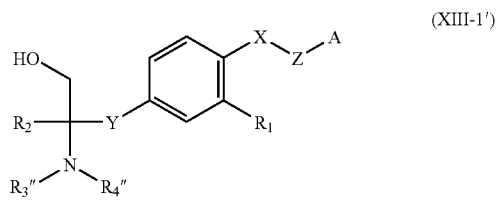

(XIII-1')

wherein $R_3''$ and $R_4''$ are alkyl having 1 to 4 carbon atoms, and X, Y Z, $R_1$, $R_2$ and A are as defined for each symbol in the formula (I), as the starting material, omitting the first step of scheme (XIII) and according to a similar method.

14) When the compound of the present invention has an asymmetric center, the compound is preferably a particular optically active form. An optically active form can be synthesized by optical resolution by HPLC or supercritical fluid chromatography (SFC) using a chiral column of the corresponding racemate. The timing of the optical resolution is not particularly limited, and a compound having a desired asymmetric center can be obtained. As a specific example of the timing of optical resolution, when R in the formula (I) is a hydrogen atom, optical resolution of the inventive compound itself can be mentioned. When an intermediate is used for the optical resolution, for example, optical resolution in the stage of phenolic intermediate (II-7) in scheme (II) and the like can be mentioned. Optical resolution conditions are, for example, mobile phase of hexane and alcohol such as ethanol and the like added with a base such as triethylamine and the like for HPLC, and mobile phase of carbon dioxide, alcohol such as ethanol and the like added with a base such as diethylamine and the like for supercritical fluid chromatography (SFC).

The compound of the present invention can be converted to an acid addition salt as necessary by a treatment with an acid in a suitable solvent (water, alcohol, ether and the like). In addition, the obtained compound of the present invention can be converted to hydrate or solvate by a treatment with water, water-containing solvent or other solvent (for example, alcohol etc.).

The compound of the present invention is useful for the treatment or prophylaxis of autoimmune diseases (e.g., rheumatoid arthritis, multiple sclerosis, encephalomyelitis, systemic lupus erythematosus, lupus nephritis, nephrosis syndrome, psoriasis, type I diabetes mellitus etc.); prophylaxis or suppression of resistance or acute rejection or chronic rejection in the transplantation of organ or tissue (including transplantation, heterologous transplantation of, for example, heart, kidney, liver, lung, bone marrow, cornea, pancreas, small intestine, extremities, muscle, nerve, fatty marrow, duodenum, skin, pancreatic islet cell and the like) in mammals such as human, dog, cat, bovine, horse, swine, monkey, mouse and the like; or treatment or prophylaxis of graft vs m host (GvH) disease due to bone marrow transplantation; and allergic diseases (e.g., atopic dermatitis, allergic rhinitis, asthma etc.).

The subject of administration of the compound of the present invention is, for example, mammals such as human, dog, cat, bovine, horse, swine, monkey, rat and the like, or the like.

In the present invention, moreover, "prophylaxis" means an act of administering the compound of the present invention or a pharmaceutical composition containing the compound to an individual who has not developed a disease, disorder or symptom. In addition, "treatment" means an act of administering the compound of the present invention or a pharmaceutical composition containing the compound to an individual who has already developed a disease, disorder or symptom. Therefore, administration to an individual who has already developed a disease, disorder or symptom for the prevention of aggravation, attack or recurrence of symptom and the like is one embodiment of the "treatment".

When the compound of the present invention is used as a medicament, it can be administered orally or parenterally in the form of a pharmaceutical composition or preparation (oral preparation, injection and the like) obtained by mixing the compound of the present invention with a pharmaceutically acceptable carrier (excipient, binder, disintegrant, corrigent, flavor, emulsifier, diluent, solubilizer and the like). The pharmaceutical composition can be formulated into a preparation according to a conventional method.

In the present specification, parenteral includes subcutaneous injection, intravenous injection, intramuscular injection, intraperitoneal injection, drip infusion or topical administration (transdermal administration, transocular administration, transpulmonary•transbronchial administration, transnasal administration or intrarectal administration and the like) and the like.

The content of the compound of the present invention that can be combined with a carrier can be changed depending on the individual to be treated and a particular administration form. However, a particular dose of a particular patient is determined according to various factors including age, body weight, general health condition, sex, diet, administration time, administration method, clearance rate and severity of particular disease during treatment.

The dose of the compound of the present invention is determined according to the age, body weight, general health condition, sex, diet, administration time, administration method, clearance rate, and the severity of the disease condition for which the patient is undergoing treatments at that time, and in consideration of other factors. The compound of the present invention is free of influence on the heart rate and can be used safely. While the daily dose varies depending on the condition and body weight of the patient, the kind of the compound, administration route and the like, it is, for example, about 0.01-50 mg/patient/day for parenteral administration (subcutaneous, intravenous, intramuscular, transdermal, transocular, transpulmonary or transbronchial, transnasal or intrarectal), and about 0.01-150 mg/patient/day for orally administration.

EXAMPLES

The present invention is explained in detail in the following by referring to Examples, which are not to be construed as limitative.

Reference Example 1

(5-formyl-2,2-dimethyl-1,3-dioxan-5-yl)carbamic acid t-butyl ester (1-1) Synthesis of (5-hydroxymethyl-2,2-dimethyl-1,3-dioxan-5-yl)carbamic acid t-butyl ester (Reference Example compound 1-1)

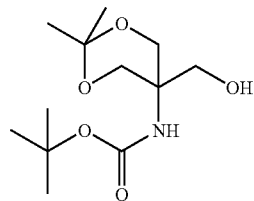

Tris(hydroxymethyl)aminomethane hydrochloride (2 g) was dissolved in N,N-dimethylformamide (50 ml), 2,2-dimethoxypropane (7.8 ml) and p-toluenesulfonic acid monohydrate (229 mg) were added, and the mixture was stirred at room temperature for 15 hr. To the mixed solution were added triethylamine (9.5 ml), methanol (20 ml), and di-t-butyl-dicarbonate (4.17 g), and the mixture was stirred at room temperature for 12 hr. Water was added to the reaction mixture, and the mixture was extracted with ethyl acetate, washed with water and saturated brine, and dried over anhydrous magnesium sulfate. The solvent was evaporated under reduced pressure to give the object product (3.11 g) as a colorless solid.

¹H-NMR(CDCl₃) δ (ppm): 1.44(3H, s), 1.46(12H, s), 3.73 (2H, d, J=6.4 Hz), 3.80(2H, d, J=11.6 Hz), 3.84(2H, d, J=11.6 Hz), 4.20(1H, brs), 5.32(1H, brs).

(1-2) Synthesis of (5-formyl-2,2-dimethyl-1,3-dioxan-5-yl)carbamic acid t-butyl ester (Reference Example compound 1-2)

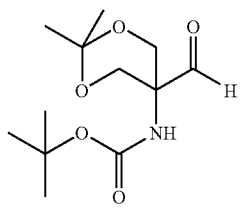

Reference Example compound 1-1 (2.96 g) was dissolved in dimethyl sulfoxide (50 ml), triethylamine (11 ml) and sulfur trioxide pyridine complex (5.4 g) were added, and the mixture was stirred at room temperature for 2 hr. Water was added to the reaction mixture, and the mixture was extracted with ethyl acetate, washed with water and saturated brine, and dried over anhydrous magnesium sulfate. The solvent was evaporated under reduced pressure. The residue was washed with diethyl ether to give the object product (2.4 g) as a colorless powder.

¹H-NMR(CDCl₃) δ (ppm): 1.46(15H, s), 3.96(2H, d, J=11.7 Hz), 4.07(2H, d, J=11.7 Hz), 5.54(1H, brs), 9.64(1H, s).

Reference Example 2

{5-[2-(4-hydroxy-3-trifluoromethylphenyl)ethyl]-2,2-dimethyl-1,3-dioxan-5-yl}carbamic acid t-butyl ester (2-1) Synthesis of 4-fluoro-3-trifluoromethylbenzoic acid benzyl ester (Reference Example compound 2-1)

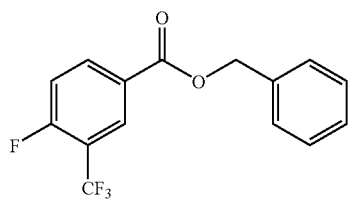

4-Fluoro-3-trifluoromethylbenzoic acid (100 g) was dissolved in N,N-dimethylformamide (400 ml), potassium carbonate (199 g) and benzyl bromide (84.0 g) were added under ice-cooling, and the mixture was stirred under ice-cooling for 20 min and further at room temperature for 2 hr. Water was added to the reaction mixture, and the mixture was extracted with ethyl acetate, washed with water and saturated brine, and dried over anhydrous magnesium sulfate. The solvent was evaporated under reduced pressure to give the object product (144 g) as a pale-yellow oil.

¹H-NMR(CDCl₃) δ (ppm): 5.38(2H, s), 7.27(1H, t, J=9.3 Hz), 7.35-7.46(5H, m), 8.27(1H, m), 8.35(1H, dd, J=6.8, 1.8 Hz).

(2-2) Synthesis of 4-benzyloxy-3-trifluoromethylbenzoic acid benzyl ester (Reference Example compound 2-2)

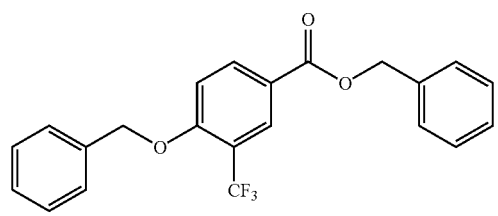

Benzyl alcohol (52.0 g) was dissolved in N,N-dimethylformamide (300 ml), sodium hydride (60%, 20.2 g) was added under ice-cooling, and the mixture was stirred under ice-cooling for 50 min. A solution of Reference Example compound 2-1 (144 g) in N,N-dimethylformamide (400 ml) was added, and the mixture was stirred under ice-cooling for 2 hr. The reaction mixture was added to water, and the mixture was extracted with ethyl acetate, washed with water and saturated brine, and dried over anhydrous magnesium sulfate. The solvent was evaporated under reduced pressure to give the object product (198 g, mixture with mineral oil contained in sodium hydride) as a pale-yellow solid.

¹H-NMR(CDCl₃) δ (ppm): 5.26(2H, s), 5.35(2H, s), 7.06 (1H, d, J=8.8 Hz), 7.31-7.45(10H, m), 8.18(1H, dd, J=8.8, 2.0 Hz), 8.32(1H, d, J=2.0 Hz).

(2-3) Synthesis of 4-benzyloxy-3-trifluoromethylbenzyl alcohol (Reference Example compound 2-3)

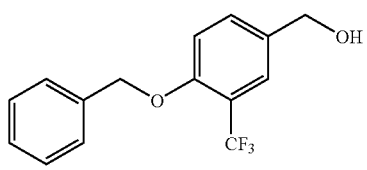

Reference Example compound 2-2 (198 g) was dissolved in tetrahydrofuran (1000 ml), lithium borohydride (15.7 g) was added, and the mixture was heated under reflux for 3 hr. After once cooling, lithium borohydride (4.0 g) was added, and the mixture was further heated under reflux for 3 hr. The reaction mixture was ice-cooled, and water (500 ml) was added to quench the reaction. The reaction mixture was added to water, and neutralized with concentrated hydrochloric acid. The mixture was extracted with ethyl acetate, washed with water and saturated brine, and dried over anhydrous magnesium sulfate. The solvent was evaporated under reduced pressure. Mineral oil and benzyl alcohol (impurities) were removed from the obtained mixture by heating in a vacuum pump under reduced pressure at 135° C. Hexane was added to the obtained residue, and the precipitated solid was collected by filtration to give the object product (99.2 g) as a white powder.

$^1$H-NMR(CDCl$_3$) δ (ppm): 1.62(1H, t, J=5.7 Hz), 4.66(2H, d, J=5.7 Hz), 5.20(2H, s), 7.02(1H, d, J=8.5 Hz), 7.30-7.33 (1H, m), 7.38(2H, t, J=7.4 Hz), 7.44(2H, d, J=7.4 Hz), 7.46 (1H, dd, J=8.5, 2.0 Hz), 7.61(1H, d, J=2.0 Hz).

(2-4) Synthesis of 4-benzyloxy-3-trifluoromethylbenzylchloride (Reference Example compound 2-4)

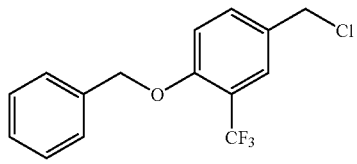

Reference Example compound 2-3 (99.2 g) was dissolved in methylene chloride (900 ml), triphenylphosphine (102 g) and N-chlorosuccinimide (49.3 g) were added under ice-cooling, and the mixture was stirred under ice-cooling for 40 min and further at room temperature for 1 hr. The reaction mixture was washed with water and saturated brine, and dried over anhydrous magnesium sulfate. The solvent was evaporated under reduced pressure. Ether (500 ml) was added, and the first precipitated triphenylphosphine oxide was filtered off. The concentrate of the filtrate was purified by silica gel column chromatography (hexane:ethyl acetate=99:1-4:1) to give the object product (99.5 g) as a colorless oil.

$^1$H-NMR(CDCl$_3$) δ (ppm): 4.56(2H, s), 5.20(2H, s), 7.01 (1H, d, J=8.6 Hz), 7.31-7.34(1H, m), 7.39(2H, t, J=7.4 Hz), 7.43(2H, d, J=7.4 Hz), 7.48(1H, dd, J=8.6, 2.0 Hz), 7.62(1H, d, J=2.0 Hz).

(2-5) Synthesis of (4-benzyloxy-3-trifluoromethyl-benzyl)triphenylphosphoniumchloride (Reference Example compound 2-5)

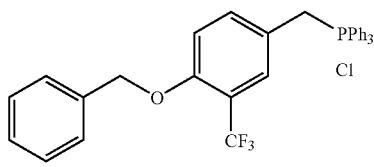

The compound (99.0 g) obtained from Reference Example compound 2-4 was dissolved in toluene (450 ml), triphenylphosphine (90.7 g) was added, and the mixture was refluxed for 8 hr. After cooling, the powder in the reaction mixture was collected by filtration, and the mixture was washed with ether to give the object compound (132 g) as a white powder. The mother liquor was concentrated, toluene (200 ml) was added, and the above-mentioned operation was repeated to give the object compound (31.0 g). The mother liquor was further treated in the same manner to give the object compound (12.3 g). The total yield was 176 g.

$^1$H-NMR (DMSO-d$_6$) δ (ppm): 5.17(2H, d, J=15.1 Hz), 5.23(2H, s). 7.02-7.04(1H, m), 7.26-7.30(2H, m), 7.31-7.37 (1H, m), 7.38-7.42(4H, m), 7.65-7.70(6H, m), 7.72-7.78(6H, m), 7.90-7.94(3H, m).

(2-6) Synthesis of {5-[2-(4-hydroxy-3-trifluoromethylphenyl)ethyl]-2,2-dimethyl-1,3-dioxan-5-yl}carbamic acid t-butyl ester (Reference Example compound 2-6)

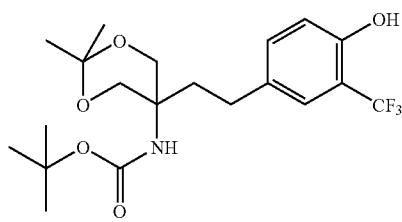

Reference Example compound 2-5 (70.3 g) was dissolved in tetrahydrofuran (500 ml), potassium t-butoxide (13.0 g) was added, and the mixture was stirred for 1 hr. A solution of Reference Example compound 1-2 (15.0 g) in tetrahydrofuran (100 ml) was added dropwise to the mixed solution under ice-cooling, and the mixture was stirred under ice-cooling for 2 hr. Water was added to the reaction mixture, and the mixture was extracted with ethyl acetate, washed with water and saturated brine, and dried over anhydrous magnesium sulfate. The solvent was evaporated under reduced pressure. The residue was purified by silica gel column chromatography (hexane:ethyl acetate=3:1) to give {5-[2-(4-benzyloxy-3-trifluoromethylphenyl)vinyl]-2,2-dimethyl-1,3-dioxan-5-yl}carbamic acid t-butyl ester as a pale-yellow oil (31.0 g). The geometric isomer ratio of the obtained compound was (E:Z=1:6). This pale-yellow oil was dissolved in ethyl acetate (200 ml), 10% palladium carbon (3.00 g) was added, and the mixture was stirred under a hydrogen atmosphere at room temperature for 7 hr. The reaction container was purged with nitrogen, the solution was filtered, and the filtrate was concentrated. The residue was washed with diisopropyl ether to give the object product (22.3 g) as a colorless powder.

$^1$H-NMR(CDCl$_3$) δ (ppm): 1.43(3H, s), 1.44(3H, s), 1.47 (9H, s), 1.91-1.98(2H, m), 2.50-2.56(2H, m), 3.69(2H, d, J=11.6 Hz), 3.89(2H, d, J=11.6 Hz), 5.02(1H, brs), 5.52(1H, brs), 6.86(1H, d, J=8.2 Hz), 7.22(1H, dd, J=8.2, 1.7 Hz), 7.29(1H, d, J=1.7 Hz).

Example 1

2-amino-2-{2-[3-cyano-4-(3-phenylpropoxy)phenyl]ethyl}propane-1,3-diol hydrochloride (1-1) Synthesis of 5-bromo-2-(3-phenylpropoxy)benzonitrile (Compound 1-1)

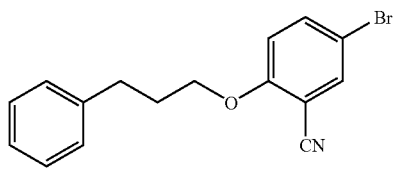

3-Phenylpropanol (2.17 g) was dissolved in N,N-dimethylformamide (32 ml), and sodium hydride (60%, 0.638 g) was added at room temperature. After stirring for 1 hr, 5-bromo-2-fluorobenzonitrile (1.60 g) was added, and the mixture was further stirred at 40-50° C. for 3 hr. The reaction mixture was poured into water, and the mixture was extracted with ethyl acetate, washed with water and saturated brine, and dried over anhydrous sodium sulfate. The solvent was evaporated under reduced pressure. The residue was purified by silica gel column chromatography to give the object product (2.30 g) as a colorless oil.

¹H-NMR(CDCl₃) δ (ppm): 2.13-2.20(2H, m), 2.85(2H, t, J=7.6 Hz), 4.03(2H, t, J=6.4 Hz), 6.78(1H, d, J=8.8 Hz), 7.19-7.22(3H, m), 7.27-7.30(2H, m), 7.57(1H, dd, J=8.8, 2.4 Hz), 7.66(1H, d, J=2.4 Hz).

(1-2) Synthesis of (5-{2-[3-cyano-4-(3-phenylpropoxy)phenyl]ethyl}-2,2-dimethyl-1,3-dioxan-5-yl) carbamic acid t-butyl ester (Compound 1-2)

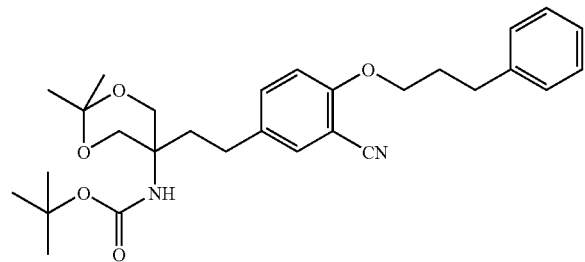

Compound 1-1 (0.720 g), (5-ethynyl-2,2-dimethyl-1,3-dioxan-5-yl)carbamic acid t-butyl ester (0.634 g) synthesized according to the known method (e.g., Tetrahedron vol.57 (2001) pages 6531-6538), 2-dicyclohexylphosphino-2',4',6'-triisopropylbiphenyl (0.050 g), bis(acetonitrile)palladium(II) dichloride (0.009 g) and cesium carbonate (0.855 g) were stirred in acetonitrile (8.7 ml) at 70° C. for 7 hr. Water was added to the reaction mixture, and the mixture was extracted with ethyl acetate, washed with saturated brine, and dried over anhydrous sodium sulfate. The solvent was evaporated under reduced pressure. The residue was purified by silica gel column chromatography to give (5-{2-[3-cyano-4-(3-phenylpropoxy)phenyl]ethynyl}-2,2-dimethyl-1,3-dioxan-5-yl) carbamic acid t-butyl ester as a pale-brown solid. This solid was dissolved in ethyl acetate (5 ml), 10% palladium carbon (containing water about 50%, 0.044 g) was added, and the mixture was stirred under a hydrogen atmosphere at room temperature for 3 hr. The solution was filtered, and the filtrate was concentrated to give the object product (0.408 g) as a brown oil.

¹H-NMR(CDCl₃) δ (ppm): 1.42(3H, s), 1.44(3H, s), 1.47 (9H, s), 1.92-1.96(2H, m), 2.12-2.18(2H, m), 2.49-2.53(2H, m), 2.85(2H, t, J=7.2 Hz), 3.68(2H, d, J=11.2 Hz), 3.86(2H, d, J=11.2 Hz), 4.01(2H, t, J=6.4 Hz), 4.97(1H, s), 6.80(1H, d, J=8.8 Hz), 7.17-7.22(3H, m), 7.25-7.31(3H, m), 7.35(1H, d, J=2.0 Hz).

(1-3) Synthesis of 2-amino-2-{2-[3-cyano-4-(3-phenylpropoxy)phenyl]ethyl}propane-1,3-diol hydrochloride (Compound 1-3)

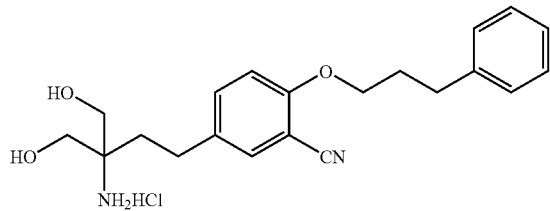

Compound 1-2 (0.408 g) was dissolved in a mixed solvent of ethanol (3 ml) and tetrahydrofuran (2 ml), p-toluenesulfonic acid monohydrate (0.028 g) was added, and the mixture was stirred at room temperature for 4.5 hr. To the reaction mixture was added saturated aqueous sodium hydrogen carbonate, and the mixture was extracted with ethyl acetate, washed with saturated brine, and dried over anhydrous sodium sulfate. The solvent was evaporated under reduced pressure. The residue was purified by silica gel column chromatography to give a compound deprotected acetal of compound 1-2 as an oil. To the obtained oil was added hydrogen chloride-containing dioxane (4 mol/l, 2 ml), and the mixture was stirred at room temperature for 2 hr. The precipitate was collected by filtration, and dried to give the object product (0.104 g) as a white powder.

MS(ESI)m/z: 355[M+H]

¹H-NMR(DMSO-d₆) δ (ppm): 1.74-1.78 (2H, m), 2.03-2.08(2H, m), 2.54-2.61(2H, m), 2.76(2H, t, J=7.6 Hz), 3.51 (4H, d, J=4.8 Hz), 4.09(2H, t, J=6.0 Hz), 5.37(2H, t, J=4.8 Hz), 7.15-7.22(4H, m), 7.27-7.30(2H, m), 7.48(1H, d, J=8.8 Hz), 7.56(1H, s), 7.85(3H, brs).

Example 2

2-amino-2-{2-[3-cyano-4-(4-phenylbutoxy)phenyl] ethyl}propane-1,3-diol hydrochloride (2-1) Synthesis of 5-bromo-2-(4-phenylbutoxy)benzonitrile (Compound 2-1)

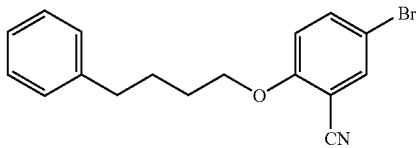

4-Phenylbutanol (0.834 g) was dissolved in N,N-dimethylformamide (10 ml), and sodium hydride (60%, 0.638 g) was added. After stirring for 30 min, 5-bromo-2-fluorobenzonitrile (0.640 g) was added, and the mixture was further stirred at 40-50° C. for 4 hr. The reaction mixture was poured into water, and the mixture was extracted with ethyl acetate, washed with water and saturated brine, and dried over anhydrous sodium sulfate. The solvent was evaporated under reduced pressure. The residue was purified by silica gel column chromatography to give the object product (1.04 g) as a colorless oil.

¹H-NMR(CDCl₃) δ (ppm): 1.81-1.89(4H, m), 2.70(2H, t, J=6.8 Hz), 4.04(2H, t, J=6.0 Hz), 6. 80(1H, d, J=9.2 Hz), 7.16-7.20(3H, m), 7.26-7.30(2H, m), 7.58(1H, dd, J=8.8, 2.4 Hz), 7.64(1H, d, J=2.4 Hz).

(2-2) Synthesis of (5-{2-[3-cyano-4-(4-phenylbutoxy)phenyl]ethyl}-2,2-dimethyl-1,3-dioxan-5-yl) carbamic acid t-butyl ester (Compound 2-2)

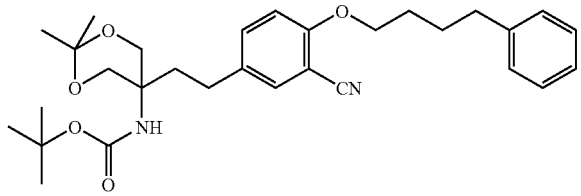

Compound 2-1 (0.544 g), (5-ethynyl-2,2-dimethyl-1,3-dioxan-5-yl)carbamic acid t-butyl ester (0.459 g), 2-dicyclohexylphosphino-2',4',6'-triisopropylbiphenyl (0.36 g), bis(acetonitrile)palladium(II) dichloride (0.007 g) and cesium carbonate (0.538 g) were stirred in acetonitrile (8.3 ml) at 70-80° C. for 2 hr. Water was added to the reaction mixture, and the mixture was extracted with ethyl acetate, washed with saturated brine, and dried over anhydrous sodium sulfate. The solvent was evaporated under reduced pressure. The residue was purified by silica gel column chromatography to give (5-{2-[3-cyano-4-(4-phenylbutoxy)phenyl]ethynyl}-2,2-dimethyl-1,3-dioxan-5-yl)carbamic acid t-butyl ester as a yellow oil. This oil was dissolved in ethyl acetate (6 ml), 10% palladium carbon (containing water about 50%, 0.080 g) was added, and the mixture was stirred under a hydrogen atmosphere at room temperature for 3.5 hr. The solution was filtered, and the filtrate was concentrated to give the object product (0.519 g) as a pale-yellow powder.

$^1$H-NMR(CDCl$_3$) δ (ppm): 1.42(3H, s), 1.43(3H, s), 1.46 (9H, s), 1.84-1.86(4H, m), 1.91-1.96(2H, m), 2.48-2.53(2H, m), 2.69(2H, t, J=6.8 Hz), 3.67(2H, d, J=11.6 Hz), 3.86(2H, d, J=11.6 Hz), 4.03(2H, t, J=5.6 Hz), 4.97(1H, s), 6.82(1H, d, J=8.8 Hz), 7.15-7.21(3H, m), 7.26-7.29(2H, m), 7.30(1H, dd, J=8.8, 2.0 Hz), 7.34(1H, d, J=2.0 Hz).

(2-3) Synthesis of 2-amino-2-{2-[3-cyano-4-(4-phenylbutoxy)phenyl]ethyl}propane-1,3-diol hydrochloride (Compound 2-3)

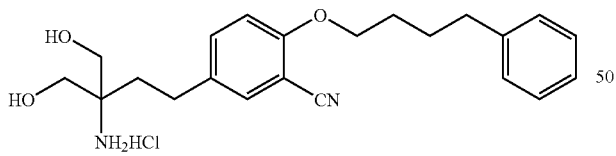

Compound 2-2 (0.519 g) was dissolved in a mixed solvent of ethanol (5 ml) and tetrahydrofuran (4 ml), p-toluenesulfonic acid monohydrate (0.035 g) was added, and the mixture was stirred at room temperature for 3.5 hr, and further at 50-60° C. for 3 hr. To the reaction mixture was added saturated aqueous sodium hydrogen carbonate, and the mixture was extracted with ethyl acetate, washed with saturated brine, and dried over anhydrous sodium sulfate. The solvent was evaporated under reduced pressure. The residue was purified by silica gel column chromatography to give a compound deprotected acetal of compound 2-2 as an oil. To the obtained oil was added hydrogen chloride-containing dioxane (4 mol/l, 2 ml), and the mixture was stirred at room temperature for 8 hr. The precipitate was collected by filtration, and dried to give the object product (0.164 g) as a black-brown powder.

MS(ESI)m/z: 369[M+H]

$^1$H-NMR(DMSO-d$_6$) δ (ppm): 1.73-1.78(6H, m), 2.54-2.59(2H, m), 2.65(2H, t, J=6.8 Hz), 3.51(4H, d, J=5.2 Hz), 4.10-4.14(2H, m), 5.36(2H, t, J=5.2 Hz), 7.15-7.22(4H, m), 7.27(1H, m), 7.28(1H, d, J=8.8 Hz), 7.48(1H, dd, J=8.8, 2.0 Hz), 7.54(1H, d, J=2.0 Hz), 7.82(3H, brs).

Example 3

2-amino-2-{2-[4-(4-cyclohexylbutoxy)-3-trifluoromethylphenyl]ethyl}propane-1,3-diol hydrochloride (3-1) Synthesis of 4'-methoxy-3'-trifluoromethylacetophenone (Compound 3-1)

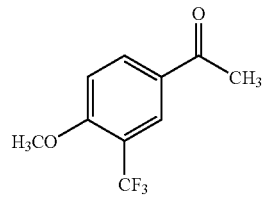

To a solution of 4'-fluoro-3'-trifluoromethylacetophenone (25.0 g) in N,N-dimethylformamide (70 ml) was added under ice-cooling sodium methoxide (7.21 g), and the mixture was stirred under ice-cooling for 2 hr and further at room temperature for 1 hr. The reaction mixture was added to water, and the mixture was extracted with ethyl acetate. The organic layer was washed with saturated brine and dried over anhydrous magnesium sulfate. The solvent was evaporated under reduced pressure to give the object product (24.3 g) as a brown solid.

$^1$H-NMR(CDCl$_3$) δ (ppm): 2.59(3H, s), 3.99(3H, s), 7.06 (1H, d, J=8.7 Hz), 8.14(1H, dd, J=2.1, 8.7 Hz), 8.19(1H, d, J=2.1 Hz).

(3-2) Synthesis of 4'-methoxy-3'-trifluoromethylphenacylbromide (Compound 3-2)

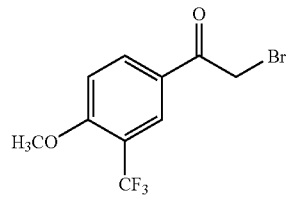

To a solution of compound 3-1 (24.3 g) in acetic acid (120 ml) was added pyridinium tribromide (90%, 39.6 g), and the mixture was stirred at 50° C. for 1 hr. The reaction mixture was added to ice water, and the mixture was extracted with ethyl acetate. The organic layer was washed successively with water, 1M aqueous sodium hydroxide solution, saturated ammonium chloride and saturated brine. The organic layer was dried over anhydrous magnesium sulfate, and the solvent was evaporated under reduced pressure to give the object product (34.2 g) as a brown solid.

¹H-NMR(CDCl₃) δ (ppm): 4.01(3H, s), 4.39(2H, s), 7.09 (1H, d,
J=8.7 Hz), 8.18(1H, dd, J=2.2, 8.7 Hz), 8.23(1H, d, J=1.9 Hz).

(3-3) Synthesis of 2-acetamide-2-[2-(4-methoxy-3-trifluoromethylphenyl)-2-oxoethyl]malonic acid diethyl ester (Compound 3-3)

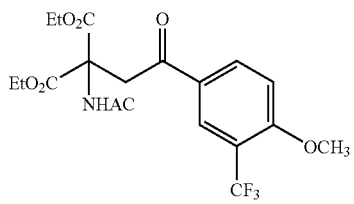

To a solution of diethyl 2-acetamidomalonate (20.1 g) in N,N-dimethylformamide (100 ml) was added under ice-cooling sodium hydride (60%, 4.07 g) in two portions, and the mixture was stirred for 30 min. A solution of compound 3-2 (33.0 g) in N,N-dimethylformamide (50 ml) was added to this solution, and the mixture was stirred under ice-cooling for 2 hr. The reaction mixture was added to ice water, and the mixture was extracted with ethyl acetate. The organic layer was washed with saturated brine and dried over anhydrous magnesium sulfate. The solvent was evaporated under reduced pressure. The obtained residue was purified by silica gel chromatography to give the object product (31.8 g) as a brown oil.

¹H-NMR(CDCl₃) δ (ppm): 1.25(6H, t, J=7.1 Hz), 1.97(3H, s), 3.98(3H, s), 4.22(2H, s), 4.27(4H, dq, J=2.4, 7.1 Hz), 7.05(1H, d, J=8.7 Hz), 7.09(1H, brs), 8.13(1H, dd, J=2.2, 8.7 Hz), 8.20(1H, d, J=2.0 Hz).

(3-4) Synthesis of 2-acetamide-2-[2-(4-methoxy-3-trifluoromethylphenyl)ethyl]malonic acid diethyl ester (Compound 3-4)

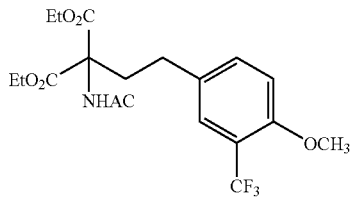

To a solution of compound 3-3 (31.5 g) in trifluoroacetic acid (230 ml) was added triethylsilane (116 ml), and the mixture was stirred at 70° C. for 13 hr. The reaction mixture was concentrated under reduced pressure, water was added, and the mixture was extracted with ethyl acetate. The organic layer was washed successively with aqueous sodium hydroxide solution and saturated brine, and dried over anhydrous magnesium sulfate. The solvent was evaporated under reduced pressure. The obtained residue was purified by silica gel chromatography to give the title compound and a mixture of the starting material as a yellow oil. To a solution of this oil in trifluoroacetic acid (230 ml) was added triethylsilane (116ml), and the mixture was stirred at 70° C. for 12 hr. The reaction mixture was concentrated under reduced pressure, water was added, and the mixture was extracted with ethyl acetate. The organic layer was washed successively with aqueous sodium hydroxide solution and saturated brine, and dried over anhydrous magnesium sulfate. The solvent was evaporated under reduced pressure. Diethyl ether was added to the obtained residue, and the precipitated solid was collected by filtration and dried to give the object product (7.91 g) as a white powder. The mother liquor was concentrated under reduced pressure, and the residue was purified by silica gel chromatography to give the object product (4.29 g). The combined yield was 12.2 g.

¹H-NMR(CDCl₃) δ (ppm): 1.25(6H, t, J=7.2 Hz), 2.02(3H, s), 2.44-2.48(2H, m), 2.62-2.68(2H, m), 3.87(3H, s), 4.15-4.27(4H, m), 6.78(1H, brs), 6.90(1H, d, J=8.4 Hz), 7.27(1H, dd, J=2.0, 8.4 Hz), 7.32(1H, d, J=2.0 Hz).

(3-5) Synthesis of N-[1,1-bis(hydroxymethyl)-3-(4-methoxy-3-trifluoromethylphenyl)propyl]acetamide (Compound 3-5)

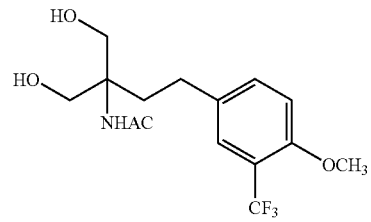

To a solution of compound 3-4 (12.2 g) in ethanol (200 ml) and water (40 ml) was added calcium chloride (6.46 g) and dissolved. To this mixture was added under ice-cooling sodium borohydride (4.40 g) in two portions, and the mixture was stirred under ice-cooling for 3 hr, and further at room temperature for 20 hr. To the reaction mixture was added under ice-cooling 1M hydrochloric acid (300 ml), the mixture was concentrated under reduced pressure, and the mixture was extracted with ethyl acetate. The organic layer was washed with saturated brine, and dried over anhydrous magnesium sulfate. The solvent was evaporated under reduced pressure to give the object product (9.88 g) as white foams.

¹H-NMR(CDCl₃) δ (ppm): 1.92-1.96(2H, m), 2.02(3H, s), 2.60-2.64(2H, m), 3.57(2H, brs), 3.64(2H, brd, J=11.6 Hz), 3.85(2H, brd, J=11.6 Hz), 3.87(3H, s), 5.94(1H, brs), 6.92 (1H, d, J=8.5 Hz), 7.32(1H, dd, J=1.9, 8.5 Hz), 7.37(1H, d, J=1.9 Hz).

(3-6) Synthesis of [3-(4-hydroxy-3-trifluoromethylphenyl)-1,1-bis(hydroxymethyl)propyl]carbamic acid t-butyl ester (Compound 3-6)

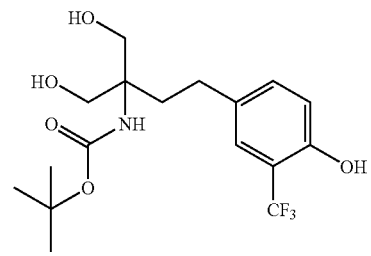

To a solution of compound 3-5 (9.70 g) in methylene chloride (90 ml) was added dropwise 1M methylene chloride solution (116 ml) of tribromide boron at −70° C. The mixture was heated to 0° C. with stirring over 1 hr, and further stirred under ice-cooling for 2 hr. To the reaction mixture was gradually added under ice-cooling methanol (200 ml), and the mixture was concentrated under reduced pressure. To a solution of the obtained residue in ethanol (50 ml) was added concentrated hydrochloric acid (50 ml), and the mixture was stirred at 70° C. for 1 hr. The reaction mixture was concentrated under reduced pressure, to a solution of the obtained residue and N,N-diisopropylethylamine (12.6 ml) in methanol (80 ml) was added under ice-cooling di-t-butyl-dicarbonate (6.94 g), and the mixture was stirred under ice-cooling for 2 hr, and further at room temperature for 4 hr. To the reaction mixture was added saturated aqueous sodium hydrogen carbonate solution (500 ml), and the mixture was concentrated under reduced pressure, and extracted with ethyl acetate. The organic layer was washed successively with saturated aqueous sodium hydrogen carbonate solution and saturated brine, and dried over anhydrous magnesium sulfate. The solvent was evaporated under reduced pressure. The obtained residue was purified by silica gel chromatography to give the object product (2.15 g) as a colorless oil.

$^1$H-NMR(CDCl$_3$) δ (ppm): 1.46(9H, s), 1.84-1.89(2H, m), 2.57-2.61(2H, m), 3.26(2H, brs), 3.66(2H, dd, J=5.9, 11.4 Hz), 3.87(2H, dd, J=5.2, 11.4 Hz), 5.04(1H, brs), 5.58(1H, brs), 6.87(1H, d, J=8.4 Hz), 7.23(1H, dd, J=1.8, 8.4 Hz), 7.30(1H, d, J=1.8 Hz).

(3-7) Synthesis of 4-bromobutylcyclohexane (Compound 3-7)

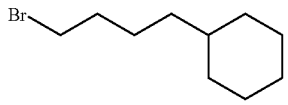

4-Cyclohexyl-1-butanol (5.00 g) was dissolved in methylene chloride (100 ml), triphenylphosphine (9.15 g) and N-bromosuccinimide (6.21 g) were added under ice-cooling, and the mixture was stirred under ice-cooling for 1 hr, and further at room temperature for 3 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (6.30 g) as a colorless oil.

$^1$H-NMR(CDCl$_3$) δ (ppm): 0.80-0.96(2H, m), 1.10-1.35 (6H, m), 1.38-1.49(2H, m), 1.60-1.77(5H, m), 1.82-1.92(2H, quint, J=7.0 Hz), 3.41(2H, t, J=7.0 Hz).

(3-8) Synthesis of {3-[4-(4-cyclohexylbutoxy)-3-trifluoromethylphenyl]-1,1-bis(hydroxymethyl)propyl}carbamic acid t-butyl ester (Compound 3-8)

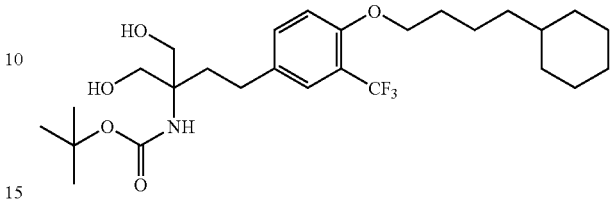

Compound 3-6 (360 mg) was dissolved in N,N-dimethylformamide (10 ml), potassium carbonate (262 mg) and compound 3-7 (250 mg) were added, and the mixture was stirred at 80° C. for 6 hr. Water was added to the reaction mixture, and the mixture was extracted with ethyl acetate, washed with water and saturated brine, and dried over anhydrous magnesium sulfate. The solvent was evaporated under reduced pressure to give the object product (520 mg) as a colorless oil.

$^1$H-NMR(CDCl$_3$) δ (ppm): 0.81-0.94(2H, m), 1.10-1.50 (6H, m), 1.40-1.50(2H, m), 1.45(9H, s), 1.61-1.82(7H, m), 1.83-1.89(2H, m), 2.57-2.62(2H, m), 3.24(2H, brs), 3.62-3.68(2H, m), 3.85-3.90(2H, m), 4.00(2H, t, J=6.4 Hz), 5.02 (1H, brs), 6.89(1H, J=8.4 Hz), 7.25-7.29(1H, m), 7.36(1H, d, J=1.8 Hz).

(3-9) Synthesis of 2-amino-2-{2-[4-(4-cyclohexylbutoxy)-3-trifluoromethylphenyl]ethyl}propane-1,3-diol hydrochloride (Compound 3-9)

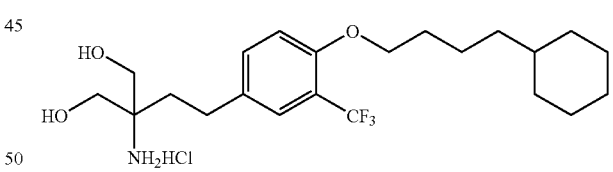

Compound 3-8 (520 mg) was dissolved in methylene chloride (5 ml), hydrogen chloride-containing dioxane (4 mol/l 5 ml) was added, and the mixture was stirred at room temperature for 12 hr. The reaction mixture was concentrated, and the residue was washed with diethyl ether to give the object product (410 mg) as a white powder.

MS(ESI)m/z: 418[M+H]

$^1$H-NMR(CD$_3$OD) S (ppm): 0.88-0.99(2H, m), 1.15-1.31 (6H, m), 1.46-1.55(2H, m), 1.60-1.81(7H, m), 1.90-1.96(2H, m), 2.63-2.69(2H, m), 3.69(4H, s), 4.04(2H, t, J=6.1 Hz), 7.07(1H, d, J=8.5 Hz), 7.39-7.45(2H, m).

Example 4

2-amino-2-{2-[4-(4-phenylbutoxy)-3-trifluoromethylphenyl]ethyl}propane-1,3-diol hydrochloride (4-1) Synthesis of {1,1-bis(hydroxymethyl)-3-[4-(4-phenylbutoxy)-3-trifluoromethylphenyl]propyl}carbamic acid t-butyl ester (Compound 4-1)

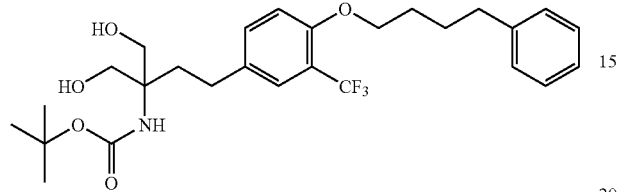

Compound 3-6 (350 mg) was dissolved in N,N-dimethylformamide (10 ml), potassium carbonate (255 mg) and 4-phenylbutylbromide (235 mg) were added, and the mixture was stirred at 80° C. for 6 hr. Water was added to the reaction mixture, and the mixture was extracted with ethyl acetate, washed with water and saturated brine, and dried over anhydrous magnesium sulfate. The solvent was evaporated under reduced pressure to give the object product (490 mg) as a colorless oil.

$^1$H-NMR(CDCl$_3$) δ (ppm): 1.45(9H, s), 1.81-1.90(6H, m), 2.57-2.62(2H, m), 2.64-2.70(2H, m), 3.24(2H, brs), 3.63-3.68(2H, m). 3.84-3.90(2H, m), 4.00(2H, t, J=6.4 Hz), 5.02(1H, brs), 6.87(1H, d, J=8.5 Hz), 7.15-7.19(3H, m), 7.24-7.31(3H, m), 7.36(1H, brs).

(4-2) Synthesis of 2-amino-2-{2-[4-(4-phenylbutoxy)-3-trifluoromethylphenyl]ethyl}propane-1,3-diol hydrochloride (Compound 4-2)

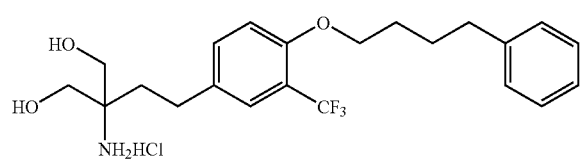

Compound 4-1 (490 mg) was dissolved in methylene chloride (7 ml), hydrogen chloride-containing dioxane (4 mol/l, 5 ml) was added, and the mixture was stirred at room temperature for 12 hr stirred for. The reaction mixture was concentrated, and the residue was washed with diethyl ether to give the object product (370 mg) as a white powder.

MS(ESI)m/z: 412[M+H]

$^1$H-NMR(CD$_3$OD) δ (ppm): 1.79-1.84(4H, m), 1.90-1.95(2H, m), 2.64-2.72(4H, m), 3.69(4H, s), 4.06(2H, t, J=5.4 Hz), 7.06(1H, d, J=8.5 Hz), 7.12-7.21(3H, m), 7.22-7.29(2H, m), 7.40(1H, d, J=8.5 Hz), 7.45(1H, brs).

Example 5

2-amino-2-{2-[4-(5-phenylpentyloxy)-3-trifluoromethylphenyl]ethyl}propane-1,3-diol hydrochloride (5-1) Synthesis of {1,1-bis(hydroxymethyl)-3-[4-(5-phenylpentyloxy)-3-trifluoromethylphenyl]propyl}carbamic acid t-butyl ester (Compound 5-1)

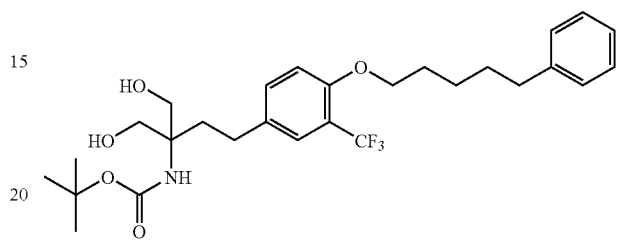

Compound 3-6 (380 mg) was dissolved in N,N-dimethylformamide (10 ml), potassium carbonate (277 mg) and 5-phenylpentylbromide (281 mg) were added, and the mixture was stirred at 80° C. for 6 hr. Water was added to the reaction mixture, and the mixture was extracted with ethyl acetate, washed with water and saturated brine, and dried over anhydrous magnesium sulfate. The solvent was evaporated under reduced pressure to give the object product (560 mg) as a colorless oil.

$^1$H-NMR(CDCl$_3$) δ (ppm): 1.45(911, s), 1.45-1.59(2H, m), 1.60-1.72(2H, m), 1.79-1.91(4H, m), 2.57-2.68(4H, m), 3.25(2H, brs), 3.63-3.68(2H, m), 3.84-3.90(2H, m), 4.00(2H, t, J=6.4 Hz), 5.02(1H, brs), 6.88(1H, d, J=8.5 Hz), 7.15-7.19(3H, m), 7.24-7.31(3H, m), 7.36(1H, brs).

(5-2) Synthesis of 2-amino-2-{2-[4-(5-phenylpentyloxy)-3-trifluoromethylphenyl]ethyl}propane-1,3-diol hydrochloride (Compound 5-2)

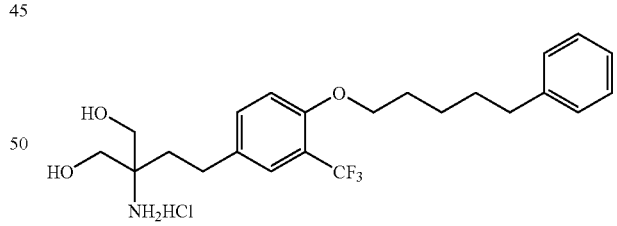

Compound 5-1 (560 mg) was dissolved in methylene chloride (5 ml), hydrogen chloride-containing dioxane (4 mol/l 5 ml) was added, and the mixture was stirred at room temperature for 12 hr. The reaction mixture was concentrated, and the residue was washed with diethyl ether to give the object product (410 mg) as a white powder.

MS(ESI)m/z: 426[M+H]

$^1$H-NMR(CD$_3$OD) δ (ppm): 1.48-1.60(2H, m), 1.64-1.75(2H, m), 1.78-1.88(2H, m), 1.92-1.96(2H, m), 2.60-2.71(4H, m), 3.68(4H, s), 4.04(2H, t, J=6.2 Hz), 7.06(1H, d, J=8.4 Hz), 7.12-7.20(3H, m), 7.22-7.27(2H, m), 7.41(1H, d, J=8.4 Hz), 7.45(1H, d, J=1.7 Hz).

Example 6

2-amino-2-{2-[4-(3-benzyloxybenzyloxy)-3-trifluoromethylphenyl]ethyl}propane-1,3-diol hydrochloride

(6-1) Synthesis of 3-benzyloxybenzylbromide (Compound 6-1)

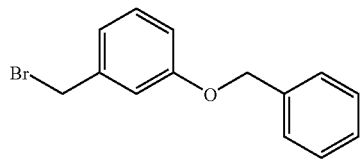

3-Benzyloxybenzyl alcohol (5.00 g) was dissolved in methylene chloride (70 ml), triphenylphosphine (6.52 g) and N-bromosuccinimide (4.43 g) were added under ice-cooling, and the mixture was stirred under ice-cooling for 1 hr, and further at room temperature for 4 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane:ethyl acetate=10:1) to give the object product (5.75 g) as a colorless oil.

$^1$H-NMR(CDCl$_3$) δ (ppm): 4.46(2H, s), 5.07(2H, s), 6.89-6.93(1H, m), 6.98-7.03(2H, m), 7.22-7.28(1H, m), 7.32-7.38 (5H, m).

(6-2) Synthesis of (5-{2-[4-(3-benzyloxybenzyloxy)-3-trifluoromethylphenyl]ethyl}-2,2-dimethyl-1,3-dioxan-5-yl)carbamic acid t-butyl ester (Compound 6-2)

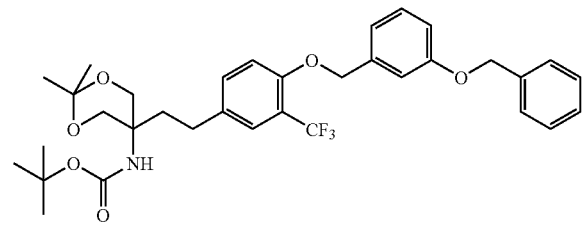

Reference Example compound 2-6 (510 mg) was dissolved in N,N-dimethylformamide (10 ml), potassium carbonate (494 mg) and compound 6-1 (396 mg) were added, and the mixture was stirred at 80° C. for 3 hr. Water was added to the reaction mixture, and the mixture was extracted with ethyl acetate, washed with water and saturated brine, and dried over anhydrous magnesium sulfate. The solvent was evaporated under reduced pressure to give the object product (810 mg) as a colorless oil.

$^1$H-NMR(CDCl$_3$) δ (ppm): 1.42(3H, s), 1.44(3H, s), 1.47 (9H, s), 1.92-1.98(2H, m), 2.51-2.57(2H, m), 3.69(2H, d, J=11.7 Hz), 3.89(2H, d, J=11.7 Hz), 4.98(1H, brs), 5.07(2H, s), 5.13(2H, s), 6.91(1H, d, J=8.6 Hz), 6.92(1H, d, J=8.0 Hz), 7.05(1H, d, J=7.5 Hz), 7.09(1H, s), 7.24-7.48(8H, m).

(6-3) Synthesis of 2-amino-{2-(2-[4-(3-benzyloxybenzyloxy)-3-trifluoromethylphenyl]ethyl}propane-1,3-diol hydrochloride (Compound 6-3)

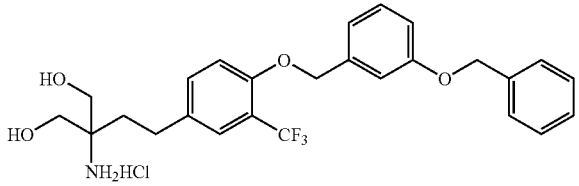

Compound 6-2 (810 mg) was dissolved in ethanol (15 ml), concentrated hydrochloric acid (2 ml) was added, and the mixture was stirred at 80° C. for 1 hr. The reaction mixture was concentrated, and the residue was washed with diethyl ether to give the object product (620 mg) as a white powder.

MS(ESI)m/z: 476[M+H]

$^1$H-NMR(CD$_3$OD) δ (ppm): 1.88-1.93(2H, m), 2.63-2.68 (2H, m), 3.67(4H, s), 5.08(2H, s), 5.18(2H, s), 6.93(1H, dd, J=8.4, 2.4 Hz), 7.02(1H, d, J=7.6 Hz), 7.09(1H, brs), 7.12(1H, d, J=8.4 Hz), 7.25-7.44(7H, m), 7.49(1H, d, 1.9 Hz).

Example 7

2-amino-2-{2-[4-(3-phenoxybenzyloxy)-3-trifluoromethylphenyl]ethyl}propane-1,3-diol hydrochloride

(7-1) Synthesis of (2,2-dimethyl-5-{2-[4-(3-phenoxybenzyloxy)-3-trifluoromethylphenyl]ethyl}-1,3-dioxan-5-yl)carbamic acid t-butyl ester (Compound 7-1)

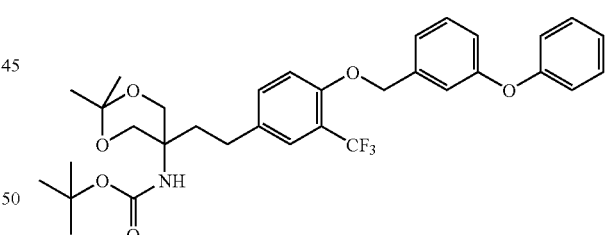

Reference Example compound 2-6 (500 mg) was dissolved in N,N-dimethylformamide (10 ml), potassium carbonate (494 mg) and 3-phenoxybenzylchloride (0.271 ml) were added, and the mixture was stirred at 80° C. for 3 hr. Water was added to the reaction mixture, and the mixture was extracted with ethyl acetate, washed with water and saturated brine, and dried over anhydrous magnesium sulfate. The solvent was evaporated under reduced pressure to give the object product (850 mg) as a colorless oil.

$^1$H-NMR(CDCl$_3$) δ (ppm): 1.42(3H, s), 1.44(3H, s), 1.47 (9H, s). 1.93-1.98(2H, m), 2.51-2.56(2H, m), 3.69(2H, d, J=11.6 Hz), 3.89(2H, d, J=11.6 Hz), 4.98(1H, brs), 5.11(2H, s), 6.89-7.18(8H, s), 7.24-7.40(4H, m).

(7-2) Synthesis of 2-amino-2-{2-[4-(3-phenoxybenzyloxy)-3-trifluoromethylphenyl]ethyl}propane-1,3-diol hydrochloride (Compound 7-2)

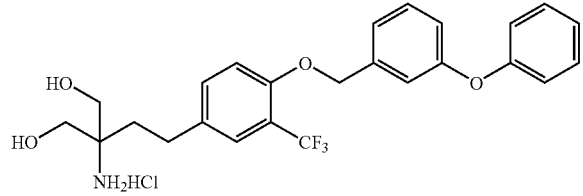

Compound 7-1 (850 mg) was dissolved in ethanol (15 ml), concentrated hydrochloric acid (2 ml) was added, and the mixture was stirred at 80° C. for 1.5 hr. The reaction mixture was concentrated, and the residue was washed with diethyl ether to give the object product (603 mg) as a white powder.

MS(ESI)m/z: 462[M+H]

$^1$H-NMR(DMSO-d$_6$) δ (ppm): 1.89-1.94(2H, m), 2.63-2.69(2H, m), 3.68(4H, s), 5.18(2H, s), 6.90-6.99(3H, m), 7.06-7.20(4H, m), 7.31-7.38(3H, m), 7.41(1H, dd, J=8.4, 1.8 Hz), 7.48(1H, d, J=1.8 Hz).

Example 8

2-amino-2-{2-[4-(3-phenylpropoxy)-3-trifluoromethylphenyl]ethyl}propane-1,3-diol hydrochloride

(8-1) Synthesis of (2,2-dimethyl-5-{2-[4-(3-phenylpropoxy)-3-trifluoromethylphenyl]ethyl}-1,3-dioxan-5-yl)carbamic acid t-butyl ester (Compound 8-1)

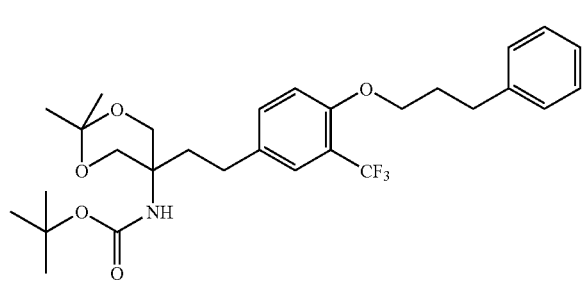

Reference Example compound 2-6 (540 mg) was dissolved in N,N-dimethylformamide (10 ml), potassium carbonate (533 mg) and 3-phenylpropylbromide (0.235 ml) were added, and the mixture was stirred at 80° C. for 3 hr. Water was added to the reaction mixture, and the mixture was extracted with ethyl acetate, washed with water and saturated brine, and dried over anhydrous magnesium sulfate. The solvent was evaporated under reduced pressure to give the object product (740 mg) as a colorless oil.

$^1$H-NMR(CDCl$_3$) δ (ppm): 1.43(3H, s), 1.44(3H, s), 1.47 (9H, s), 1.93-1.98(2H, m), 2.09-2.15(2H, m), 2.51-2.56(2H, m), 2.83(2H, t, J=7.5 Hz), 3.69(2H, d, J=11.6 Hz), 3.89(2H, d, J=11.6 Hz), 3.99(2H, t, J=6.0 Hz), 4.98(1H, brs), 6.83(1H, d, J=8.5 Hz), 7.18-7.22(3H, m), 7.24-7.31(3H, m), 7.37(1H, d, J=2.0 Hz).

(8-2) Synthesis of 2-amino-2-{2-[4-(3-phenylpropoxy)-3-trifluoromethylphenyl]ethyl}propane-1,3-diol hydrochloride (Compound 8-2)

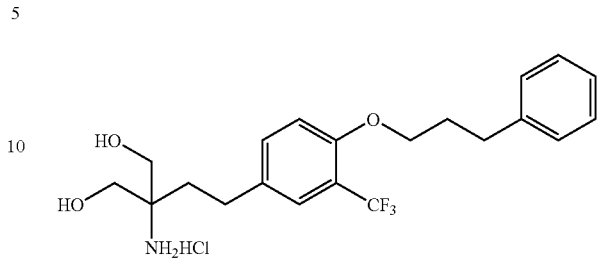

Compound 8-1 (740 mg) was dissolved in ethanol (20 ml), concentrated hydrochloric acid (3 ml) was added, and the mixture was stirred at 80° C. for 2.5 hr. The reaction mixture was concentrated, and the residue was washed with diethyl ether to give the object product (540 mg) as a white powder.

MS(ESI)m/z: 398[M+H]

$^1$H-NMR(CD$_3$OD) δ (ppm): 1.90-1.95(2H, m), 2.04-2.12 (2H, m), 2.63-2.68(2H, m), 2.81(2H, t, J=7.4 Hz), 3.68(4H, s), 4.01(2H, t, J=6.0 Hz), 7.23(1H, d, J=8.5 Hz), 7.12-7.28(5H, m), 7.40(1H, dd, J=8.5, 1.6 Hz), 7.48(1H, d, J=1.6 Hz).

Example 9

2-amino-2-{2-[4-(3-cyclohexylpropoxy)-3-trifluoromethylphenyl]ethyl}propane-1,3-diol hydrochloride

(9-1) Synthesis of 3-bromopropylcyclohexane (Compound 9-1)

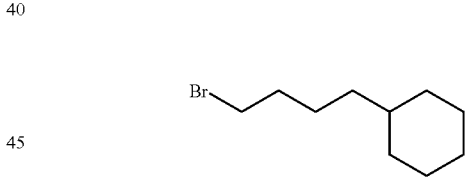

3-Cyclohexyl-1-propanol (5.00 g) was dissolved in methylene chloride (50 ml), triphenylphosphine (10.2 g) and N-bromosuccinimide (6.90 g) were added under ice-cooling, and the mixture was stirred under ice-cooling for 1 hr, and further at room temperature for 1 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (7.17 g) as a colorless oil.

$^1$H-NMR(CDCl$_3$) δ (ppm): 0.81-0.96(2H, m), 1.10-1.45 (6H, m), 1.60-1.78(5H, m), 1.82-1.92(2H, quint, J=7.0 Hz), 3.39(2H, t, J=7.0 Hz).

(9-2) Synthesis of (5-{2-[4-(3-cyclohexylpropyl)-3-trifluoromethylphenyl]ethyl}-2,2-dimethyl-1,3-dioxan-5-yl)carbamic acid t-butyl ester (Compound 9-2)

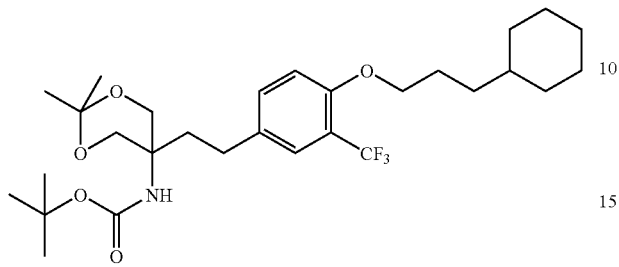

Reference Example compound 2-6 (500 mg) was dissolved in N,N-dimethylformamide (10 ml), potassium carbonate (493 mg) and compound 9-1 (293 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (740 mg) as a colorless oil.

$^1$H-NMR(CDCl$_3$) δ (ppm): 0.81-0.95(2H, m), 1.10-1.39 (7H, m), 1.42(3H, s), 1.44(3H, m), 1.47(9H, s), 1.61-1.84(6H, m), 1.91-1.98(2H, m), 2.51-2.57(2H, m), 3.68(2H, d, J=11.7 Hz), 3.87(2H, d, J=11.7 Hz), 3.98(2H, t, J=6.4 Hz), 4.98(1H, brs), 6.87(1H, d, J=8.5 Hz), 7.25-7.28(1H, m), 7.34(1H, d, J=1.9 Hz).

(9-3) Synthesis of 2-amino-2-{2-[4-(3-cyclohexylpropoxy)-3-trifluoromethylphenyl]ethyl}propane-1,3-diol hydrochloride (Compound 9-3)

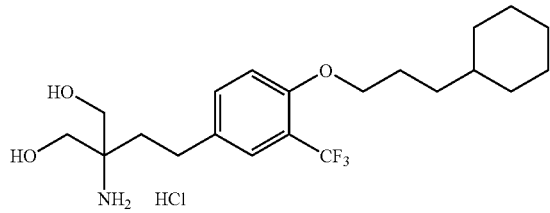

Compound 9-2 (760 mg) was dissolved in ethanol (15 ml), concentrated hydrochloric acid (3 ml) was added, and the mixture was stirred at 80° C. for 2.5 hr. The reaction mixture was concentrated, and the residue was washed with diethyl ether to give the object product (525 mg) as a white powder. MS(ESI)m/z: 404[M+H]

$^1$H-NMR(CD$_3$OD) δ (ppm): 0.88-0.98(2H, m), 1.15-1.33 (4H, m), 1.34-1.41(2H, m), 1.61-1.83(7H, m), 1.89-1.96(2H, m), 2.63-2.68(2H, m), 3.68(4H, s), 4.03(2H, t, J=6.2 Hz), 7.07(1H, d, J=8.4 Hz), 7.41(1H, dd, J=8.4, 1.7 Hz), 7.45(1H, d, J=1.7 Hz).

Example 10

2-amino-2-(2-{4-[3-(4-methoxyphenyl)propoxy]-3-trifluoromethylphenyl}ethyl)propane-1,3-diol hydrochloride (10-1) Synthesis of 1-(3-bromopropyl)-4-methoxybenzene (Compound 10-1)

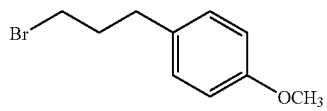

3-(4-Methoxyphenyl)-1-propanol (5.00 g) was dissolved in methylene chloride (50 ml), triphenylphosphine (8.86 g) and N-bromosuccinimide (5.94 g) were added under ice-cooling, and the mixture was stirred under ice-cooling for 1 hr, and further at room temperature for 5 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane:ethyl acetate=100:1-3:1) to give the object product (990 mg) as a colorless oil.

$^1$H-NMR(CDCl$_3$) δ (ppm): 2.14(2H, quint, J=6.5 Hz), 2.72 (2H, t, J=7.2 Hz), 3.38(2H, t, J=6.5 Hz), 3.78(3H, s), 6.84(2H, d, J=8.6 Hz), 7.11(2H, d, J=8.6 Hz).

(10-2) Synthesis of [5-(2-{4-[3-(4-methoxyphenyl)propoxy]-3-trifluoromethylphenyl}ethyl)-2,2-dimethyl-1,3-dioxan-5-yl]carbamic acid t-butyl ester (Compound 10-2)

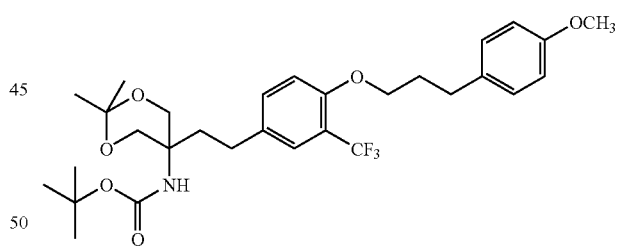

Reference Example compound 2-6 (500 mg) was dissolved in N,N-dimethylformamide (10 ml), potassium carbonate (493 mg) and compound 10-1 (327 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (730 mg) as a brown oil.

$^1$H-NMR(CDCl$_3$) δ (ppm): 1.42(3H, s), 1.44(3H, s), 1.47 (9H, s), 1.93-1.98(2H, m), 2.04-2.09(2H, m), 2.51-2.64(2H, m), 2.77(2H, t, J=7.5 Hz), 3.69(2H, d, J=11.7 Hz), 3.78(3H, s), 3.89(2H, d, J=11.7 Hz), 3.97(2H, t, J=6.0 Hz), 4.98(1H, brs), 6.81-6.85(3H, m), 7.11(2H, d, J=8.6 Hz), 7.24-7.26(1H, m), 7.36(1H, d, J=1.8 Hz).

(10-3) Synthesis of 2-amino-2-(2-{4-[3-(4-methoxyphenyl)propoxy]-3-trifluoromethylphenyl}ethyl)propane-1,3-diol hydrochloride (Compound 10-3)

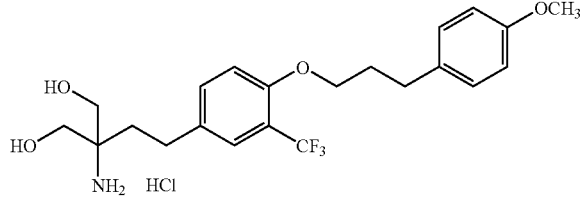

Compound 10-2 (730 mg) was dissolved in ethanol (20 ml), concentrated hydrochloric acid (2 ml) was added, and the mixture was stirred at 80° C. for 2.5 hr. The reaction mixture was concentrated, and the residue was washed with diethyl ether to give the object product (550 mg) as a white powder.

MS(ESI)m/z: 428[M+H]

$^1$H-NMR(DMSO-$d_6$) δ (ppm): 1.73-1.80(2H, m), 1.91-2.02(2H, m), 2.57-2.63(2H, m), 2.68(2H, t, J=7.4 Hz), 3.50 (4H, brs), 3.71(3H, s), 4.03(2H, t, J=5.8 Hz), 5.34(2H, brs), 6.84(2H, d, J=8.2 Hz), 7.10(2H, d, J=8.2 Hz), 7.15(1H, d, J=8.4 Hz), 7.43(1H, d, J=8.4 Hz), 7.47(1H, brs), 7.68(3H, brs).

Example 11

2-amino-2-(2-{3-trifluoromethyl-4-[3-(4-trifluoromethylphenyl)propoxy]phenyl}ethyl)propane-1,3-diol hydrochloride

(11-1) Synthesis of 3-(4-trifluoromethylphenyl)-1-propanol (Compound 11-1)

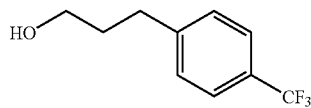

4-Trifluoromethylcinnamic acid (10.0 g) was dissolved in methanol (20 ml) and tetrahydrofuran (50 ml), 10% palladium carbon (5.00 g) was added, and the mixture was stirred under a hydrogen atmosphere at room temperature for 10 hr. The reaction container was purged with nitrogen, the solution was filtered, and the filtrate was concentrated to give a colorless powder (10.5 g). The colorless powder was dissolved in tetrahydrofuran (100 ml), and a tetrahydrofuran-borane·tetrahydrofuran solution (1 mol/l, 59.5 ml) was added dropwise to the mixture under ice-cooling, and the mixture was stirred under ice-cooling for 30 min, and further at room temperature for 16 hr. To the reaction mixture was added water, 1 mol/l aqueous hydrochloric acid solution was added, and the mixture was extracted with ethyl acetate, washed with water, saturated aqueous sodium hydrogen carbonate solution and saturated brine, and dried over anhydrous magnesium sulfate. The solvent was evaporated under reduced pressure to give the object product (9.53 g) as a colorless oil.

$^1$H-NMR(CDCl$_3$) δ (ppm): 1.54(1H, brs), 1.87-1.94(2H, m), 2.78(2H, t, J=7.7 Hz), 3.68(2H, t, J=6.3 Hz), 7.31(2H, d, J=8.0 Hz), 7.54(2H, d, J=8.0 Hz).

(11-2) Synthesis of 1-(3-bromopropyl)-4-trifluoromethylbenzene (Compound 11-2)

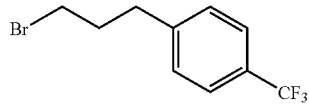

Compound 11-1 (9.53 g) was dissolved in methylene chloride (100 ml), triphenylphosphine (13.3 g) and N-bromosuccinimide (8.97 g) were added under ice-cooling, and the mixture was stirred under ice-cooling for 1 hr, and further at room temperature for 3 hr. The reaction mixture was washed with water and saturated brine, and dried over anhydrous magnesium sulfate. The solvent was evaporated under reduced pressure. Diethyl ether (200 ml) was added, and the precipitated triphenylphosphine oxide was filtered off. The concentrate of the filtrate was purified by silica gel column chromatography (hexane alone) to give the object product (10.1 g) as a colorless oil.

$^1$H-NMR(CDCl$_3$) δ (ppm): 2.18(2H, quint, J=7.4 Hz), 2.85 (2H, t, J=7.4 Hz), 3.39(2H, t, J=6.4 Hz), 7.32(2H, d, J=8.0 Hz), 7.55(2H, d, J=8.0 Hz).

(11-3) Synthesis of [2,2-dimethyl-5-(2-{3-trifluoromethyl-4-[3-(4-trifluoromethylphenyl)propoxy]phenyl}ethyl)-1,3-dioxan-5-yl]carbamic acid t-butyl ester (Compound 11-3)

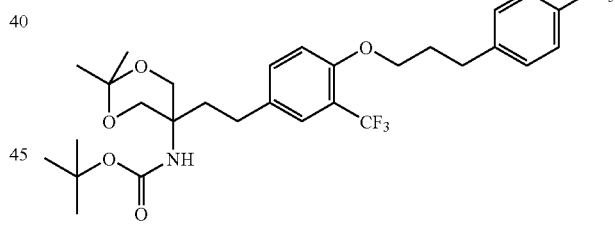

Reference Example compound 2-6 (500 mg) was dissolved in N,N-dimethylformamide (10 ml), potassium carbonate (493 mg) and compound 11-2 (382 mg) were added, and the mixture was stirred at 80° C. for 2.5 hr. Water was added to the reaction mixture, and the mixture was extracted with ethyl acetate, washed with water and saturated brine, and dried over anhydrous magnesium sulfate. The solvent was evaporated under reduced pressure to give the object product (800 mg) as a pale-yellow solid.

$^1$H-NMR(CDCl$_3$) δ (ppm): 1.42(3H, s), 1.44(3H, s), 1.47 (9H, s), 1.93-1.99(2H, m), 2.10-2.18(2H, m), 2.51-2.57(2H, m), 2.90(2H, t, J=7.5 Hz), 3.69(2H, d, J=11.7 Hz), 3.89(2H, d, J=11.7 Hz), 3.98(2H, t, J=5.9 Hz), 4.98(1H, brs), 6.83(1H, d, J=8.5 Hz), 7.25-7.32(3H, m), 7.38(1H, d, J=1.6 Hz), 7.53(2H, d, J=8.1 Hz).

(11-4) Synthesis of 2-amino-2-(2-{3-trifluoromethyl-4-[3-(4-trifluoromethylphenyl)propoxy]phenyl}ethyl)propane-1,3-diol hydrochloride (Compound 11-4)

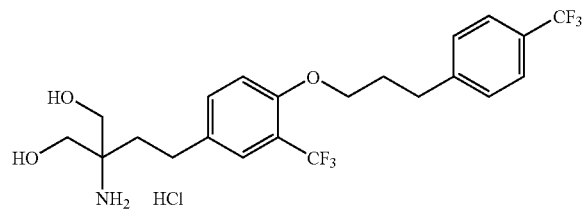

Compound 11-3 (800 mg) was dissolved in ethanol (20 ml), concentrated hydrochloric acid (2 ml) was added, and the mixture was stirred at 80° C. for 2.5 hr. The reaction mixture was concentrated, and the residue was washed with diethyl ether to give the object product (592 mg) as a white powder.

MS(ESI)m/z: 466[M+H]

$^1$H-NMR(DMSO-d$_6$) δ (ppm): 1.73-1.79(2H, m), 2.02-2.08(2H, m), 2.58-2.64(2H, m), 2.84(2H, t, J=7.5 Hz), 3.52 (4H, d, J=4-6 Hz), 4.06(2H, t, J=6.1 Hz), 5.36(2H, t, J=4.8 Hz), 7.17(1H, d, J=8.5 Hz), 7.42-7.48(4H, m), 7.65(2H, d, J=8.2 Hz), 7.78(3H, brs).

Example 12

2-amino-2-(2-{3-trifluoromethyl-4-[3-(3-trifluoromethylphenyl)propoxy]phenyl}ethyl)propane-1,3-diol hydrochloride (12-1) Synthesis of 3-(3-trifluoromethylphenyl)-1-propanol (Compound 12-1)

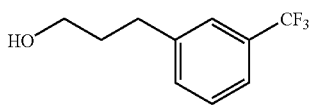

3-Trifluoromethylcinnamic acid (10.0 g) was dissolved in methanol (50 ml) and tetrahydrofuran (30 ml), 10% palladium carbon (5.00 g) was added, and the mixture was stirred under a hydrogen atmosphere at room temperature for 11 hr. The reaction container was purged with nitrogen, the solution was filtered, and the filtrate was concentrated to give a white powder (10.4 g). The white powder was dissolved in tetrahydrofuran (100 ml), and a tetrahydrofuran-borane·tetrahydrofuran solution (1 mol/l, 60.2 ml) was added dropwise to the mixture under ice-cooling, and the mixture was stirred under ice-cooling for 30 min, and further at room temperature for 16 hr. To the reaction mixture was added water, 1 mol/l aqueous hydrochloric acid solution was added, and the mixture was extracted with ethyl acetate, washed with water, saturated aqueous sodium hydrogen carbonate solution and saturated brine, and dried over anhydrous magnesium sulfate. The solvent was evaporated under reduced pressure to give the object product (9.00 g) as a pale-yellow oil.

$^1$H-NMR(CDCl$_3$) δ (ppm): 1.56(1H, brs), 1.87-1.95(2H, m), 2.78(2H, t, J=7.5 Hz), 3.69(2H, t, J=6.4 Hz), 7.38-7.48 (4H, m).

(12-2) Synthesis of 1-(3-bromopropyl)-3-trifluoromethylbenzene (Compound 12-2)

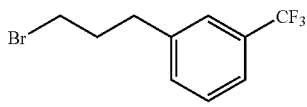

Compound 12-1 (9.00 g) was dissolved in methylene chloride (80 ml), triphenylphosphine (12.8 g) and N-bromosuccinimide (8.63 g) were added under ice-cooling, and the mixture was stirred under ice-cooling for 1 hr, and further at room temperature for 3 hr. The reaction mixture was washed with water and saturated brine, and dried over anhydrous magnesium sulfate. The solvent was evaporated under reduced pressure. Diethyl ether (200 ml) was added, and the precipitated triphenylphosphine oxide was filtered off. The concentrate of the filtrate was purified by silica gel column chromatography (hexane alone) to give the object product (8.59 g) as a colorless oil.

$^1$H-NMR(CDCl$_3$) δ (ppm): 2.17-2.23(2H, m), 2.85(2H, t, J=7.5 Hz), 3.40(2H, t, J=6.4 Hz), 7.38-7.49(4H, m).

(12-3) Synthesis of [2,2-dimethyl-5-(2-{3-trifluoromethyl-4-[3-(3-trifluoromethylphenyl)propoxy]phenyl}ethyl)-1,3-dioxan-5-yl]carbamic acid t-butyl ester (Compound 12-3)

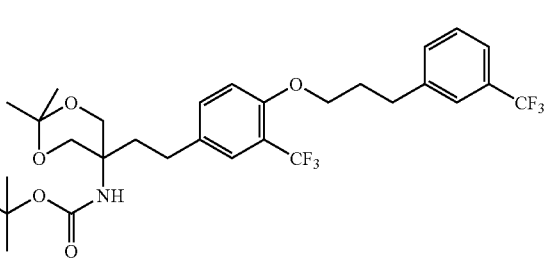

Reference Example compound 2-6 (500 mg) was dissolved in N,N-dimethylformamide (10 ml), potassium carbonate (493 mg) and compound 12-2 (382 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (810 mg) as a white solid.

$^1$H-NMR(CDCl$_3$) δ (ppm): 1.43(3H, s), 1.44(3H, s), 1.47 (9H, s), 1.93-1.98(2H, m), 1.99-2.15(2H, m), 2.51-2.57(2H, m), 2.90(2H, t, J=7.6 Hz), 3.69(2H, d, J=11.7 Hz), 3.89(2H, d, J=11.7 Hz), 3.99(2H, t, J=5.9 Hz), 4.98(1H, brs), 6.84(1H, d, J=8.4 Hz), 7.25-7.28(1H, m), 7.35-7.40(3H, m), 7.45(2H, brs).

(12-4) Synthesis of 2-amino-2-(2-{3-trifluoromethyl-4-[3-(3-trifluoromethylphenyl)propoxy]phenyl}ethyl)propane-1,3-diol hydrochloride (Compound 12-4)

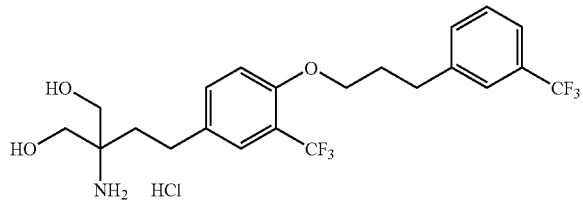

Compound 12-3 (810 mg) was dissolved in ethanol (20 ml), concentrated hydrochloric acid (2 ml) was added, and the mixture was stirred at 80° C. for 2.5 hr. The reaction mixture was concentrated, and the residue was washed with diethyl ether to give the object product (600 mg) as a white powder.

MS(ESI)m/z: 466[M+H]

$^1$H-NMR(DMSO-$d_6$) δ (ppm): 1.71-1.76(2H, m), 2.04-2.08(2H, m), 2.57-2.62(2H, m), 2.85(2H, t, J=7.5 Hz), 3.49 (4H, brs), 4.05(2H, t, J=6.0 Hz), 5.29(2H, brs), 7.16(1H, d, J=8.5 Hz), 7.43(1H, d, J=8.5 Hz), 7.47(1H, d, J=1.5 Hz), 7.50-7.58(4H, m).

Example 13

2-amino-2-(2-{4-[3-(4-methylphenyl)propoxy]-3-trifluoromethylphenyl}ethyl)propane-1,3-diol hydrochloride (13-1) Synthesis of 3-(4-methylphenyl)-1-propanol (Compound 13-1)

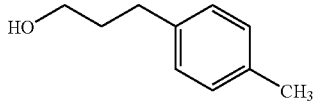

To a suspension of lithium aluminum hydride (585 mg) and tetrahydrofuran (50 ml) was added dropwise a solution of 4-methylcinnamic acid (1.00 g) in tetrahydrofuran (20 ml) under ice-cooling, and the mixture was stirred under ice-cooling for 1.5 hr. To the reaction solution was slowly added dropwise a saturated aqueous sodium sulfate solution to quench the reaction, the solution was filtered, and the filtrate was concentrated to give a colorless oil (1.05 g). The colorless oil was dissolved in ethyl acetate (30 ml), 10% palladium carbon (200 mg) was added, and the mixture was stirred under a hydrogen atmosphere at room temperature for 2 hr. The reaction container was purged with nitrogen, the solution was filtered, and the filtrate was concentrated to give the object product (690 mg) as a colorless oil.

$^1$H-NMR(CDCl$_3$) δ (ppm): 1.22(1H, brs), 1.84-1.92(2H, m), 2.31(3H, s), 2.67(2H, t, J=7.5 Hz), 3.67(2H, t, J=6.1 Hz), 7.09(4H, s).

(13-2) Synthesis of 1-(3-bromopropyl)-4-methylbenzene (Compound 13-2)

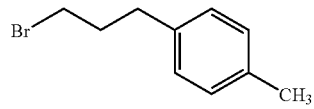

Compound 13-1 (690 mg) was dissolved in methylene chloride (30 ml), triphenylphosphine (1.33 g) and N-bromosuccinimide (899 mg) were added under ice-cooling, and the mixture was stirred under ice-cooling for 1 hr, and further at room temperature for 3 hr. The reaction mixture was washed with water and saturated brine, and dried over anhydrous magnesium sulfate. The solvent was evaporated under reduced pressure. Diethyl ether (50 ml) was added, and the precipitated triphenylphosphine oxide was filtered off. The concentrate of the filtrate was purified by silica gel column chromatography (hexane alone) to give the object product (830 mg) as a colorless oil.

$^1$H-NMR(CDCl$_3$) δ (ppm): 2.11-2.18(2H, m), 2.32(3H, s), 2.74(2H, t, J=7.5 Hz), 3:67(2H, t, J=6.6 Hz), 7.07-7.11(4H, m).

(13-3) Synthesis of [2,2-dimethyl-5-(2-{4-[3-(4-methylphenyl)propoxy]-3-trifluoromethylphenyl}ethyl)-1,3-dioxan-5-yl]carbamic acid t-butyl ester (Compound 13-3)

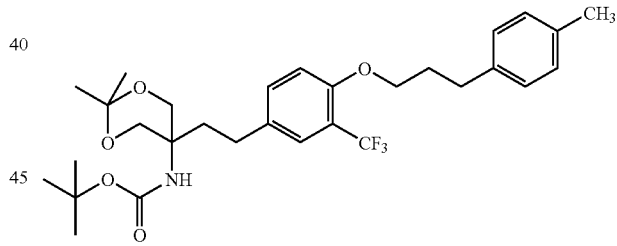

Reference Example compound 2-6 (500 mg) was dissolved in N,N-dimethylformamide (10 ml), potassium carbonate (493 mg) and compound 13-2 (305 mg) were added, and the mixture was stirred at 80° C. for 1.5 hr. Water was added to the reaction mixture, and the mixture was extracted with ethyl acetate, washed with water and saturated brine, and dried over anhydrous magnesium sulfate. The solvent was evaporated under reduced pressure to give the object product (790 mg) as a colorless oil.

$^1$H-NMR(CDCl$_3$) δ (ppm): 1.42 (3H, s), 1.44 (3H, s), 1.47 (9H, s), 1.93-1.98(2H, m), 2.07-2.14(2H, m), 2.31(3H, s), 2.51-2.57(2H, m), 2.78(2H, t, J=7.5 Hz), 3.69(2H, d, J=11.7 Hz), 3.89(2H, d, J=11.7 Hz), 3.98(2H, t, J=6.1 Hz), 4.98(1H, brs), 6.83(1H, d, J=8.5 Hz), 7.09(4H, brs), 7.23-7.26(1H, m), 7.36(1H, d, J=2.0 Hz).

(13-4) Synthesis of 2-amino-2-(2-{4-[3-(4-methylphenyl)propoxy]-3-trifluoromethylphenyl}ethyl)propane-1,3-diol hydrochloride (Compound 13-4)

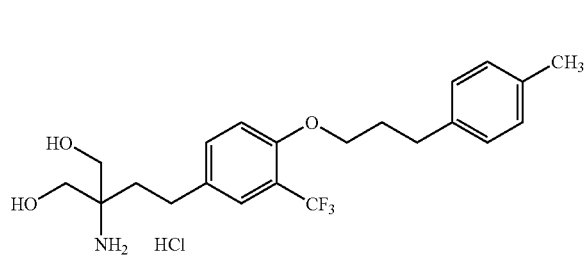

Compound 13-3 (790 mg) was dissolved in ethanol (20 ml), concentrated hydrochloric acid (2 ml) was added, and the mixture was stirred at 80° C. for 2 hr. The reaction mixture was concentrated, and the residue was washed with diethyl ether to give the object product (540 mg) as a white powder.

MS(ESI)m/z: 412[M+H]

$^1$H-NMR(DMSO-$d_6$) δ (ppm): 1.73-1.78(2H, m), 1.96-2.04(2H, m), 2.25(3H, s), 2.58-2.63(2H, m), 2.69(2H, t, J=7.5 Hz), 3.51(4H, d, J=3.3 Hz), 4.03(2H, t, J=5.9 Hz), 5.35(2H, brs), 7.08(4H, s), 7.15(1H, d, J=8.7 Hz), 7.43(1H, d, J=8.7 Hz), 7.47(1H, brs), 25 7.71(3H, brs).

Example 14

2-amino-2-(2-{4-[3-(2-methylphenyl)propoxy]-3-trifluoromethylphenyl}ethyl)propane-1,3-diol hydrochloride (14-1) Synthesis of 3-(2-methylphenyl)-1-propanol (Compound 14-1)

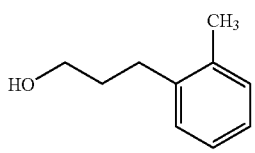

To a suspension of lithium aluminum hydride (1.74 g) and tetrahydrofuran (100 ml) was added dropwise a solution of 2-methylcinnamic acid (3.00 g) in tetrahydrofuran (30 ml) under ice-cooling, and the mixture was stirred under ice-cooling for 4.5 hr. To the reaction solution was slowly added dropwise a saturated aqueous sodium sulfate solution to quench the reaction, the solution was filtered, and the filtrate was concentrated to give a yellow oil (3.17 g). The yellow oil was dissolved in ethyl acetate (30 ml), 10% palladium carbon (500 mg) was added, and the mixture was stirred under a hydrogen atmosphere at room temperature for 2 hr. The reaction container was purged with nitrogen, the solution was filtered, and the filtrate was concentrated to give the object product (3.10 g) as a colorless oil.

$^1$H-NMR(CDCl$_3$) δ (ppm): 1.26(1H, brs), 1.84-1.90(2H, m), 2.32(3H, s), 2.70(2H, t, J=7.8 Hz), 3.72(2H, t, J=6.2 Hz), 7.08-7.20(4H, m).

(14-2) Synthesis of 1-(3-bromopropyl)-2-methylbenzene (Compound 14-2)

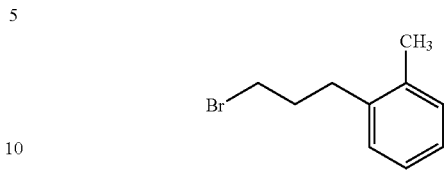

Compound 14-1 (3.10 g) was dissolved in methylene chloride (70 ml), triphenylphosphine (5.28 g) and N-bromosuccinimide (3.58 g) were added under ice-cooling, and the mixture was stirred under ice-cooling for 1 hr, and further at room temperature for 12 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (2.67 g) as a pale-yellow oil.

$^1$H-NMR(CDCl$_3$) δ (ppm): 2.09-2.17(2H, m), 2.32(3H, s), 2.77(2H, t, J=7.8 Hz), 3.72(2H, t, J=6.4 Hz), 7.11-7.17(4H, m).

(14-3) Synthesis of [2,2-dimethyl-5-(2-{4-[3-(2-methylphenyl)propoxy]-3-trifluoromethylphenyl}ethyl)-1,3-dioxan-5-yl]carbamic acid t-butyl ester (Compound 14-3)

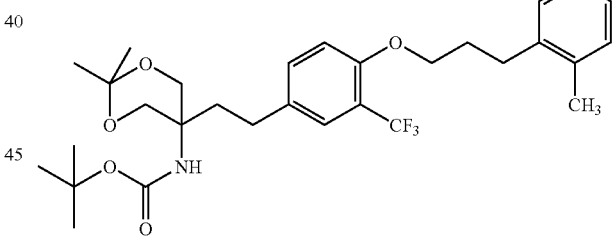

Reference Example compound 2-6 (500 mg) was dissolved in N,N-dimethylformamide (10 ml), potassium carbonate (493 mg) and compound 14-2 (305 mg) were added, and the mixture was stirred at 80° C. for 3 hr. Water was added to the reaction mixture, and the mixture was extracted with ethyl acetate, washed with water and saturated brine, and dried over anhydrous magnesium sulfate. The solvent was evaporated under reduced pressure to give the object product (750 mg) as a colorless oil.

$^1$H-NMR(CDCl$_3$) δ (ppm): 1.43(3H, s), 1.44(3H, s), 1.47(9H, s), 1.94-1.98(2H, m), 2.03-2.11(2H, m), 2.32(3H, s), 2.52-2.57(2H, m), 2.83(2H, t, J=7.6 Hz), 3.69(2H, d, J=11.7 Hz), 3.89(2H, d, J=11.7 Hz), 4.03(2H, t, J=5.9 Hz), 4.98(1H, brs), 6.86(1H, d, J=8.5 Hz), 7.09-7.16(4H, m), 7.28(1H, d, J=2.0 Hz), 7.37(1H, d, J=2.0 Hz).

(14-4) Synthesis of 2-amino-2-(2-{4-[3-(2-methylphenyl)propoxy]-3-trifluoromethylphenyl}ethyl)propane-1,3-diol hydrochloride (Compound 14-4)

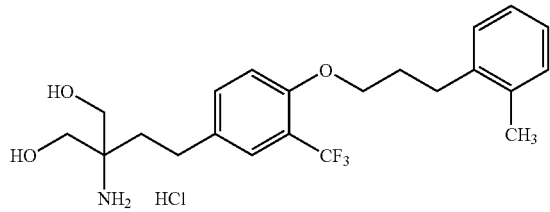

Compound 14-3 (750 mg) was dissolved in ethanol (20 ml), concentrated hydrochloric acid (2 ml) was added, and the mixture was stirred at 80° C. for 2 hr. The reaction mixture was concentrated, and the residue was washed with diethyl ether to give the object product (510 mg) as a white powder.

MS(ESI)m/z: 412[M+H]

$^1$H-NMR(DMSO-$d_6$) δ (ppm): 1.67-1.73(2H, m), 1.85-1.90(2H, m), 2.18(3H, s), 2.52-2.57(2H, m), 2.67(2H, t, J=7.8 Hz), 3.45(4H, d, J=4.3 Hz), 4.02(2H, t, J=5.8 Hz), 5.30(2H, t, J=4.6 Hz), 6.99-7.08(4H, m), 7.10(1H, d, J=8.4 Hz), 7.37(1H, d, J=8.4 Hz), 7.41(1H, d, J=1.7 Hz), 7.74(3H, brs).

Example 15

2-amino-2-(2-{4-[3-(3-methylphenyl)propoxy]-3-trifluoromethylphenyl}ethyl)propane-1,3-diol hydrochloride

(15-1) Synthesis of 3-(3-methylphenyl)-1-propanol (Compound 15-1)

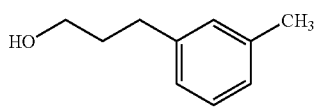

To a suspension of lithium aluminum hydride (1.75 g) and tetrahydrofuran (100 ml) was added dropwise a solution of 3-methylcinnamic acid (3.00 g) in tetrahydrofuran (30 ml) under ice-cooling, and the mixture was stirred under ice-cooling for 1 hr, and further at room temperature for 15.5 hr. To the reaction solution was slowly added dropwise a saturated aqueous sodium sulfate solution to quench the reaction, the solution was filtered, and the filtrate was concentrated to give a yellow oil (2.97 g). The yellow oil was dissolved in ethyl acetate (30 ml), 10% palladium carbon (500 mg) was added, and the mixture was stirred under a hydrogen atmosphere at room temperature for 2 hr. The reaction container was purged with nitrogen, the solution was filtered, and the filtrate was concentrated. The residue was purified by silica gel column chromatography (hexane:ethyl acetate=2:1-1:1) to give the object product (1.88 g) as a colorless oil.

$^1$H-NMR(CDCl$_3$) δ (ppm): 1.26(1H, brs), 1.85-1.93(2H, m), 2.33(3H, s), 2.67(2H, t, J=7.5 Hz), 3.72(2H, t, J=6.4 Hz), 6.99-7.02(3H, m), 7.18(1H, t, J=7.5 Hz).

(15-2) Synthesis of 1-(3-bromopropyl)-3-methylbenzene (Compound 15-2)

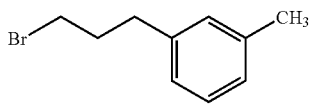

Compound 15-1 (1.88 g) was dissolved in methylene chloride (50 ml), triphenylphosphine (3.64 g) and N-bromosuccinimide (2.46 g) were added under ice-cooling, and the mixture was stirred under ice-cooling for 1 hr, and further at room temperature for 12 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane:ethyl acetate=100:1) to give the object product (2.25 g) as a colorless oil.

$^1$H-NMR(CDCl$_3$) δ (ppm): 2.09-2.17(2H, m), 2.33(3H, s), 2.74(2H, t, J=7.4 Hz), 3.40(2H, t, J=6.5 Hz), 6.98-7.03(3H, m), 7.18(1H, t, J=7.4 Hz).

(15-3) Synthesis of [2,2-dimethyl-5-(2-{4-[3-(3-methylphenyl)propoxy]-3-trifluoromethylphenyl}ethyl)-1,3-dioxan-5-yl]carbamic acid t-butyl ester (Compound 15-3)

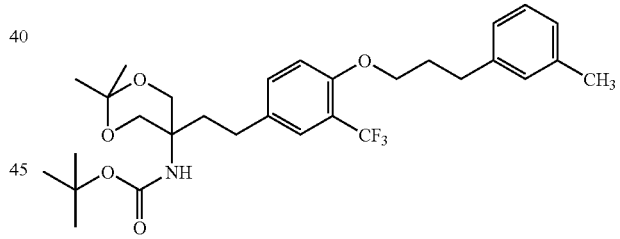

Reference Example compound 2-6 (500 mg) was dissolved in N,N-dimethylformamide (10 ml), potassium carbonate (493 mg) and compound 15-2 (305 mg) were added, and the mixture was stirred at 80° C. for 1.5 hr. Water was added to the reaction mixture, and the mixture was extracted with ethyl acetate, washed with water and saturated brine, and dried over anhydrous magnesium sulfate. The solvent was evaporated under reduced pressure to give the object product (720 mg) as a white solid.

$^1$H-NMR(CDCl$_3$) δ (ppm): 1.42(3H, s), 1.44(3H, s), 1.47(9H, s), 1.93-1.98(2H, m), 2.05-2.12(2H, m), 2.32(3H, s), 2.51-2.57(2H, m), 2.78(2H, t, J=7.6 Hz), 3.69(2H, d, J=11.7 Hz), 3.89(2H, J=11.7 Hz), 3.99(2H, t, J=6.0 Hz), 4.97(1H, brs), 6.84(1H, J=8.5 Hz), 6.98-7.01(3H, m), 7.17(1H, t, J=7.4 Hz), 7.23-7.26(1H, m), 7.36(1H, d, J=1.7 Hz).

(15-4) Synthesis of 2-amino-2-(2-{4-[3-(3-methylphenyl)propoxy]-3-trifluoromethylphenyl}ethyl)propane-1,3-diol hydrochloride (Compound 15-4)

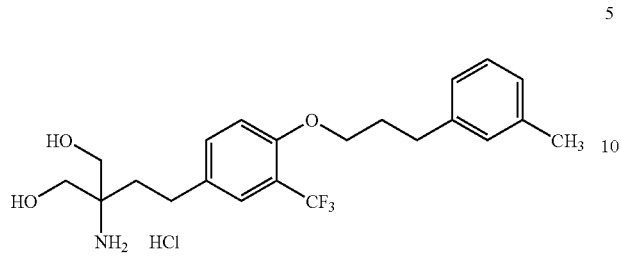

Compound 15-3 (720 mg) was dissolved in ethanol (20 ml), concentrated hydrochloric acid (2 ml) was added, and the mixture was stirred at 80° C. for 2 hr. The reaction mixture was concentrated, and the residue was washed with diethyl ether to give the object product (530 mg) as a white powder.

MS(ESI)m/z: 412[M+H]

$^1$H-NMR(DMSO-$d_6$) δ (ppm): 1.73-1.78(2H, m), 1.97-2.03(2H, m), 2.26(3H, s), 2.58-2.63(2H, m), 2.70(2H, t, J=7.5 Hz), 3.51(4H, d, J=3.9 Hz), 4.04(2H, t, J=6.1 Hz), 5.34(2H, brs), 6.96-7.01(3H, m), 7.16(2H, t, J=7.5 Hz), 7.43(1H, d, J=8.6 Hz), 7.47(1H, d, J=1.6 Hz), 7.69(3H, brs).

Example 16

2-amino-2-(2-{4-[3-(3-methoxyphenyl)propoxy]-3-trifluoromethylphenyl}ethyl)propane-1,3-diol hydrochloride

(16-1) Synthesis of 3-(3-methoxyphenyl)-1-propanol (Compound 16-1)

To a suspension of lithium aluminum hydride (1.60 g) and tetrahydrofuran (80 ml) was added dropwise a solution of 3-methoxycinnamic acid (3.00 g) in tetrahydrofuran (30 ml) under ice-cooling, and the mixture was stirred under ice-cooling for 1 hr, and further at room temperature for 15.5 hr. To the reaction solution was slowly added dropwise a saturated aqueous sodium sulfate solution to quench the reaction, the solution was filtered, and the filtrate was concentrated to give a yellow oil (2.75 g). The yellow oil was dissolved in ethyl acetate (30 ml), 10% palladium carbon (800 mg) was added, and the mixture was stirred under a hydrogen atmosphere at room temperature for 2 hr. The reaction container was purged with nitrogen, the solution was filtered, and the filtrate was concentrated. The residue was purified by silica gel column chromatography (hexane:ethyl acetate=1:3-1:4) to give the object product (2.00 g) as a colorless oil.

$^1$H-NMR(CDCl$_3$) δ (ppm): 1.26(1H, brs), 1.86-1.93(2H, m), 2.69(2H, t, J=7.6 Hz), 3.68(2H, t, J=6.4 Hz), 3.80(3H, s), 6.72-6.75(2H, m), 6.80(1H, d, J=7.6 Hz), 7.18(1H, t, J=7.6 Hz).

(16-2) Synthesis of 1-(3-bromopropyl)-3-methoxybenzene (Compound 16-2)

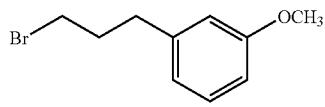

Compound 16-1 (2.00 g) was dissolved in methylene chloride (50 ml), triphenylphosphine (3.58 g) and N-bromosuccinimide (2.40 g) were added under ice-cooling, and the mixture was stirred under ice-cooling for 1 hr, and further at room temperature for 15 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (2.07 g) as a pale-yellow oil.

$^1$H-NMR(CDCl$_3$) δ (ppm): 2.13-2.20(2H, m), 2.76(2H, t, J=7.4 Hz), 3.40(2H, t, J=6.6 Hz), 3.80(3H, s), 6.74-6.70(3H, m), 7.18-7.23(1H, m).

(16-3) Synthesis of [5-(2-{4-[3-(3-methoxyphenyl)propoxy]-3-trifluoromethylphenyl}ethyl)-2,2-dimethyl-1,3-dioxan-5-yl]carbamic acid t-butyl ester (Compound 16-3)

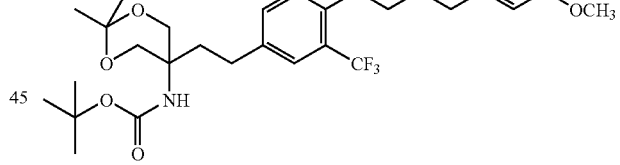

Reference Example compound 2-6 (500 mg) was dissolved in N,N-dimethylformamide (10 ml), potassium carbonate (493 mg) and compound 16-2 (328 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (800 mg) as a white solid.

$^1$H-NMR(CDCl$_3$) δ (ppm): 1.42(3H, s), 1.44(3H, s), 1.47(9H, s), 1.93-1.98(2H, m), 2.08-2.12(2H, m), 2.51-2.56(2H, m), 2.81(2H, t, J=7.5 Hz), 3.69(2H, d, J=11.7 Hz), 3.76(3H, s), 3.89(2H, d, J=11.7 Hz), 3.99(2H, t, J=6.0 Hz), 4.98(1H, brs), 6.72-6.84(4H, m), 7.19(1H, t, J=7.5 Hz), 7.24(1H, d, J=1.8 Hz), 7.36(1H, d, J=1.8 Hz).

(16-4) Synthesis of 2-amino-2-(2-{4-[3-(3-methoxyphenyl)propoxy]-3-trifluoromethylphenyl}ethyl)propane-1,3-diol hydrochloride (Compound 16-4)

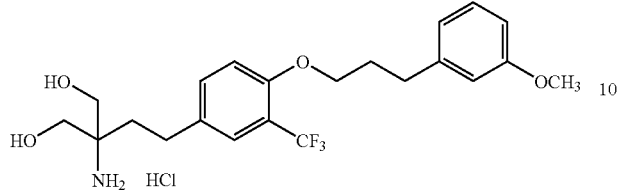

Compound 16-3 (800 mg) was dissolved in ethanol (20 ml), concentrated hydrochloric acid (2 ml) was added, and the mixture was stirred at 80° C. for 2 hr. The reaction mixture was concentrated, and the residue was washed with diethyl ether to give the object product (560 mg) as a white powder.

MS(ESI)m/z: 428[M+H]

$^1$H-NMR(DMSO-$d_6$) δ (ppm): 1.73-1.78(2H, m), 1.99-2.05(2H, m), 2.57-2.63(2H, m), 2.72(2H, t, J=7.4 Hz), 3.51 (4H, d, J=4.8 Hz), 3.69(3H, s), 4.03(2H, t, J=6.1 Hz), 5.34 (2H, t, J=4.8 Hz), 6.73-6.78(3H, m), 7.14-7.22(2H, m), 7.43 (1H, d, J=8.7 Hz), 7.47(1H, brs), 7.69(3H, brs).

Example 17

2-amino-2-(2-{4-[3-(2-methoxyphenyl)propoxy]-3-trifluoromethylphenyl}ethyl)propane-1,3-diol hydrochloride (17-1) Synthesis of 3-(2-methoxyphenyl)-1-propanol (Compound 17-1)

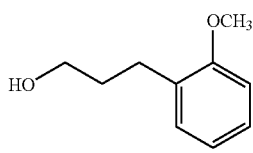

To a suspension of lithium aluminum hydride (1.60 g) and tetrahydrofuran (70 ml) was added dropwise a solution of 2-methoxycinnamic acid (3 g) in tetrahydrofuran (30 ml) under ice-cooling, and the mixture was stirred under ice-cooling for 1 hr, and further at room temperature for 15.5 hr. To the reaction solution was slowly added dropwise a saturated aqueous sodium sulfate solution to quench the reaction, the solution was filtered, and the filtrate was concentrated to give a colorless oil (2.95 g). The colorless oil was dissolved in ethyl acetate (30 ml), 10% palladium carbon (700 mg) was added, and the mixture was stirred under a hydrogen atmosphere at room temperature for 2 hr. The reaction container was purged with nitrogen, the solution was filtered, and the filtrate was concentrated. The residue was purified by silica gel column chromatography (hexane:ethyl acetate=2:1-1:2) to give the object product (2.00 g) as a colorless oil.

$^1$H-NMR(CDCl$_3$) δ (ppm): 1.26(1H, brs), 1.81-1.89(2H, m), 2.73(2H, t, J=7.3 Hz), 3.60(2H, brs), 3.84(3H, s), 6.85-6.92(2H, m), 7.13-7.21(2H, m).

(17-2) Synthesis of 1-(3-bromopropyl)-2-methoxybenzene (Compound 17-2)

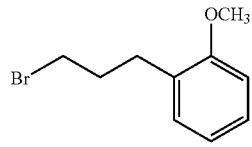

Compound 17-1 (2.00 g) was dissolved in methylene chloride (50 ml), triphenylphosphine (3.58 g) and N-bromosuccinimide (2.40 g) were added under ice-cooling, and the mixture was stirred under ice-cooling for 1 hr, and further at room temperature for 15 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (2.24 g) as a pale-brown oil.

$^1$H-NMR(CDCl$_3$) δ (ppm): 2.11-2.18(2H, m), 2.76(2H, t, J=7.3 Hz), 3.40(2H, t, J=6.9 Hz), 3.82(3H, s), 6.83-6.90(2H, m), 7.13-7.22(2H, m).

(17-3) Synthesis of [5-(2-{4-[3-(2-methoxyphenyl)propoxy]-3-trifluoromethylphenyl}ethyl)-2,2-dimethyl-1,3-dioxan-5-yl]carbamic acid t-butyl ester (Compound 17-3)

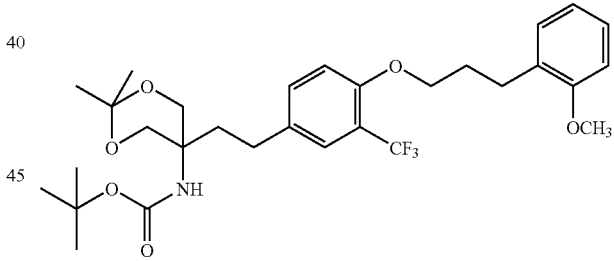

Reference Example compound 2-6 (500 mg) was dissolved in N,N-dimethylformamide (10 ml), potassium carbonate (493 mg) and compound 17-2 (328 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (780 mg) as a white solid.

$^1$H-NMR(CDCl$_3$) δ (ppm): 1.42(3H, s), 1.44(3H, s), 1.47 (9H, s), 1.93-1.98(2H, m), 2.06-2.10(2H, m), 2.51-2.56(2H, m), 2.81(2H, t, J=7.4 Hz), 3.69(2H, d, J=11.7 Hz), 3.80(3H, s), 3.89(2H, d, J=11.7 Hz), 3.99(2H, t, J=6.0 Hz), 4.98(1H, brs), 6.83-6.88(3H, m), 7.13(1H, d, J=7.0 Hz), 7.18 (1H, t, J=7.8 Hz), 7.24(1H, brs), 7.36(1H, d, J=1.4 Hz).

(17-4) Synthesis of 2-amino-2-(2-{4-[3-(2-methoxyphenyl)propoxy]-3-trifluoromethylphenyl}ethyl)propane-1,3-diol hydrochloride (Compound 17-4)

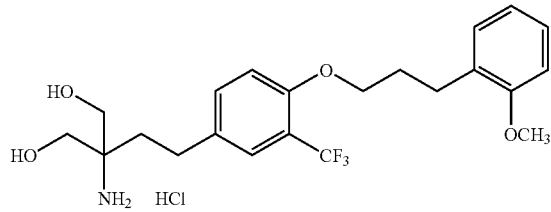

Compound 17-3 (780 mg) was dissolved in ethanol (20 ml), concentrated hydrochloric acid (2 ml) was added, and the mixture was stirred at 80° C. for 2 hr. The reaction mixture was concentrated, and the residue was washed with diethyl ether to give the object product (560 mg) as a white powder.

MS(ESI)m/z: 428[M+H]

$^1$H-NMR(DMSO-$d_6$) δ (ppm): 1.74-1.79(2H, m), 1.94-2.04(2H, m), 2.57-2.64(2H, m), 2.72(2H, t, J=7.5 Hz), 3.52 (4H, d, J=4.3 Hz), 3.75(3H, s), 4.04(2H, t, J=6.0 Hz), 5.36 (2H, brs), 6.85(1H, t, J=7.3 Hz), 6.95(1H, d, J=8.2 Hz), 7.08 (1H, d, J=7.3 Hz), 7.13-7.18(2H, m), 7.43(1H, d, J=8.5 Hz), 7.47(1H, brs), 7.77(3H, brs).

Example 18

2-amino-2-(2-{4-[3-(3,4-dimethoxyphenyl)propoxy]-3-trifluoromethylphenyl}ethyl)propane-1,3-diol hydrochloride

(18-1) Synthesis of 3-(3,4-dimethoxyphenyl)-1-propanol (Compound 18-1)

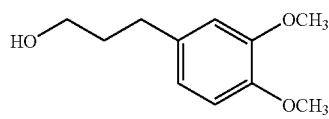

To a suspension of lithium aluminum hydride (1.37 g) and tetrahydrofuran (70 ml) was added dropwise a solution of 3,4-dimethoxycinnamic acid (3.00 g) in tetrahydrofuran (30 ml) under ice-cooling, and the mixture was stirred under ice-cooling for 1 hr, and further at room temperature for 15.5 hr. To the reaction solution was slowly added dropwise a saturated aqueous sodium sulfate solution to quench the reaction, the solution was filtered, and the filtrate was concentrated to give a colorless oil (2.96 g). The colorless oil was dissolved in ethyl acetate (50 ml), 10% palladium carbon (1.00 g) was added, and the mixture was stirred under a hydrogen atmosphere at room temperature for 2 hr. The reaction container was purged with nitrogen, the solution was filtered, and the filtrate was concentrated. The residue was purified by silica gel column chromatography (hexane:ethyl acetate=1:1-1:3) to give the object product (2.00 g) as a pale-yellow oil.

1H-NMR(CDCl$_3$) δ (ppm): 1.21-1.25(1H, m), 1.84-1.92 (2H, m), 2.66(2H, t, J=7.8 Hz), 3.69(2H, q, J=6.1 Hz), 3.86 (3H, s), 3.87(3H, s), 6.73-6.75(2H, m), 6.78-6.81(1H, m).

(18-2) Synthesis of 1-(3-bromopropyl)-3,4-dimethoxybenzene (Compound 18-2)

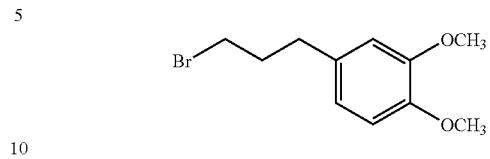

Compound 18-1 (2.00 g) was dissolved in methylene chloride (50 ml), triphenylphosphine (2.97 g) and N-bromosuccinimide (1.99 g) were added under ice-cooling, and the mixture was stirred under ice-cooling for 1 hr, and further at room temperature for 15 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane:ethyl acetate=5:1-3:1) to give the object product (2.17 g) as a pale-brown oil.

$^1$H-NMR(CDCl$_3$) δ (ppm): 2.11-2.18(2H, m), 2.73(2H, t, J=7.3 Hz), 3.40(2H, t, J=6.5 Hz), 3.86(3H, s), 3.88(3H, s), 6.72-6.75(2H, m), 6.79-6.81(1H, m).

(18-3) Synthesis of [5-(2-{4-[3-(3,4-dimethoxyphenyl)propoxy]-3-trifluoromethylphenyl}ethyl)-2,2-dimethyl-1,3-dioxan-5-yl]carbamic acid t-butyl ester (Compound 18-3)

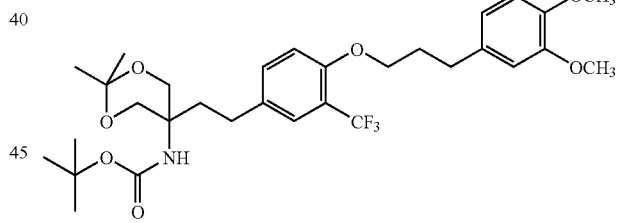

Reference Example compound 2-6 (500 mg) was dissolved in N,N-dimethylformamide (10 ml), potassium carbonate (493 mg) and compound 18-2 (371 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (1.00 g) as a pale-yellow solid.

$^1$H-NMR(CDCl$_3$) δ (ppm): 1.42(3H, s), 1.44(3H, s), 1.47 (9H, s), 1.93-1.98(2H, m), 2.05-2.10(2H, m), 2.51-2.56(2H, m), 2.78(2H, t, J=7.3 Hz), 3.69(2H, d, J=11.7 Hz), 3.79(3H, s), 3.84-3.90(5H, m), 3.97(2H, t, J=5.9 Hz), 4.98(1H, brs), 6.71-6.75(2H, m), 6.77-6.84(2H, m), 7.24-7.26(1H, m), 7.37 (1H, d, J=1.6 Hz).

(18-4) Synthesis of 2-amino-2-(2-{4-[3-(3,4-dimethoxyphenyl)propoxy]-3-trifluoromethylphenyl}ethyl)propane-1,3-diol hydrochloride (Compound 18-4)

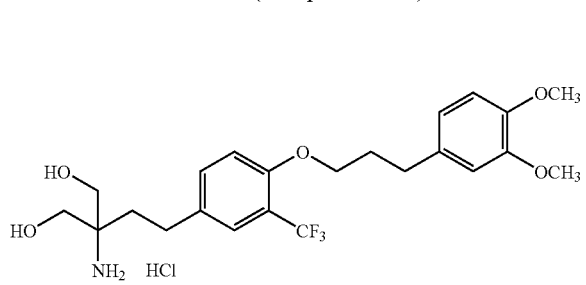

Compound 18-3 (1.00 g) was dissolved in ethanol (20 ml), concentrated hydrochloric acid (2 ml) was added, and the mixture was stirred at 80° C. for 2.5 hr. The reaction mixture was concentrated, and the residue was washed with diethyl ether to give the object product (580 mg) as a pale-yellow powder.

MS(ESI)m/z: 458[M+H]

$^1$H-NMR(DMSO-$d_6$) δ (ppm): 1.73-1.78(2H, m), 1.97-2.04(2H, m), 2.57-2.64(2H, m), 2.68(2H, t, J=7.3 Hz), 3.52 (4H, d, J=4.7 Hz), 3.66(3H, s), 3.70(3H, s), 4.02(2H, t, J=6.0 Hz), 5.36(2H, t, J=4.7 Hz), 6.69(1H, dd, J=8.4, 1.5 Hz), 6.76(1H, d, J=1.5 Hz), 6.84(1H, d, J=8.0 Hz), 7.15(1H, d, J=8.4 Hz), 7.43(1H, d, J=8.4 Hz), 7.47(1H, s), 7.76(3H, brs).

Example 19

2-amino-2-(2-{4-[3-(2,4-dimethoxyphenyl)propoxy]-3-trifluoromethylphenyl}ethyl)propane-1,3-diol hydrochloride (19-1) Synthesis of 3-(2,4-dimethoxyphenyl)-1-propanol (Compound 19-1)

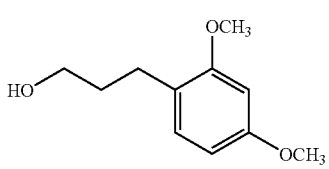

To a suspension of lithium aluminum hydride (2.28 g) and tetrahydrofuran (100 ml) was added dropwise a solution of 2,4-dimethoxycinnamic acid (5.00 g) in tetrahydrofuran (50 ml) under ice-cooling, and the mixture was stirred under ice-cooling for 1 hr, and further at room temperature for 2 hr. To the reaction solution was slowly added dropwise a saturated aqueous sodium sulfate solution to quench the reaction, the solution was filtered, and the filtrate was concentrated to give a yellow oil (4.30 g). The a yellow oil was dissolved in ethyl acetate (50 ml), 10% palladium carbon (1.00 g) was added, and the mixture was stirred under a hydrogen atmosphere at room temperature for 2 hr. The reaction container was purged with nitrogen, the solution was filtered, and the filtrate was concentrated. The residue was purified by silica gel column chromatography (hexane:ethyl acetate=1:1-1:2) to give the object product (2.68 g) as a yellow oil.

$^1$H-NMR(CDCl$_3$) δ (ppm): 1.54(1H, brs), 1.77-1.85(2H, m), 2.65(2H, t, J=7.3 Hz), 3.59(2H, q, J=6.2 Hz), 3.81(3H, s), 3.83(3H, s), 6.42-6.47(2H, m), 7.04(1H, d, J=7.9 Hz).

(19-2) Synthesis of 1-(3-bromopropyl)-2,4-dimethoxybenzene (Compound 19-2)

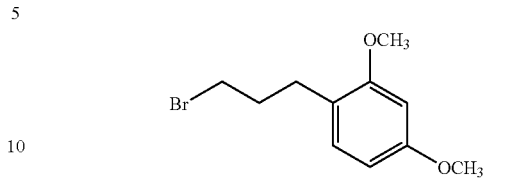

Compound 19-1 (2.68 g) was dissolved in methylene chloride (30 ml), triphenylphosphine (3.99 g) and N-bromosuccinimide (2.69 g) were added under ice-cooling, and the mixture was stirred under ice-cooling for 2 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane:ethyl acetate=50:1) to give the object product (2.71 g) as a pale-brown oil.

$^1$H-NMR(CDCl$_3$) δ (ppm): 2.07-2.14(2H, m), 2.69(2H, t, J=7.2 Hz), 3.39(2H, t, J=6.7 Hz), 3.79(6H, s), 6.40-6.45(2H, m), 7.04(1H, d, J=8.0 Hz).

(19-3) Synthesis of [5-(2-{4-[3-(2,4-dimethoxyphenyl)propoxy]-3-trifluoromethylphenyl}ethyl)-2,2-dimethyl-1,3-dioxan-5-yl]carbamic acid t-butyl ester (Compound 19-3)

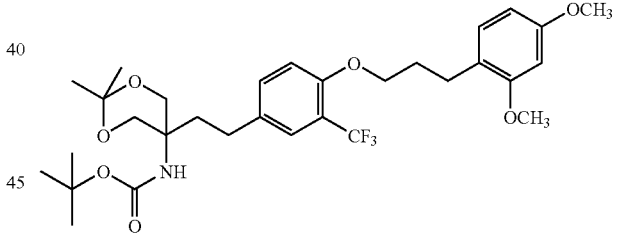

Reference Example compound 2-6 (500 mg) was dissolved in N,N-dimethylformamide (10 ml), potassium carbonate (493 mg) and compound 19-2 (371 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (930 mg) as a colorless oil.

$^1$H-NMR(CDCl$_3$) δ (ppm): 1.42(3H, s), 1.44(3H, s), 1.47 (9H, s), 1.93-1.98(2H, m), 2.02-2.06(2H, m), 2.51-2.56(2H, m), 2.74(2H, t, J=7.4 Hz), 3.69(2H, d, J=11.8 Hz), 3.77(3H, s), 3.79(3H, s), 3.87-3.90(2H, m), 3.97(2H, t, J=6.1 Hz), 4.98(1H, brs), 6.39(1H, dd, J=8.1, 2.3 Hz), 6.44(1H, d, J=2.3 Hz), 6.84(1H, d, J=8.5 Hz), 7.01(1H, d, J=8.1 Hz), 7.24-7.26(1H, m), 7.36(1H, d, J=1.8 Hz).

(19-4) Synthesis of 2-amino-2-(2-{4-[3-(2,4-dimethoxyphenyl)propoxy]-3-trifluoromethylphenyl}ethyl)propane-1,3-diol hydrochloride (Compound 19-4)

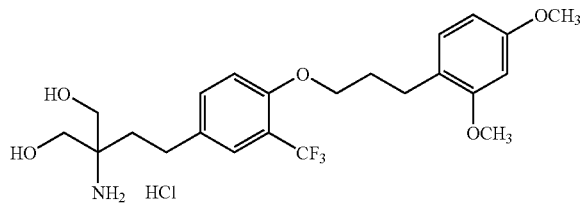

Compound 19-3 (930 mg) was dissolved in ethanol (20 ml), concentrated hydrochloric acid (2 ml) was added, and the mixture was stirred at 80° C. for 1.5 hr. The reaction mixture was concentrated, and the residue was washed with diethyl ether to give a white powder. The white powder was purified by HPLC, and the obtained residue was converted to hydrochloride by adding hydrogen chloride containing ether (1 mol/l, 15 ml). The precipitate was collected by filtration and dried to give the object product (460 mg) as a white powder.

MS(ESI)m/z: 458[M+H]

$^1$H-NMR(DMSO-d$_6$) δ (ppm): 1.79-1.84(2H, m), 1.96-2.00(2H, m), 2.64-2.72(4H, m), 3.57(4H, d, J=4.1 Hz), 3.78 (3H, s), 3.79(3H, s), 4.07(2H, t, J=6.1 Hz), 5.40(2H, brs), 6.48(1H, dd, J=8.1, 2.3 Hz), 6.58(1H, d, J=2.3 Hz), 7.03(1H, d, J=8.1 Hz), 7.19(1H, d, J=8.5 Hz), 7.49(1H, d, J=8.5 Hz), 7.52(1H, s), 7.75(3H, brs).

Example 20

2-amino-2-(2-{4-[3-(4-fluorophenyl)propoxy]-3-trifluoromethylphenyl}ethyl)propane-1,3-diol hydrochloride

(20-1) Synthesis of 3-(4-fluorophenyl)-1-propanol (Compound 20-1)

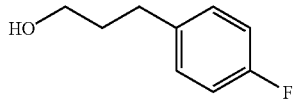

4-Fluorocinnamic acid (10.0 g) was dissolved in methanol (10 ml) and tetrahydrofuran (100 ml), 10% palladium carbon (2.00 g) was added, and the mixture was stirred under a hydrogen atmosphere at room temperature for 5 hr. The reaction container was purged with nitrogen, the solution was filtered, and the filtrate was concentrated to give a colorless powder (10.2 g). The colorless powder was dissolved in tetrahydrofuran (100 ml), and a tetrahydrofuran-borane.tetrahydrofuran solution (1 mol/l, 72.2 ml) was added dropwise to the mixture under ice-cooling, and the mixture was stirred under ice-cooling for 30 min, and further at room temperature for 2 hr. To the reaction mixture was added water, 1 mol/l aqueous hydrochloric acid solution was added, and the mixture was extracted with ethyl acetate, washed with water, saturated aqueous sodium hydrogen carbonate solution and saturated brine, and dried over anhydrous magnesium sulfate. The solvent was evaporated under reduced pressure to give the object product (9.39 g) as a colorless oil.

$^1$H-NMR(CDCl$_3$) δ (ppm): 1.22-1.25(1H, m), 1.83-1.91 (2H, m), 2.69(2H, t, J=7.6 Hz), 3.67(2H, q, J=6.1 Hz), 6.94-6.99(2H, m), 7.13-7.17(2H, m).

(20-2) Synthesis of 1-(3-bromopropyl)-4-fluorobenzene (Compound 20-2)

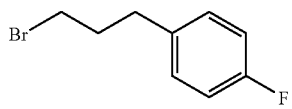

Compound 20-1 (9.39 g) was dissolved in diethyl ether (100 ml), phosphorus tribromide (8.58 ml) was added under ice-cooling, and the mixture was stirred under ice-cooling for 3.5 hr. To the reaction mixture was slowly added water, and the mixture was extracted with diethyl ether. The organic layer was washed with saturated brine and dried over anhydrous magnesium sulfate. The solvent was evaporated under reduced pressure to give the object product (4.93 g) as a pale-yellow oil.

$^1$H-NMR(CDCl$_3$) δ (ppm): 2.10-2.18(2H, m), 2.76(2H, t, J=7.3 Hz), 3.38(2H, t, J=6.5 Hz), 6.98(2H, t, J=8.3 Hz), 7.15(2H, t, J=6.5 Hz).

(20-3) Synthesis of [5-(2-{4-[3-(4-fluorophenyl)propoxy]-3-trifluoromethylphenyl}ethyl)-2,2-dimethyl-1,3-dioxan-5-yl]carbamic acid t-butyl ester (Compound 20-3)

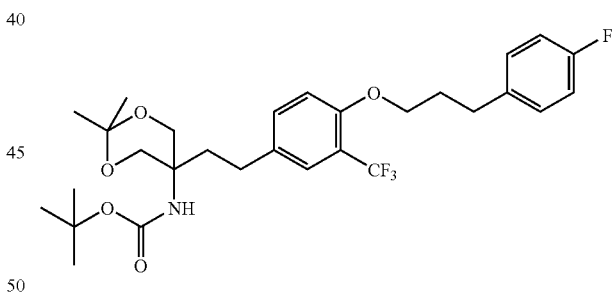

Reference Example compound 2-6 (500 mg) was dissolved in N,N-dimethylformamide (10 ml), potassium carbonate (493 mg) and compound 20-2 (310 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (720 mg) as a white solid.

$^1$H-NMR(CDCl$_3$) δ (ppm): 1.42(3H, s), 1.44(3H, s), 1.47 (9H, s), 1.93-1.98(2H, m), 2.04-2.11(2H, m), 2.52-2.56(2H, m), 2.80(2H, t, J=7.5 Hz), 3.69(2H, d, J=11.7 Hz), 3.89(2H, d, J=11.7 Hz), 3.97(2H, t, J=5.9 Hz), 4.97(1H, brs), 6.83(1H, d, J=8.5 Hz), 6.93-6.98(2H, m), 7.12-7.16(2H, m), 7.25-7.27 (1H, m), 7.37(1H, d, J=1.9 Hz).

(20-4) Synthesis of 2-amino-2-(2-{4-[3-(4-fluorophenyl)propoxy]-3-trifluoromethylphenyl}ethyl)propane-1,3-diol hydrochloride (Compound 20-4)

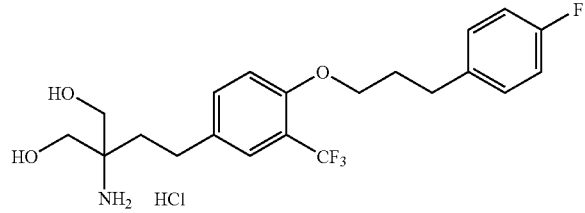

Compound 20-3 (720 mg) was dissolved in ethanol (20 ml), concentrated hydrochloric acid (1.5 ml) was added, and the mixture was stirred at 80° C. for 2.5 hr. The reaction mixture was concentrated, and the residue was washed with diethyl ether to give the object product (523 mg) as a white powder.

MS(ESI)m/z: 416[M+H]
$^1$H-NMR(DMSO-d$_6$) δ (ppm): 1.74-1.79(2H, m), 1.98-2.05(2H, m), 2.59-2.64(2H, m), 2.74(2H, t, J=7.5 Hz), 3.52 (4H, d, J=4.7 Hz), 4.04(2H, t, J=6.1 Hz), 5.37(2H, t, J=4.7 Hz), 7.07-7.17(3H, m), 7.20-7.24(2H, m), 7.44(1H, dd, J=8.5, 1.7 Hz),7.47(1H, brs), 7.80(3H, brs).

Example 21

2-amino-2-(2-{4-[3-(3,4-methylenedioxyphenyl)propoxy]-3-trifluoromethylphenyl}ethyl)propane-1,3-diol hydrochloride (21-1) Synthesis of 3-(3,4-methylenedioxyphenyl)-1-propanol (Compound 21-1)

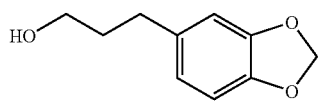

3,4-Methylenedioxycinnamic acid (10.0 g) was dissolved in methanol (30 ml) and tetrahydrofuran (50 ml), 10% palladium carbon (2.00 g) was added, and the mixture was stirred under a hydrogen atmosphere at room temperature for 6 hr. The reaction container was purged with nitrogen, the solution was filtered, and the filtrate was concentrated to give a colorless powder (9.88 g). The colorless powder was dissolved in tetrahydrofuran (100 ml), and a tetrahydrofuran-borane.tetrahydrofuran solution (1 mol/l, 61.1 ml) was added dropwise to the mixture under ice-cooling, and the mixture was stirred under ice-cooling for 30 min, and further at room temperature for 12 hr. To the reaction mixture was added water, 1 mol/l aqueous hydrochloric acid solution was added, and the mixture was extracted with ethyl acetate, washed with water, saturated aqueous sodium hydrogen carbonate solution and saturated brine, and dried over anhydrous magnesium sulfate. The solvent was evaporated under reduced pressure to give the object product (9.72 g) as a pale-yellow oil.

$^1$H-NMR(CDCl$_3$) δ (ppm): 1.21-1.26(1H, m), 1.82-1.89 (2H, m), 2.64(2H, t, J=7.6 Hz), 3.67(2H, q, J=6.0 Hz), 5.92 (2H, s), 6.63-6.66(1H, m), 6.69-6.74(2H, m).

(21-2) Synthesis of 1-(3-bromopropyl)-3,4-methylenedioxybenzene (Compound 21-2)

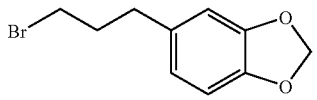

Compound 21-1 (9.72 g) was dissolved in diethyl ether (100 ml), phosphorus tribromide (5.27 ml) was added under ice-cooling, and the mixture was stirred under ice-cooling for 6.5 hr. To the reaction mixture was slowly added water was added, and the mixture was extracted with diethyl ether. The organic layer was washed with saturated brine and dried over anhydrous magnesium sulfate. The solvent was evaporated under reduced pressure to give the object product (5.05 g) as a pale-yellow oil.

$^1$H-NMR(CDCl$_3$) δ (ppm): 2.08-2.15(2H, m), 2.70(2H, t, J=7.3 Hz), 3.38(2H, t, J=6.5 Hz), 5.92(2H, s), 6.63-6.69(2H, m), 6.74(1H, d, J=7.8 Hz).

(21-3) Synthesis of [2,2-dimethyl-5-(2-{4-[3-(3,4-methylenedioxyphenyl)propoxy]-3-trifluoromethylphenyl}ethyl)-1,3-dioxan-5-yl]carbamic acid t-butyl ester (Compound 21-3)

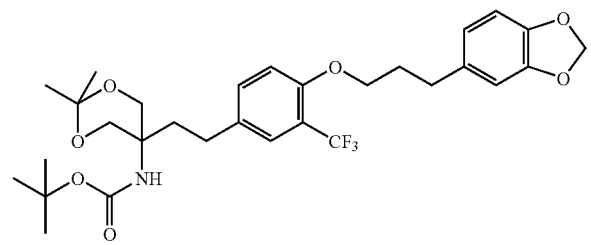

Reference Example compound 2-6 (500 mg) was dissolved in N,N-dimethylformamide (10 ml), potassium carbonate (493 mg) and compound 21-2 (388 mg) were added, and the mixture was stirred at 80° C. for 1 hr. Water was added to the reaction mixture, and the mixture was extracted with ethyl acetate, washed with water and saturated brine, and dried over anhydrous magnesium sulfate. The solvent was evaporated under reduced pressure to give the object product (860 mg) as a yellow oil.

$^1$H-NMR(CDCl$_3$) δ (ppm): 1.42(3H, s), 1.44(3H, s), 1.47 (9H, s), 1.93-1.98(2H, m), 2.04-2.09(2H, m), 2.51-2.56(2H, m), 2.75(2H, t, J=7.4 Hz), 3.69(2H, d, J=11.7 Hz), 3.89(2H, d, J=11.7 Hz), 3.97(2H, t, J=5.9 Hz), 4.97(1H, brs), 5.91(2H, s), 6.62-6.73(3H, m), 6.83(1H, d, J=8.5 Hz), 7.25-7.26(1H, m), 7.36(1H, J=1.8 Hz).

(21-4) Synthesis of 2-amino-2-(2-{4-[3-(3,4-methyl-enedioxyphenyl)propoxy]-3-trifluoromethylphenyl}ethyl)propane-1,3-diol hydrochloride (Compound 21-4)

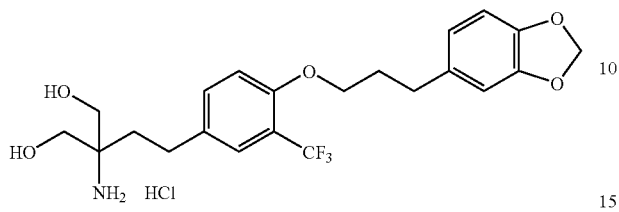

Compound 21-3 (860 mg) was dissolved in ethanol (15 ml), concentrated hydrochloric acid (1.5 ml) was added, and the mixture was stirred at 80° C. for 2 hr. The reaction mixture was concentrated, and the residue was washed with diethyl ether to give the object product (570 mg) as a white powder.
MS(ESI)m/z: 442[M+H]
$^1$H-NMR(DMSO-$d_6$) δ (ppm): 1.70-1.75(2H, m), 1.91-1.99(2H, m), 2.54-2.59(2H, m), 2.62(2H, t, J=7.4 Hz), 3.47(4H, d, J=4.7 Hz), 3.98(2H, t, J=6.1 Hz), 5.32(2H, t, J=4.7 Hz), 5.91(2H, s), 6.59(1H, dd, J=7.8, 1.3 Hz), 6.73-6.77(2H, m), 7.11(1H, d, J=8.5 Hz), 7.37-7.43(2H, m), 7.70(3H, brs).

Example 22

2-amino-2-(2-{4-[3-(2-fluorophenyl)propoxy]-3-trifluoromethylphenyl}ethyl)propane-1,3-diol hydrochloride (22-1) Synthesis of 3-(2-fluorophenyl)-1-propanol (Compound 22-1)

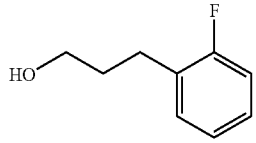

2-Fluorocinnamic acid (10.0 g) was dissolved in methanol (20 ml) and tetrahydrofuran (30 ml), 10% palladium carbon (5.00 g) was added, and the mixture was stirred under a hydrogen atmosphere at room temperature for 4 hr. The reaction container was purged with nitrogen, the solution was filtered, and the filtrate was concentrated to give a white powder (10.3 g). The white powder was dissolved in tetrahydrofuran (100 ml), and a tetrahydrofuran-borane.tetrahydrofuran solution (1 mol/l, 78.3 ml) was added dropwise to the mixture under ice-cooling, and the mixture was stirred under ice-cooling for 30 min, and further at room temperature for 1.5 hr. To the reaction mixture was added water, 1 mol/l aqueous hydrochloric acid solution was added, and the mixture was extracted with ethyl acetate, washed with water, saturated aqueous sodium hydrogen carbonate solution and saturated brine, and dried over anhydrous magnesium sulfate. The solvent was evaporated under reduced pressure to give the object product (8.68 g) as a colorless oil.
$^1$H-NMR(CDCl$_3$) δ (ppm): 1.52-1.58(1H, m), 1.85-1.92(2H, m), 2.75(2H, t, J=7.6 Hz), 3.68(2H, t, J=6.3 Hz), 6.98-7.08(2H, m), 7.14-7.20(2H, m).

(22-2) Synthesis of 1-(3-bromopropyl)-2-fluorobenzene (Compound 22-2)

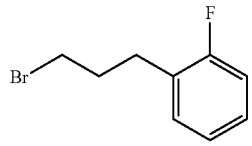

Compound 22-1 (8.68 g) was dissolved in diethyl ether (100 ml), phosphorus tribromide (6.35 ml) was added under ice-cooling, and the mixture was stirred under ice-cooling for 3 hr. To the reaction mixture was slowly added water was added, and the mixture was extracted with diethyl ether. The organic layer was washed with saturated brine and dried over anhydrous magnesium sulfate. The solvent was evaporated under reduced pressure to give the object product (5.00 g) as a yellow oil.
$^1$H-NMR(CDCl$_3$) δ (ppm): 2.13-2.21(2H, m), 2.81(2H, t, J=7.4 Hz), 3.40(2H, t, J=6.6 Hz), 6.99-7.08(2H, m), 7.16-7.23(2H, m).

(22-3) Synthesis of [5-(2-{4-[3-(2-fluorophenyl)propoxy]-3-trifluoromethylphenyl}ethyl)-2,2-dimethyl-1,3-dioxan-5-yl]carbamic acid t-butyl ester (Compound 22-3)

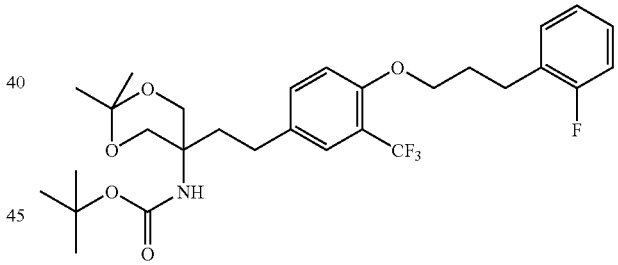

Reference Example compound 2-6 (500 mg) was dissolved in N,N-dimethylformamide (10 ml), potassium carbonate (493 mg) and compound 22-2 (310 mg) were added, and the mixture was stirred at 80° C. for 1 hr. Water was added to the reaction mixture, and the mixture was extracted with ethyl acetate, washed with water and saturated brine, and dried over anhydrous magnesium sulfate. The solvent was evaporated under reduced pressure to give the object product (740 mg) as a white solid.
$^1$H-NMR(CDCl$_3$) δ (ppm): 1.42(3H, s), 1.44(3H, s), 1.47(9H, s), 1.93-1.98(2H, m), 2.09-2.15(2H, m), 2.51-2.56(2H, m), 2.86(2H, t, J=7.5 Hz), 3.69(2H, d, J=11.7 Hz), 3.89(2H, d, J=11.7 Hz), 4.00(2H, t, J=6.1 Hz), 4.97(1H, brs), 6.84(1H, d, J=8.5 Hz), 6.98-7.05(2H, m), 7.16-7.19(2H, m), 7.27(1H, brs), 7.37(1H, brs).

(22-4) Synthesis of 2-amino-2-(2-{4-[3-(2-fluorophenyl)propoxy]-3-trifluoromethylphenyl}ethyl)propane-1,3-diol hydrochloride (Compound 22-4)

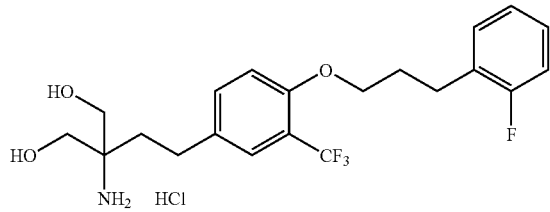

Compound 22-3 (740 mg) was dissolved in ethanol (15 ml), concentrated hydrochloric acid (1.5 ml) was added, and the mixture was stirred at 80° C. for 2.5 hr. The reaction mixture was concentrated, and the residue was washed with diethyl ether to give the object product (540 mg) as a white powder.

MS(ESI)m/z: 416[M+H]

$^1$H-NMR(DMSO-$d_6$) δ (ppm): 1.71-1.75(2H, m), 1.95-1.99(2H, m), 2.55-2.60(2H, m), 2.75(2H, t, J=7.6 Hz), 3.48 (4H, d, J=4.5 Hz), 4.04(2H, t, J=5.9 Hz), 5.33(2H, t, J=4.5 Hz), 7.07-7.13(3H, m), 7.21-7.25(2H, m), 7.40(1H, d, J=8.6 Hz), 7.44(1H, brs), 7.73(3H, brs).

Example 23

2-amino-2-(2-{4-[3-(3-fluorophenyl)propoxy]-3-trifluoromethylphenyl}ethyl)propane-1,3-diol hydrochloride (23-1) Synthesis of 3-(3-fluorophenyl)-1-propanol (Compound 23-1)

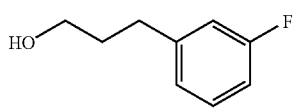

3-Fluorocinnamic acid (10.0 g) was dissolved in methanol (20 ml) and tetrahydrofuran (30 ml), 10% palladium carbon (3.00 g) was added, and the mixture was stirred under a hydrogen atmosphere at room temperature for 6 hr. The reaction container was purged with nitrogen, the solution was filtered, and the filtrate was concentrated to give a yellow powder (10.6 g). The yellow powder was dissolved in tetrahydrofuran (100 ml), and a tetrahydrofuran-borane tetrahydrofuran solution (1 mol/l, 78.3 ml) was added dropwise to the mixture under ice-cooling, and the mixture was stirred under ice-cooling for 30 min, and further at room temperature for 4 hr. To the reaction mixture was added water, 1 mol/l aqueous hydrochloric acid solution was added, and the mixture was extracted with ethyl acetate, washed with water, saturated aqueous sodium hydrogen carbonate solution and saturated brine, and dried over anhydrous magnesium sulfate. The solvent was evaporated under reduced pressure to give the object product (10.0 g) as a colorless oil.

$^1$H-NMR(CDCl$_3$) δ (ppm): 1.25(1H, brs), 1.85-1.93(2H, m), 2.72(2H, t, J=7.6 Hz), 3.68(2H, t, J=6.4 Hz), 6.86-6.92(2H, m), 6.97(1H, d, J=7.5 Hz), 7.20-7.25(1H, m).

(23-2) Synthesis of 1-(3-bromopropyl)-3-fluorobenzene (Compound 23-2)

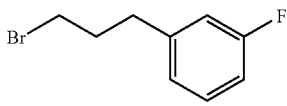

Compound 23-1 (10.0 g) was dissolved in methylene chloride (100 ml), triphenylphosphine (17.5 g) and N-bromosuccinimide (11.8 g) were added under ice-cooling, and the mixture was stirred under ice-cooling for 3.5 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (11.1 g) as a colorless oil.

$^1$H-NMR(CDCl$_3$) δ (ppm): 2.12-2.20(2H, m), 2.78(2H, t, J=7.3 Hz), 3.39(2H, t, J=6.4 Hz), 6.88-6.92(2H, m), 6.98(1H, d, J=7.6 Hz), 7.22-7.28(1H, m).

(23-3) Synthesis of [5-(2-{4-[3-(3-fluorophenyl)propoxy]-3-trifluoromethylphenyl}ethyl)-2,2-dimethyl-1,3-dioxan-5-yl]carbamic acid t-butyl ester (Compound 23-3)

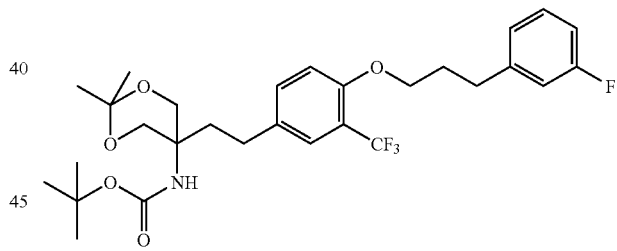

Reference Example compound 2-6 (500 mg) was dissolved in N,N-dimethylformamide (10 ml), potassium carbonate (493 mg) and compound 23-2 (310 mg) were added, and the mixture was stirred at 80° C. for 3 hr. Water was added to the reaction mixture, and the mixture was extracted with ethyl acetate, washed with water and saturated brine, and dried over anhydrous magnesium sulfate. The solvent was evaporated under reduced pressure to give the object product (700 mg) as a white solid.

$^1$H-NMR(CDCl$_3$) δ (ppm): 1.42(3H, s), 1.44(3H, s), 1.47 (9H, s), 1.93-1.98(2H, m), 2.08-2.14(2H, m), 2.52-2.56(2H, m), 2.83(2H, t, J=7.5 Hz), 3.69(2H, d, J=11.7 Hz), 3.89(2H, d, J=11.7 Hz), 3.98(2H, t, J=5.9 Hz), 4.97(1H, brs), 6.83(1H, d, J=8.4 Hz), 6.88-6.92(2H, m), 6.97(1H, d, J=7.6 Hz), 7.20-7.27(2H, m), 7.37(1H, brs).

(23-4) Synthesis of 2-amino-2-(2-{4-[3-(3-fluorophenyl)propoxy]-3-trifluoromethylphenyl}ethyl)propane-1,3-diol hydrochloride (Compound 23-4)

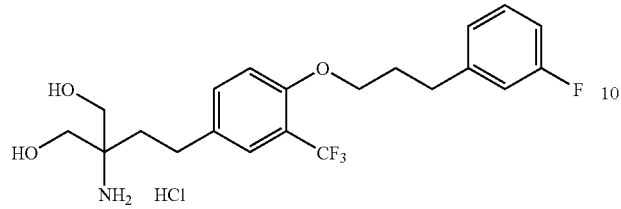

Compound 23-3 (700 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give the object product (525 mg) as a white powder.
MS(ESI)m/z: 416[M+H]
$^1$H-NMR(DMSO-$d_6$) δ (ppm): 1.74-1.78(2H, m), 2.00-2.08(2H, m), 2.58-2.63(2H, m), 2.77(2H, t, J=7.5 Hz), 3.51 (4H, d, J=4.8 Hz), 4.04(2H, t, J=6.1 Hz), 5.36(2H, t, J=4.8 Hz), 7.01-7.05(3H, m), 7.16(1H, d, J=8.5 Hz), 7.29-7.33(1H, m), 7.44(1H, d, J=8.5 Hz), 7.47(1H, brs), 7.75(3H, brs).

Example 24

2-amino-2-(2-{3-trifluoromethyl-4-[3-(2-trifluoromethylphenyl)propoxy]phenyl}ethyl)propane-1,3-diol hydrochloride (24-1) Synthesis of 3-(2-trifluoromethylphenyl)-1-propanol (Compound 24-1)

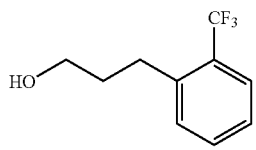

2-Trifluoromethylcinnamic acid (5.43 g) was dissolved in methanol (30 ml) and tetrahydrofuran (30 ml), 10% palladium carbon (2.00 g) was added, and the mixture was stirred under a hydrogen atmosphere at room temperature for 15 hr. The reaction container was purged with nitrogen, the solution was filtered, and the filtrate was concentrated to give a white powder (5.8 g). The white powder was dissolved in tetrahydrofuran (100 ml), and a tetrahydrofuran-borane.tetrahydrofuran solution (1 mol/l, 32.4 ml) was added dropwise to the mixture under ice-cooling, and the mixture was stirred under ice-cooling for 30 min, and further at room temperature for 18 hr. To the reaction mixture were added water and 1 mol/l aqueous hydrochloric acid solution, and the mixture was extracted with ethyl acetate, washed with water, saturated aqueous sodium hydrogen carbonate solution and saturated brine, and dried over anhydrous magnesium sulfate. The solvent was evaporated under reduced pressure to give the object product (5.07 g) as a pale-yellow oil.
$^1$H-NMR(CDCl$_3$) δ (ppm): 1.55(1H, brs), 1.86-1.94(2H, m), 2.88(2H, t, J=7.9 Hz), 3.73(2H, t, J=6.3 Hz), 7.29(1H, t, J=7.8 Hz), 7.36(1H, d, J=7.8 Hz), 7.47(1H, d, J=7.8 Hz), 7.47(1H, d, J=7.8 Hz).

(24-2) Synthesis of 1-(3-bromopropyl)-2-trifluoromethylbenzene (Compound 24-2)

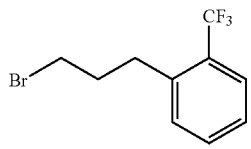

Compound 24-1 (5.07 g) was dissolved in methylene chloride (50 ml), triphenylphosphine (7.24 g) and N-bromosuccinimide (4.86 g) were added under ice-cooling, and the mixture was stirred under ice-cooling for 4.5 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (5.32 g) as a colorless oil.
$^1$H-NMR(CDCl$_3$) δ (ppm): 2.14-2.21(2H, m), 2.95(2H, t, J=7.7 Hz), 3.45(2H, t, J=6.6 Hz), 7.29-7.36(2H, m), 7.48(1H, t, J=7.6 Hz), 7.63(1H, d, J=7.6 Hz).

(24-3) Synthesis of [2,2-dimethyl-5-(2-{3-trifluoromethyl-4-[3-(2-trifluoromethylphenyl)propoxy]phenyl}ethyl)-1,3-dioxan-5-yl]carbamic acid t-butyl ester (Compound 24-3)

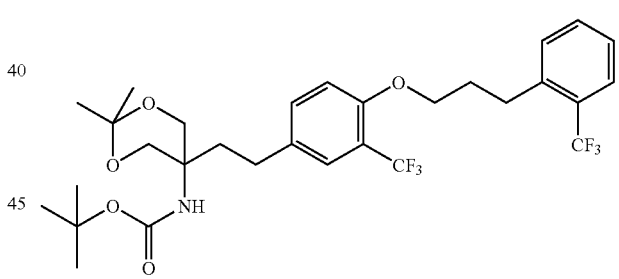

Reference Example compound 2-6 (500 mg) was dissolved in N,N-dimethylformamide (10 ml), potassium carbonate (493 mg) and compound 24-2 (382 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (800 mg) as a white solid.
$^1$H-NMR(CDCl$_3$) δ (ppm): 1.43(3H, s), 1.44(3H, s), 1.47 (9H, s), 1.94-1.99(2H, m), 2.11-2.14(2H, m), 2.52-2.57(2H, m), 3.00(2H, t, J=7.8 Hz), 3.69(2H, d, J=11.7 Hz), 3.89(2H, d, J=11.7 Hz), 4.05(2H, t, J=5.9 Hz), 4.98(1H, brs), 6.87(1H, d, J=8.5 Hz), 7.29(2H, t, J=7.3 Hz), 7.34-7.38(2H, m), 7.46(1H, t, J=7.6 Hz), 7.62(1H, d, J=7.6 Hz).

(24-4) Synthesis of 2-amino-2-(2-{3-trifluoromethyl-4-[3-(2-trifluoromethylphenyl)propoxy]phenyl}ethyl)propane-1,3-diol hydrochloride (Compound 24-4)

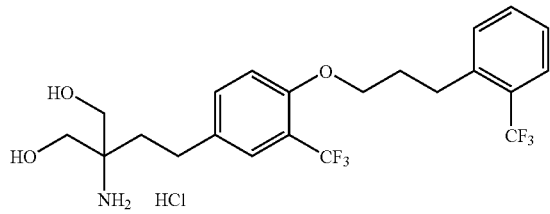

Compound 24-3 (800 mg) was dissolved in ethanol (15 ml), concentrated hydrochloric acid (1.5 ml) was added, and the mixture was stirred at 80° C. for 2.5 hr. The reaction mixture was concentrated, and the residue was washed with diethyl ether to give the object product (600 mg) as a white powder.

MS(ESI)m/z: 466[M+H]

$^1$H-NMR(DMSO-d$_6$) δ (ppm): 1.75-1.80(2H, m), 2.00-2.05(2H, m), 2.59-2.64(2H, m), 2.94(2H, t, J=7.8 Hz), 3.52 (4H, d, J=4.9 Hz), 4.15(2H, t, J=5.8 Hz), 5.37(2H, t, J=4.9 Hz), 7.19(1H, t, J=8.5 Hz), 7.42-7.52(4H, m), 7.62(1H, t, J=7.7 Hz), 7.68(1H, J=7.7 Hz), 7.77(3H, brs).

Example 25

2-amino-2-(2-{4-[3-(3-chlorophenyl)propoxy]-3-trifluoromethylphenyl}ethyl)propane-1,3-diol hydrochloride (25-1) Synthesis of 3-(3-chlorophenyl)-1-propanol (Compound 25-1)

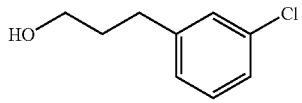

3-(3-Chlorophenyl)propionic acid (5.00 g) was dissolved in tetrahydrofuran (100 ml), a tetrahydrofuran-borane.tetrahydrofuran solution (1 mol/l, 34.5 ml) was added dropwise to the mixture under ice-cooling, and the mixture was stirred under ice-cooling for 30 min, and further at room temperature for 15 hr. To the reaction mixture was added water, 1 mol/l aqueous hydrochloric acid solution was added, and the mixture was extracted with ethyl acetate, washed with water, saturated aqueous sodium hydrogen carbonate solution and saturated brine, and dried over anhydrous magnesium sulfate. The solvent was evaporated under reduced pressure to give the object product (3.48 g) as a colorless oil.

$^1$H-NMR(CDCl$_3$) δ (ppm): 1.56(1H, brs), 1.84-1.92(2H, m), 2.70(2H, t, J=7.7 Hz), 3.67(2H, t, J=6.4 Hz), 7.06-7.16 (1H, m), 7.18-7.23(3H, m).

(25-2) Synthesis of 1-(3-bromopropyl)-3-chlorobenzene (Compound 25-2)

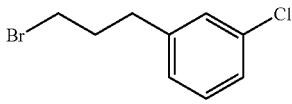

Compound 25-1 (1.00 g) was dissolved in methylene chloride (100 ml), triphenylphosphine (1.71 g) and N-bromosuccinimide (1.15 g) were added under ice-cooling, and the mixture was stirred under ice-cooling for 5 hr. The reaction mixture was washed with water and saturated brine, and dried over anhydrous magnesium sulfate. The solvent was evaporated under reduced pressure. Diethyl ether (50 ml) was added, and the precipitated triphenylphosphine oxide was filtered off. The concentrate of the filtrate was purified by silica gel column chromatography (hexane alone) to give the object product (970 mg) as a colorless oil.

$^1$H-NMR(CDCl$_3$) δ (ppm): 2.12-2.19(2H, m), 2.76(2H, t, J=7.4 Hz), 3.39(2H, t, J=6.5 Hz), 7.08(1H, d, J=7.0 Hz), 7.18-7.24(3H, m).

(25-3) Synthesis of [5-(2-{4-[3-(3-chlorophenyl)propoxy]-3-trifluoromethylphenyl}ethyl)-2,2-dimethyl-1,3-dioxan-5-yl]carbamic acid t-butyl ester (Compound 25-3)

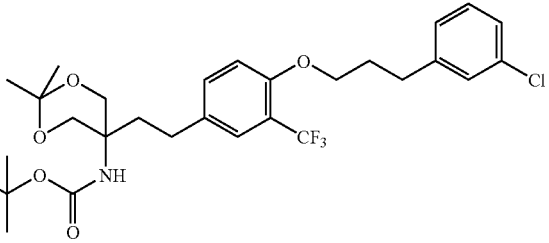

Reference Example compound 2-6 (500 mg) was dissolved in N,N-dimethylformamide (10 ml), potassium carbonate (493 mg) and compound 25-2 (333 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (760 mg) as a colorless oil.

$^1$H-NMR(CDCl$_3$) δ (ppm): 1.43(3H, s), 1.45(3H, s), 1.47 (9H, s), 1.93-1.98(2H, m), 2.07-2.12(2H, m), 2.52-2.56(2H, m), 2.81(2H, t, J=7.6 Hz), 3.69(2H, d, J=11.6 Hz), 3.89(2H, d, J=11.6 Hz), 3.98(2H, t, J=5.9 Hz), 4.98(1H, brs), 6.84(1H, d, J=8.4 Hz), 7.07(1H, t, J=7.1 Hz), 7.15-7.22(3H, m), 7.27(1H, brs), 7.37(1H, d, J=1.8 Hz).

(25-4) Synthesis of 2-amino-2-(2-{4-[3-(3-chlorophenyl)propoxy]-3-trifluoromethylphenyl}ethyl)propane-1,3-diol hydrochloride (Compound 25-4)

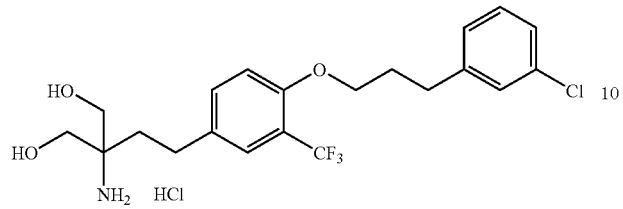

Compound 25-3 (760 mg) was dissolved in ethanol (15 ml), concentrated hydrochloric acid (1.5 ml) was added, and the mixture was stirred at 80° C. for 2 hr. The reaction mixture was concentrated, and the residue was washed with diethyl ether to give the object product (560 mg) as a white powder.

MS(ESI)m/z: 432[M+H]

$^1$H-NMR(DMSO-d$_6$) δ (ppm): 1.74-1.80(2H, m), 2.00-2.06(2H, m), 2.59-2.63(2H, m), 2.75(2H, t, J=7.5 Hz), 3.52 (4H, d, J=4.9 Hz), 4.04(2H, t, J=6.0 Hz), 5.37(2H, t, J=4.9 Hz), 7.17(2H, d, J=8.2 Hz), 7.24-7.32(3H, m), 7.44(1H, d, J=8.9 Hz), 7.48(1H, brs), 7.81(3H, brs).

Example 26

2-amino-2-(2-{4-[3-(4-chlorophenyl)propoxy]-3-trifluoromethylphenyl}ethyl)propane-1,3-diol hydrochloride (26-1) Synthesis of 1-(3-bromopropyl)-4-chlorobenzene (Compound 26-1)

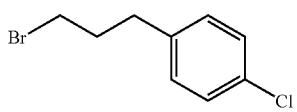

3-(4-Chlorophenyl)-1-propanol (1.00 g) was dissolved in methylene chloride (30 ml), triphenylphosphine (1.66 g) and N-bromosuccinimide (1.11 g) were added under ice-cooling, and the mixture was stirred under ice-cooling for 6 hr. The reaction mixture was washed with water and saturated brine, and dried over anhydrous magnesium sulfate. The solvent was evaporated under reduced pressure. Diethyl ether (50 ml) was added, and the precipitated triphenylphosphine oxide was filtered off. The concentrate of the filtrate was purified by silica gel column chromatography (hexane alone) to give the object product (1.30 g) as a colorless oil.

$^1$H-NMR(CDCl$_3$) δ (ppm): 2.10-2.18(2H, m), 2.76(2H, t, J=7.3 Hz), 3.38(2H, t, J=6.5 Hz), 7.13(2H, d, J=8.3 Hz), 7.31-7.35(2H, m).

(26-2) Synthesis of 2-amino-2-(2-{4-[3-(4-chlorophenyl)propoxy]-3-trifluoromethylphenyl}ethyl)propane-1,3-diol hydrochloride (Compound 26-2)

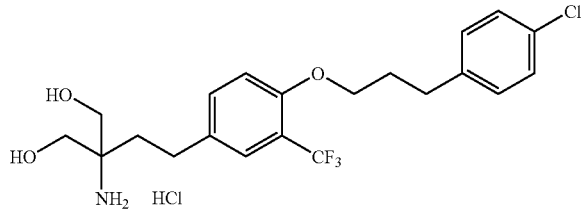

Reference Example compound 2-6 (500 mg) was dissolved in N,N-dimethylformamide (10 ml), potassium carbonate (493 mg) and compound 26-1 (334 mg) were added, and the mixture was stirred at 80° C. for 1 hr. Water was added to the reaction mixture, and the mixture was extracted with ethyl acetate, washed with water and saturated brine, and dried over anhydrous magnesium sulfate. The solvent was evaporated under reduced pressure to give a yellow oil (860 mg). The yellow oil was dissolved in ethanol (15 ml), concentrated hydrochloric acid (1.5 ml) was added, and the mixture was stirred at 80° C. for 1 hr. The reaction mixture was concentrated, and the residue was washed with diethyl ether to give a white powder. The white powder was purified by HPLC, the obtained residue was converted to hydrochloride by adding hydrogen chloride containing ether (1 mol/l, 15 ml), and the precipitate was collected by filtration and dried to give the object product (130 mg) as a white powder.

MS(ESI)m/z: 432[M+H]

$^1$H-NMR(DMSO-d$_6$) δ (ppm): 1.74-1.79(2H, m), 1.97-2.05(2H, m), 2.58-2.63(2H, m), 2.74(2H, t, J=7.5 Hz), 3.52 (4H, d, J=4.8 Hz), 4.03(2H, t, J=6.0 Hz), 5.37(2H, t, J=4.8 Hz), 7.16(1H, d, J=8.5 Hz), 7.22(2H, d, J=8.2 Hz), 7.34(2H, d, J=8.2 Hz), 7.43(1H, d, J=8.3 Hz), 7.47(1H, brs), 7.78(3H, brs).

Example 27

2-amino-2-methyl-4-{3-trifluoromethyl-4-[3-(4-trifluoromethylphenyl)propoxy]phenyl}butanol hydrochloride (27-1) Synthesis of (2-hydroxy-1-hydroxymethyl-1-methyl)ethylcarbamic acid t-butyl ester (Compound 27-1)

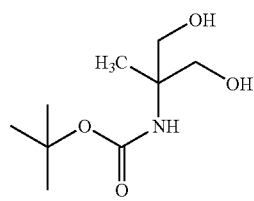

2-Amino-2-methyl-1,3-propanediol hydrochloride (14.0 g) was dissolved in methanol (200 ml), N,N-diisopropylethylamine (46.3 ml) and di-t-butyl-dicarbonate (43.7 g) were added under ice-cooling, and the mixture was stirred under ice-cooling for 40 min and further at room temperature for 27 hr. To the reaction mixture was added 1M aqueous sodium hydroxide solution (100 ml) under ice-cooling, the mixture was stirred for 40 min, and methanol was evaporated under reduced pressure. Water was added and the mixture was extracted with ethyl acetate. The organic layer was washed with saturated brine and dried over anhydrous magnesium sulfate. The solvent was evaporated under reduced pressure to give the object product (25.3 g) as a white powder.

$^1$H-NMR(CDCl$_3$) δ (ppm): 1.17(3H, s), 1.44(9H, s), 3.45 (2H, brs), 3.62(2H, dd, J=7.1, 11.3 Hz), 3.78(2H, dd, J=5.4, 11.3 Hz), 4.96(1H, brs).

(27-2) Synthesis of (1-hydroxymethyl-2-methoxymethoxy-1-methyl)ethylcarbamic acid t-butyl ester (Compound 27-2)

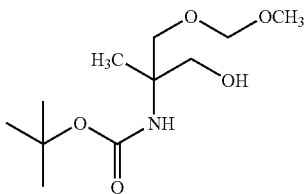

To a solution of compound 27-1 (25.3 g) in methylene chloride (300 ml) were added N,N-diisopropylethylamine (26.8 ml) and methoxymethylchloride (11.6 ml) under ice-cooling, and the mixture was stirred under ice-cooling for 20 min and further at room temperature for 22 hr. Water was added to the reaction mixture, and the mixture was extracted with methylene chloride. The organic layer was washed with water and saturated brine, and dried over anhydrous magnesium sulfate. The solvent was evaporated under reduced pressure. The obtained residue was purified by silica gel chromatography to give the object product (14.2 g) as a colorless oil.

$^1$H-NMR(CDCl$_3$) δ (ppm): 1.26(3H, s), 1.44(9H, s), 3.38 (3H, s), 3.57(1H, d, J=9.7 Hz), 3.61(1H, dd, J=7.8, 11.5 Hz), 3.66(1H, J=9.7 Hz), 3.71(1H, dd, J=5.0, 11.5 Hz), 3.91(1H, brs), 4.64(2H, s), 5.10(1H, brs).

(27-3) Synthesis of (1-formyl-2-methoxymethoxy-1-methyl)ethylcarbamic acid t-butyl ester (Compound 27-3)

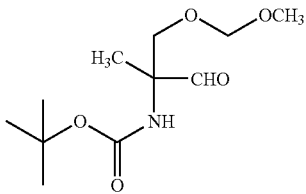

To a mixed solution of compound 27-2 (14.2 g) and sodium bromide (5.86 g) in toluene (100 ml), ethyl acetate (100 ml) and water (20 ml) were added 2,2,6,6-tetramethylpiperidine 1-oxyl and free radical (178 mg) under ice-cooling, and then 10% aqueous sodium hypochlorite solution (46.7 g) and a solution of sodium hydrogen carbonate (13.8 g) in water (150 ml) were added dropwise over 1.5 hr. The mixture was further stirred under ice-cooling for 1.5 hr. The organic layer was partitioned, washed with water and saturated-brine, and dried over anhydrous magnesium sulfate. The solvent was evaporated under reduced pressure to give the object product (13.1 g) as a pale-brown oil.

$^1$H-NMR(CDCl$_3$) δ (ppm): 1.39(3H, s), 1.45(9H, s), 3.34 (3H, s), 3.75(2H, s), 4.60(2H, s), 5.39(1H, brs), 9.51(1H, s).

(27-4) Synthesis of [3-(4-hydroxy-3-trifluoromethylphenyl)-1-(methoxymethoxy)methyl-1-methyl]propylcarbamic acid t-butyl ester (Compound 27-4)

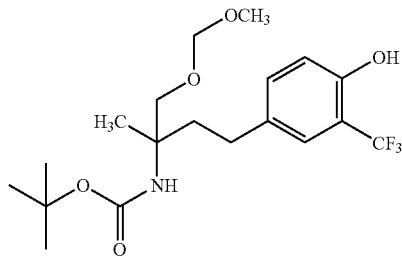

Reference Example compound 2-5 (21.8 g) was suspended in tetrahydrofuran (200 ml), potassium t-butoxide (4.35 g) was added under ice-cooling, and the mixture was stirred for 1 hr. To the mixed solution was added a solution of compound 27-3 (4.80 g) in tetrahydrofuran (40 ml), and the mixture was stirred under ice-cooling for 1.5 hr, and at room temperature for 1 hr. The reaction mixture was added to water, and the mixture was extracted with ethyl acetate. The organic layer was washed with saturated brine and dried over anhydrous magnesium sulfate. The solvent was evaporated under reduced pressure. The obtained residue was purified by silica gel column chromatography to give [3-(4-benzyloxy-3-trifluoromethylphenyl)-1-(methoxymethoxy)methyl-1-methyl]allylcarbamic acid t-butyl ester (8.45 g) as a colorless oil. The geometric isomer ratio of the obtained compound was (E:Z=3:7). To a solution of the oil in 1,4-dioxane (150 ml) was added 10% palladium carbon (containing water about 50%, 845 mg), and the mixture was stirred under a hydrogen atmosphere at room temperature for 24 hr. The reaction mixture was filtered through celite and concentrated to give the object product (6.92 g) as a colorless oil.

$^1$H-NMR(CDCl$_3$) δ (ppm): 1.34(3H, s), 1.45(9H, s), 1.88-1.95(1H, m), 2.00-2.08(1H, m), 2.52-2.60(2H, m), 3.38(3H, s), 3.47(1H, d, J=9.5 Hz), 3.65(1H, d, J=9.5 Hz), 4.65(2H, s), 4.78(1H, brs), 5.98(1H, brs), 6.85(1H, d, J=8.4 Hz), 7.18(1H, dd, J=1.5, 8.4 Hz), 7.29(1H, d, J=1.5 Hz).

(27-5) Synthesis of (1-(methoxymethoxy)methyl-1-methyl-3-{3-trifluoromethyl-4-[3-(4-trifluoromethylphenyl)propoxy]phenyl})propylcarbamic acid t-butyl ester (Compound 27-5)

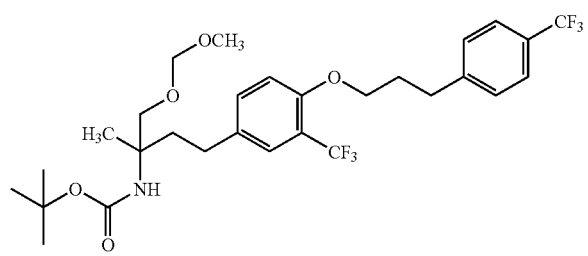

To a solution of compound 27-4 (480 mg) in N,N-dimethylformamide (1 ml) were added potassium carbonate (488 mg) and compound 11-2 (378 mg), and the mixture was stirred at 80° C. for 1.5 hr. The reaction mixture was added to water, and the mixture was extracted with ethyl acetate. The organic layer was washed with saturated brine and dried over anhydrous magnesium sulfate. The solvent was evaporated under reduced pressure to give the object product (700 mg) as a pale-yellow oil.

$^1$H-NMR(CDCl$_3$) δ (ppm): 1.34(3H, s), 1.45(9H, s), 1.88-1.99(1H, m), 2.00-2.21(3H, m), 2.58(2H, t, J=8.5 Hz), 2.88-2.92(2H, m), 3.38(3H, s), 3.48(1H, d, J=9.5 Hz), 3.64(1H, d, J=9.5 Hz), 3.98(2H, t, J=5.4 Hz), 4.64(2H, s), 4.72(1H, brs), 6.83(1H, d, J=8.2 Hz), 7.25-7.32(2H, m), 7.38(1H, brs), 7.52-7.57(3H, m).

(27-6) Synthesis of 2-amino-2-methyl-4-{3-trifluoromethyl-4-[3-(4-trifluoromethylphenyl)propoxy]phenyl}butanol hydrochloride (Compound 27-6)

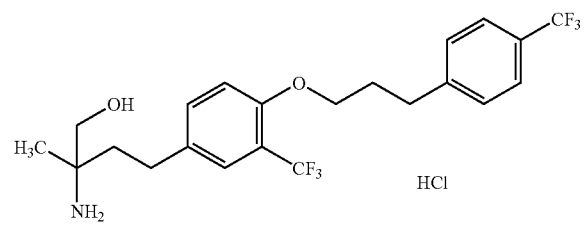

To a solution of compound 27-5 (400 mg) in ethanol (15 ml) was added concentrated hydrochloric acid (1.5 ml), and the mixture was stirred at 80° C. for 1.5 hr. The reaction mixture was concentrated, and the residue was washed with diisopropyl ether to give the object product (440 mg) as a pale-red powder.

MS(ESI)m/z: 450[M+H]

$^1$H-NMR(DMSO-d$_6$) δ (ppm): 1.21(3H, s), 1.70-1.85(2H, m), 2.02-2.10(2H, m), 2.62(2H, t, J=8.7 Hz), 2.84(2H, t, J=7.5 Hz), 3.41(1H, dd, J=4.8, 11.2 Hz), 3.48(1H, dd, J=4.8, 11.2 Hz), 4.06(2H, t, J=6.0 Hz), 5.50(1H, t, J=5.0 Hz), 7.17 (1H, d, J=8.5 Hz), 7.42-7.48(4H, m), 7.65(2H, d, J=8.0 Hz), 7.90(3H, brs).

Example 28

(S)-2-amino-2-methyl-4-{3-trifluoromethyl-4-[3-(4-trifluoromethylphenyl)propoxy]phenyl}butanol hydrochloride

(28-1) Synthesis of (S)-2-amino-2-methyl-4-{3-trifluoromethyl-4-[3-(4-trifluoromethylphenyl)propoxy]phenyl}butanol (Compound 28-1-1) and (R)-2-amino-2-methyl-4-{3-trifluoromethyl-4-[3-(4-trifluoromethylphenyl)propoxy]phenyl}butanol (Compound 28-1-2)

compound 28-1-1

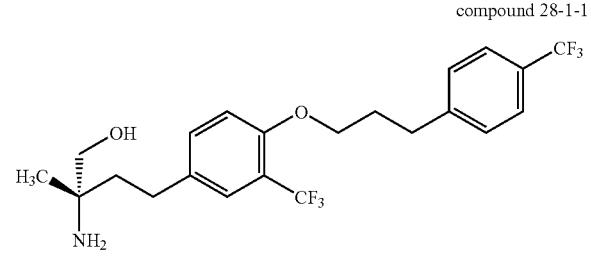

compound 28-1-2

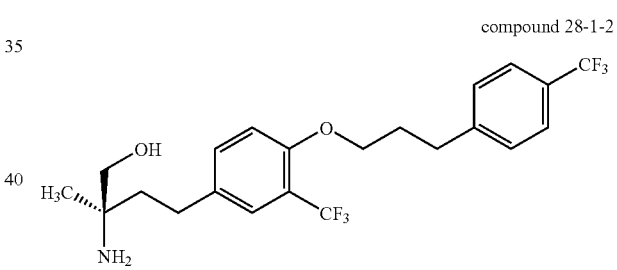

To a solution of compound 27-5 (1.90 g) in ethanol (15 ml) was added concentrated hydrochloric acid (1.5 ml), and the mixture was stirred at 80° C. for 1.5 hr. The reaction mixture was concentrated, chloroform (50 ml) and 1M aqueous sodium hydroxide solution (50 ml) were added, and the mixture was stirred at 50° C. for 1 hr. The mixture was extracted with chloroform. The organic layer was washed with saturated brine and dried over anhydrous sodium sulfate, and the solvent was evaporated under reduced pressure to give a mixture (1.24 g) of compound 28-1-1 and compound 28-1-2. The mixture (1.24 g) was separated by HPLC using CHIRALPAK (registered trade mark) AD-H (hexane/ethanol/isopropylamine) to give both enantiomers as colorless oil. The primary peak with a shorter retention time was S-configuration (0.41 g, compound 28-1-1), and the secondary peak with a longer retention time was R-configuration (0.53 g, compound 28-1-2).

(28-2) Synthesis of (S)-2-amino-2-methyl-4-{3-trifluoromethyl-4-[3-(4-trifluoromethylphenyl)propoxy]phenyl}butanol hydrochloride (Compound 28-2)

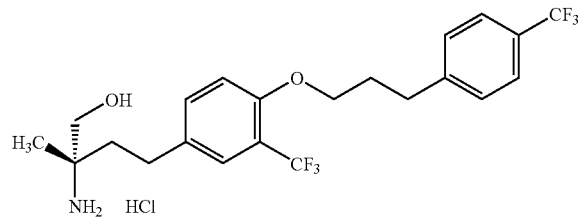

Compound 28-1-1 (0.41 g) was dissolved in methanol (5 ml) and methylene chloride (10 ml), hydrogen chloride-containing ether (1 mol/l, 15 ml) was added, and the mixture was stirred at room temperature for 30 min. The precipitate was collected by filtration and dried to give the object product (424 mg) as a white powder.

MS(ESI)m/z: 450[M+H]

$^1$H-NMR(DMSO-$d_6$) δ (ppm): 1.21(3H, s), 1.71-1.86(2H, m), 2.02-2.11(2H, m), 2.62(2H, t, J=8.7 Hz), 2.84(2H, t, J=7.5 Hz), 3.41(1H, dd, J=5.3, 11.3 Hz), 3.48(1H, dd, J=5.3, 11.3 Hz), 4.06(2H, t, J=6.0 Hz), 5.53(1H, t, J=5.2 Hz), 7.17 (1H, d, J=8.5 Hz), 7.42-7.48(4H, m), 7.65(2H, d, J=8.1 Hz), 7.91(3H, brs).

Example 29

(R)-2-amino-2-methyl-4-{3-trifluoromethyl-4-[3-(4-trifluoromethylphenyl)propoxy]phenyl}butanol hydrochloride (29-1) Synthesis of (R)-2-amino-2-methyl-4-{3-trifluoromethyl-4-[3-(4-trifluoromethylphenyl)propoxy]phenyl}butanol hydrochloride (Compound 29-1)

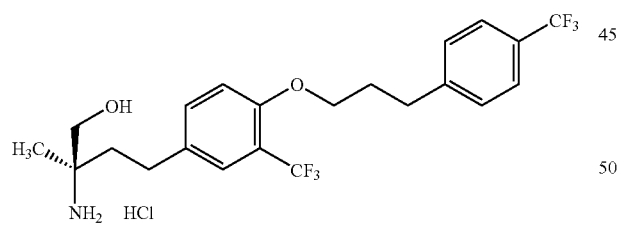

Compound 28-1-2 (0.53 g) was dissolved in methanol (5 ml) and methylene chloride (10 ml), hydrogen chloride-containing ether (1 mol/l, 15 ml) was added, and the mixture was stirred at room temperature for 30 min. The precipitate was collected by filtration and dried to give the object product (427 mg) as a white powder.

MS(ESI)m/z: 450[M+H]

$^1$H-NMR(DMSO-$d_6$) δ (ppm): 1.20(3H, s), 1.71-1.84(2H, m), 2.01-2.10(2H, m), 2.61(2H, t, J=8.7 Hz), 2.84(2H, t, J=7.5 Hz), 3.40(1H, dd, J=5.2, 11.5 Hz), 3.48(1H, dd, J=5.2, 11.5 Hz), 4.06(2H, t, J=6.0 Hz), 5.53(1H, t, J=5.2 Hz), 7.17 (1H, d, J=8.6 Hz), 7.42-7.48(4H, m), 7.65(2H, d, J=8.0 Hz), 7.86(3H, brs).

Example 30

2-amino-2-ethyl-4-{3-trifluoromethyl-4-[3-(4-trifluoromethylphenyl)propoxy]phenyl}butanol hydrochloride (30-1) Synthesis of [1,1-bis(hydroxymethyl)propyl]carbamic acid t-butyl ester (Compound 30-1)

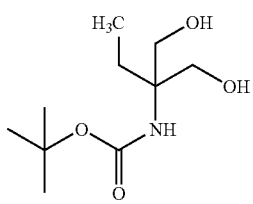

To a solution of 2-amino-2-ethyl-1,3-propanediol (22.0 g) and N,N-diisopropylethylamine (64.3 ml) in methanol (500 ml) was added di-t-butyl-dicarbonate (60.5 g) under ice-cooling, and the mixture was stirred under ice-cooling for 40 min and further at room temperature for 16 hr. To the reaction mixture was added 1M aqueous sodium hydroxide solution (184 ml) under ice-cooling, and the mixture was stirred for 40 min, and methanol was removed under reduced pressure. Water was added and the mixture was extracted with ethyl acetate. The organic layer was washed with saturated brine and dried over anhydrous magnesium sulfate. The solvent was evaporated under reduced pressure to give the object product (41.0 g) as a colorless oil.

$^1$H-NMR(CDCl$_3$) δ (ppm): 0.90(3H, t, J=7.5 Hz), 1.45(9H, s), 1.59(2H, q, J=7.5 Hz), 3.45(2H, brs), 3.60(2H, dd, J=6.9, 11.6 Hz), 3.84(2H, dd, J=4.8, 11.6 Hz), 4.89(1H, brs).

(30-2) Synthesis of [1-hydroxymethyl-1-(methoxymethoxy)methyl]propylcarbamic acid t-butyl ester (Compound 30-2)

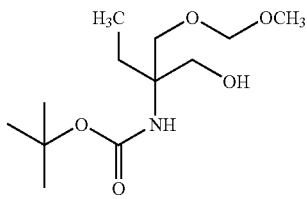

To a solution of compound 30-1 (41.0 g) in methylene chloride (400 ml) were added, N,N-diisopropylethylamine (40.7 ml) and methoxymethylchloride (17.6 ml) were added under ice-cooling, and the mixture was stirred under ice-cooling for 40 min and further at room temperature for 4 hr. Water was added to the reaction mixture, and the mixture was extracted with methylene chloride. The organic layer was washed with saturated brine and dried over anhydrous magnesium sulfate. The solvent was evaporated under reduced pressure. The obtained residue was purified by silica gel chromatography to give the object product (21.3 g) as a colorless oil.

$^1$H-NMR(CDCl$_3$) δ (ppm): 0.89(3H, t, J=7.5 Hz), 1.44(9H, s), 1.55-1.62(1H, m), 1.75-1.84(1H, m), 3.38(3H, s), 3.49(1H, d, J=9.8 Hz), 3.68(2H, d, J=6.6 Hz), 3.74(1H, d, J=9.8 Hz), 4.04(1H, brs), 4.63(2H, s), 5.05(1H, brs).

(30-3) Synthesis of [1-formyl-1-(methoxymethoxy)methyl]propylcarbamic acid t-butyl ester (Compound 30-3)

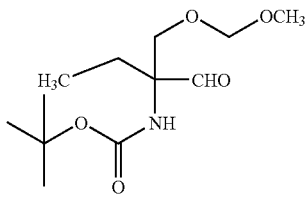

To a mixed solution of compound 30-2 (21.3 g) and sodium bromide (8.32 g) in toluene (170 ml), ethyl acetate (170 ml) and water (30 ml) were added 2,2,6,6-tetramethylpiperidine 1-oxyl, free radical (253 mg), and then 10% aqueous sodium hypochlorite solution (66.3 g) and a solution of sodium hydrogen carbonate (19.6 g) in water (200 ml) was added dropwise over 1.5 hr. The mixture was further stirred under ice-cooling for 1.5 hr, a solution of 10% aqueous sodium hypochlorite solution (22.1 g) and sodium hydrogen carbonate (6.53 g) in water (67 ml) was added dropwise over 30 min, and the mixture was further stirred for 30 min. The organic layer was partitioned, and diluted with ethyl acetate (200 ml). The organic layer was washed with saturated brine and dried over anhydrous magnesium sulfate. The solvent was evaporated under reduced pressure to give the object product (22.0 g) as a pale-brown oil.

$^1$H-NMR(CDCl$_3$) δ (ppm): 0.81(3H, t, J=7.5 Hz), 1.45(9H, s), 1.74-1.83(1H, m), 2.04-2.11(1H, m), 3.32(3H, s), 3.81(1H, d, J=10.0 Hz), 4.03(1H, d, J=10.0 Hz), 4.59(2H, s), 5.37(1H, brs), 9.39(1H, s).

(30-4) Synthesis of [1-ethyl-3-(4-hydroxy-3-trifluoromethylphenyl)-1-(methoxymethoxy)methyl]propylcarbamic acid t-butyl ester (Compound 30-4)

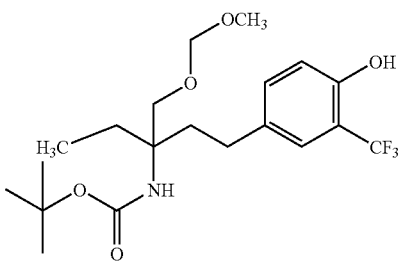

Reference Example compound 2-5 (26.3 g) was suspended in tetrahydrofuran (120 ml), potassium t-butoxide (5.24 g) was added under ice-cooling, and the mixture was stirred for 50 min. To the mixed solution was added a solution of compound 30-3 (6.10 g) in tetrahydrofuran (80 ml), and the mixture was stirred under ice-cooling for 2 hr, and at room temperature for 4 hr. The reaction mixture was added to brine, and the mixture was extracted with ethyl acetate. The organic layer was washed with saturated brine and dried over anhydrous magnesium sulfate. The solvent was evaporated under reduced pressure. The obtained residue was purified by silica gel column chromatography to give [1-ethyl-3-(4-benzyloxy-3-trifluoromethylphenyl)-1-(methoxymethoxy)methyl]allylcarbamic acid t-butyl ester (10.3 g) as a colorless oil. The geometric isomer ratio of the obtained compound was (E:Z=1:2.8). To a solution of this oil in 1,4-dioxane (200 ml) was added 10% palladium carbon (containing water about 50%, 2 g), and the mixture was stirred under a hydrogen atmosphere at room temperature for 9 hr. The reaction mixture was filtered through celite and concentrated to give the object product (8.67 g) as a white powder.

$^1$H-NMR(CDCl$_3$) δ (ppm): 0.89(3H, t, J=7.5 Hz), 1.45(9H, s), 1.65-1.74(1H, m), 1.76-1.86(1H, m), 1.93-1.97 (2H, m), 2.52-2.56(2H, m), 3.39(3H, s), 3.57(1H, d, J=9.7 Hz), 3.63(1H, d, J=9.7 Hz), 4.64(3H, m), 5.85(1H, brs), 6.85 (1H, d, J=8.3 Hz), 7.20(1H, brd, J=8.3 Hz), 7.29(1H, d, J=1.4 Hz).

(30-5) Synthesis of [1-ethyl-1-(methoxymethoxy)methyl-3-{3-trifluoromethyl-4-[3-(4-trifluoromethylphenyl)propoxy]phenyl}]propylcarbamic acid t-butyl ester (Compound 30-5)

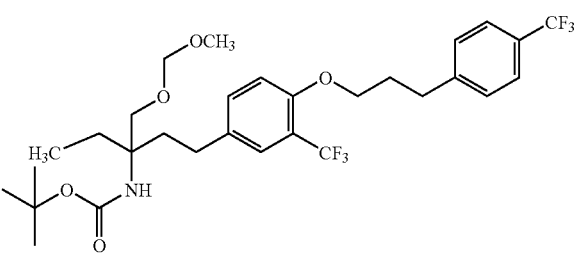

To a solution of compound 30-4 (500 mg) in N,N-dimethylformamide (10 ml) were added potassium carbonate (492 mg) and compound 11-2 (381 mg), and the mixture was stirred at 80° C. for 1 hr. The reaction mixture was added to water, and the mixture was extracted with ethyl acetate. The organic layer was washed with saturated brine and dried over anhydrous magnesium sulfate. The solvent was evaporated under reduced pressure to give the object product (740 mg) as a colorless oil.

$^1$H-NMR(CDCl$_3$) δ (ppm): 0.90(3H, t, J=7.4 Hz), 1.45(9H, s), 1.68-1.88(2H, m), 1.92-1.99(2H, m), 2.10-2.16 (2H, m), 2.53-2.58(2H, m), 2.90(2H, t, J=7.4 Hz), 3.38(3H, s), 3.57(1H, d, J=9.8 Hz), 3.63(1H, d, J=9.8 Hz), 3.98(2H, t, J=5.8 Hz), 4.60(1H, brs), 4.64(2H, s), 6.83(1H, d, J=8.4 Hz), 7.25-7.32(3H, m), 7.38(1H, brs), 7.52-7.56(2H, m).

(30-6) Synthesis of 2-amino-2-ethyl-4-{3-trifluoromethyl-4-[3-(4-trifluoromethylphenyl)propoxy]phenyl}butanol hydrochloride (Compound 30-6)

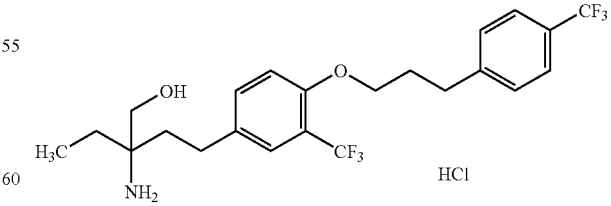

To a solution of compound 30-5 (740 mg) in ethanol (15 ml) was added concentrated hydrochloric acid (1.5 ml), and the mixture was stirred at 80° C. for 2 hr. The reaction mixture was concentrated, and the residue was washed with diethyl ether to give the object product (550 mg) as a white powder.

MS(ESI)m/z: 464[M+H]

$^1$H-NMR(DMSO-$d_6$) δ (ppm): 0.90(3H, t, J=7.4 Hz), 1.58-1.69(2H, m), 1.70-1.79(2H, m), 2.01-2.10(2H, m), 2.56-2.62(2H, m), 2.84(2H, t, J=7.5 Hz), 3.47(2H, brs), 4.06(2H, t, J=5.9 Hz), 5.45(1H, brs), 7.17(1H, d, J=8.5 Hz), 7.42-7.48(4H, m), 7.65(2H, d, J=8.0 Hz), 7.80(3H, brs).

Example 31

(S)-2-amino-2-ethyl-4-{3-trifluoromethyl-4-[3-(4-trifluoromethylphenyl)propoxy]phenyl}butanol hydrochloride (31-1) Synthesis of (S)-2-amino-2-ethyl-4-{3-trifluoromethyl-4-[3-(4-trifluoromethylphenyl)propoxy]phenyl}butanol (Compound 31-1-1) and (R)-2-amino-2-ethyl-4-{3-trifluoromethyl-4-[3-(4-trifluoromethylphenyl)propoxy]phenyl}butanol (Compound 31-1-2)

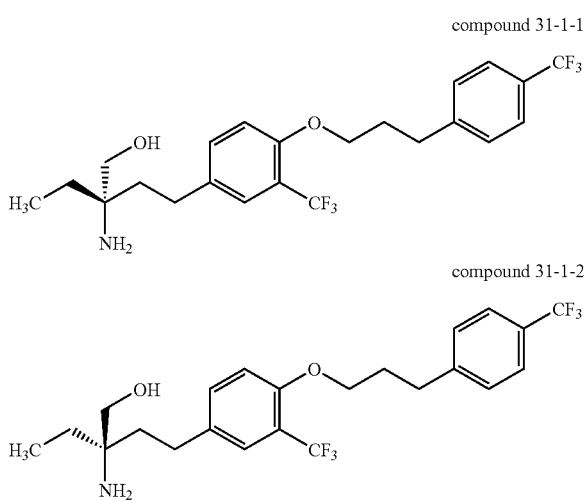

compound 31-1-1 compound 31-1-2

To a solution of compound 30-5 (1.64 g) in ethanol (20 ml) was added concentrated hydrochloric acid (3.0 ml), and the mixture was stirred at 80° C. for 2.5 hr. The reaction mixture was concentrated, chloroform (50 ml) and 1M aqueous sodium hydroxide solution (50 ml) were added, and the mixture was stirred at 50° C. for 1 hr. The mixture was extracted with chloroform. The organic layer was washed with saturated brine and dried over anhydrous sodium sulfate, and the solvent was evaporated under reduced pressure to give a mixture (1.18 g) of compound 31-1-1 and compound 31-1-2. The mixture (1.18 g) was separated by HPLC using CHIRALPAK (registered trade mark) AD-H (hexane/ethanol/isopropylamine) to give both enantiomers as colorless oil. The primary peak with a shorter retention time was S-configuration (0.36 g, compound 31-1-1), and the secondary peak with a longer retention time was R-configuration (0.36 g, compound 31-1-2).

(31-2) Synthesis of (S)-2-amino-2-ethyl-4-{3-trifluoromethyl-4-[3-(4-trifluoromethylphenyl)propoxy]phenyl}butanol hydrochloride (Compound 31-2)

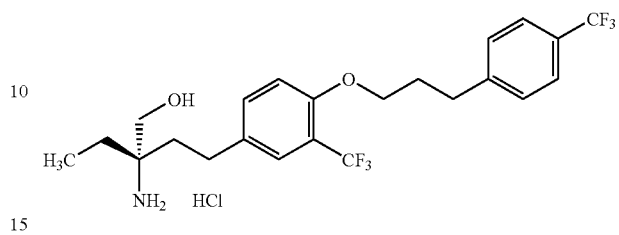

Compound 31-1-1 (0.36 g) was dissolved in methanol (5 ml) and methylene chloride (10 ml), hydrogen chloride-containing ether (1 mol/l, 15 ml) was added, and the mixture was stirred at room temperature for 30 min. The precipitate was collected by filtration and dried to give the object product (370 mg) as a white powder.

MS(ESI)m/z: 464[M+H]

$^1$H-NMR(DMSO-$d_6$) δ (ppm): 0.90(3H, t, J=7.5 Hz), 1.58-1.68(2H, m), 1.70-1.78(2H, m), 2.04-2.10(2H, m), 2.56-2.62(2H, m), 2.84(2H, t, J=7.5 Hz), 3.47(2H, brs), 4.06(2H, t, J=6.0 Hz), 5.48(1H, brs), 7.17(1H, d, J=8.5 Hz), 7.42-7.48(4H, m), 7.65(2H, d, J=8.0 Hz), 7.81(3H, brs).

Example 32

(R)-2-amino-2-ethyl-4-{3-trifluoromethyl-4-[3-(4-trifluoromethylphenyl)propoxy]phenyl}butanol hydrochloride (32-1) Synthesis of (R)-2-amino-2-ethyl-4-{3-trifluoromethyl-4-[3-(4-trifluoromethylphenyl)propoxy]phenyl}butanol hydrochloride (Compound 32-1)

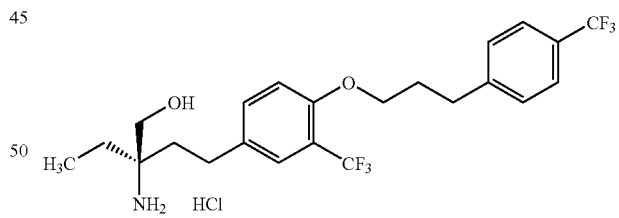

Compound 31-1-2 (0.36 g) was dissolved in methanol (5 ml) and methylene chloride (10 ml), hydrogen chloride-containing ether (1 mol/l, 15 ml) was added, and the mixture was stirred at room temperature for 30 min. The precipitate was collected by filtration and dried to give the object product (370 mg) as a white powder.

MS(ESI)m/z: 464 [M+H]

$^1$H-NMR(DMSO-$d_6$) δ (ppm): 0.90(3H, t, J=7.5 Hz), 1.58-1.68(2H, m), 1.70-1.78(2H, m), 2.02-2.09(2H, m), 2.54-2.61(2H, m), 2.84(2H, t, J=7.5 Hz), 3.47(2H, brs), 4.06(2H, t, J=6.0 Hz), 5.48(1H, brs), 7.17(1H, d, J=8.5 Hz), 7.42-7.48(4H, m), 7.65(2H, d, J=8.1 Hz), 7.79(3H, brs).

Example 33

2-amino-2-(2-{4-[2-(4-methylphenyl)ethoxy]-3-trifluoromethylphenyl}ethyl)propane-1,3-diol hydrochloride

(33-1) Synthesis of 2-(4-methylphenyl)-1-ethanol (Compound 33-1)

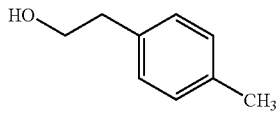

To a suspension of lithium aluminum hydride (1.40 g) and tetrahydrofuran (40 ml) was added dropwise a solution of 4-methylphenylmethyl acetate ester (5.00 g) in tetrahydrofuran (20 ml) under ice-cooling, and the mixture was stirred under ice-cooling for 1.5 hr. To the reaction solution was slowly added dropwise a saturated aqueous sodium sulfate solution to quench the reaction, the solution was filtered, and the filtrate was concentrated. The obtained residue was purified by silica gel column chromatography (hexane:ethyl acetate=3:1-2:1) to give the object product (3.96 g) as a colorless oil.

$^1$H-NMR(CDCl$_3$) δ (ppm): 1.35(1H, t, J=5.9 Hz), 2.33(3H, s), 2.83(2H, t, J=6.5 Hz), 3.84(2H, q, J=6.3 Hz), 7.12(4H, s).

(33-2) Synthesis of [2,2-dimethyl-5-(2-{4-[2-(4-methylphenyl)ethoxy]-3-trifluoromethylphenyl}ethyl)-1,3-dioxan-5-yl]carbamic acid t-butyl ester (Compound 33-2)

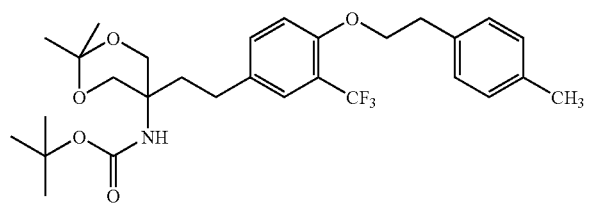

Triphenylphosphine (632 mg) was dissolved in tetrahydrofuran (10 ml), diisopropyl azodicarboxylate (40% toluene solution, 1.28 ml), compound 33-1 (324 mg) and Reference Example compound 2-6 (500 mg) were added, and the mixture was stirred at room temperature for 10 hr. Water was added to the reaction mixture, and the mixture was extracted with ethyl acetate, washed with saturated brine, and dried over anhydrous magnesium sulfate. The solvent was evaporated under reduced pressure. The obtained residue was purified by silica gel column chromatography (hexane:ethyl acetate=4:1-2:1) to give the object product (820 mg) as a colorless oil.

$^1$H-NMR(CDCl$_3$) δ (ppm): 1.42(3H, s), 1.44(3H, s), 1.47 (9H, s), 1.92-1.97(2H, m), 2.33(3H, s), 2.50-2.56(2H, m), 3.07(2H, t, J=7.0 Hz), 3.68(2H, d, J=11.7 Hz), 3.83-3.90(2H, m), 4.16(2H, t, J=6.9 Hz), 4.98(1H, brs), 6.85(1H, d, J=8.4 Hz), 7.09-7.20(4H, m), 7.23-7.26(1H, m), 7.34(1H, d, J=1.8 Hz).

(33-3) Synthesis of 2-amino-2-(2-{4-[2-(4-methylphenyl)ethoxy]-3-trifluoromethylphenyl}ethyl)propane-1,3-diol hydrochloride (Compound 33-3)

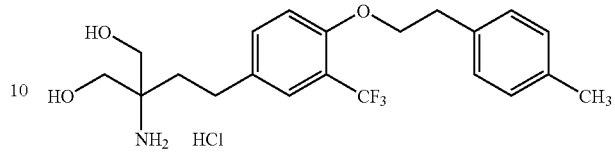

Compound 33-2 (820 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give a white powder. 90 mg from the white powder was purified by HPLC, and hydrogen chloride-containing ether (1 mol/l, 10 ml) was added the obtained residue to give hydrochloride. The precipitate was collected by filtration and dried to give the object product (75 mg) as a white powder.

MS(ESI)m/z: 398 [M+H]

$^1$H-NMR(DMSO-d$_6$) δ (ppm): 1.72-1.77(2H, m), 2.26(3H, s), 2.56-2.63(2H, m), 2.98(2H, t, J=6.6 Hz), 3.51 (4H, d, J=4.8 Hz), 4.23(2H, t, J=6.6 Hz), 5.39(2H, brs), 7.10 (2H, d, J=7.8 Hz), 7.20(3H, d, J=7.8 Hz), 7.41-7.45(2H, m), 7.80(3H, brs).

Example 34

2-(2-{4-[2-(4-acetylphenyl)ethoxy]-3-trifluoromethylphenyl}ethyl)-2-aminopropane-1,3-diol hydrochloride

(34-1) Synthesis of 4-acetylphenethylacetate (Compound 34-1)

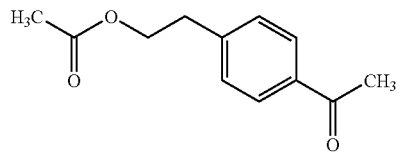

To a solution of aluminum chloride (20.8 g) and 1,2-dichloroethane (100 ml) was added acetyl chloride (7.39 ml) under ice-cooling, and the mixture was stirred under ice-cooling for 15 min. A solution of phenethylacetate (8.54 g) in 1,2-dichloroethane (50 ml) was added dropwise under ice-cooling, and the mixture was stirred under ice-cooling for 2 hr. To the reaction solution was slowly added dropwise ice-cooled water to quench the reaction, and the mixture was extracted with methylene chloride. The organic layer was washed successively with 1M aqueous sodium hydroxide solution and saturated brine, and dried over anhydrous magnesium sulfate. The solvent was evaporated under reduced pressure. The obtained residue was purified by silica gel column chromatography (hexane:ethyl acetate=3:1-1:1) to give the object product (8.65 g) as a yellow oil.

¹H-NMR(CDCl₃) δ (ppm): 2.03(3H, s), 2.60(3H, s), 3.00 (2H, t, J=6.8 Hz), 4.31(2H, t, J=6.8 Hz), 7.32(2H, d, J=7.7 Hz), 7.91(2H, d, J=7.7 Hz).

(34-2) Synthesis of 4-acetylphenethyl alcohol (Compound 34-2)

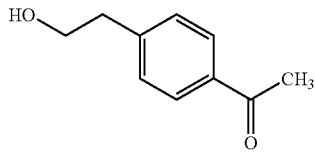

To a solution of compound 34-1 (3.65 g) in tetrahydrofuran (30 ml) were added 1M aqueous sodium hydroxide solution (40 ml) and methanol (20 ml), and the mixture was stirred at room temperature for 1 hr. Water was added to the reaction mixture, and the mixture was extracted with ethyl acetate, washed with saturated brine, and dried over anhydrous magnesium sulfate. The solvent was evaporated under reduced pressure. The obtained residue was purified by silica gel column chromatography (hexane:ethyl acetate=1:2-1:3) to give the object product (2.73 g) as a yellow oil.

¹H-NMR(CDCl₃) δ (ppm): 1.39(1H, t, J=5.6 Hz), 2.60(3H, s), 2.94(2H, t, J=6.5 Hz), 3.88-3.93(2H, m), 7.34(2H, d, J=8.1 Hz), 7.92(2H, d, J=8.1 Hz).

(34-3) Synthesis of 2-(2-{4-[2-(4-acetylphenyl)ethoxy]-3-trifluoromethylphenyl}ethyl)-2-aminopropane-1,3-diol hydrochloride (Compound 34-3)

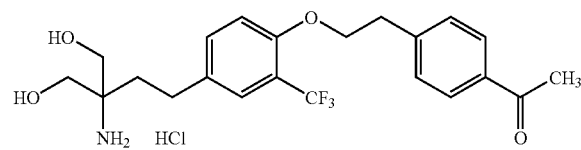

Triphenylphosphine (632 mg) was dissolved in tetrahydrofuran (10 ml), diisopropyl azodicarboxylate (40% toluene solution, 1.28 ml), compound 34-2 (391 mg) and Reference Example compound 2-6 (500 mg) were added, and the mixture was stirred at room temperature for 18 hr. Water was added to the reaction mixture, and the mixture was extracted with ethyl acetate, washed with saturated brine, and dried over anhydrous magnesium sulfate. The solvent was evaporated under reduced pressure. To a solution of the obtained residue in ethanol (15 ml) was added concentrated hydrochloric acid (1.5 ml), and the mixture was stirred at 80° C. for 2.5 hr. The reaction mixture was concentrated, and the residue was washed with diethyl ether to give a white powder. The white powder was purified by HPLC, the obtained residue was converted to hydrochloride by adding hydrogen chloride containing ether (1 mol/l, 15 ml), and the precipitate was collected by filtration and dried to give the object product (206 mg) as a white powder.

MS(ESI)m/z: 426[M+H]

¹H-NMR(DMSO-d₆) δ (ppm): 1.72-1.77(2H, m), 2.56(3H, s), 2.56-2.63(2H, m), 3.12(2H, t, J=6.3 Hz), 3.51 (4H, d, J=4.8 Hz), 4.31(2H, t, J=6.3 Hz), 5.39(2H, brs), 7.21 (1H, d, J=8.8 Hz), 7.43-7.48(4H, m), 7.82(3H, brs), 7.89(2H, d, J=8.0 Hz).

Example 35

2-amino-2-(2-{4-[3-(3,5-dichlorophenyl)propoxy]-3-trifluoromethylphenyl}ethyl)propane-1,3-diol hydrochloride (35-1) Synthesis of 3-(3,5-dichlorophenyl)-2-propyne-1-ol (Compound 35-1)

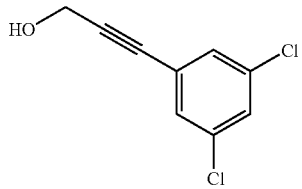

A mixture of 3,5-dichloroiodobenzene (2.50 g), copper(I) iodide (34.9 mg), triphenylphosphine (120 mg), tris(dibenzylideneacetone)dipalladium(0) chloroform adduct (189 mg), propargyl alcohol (0.596 ml), diisopropylethylamine (6.38 ml) and tetrahydrofuran (50 ml) was stirred at room temperature for 4 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=95:5-80:20) to give the object product (1.73 g) as a brown solid.

¹H-NMR(CDCl₃) δ (ppm): 1.68(1H, t, J=6.3 Hz), 4.49(2H, d, J=6.3 Hz), 7.31-7.33(3H, m).

(35-2) Synthesis of 3-(3,5-dichlorophenyl)-1-propanol (Compound 35-2)

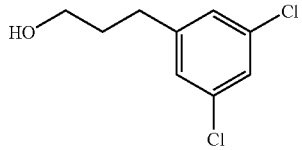

A suspension of compound 35-1 (1.73 g) and chlorotris(triphenylphosphine)rhodium(I) (1.00 g) in toluene (90 ml) was stirred under a hydrogen atmosphere at 60° C. for 10 hr. The reaction mixture was filtered through celite and concentrated. The obtained residue was purified by silica gel column chromatography (hexane:ethyl acetate=98:2-80:20) to give the object product (1.22 g) as a brown oil.

¹H-NMR(CDCl₃) δ (ppm): 1.31(1H, brs), 1.83-1.90(2H, m), 2.68(2H, t, J=7.7 Hz), 3.65-3.69(2H, m), 7.09(2H, d, J=1.7 Hz), 7.20(1H, t, J=1.8 Hz).

(35-3) Synthesis of 1-(3-bromopropyl)-3,5-dichlorobenzene (Compound 35-3)

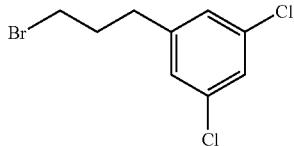

Compound 35-2 (1.23 g) was dissolved in methylene chloride (30 ml), triphenylphosphine (1.75 g) and N-bromosuccinimide (1.17 g) were added under ice-cooling, and the mixture was stirred under ice-cooling for 2 hr, and at room temperature for 12 hr. The reaction mixture was washed with water and saturated brine, and dried over anhydrous magnesium sulfate. The solvent was evaporated under reduced pressure. Diethyl ether (50 ml) was added, and the precipitated triphenylphosphine oxide was filtered off. The concentrate of the filtrate was purified by silica gel column chromatography (hexane alone) to give the object product (1.30 g) as a colorless oil.

$^1$H-NMR(CDCl$_3$) δ (ppm): 2.13-2.17(2H, m), 2.75(2H, t, J=7.2 Hz), 3.39(2H, t, J=6.3 Hz), 7.09(2H, s), 7.22(1H, s).

(35-4) Synthesis of [5-(2-{4-[3-(3,5-dichlorophenyl)propoxy]-3-trifluoromethylphenyl}ethyl)-2,2-dimethyl-1,3-dioxan-5-yl]carbamic acid t-butyl ester (Compound 35-4)

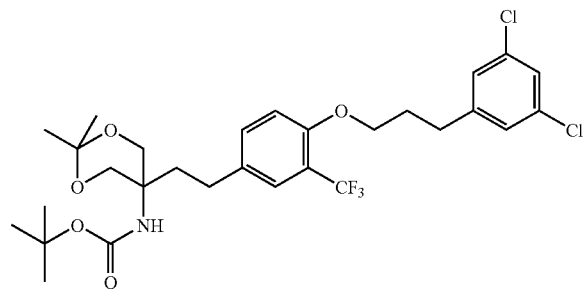

Reference Example compound 2-6 (500 mg) was dissolved in N,N-dimethylformamide (10 ml), potassium carbonate (494 mg) and compound 35-3 (383 mg) were added, and the mixture was stirred at 80° C. for 1 hr. Water was added to the reaction mixture, and the mixture was extracted with ethyl acetate, washed with water and saturated brine, and dried over anhydrous magnesium sulfate. The solvent was evaporated under reduced pressure to give the object product (790 mg) as a colorless oil.

$^1$H-NMR(CDCl$_3$) δ (ppm): 1.42(3H, s), 1.44(3H, s), 1.47 (9H, s), 1.94-1.99(2H, m), 2.01-2.11(2H, m), 2.52-2.57(2H, m), 2.77-2.82(2H, m), 3.69(2H, d, J=11.7 Hz), 3.89(2H, d, J=11.7 Hz), 3.99(2H, t, J=5.6 Hz), 4.99(1H, brs), 6.84(1H, d, J=8.5 Hz), 7.09(2H, brs), 7.20(1H, brs), 7.26-7.29(1H, m), 7.38(1H, brs).

(35-5) Synthesis of 2-amino-2-(2-{4-[3-(3,5-dichlorophenyl)propoxy]-3-trifluoromethylphenyl}ethyl)propane-1,3-diol hydrochloride (Compound 35-5)

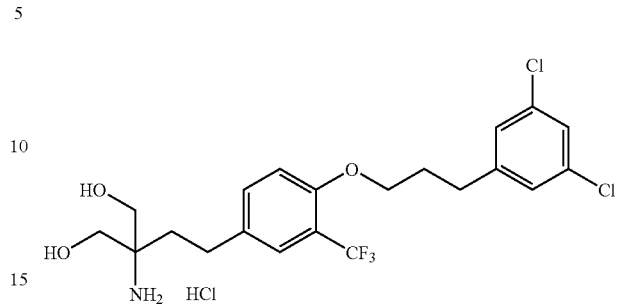

Compound 35-4 (790 mg) was dissolved in ethanol (15 ml), concentrated hydrochloric acid (1.5 ml) was added, and the mixture was stirred at 80° C. for 2 hr. The reaction mixture was concentrated, and the residue was washed with diethyl ether to give the object product (590 mg) as a white powder.

MS(ESI)m/z: 466[M+H]

$^1$H-NMR(DMSO-d$_6$) δ (ppm): 1.74-1.81(2H, m), 2.01-2.09(2H, m), 2.58-2.63(2H, m), 2.76(2H, t, J=7.5 Hz), 3.52 (4H, d, J=5.0 Hz), 4.04(2H, t, J=6.1 Hz), 5.39(2H, t, J=5.0 Hz), 7.17(1H, d, J=8.6 Hz), 7.27(1H, s), 7.28(1H, s), 7.42-7.45(2H, m), 7.48(1H, brs), 7.80(3H, brs).

Example 36

2-amino-2-(2-{4-[3-(3,5-dimethylphenyl)propoxy]-3-trifluoromethylphenyl}ethyl)propane-1,3-diol hydrochloride

(36-1) Synthesis of 3-(3,5-dimethylphenyl)-2-propyne-1-ol (Compound 36-1)

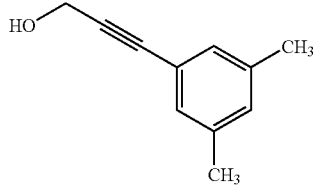

A mixture of 1-iodo-3,5-dimethylbenzene (5.00 g), copper (I) iodide (82.1 mg), triphenylphosphine (283 mg), tris(dibenzylideneacetone)dipalladium(0) chloroform adduct (446 mg), propargyl alcohol (1.40 ml), diisopropylethylamine (15.0 ml) and tetrahydrofuran (100 ml) was stirred at room temperature for 10 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=98:2-90:10) to give the object product (2.39 g) as a brown oil.

$^1$H-NMR(CDCl$_3$) δ (ppm): 1.65(1H, t, J=6.1 Hz), 2.28(6H, s), 4.48(2H, d, J=6.2 Hz), 6.96(1H, brs), 7.07(2H, brs).

(36-2) Synthesis of 3-(3,5-dimethylphenyl)-1-propanol (Compound 36-2)

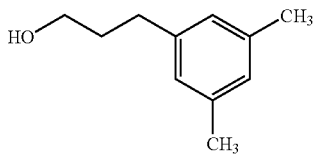

A solution of compound 36-1 (2.39 g) and 10% palladium carbon (0.50 g) in 1,4-dioxane (40 ml) was stirred under a hydrogen atmosphere at room temperature for 22 hr. The reaction mixture was filtered through celite and concentrated to give the object product (2.37 g) as a brown oil.
$^1$H-NMR(CDCl$_3$) δ (ppm): 1.26(1H, brs), 1.84-1.91(2H, m), 2.29(6H, s), 2.63(2H, t, J=7.7 Hz), 3.68(2H, t, J=6.3 Hz), 6.82-6.83(3H, m).

(36-3) Synthesis of 1-(3-bromopropyl)-3,5-dimethylbenzene (Compound 36-3)

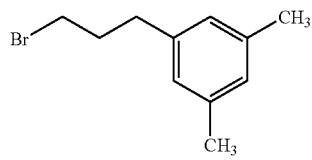

Compound 36-2 (2.36 g) was dissolved in methylene chloride (50 ml), triphenylphosphine (4.19 g) and N-bromosuccinimide (2.81 g) were added under ice-cooling, and the mixture was stirred under ice-cooling for 1 hr, and at room temperature for 3 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (2.82 g) as a colorless oil.
$^1$H-NMR(CDCl$_3$) δ (ppm): 2.12-2.18(2H, m), 2.29(6H, s), 2.69(2H, t, J=7.3 Hz), 3.40(2H, t, J=6.6 Hz), 6.81(2H, s), 6.85(1H, s).

(36-4) Synthesis of [2,2-dimethyl-5-(2-{4-[3-(3,5-dimethylphenyl)propoxy]-3-trifluoromethylphenyl}ethyl)-1,3-dioxan-5-yl]carbamic acid t-butyl ester (Compound 36-4)

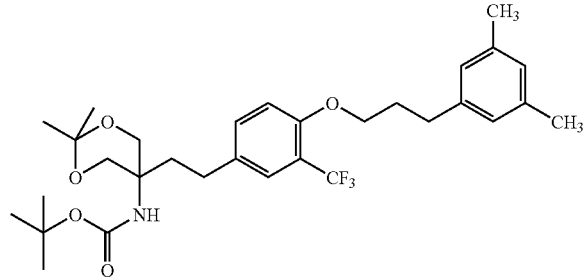

Reference Example compound 2-6 (500 mg) was dissolved in N,N-dimethylformamide (10 ml), potassium carbonate (494 mg) and compound 36-3 (325 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (750 mg) as a colorless oil.
$^1$H-NMR(CDCl$_3$) δ (ppm): 1.43(3H, s), 1.44(3H, s), 1.47 (9H, s), 1.93-1.98(2H, m), 2.03-2.12(2H, m), 2.28(6H, s), 2.51-2.56(2H, m), 2.72-2.76(2H, m), 3.69(2H, d, J=11.8 Hz), 3.89(2H, d, J=11.8 Hz), 3.99(2H, t, J=6.1 Hz), 4.99(1H, brs), 6.82-6.85(4H, m), 7.25-7.27(1H, m), 7.36(1H, brs).

(36-5) Synthesis of 2-amino-2-(2-{4-[3-(3,5-dimethylphenyl)propoxy]-3-trifluoromethylphenyl}ethyl)propane-1,3-diol hydrochloride (Compound 36-5)

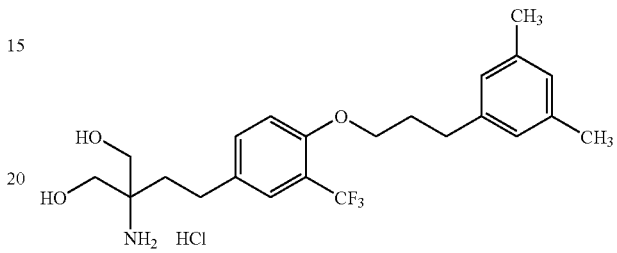

Compound 36-4 (750 mg) was dissolved in ethanol (15 ml), concentrated hydrochloric acid (1.5 ml) was added, and the mixture was stirred at 80° C. for 2 hr. The reaction mixture was concentrated, and the residue was washed with diethyl ether to give the object product (540 mg) as a white powder.
MS(ESI)m/z: 426[M+H]
$^1$H-NMR(DMSO-d$_6$) δ (ppm): 1.74-1.79(2H, m), 1.96-2.04(2H, m), 2.51(6H, s), 2.58-2.63(2H, m), 2.66(2H, t, J=7.4 Hz), 3.51(4H, d, J=6.0 Hz), 4.04(2H, t, J=6.0 Hz), 5.39(2H, t, J=4.8 Hz), 6.79-6.81(3H, m), 7.16(1H, d, J=8.5 Hz), 7.44(1H, d, J=8.5 Hz), 7.48(1H, brs), 7.79(3H, brs).

Example 37

2-amino-2-(2-{4-[3-(3,4-dimethylphenyl)propoxy]-3-trifluoromethylphenyl}ethyl)propane-1,3-diol hydrochloride

(37-1) Synthesis of 3-(3,4-dimethylphenyl)-2-propyne-1-ol (Compound 37-1)

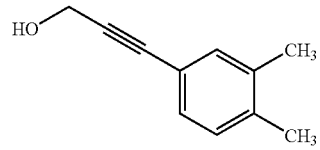

A mixture of 1-iodo-3,4-dimethylbenzene (5.00 g), copper (I) iodide (82.1 mg), triphenylphosphine (283 mg), tris(dibenzylideneacetone)dipalladium(0) chloroform adduct (446 mg), propargyl alcohol (1.40 ml), diisopropylethylamine (15.0 ml) and tetrahydrofuran (100 ml) was stirred at room temperature for 5 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=98:2-80:20) to give the object product (2.12 g) as a brown oil.

¹H-NMR(CDCl₃) δ (ppm): 1.64(1H, t, J=6.2 Hz), 2.23(3H, s), 2.26(3H, s), 4.48(2H, d, J=6.0 Hz), 7.07(1H, d, J=7.7 Hz), 7.18(1H, d, J=7.7 Hz), 7.22(1H, s).

(37-2) Synthesis of 3-(3,4-dimethylphenyl)-1-propanol (Compound 37-2)

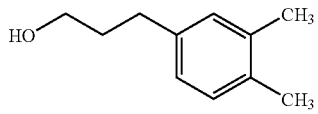

A solution of compound 37-1 (2.12 g) and 10% palladium carbon (1.00 g) in 1,4-dioxane (100 ml) was stirred under a hydrogen atmosphere at room temperature for 16 hr. The reaction mixture was filtered through celite and concentrated to give the object product (2.11 g) as a brown oil.

¹H-NMR(CDCl₃) δ (ppm): 1.28(1H, brs), 1.84-1.91(2H, m), 2.23(3H, s), 2.24(3H, s), 2.64(2H, t, J=7.7 Hz), 3.68(2H, t, J=6.4 Hz), 6.94(1H, d, J=7.6 Hz), 6.80(1H, s), 7.05(1H, d, J=7.6 Hz).

(37-3) Synthesis of 1-(3-bromopropyl)-3,4-dimethylbenzene (Compound 37-3)

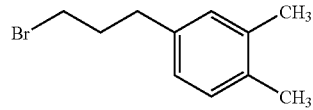

Compound 37-2 (1.95 g) was dissolved in methylene chloride (50 ml), triphenylphosphine (3.46 g) and N-bromosuccinimide (2.33 g) were added under ice-cooling, and the mixture was stirred under ice-cooling for 2 hr, and at room temperature for 2 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (2.20 g) as a colorless oil.

¹H-NMR(CDCl₃) δ (ppm): 2.10-2.18(2H, m), 2.23(3H, s), 2.24(3H, s), 2.71(2H, t, J=7.3 Hz), 3.40(2H, t, J=6.6 Hz), 6.93(1H, d, J=7.5 Hz), 6.96(1H, s), 7.06(1H, d, J=7.5 Hz).

(37-4) Synthesis of [2,2-dimethyl-5-(2-{4-[3-(3,4-dimethylphenyl)propoxy]-3-trifluoromethylphenyl}ethyl)-1,3-dioxan-5-yl]carbamic acid t-butyl ester (Compound 37-4)

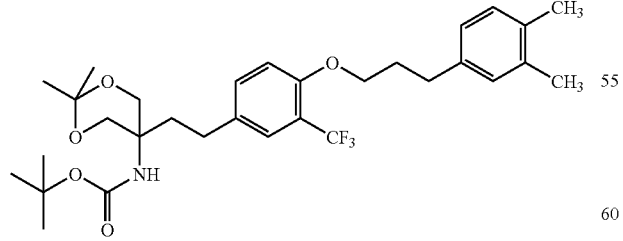

Reference Example compound 2-6 (432 mg) was dissolved in N,N-dimethylformamide (10 ml), potassium carbonate (427 mg) and compound 37-3 (281 mg) were added, and the mixture was stirred at 80° C. for 1.5 hr. Water was added to the reaction mixture, and the mixture was extracted with ethyl acetate, washed with water and saturated brine, and dried over anhydrous magnesium sulfate. The solvent was evaporated under reduced pressure to give the object product (640 mg) as a colorless oil.

¹H-NMR(CDCl₃) δ (ppm): 1.43(3H, s), 1.44(3H, s), 1.47(9H, s), 1.93-1.98(2H, m), 2.04-2.12(2H, m), 2.23(6H, s), 2.51-2.56(2H, m), 2.73-2.77(2H, m), 3.69(2H, d, J=11.8 Hz), 3.89(2H, d, J=11.8 Hz), 3.99(2H, t, J=6.1 Hz), 4.99(1H, brs), 6.84(1H, d, J=8.5 Hz), 6.93(1H, d, J=7.5 Hz), 6.97(1H, s), 7.04(1H, d, J=7.5 Hz), 7.24-7.26(1H, m), 7.36(1H, d, J=1.9 Hz).

(37-5) Synthesis of 2-amino-2-(2-{4-[3-(3,4-dimethylphenyl)propoxy]-3-trifluoromethylphenyl}ethyl)propane-1,3-diol hydrochloride (Compound 37-5)

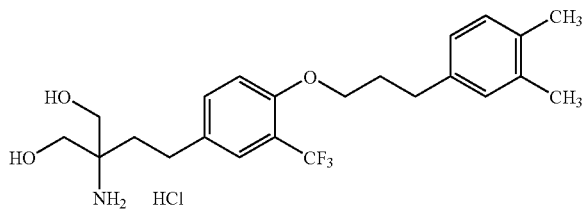

Compound 37-4 (640 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give the object product (470 mg) as a white powder.

MS(ESI)m/z: 426[M+H]

¹H-NMR(DMSO-d₆) δ (ppm): 1.74-1.79(2H, m), 1.95-2.02(2H, m), 2.17(6H, s), 2.58-2.63(2H, m), 2.66(2H, t, J=7.5 Hz), 3.52(4H, d, J=4.8 Hz), 4.03(2H, t, J=6.1 Hz), 5.39(2H, t, J=5.1 Hz), 6.89(1H, d, J=7.3 Hz), 6.96(1H, s), 7.02(1H, d, J=7.7 Hz), 7.15(1H, d, J=8.5 Hz), 7.43(1H, d, J=8.5 Hz), 7.48(1H, d, J=1.4 Hz), 7.80(3H, brs).

Example 38

2-amino-2-(2-{4-[3-(3,4-dichlorophenyl)propoxy]-3-trifluoromethylphenyl}ethyl)propane-1,3-diol hydrochloride (38-1) Synthesis of 3-(3,4-dichlorophenyl)-2-propyne-1-ol (Compound 38-1)

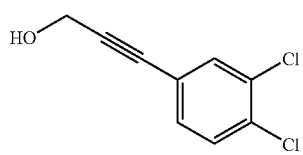

A mixture of 3,4-dichloroiodobenzene (5.00 g), copper(I) iodide (69.8 mg), triphenylphosphine (240 mg), tris(dibenzylideneacetone)dipalladium(0) chloroform adduct (378 mg), propargyl alcohol (1.19 ml), diisopropylethylamine (12.8 ml) and tetrahydrofuran (80 ml) was stirred at room temperature for 5 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=98:2-80:20) to give the object product (3.21 g) as a pale-brown solid.

$^1$H-NMR(CDCl$_3$) δ (ppm): 1.65(1H, t, J=6.2 Hz), 4.49(2H, J=6.2 Hz), 7.26(1H, dd, J=1.6, 8.4 Hz), 7.39(1H, d, J=8.4 Hz), 7.52(1H, d, J=1.6 Hz).

(38-2) Synthesis of 3-(3,4-dichlorophenyl)-1-propanol (Compound 38-2)

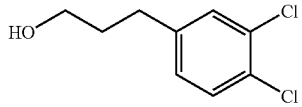

A suspension of Compound 38-1 (3.21 g) and chlorotris(triphenylphosphine)rhodium(I) (1.60 g) in toluene (100 ml) was stirred under a hydrogen atmosphere at 60° C. for 10 hr. The reaction mixture was filtered through celite and concentrated. The obtained residue was purified by silica gel column chromatography (hexane:ethyl acetate=98:2-80:20) to give the object product (2.83 g) as a brown oil.

$^1$H-NMR(CDCl$_3$) δ (ppm): 1.33(1H, brs), 1.83-1.90(2H, m), 2.68(2H, t, J=7.7 Hz), 3.67(2H, t, J=6.3 Hz), 7.04(1H, dd, J=8.1, 1.8 Hz), 7.29(1H, d, J=1.8 Hz), 7.34(1H, d, J=8.1 Hz).

(38-3) Synthesis of 1-(3-bromopropyl)-3,4-dichlorobenzene (Compound 38-3)

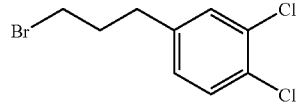

Compound 38-2 (2.82 g) was dissolved in methylene chloride (50 ml), triphenylphosphine (4.02 g) and N-bromosuccinimide (2.71 g) were added under ice-cooling, and the mixture was stirred under ice-cooling for 1 hr, and at room temperature for 2 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (3.42 g) as a colorless oil.

$^1$H-NMR(CDCl$_3$) δ (ppm): 2.10-2.18(2H, m), 2.75(2H, t, J=7.3 Hz), 3.38(2H, t, J=6.5 Hz), 7.04(1H, dd, J=8.3, 1.9 Hz), 7.30(1H, d, 1.9 Hz), 7.36(1H, d, J=8.3 Hz).

(38-4) Synthesis of [5-(2-{4-[3-(3,4-dichlorophenyl)propoxy]-3-trifluoromethylphenyl}ethyl)-2,2-dimethyl-1,3-dioxan-5-yl]carbamic acid t-butyl ester (Compound 38-4)

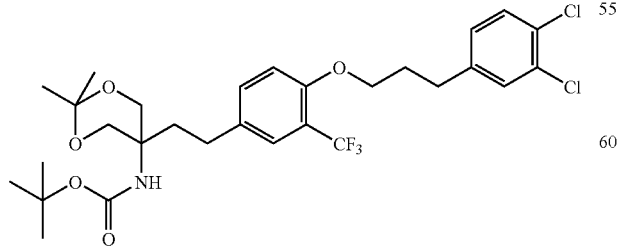

Reference Example compound 2-6 (500 mg) was dissolved in N,N-dimethylformamide (10 ml), potassium carbonate (494 mg) and compound 38-3 (383 mg) were added, and the mixture was stirred at 80° C. for 1 hr. Water was added to the reaction mixture, and the mixture was extracted with ethyl acetate, washed with water and saturated brine, and dried over anhydrous magnesium sulfate. The solvent was evaporated under reduced pressure to give the object product (790 mg) as a colorless oil.

$^1$H-NMR(CDCl$_3$) δ (ppm): 1.43(3H, s), 1.44(3H, s), 1.47 (9H, s), 1.93-2.05(2H, m), 2.04-2.12(2H, m), 2.52-2.56(2H, m), 2.80(2H, t, J=7.5 Hz), 3.69(2H, d, J=11.7 Hz), 3.89(2H, d, J=11.7 Hz), 3.97(2H, t, J=5.8 Hz), 5.00(1H, brs), 6.83(1H, d, J=8.4 Hz), 7.03(1H, dd, J=8.4, 1.9 Hz), 7.28-7.30(2H, m), 7.33(1H, d, J=8.2 Hz), 7.37-7.38(1H, m).

(38-5) Synthesis of 2-amino-2-(2-{4-[3-(3,4-dichlorophenyl)propoxy]-3-trifluoromethylphenyl}ethyl)propane-1,3-diol hydrochloride (Compound 38-5)

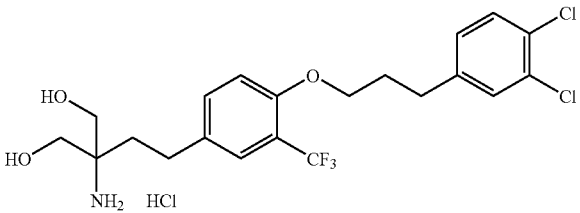

Compound 38-4 (790 mg) was dissolved in ethanol (15 ml), concentrated hydrochloric acid (1.5 ml) was added, and the mixture was stirred at 80° C. for 2 hr. The reaction mixture was concentrated, and the residue was washed with diethyl ether to give the object product (590 mg) as a white powder.

MS(ESI)m/z: 466[M+H]

$^1$H-NMR(DMSO-d$_6$) δ (ppm): 1.73-1.79(2H, m), 1.99-2.08(2H, m), 2.58-2.63(2H, m), 2.75(2H, t, J=7.5 Hz), 3.51 (4H, d, J=4.5 Hz), 4.04(2H, t, J=6.0 Hz), 5.39(2H, t, J=4.8 Hz), 7.17(1H, d, J=8.6 Hz), 7.20(1H, dd, J=8.4, 1.9 Hz), 7.44(1H, d, J=8.6 Hz), 7.47-7.49(2H, m), 7.54(1H, d, J=8.4 Hz), 7.76(3H, brs).

Example 39

2-amino-2-(2-{4-[3-(4-ethylphenyl)propoxy]-3-trifluoromethylphenyl}ethyl)propane-1,3-diol hydrochloride (39-1) Synthesis of 3-(4-ethylphenyl)-2-propyne-1-ol (Compound 39-1)

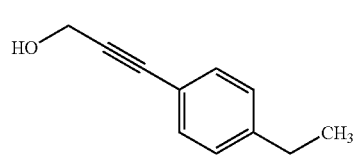

A mixture of 4-ethyliodobenzene (5.00 g), copper(I) iodide (82.1 mg), triphenylphosphine (283 mg), tris(dibenzylideneacetone)dipalladium(0) chloroform adduct (446 mg), propargyl alcohol (1.40 ml), diisopropylethylamine (15.0 ml) and tetrahydrofuran (100 ml) was stirred at room temperature for 12 hr. The reaction mixture was added to water, and the mixture was extracted with ethyl acetate, washed with saturated brine, and dried over anhydrous magnesium sulfate. The solvent was evaporated under reduced pressure. The residue was purified by silica gel column chromatography (hexane: ethyl acetate=98:2-80:20) to give the object product (2.10 g) as a brown oil.

$^{1}$H-NMR(CDCl$_{3}$) δ (ppm): 1.23(3H, t, J=7.6 Hz), 1.65(1H, t, J=6.0 Hz), 2.64(2H, q, J=7.6 Hz), 4.49(2H, d, J=5.9 Hz), 7.15(2H, d, J=7.6 Hz), 7.36(2H, d, J=7.6 Hz).

(39-2) Synthesis of 3-(4-ethylphenyl)-1-propanol (Compound 39-2)

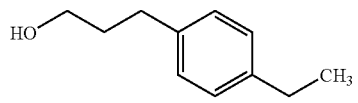

A solution of compound 39-1 (2.10 g) and 10% palladium carbon (1.00 g) in 1,4-dioxane (80 ml) was stirred under a hydrogen atmosphere at room temperature for 10 hr. The reaction mixture was filtered through celite and concentrated to give the object product (1.98 g) as a brown oil.

$^{1}$H-NMR(CDCl$_{3}$) δ (ppm): 1.22(3H, t, J=7.6 Hz), 1.29(1H, brs), 1.85-1.92(2H, m), 2.62(2H, q, J=7.6 Hz), 2.68(2H, t, J=7.7 Hz), 3.68(2H, t, J=6.4 Hz), 7.12(4H, s).

(39-3) Synthesis of 1-(3-bromopropyl)-4-ethylbenzene (Compound 39-3)

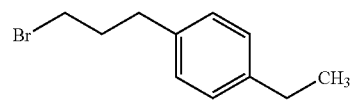

Compound 39-2 (1.97 g) was dissolved in methylene chloride (40 ml), triphenylphosphine (3.50 g) and N-bromosuccinimide (2.35 g) were added under ice-cooling, and the mixture was stirred under ice-cooling for 1 hr, and at room temperature for 1 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (2.26 g) as a colorless oil.

$^{1}$H-NMR(CDCl$_{3}$) δ (ppm): 1.22(3H, t, J=7.5 Hz), 2.10-2.18(2H, m), 2.62(2H, q, J=7.5 Hz), 2.75(2H, t, J=7.3 Hz), 3.40(2H, t, J=6.5 Hz), 7.10-7.13(4H, m).

(39-4) Synthesis of [5-(2-{4-[3-(4-ethylphenyl)propoxy]-3-trifluoromethylphenyl}ethyl)-2,2-dimethyl-1,3-dioxan-5-yl]carbamic acid t-butyl ester (Compound 39-4)

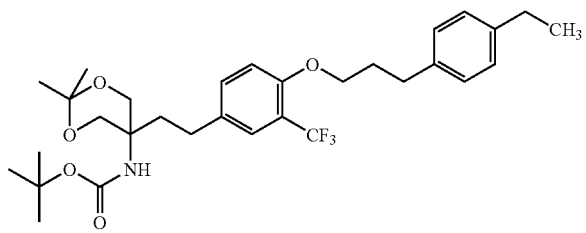

Reference Example compound 2-6 (500 mg) was dissolved in N,N-dimethylformamide (10 ml), potassium carbonate (494 mg) and compound 39-3 (325 mg) were added, and the mixture was stirred at 80° C. for 1.5 hr. Water was added to the reaction mixture, and the mixture was extracted with ethyl acetate, washed with water and saturated brine, and dried over anhydrous magnesium sulfate. The solvent was evaporated under reduced pressure to give the object product (770 mg) as a colorless oil.

$^{1}$H-NMR(CDCl$_{3}$) δ (ppm): 1.20-1.28(3H, m), 1.43(3H, s), 1.44(3H, s), 1.47(9H, s), 1.93-1.98(2H, m), 2.04-2.13(2H, m), 2.51-2.56(2H, m), 2.58-2.64(2H, m), 2.77-2.81(2H, m), 3.69(2H, d, J=11.8 Hz), 3.89(2H, d, J=11.8 Hz), 3.98(2H, t, J=6.1 Hz), 4.99(1H, brs), 6.84(1H, d, J=8.5 Hz), 7.11(4H, s), 7.24-7.26(1H, m), 7.36(1H, d, J=1.6 Hz).

(39-5) Synthesis of 2-amino-2-(2-{4-[3-(4-ethylphenyl)propoxy]-3-trifluoromethylphenyl}ethyl)propane-1,3-diol hydrochloride (Compound 39-5)

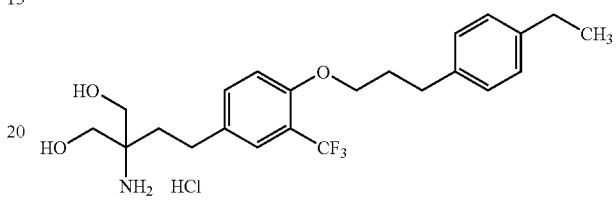

Compound 39-4 (770 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give the object product (540 mg) as a white powder.

MS(ESI)m/z: 426[M+H]

$^{1}$H-NMR(DMSO-d$_{6}$) δ (ppm): 1.51(3H, t, J=7.8 Hz), 1.74-1.78(2H, m), 1.98-2.06(2H, m), 2.55(2H, q, J=7.8 Hz), 2.58-2.64(2H, m), 2.70(2H, t, J=7.5 Hz), 3.52(4H, d, J=4.6 Hz), 4.03(2H, t, J=6.0 Hz), 5.40(2H, t, J=4.8 Hz), 7.08-7.16(5H, s), 7.44(1H, d, J=8.5 Hz), 7.48(1H, d, J=1.6 Hz), 7.81(3H, brs).

Example 40

2-amino-2-(2-{4-[3-(3-bromophenyl)propoxy]-3-trifluoromethylphenyl}ethyl)propane-1,3-diol hydrochloride (40-1) Synthesis of 3-(3-bromophenyl)-2-propyne-1-ol (Compound 40-1)

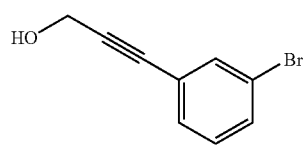

A mixture of 3-bromoiodobenzene (5.00 g), copper(I) iodide (67.4 mg), triphenylphosphine (232 mg), tris(dibenzylideneacetone)dipalladium(0) chloroform adduct (366 mg), propargyl alcohol (1.15 ml), diisopropylethylamine (12.3 ml) and tetrahydrofuran (90 ml) was stirred at room temperature for 15 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=98:2-70:30) to give the object product (3.42 g) as a brown oil.

$^1$H-NMR(CDCl$_3$) δ (ppm): 1.67(1H, t, J=6.2 Hz), 4.50(2H, d, J=6.2 Hz), 7.19(1H, t, J=7.9 Hz), 7.36(1H, d, J=7.8 Hz), 7.46(1H, d, J=7.8 Hz), 7.59(1H, t, J=1.7 Hz).

(40-2) Synthesis of 3-(3-bromophenyl)-1-propanol (Compound 40-2)

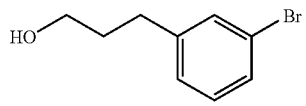

A suspension of compound 40-1 (3.42 g) and chlorotris(triphenylphosphine)rhodium(I) (1.70 g) in toluene (130 ml) was stirred under a hydrogen atmosphere at 60° C. for 9 hr. The reaction mixture was filtered through celite and concentrated. The obtained residue was purified by silica gel column chromatography (hexane:ethyl acetate=98:2-80:20) to give the object product (2.79 g) as a brown oil.

$^1$H-NMR(CDCl$_3$) δ (ppm): 1.28(1H, t, J=4.4 Hz), 1.84-1.91(2H, m), 2.69(2H, t, J=7.7 Hz), 3.65-3.69(2H, m), 7.11-7.14(1H, m), 7.16(1H, t, J=7.7 Hz), 7.31-7.34(1H, m), 7.36(1H, brs).

(40-3) Synthesis of 3-bromo-1-(3-bromopropyl)benzene (Compound 40-3)

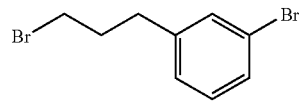

Compound 40-2 (2.78 g) was dissolved in methylene chloride (40 ml), triphenylphosphine (3.72 g) and N-bromosuccinimide (2.53 g) were added under ice-cooling, and the mixture was stirred under ice-cooling for 2 hr, and at room temperature for 12 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (1.34 g) as a colorless oil.

$^1$H-NMR(CDCl$_3$) δ (ppm): 2.12-2.19(2H, m), 2.76(2H, t, J=7.3 Hz), 3.39(2H, t, J=6.5 Hz), 7.12-7.18(2H, m), 7.33-7.35(2H, m).

(40-4) Synthesis of [5-(2-{4-[3-(3-bromophenyl)propoxy]-3-trifluoromethylphenyl}ethyl)-2,2-dimethyl-1,3-dioxan-5-yl]carbamic acid t-butyl ester (Compound 40-4)

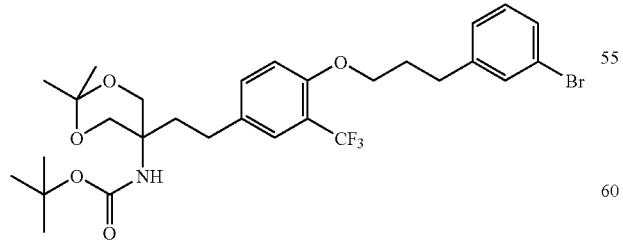

Reference Example compound 2-6 (500 mg) was dissolved in N,N-dimethylformamide (10 ml), potassium carbonate (494 mg) and compound 40-3 (479 mg) were added, and the mixture was stirred at 80° C. for 1.5 hr. Water was added to the reaction mixture, and the mixture was extracted with ethyl acetate, washed with water and saturated brine, and dried over anhydrous magnesium sulfate. The solvent was evaporated under reduced pressure to give the object product (980 mg) as a white solid.

$^1$H-NMR(CDCl$_3$) δ (ppm): 1.43(3H, s), 1.44(3H, s), 1.47(9H, s), 1.93-1.98(2H, m), 2.07-2.12(2H, m), 2.51-2.56(2H, m), 2.78-2.82(2H, m), 3.69(2H, d, J=11.7 Hz), 3.89(2H, d, J=11.7 Hz), 3.98(2H, t, J=5.9 Hz), 4.99(1H, brs), 6.84(1H, d, J=8.5 Hz), 7.12-7.17(2H, m), 7.26-7.28(1H, m), 7.30-7.34 (3H, m).

(40-5) Synthesis of 2-amino-2-(2-{4-[3-(3-bromophenyl)propoxy]-3-trifluoromethylphenyl}ethyl)propane-1,3-diol hydrochloride (Compound 40-5)

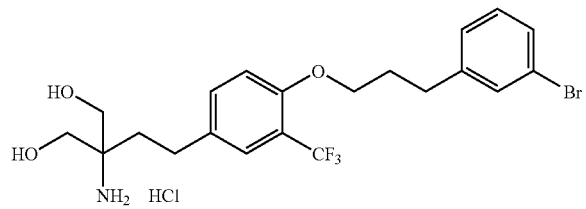

Compound 40-4 (980 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give the object product (590 mg) as a white powder.

MS(ESI)m/z: 476, 478[M+H]

$^1$H-NMR(DMSO-d$_6$) δ (ppm): 1.74-1.79(2H, m), 2.00-2.06(2H, m), 2.58-2.63(2H, m), 2.75(2H, t, J=7.5 Hz), 3.52 (4H, d, J=4.5 Hz), 4.04(2H, t, J=6.0 Hz), 5.40(2H, t, J=4.9 Hz), 7.15-7.28(3H, m), 7.38-7.46(3H, m), 7.48(1H, brs), 7.81 (3H, brs).

Example 41

2-amino-2-(2-{4-[3-(4-bromophenyl)propoxy]-3-trifluoromethylphenyl}ethyl)propane-1,3-diol hydrochloride (41-1) Synthesis of 3-(4-bromophenyl)-2-propyne-1-ol (Compound 41-1)

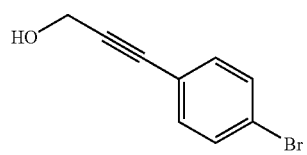

A mixture of 4-bromoiodobenzene (8.00 g), copper(I) iodide (108 mg), triphenylphosphine (372 mg), tris(dibenzylideneacetone)dipalladium(0) chloroform adduct (586 mg), propargyl alcohol (1.84 ml), diisopropylethylamine (19.7 ml) and tetrahydrofuran (100 ml) was stirred at room temperature for 13 hr. The reaction mixture was added to water, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=98:2-90:10) to give the object product (4.34 g) as a brown oil.

$^1$H-NMR(CDCl$_3$) δ (ppm): 1.64(1H, t, J=6.2 Hz), 4.48(2H, d, J=6.2 Hz), 7.30(2H, d, J=8.4 Hz), 7.45(2H, d, J=8.4 Hz).

(41-2) Synthesis of 3-(4-bromophenyl)-1-propanol (Compound 41-2)

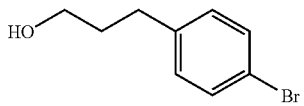

A suspension of compound 41-1 (4.34 g) and chlorotris(triphenylphosphine)rhodium(I) (2.50 g) in toluene (170 ml) was stirred under a hydrogen atmosphere at 60° C. for 7 hr. The reaction mixture was filtered through celite and concentrated. The obtained residue was purified by silica gel column chromatography (hexane:ethyl acetate=98:2-70:30) to give the object product (3.62 g) as a brown oil.

$^1$H-NMR(CDCl$_3$) δ (ppm): 1.28(1H, brs), 1.83-1.90(2H, m), 2.67(2H, t, J=7.7 Hz), 3.67(2H, t, J=6.3 Hz), 7.08(2H, d, J=8.2 Hz), 7.40(2H, d, J=8.2 Hz).

(41-3) Synthesis of 4-bromo-1-(3-bromopropyl)benzene (Compound 41-3)

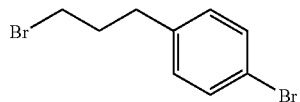

Compound 41-2 (3.63 g) was dissolved in methylene chloride (40 ml), triphenylphosphine (4.88 g) and N-bromosuccinimide (3.31 g) were added under ice-cooling, and the mixture was stirred under ice-cooling for 2 hr, and at room temperature for 4 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (1.87 g) as a colorless oil.

$^1$H-NMR(CDCl$_3$) δ (ppm): 2.10-2.17(2H, m), 2.74(2H, t, J=7.4 Hz), 3.38(2H, t, J=6.5 Hz), 7.08(2H, d, J=8.3 Hz), 7.41(2H, dd, J=8.3, 1.9 Hz).

(41-4) Synthesis of [5-(2-{4-[3-(4-bromophenyl)propoxy]-3-trifluoromethylphenyl}ethyl)-2,2-dimethyl-1,3-dioxan-5-yl]carbamic acid t-butyl ester (Compound 41-4)

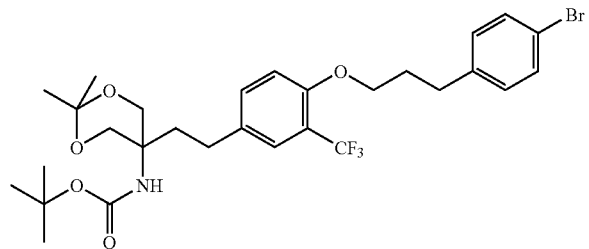

Reference Example compound 2-6 (500 mg) was dissolved in N,N-dimethylformamide (10 ml), potassium carbonate (494 mg) and compound 41-3 (447 mg) were added, and the mixture was stirred at 80° C. for 1.5 hr. Water was added to the reaction mixture, and the mixture was extracted with ethyl acetate, washed with water and saturated brine, and dried over anhydrous magnesium sulfate. The solvent was evaporated under reduced pressure to give the object product (820 mg) as a white solid.

$^1$H-NMR(CDCl$_3$) δ (ppm): 1.43(3H, s), 1.44(3H, s), 1.47(9H, s), 1.93-1.98(2H, m), 2.06-2.10(2H, m), 2.51-2.56(2H, m), 2.77-2.81(2H, m), 3.69(2H, d, J=11.7 Hz), 3.89(2H, d, J=11.7 Hz), 3.96(2H, t, J=6.0 Hz), 5.00(1H, brs), 6.83(1H, d, J=8.5 Hz), 7.05-7.09(2H, m), 7.24-7.27(1H, m), 7.36-7.43 (3H, m).

(41-5) Synthesis of 2-amino-2-(2-{4-[3-(4-bromophenyl)propoxy]-3-trifluoromethylphenyl}ethyl)propane-1,3-diol hydrochloride (Compound 41-5)

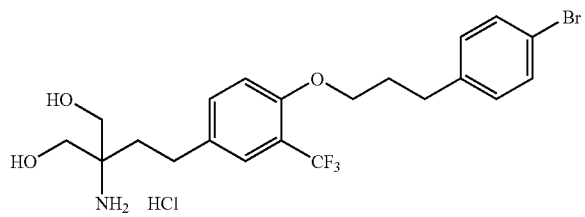

Compound 41-4 (820 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give the object product (600 mg) as a white powder.

MS(ESI)m/z: 476, 478[M+H]

$^1$H-NMR(DMSO-d$_6$) δ (ppm): 1.74-1.79(2H, m), 1.97-2.04(2H, m), 2.58-2.63(2H, m), 2.75(2H, t, J=7.5 Hz), 3.52 (4H, d, J=4.7 Hz), 4.03(2H, t, J=6.0 Hz), 5.39(2H, t, J=4.9 Hz), 7.14-7.18(3H, m), 7.42-7.48(4H, m), 7.83(3H, brs).

Example 42

2-amino-2-(2-{4-[3-(4-methoxy-3-methylphenyl)propoxy]-3-trifluoromethylphenyl}ethyl)propane-1,3-diol hydrochloride (42-1) Synthesis of 1-(4-methoxy-3-methylphenyl)-3-(tetrahydro-2H-pyran-2-yloxy)-1-propyne (Compound 42-1)

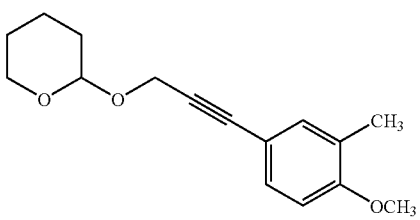

A mixture of 4-bromo-2-methylanisole (3.02 g), cesium carbonate (12.7 g), 2-(2-propynyloxy)tetrahydropyran (3.16 ml), 2-dicyclohexylphosphino-2',4',6'-triisopropylbiphenyl (429 mg), bis(acetonitrile)palladium(II) dichloride (77.8 mg) and acetonitrile (100 ml) was stirred at 80° C. for 5 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=100:0-90:10) to give the object product (1.76 g) as a pale-brown oil.

$^1$H-NMR(CDCl$_3$) δ (ppm): 1.54-1.70(4H, m), 1.73-1.90 (2H, m), 2.17(3H, s), 3.54-3.59(1H, m), 3.83(3H, s), 3.85-3.92(1H, m), 4.44(1H, d, J=15.6 Hz), 4.50(1H, d, J=15.6 Hz), 4.90(1H, t, J=3.4 Hz), 6.74(1H, d, J=8.2 Hz), 7.24(1H, s), 7.28(1H, dd, J=1.7, 8.2 Hz).

(42-2) Synthesis of 1-(4-methoxy-3-methylphenyl)-3-(tetrahydro-2H-pyran-2-yloxy)propane (Compound 42-2)

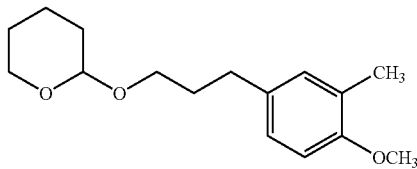

A solution of compound 42-1 (1.76 g) and 10% palladium carbon (0.90 g) in 1,4-dioxane (25 ml) was stirred under a hydrogen atmosphere at room temperature for 5 hr. The reaction mixture was filtered through celite and concentrated to give the object product (1.78 g) as a yellow oil.

$^1$H-NMR(CDCl$_3$) δ (ppm): 1.51-1.61(4H, m), 1.70-1.76 (1H, m), 1.81-1.92(3H, m), 2.19(3H, s), 2.55-2.68(2H, m), 3.40(1H, dt, J=9.9, 6.4 Hz), 3.47-3.53(1H, m), 3.76(1H, dt, J=9.6, 6.5 Hz), 3.80(3H, s), 3.85-3.91(1H, m), 4.58(1H, t, J=3.6 Hz), 6.73-6.76(1H, m), 6.97-6.99(2H, m).

(42-3) Synthesis of 3-(4-methoxy-3-methylphenyl)-1-propanol (Compound 42-3)

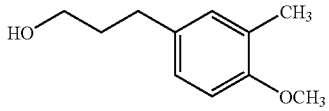

A solution of compound 42-2 (1.78 g) and p-toluenesulfonic acid monohydrate (17.0 mg) in methanol (100 ml) was stirred at room temperature for 3 hr. To the reaction mixture was added saturated aqueous sodium hydrogen carbonate, and methanol was evaporated under reduced pressure. Water was added to the obtained mixture, and the mixture was extracted with ethyl acetate. The organic layer was washed with saturated brine and dried over anhydrous magnesium sulfate, and the solvent was concentrated under reduced pressure to give the object product (1.03 g) as a pale-yellow solid.

$^1$H-NMR(CDCl$_3$) δ (ppm): 1.26(1H, brs), 1.83-1.90(2H, m), 2.20(3H, s), 2.62(2H, t, J=7.6 Hz), 3.67(2H, t, J=6.4 Hz), 3.81(3H, s), 6.75(1H, d, J=8.8 Hz), 6.97-6.99(2H, m).

(42-4) Synthesis of 1-(3-bromopropyl)-4-methoxy-3-methylbenzene (Compound 42-4)

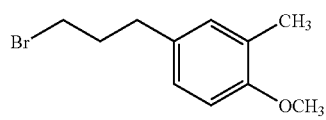

Compound 42-3 (860 mg) was dissolved in methylene chloride (30 ml), triphenylphosphine (1.39 g) and N-bromosuccinimide (0.934 g) were added under ice-cooling, and the mixture was stirred under ice-cooling for 2 hr, and at room temperature for 2 hr. The reaction mixture was washed with water and saturated brine, and dried over anhydrous magnesium sulfate. The solvent was evaporated under reduced pressure. Diethyl ether (50 ml) was added, and the precipitated triphenylphosphine oxide was filtered off. The concentrate of the filtrate was purified by silica gel column chromatography (hexane alone) to give the object product (800 mg) as a colorless oil.

$^1$H-NMR(CDCl$_3$) δ (ppm): 2.09-2.16(2H, m), 2.20(3H, s), 2.68(2H, t, J=7.3 Hz), 3.39(2H, t, J=6.5 Hz), 3.81(3H, s), 6.75(1H, d, J=8.0 Hz), 6.96-6.99(2H, m).

(42-5) Synthesis of [2,2-dimethyl-5-(2-{4-[3-(4-methoxy-3-methylphenyl)propoxy]-3-trifluoromethylphenyl}ethyl)-1,3-dioxan-5-yl]carbamic acid t-butyl ester (Compound 42-5)

Reference Example compound 2-6 (500 mg) was dissolved in N,N-dimethylformamide (10 ml), potassium carbonate (494 mg) and compound 42-4 (348 mg) were added, and the mixture was stirred at 80° C. for 1.5 hr. Water was added to the reaction mixture, and the mixture was extracted with ethyl acetate, washed with water and saturated brine, and dried over anhydrous magnesium sulfate. The solvent was evaporated under reduced pressure to give the object product (810 mg) as a colorless oil.

$^1$H-NMR(CDCl$_3$) δ (ppm): 1.43(3H, s), 1.44(3H, s), 1.47 (9H, s), 1.93-1.98(2H, m), 2.03-2.12(2H, m), 2.19(3H, s), 2.51-2.55(2H, m), 2.71-2.75(2H, m), 3.69(2H, d, J=11.7 Hz), 3.80(3H, s), 3.89(2H, d, J=11.7 Hz), 3.98(2H, t, J=6.1 Hz), 4.99(1H, brs), 6.72-6.76(1H, m), 6.84(1H, d, J=8.5 Hz), 6.96-6.99(2H, m), 7.24-7.26(1H, m), 7.36(1H, d, J=1.6 Hz).

(42-6) Synthesis of 2-amino-2-(2-{4-[3-(4-methoxy-3-methylphenyl)propoxy]-3-trifluoromethylphenyl}ethyl)propane-1,3-diol hydrochloride (Compound 42-6)

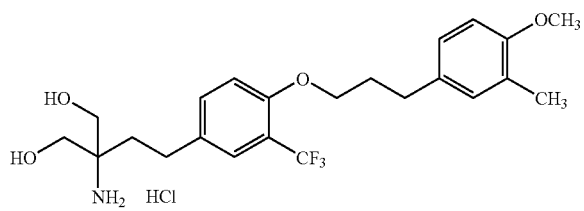

Compound 42-5 (810 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give the object product (570 mg) as a white powder.

MS(ESI)m/z: 442[M+H]

$^1$H-NMR(DMSO-d$_6$) δ (ppm): 1.74-1.78(2H, m), 1.95-2.00(2H, m), 2.10(3H, s), 2.58-2.66(4H, m), 3.52(4H, d, J=4.5 Hz), 3.73(3H, s), 4.02(2H, t, J=6.0 Hz), 5.39(2H, t, J=4.9 Hz), 6.80-6.83(1H, m), 6.94-6.96(2H, m), 7.15(1H, d, J=8.6 Hz), 7.43(1H, d, J=8.6 Hz), 7.48(1H, d, J=1.4 Hz), 7.80(3H, brs).

Example 43

2-amino-2-(2-{4-[2-(4-ethylphenyl) ethoxy]-3-trifluoromethylphenyl}ethyl)propane-1,3-diol hydrochloride

(43-1) Synthesis of 4-ethylphenethylacetate (Compound 43-1)

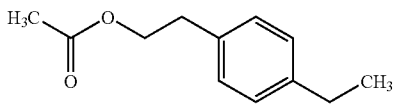

To a solution of compound 34-1 (5.00 g) in methylene chloride (20 ml) were added trifluoroacetic acid (20 ml) and triethylsilane (12 ml), and the mixture was stirred under ice-cooling for 1 hr, and at room temperature for 15 hr. Water was added to the reaction mixture, and the mixture was extracted with chloroform. The organic layer was washed successively with 1M aqueous sodium hydroxide solution and saturated brine, and dried over anhydrous magnesium sulfate. The solvent was evaporated under reduced pressure. The obtained residue was purified by silica gel chromatography (hexane:ethyl acetate=30:1-10:1) to give the object product (5.32 g) as a colorless oil.

$^1$H-NMR(CDCl$_3$) δ (ppm): 1.22(3H, t, J=7.5 Hz), 2.04(3H, s), 2.63(2H, q, J=7.5 Hz), 2.90(2H, t, J=7.0 Hz), 4.26(2H, t, J=7.0 Hz), 7.14(4H, s).

(43-2) Synthesis of 4-ethylphenethyl alcohol (Compound 43-2)

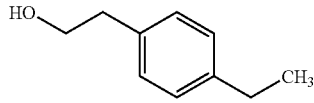

To a solution of compound 43-1 (5.32 g) in tetrahydrofuran (30 ml) were added 1M aqueous sodium hydroxide solution (40 ml) and methanol (30 ml), and the mixture was stirred at room temperature for 4 hr. Water was added to the reaction mixture, and the mixture was extracted with ethyl acetate, washed with saturated brine, and dried over anhydrous magnesium sulfate. The solvent was evaporated under reduced pressure. The obtained residue was purified by silica gel column chromatography (hexane:ethyl acetate=2:1-1:1) to give the object product (3.35 g) as a colorless oil.

$^1$H-NMR(CDCl$_3$) δ (ppm): 1.21-1.26(3H, m), 1.37(1H, t, J=5.9 Hz), 2.60-2.66(2H, m), 2.85(2H, t, J=6.5 Hz), 3.85(2H, q, J=6.3 Hz), 7.15(4H, s).

(43-3) Synthesis of 2-amino-2-(2-{4-[2-(4-ethylphenyl)ethoxy]-3-trifluoromethylphenyl}ethyl)propane-1,3-diol hydrochloride (Compound 43-3)

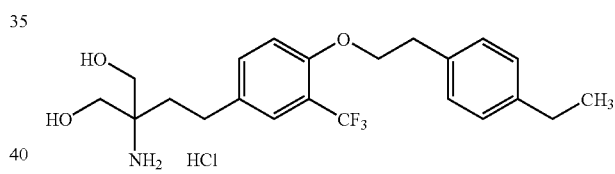

Triphenylphosphine (632 mg) was dissolved in tetrahydrofuran (10 ml), diisopropyl azodicarboxylate (40% toluene solution, 1.28 ml), compound 43-2 (356 mg) and Reference Example compound 2-6 (500 mg) were added, and the mixture was stirred at room temperature for 18 hr. Water was added to the reaction mixture, and the mixture was extracted with ethyl acetate, washed with saturated brine, and dried over anhydrous magnesium sulfate. The solvent was evaporated under reduced pressure. To a solution of the obtained residue in ethanol (15 ml) was added concentrated hydrochloric acid (1.5 ml), and the mixture was stirred at 80° C. for 2 hr. The reaction mixture was concentrated, and the residue was washed with diethyl ether to give the object product (360 mg) as a white powder.

MS(ESI)m/z: 412[M+H]

$^1$H-NMR(DMSO-d$_6$) δ (ppm): 1.15(3H, t, J=7.4 Hz), 1.73-1.78(2H, m), 2.50-2.62(4H, m), 2.99(2H, t, J=6.5 Hz), 3.51 (4H, d, J=4.7 Hz), 4.23(2H, t, J=6.8 Hz), 5.39(2H, t, J=4.9 Hz), 7.13(2H, d, J=7.8 Hz), 7.18-7.23(3H, m), 7.42-7.45(2H, m), 7.81(3H, brs).

Example 44

2-amino-2-(2-{4-[3-(4-fluoro-3-methylphenyl)propoxy]-3-trifluoromethylphenyl}ethyl)propane-1,3-diol hydrochloride

(44-1) Synthesis of 1-(4-fluoro-3-methylphenyl)-3-(tetrahydro-2H-pyran-2-yloxy)-1-propyne (Compound 44-1)

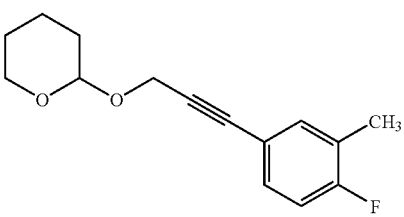

A mixture of 5-bromo-2-fluorotoluene (10.0 g), cesium carbonate (45.0 g), 2-(2-propynyloxy)tetrahydropyran (11.2 ml), 2-dicyclohexylphosphino-2',4',6'-triisopropylbiphenyl (1.51 g), bis(acetonitrile)palladium(II) dichloride (274 mg) and acetonitrile (300 ml) was stirred at 85° C. for 10 hr. The reaction mixture was added to water, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=98:2-90:10) to give the object product (8.08 g) as a yellow oil.

$^1$H-NMR(CDCl$_3$) δ (ppm): 1.53-1.70(4H, m), 1.73-1.90 (2H, m), 2.24(3H, d, J=1.4 Hz), 3.54-3.59(1H, m), 3.86-3.92 (1H, m), 4.43(1H, d, J=15.8 Hz), 4.49(1H, d, J=15.8 Hz), 4.89(1H, t, J=3.4 Hz), 6.93(1H, t, J=8.9 Hz), 7.23-7.30(2H, m).

(44-2) Synthesis of 1-(4-fluoro-3-methylphenyl)-3-(tetrahydro-2H-pyran-2-yloxy)propane (Compound 44-2)

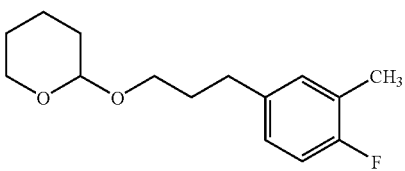

A solution of compound 44-1 (8.08 g) and 10% palladium carbon (2.02 g) in 1,4-dioxane (150 ml) was stirred under a hydrogen atmosphere at room temperature for 9 hr. The reaction mixture was filtered through celite and concentrated to give the object product (8.07 g) as a colorless oil.

$^1$H-NMR(CDCl$_3$) δ (ppm): 1.51-1.63(4H, m), 1.70-1.76 (1H, m), 1.80-1.92(3H, m), 2.24(3H, d, J=1.4 Hz), 2.58-2.70 (2H, m), 3.39(1H, dt, J=9.6, 6.6 Hz), 3.47-3.53(1H, m), 3.76 (1H, dt, J=9.5, 6.7 Hz), 3.84-3.90(1H, m), 4.57(1H, t, J=3.5 Hz), 6.89(1H, t, J=8.9 Hz), 6.94-7.01(2H, m).

(44-3) Synthesis of 3-(4-fluoro-3-methylphenyl)-1-propanol (Compound 44-3)

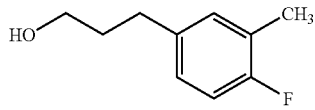

A solution of compound 44-2 (8.07 g) and p-toluenesulfonic acid monohydrate (15.0 mg) in methanol (120 ml) was stirred at room temperature for 18 hr. To the reaction mixture was added saturated aqueous sodium hydrogen carbonate, and methanol was evaporated under reduced pressure. Water was added to the obtained mixture, and the mixture was extracted with ethyl acetate. The organic layer was washed with saturated brine and dried over anhydrous magnesium sulfate, and the solvent was concentrated under reduced pressure to give the object product (5.48 g) as a pale-yellow oil.

$^1$H-NMR(CDCl$_3$) δ (ppm): 1.28(1H, brs), 1.82-1.89(2H, m), 2.25(3H, d, J=1.4 Hz), 2.64(2H, t, J=7.6 Hz), 3.67(2H, t, J=6.2 Hz), 6.90(1H, t, J=8.9 Hz), 6.94-7.01(2H, m).

(44-4) Synthesis of 1-(3-bromopropyl)-4-fluoro-3-methylbenzene (Compound 44-4)

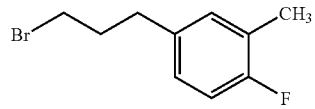

Compound 44-3 (5.47 g) was dissolved in methylene chloride (30 ml), triphenylphosphine (9.39 g) and N-bromosuccinimide (6.37 g) were added under ice-cooling, and the mixture was stirred under ice-cooling for 2 hr, and at room temperature for 4 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (3.10 g) as a colorless oil.

$^1$H-NMR(CDCl$_3$) δ (ppm): 2.09-2.16(2H, m), 2.25(3H, d, J=1.5 Hz), 2.71(2H, t, J=7.3 Hz), 3.38(2H, t, J=6.4 Hz), 6.88-7.00(3H, m).

(44-5) Synthesis of [5-(2-{4-[3-(4-fluoro-3-methylphenyl)propoxy]-3-trifluoromethylphenyl}ethyl)-2,2-dimethyl-1,3-dioxan-5-yl]carbamic acid t-butyl ester (Compound 44-5)

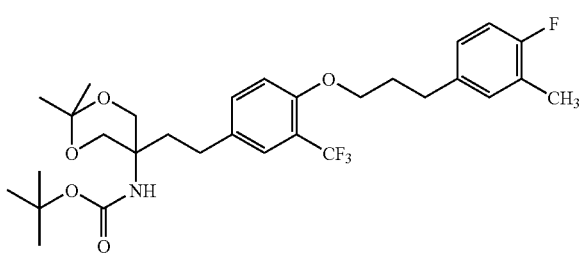

Reference Example compound 2-6 (500 mg) was dissolved in N,N-dimethylformamide (10 ml), potassium carbonate (494 mg) and compound 44-4 (331 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (800 mg) as a white solid.

$^1$H-NMR(CDCl$_3$) δ (ppm): 1.43(3H, s), 1.44(3H, s), 1.47 (9H, s), 1.93-1.98(2H, m), 2.04-2.12(2H, m), 2.23(3H, d, J=1.7 Hz), 2.51-2.56(2H, m), 2.75(2H, t, J=7.5 Hz), 3.69(2H, d, J=11.7 Hz), 3.88(2H, d, J=11.7 Hz), 3.97(2H, t, J=6.0 Hz), 4.99(1H, brs), 6.82-7.00(4H, m), 7.25-7.26(1H, m), 7.37(1H, d, J=1.9 Hz).

(44-6) Synthesis of 2-amino-2-(2-{4-[3-(4-fluoro-3-methylphenyl)propoxy]-3-trifluoromethylphenyl}ethyl)propane-1,3-diol hydrochloride (Compound 44-6)

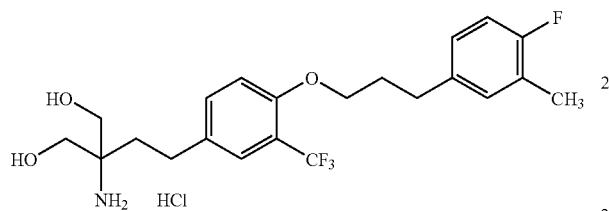

Compound 44-5 (800 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give the object product (540 mg) as a white powder.

MS(ESI)m/z: 430[M+H]

$^1$H-NMR(DMSO-d$_6$) δ (ppm): 1.73-1.78(2H, m), 1.97-2.03(2H, m), 2.19(3H, brs), 2.58-2.63(2H, m), 2.69(2H, t, J=7.5 Hz), 3.51(4H, d, J=4.2 Hz), 4.03(2H, t, J=6.0 Hz), 5.38(2H, brs), 7.01-7.03(2H, m), 7.10(1H, d, J=7.4 Hz), 7.16 (1H, d, J=8.6 Hz), 7.44(1H, d, J=8.6 Hz), 7.48(1H, brs), 7.76(3H, brs).

Example 45

2-amino-2-(2-{4-[3-(2-fluoro-5-methylphenyl)propoxy]-3-trifluoromethylphenyl}ethyl)propane-1,3-diol hydrochloride (45-1) Synthesis of 1-(2-fluoro-5-methylphenyl)-3-(tetrahydro-2H-pyran-2-yloxy)-1-propyne (Compound 45-1)

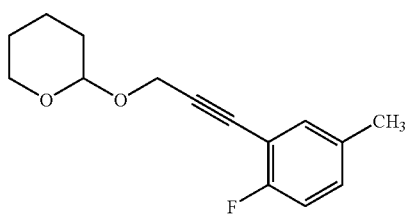

A mixture of 3-bromo-4-fluorotoluene (10.0 g), cesium carbonate (45.0 g), 2-(2-propynyloxy)tetrahydropyran (11.2 ml), 2-dicyclohexylphosphino-2',4',6'-triisopropylbiphenyl (1.51 g), bis(acetonitrile)palladium(II) dichloride (274 mg) and acetonitrile (250 ml) was stirred at 90° C. for 11 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=99:1-95:5) to give the object product (8.32 g) as a pale-brown oil.

$^1$H-NMR(CDCl$_3$) δ (ppm): 1.52-1.70(4H, m), 1.74-1.90 (2H, m), 2.29(3H, s), 3.55-3.59(1H, m), 3.87-3.92(1H, m), 4.49(1H, d, J=15.8 Hz), 4.53(1H, d, J=15.8 Hz), 4.92(1H, t, J=3.4 Hz), 6.94(1H, t, J=8.8 Hz), 7.06-7.10(1H, m), 7.24(1H, dd, J=2.0, 6.6 Hz).

(45-2) Synthesis of 1-(2-fluoro-5-methylphenyl)-3-(tetrahydro-2H-pyran-2-yloxy)propane (Compound 45-2)

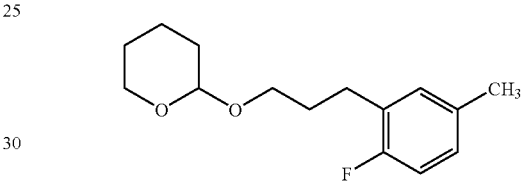

A solution of compound 45-1 (8.32 g) and 10% palladium carbon (2.00 g) in 1,4-dioxane (40 ml) was stirred under a hydrogen atmosphere at room temperature for 4 hr. The reaction mixture was filtered through celite and concentrated to give the object product (8.32 g) as a colorless oil.

$^1$H-NMR(CDCl$_3$) δ (ppm): 1.51-1.63(4H, m), 1.70-1.76 (1H, m), 1.80-1.94(3H, m), 2.28(3H, s), 2.63-2.76(2H, m), 3.40(1H, dt, J=9.6, 6.6 Hz), 3.47-3.53(1H, m), 3.78(1H, dt, J=9.6, 6.6 Hz), 3.85-3.90(1H, m), 4.58(1H, t, J=3.5 Hz), 6.87(1H, t, J=9.0 Hz), 6.92-6.96(1H, m), 7.00(1H, dd, J=1.6, 7.4 Hz).

(45-3) Synthesis of 3-(2-fluoro-5-methylphenyl)-1-propanol (Compound 45-3)

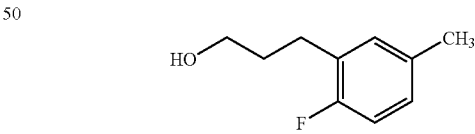

A solution of compound 45-2 (8.32 g) and p-toluenesulfonic acid monohydrate (20.0 mg) in methanol (200 ml) was stirred at room temperature for 14 hr. To the reaction mixture was added saturated aqueous sodium hydrogen carbonate, and methanol was evaporated under reduced pressure. Water was added to the obtained mixture, and the mixture was extracted with ethyl acetate. The organic layer was washed with saturated brine and dried over anhydrous magnesium sulfate, and the solvent was concentrated under reduced pressure to give the object product (5.53 g) as a pale-yellow oil.

¹H-NMR(CDCl₃) δ (ppm): 1.34(1H, t, J=4.5 Hz), 1.84-1.91(2H, m), 2.29(3H, s), 2.70(2H, t, J=7.6 Hz), 3.65-3.69 (2H, m), 6.86-6.91(1H, m), 6.94-6.96(1H, m), 6.98-7.00(1H, m).

(45-4) Synthesis of 1-(3-bromopropyl)-2-fluoro-5-methylbenzene (Compound 45-4)

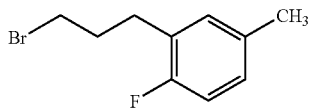

Compound 45-3 (5.54 g) was dissolved in methylene chloride (30 ml), triphenylphosphine (9.49 g) and N-bromosuccinimide (6.44 g) were added under ice-cooling, and the mixture was stirred under ice-cooling for 2 hr, and at room temperature for 5 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (3.78 g) as a pale-yellow oil.

¹H-NMR(CDCl₃) δ (ppm): 2.12-2.19(2H, m), 2.29(3H, s), 2.76(2H, t, J=7.4 Hz), 3.41(2H, t, J=6.6 Hz), 6.87-6.92(1H, m), 6.95-7.00(2H, m).

(45-5) Synthesis of [5-(2-{4-[3-(2-fluoro-5-methylphenyl)propoxy]-3-trifluoromethylphenyl}ethyl)-2,2-dimethyl-1,3-dioxan-5-yl]carbamic acid t-butyl ester (Compound 45-5)

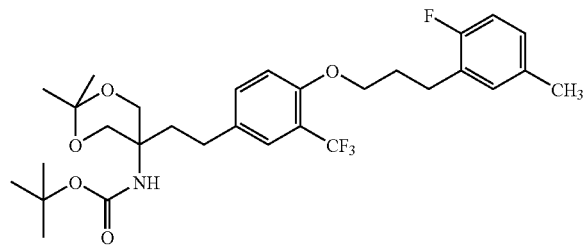

Reference Example compound 2-6 (500 mg) was dissolved in N,N-dimethylformamide (10 ml), potassium carbonate (494 mg) and compound 45-4 (331 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure. The obtained residue was purified by silica gel column chromatography (hexane:ethyl acetate=3:1-2:1) to give the object product (640 mg) as a white solid.

¹H-NMR(CDCl₃) δ (ppm): 1.43(3H, s), 1.44(3H, s), 1.47 (9H, s), 1.93-1.98(2H, m), 2.04-2.13(2H, m), 2.26(3H, s), 2.51-2.56(2H, m), 2.80(2H, t, J=7.5 Hz), 3.69(2H, d, J=11.7 Hz), 3.89(2H, J=11.7 Hz), 4.00(2H, t, J=6.1 Hz), 4.99(1H, brs), 6.84-6.90(2H, m), 6.93-6.98(2H, m), 7.25-7.26(1H, m), 7.37(1H, d, J=1.8 Hz).

(45-6) Synthesis of 2-amino-2-(2-{4-[3-(2-fluoro-5-methylphenyl)propoxy]-3-trifluoromethylphenyl}ethyl)propane-1,3-diol hydrochloride (Compound 45-6)

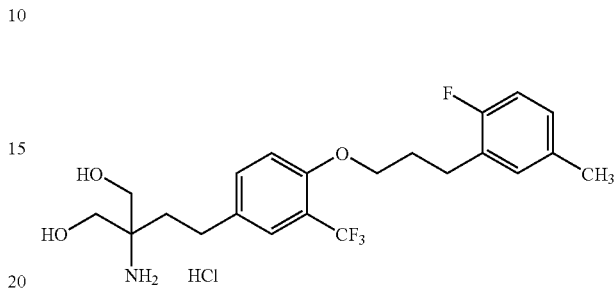

Compound 45-5 (640 mg) was dissolved in ethanol (15 ml), concentrated hydrochloric acid (1.5 ml) was added, and the mixture was stirred at 80° C. for 2 hr. The reaction mixture was concentrated, and the residue was washed with diethyl ether to give the object product (480 mg) as a white powder.

MS(ESI)m/z: 430[M+H]

¹H-NMR(DMSO-d₆) δ (ppm): 1.74-1.79(2H, m), 1.97-2.01(2H, m), 2.24(3H, s), 2.59-2.64(2H, m), 2.71-2.76(2H, m), 3.52(4H, J=4.4 Hz), 4.08(2H, t, J=5.9 Hz), 5.40(2H, t, J=4.8 Hz), 7.00-7.08(3H, m), 7.17(1H, d, J=8.5 Hz), 7.45(1H, d, J=8.5 Hz), 7.48(1H, brs), 7.83(3H, brs).

Example 46

2-amino-2-(2-{4-[3-(2-thienyl)propoxy]-3-trifluoromethylphenyl}ethyl)propane-1,3-diol hydrochloride (46-1) Synthesis of 3-(2-thienyl)-2-propyne-1-ol (Compound 46-1)

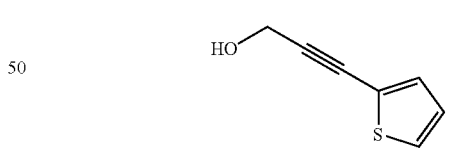

A mixture of 2-iodothiophene(5.00 g), copper(I) iodide (91 mg), triphenylphosphine (315 mg), tris(dibenzylideneacetone)dipalladium(0) chloroform adduct (497 mg), propargyl alcohol (1.54 ml), diisopropylethylamine (16.6 ml) and tetrahydrofuran (50 ml) was stirred at room temperature for 20 hr. The reaction mixture was added to water, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=3:1-2:1) to give the object product (1.45 g) as a brown oil.

$^1$H-NMR(CDCl$_3$) δ (ppm): 1.66(1H, t, J=6.2 Hz), 4.51(2H, d, J=6.1 Hz), 6.96-6.99(1H, m), 7.21-7.22(1H, m), 7.27(1H, s).

(46-2) Synthesis of 3-(2-thienyl)-1-propanol (Compound 46-2)

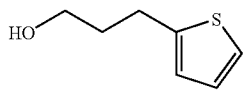

A solution of compound 46-1 (1.45 g) and 10% palladium carbon (1.00 g) in ethyl acetate (30 ml) was stirred under a hydrogen atmosphere at room temperature for 23 hr The reaction mixture was filtered through celite and concentrated. The residue was purified by silica gel column chromatography (hexane:ethyl acetate=2:1) to give the object product (1.29 g) as a yellow oil.

$^1$H-NMR(CDCl$_3$) δ (ppm): 1.31(1H, brs), 1.91-1.99(2H, m), 2.95(2H, t, J=7.6 Hz), 3.71(2H, brs), 6.81(1H, d, J=2.8 Hz), 6.91-6.93(1H, m), 7.11-7.13(1H, m).

(46-3) Synthesis of 2-(3-bromopropyl)thiophene (Compound 46-3)

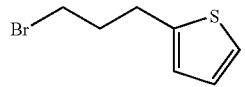

Compound 46-2 (1.29 g) was dissolved in methylene chloride (30 ml), triphenylphosphine (2.62 g) and N-bromosuccinimide (1.76 g) were added under ice-cooling, and the mixture was stirred under ice-cooling for 2 hr. The reaction mixture was washed with water and saturated brine, and dried over anhydrous magnesium sulfate. The solvent was evaporated under reduced pressure. Diethyl ether (50 ml) was added, and the precipitated triphenylphosphine oxide was filtered off. The concentrate of the filtrate was purified by silica gel column chromatography (hexane alone) to give the object product (760 mg) as a pale-yellow oil.

$^1$H-NMR(CDCl$_3$) δ (ppm): 2.17-2.25(2H, m), 3.02(2H, t, J=7.2 Hz), 3.43(2H, t, J=6.5 Hz), 6.84(1H, d, J=2.9 Hz), 6.92-6.94(1H, m), 7.13-7.15(1H, m).

(46-4) Synthesis of [2,2-dimethyl-5-(2-{4-[3-(2-thienyl)propoxy]-3-trifluoromethylphenyl}ethyl)-1,3-dioxan-5-yl]carbamic acid t-butyl ester (Compound 46-4)

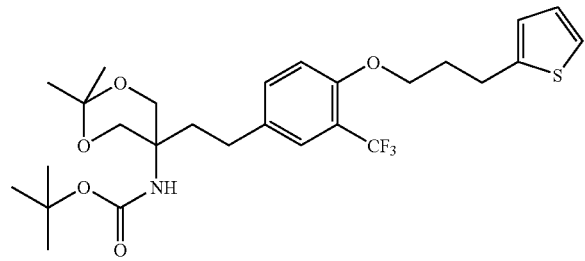

Reference Example compound 2-6 (500 mg) was dissolved in N,N-dimethylformamide (10 ml), potassium carbonate (493 mg) and compound 46-3 (293 mg) were added, and the mixture was stirred at 80° C. for 1.5 hr. Water was added to the reaction mixture, and the mixture was extracted with ethyl acetate, washed with water and saturated brine, and dried over anhydrous magnesium sulfate. The solvent was evaporated under reduced pressure to give the object product (740 mg) as a yellow oil.

$^1$H-NMR(CDCl$_3$) δ (ppm): 1.43(3H, s), 1.44(3H, s), 1.47 (9H, s), 1.93-1.98(2H, m), 2.10-2.21(2H, m), 2.51-2.56(2H, m), 3.06(2H, t, J=7.3 Hz), 3.69(2H, d, J=11.8 Hz), 3.89(2H, d, J=11.8 Hz), 4.02(2H, t, J=5.9 Hz), 4.99(1H, brs), 6.80(1H, d, J=3.0 Hz), 6.85(1H, d, J=8.5 Hz), 6.91(1H, dd, J=5.1, 3.5 Hz), 7.12(1H, J=5.8 Hz), 7.26-7.27(1H, m), 7.36(1H, brd, J=1.4 Hz).

(46-5) Synthesis of 2-amino-2-(2-{4-[3-(2-thienyl) propoxy]-3-trifluoromethylphenyl}ethyl)propane-1, 3-diol hydrochloride (Compound 46-5)

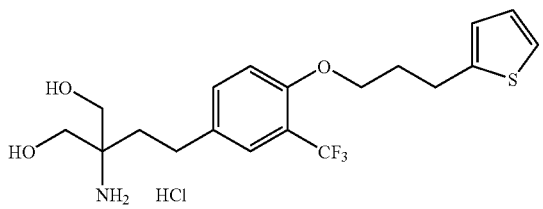

Compound 46-4 (740 mg) was dissolved in ethanol (15 ml), concentrated hydrochloric acid (1.5 ml) was added, and the mixture was stirred at 80° C. for 2.5 hr. The reaction mixture was concentrated, and the residue was washed with diethyl ether to give a white powder. The white powder was purified by HPLC, the obtained residue was converted to hydrochloride by adding hydrogen chloride containing ether (1 mol/l, 15 ml), and the precipitate was collected by filtration and dried to give the object product (360 mg) as a white powder.

MS(ESI)m/z: 404[M+H]

$^1$H-NMR(DMSO-d$_6$) δ (ppm): 1.74-1.79(2H, m), 2.02-2.08(2H, m), 2.59-2.63(2H, m), 2.96(2H, t, J=7.3 Hz), 3.52 (4H, d, J=4.6 Hz), 4.08(2H, t, J=5.9 Hz), 5.39(2H, t, J=4.9 Hz), 6.85(1H, d, J=3.0 Hz), 6.93-6.95(1H, m), 7.17(1H, d, J=8.6 Hz), 7.31-7.33(1H, m), 7.44(1H, d, J=8.6 Hz), 7.48(1H, s), 7.82(3H, brs).

Example 47

2-amino-2-(2-{4-[3-(3-ethylphenyl)propoxy]-3-trifluoromethylphenyl}ethyl)propane-1,3-diol hydrochloride (47-1) Synthesis of 1-(3-ethylphenyl)-3-(tetrahydro-2H-pyran-2-yloxy)-1-propyne (Compound 47-1)

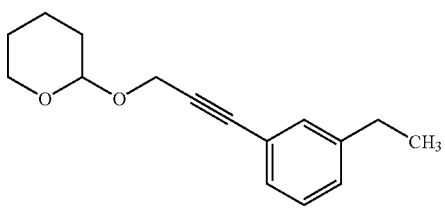

A mixture of 1-bromo-3-ethylbenzene (9.79 g), cesium carbonate (45.0 g), 2-(2-propynyloxy)tetrahydropyran (11.2 ml), 2-dicyclohexylphosphino-2',4',6'-triisopropylbiphenyl (1.51 g), bis(acetonitrile)palladium(II) dichloride (274 mg) and acetonitrile (300 ml) was stirred at 90° C. for 10 hr. The reaction mixture was added to water, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=99:1-95:5) to give the object product (5.25 g) as a yellow oil.

$^1$H-NMR(CDCl$_3$) δ (ppm): 1.22(3H, t, J=7.5 Hz), 1.53-1.71(4H, m), 1.74-1.91(2H, m), 2.62(2H, q, J=7.5 Hz), 3.54-3.60(1H, m), 3.87-3.92(1H, m), 4.46(1H, d, J=15.7 Hz), 4.51(1H, d, J=15.7 Hz), 4.91(1H, t, J=3.4 Hz), 7.14-7.16(1H, m), 7.22(1H, t, J=7.5 Hz), 7.26-7.28(1H, m), 7.30(1H, brs).

(47-2) Synthesis of 1-(3-ethylphenyl)-3-(tetrahydro-2H-pyran-2-yloxy)propane (Compound 47-2)

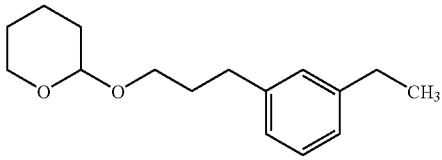

A solution of compound 47-1 (5.25 g) and 10% palladium carbon (1.06 g) in 1,4-dioxane (120 ml) was stirred under a hydrogen atmosphere at room temperature for 10 hr. The reaction mixture was filtered through celite and concentrated to give the object product (5.31 g) as a pale-yellow oil.

$^1$H-NMR(CDCl$_3$) δ (ppm): 1.23(3H, t, J=7.5 Hz), 1.51-1.63(4H, m), 1.69-1.76(1H, m), 1.81-1.88(1H, m), 1.93(2H, quint, J=7.1 Hz), 2.62(2H, q, J=7.6 Hz), 2.63-2.75(2H, m), 3.41(1H, dt, J=9.7, 6.6 Hz), 3.47-3.53(1H, m), 3.78(1H, dt, J=9.8, 6.5 Hz), 3.85-3.91(1H, m), 4.58(1H, t, J=3.6 Hz), 7.00-7.04(3H, m), 7.20(1H, t, J=7.4 Hz).

(47-3) Synthesis of 3-(3-ethylphenyl)-1-propanol (Compound 47-3)

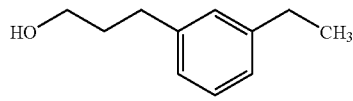

A solution of compound 47-2 (5.31 g) and p-toluenesulfonic acid monohydrate (10.0 mg) in methanol (100 ml) was stirred at room temperature for 21 hr. To the reaction mixture was added saturated aqueous sodium hydrogen carbonate, and methanol was evaporated under reduced pressure. Water was added to the obtained mixture, and the mixture was extracted with ethyl acetate. The organic layer was washed with saturated brine and dried over anhydrous magnesium sulfate, and the solvent was concentrated under reduced pressure to give the object product (3.53 g) as a pale-yellow oil.

$^1$H-NMR(CDCl$_3$) δ (ppm): 1.23(3H, t, J=7.5 Hz), 1.28(1H, brs), 1.86-1.94(2H, m), 2.63(2H, q, J=7.6 Hz), 2.69(2H, t, J=7.7 Hz), 3.68(2H, m), 7.01-7.04(3H, m), 7.19-7.23(1H, m).

(47-4) Synthesis of 1-(3-bromopropyl)-3-ethylbenzene (Compound 47-4)

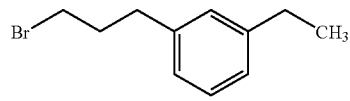

Compound 47-3 (3.53 g) was dissolved in methylene chloride (30 ml), triphenylphosphine (6.19 g) and N-bromosuccinimide (4.20 g) were added under ice-cooling, and the mixture was stirred under ice-cooling for 1 hr, and at room temperature for 5 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (4.29 g) as a colorless oil.

$^1$H-NMR(CDCl$_3$) δ (ppm): 1.23(3H, t, J=7.5 Hz), 2.14-2.20(2H, m), 2.63(2H, q, J=7.5 Hz), 2.75(2H, t, J=7.4 Hz), 3.40(2H, t, J=6.6 Hz), 7.00-7.05(3H, m), 7.21(1H, t, J=7.4 Hz).

(47-5) Synthesis of [2,2-dimethyl-5-(2-{4-[3-(3-ethylphenyl)propoxy]-3-trifluoromethylphenyl}ethyl)-1,3-dioxan-5-yl]carbamic acid t-butyl ester (Compound 47-5)

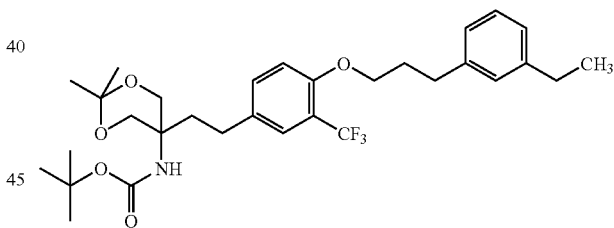

Reference Example compound 2-6 (500 mg) was dissolved in N,N-dimethylformamide (10 ml), potassium carbonate (494 mg) and compound 47-4 (325 mg) were added, and the mixture was stirred at 80° C. for 1.5 hr. Water was added to the reaction mixture, and the mixture was extracted with ethyl acetate, washed with water and saturated brine, and dried over anhydrous magnesium sulfate. The solvent was evaporated under reduced pressure to give the object product (790 mg) as a colorless oil.

$^1$H-NMR(CDCl$_3$) δ (ppm): 1.20(3H, t, J=7.7 Hz), 1.43(3H, s), 1.44(3H, s), 1.47(9H, s), 1.93-1.99(2H, m), 2.08-2.12(2H, m), 2.51-2.56(2H, m), 2.61(2H, q, J=7.7 Hz), 2.80(2H, t, J=7.5 Hz), 3.69(2H, d, J=11.7 Hz), 3.89(2H, d, J=11.7 Hz), 3.99(2H, t, J=6.0 Hz), 4.98(1H, brs), 6.84(1H, d, J=8.4 Hz), 7.00-7.03(3H, m), 7.20(1H, t, J=7.7 Hz), 7.24-7.26(1H, m), 7.37(1H, J=1.9 Hz).

(47-6) Synthesis of 2-amino-2-(2-{4-[3-(3-ethylphenyl)propoxy]-3-trifluoromethylphenyl}ethyl)propane-1,3-diol hydrochloride (Compound 47-6)

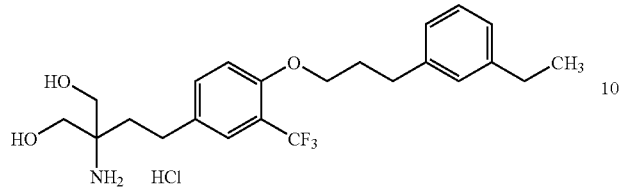

Compound 47-5 (790 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give the object product (570 mg) as a white powder.

MS(ESI)m/z: 426[M+H]

$^1$H-NMR(DMSO-$d_6$) δ (ppm): 1.13(3H, t, J=7.5 Hz), 1.74-1.79(2H, m), 1.98-2.02(2H, m), 2.50-2.63(4H, m), 2.71(2H, t, J=7.5 Hz), 3.52(4H, d, J=4.3 Hz), 4.03(2H, t, J=6.1 Hz), 5.39(2H, brs), 6.98-7.02(3H, m), 7.14-7.20(2H, m), 7.44(1H, d, J=8.6 Hz), 7.48(1H, s), 7.82(3H, brs).

Example 48

2-amino-2-(2-{4-[3-(5-methyl-2-thienyl)propoxy]-3-trifluoromethylphenyl}ethyl)propane-1,3-diol hydrochloride (48-1) Synthesis of 3-(5-methyl-2-thienyl)-2-propyne-1-ol (Compound 48-1)

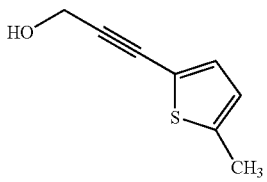

A mixture of 2-iodo-5-methylthiophene (5.00 g), copper(I) iodide (82 mg), triphenylphosphine (286 mg), tris(dibenzylideneacetone)dipalladium(0) chloroform adduct (445 mg), propargyl alcohol (1.91 ml), diisopropylethylamine (15.1 ml) and tetrahydrofuran (30 ml) was stirred at room temperature for 20 hr. The reaction mixture was added to water, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=3:1-2:1) to give the object product (1.48 g) as a brown oil.

$^1$H-NMR(CDCl$_3$) δ (ppm): 1.64(1H, t, J=6.2 Hz), 2.46(3H, s), 4.49(2H, d, J=6.1 Hz), 6.62(1H, d, J=4.2 Hz), 7.02(1H, d, J=3.6 Hz).

(48-2) Synthesis of 3-(5-methyl-2-thienyl)-1-propanol (Compound 48-2)

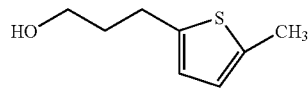

A solution of compound 48-1 (1.48 g) and 10% palladium carbon (1.00 g) in ethyl acetate (30 ml) was stirred under a hydrogen atmosphere at room temperature for 6 hr. The reaction mixture was filtered through celite and concentrated. The residue was purified by silica gel column chromatography (hexane:ethyl acetate=2:1-1:1) to give the object product (1.23 g) as a brown oil.

$^1$H-NMR(CDCl$_3$) δ (ppm): 1.28(1H, brs), 1.87-2.05(2H, m), 2.43(3H, s), 2.85(2H, t, J=7.5 Hz), 3.67-3.73(2H, m), 6.55(1H, d, J=2.8 Hz)6.58(1H, d, J=3.2 Hz).

(48-3) Synthesis of 2-(3-bromopropyl)-5-methylthiophene (Compound 48-3)

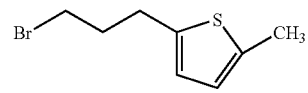

Compound 48-2 (1.23 g) was dissolved in methylene chloride (30 ml), triphenylphosphine (2.27 g) and N-bromosuccinimide (1.54 g) were added under ice-cooling, and the mixture was stirred under ice-cooling for 1 hr, and at room temperature for 2 hr. The reaction mixture was washed with water and saturated brine, and dried over anhydrous magnesium sulfate. The solvent was evaporated under reduced pressure. Diethyl ether (50 ml) was added, and the precipitated triphenylphosphine oxide was filtered off. The concentrate of the filtrate was purified by silica gel column chromatography (hexane alone) to give the object product (650 mg) as a yellow oil.

$^1$H-NMR(CDCl$_3$) δ (ppm): 2.13-2.20(2H, m), 2.43(3H, s), 2.92(2H, t, J=7.2 Hz), 3.43(2H, t, J=6.4 Hz), 6.55(1H, d, J=2.6 Hz), 6.60(1H, d, J=3.4 Hz).

(48-4) Synthesis of [2,2-dimethyl-5-(2-{4-[3-(5-methyl-2-thienyl)propoxy]-3-trifluoromethylphenyl}ethyl)-1,3-dioxan-5-yl]carbamic acid t-butyl ester (Compound 48-4)

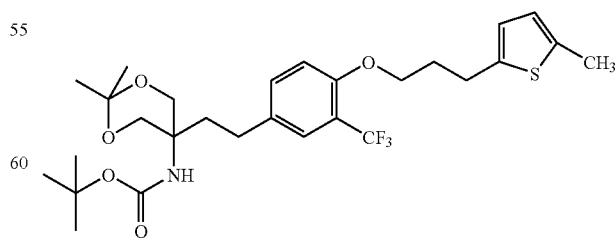

Reference Example compound 2-6 (500 mg) was dissolved in N,N-dimethylformamide (10 ml), potassium carbonate (493 mg) and compound 48-3 (313 mg) were added, and the mixture was stirred at 80° C. for 1 hr. Water was added to the reaction mixture, and the mixture was extracted with ethyl acetate, washed with water and saturated brine, and dried over anhydrous magnesium sulfate. The solvent was evaporated under reduced pressure to give the object product (710 mg) as a yellow oil.

$^1$H-NMR(CDCl$_3$) δ (ppm): 1.43(3H, s), 1.44(3H, s), 1.47 (9H, s), 1.93-1.98(2H, m), 2.09-2.19(2H, m), 2.42(3H, s), 2.51-2.56(2H, m), 2.97(2H, t, J=7.3 Hz), 3.69(2H, d, J=11.7 Hz), 3.89(2H, d, J=11.7 Hz), 4.02(2H, t, J=5.9 Hz), 4.99(1H, brs), 6.53(1H, J=2.7 Hz), 6.56(1H, d, J=3.2 Hz), 6.85(1H, d, J=8.5 Hz), 7.25-7.26(1H, m), 7.36(1H, d, J=1.6 Hz).

(48-5) Synthesis of 2-amino-2-(2-{4-[3-(5-methyl-2-thienyl)propoxy]-3-trifluoromethylphenyl}ethyl)propane-1,3-diol hydrochloride (Compound 48-5)

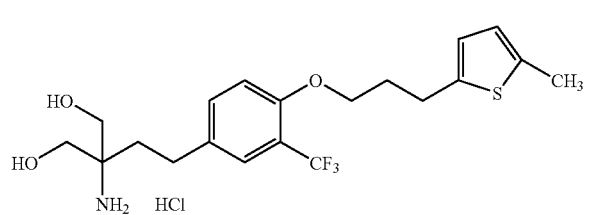

Compound 48-4 (710 mg) was dissolved in ethanol (15 ml), concentrated hydrochloric acid (1.5 ml) was added, and the mixture was stirred at 80° C. for 2 hr. The reaction mixture was concentrated, and the residue was washed with diethyl ether to give a white powder. The white powder was purified by HPLC, the obtained residue was converted to hydrochloride by adding hydrogen chloride containing ether (1 mol/l, 15 ml), and the precipitate was collected by filtration and dried to give the object product (480 mg) as a white powder.
MS(ESI)m/z: 418[M+H]
$^1$H-NMR(DMSO-d$_6$) δ (ppm): 1.74-1.79(2H, m), 1.98-2.04(2H, m), 2.37(3H, s), 2.59-2.64(2H, m), 2.87(2H, t, J=7.4 Hz), 3.52(4H, d, J=4.6 Hz), 4.07(2H, t, J=6.0 Hz), 5.40(2H, t, J=4.9 Hz), 6.59(2H, s), 7.16(1H, d, J=8.6 Hz), 7.45(1H, d, J=8.6 Hz), 7.48(1H, s), 7.85(3H, brs).

Example 49

2-amino-2-(2-{4-[3-(2,3-dimethylphenyl)propoxy]-3-trifluoromethylphenyl}ethyl)propane-1,3-diol hydrochloride (49-1) Synthesis of 3-(2,3-dimethylphenyl)-2-propyne-1-ol (Compound 49-1)

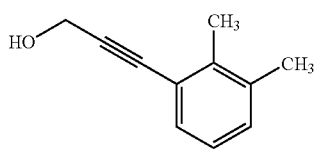

A mixture of 1-iodo-2,3-dimethylbenzene (5.00 g), copper (I) iodide (82.1 mg), triphenylphosphine (283 mg), tris (dibenzylideneacetone)dipalladium(0) chloroform adduct (446 mg), propargyl alcohol (1.40 ml), diisopropylethylamine (15.0 ml) and tetrahydrofuran (100 ml) was stirred at room temperature for 19 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=100:0-70:30) to give the object product (1.91 g) as a brown oil.

$^1$H-NMR(CDCl$_3$) δ (ppm): 1.66(1H, t, J=6.2 Hz), 2.27(3H, s), 2.38(3H, s), 4.54(2H, d, J=6.2 Hz), 7.04(1H, t, J=7.6 Hz), 7.11(1H, d, J=7.4 Hz), 7.28(1H, d, J=7.6 Hz).

(49-2) Synthesis of 3-(2,3-dimethylphenyl)-1-propanol (Compound 49-2)

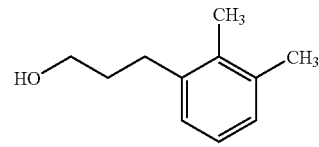

A solution of compound 49-1 (1.91 g) and 10% palladium carbon (0.95 g) in 1,4-dioxane (80 ml) was stirred under a hydrogen atmosphere at room temperature for 15 hr. The reaction mixture was filtered through celite and concentrated to give the object product (1.93 g) as a brown oil.

$^1$H-NMR(CDCl$_3$) δ (ppm): 1.29(1H, t, J=5.0 Hz), 1.80-1.88(2H, m), 2.22(3H, s), 2.28(3H, s), 2.71-2.74(2H, m), 3.69-3.73(2H, m), 6.99-7.06(3H, m).

(49-3) Synthesis of 1-(3-bromopropyl)-2,3-dimethylbenzene (Compound 49-3)

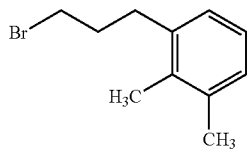

Compound 49-2 (1.83 g) was dissolved in methylene chloride (40 ml), triphenylphosphine (3.25 g) and N-bromosuccinimide (2.18 g) were added under ice-cooling, and the mixture was stirred under ice-cooling for 2 hr. Water was added to the reaction mixture, and the mixture was extracted with methylene chloride, washed with saturated brine, and dried over anhydrous sodium sulfate. The solvent was evaporated under reduced pressure. Diethyl ether was added, and the precipitated triphenylphosphine oxide was filtered off. The concentrate of the filtrate was purified by silica gel column chromatography (hexane alone) to give the object product (2.12 g) as a colorless oil.

$^1$H-NMR(DMSO-d$_6$) δ (ppm): 1.96-2.03(2H, m), 2.16(3H, s), 2.22(3H, s), 2.71(2H, t, J=7.8 Hz), 3.55(2H, t, J=6.5 Hz), 6.97-7.00(3H, m).

(49-4) Synthesis of [2,2-dimethyl-5-(2-{4-[3-(2,3-dimethylphenyl)propoxy]-3-trifluoromethylphenyl}ethyl)-1,3-dioxan-5-yl]carbamic acid t-butyl ester (Compound 49-4)

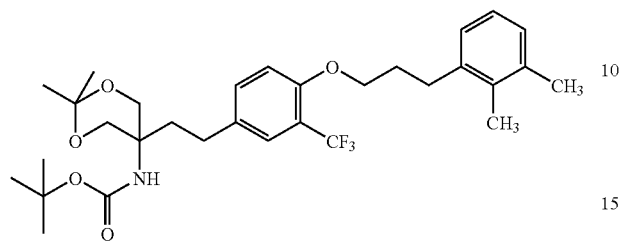

Reference Example compound 2-6 (500 mg) was dissolved in N,N-dimethylformamide (10 ml), potassium carbonate (494 mg) and compound 49-3 (325 mg) were added, and the mixture was stirred at 80° C. for 1 hr. Water was added to the reaction mixture, and the mixture was extracted with ethyl acetate, washed with water and saturated brine, and dried over anhydrous sodium sulfate. The solvent was evaporated under reduced pressure to give the object product (670 mg) as a white solid.

$^1$H-NMR(DMSO-$d_6$) δ (ppm): 1.32(3H, s), 1.33(3H, s), 1.40(9H, s), 1.88-1.95(4H, m), 2.15(3H, s), 2.22(3H, s), 2.45-2.50(2H, m), 2.72-2.78(2H, m), 3.66(2H, d, J=11.6 Hz), 3.88 (2H, d, J=11.3 Hz), 4.07(2H, t, J=5.7 Hz), 6.65(1H, brs), 6.94-7.01(3H, m), 7.14(1H, d, J=8.4 Hz), 7.37-7.40(1H, m), 7.40(1H, s).

(49-5) Synthesis of 2-amino-2-(2-{4-[3-(2,3-dimethylphenyl)propoxy]-3-trifluoromethylphenyl}ethyl) propane-1,3-diol hydrochloride (Compound 49-5)

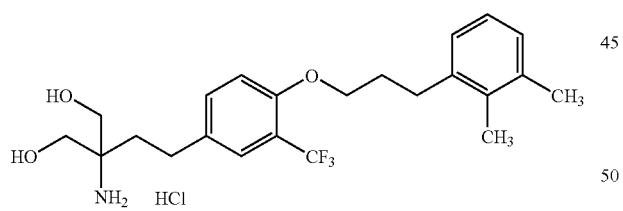

Compound 49-4 (670 mg) was dissolved in ethanol (15 ml), concentrated hydrochloric acid (1.5 ml) was added, and the mixture was stirred at 80° C. for 1 hr. The reaction mixture was concentrated, and the residue was washed with diethyl ether to give the object product (490 mg) as a white powder.

MS(ESI)m/z: 426[M+H]

$^1$H-NMR(DMSO-$d_6$) δ (ppm): 1.75-1.79(2H, m), 1.89-1.96(2H, m), 2.16(3H, s), 2.22(3H, s), 2.58-2.63(2H, m), 2.76(2H, t, J=7.6 Hz), 3.52(4H, d, J=5.1 Hz), 4.08(2H, t, J=5.8 Hz), 5.40(2H, t, J=5.0 Hz), 6.94-6.99(3H, m), 7.17(1H, d, J=8.5 Hz), 7.44(1H, d, J=8.6 Hz), 7.48(1H, s), 7.82(3H, brs).

Example 50

2-amino-2-[2-(4-{3-[3,5-bis(trifluoromethyl)phenyl]propoxyl}-3-trifluoromethylphenyl)ethyl]propane-1,3-diol hydrochloride

(50-1) Synthesis of 3-[3,5-bis(trifluoromethyl)phenyl]-2-propyne-1-ol (Compound 50-1)

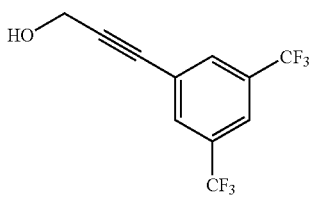

A mixture of 1-iodo-3,5-bis(trifluoromethyl)benzene (5.00 g), copper(I) iodide (56.0 mg), triphenylphosphine (193 mg), tris(dibenzylideneacetone)dipalladium(0) chloroform adduct (304 mg), propargyl alcohol (0.954 ml), diisopropylethylamine (10.2 ml) and tetrahydrofuran (100 ml) was stirred at room temperature for 6 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=99:1-80:20) to give the object product (3.81 g) as a brown oil.

$^1$H-NMR(CDCl$_3$) δ (ppm): 1.76(1H, t, J=6.3 Hz), 4.53(2H, d, J=6.2 Hz), 7.82(1H, brs), 7.87(2H, brs).

(50-2) Synthesis of 3-[3,5-bis(trifluoromethyl)phenyl]-1-propanol (Compound 50-2)

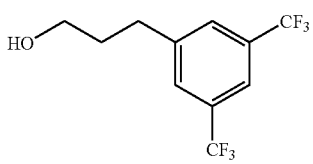

A solution of compound 50-1 (3.81 g) and 10% palladium carbon (1.50 g) in 1,4-dioxane (60 ml) was stirred under a hydrogen atmosphere at room temperature for 20 hr. The reaction mixture was filtered through celite and concentrated to give the object product (3.47 g) as a brown oil.

$^1$H-NMR(CDCl$_3$) δ (ppm): 1.36(1H, brs), 1.90-1.97(2H, m), 2.87(2H, t, J=7.8 Hz), 3.71(2H, t, J=6.2 Hz), 7.66(2H, brs), 7.72(1H, brs).

(50-3) Synthesis of 1-(3-bromopropyl)-3,5-bis(trifluoromethyl)benzene (Compound 50-3)

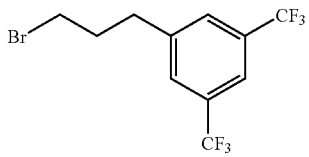

Compound 50-2 (3.48 g) was dissolved in methylene chloride (45 ml), triphenylphosphine (3.73 g) and N-bromosuccinimide (2.5 g) were added under ice-cooling, and the mixture was stirred under ice-cooling for 1.5 hr. Water was added to the reaction mixture, and the mixture was extracted with methylene chloride, washed with saturated brine, and dried over anhydrous sodium sulfate. The solvent was evaporated under reduced pressure. Diethyl ether was added, and the precipitated triphenylphosphine oxide was filtered off. The concentrate of the filtrate was purified by silica gel column chromatography (hexane alone) to give the object product (3.27 g) as a yellow oil.

$^1$H-NMR(DMSO-$d_6$) δ (ppm): 2.18(2H, quint, J=6.8 Hz), 2.92(2H, t, J=7.9 Hz), 3.53(2H, t, J=6.8 Hz), 7.93(1H, s), 7.98(2H, s).

(50-4) Synthesis of 2-amino-2-[2-(4-{3-[3,5-bis(trifluoromethyl)phenyl]propoxy}-3-trifluoromethylphenyl)ethyl]propane-1,3-diol hydrochloride (Compound 50-4)

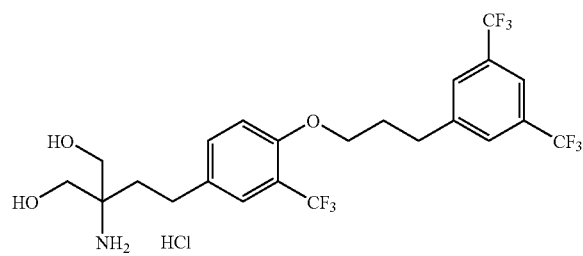

Reference Example compound 2-6 (500 mg) was dissolved in N,N-dimethylformamide (10 ml), potassium carbonate (494 mg) and compound 50-3 (480 mg) were added, and the mixture was stirred at 80° C. for 2 hr. Water was added to the reaction mixture, and the mixture was extracted with ethyl acetate, washed with water and saturated brine, and dried over anhydrous sodium sulfate. The solvent was evaporated under reduced pressure. The obtained pale-yellow oil was dissolved in ethanol (15 ml), concentrated hydrochloric acid (1.5 ml) was added, and the mixture was stirred at 80° C. for 1 hr. The reaction mixture was concentrated, and the residue was washed with diethyl ether to give the object product (630 mg) as a white powder.

MS(ESI)m/z: 534[M+H]

$^1$H-NMR(DMSO-$d_6$) δ (ppm): 1.73-1.78(2H, m), 2.10-2.13(2H, m), 2.57-2.61(2H, m), 2.95(2H, t, J=7.4 Hz), 3.51 (4H, d, J=5.1 Hz), 4.05(2H, t, J=6.0 Hz), 5.39(2H, t, J=5.0 Hz), 7.17(1H, d, J=8.4 Hz), 7.43(1H, d, J=8.6 Hz), 7.47(1H, s), 7.77(3H, brs), 7.92(3H, s).

Example 51

2-amino-2-{2-[3-difluoromethyl-4-(3-phenylpropoxy)phenyl]ethyl}propane-1,3-diol hydrochloride

(51-1) Synthesis of 2-benzyloxy-5-bromobenzaldehyde (Compound 51-1)

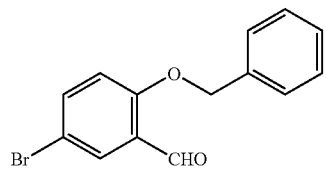

To a suspension of 5-bromosalicylaldehyde (25.0 g) and potassium carbonate (51.4 g) in N,N-dimethylformamide (250 ml) was added benzyl bromide (15.4 ml) under ice-cooling, and the mixture was stirred under ice-cooling for 40 min, and further at room temperature for 15 hr. The reaction mixture was added to water, and the mixture was extracted with ethyl acetate, washed with 0.1M aqueous sodium hydroxide solution and then saturated brine, and dried over anhydrous magnesium sulfate. The solvent was evaporated under reduced pressure, and the obtained residue was suspended in hexane (200 ml) and collected by filtration to give the object product (32.7 g) as a pale-yellow powder.

$^1$H-NMR(CDCl$_3$) δ (ppm): 5.19(2H, s), 6.95(1H, d, J=8.8 Hz), 7.34-7.43(5H, m), 7.61(1H, dd, J=2.8, 8.8 Hz), 7.95(1H, d, J=2.8 Hz), 10.46(1H, s).

(51-2) Synthesis of 1-benzyloxy-4-bromo-2-difluoromethylbenzene (Compound 51-2)

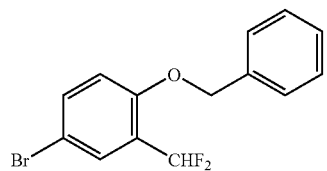

To a solution of compound 51-1 (2.70 g) in methylene chloride (5 ml) was added a solution of diethylaminosulfur trifluoride (DAST, 1.66 g) in methylene chloride (5 ml), and the mixture was stirred at room temperature for 21 hr. The reaction mixture was added to water, and the mixture was extracted with methylene chloride. The organic layer was washed with saturated brine, and dried over anhydrous magnesium sulfate. The solvent was evaporated under reduced pressure, and the obtained residue was purified by silica gel chromatography to give the object product (2.16 g) as a colorless oil.

$^1$H-NMR(CDCl$_3$) δ (ppm): 5.11(2H, s), 6.86(1H, d, J=9.1 Hz), 6.95(1H, t, J=55.3 Hz), 7.33-7.42(5H, m), 7.49(1H, dd, J=1.6, 9.8 Hz), 7.69(1H, d, J=1.9 Hz).

(51-3) Synthesis of {5-[(4-benzyloxy-3-difluoromethylphenyl)ethynyl]-2,2-dimethyl-1,3-dioxan-5-yl}carbamic acid t-butyl ester (Compound 51-3)

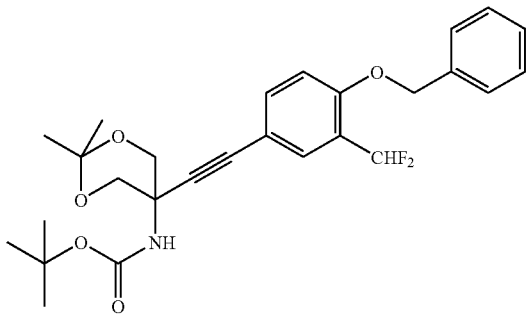

Compound 51-2 (9.48 g), (5-ethynyl-2,2-dimethyl-1,3-dioxan-5-yl)carbamic acid t-butyl ester (7.34 g) synthesized according to the known method (e.g., Tetrahedron vol. 57 (2001) 15 pages 6531-6538), 2-dicyclohexylphosphino-2',4',6'-triisopropylbiphenyl (868 mg), bis(acetonitrile)palladium (II) dichloride (157 mg) and cesium carbonate (25.6 g) were stirred in acetonitrile (200 ml) at 80° C. for 8 hr. Water was added to the reaction mixture, and the mixture was extracted with ethyl acetate, washed with saturated brine, and dried over anhydrous sodium sulfate. The solvent was evaporated under reduced pressure. The residue was purified by silica gel column chromatography to give the object product (11.1 g) as a pale-brown oil.

$^1$H-NMR(CDCl$_3$) δ (ppm): 1.45(3H, s), 1.48(9H, s), 1.50 (3H, s), 4.03(2H, d, J=11.2 Hz), 4.10(2H, d, J=11.2 Hz), 5.13(2H, s), 5.20(1H, brs), 6.91(1H, d, J=8.6 Hz), 6.94(1H, t, J=55.4 Hz), 7.33-7.40(5H, m), 7.46(1H, d, J=8.6 Hz), 7.65 (1H, s).

(51-4) Synthesis of {5-[2-(3-difluoromethyl-4-hydroxyphenyl)ethyl]-2,2-dimethyl-1,3-dioxan-5-yl}carbamic acid t-butyl ester (Compound 51-4)

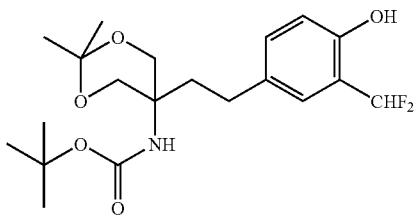

Compound 51-3 (11.1 g) was dissolved in 1,4-dioxane (250 ml), 10% palladium carbon (3.5 g) was added, and the mixture was stirred under a hydrogen atmosphere at room temperature for 3.5 hr. The reaction container was purged with nitrogen, the solution was filtered, and the filtrate was concentrated. The residue was suspended in a mixed solution of diisopropyl ether and hexane and collected by filtration to give the object product (8.17 g) as a white powder.

$^1$H-NMR(CDCl$_3$) δ (ppm): 1.43(3H, s), 1.44(3H, s), 1.48 (9H, s), 1.92-1.96(2H, m), 2.50-2.54(2H, m), 3.69(2H, d, J=11.7 Hz), 3.89(2H, d, J=11.7 Hz), 5.03(1H, brs), 5.57(1H, brs), 6.77(1H, d, J=8.4 Hz), 6.84(1H, t, J=55.5 Hz), 7.12(1H, d, J=8.4 Hz), 7.23(1H, s).

(51-5) Synthesis of 2-amino-2-{2-[3-difluoromethyl-4-(3-phenylpropoxy)phenyl]ethyl}propane-1,3-diol hydrochloride (Compound 51-5)

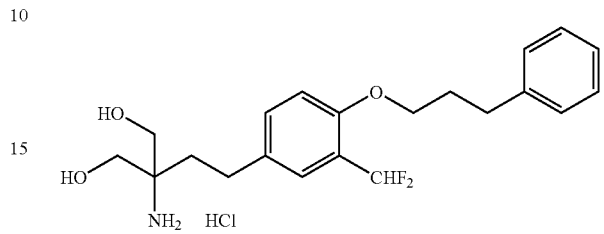

Compound 51-4 (600 mg) was dissolved in N,N-dimethylformamide (10 ml), sodium hydride (66 mg) and 3-phenylpropylbromide (0.272 ml) were added, and the mixture was stirred under ice-cooling for 1 hr, and at room temperature for 2 hr. Water was added to the reaction mixture, and the mixture was extracted with ethyl acetate, washed with water and saturated brine, and dried over anhydrous magnesium sulfate. The solvent was evaporated under reduced pressure. To a solution of the obtained residue in ethanol (15 ml) was added concentrated hydrochloric acid (1.5 ml), and the mixture was stirred at 80° C. for 1 hr. The reaction mixture was concentrated, and the residue was washed with diethyl ether to give a white powder. The white powder was purified by HPLC, the obtained residue was converted to hydrochloride by the addition of hydrogen chloride containing ether (1 mol/l, 10 ml), and the precipitate was collected by filtration and dried to give the object product (98 mg) as a white powder.

MS(ESI)m/z: 380[M+H]

$^1$H-NMR(DMSO-d$_6$) δ (ppm): 1.73-1.78(2H, m), 2.00-2.08(2H, m), 2.56-2.62(2H, m), 2.75(2H, t, J=7.5 Hz), 3.52 (4H, d, J=4.8 Hz), 4.01(2H, t, J=6.1 Hz), 5.39(2H, J=4.6 Hz), 7.04(1H, d, J=8.6 Hz), 7.06(1H, t, J=51.9 Hz), 7.15-7.25(3H, m), 7.26-7.33(3H, m), 7.37(1H, brs), 7.79(3H, brs).

Example 52

2-amino-2-(2-{5-[3-(4-trifluoromethoxyphenyl)propoxy]-3-trifluoromethylphenyl}ethyl)propane-1,3-diol hydrochloride (52-1) Synthesis of 3-(4-trifluoromethoxyphenyl)-2-propyne-1-ol (Compound 52-1)

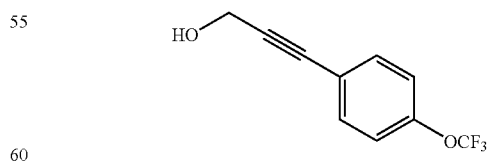

A mixture of 1-iodo-4-(trifluoromethoxy)benzene (5.00 g), copper(I) iodide (66.3 mg), triphenylphosphine (228 mg), tris(dibenzylideneacetone)dipalladium(0) chloroform adduct (360 mg), propargyl alcohol (1.13 ml), diisopropylethylamine (12.1 ml) and tetrahydrofuran (100 ml) was stirred at room temperature for 21 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=99:1-80:20) to give the object product (3.46 g) as a brown oil.

¹H-NMR(CDCl₃) δ (ppm): 1.73(1H, t, J=6.1 Hz), 4.50(2H, d, J=6.4 Hz), 7.16(2H, d, J=8.2 Hz), 7.46(2H, d, J=8.6 Hz).

(52-2) Synthesis of 3-(4-trifluoromethoxyphenyl)-1-propanol (Compound 52-2)

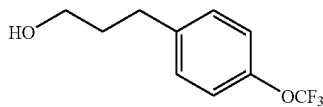

A solution of compound 52-1 (3.46 g) and 10% palladium carbon (0.80 g) in 1,4-dioxane (70 ml) was stirred under a hydrogen atmosphere at room temperature for 24 hr. The reaction mixture was filtered through celite and concentrated to give the object product (3.33 g) as a brown oil.

¹H-NMR(CDCl₃) δ (ppm): 1.29(1H, brs), 1.85-1.92(2H, m), 2.72(2H, t, J=7.8 Hz), 3.68(2H, t, J=6.3 Hz), 7.13(2H, d, J=8.2 Hz), 7.21(2H, d, J=8.6 Hz).

(52-3) Synthesis of 1-(3-bromopropyl)-4-trifluoromethoxybenzene (Compound 52-3)

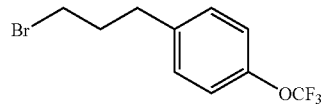

Compound 52-2 (3.33 g) was dissolved in methylene chloride (30 ml), triphenylphosphine (4.35 g) and N-bromosuccinimide (2.95 g) were added under ice-cooling, and the mixture was stirred under ice-cooling for 1 hr, and further at room temperature for 3 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (1.39 g) as a yellow oil.

¹H-NMR(CDCl₃) δ (ppm): 2.12-2.19(2H, m), 2.79(2H, t, J=7.4 Hz), 3.39(2H, t, J=6.5 Hz), 7.14(2H, d, J=8.3 Hz), 7.22(2H, d, J=8.6 Hz).

(52-4) Synthesis of [2,2-dimethyl-5-(2-{4-[3-(4-trifluoromethoxyphenyl)propoxy]-3-trifluoromethylphenyl}ethyl)-1,3-dioxan-5-yl]carbamic acid t-butyl ester (Compound 52-4)

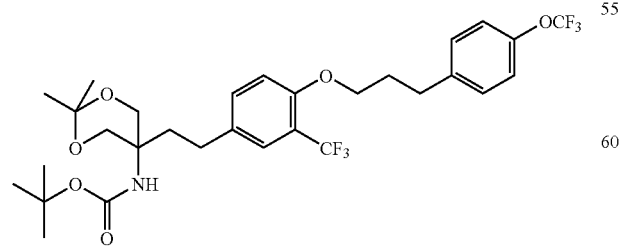

Reference Example compound 2-6 (500 mg) was dissolved in N,N-dimethylformamide (10 ml), potassium carbonate (494 mg) and compound 52-3 (405 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (790 mg) as a pale-yellow oil.

¹H-NMR(CDCl₃) δ (ppm): 1.43(3H, s), 1.44(3H, s), 1.47 (9H, s), 1.93-1.98(2H, m), 2.05-2.13(2H, m), 2.52-2.56(2H, m), 2.84(2H, t, J=7.5 Hz), 3.69(2H, d, J=11.7 Hz), 3.89(2H, d, J=11.7 Hz), 3.98(2H, t, J=5.9 Hz), 4.99(1H, brs), 6.84(1H, d, J=8.5 Hz), 7.10-7.14(2H, m), 7.19-7.22(2H, m), 7.26-7.28 (1H, m), 7.37(1H, d, J=1.6 Hz).

(52-5) Synthesis of 2-amino-2-(2-{4-[3-(4-trifluoromethoxyphenyl)propoxy]-3-trifluoromethylphenyl}ethyl)propane-1,3-diol hydrochloride (Compound 52-5)

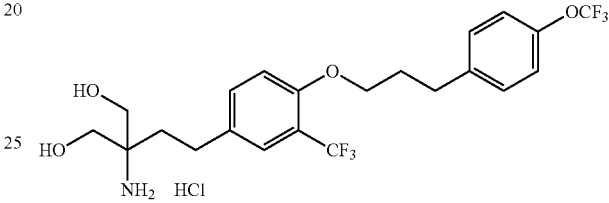

Compound 52-4 (790 mg) was dissolved in ethanol (15 ml), concentrated hydrochloric acid (1.5 ml) was added, and the mixture was stirred at 80° C. for 2 hr. The reaction mixture was concentrated, and the residue was washed with diethyl ether to give the object product (600 mg) as a white powder.

MS(ESI)m/z: 482[M+H]

¹H-NMR(DMSO-d₆) δ (ppm): 1.74-1.80(2H, m), 1.98-2.07(2H, m), 2.59-2.64(2H, m), 2.78(2H, t, J=7.5 Hz), 3.52 (4H, d, J=4.6 Hz), 4.05(2H, t, J=6.1 Hz), 5.40(2H, t, J=5.0 Hz), 7.17(1H, d, J=8.5 Hz), 7.26-7.34(4H, m), 7.45(1H, d, J=8.5 Hz), 7.48(1H, brs), 7.85(3H, brs).

Example 53

2-amino-2-(2-{4-[3-(3,4-difluorophenyl)propoxy]-3-trifluoromethylphenyl}ethyl)propane-1,3-diol hydrochloride (53-1) Synthesis of 3-(3,4-difluorophenyl)-2-propyne-1-ol (Compound 53-1)

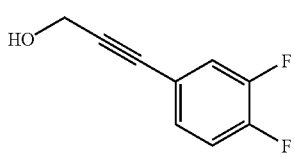

A mixture of 3,4-difluoroiodobenzene (5.00 g), copper(I) iodide (79.4 mg), triphenylphosphine (273 mg), tris(dibenzylideneacetone)dipalladium(0) chloroform adduct (432 mg), propargyl alcohol (1.35 ml), diisopropylethylamine (14.5 ml) and tetrahydrofuran (100 ml) was stirred at room temperature for 15 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=100:0-80:20) to give the object product (3.25 g) as a brown oil.

$^1$H-NMR(CDCl$_3$) δ (ppm): 1.69(1H, t, J=6.2 Hz), 4.48(2H, d, J=6.2 Hz), 7.10(1H, dt, J=10.0, 8.2 Hz), 7.16-7.19(1H, m), 7.22-7.27(1H, m).

(53-2) Synthesis of 3-(3,4-difluorophenyl)-1-propanol (Compound 53-2)

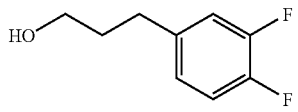

A solution of compound 53-1 (3.25 g) and 10% palladium carbon (0.75 g) in 1,4-dioxane (70 ml) was stirred under a hydrogen atmosphere at room temperature for 10 hr. The reaction mixture was filtered through celite and concentrated to give the object product (3.12 g) as a brown oil.

$^1$H-NMR(CDCl$_3$) δ (ppm): 1.28(1H, brs), 1.83-1.90(2H, m), 2.68(2H, t, J=7.7 Hz), 3.64-3.68(2H, m), 6.88-6.91(1H, m), 6.97-7.03(1H, m), 7.06(1H, dt, J=10.5, 8.2 Hz).

(53-3) Synthesis of 1-(3-bromopropyl)-3,4-difluorobenzene (Compound 53-3)

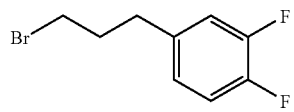

Compound 53-2 (3.11 g) was dissolved in methylene chloride (60 ml), triphenylphosphine (5.21 g) and N-bromosuccinimide (3.54 g) were added under ice-cooling, and the mixture was stirred under ice-cooling for 2 hr. Water was added to the reaction mixture, and the mixture was extracted with methylene chloride and washed with saturated brine, and dried over anhydrous sodium sulfate. The solvent was evaporated under reduced pressure. Diethyl ether was added, and the precipitated triphenylphosphine oxide was filtered off. The concentrate of the filtrate was purified by silica gel column chromatography (hexane alone) to give the object product (3.6 g) as a yellow oil.

$^1$H-NMR(DMSO-d$_6$) δ (ppm): 2.06-2.13(2H, m), 2.71(2H, t, J=7.8 Hz), 3.50(2H, t, J=6.7 Hz), 7.05-7.08(1H, m), 7.28-7.34(2H, m).

(53-4) Synthesis of 2-amino-2-(2-{4-[3-(3,4-difluorophenyl)propoxy]-3-trifluoromethylphenyl}ethyl)propane-1,3-diol hydrochloride (Compound 53-4)

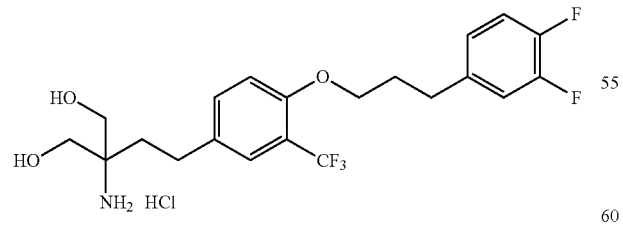

Reference Example compound 2-6 (500 mg) was dissolved in N,N-dimethylformamide (10 ml), potassium carbonate (494 mg) and compound 53-3 (340 mg) were added, and the mixture was stirred at 80° C. for 1.5 hr. Water was added to the reaction mixture, and the mixture was extracted with ethyl acetate, washed with water and saturated brine, and dried over anhydrous sodium sulfate. The solvent was evaporated under reduced pressure. The obtained colorless oil was dissolved in ethanol (15 ml), concentrated hydrochloric acid (1.5 ml) was added, and the mixture was stirred at 80° C. for 1 hr. The reaction mixture was concentrated, and the residue was washed with diethyl ether to give the object product (475 mg) as a white powder.

MS(ESI)m/z: 434[M+H]

$^1$H-NMR(DMSO-d$_6$) δ (ppm): 1.74-1.79(2H, m), 1.99-2.06(2H, m), 2.59-2.63(2H, m), 2.74(2H, t, J=7.4 Hz), 3.52 (4H, d, J=5.2 Hz), 4.04(2H, t, J=6.1 Hz), 5.40(2H, t, J=5.2 Hz), 7.01-7.04(1H, m), 7.17(1H, d, J=8.5 Hz), 7.26-7.37(2H, m), 7.44(1H, d, J=8.6 Hz), 7.48(1H, d, J=1.4 Hz), 7.87(3H, brs).

Example 54

2-amino-2-(2-{4-[3-(3-chloro-2-methylphenyl)propoxy]-3-trifluoromethylphenyl}ethyl)propane-1,3-diol hydrochloride (54-1) Synthesis of 3-(3-chloro-2-methylphenyl)-2-propyne-1-ol (Compound 54-1)

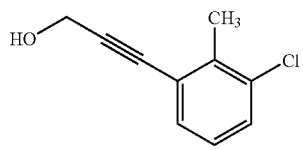

A mixture of 2-chloro-6-iodotoluene (5.00 g), copper(I) iodide (75.4 mg), triphenylphosphine (260 mg), tris(dibenzylideneacetone)dipalladium(0) chloroform adduct (410 mg), propargyl alcohol (1.29 ml), diisopropylethylamine (13.8 ml) and tetrahydrofuran (100 ml) was stirred at room temperature for 25 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=100:0-80:20) to give the object product (2.58 g) as a brown oil.

$^1$H-NMR(CDCl$_3$) δ (ppm): 1.74(1H, t, J=5.6 Hz), 2.50(3H, s), 4.54(2H, d, J=5.6 Hz), 7.07(1H, t, J=7.9 Hz), 7.31-7.33 (2H, m).

(54-2) Synthesis of 3-(3-chloro-2-methylphenyl)-1-propanol (Compound 54-2)

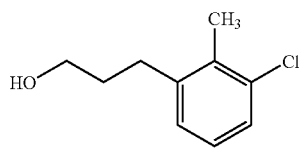

A suspension of Compound 54-1 (2.58 g) and chlorotris (triphenylphosphine)rhodium(I) (1.50 g) in toluene (80 ml) was stirred under a hydrogen atmosphere at 60° C. for 11 hr. The reaction mixture was filtered through celite and concentrated. The obtained residue was purified by silica gel column chromatography (hexane:ethyl acetate=99:1-80:20) to give the object product (2.11 g) as a brown oil.

$^1$H-NMR(CDCl$_3$) δ (ppm): 1.34(1H, brs), 1.80-1.87(2H, m), 2.36(3H, s), 2.75(2H, t, J=7.8 Hz), 3.70(2H, t, J=6.4 Hz), 7.02-7.07(2H, m), 7.20-7.24(1H, m).

(54-3) Synthesis of 1-(3-bromopropyl)-3-chloro-2-methylbenzene (Compound 54-3)

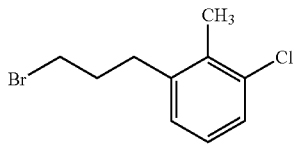

Compound 54-2 (2.10 g) was dissolved in methylene chloride (40 ml), triphenylphosphine (3.30 g) and N-bromosuccinimide (2.23 g) were added under ice-cooling, and the mixture was stirred under ice-cooling for 2 hr. Water was added to the reaction mixture, and the mixture was extracted with methylene chloride and washed with saturated brine, and dried over anhydrous sodium sulfate. The solvent was evaporated under reduced pressure. Diethyl ether was added, and the precipitated triphenylphosphine oxide was filtered off. The concentrate of the filtrate was purified by silica gel column chromatography (hexane alone) to give the object product (2.56 g) as a colorless oil.

$^1$H-NMR(DMSO-d$_6$) δ (ppm): 1.99-2.06(2H, m), 2.32(3H, s), 2.77(2H, t, J=7.8 Hz), 3.56(2H, t, J=6.5 Hz), 7.14-7.15(2H, m), 7.26-7.30(1H, m).

(54-4) Synthesis of 2-amino-2-(2-{4-[3-(3-chloro-2-methylphenyl)propoxy]-3-trifluoromethylphenyl}ethyl)propane-1,3-diol hydrochloride (Compound 54-4)

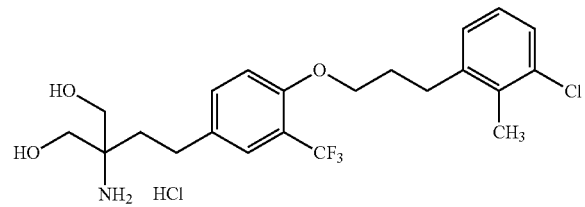

Reference Example compound 2-6 (500 mg) was dissolved in N,N-dimethylformamide (10 ml), potassium carbonate (494 mg) and compound 54-3 (355 mg) were added, and the mixture was stirred at 80° C. for 2 hr. Water was added to the reaction mixture, and the mixture was extracted with ethyl acetate, washed with water and saturated brine, and dried over anhydrous sodium sulfate. The solvent was evaporated under reduced pressure. The obtained white solid was dissolved in ethanol (15 ml), concentrated hydrochloric acid (1.5 ml) was added, and the mixture was stirred at 80° C. for 1 hr. The reaction mixture was concentrated, and the residue was washed with diethyl ether to give the object product (535 mg) as a white powder.

MS(ESI)m/z: 446[M+H]

$^1$H-NMR(DMSO-d$_6$) δ (ppm): 1.74-1.79(2H, m), 1.92-1.98(2H, m), 2.31(3H, s), 2.58-2.63(2H, m), 2.82(2H, t, J=7.6 Hz), 3.52(4H, d, J=5.2 Hz), 4.09(2H, t, J=5.8 Hz), 5.40(2H, t, J=5.2 Hz), 7.13(1H, s), 7.14(1H, d, J=3.6 Hz), 7.18(1H, d, J=8.6 Hz), 7.28(1H, q, J=3.2 Hz), 7.45(1H, d, J=8.6 Hz), 7.48(1H, s), 7.81(3H, brs).

Example 55

2-amino-2-(2-{4-[3-(3-chloro-4-methylphenyl)propoxy]-3-trifluoromethylphenyl}ethyl)propane-1,3-diol hydrochloride (55-1) Synthesis of 3-(3-chloro-4-methylphenyl)-2-propyne-1-ol (Compound 55-1)

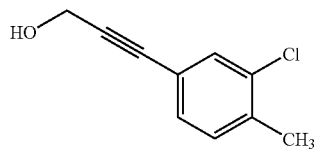

A mixture of 2-chloro-4-iodotoluene (5.00 g), copper(I) iodide (75.4 mg), triphenylphosphine (260 mg), tris(dibenzylideneacetone)dipalladium(0) chloroform adduct (410 mg), propargyl alcohol (1.29 ml), diisopropylethylamine (13.8 ml) and tetrahydrofuran (100 ml) was stirred at room temperature for 25 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=100:0-80:20) to give the object product (2.80 g) as a brown oil.

$^1$H-NMR(CDCl$_3$) δ (ppm): 1.65(1H, t, J=6.2 Hz), 2.37(3H, s), 4.48(2H, d, J=6.2 Hz), 7.16(1H, d, J=7.9 Hz), 7.22(1H, d, J=7.9 Hz), 7.42(1H, d, J=1.2 Hz).

(55-2) Synthesis of 3-(3-chloro-4-methylphenyl)-1-propanol (Compound 55-2)

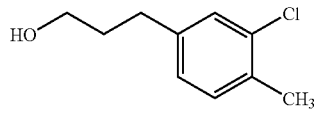

A suspension of compound 55-1 (2.80 g) and chlorotris(triphenylphosphine)rhodium(I) (1.50 g) in toluene (80 ml) was stirred under a hydrogen atmosphere at 60° C. for 11 hr. The reaction mixture was filtered through celite and concentrated. The obtained residue was purified by silica gel column chromatography (hexane:ethyl acetate=99:1-75:25) to give the object product (2.35 g) as a brown oil.

$^1$H-NMR(CDCl$_3$) δ (ppm): 1.29(1H, brs), 1.83-1.90(2H, m), 2.33(3H, s), 2.66(2H, t, J=7.7 Hz), 3.67(2H, t, J=6.2 Hz), 6.99(1H, dd, J=1.2, 7.8 Hz), 7.13(1H, d, J=7.8 Hz), 7.18(1H, d, J=1.2 Hz).

(55-3) Synthesis of 1-(3-bromopropyl)-3-chloro-4-methylbenzene (Compound 55-3)

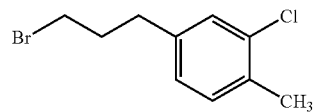

Compound 55-2 (2.34 g) was dissolved in methylene chloride (40 ml), triphenylphosphine (3.66 g) and N-bromosuccinimide (2.48 g) were added under ice-cooling, and the mixture was stirred under ice-cooling for 3 hr. Water was added to the reaction mixture, and the mixture was extracted with methylene chloride and washed with saturated brine, and dried over anhydrous sodium sulfate. The solvent was evaporated under reduced pressure. Diethyl ether was added, and the precipitated triphenylphosphine oxide was filtered off. The concentrate of the filtrate was purified by silica gel column chromatography (hexane alone) to give the object product (2.88 g) as a colorless oil.

$^1$H-NMR(DMSO-$d_6$) δ (ppm): 2.04-2.11(2H, m), 2.28(3H, s), 2.67(2H, t, J=7.8 Hz), 3.48(2H, t, J=6.6 Hz), 7.09(1H, dd, J=7.8, 1.8 Hz), 7.26(1H, d, J=7.8 Hz), 7.27(1H, s).

(55-4) Synthesis of 2-amino-2-(2-{4-[3-(3-chloro-4-methylphenyl)propoxy]-3-trifluoromethylphenyl}ethyl)propane-1,3-diol hydrochloride (Compound 55-4)

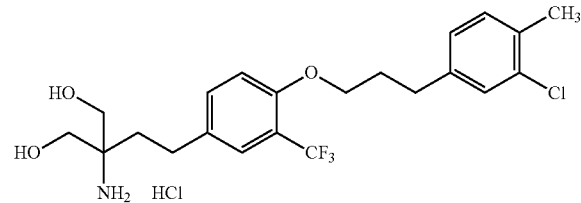

Reference Example compound 2-6 (500 mg) was dissolved in N,N-dimethylformamide (10 ml), potassium carbonate (494 mg) and compound 55-3 (355 mg) were added, and the mixture was stirred at 80° C. for 3 hr. Water was added to the reaction mixture, and the mixture was extracted with ethyl acetate, washed with water and saturated brine, and dried over anhydrous sodium sulfate. The solvent was evaporated under reduced pressure. The obtained colorless oil was dissolved in ethanol (15 ml), concentrated hydrochloric acid (1.5 ml) was added, and the mixture was stirred at 80° C. for 1 hr. The reaction mixture was concentrated, and the residue was washed with diethyl ether to give the object product (458 mg) as a white powder.

MS(ESI)m/z: 446[M+H]

$^1$H-NMR(DMSO-$d_6$) δ (ppm): 1.74-1.78(2H, m), 1.97-2.04(2H, m), 2.28(3H, s), 2.57-2.62(2H, m), 2.71(2H, t, J=7.6 Hz), 3.51(4H, d, J=5.0 Hz), 4.02(2H, t, J=6.1 Hz), 5.39(2H, t, J=5.0 Hz), 7.06(1H, d, J=7.8 Hz), 7.16(1H, d, J=8.5 Hz), 7.24(1H, s), 7.25(1H, d, J=8.1 Hz), 7.43(1H, d, J=8.5 Hz), 7.47(1H, d, J=1.5 Hz), 7.78(3H, brs).

Example 56

2-amino-2-(2-{4-[3-(1-indanon-5-yl)propoxy]-3-trifluoromethylphenyl}ethyl)propane-1,3-diol hydrochloride (56-1) Synthesis of 1-(1-indanon-5-yl)-3-(tetrahydro-2H-pyran-2-yloxy)-1-propyne (Compound 56-1)

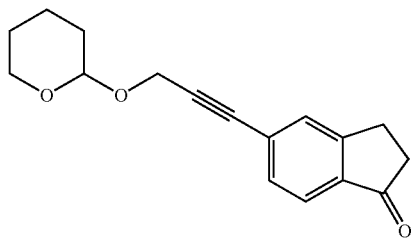

A mixture of 5-bromo-1-indanone (10.0 g), cesium carbonate (40.3 g), 2-(2-propynyloxy)tetrahydropyran (10.0 ml), 2-dicyclohexylphosphino-2',4',6'-triisopropylbiphenyl (1.40 g), bis(acetonitrile)palladium(II) dichloride (246 mg) and acetonitrile (200 ml) was stirred at 90° C. for 6 hr. The reaction mixture was added to water, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=3:1-2:1) to give the object product (7.87 g) as a brown oil.

$^1$H-NMR(CDCl$_3$) δ (ppm): 1.53-1.91(6H, m), 2.69-2.72 (2H, m), 3.12(2H, t, J=6.0 Hz), 3.55-3.60(1H, m), 3.86-3.93 (1H, m), 4.48(1H, d, J=15.9 Hz), 4.55(1H, d, J=15.9 Hz), 4.90(1H, t, J=3.3 Hz), 7.43(1H, d, J=7.9 Hz), 7.55(1H, s), 7.69(1H, d, J=7.9 Hz).

(56-2) Synthesis of 3-(1-indanon-5-yl)-1-propanol (Compound 56-2)

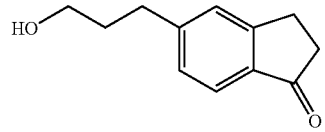

A solution of compound 56-1 (7.87 g) and 10% palladium carbon (3.00 g) in ethyl acetate (50 ml) was stirred under a hydrogen atmosphere at room temperature for 12 hr. The reaction mixture was filtered through celite and concentrated. The residue was purified by silica gel column chromatography to give 1-(1-indanon-5-yl)-3-(tetrahydro-2H-pyran-2-yloxy)propane (6.24 g) as a yellow oil. A solution of 2.02 g of the yellow oil and p-toluenesulfonic acid monohydrate (10.0 mg) in methanol (30 ml) was stirred at room temperature for 6 hr. To the reaction mixture was added saturated aqueous sodium hydrogen carbonate, and methanol was evaporated under reduced pressure. Water was added to the obtained mixture, and the mixture was extracted with ethyl acetate. The organic layer was washed with saturated brine and dried over anhydrous magnesium sulfate, and the solvent was concentrated under reduced pressure. The residue was purified by silica gel column chromatography (hexane:ethyl acetate=1:1-1:4) to give the object product (1.15 g) as a brown oil.

$^1$H-NMR(CDCl$_3$) δ (ppm): 1.32(1H, t, J=5.1 Hz), 1.89-1.96(2H, m), 2.67-2.70(2H, m), 2.81(2H, t, J=7.6 Hz), 3.09-3.13(2H, m), 3.67-3.72(2H, m), 7.22(1H, d, J=7.9 Hz), 7.31 (1H, s), 7.69(1H, d, J=7.9 Hz).

(56-3) Synthesis of 5-(3-bromopropyl)-1-indanone (Compound 56-3)

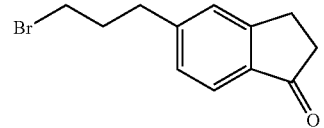

Compound 56-2 (1.15 g) was dissolved in methylene chloride (20 ml), triphenylphosphine (1.74 g) and N-bromosuccinimide (1.18 g) were added under ice-cooling, and the mixture was stirred under ice-cooling for 2 hr, and further at room temperature for 15 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography to give the object product (430 mg) as a yellow oil.

$^1$H-NMR(CDCl$_3$) δ (ppm): 2.16-2.24(2H, m), 2.67-2.73 (2H, m), 2.87(2H, t, J=7.4 Hz), 3.12(2H, t, J=5.9 Hz), 3.40 (2H, t, J=6.5 Hz), 7.22(1H, d, J=7.9 Hz), 7.31(1H, s), 7.70 (1H, d, J=7.9 Hz).

(56-4) Synthesis of [5-(2-{4-[3-(1-indanon-5-yl) propoxy]-3-trifluoromethylphenyl}ethyl)-2,2-dimethyl-1,3-dioxan-5-yl]carbamic acid t-butyl ester (Compound 56-4)

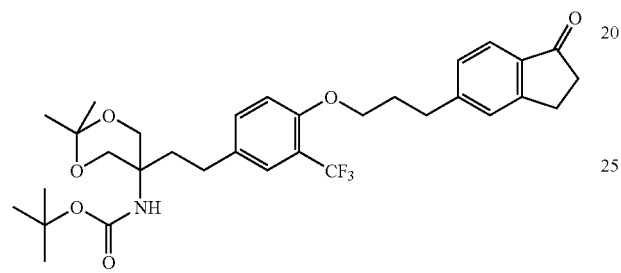

Reference Example compound 2-6 (500 mg) was dissolved in N,N-dimethylformamide (10 ml), potassium carbonate (494 mg) and compound 56-3 (430 mg) were added, and the mixture was stirred at 80° C. for 1 hr. Water was added to the reaction mixture, and the mixture was extracted with ethyl acetate, washed with water and saturated brine, and dried over anhydrous magnesium sulfate. The solvent was evaporated under reduced pressure to give the object product (840 mg) as a yellow oil.

$^1$H-NMR(CDCl$_3$) δ (ppm): 1.43(3H, s), 1.44(3H, s), 1.47 (9H, s), 1.93-1.99(2H, m), 2.12-2.17(2H, m), 2.52-2.57(2H, m), 2.66-2.71(2H, m), 2.92(2H, t, J=7.5 Hz), 3.08-3.14(2H, m), 3.69(2H, d, J=11.7 Hz), 3.89(2H, d, J=11.7 Hz), 4.00(2H, t, J=5.9 Hz), 4.98(1H, brs), 6.84(1H, d, J=8.5 Hz), 7.21(1H, d, J=7.8 Hz), 7.26-7.30(1H, m), 7.31(1H, s), 7.38(1H, d, J=1.4 Hz), 7.68(1H, d, J=7.8 Hz).

(56-5) Synthesis of 2-amino-2-(2-{4-[3-(1-indanon-5-yl)propoxy]-3-trifluoromethylphenyl}ethyl)propane-1,3-diol hydrochloride (Compound 56-5)

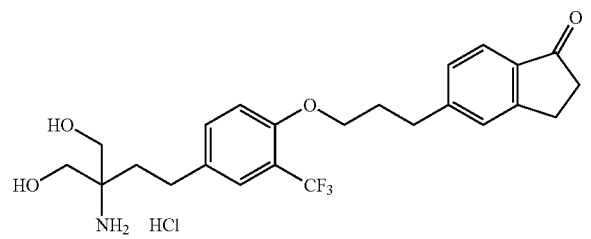

Compound 56-4 (840 mg) was dissolved in ethanol (15 ml), concentrated hydrochloric acid (1.5 ml) was added, and the mixture was stirred at 80° C. for 1 hr. The reaction mixture was concentrated, and the residue was washed with diethyl ether to give a white powder. The white powder was purified by HPLC, the obtained residue was converted to hydrochloride by adding hydrogen chloride containing ether (1 mol/l, 15 ml), and the precipitate was collected by filtration and dried to give the object product (410 mg) as a white powder.

MS(ESI)m/z: 452[M+H]

$^1$H-NMR(DMSO-d$_6$) δ (ppm): 1.74-1.79(2H, m), 2.04-2.08(2H, m), 2.59-2.63(4H, m), 2.85(2H, t, J=7.5 Hz), 3.06 (2H, t, J=5.8 Hz), 3.52(4H, d, J=4.6 Hz), 4.07(2H, t, J=6.0 Hz), 5.39(2H, t, J=4.9 Hz), 7.17(1H, d, J=8.6 Hz), 7.26(1H, d, J=7.8 Hz), 7.41-7.48(3H, m), 7.56(1H, d, J=7.8 Hz), 7.78(3H, brs).

Example 57

2-amino-2-(2-{4-[3-(2-chloro-5-trifluoromethylphenyl)propoxy]-3-trifluoromethylphenyl}ethyl)propane-1,3-diol hydrochloride (57-1) Synthesis of 3-(2-chloro-5-trifluoromethylphenyl)-2-propyne-1-ol (Compound 57-1)

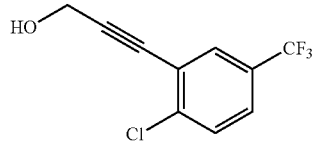

A mixture of 4-chloro-3-iodobenzotrifluoride (10.0 g), copper(I) iodide (124 mg), triphenylphosphine (428 mg), tris(dibenzylideneacetone)dipalladium(0) chloroform adduct (675 mg), propargyl alcohol (2.12 ml), diisopropylethylamine (22.6 ml) and tetrahydrofuran (180 ml) was stirred at room temperature for 15 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=99:1-80:20) to give the object product (7.63 g) as a brown oil.

$^1$H-NMR(CDCl$_3$) δ (ppm): 1.73(1H, t, J=6.3 Hz), 4.57(2H, d, J=6.3 Hz), 7.50(1H, dd, J=1.7, 8.5 Hz), 7.53(1H, d, J=8.5 Hz), 7.74(1H, d, J=1.7 Hz).

(57-2) Synthesis of 3-(2-chloro-5-trifluoromethylphenyl)-1-propanol (Compound 57-2)

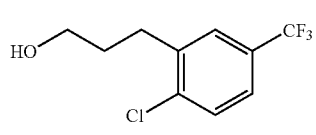

A suspension of compound 57-1 (7.63 g) and chlorotris (triphenylphosphine)rhodium(I) (2.00 g) in toluene (100 ml) was stirred under a hydrogen atmosphere at 60° C. for 10 hr. The reaction mixture was filtered through celite and concentrated. The obtained residue was purified by silica gel column chromatography (hexane:ethyl acetate=100:0-70:30) to give the object product (6.33 g) as a brown oil.

¹H-NMR(CDCl₃) δ (ppm): 1.37(1H, brs), 1.88-1.95(2H, m), 2.90(2H, t, J=7.8 Hz), 3.72(2H, brs), 7.41(1H, dd, J=1.7, 8.3 Hz), 7.46(1H, d, J=8.3 Hz), 7.51(1H, d, J=1.7 Hz).

(57-3) Synthesis of 1-(3-bromopropyl)-2-chloro-5-trifluoromethylbenzene (Compound 57-3)

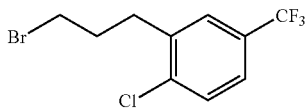

Compound 57-2 (6.32 g) was dissolved in methylene chloride (30 ml), triphenylphosphine (7.64 g) and N-bromosuccinimide (5.18 g) were added under ice-cooling, and the mixture was stirred under ice-cooling for 2 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (7.53 g) as a colorless oil.

¹H-NMR(CDCl₃) δ (ppm): 2.16-2.24(2H, m), 2.96(2H, t, J=7.5 Hz), 3.44(2H, t, J=6.4 Hz), 7.41-7.51(3H, m).

(57-4) Synthesis of [5-(2-{4-[3-(2-chloro-5-trifluoromethylphenyl)propoxy]-3-trifluoromethylphenyl}ethyl)-2,2-dimethyl-1,3-dioxan-5-yl]carbamic acid t-butyl ester (Compound 57-4)

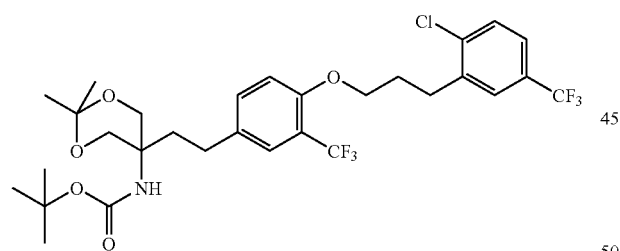

Reference Example compound 2-6 (500 mg) was dissolved in N,N-dimethylformamide (10 ml), potassium carbonate (494 mg) and compound 57-3 (431 mg) were added, and the mixture was stirred at 80° C. for 1.5 hr. Water was added to the reaction mixture, and the mixture was extracted with ethyl acetate, washed with water and saturated brine, and dried over anhydrous magnesium sulfate. The solvent was evaporated under reduced pressure to give the object product (870 mg) as a white solid.

¹H-NMR(CDCl₃) δ (ppm): 1.43(3H, s), 1.44(3H, s), 1.48 (9H, s), 1.93-1.99(2H, m), 2.10-2.17(2H, m), 2.52-2.57(2H, m), 3.10(2H, t, J=7.6 Hz), 3.69(2H, d, J=11.7 Hz), 3.89(2H, d, J=11.7 Hz), 4.03(2H, t, J=5.9 Hz), 5.00(1H, brs), 6.86(1H, d, J=8.4 Hz), 7.26-7.29(1H, m), 7.37-7.48(4H, m).

(57-5) Synthesis of 2-amino-2-(2-{4-[3-(2-chloro-5-trifluoromethylphenyl)propoxy]-3-trifluoromethylphenyl}ethyl)propane-1,3-diol hydrochloride (Compound 57-5)

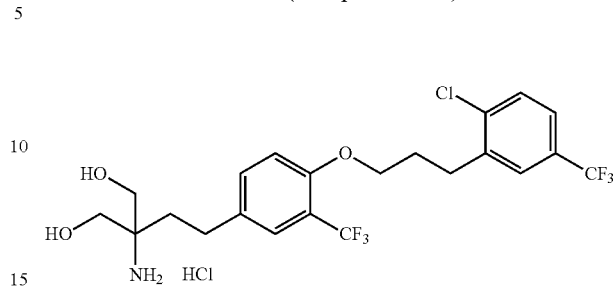

Compound 57-4 (870 mg) was dissolved in ethanol (15 ml), concentrated hydrochloric acid (1.5 ml) was added, and the mixture was stirred at 80° C. for 2 hr. The reaction mixture was concentrated, and the residue was washed with diethyl ether to give the object product (630 mg) as a white powder.

MS(ESI)m/z: 500[M+H]

¹H-NMR(DMSO-d₆) δ (ppm): 1.75-1.80(2H, m), 2.03-2.08(2H, m), 2.60-2.64(2H, m), 2.96(2H, t, J=7.5 Hz), 3.53 (4H, d, J=4.0 Hz), 4.10(2H, t, J=5.7 Hz), 5.41(2H, brs), 7.18 (1H, d, J=8.5 Hz), 7.46(1H, d, J=8.5 Hz), 7.49(1H, s), 7.60-7.70(3H, m), 7.86(3H, brs).

Example 58

2-amino-2-(2-{4-[3-(3-trifluoromethoxyphenyl)propoxy]-3-trifluoromethylphenyl}ethyl)propane-1,3-diol hydrochloride (58-1) Synthesis of 3-(3-trifluoromethoxyphenyl)-2-propyne-1-ol (Compound 58-1)

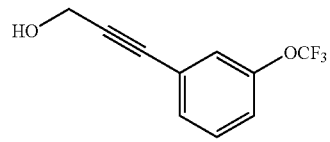

A mixture of 1-iodo-3-(trifluoromethoxy)benzene (5.00 g), copper(I) iodide (66.3 mg), triphenylphosphine (228 mg), tris(dibenzylideneacetone)dipalladium(0) chloroform adduct (360 mg), propargyl alcohol (1.13 ml), diisopropylethylamine (12.1 ml) and tetrahydrofuran (100 ml) was stirred at room temperature for 15 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=100:0-80:20) to give the object product (3.28 g) as a brown oil.

¹H-NMR(CDCl₃) δ (ppm): 1.71(1H, t, J=6.2 Hz), 4.51(2H, d, J=6.2 Hz), 7.18-7.20(1H, m), 7.29(1H, brs), 7.34(1H, t, J=7.6 Hz), 7.36-7.38(1H, m).

(58-2) Synthesis of 3-(3-trifluoromethoxyphenyl)-1-propanol (Compound 58-2)

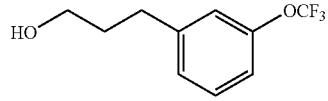

A solution of compound 58-1 (3.28 g) and 10% palladium carbon (0.75 g) in 1,4-dioxane (70 ml) was stirred under a hydrogen atmosphere at room temperature for 10 hr. The reaction mixture was filtered through celite and concentrated to give the object product (3.17 g) as a brown oil.

$^1$H-NMR(CDCl$_3$) δ (ppm): 1.30(1H, brs), 1.86-1.93(2H, m), 2.74(2H, t, J=7.8 Hz), 3.68(2H, t, J=6.0 Hz), 7.04-7.06 (2H, m), 7.13(1H, d, J=7.6 Hz), 7.28-7.32(1H, m).

(58-3) Synthesis of 1-(3-bromopropyl)-3-trifluoromethoxybenzene (Compound 58-3)

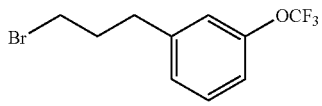

Compound 58-2 (3.15 g) was dissolved in methylene chloride (50 ml), triphenylphosphine (4.13 g) and N-bromosuccinimide (2.79 g) were added under ice-cooling, and the mixture was stirred under ice-cooling for 1 hr, and further at room temperature for 3 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (3.54 g) as a yellow oil.

$^1$H-NMR(CDCl$_3$) δ (ppm): 2.13-2.20(2H, m), 2.80(2H, t, J=7.4 Hz), 3.39(2H, t, J=6.4 Hz), 7.05-7.08(2H, m), 7.14(1H, d, J=7.7 Hz), 7.31(1H, t, J=7.7 Hz).

(58-4) Synthesis of [2,2-dimethyl-5-(2-{4-[3-(3-trifluoromethoxyphenyl)propoxy]-3-trifluoromethylphenyl}ethyl)-1,3-dioxan-5-yl]carbamic acid t-butyl ester (Compound 58-4)

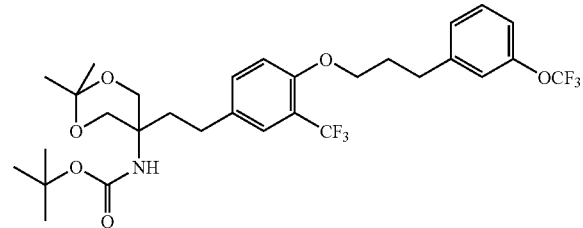

Reference Example compound 2-6 (500 mg) was dissolved in N,N-dimethylformamide (10 ml), potassium carbonate (494 mg) and compound 58-3 (405 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (790 mg) as a white solid.

$^1$H-NMR(CDCl$_3$) δ (ppm): 1.43(3H, s), 1.44(3H, s), 1.47 (9H, s), 1.93-1.98(2H, m), 2.08-2.15(2H, m), 2.52-2.57(2H, m), 2.86(2H, t, J=7.5 Hz), 3.69(2H, d, J=11.8 Hz), 3.89(2H, d, J=11.8 Hz), 3.98(2H, t, J=5.9 Hz), 4.99(1H, brs), 6.83(1H, d, J=8.4 Hz), 7.03-7.05(2H, m), 7.13(1H, d, J=7.8 Hz), 7.25-7.31(2H, m), 7.37(1H, d, J=1.8 Hz).

(58-5) Synthesis of 2-amino-2-(2-{4-[3-(3-trifluoromethoxyphenyl)propoxy]-3-trifluoromethylphenyl}ethyl)propane-1,3-diol hydrochloride (Compound 58-5)

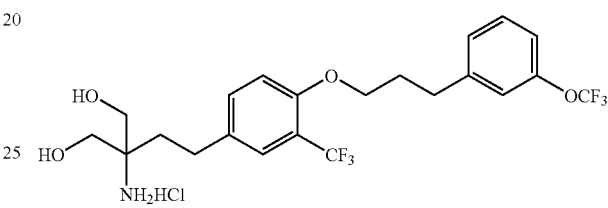

Compound 58-4 (790 mg) was dissolved in ethanol (15 ml), concentrated hydrochloric acid (1.5 ml) was added, and the mixture was stirred at 80° C. for 2 hr. The reaction mixture was concentrated, and the residue was washed, with diethyl ether to give the object product (590 mg) as a white powder.

MS(ESI)m/z: 482[M+H]

$^1$H-NMR(DMSO-d$_6$) δ (ppm): 1.74-1.79(2H, m), 2.01-2.08(2H, m), 2.59-2.64(2H, m), 2.80(2H, t, J=7.4 Hz), 3.52 (4H, d, J=4.6 Hz), 4.04(2H, t, J=6.1 Hz), 5.40(2H, t, J=5.0 Hz), 7.14-7.19(3H, m), 7.25(1H, d, J=7.6 Hz), 7.40-7.45(2H, m), 7.48(1H, d, J=1.3 Hz), 7.84(3H, brs).

Example 59

2-amino-2-(2-{4-[3-(2-naphthyl)propoxy]-3-trifluoromethylphenyl}ethyl)propane-1,3-diol hydrochloride (59-1) Synthesis of 3-(2-naphthyl)-1-propanol (Compound 59-1)

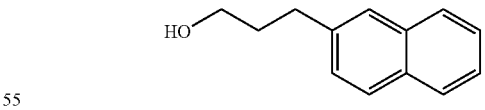

3-(2-Naphthyl)acrylic acid (5.00 g) was dissolved in methanol (30 ml) and tetrahydrofuran (50 ml), 10% palladium carbon (2.40 g) was added, and the mixture was stirred under a hydrogen atmosphere at room temperature for 15 hr. The reaction container was purged with nitrogen, the solution was filtered, and the filtrate was concentrated to give a pale-yellow solid (4.86 g). The pale-yellow solid was dissolved in tetrahydrofuran (100 ml), and a tetrahydrofuran-borane.tetrahydrofuran solution (1 mol/l, 27.0 ml) was added dropwise to the mixture under ice-cooling, and the mixture was stirred under ice-cooling for 1 hr, and further at room temperature for 18 hr. To the reaction mixture was added water, and 1M aqueous hydrochloric acid solution was added. The mixture was extracted with ethyl acetate, washed with water, saturated aqueous sodium hydrogen carbonate solution and saturated brine, and dried over anhydrous magnesium sulfate. The solvent was evaporated under reduced pressure to give the object product (4.33 g) as a colorless oil.

$^1$H-NMR(CDCl$_3$) δ (ppm): 1.26(1H, t, J=7.1 Hz), 1.95-2.02(2H, m), 2.88(2H, t, J=7.6 Hz), 3.71(2H, t, J=6.5 Hz), 7.35(1H, dd, J=8.3, 1.3 Hz), 7.39-7.47(2H, m), 7.64(1H, s), 7.76-7.81(3H, m).

(59-2) Synthesis of 2-(3-bromopropyl)naphthalene (Compound 59-2)

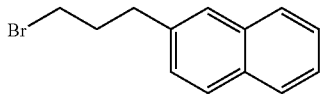

Compound 59-1 (4.33 g) was dissolved in methylene chloride (50 ml), triphenylphosphine (6.69 g) and N-bromosuccinimide (4.54 g) were added under ice-cooling, and the mixture was stirred under ice-cooling for 2 hr, and further at room temperature for 21 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography to give the object product (4.95 g) as a colorless oil.

$^1$H-NMR(CDCl$_3$) δ (ppm): 2.22-2.30(2H, m), 2.95(2H, t, J=7.3 Hz), 3.43(2H, t, J=6.5 Hz), 7.34(1H, dd, J=8.5, 1.3 Hz), 7.41-7.48(2H, m), 7.65(1H, s), 7.77-7.82(3H, m).

(59-3) Synthesis of [2,2-dimethyl-5-(2-{4-[3-(2-naphthyl)propoxy]-3-trifluoromethylphenyl}ethyl)-1,3-dioxan-5-yl]carbamic acid t-butyl ester (Compound 59-3)

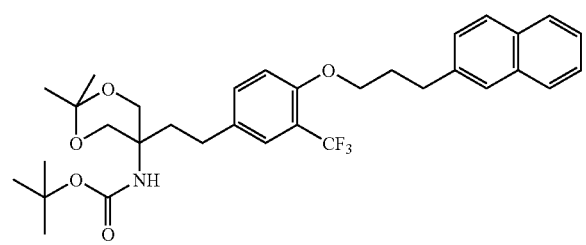

Reference Example compound 2-6 (500 mg) was dissolved in N,N-dimethylformamide (10 ml), potassium carbonate (494 mg) and compound 59-2 (356 mg) were added, and the mixture was stirred at 80° C. for 1.5 hr. Water was added to the reaction mixture, and the mixture was extracted with ethyl acetate, washed with water and saturated brine, and dried over anhydrous magnesium sulfate. The solvent was evaporated under reduced pressure. The obtained residue was purified by silica gel column chromatography to give the object product (500 mg) as a white solid.

$^1$H-NMR(CDCl$_3$) δ (ppm): 1.43(3H, s), 1.44(3H, s), 1.47 (9H, s), 1.93-1.98(2H, m), 2.16-2.24(2H, m), 2.51-2.56(2H, m), 3.00(2H, t, J=7.5 Hz), 3.69(2H, d, J=11.7 Hz), 3.89(2H, d, J=11.7 Hz), 4.01(2H, t, J=6.0 Hz), 4.99(1H, brs), 6.83(1H, d, J=8.5 Hz), 7.24(1H, brd, J=1.8 Hz), 7.33-7.40(2H, m), 7.41-7.46(2H, m), 7.63(1H, brs), 7.74-7.81(3H, m).

(59-4) Synthesis of 2-amino-2-(2-{4-[3-(2-naphthyl) propoxy]-3-trifluoromethylphenyl}ethyl)propane-1,3-diol hydrochloride (Compound 59-4)

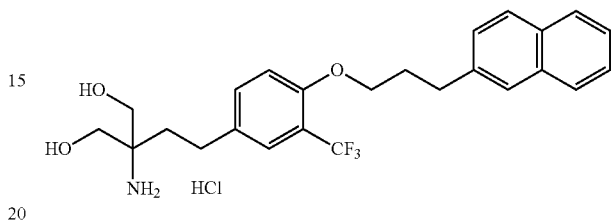

Compound 59-3 (500 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give the object product (400 mg) as a white powder.

MS(ESI)m/z: 448[M+H]

$^1$H-NMR(DMSO-d$_6$) δ (ppm): 1.73-1.78(2H, m), 2.09-2.18(2H, m), 2.57-2.62(2H, m), 2.92(2H, t, J=7.5 Hz), 3.51 (4H, d, J=4.2 Hz), 4.09(2H, t, J=6.1 Hz), 5.36(2H, brs), 7.17 (1H, d, J=8.6 Hz), 7.38-7.49(5H, m), 7.70(4H, brs), 7.81-7.87 (3H, m).

Example 60

2-amino-2-(2-{4-[3-(2,3-dichlorophenyl)propoxy]-3-trifluoromethylphenyl}ethyl)propane-1,3-diol hydrochloride (60-1) Synthesis of 3-(2,3-dichlorophenyl)-2-propyne-1-ol (Compound 60-1)

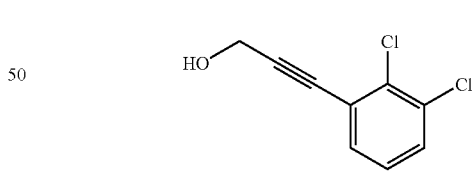

A mixture of 2,3-dichloroiodobenzene (5.00 g), copper(I) iodide (69.8 mg), triphenylphosphine (240 mg), tris(dibenzylideneacetone)dipalladium(0) chloroform adduct (378 mg), propargyl alcohol (1.19 ml), diisopropylethylamine (12.8 ml) and tetrahydrofuran (100 ml) was stirred at room temperature for 25 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=100:0-80:20) to give the object product (3.12 g) as a brown solid.

¹H-NMR(CDCl₃) δ (ppm): 1.75(1H, t, J=6.3 Hz), 4.56(2H, d, J=6.3 Hz), 7.15(1H, t, J=7.9 Hz), 7.39(1H, dd, J=7.9, 1.3 Hz), 7.42(1H, dd, J=8.4, 1.3 Hz).

(60-2) Synthesis of 3-(2,3-dichlorophenyl)-1-propanol (Compound 60-2)

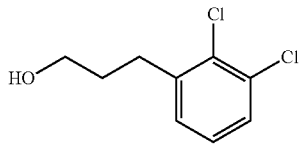

A suspension of compound 60-1 (3.12 g) and chlorotris(triphenylphosphine)rhodium(I) (1.80 g) in toluene (80 ml) was stirred under a hydrogen atmosphere at 60° C. for 10 hr. The reaction mixture was concentrated, diisopropyl ether was added and the mixture was filtered through celite. The filtrate was concentrated and the obtained residue was purified by silica gel column chromatography (hexane:ethyl acetate=99:1-80:20) to give the object product (2.66 g) as a brown oil.

¹H-NMR(CDCl₃) δ (ppm): 1.35(1H, brs), 1.86-1.93(2H, m), 2.86-2.90(2H, m), 3.70(2H, t, J=6.3 Hz), 7.12(1H, t, J=7.3 Hz), 7.16(1H, dd, J=7.6, 2.2 Hz), 7.32(1H, dd, J=7.6, 2.2 Hz).

(60-3) Synthesis of 1-(3-bromopropyl)-2,3-dichlorobenzene (Compound 60-3)

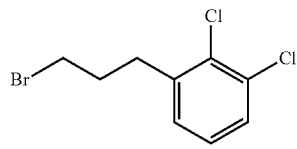

Compound 60-2 (2.67 g) was dissolved in methylene chloride (30 ml), triphenylphosphine (3.76 g) and N-bromosuccinimide (2.55 g) were added under ice-cooling, and the mixture was stirred under ice-cooling for 3 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (3.25 g) as a colorless oil.

¹H-NMR(CDCl₃) δ (ppm): 2.15-2.22(2H, m), 2.95(2H, t, J=7.5 Hz), 3.42(2H, t, J=6.5 Hz), 7.11-7.19(2H, m), 7.33-7.36(1H, m).

(60-4) Synthesis of [5-(2-{4-[3-(2,3-dichlorophenyl)propoxy]-3-trifluoromethylphenyl}ethyl)-2,2-dimethyl-1,3-dioxan-5-yl]carbamic acid t-butyl ester (Compound 60-4)

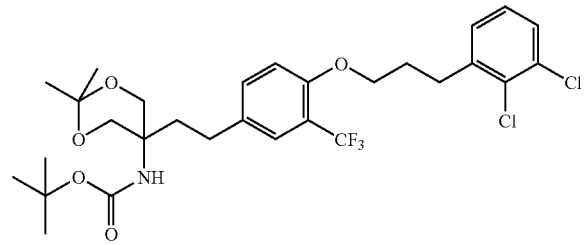

Reference Example compound 2-6 (500 mg) was dissolved in N,N-dimethylformamide (10 ml), potassium carbonate (494 mg) and compound 60-3 (383 mg) were added, and the mixture was stirred at 80° C. for 1 hr. Water was added to the reaction mixture, and the mixture was extracted with ethyl acetate, washed with water and saturated brine, and dried over anhydrous magnesium sulfate. The solvent was evaporated under reduced pressure to give the object product (770 mg) as a colorless oil.

¹H-NMR(CDCl₃) δ (ppm): 1.43(3H, s), 1.44(3H, s), 1.48(9H, s), 1.94-1.98(2H, m), 2.10-2.19(2H, m), 2.52-2.57(2H, m), 3.00(2H, t, J=7.5 Hz), 3.69(2H, d, J=11.7 Hz), 3.89(2H, d, J=11.7 Hz), 4.00(2H, t, J=5.9 Hz), 4.98(1H, brs), 6.85(1H, d, J=8.5 Hz), 7.07-7.19(2H, m), 7.25-7.36(2H, m), 7.38(1H, d, J=1.6 Hz).

(60-5) Synthesis of 2-amino-2-(2-{4-[3-(2,3-dichlorophenyl)propoxy]-3-trifluoromethylphenyl}ethyl)propane-1,3-diol hydrochloride (Compound 60-5)

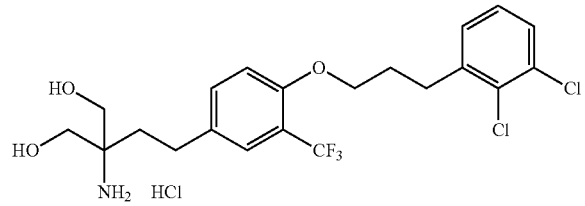

Compound 60-4 (770 mg) was dissolved in ethanol (15 ml), concentrated hydrochloric acid (1.5 ml) was added, and the mixture was stirred at 80° C. for 2 hr. The reaction mixture was concentrated, and the residue was washed with diethyl ether to give the object product (530 mg) as a white powder.

MS(ESI)m/z: 466[M+H]

¹H-NMR(DMSO-d₆) δ (ppm): 1.74-1.79(2H, m), 1.99-2.05(2H, m), 2.58-2.63(2H, m), 2.94(2H, t, J=7.6 Hz), 3.52(4H, d, J=4.2 Hz), 4.10(2H, t, J=5.8 Hz), 5.39(2H, t, J=4.6 Hz), 7.18(1H, d, J=8.6 Hz), 7.31(2H, d, J=4.8 Hz), 7.45(1H, d, J=8.6 Hz), 7.48-7.52(2H, m), 7.75(3H, brs).

Example 61

2-amino-2-(2-{4-[3-(3-chloro-4-fluorophenyl)propoxy]-3-trifluoromethylphenyl}ethyl)propane-1,3-diol hydrochloride (61-1) Synthesis of 3-(3-chloro-4-fluorophenyl)-2-propyne-1-ol (Compound 61-1)

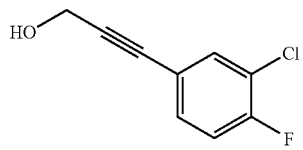

A mixture of 3-chloro-4-fluoroiodobenzene (5.00 g), copper(I) iodide (74.3 mg), triphenylphosphine (256 mg), tris(dibenzylideneacetone)dipalladium(0) chloroform adduct (404 mg), propargyl alcohol (1.27 ml), diisopropylethylamine (13.6 ml) and tetrahydrofuran (80 ml) was stirred at room temperature for 8 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=99:1-80:20) to give the object product (3.20 g) as a brown oil.

$^1$H-NMR(CDCl$_3$) δ (ppm): 1.66(1H, t, J=6.2 Hz), 4.48(2H, d, J=6.2 Hz), 7.09(1H, t, J=8.7 Hz), 7.29-7.33(1H, m), 7.49 (1H, dd, J=2.1, 7.0 Hz).

(61-2) Synthesis of 3-(3-chloro-4-fluorophenyl)-1-propanol (Compound 61-2)

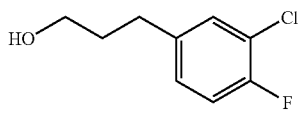

A suspension of Compound 61-1 (3.20 g) and chlorotris (triphenylphosphine)rhodium(I) (3.00 g) in toluene (70 ml) was stirred under a hydrogen atmosphere at 65° C. for 10 hr. The reaction mixture was concentrated, diisopropyl ether was added and the mixture was filtered through celite. The filtrate was concentrated and the obtained residue was purified by silica gel column chromatography (hexane:ethyl acetate=99:1-75:25) to give the object product (2.47 g) as a brown oil.

$^1$H-NMR(CDCl$_3$) δ (ppm): 1.32(1H, brs), 1.82-1.90(2H, m), 2.68(2H, t, J=7.7 Hz), 3.67(2H, t, J=6.3 Hz), 7.04-7.06 (2H, m), 7.23(1H, d, J=7.4 Hz).

(61-3) Synthesis of 1-(3-bromopropyl)-3-chloro-4-fluorobenzene (Compound 61-3)

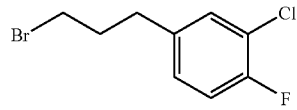

Compound 61-2 (2.47 g) was dissolved in methylene chloride (20 ml), triphenylphosphine (3.78 g) and N-bromosuccinimide (2.56 g) were added under ice-cooling, and the mixture was stirred under ice-cooling for 1 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (3.06 g) as a colorless oil.

$^1$H-NMR(CDCl$_3$) δ (ppm): 2.10-2.17(2H, m), 2.75(2H, t, J=7.4 Hz), 3.38(2H, t, J=6.4 Hz), 7.05-7.07(2H, m), 7.23(1H, d, J=7.1 Hz).

(61-4) Synthesis of [5-(2-{4-[3-(3-chloro-4-fluorophenyl)propoxy]-3-trifluoromethylphenyl}ethyl)-2,2-dimethyl-1,3-dioxan-5-yl]carbamic acid t-butyl ester (Compound 61-4)

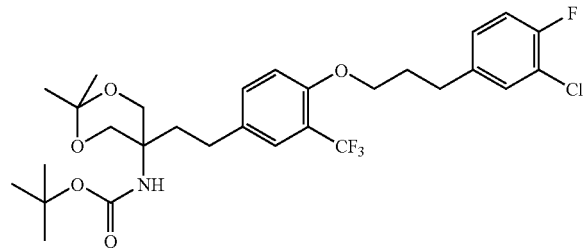

Reference Example compound 2-6 (500 mg) was dissolved in N,N-dimethylformamide (10 ml), potassium carbonate (494 mg) and compound 61-3 (360 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (740 mg) as a white solid.

$^1$H-NMR(CDCl$_3$) δ (ppm): 1.43(3H, s), 1.44(3H, s), 1.47 (9H, s), 1.94-1.98(2H, m), 2.05-2.14(2H, m), 2.52-2.57(2H, m), 2.79(2H, t, J=7.5 Hz), 3.69(2H, d, J=11.7 Hz), 3.89(2H, d, J=11.7 Hz), 3.97(2H, t, J=5.8 Hz), 4.99(1H, brs), 6.84(1H, d, J=8.5 Hz), 7.02-7.07(2H, m), 7.22(1H, d, J=7.4 Hz), 7.25-7.28(1H, m), 7.37(1H, d, J=1.6 Hz).

(61-5) Synthesis of 2-amino-2-(2-{4-[3-(3-chloro-4-fluorophenyl)propoxy]-3-trifluoromethylphenyl}ethyl)propane-1,3-diol hydrochloride (Compound 61-5)

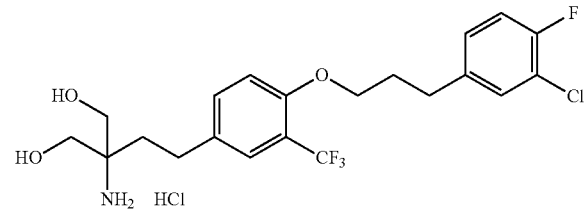

Compound 61-4 (740 mg) was dissolved in ethanol (15 ml), concentrated hydrochloric acid (1.5 ml) was added, and the mixture was stirred at 80° C. for 2 hr. The reaction mixture was concentrated, and the residue was washed with diethyl ether to give the object product (520 mg) as a white powder.

MS(ESI)m/z: 450[M+H]

$^1$H-NMR(DMSO-d$_6$) δ (ppm): 1.74-1.79(2H, m), 1.98-2.05(2H, m), 2.58-2.63(2H, m), 2.74(2H, t, J=7.5 Hz), 3.52 (4H, d, J=5.2 Hz), 4.03(2H, t, J=6.0 Hz), 5.40(2H, t, J=5.1 Hz), 7.17(1H, d, J=8.7 Hz), 7.18-7.22(1H, m), 7.32(1H, t, J=8.7 Hz), 7.40-7.46(2H, m), 7.47(1H, brs), 7.86(3H, brs).

Example 62

2-amino-2-(2-{4-[3-(2,5-dimethylphenyl)propoxy]-3-trifluoromethylphenyl}ethyl)propane-1,3-diol hydrochloride (62-1) Synthesis of 3-(2,5-dimethylphenyl)-2-propyne-1-ol (Compound 62-1)

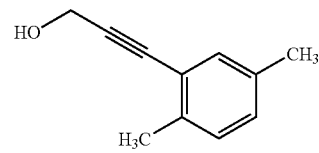

A mixture of 1-iodo-2,5-dimethylbenzene (5.00 g), copper (I) iodide (82.1 mg), triphenylphosphine (283 mg), tris (dibenzylideneacetone)dipalladium(0) chloroform adduct (446 mg), propargyl alcohol (1.40 ml), diisopropylethylamine (15.0 ml) and tetrahydrofuran (100 ml) was stirred at room temperature for 5 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=99:1-80:20) to give the object product (1.70 g) as a brown oil.

$^1$H-NMR(CDCl$_3$) δ (ppm): 1.64(1H, t, J=6.2 Hz), 2.28(3H, s), 2.38(3H, s), 4.53(2H, d, J=6.2 Hz), 7.03(1H, dd, J=1.0, 7.8 Hz), 7.08(1H, d, J=7.8 Hz), 7.23(1H, s).

(62-2) Synthesis of 3-(2,5-dimethylphenyl)-1-propanol (Compound 62-2)

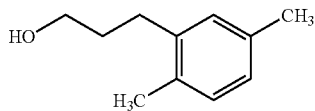

A solution of compound 62-1 (1.70 g) and 10% palladium carbon (0.50 g) in 1,4-dioxane (70 ml) was stirred under a hydrogen atmosphere at room temperature for 9 hr. The reaction mixture was filtered through celite and concentrated to give the object product (1.69 g) as a dark-green oil.

$^1$H-NMR(CDCl$_3$) δ (ppm): 1.30(1H, brs), 1.81-1.88(2H, m), 2.27(3H, s), 2.29(3H, s), 2.64-2.68(2H, m), 3.70-3.72 (2H, m), 6.92(1H, d, J=7.6 Hz), 6.97(1H, s), 7.03(1H, d, J=7.6 Hz).

(62-3) Synthesis of 1-(3-bromopropyl)-2,5-dimethylbenzene (Compound 62-3)

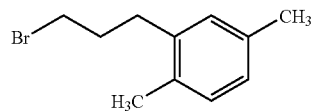

Compound 62-2 (1.64 g) was dissolved in methylene chloride (33 ml), triphenylphosphine (2.90 g) and N-bromosuccinimide (1.95 g) were added under ice-cooling, and the mixture was stirred under ice-cooling for 3.5 hr. Water was added to the reaction mixture, and the mixture was extracted with methylene chloride and washed with saturated brine, and dried over anhydrous sodium sulfate. The solvent was evaporated under reduced pressure. Diethyl ether was added, and the precipitated triphenylphosphine oxide was filtered off. The concentrate of the filtrate was purified by silica gel column chromatography (hexane alone) to give the object product (1.97 g) as a colorless oil.

$^1$H-NMR(DMSO-d$_6$) δ (ppm): 1.98-2.05(2H, m), 2.21(3H, s), 2.23(3H, s), 2.65(2H, t, J=7.9 Hz), 3.56(2H, t, J=6.4 Hz), 6.90(1H, d, J=7.5 Hz), 6.95(1H, s), 7.02(1H, d, J=7.6 Hz).

(62-4) Synthesis of 2-amino-2-(2-{4-[3-(2,5-dimethylphenyl)propoxy]-3-trifluoromethylphenyl}ethyl)propane-1,3-diol hydrochloride (Compound 62-4)

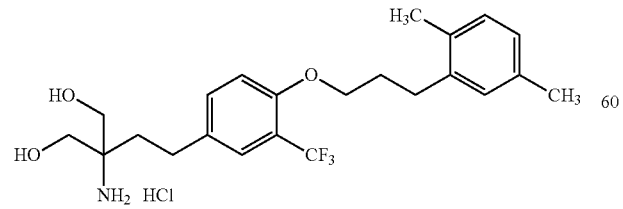

Reference Example compound 2-6 (500 mg) was dissolved in N,N-dimethylformamide (10 ml), potassium carbonate (494 mg) and compound 62-3 (330 mg) were added, and the mixture was stirred at 80° C. for 4 hr. Water was added to the reaction mixture, and the mixture was extracted with ethyl acetate, washed with water and saturated brine, and dried over anhydrous sodium sulfate. The solvent was evaporated under reduced pressure. The obtained white solid was dissolved in ethanol (15 ml), concentrated hydrochloric acid (1.5 ml) was added, and the mixture was stirred at 80° C. for 3.5 hr. The reaction mixture was concentrated, and the residue was washed with diethyl ether to give the object product (440 mg) as a white powder.

MS(ESI)m/z: 426[M+H]

$^1$H-NMR(DMSO-d$_6$) δ (ppm): 1.75-1.79(2H, m), 1.90-1.96(2H, m), 2.20(3H, s), 2.21(3H, s), 2.59-2.63(2H, m), 2.69(2H, t, J=7.7 Hz), 3.52(4H, d, J=5.1 Hz), 4.09(2H, t, J=5.8 Hz), 5.40(2H, t, J=5.2 Hz), 6.89(1H, d, J=7.5 Hz), 6.94(1H, s), 7.01(1H, d, J=7.6 Hz), 7.18(1H, d, J=8.6 Hz), 7.45(1H, d, J=8.6 Hz), 7.48(1H, s), 7.84(3H, brs).

Example 63

2-amino-2-(2-{4-[3-(3-chloro-2-fluorophenyl)propoxy]-3-trifluoromethylphenyl}ethyl)propane-1,3-diol hydrochloride (63-1) Synthesis of 3-(3-chloro-2-fluorophenyl)-2-propyne-1-ol (Compound 63-1)

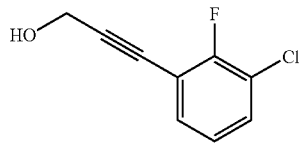

A mixture of 3-chloro-2-fluoroiodobenzene (5.00 g), copper(I) iodide (74.3 mg), triphenylphosphine (256 mg), tris(dibenzylideneacetone)dipalladium(0) chloroform adduct (404 mg), propargyl alcohol (1.27 ml), diisopropylethylamine (13.6 ml) and tetrahydrofuran (90 ml) was stirred at room temperature for 8 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=99:1-80:20) to give the object product (3.15 g) as a brown oil.

$^1$H-NMR(CDCl$_3$) δ (ppm): 1.73(1H, t, J=6.3 Hz), 4.54(2H, d, J=6.3 Hz), 7.04(1H, t, J=7.8 Hz), 7.31-7.39(2H, m).

(63-2) Synthesis of 3-(3-chloro-2-fluorophenyl)-1-propanol (Compound 63-2)

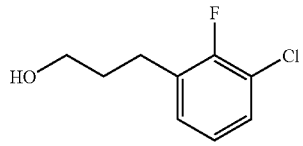

A suspension of Compound 63-1 (3.15 g) and chlorotris(triphenylphosphine)rhodium(I) (3.00 g) in toluene (90 ml) was stirred under a hydrogen atmosphere at 60° C. for 11 hr. The reaction mixture was concentrated, diisopropyl ether was added and the mixture was filtered through celite. The filtrate was concentrated and the obtained residue was purified by silica gel column chromatography (hexane:ethyl acetate=99:1-80:20) to give the object product (2.48 g) as a brown oil.

$^1$H-NMR(CDCl$_3$) δ (ppm): 1.36(1H, brs), 1.88(2H, quint, J=7.0 Hz), 2.77(2H, t, J=7.9 Hz), 3.68(2H, t, J=6.3 Hz), 7.00(1H, t, J=7.9 Hz), 7.09-7.13(1H, m), 7.22-7.26(1H, m).

(63-3) Synthesis of 1-(3-bromopropyl)-3-chloro-2-fluorobenzene (Compound 63-3)

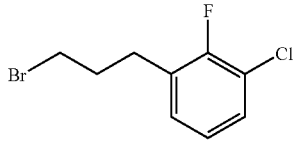

Compound 63-2 (2.48 g) was dissolved in methylene chloride (45 ml), triphenylphosphine (3.80 g) and N-bromosuccinimide (2.57 g) were added under ice-cooling, and the mixture was stirred under ice-cooling for 2 hr. Water was added to the reaction mixture, and the mixture was extracted with methylene chloride and washed with saturated brine, and dried over anhydrous sodium sulfate. The solvent was evaporated under reduced pressure. Diethyl ether was added, and the precipitated triphenylphosphine oxide was filtered off. The concentrate of the filtrate was purified by silica gel column chromatography (hexane alone) to give the object product (2.88 g) as a colorless oil.

$^1$H-NMR(DMSO-d$_6$) δ (ppm): 2.06-2.13(2H, m), 2.79(2H, t, J=7.8 Hz), 3.54(2H, t, J=6.4 Hz), 7.17(1H, t, J=8.0 Hz), 7.30(1H, dd, J=7.5, 1.0 Hz), 7.44(1H, dd, J=8.1, 1.4 Hz).

(63-4) Synthesis of 2-amino-2-(2-{4-[3-(3-chloro-2-fluorophenyl)propoxy]-3-trifluoromethylphenyl}ethyl)propane-1,3-diol hydrochloride (Compound 63-4)

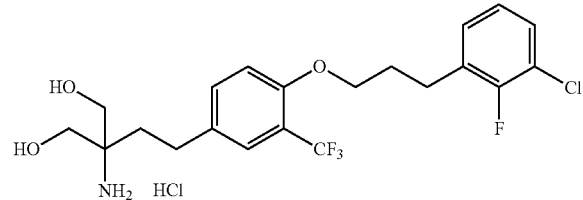

Reference Example compound 2-6 (500 mg) was dissolved in N,N-dimethylformamide (10 ml), potassium carbonate (494 mg) and compound 63-3 (330 mg) were added, and the mixture was stirred at 80° C. for 3 hr. Water was added to the reaction mixture, and the mixture was extracted with ethyl acetate, washed with water and saturated brine, and dried over anhydrous sodium sulfate. The solvent was evaporated under reduced pressure. The obtained white solid was dissolved in ethanol (15 ml), concentrated hydrochloric acid (1.5 ml) was added, and the mixture was stirred at 80° C. for 3.5 hr. The reaction mixture was concentrated, and the residue was washed with diethyl ether to give the object product (467 mg) as a white powder.

MS(ESI)m/z: 450[M+H]

$^1$H-NMR(DMSO-d$_6$) δ (ppm): 1.75-1.79(2H, m), 1.99-2.05(2H, m), 2.59-2.63(2H, m), 2.83(2H, t, J=7.7 Hz), 3.52 (4H, d, J=5.2 Hz), 4.08(2H, t, J=5.9 Hz), 5.41(2H, t, J=5.1 Hz), 7.14-7.18(2H, m), 7.26(1H, dd, J=7.8, 1.2 Hz), 7.41-7.46(2H, m), 7.48(1H, s), 7.85(3H, brs).

Example 64

2-amino-2-(2-{4-[3-(5-chloro-2-fluorophenyl)propoxy]-3-trifluoromethylphenyl}ethyl)propane-1,3-diol hydrochloride (64-1) Synthesis of 3-(5-chloro-2-fluorophenyl)-2-propyne-1-ol (Compound 64-1)

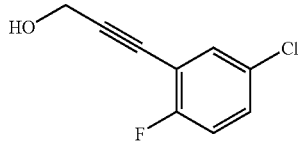

A mixture of 5-chloro-2-fluoroiodobenzene (5.00 g), copper(I) iodide (74.3 mg), triphenylphosphine (256 mg), tris(dibenzylideneacetone)dipalladium(0) chloroform adduct (404 mg), propargyl alcohol (1.27 ml), diisopropylethylamine (13.6 ml) and tetrahydrofuran (100 ml) was stirred at room temperature for 8 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=99:1-80:20) to give the object product (2.82 g) as a brown oil.

$^1$H-NMR(CDCl$_3$) δ (ppm): 1.71(1H, t, J=6.3 Hz), 4.53(2H, d, J=6.3 Hz), 7.02(1H, t, J=8.7 Hz), 7.25-7.29(1H, m), 7.41 (1H, dd, J=2.8, 6.2 Hz).

(64-2) Synthesis of 3-(5-chloro-2-fluorophenyl)-1-propanol (Compound 64-2)

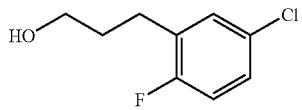

A suspension of compound 64-1 (2.81 g) and chlorotris(triphenylphosphine)rhodium(I) (3.00 g) in toluene (90 ml) was stirred under a hydrogen atmosphere at 60° C. for 11 hr. The reaction mixture was concentrated, diisopropyl ether was added and the mixture was filtered through celite. The filtrate was concentrated and the obtained residue was purified by silica gel column chromatography (hexane:ethyl acetate=99:1-80:20) to give the object product (2.31 g) as a brown oil.

$^1$H-NMR(CDCl$_3$) δ (ppm): 1.36(1H, brs), 1.84-1.91(2H, m), 2.72(2H, t, J=7.7 Hz), 3.68(2H, t, J=6.3 Hz), 6.95(1H, t, J=9.0 Hz), 7.12-7.16(1H, m), 7.19(1H, dd, J=2.6, 6.5 Hz).

(64-3) Synthesis of 1-(3-bromopropyl)-5-chloro-2-fluorobenzene (Compound 64-3)

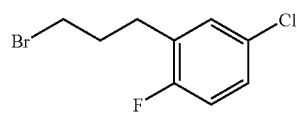

Compound 64-2 (2.28 g) was dissolved in methylene chloride (40 ml), triphenylphosphine (3.50 g) and N-bromosuccinimide (2.37 g) were added under ice-cooling, and the mixture was stirred under ice-cooling for 5 hr. Water was added to the reaction mixture, and the mixture was extracted with methylene chloride and washed with saturated brine, and dried over anhydrous sodium sulfate. The solvent was evaporated under reduced pressure. Diethyl ether was added, and the precipitated triphenylphosphine oxide was filtered off. The concentrate of the filtrate was purified by silica gel column chromatography (hexane alone) to give the object product (2.70 g) as a colorless oil.

$^1$H-NMR(DMSO-$d_6$) δ (ppm): 2.05-2.12(2H, m), 2.74(2H, t, J=7.8 Hz), 3.53(2H, t, J=6.4 Hz), 7.22(1H, t, J=9.0 Hz), 7.32(1H, ddd, J=8.6, 4.4, 2.7 Hz), 7.41(1H, dd, J=6.4, 2.7 Hz).

(64-4) Synthesis of 2-amino-2-(2-{4-[3-(5-chloro-2-fluorophenyl)propoxy]-3-trifluoromethylphenyl}ethyl)propane-1,3-diol hydrochloride (Compound 64-4)

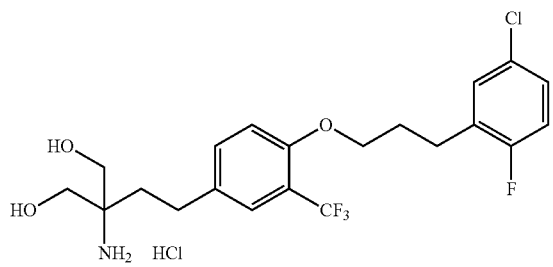

Reference Example compound 2-6 (500 mg) was dissolved in N,N-dimethylformamide (10 ml), potassium carbonate (494 mg) and compound 64-3 (360 mg) were added, and the mixture was stirred at 80° C. for 4 hr. Water was added to the reaction mixture, and the mixture was extracted with ethyl acetate, washed with water and saturated brine, and dried over anhydrous sodium sulfate. The solvent was evaporated under reduced pressure. The obtained white solid was dissolved in ethanol (15 ml), concentrated hydrochloric acid (1.5 ml) was added, and the mixture was stirred at 80° C. for 4 hr. The reaction mixture was concentrated, and the residue was washed with diethyl ether to give the object product (478 mg) as a white powder.

MS(ESI)m/z: 450[M+H]

$^1$H-NMR(DMSO-$d_6$) δ (ppm): 1.74-1.79(2H, m), 1.98-2.05(2H, m), 2.58-2.63(2H, m), 2.78(2H, t, J=7.8 Hz), 3.52 (4H, d, J=5.0 Hz), 4.08(2H, t, J=5.8 Hz), 5.40(2H, t, J=5.0 Hz), 7.16-7.23(2H, m), 7.32(1H, ddd, J=8.6, 4.4, 2.7 Hz), 7.36(1H, dd, J=6.5, 2.7 Hz), 7.44(1H, d, J=8.6 Hz), 7.47(1H, s), 7.83(3H, brs).

Example 65

2-amino-2-(2-{4-[3-(2,4-difluorophenyl)propoxy]-3-trifluoromethylphenyl}ethyl)propane-1,3-diol hydrochloride (65-1) Synthesis of 3-(2,4-difluorophenyl)-2-propyne-1-ol (Compound 65-1)

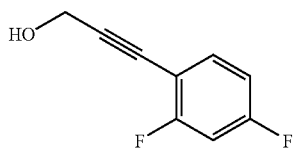

A mixture of 2,4-difluoroiodobenzene (5.00 g), copper(I) iodide (79.4 mg), triphenylphosphine (273 mg), tris(dibenzylideneacetone)dipalladium(0) chloroform adduct (432 mg), propargyl alcohol (1.35 ml), diisopropylethylamine (14.5 ml) and tetrahydrofuran (80 ml) was stirred at room temperature for 15 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=99:1-80:20) to give the object product (1.03 g) as a brown oil.

$^1$H-NMR(CDCl$_3$) δ (ppm): 1.71(1H, t, J=6.2 Hz), 4.52(2H, d, J=6.2 Hz), 6.81-6.88(2H, m), 7.39-7.45(1H, m).

(65-2) Synthesis of 3-(2,4-difluorophenyl)-1-propanol (Compound 65-2)

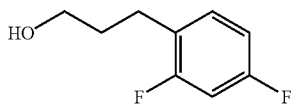

A solution of compound 65-1 (1.03 g) and 10% palladium carbon (0.50 g) in 1,4-dioxane (60 ml) was stirred under a hydrogen atmosphere at room temperature for 9 hr. The reaction mixture was filtered through celite and concentrated to give the object product (0.99 g) as a dark-green oil.

$^1$H-NMR(CDCl$_3$) δ (ppm): 1.32(1H, brs), 1.85(2H, quint, J=7.0 Hz), 2.71(2H, t, J=7.6 Hz), 3.67(2H, t, J=6.1 Hz), 6.75-6.83(2H, m), 7.13-7.19(1H, m).

(65-3) Synthesis of 1-(3-bromopropyl)-2,4-difluorobenzene (Compound 65-3)

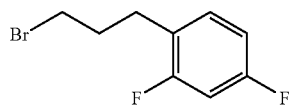

Compound 65-2 (940 mg) was dissolved in methylene chloride (10 ml), triphenylphosphine (1.58 g) and N-bromosuccinimide (1.07 g) were added under ice-cooling, and the mixture was stirred under ice-cooling for 1 hr, and at room temperature for 1 hr. The reaction mixture was washed with water and saturated brine, and dried over anhydrous magnesium sulfate. The solvent was evaporated under reduced pressure. Diethyl ether (50 ml) was added, and the precipitated triphenylphosphine oxide was filtered off. The concentrate of the filtrate was purified by silica gel column chromatography (hexane alone) to give the object product (1.03 g) as a colorless oil.

$^1$H-NMR(CDCl$_3$) δ (ppm): 2.10-2.17(2H, m), 2.78(2H, t, J=7.4 Hz), 3.39(2H, t, J=6.6 Hz), 6.75-6.83(2H, m), 7.14-7.21(1H, m).

(65-4) Synthesis of [5-(2-{4-[3-(2,4-difluorophenyl)propoxy]-3-trifluoromethylphenyl}ethyl)-2,2-dimethyl-1,3-dioxan-5-yl]carbamic acid t-butyl ester (Compound 65-4)

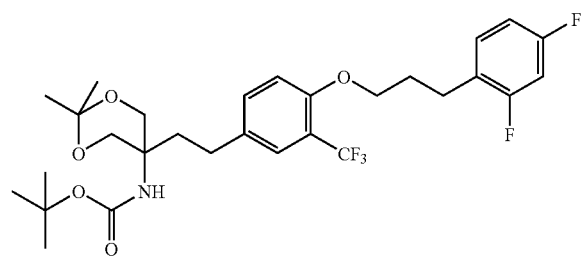

Reference Example compound 2-6 (500 mg) was dissolved in N,N-dimethylformamide (10 ml), potassium carbonate (494 mg) and compound 65-3 (336 mg) were added, and the mixture was stirred at 80° C. for 1 hr. Water was added to the reaction mixture, and the mixture was extracted with ethyl acetate, washed with water and saturated brine, and dried over anhydrous magnesium sulfate. The solvent was evaporated under reduced pressure to give the object product (730 mg) as a white solid.

$^1$H-NMR(CDCl$_3$) δ (ppm): 1.43(3H, s), 1.44(3H, s), 1.47 (9H, s), 1.93-1.98(2H, m), 2.05-2.11(2H, m), 2.52-2.57(2H, m), 2.82(2H, t, J=7.4 Hz), 3.69(2H, d, J=11.7 Hz), 3.89(2H, d, J=11.7 Hz), 3.98(2H, t, J=5.9 Hz), 4.99(1H, $_{brs}$), 6.75-6.81 (2H, m), 6.84(1H, d, J=8.5 Hz), 7.12-7.18(1H, m), 7.26-7.28 (1H, m), 7.37(1H, d, J=1.8 Hz).

(65-5) Synthesis of 2-amino-2-(2-{4-[3-(2,4-difluorophenyl)propoxy]-3-trifluoromethylphenyl}ethyl) propane-1,3-diol hydrochloride (Compound 65-5)

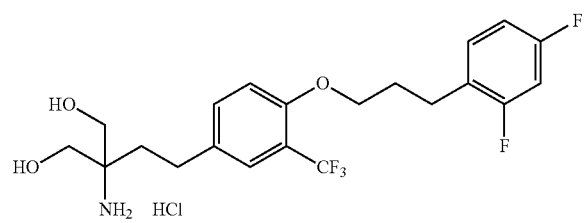

Compound 65-4 (730 mg) was dissolved in ethanol (15 ml), concentrated hydrochloric acid (1.5 ml) was added, and the mixture was stirred at 80° C. for 2 hr. The reaction mixture was concentrated, and the residue was washed with diethyl ether to give the object product (480 mg) as a white powder.

MS(ESI)m/z: 434[M+H]

$^1$H-NMR(DMSO-d$_6$) δ (ppm): 1.74-1.79(2H, m), 1.97-2.01(2H, m), 2.58-2.63(2H, m), 2.76(2H, t, J=7.5 Hz), 3.52 (4H, d, J=5.0 Hz), 4.06(2H, t, J=5.9 Hz), 5.39(2H, t, J=5.0 Hz), 7.02(1H, td, J=8.5, 2.4 Hz), 7.15-7.20(2H, m), 7.28-7.34 (1H, m), 7.44(1H, d, J=8.5 Hz), 7.48(1H, d, J=1.5 Hz), 7.81 (3H, brs).

Example 66

2-amino-2-(2-{4-[3-(2,5-dichlorophenyl)propoxy]-3-trifluoromethylphenyl}ethyl)propane-1,3-diol hydrochloride (66-1) Synthesis of 3-(2,5-dichlorophenyl)-2-propyne-1-ol (Compound 66-1)

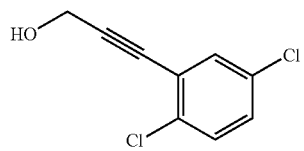

A mixture of 2,5-dichloroiodobenzene (5.00 g), copper(I) iodide (69.8 mg), triphenylphosphine (240 mg), tris(dibenzylideneacetone)dipalladium(0) chloroform adduct (378 mg), propargyl alcohol (1.19 ml), diisopropylethylamine (12.8 ml) and tetrahydrofuran (100 ml) was stirred at room temperature for 25 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=100:0-80:20) to give the object product (3.38 g) as a brown solid.

$^1$H-NMR(CDCl$_3$) δ (ppm): 1.74(1H, t, J=6.3 Hz), 4.55(2H, d, J=6.3 Hz), 7.23(1H, dd, J=2.3, 8.6 Hz), 7.32(1H, d, J=8.6 Hz), 7.46(1H, d, J=2.3 Hz).

(66-2) Synthesis of 3-(2,5-dichlorophenyl)-1-propanol (Compound 66-2)

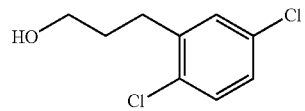

A suspension of compound 66-1 (3.38 g) and chlorotris(triphenylphosphine)rhodium(I) (1.80 g) in toluene (80 ml) was stirred under a hydrogen atmosphere at 60° C. for 10 hr. The reaction mixture was concentrated, diisopropyl ether was added and the mixture was filtered through celite. The filtrate was concentrated and the obtained residue was purified by silica gel column chromatography (hexane:ethyl acetate=99:1-80:20) to give the object product (2.74 g) as a brown oil.

$^1$H-NMR(CDCl$_3$) δ (ppm): 1.36(1H, brs), 1.85-1.92(2H, m), 2.81(2H, t, J=7.8 Hz), 3.70(2H, t, J=6.2 Hz), 7.12(1H, dd, J=2.5, 8.6 Hz), 7.24(1H, d, J=2.5 Hz), 7.27(1H, d, J=8.6 Hz).

(66-3) Synthesis of 1-(3-chloropropyl)-2,5-dichlorobenzene (Compound 66-3)

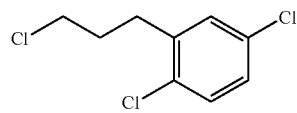

Compound 66-2 (1.73 g) was dissolved in methylene chloride (20 ml), triphenylphosphine (2.43 g) and N-chlorosuccinimide (1.24 g) were added under ice-cooling, and the mixture was stirred under ice-cooling for 1 hr, and at room temperature for 2.5 hr. The reaction mixture was washed with water and saturated brine, and dried over anhydrous magnesium sulfate. The solvent was evaporated under reduced pressure. Diethyl ether (50 ml) was added, and the precipitated triphenylphosphine oxide was filtered off. The concentrate of the filtrate was purified by silica gel column chromatography (hexane alone) to give the object product (1.76 g) as a colorless oil.

$^1$H-NMR(CDCl$_3$) δ (ppm): 2.05-2.13(2H, m), 2.87(2H, t, J=7.4 Hz), 3.56(2H, t, J=6.5 Hz), 7.12-7.16(1H, m), 7.23-7.29(2H, m).

(66-4) Synthesis of [5-(2-{4-[3-(2,5-dichlorophenyl) propoxy]-3-trifluoromethylphenyl}ethyl)-2,2-dimethyl-1,3-dioxan-5-yl]carbamic acid t-butyl ester (Compound 66-4)

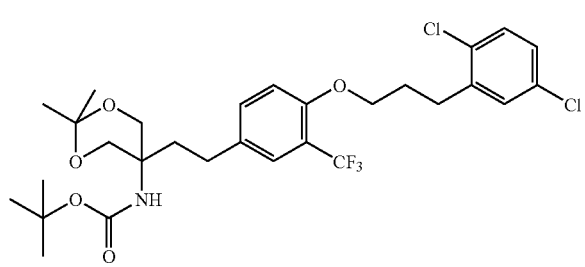

Reference Example compound 2-6 (500 mg) was dissolved in N,N-dimethylformamide (10 ml), potassium carbonate (494 mg) and compound 66-3 (320 mg) were added, and the mixture was stirred at 80° C. for 7.5 hr. Water was added to the reaction mixture, and the mixture was extracted with ethyl acetate, washed with water and saturated brine, and dried over anhydrous magnesium sulfate. The solvent was evaporated under reduced pressure to give the object product (740 mg) as a pale-yellow solid.

$^1$H-NMR(CDCl$_3$) δ (ppm): 1.43(3H, s), 1.44(3H, s), 1.48 (9H, s), 1.94-1.98(2H, m), 2.04-2.13(2H, m), 2.52-2.57(2H, m), 2.89-2.94(2H, m), 3.69(2H, d, J=11.7 Hz), 3.89(2H, d, J=11.7 Hz), 4.03(2H, t, J=5.9 Hz), 4.99(1H, brs), 6.86(1H, d, J=8.5 Hz), 7.13(1H, td, J=8.5, 2.4 Hz), 7.21-7.29(3H, m), 7.38(1H, d, J=1.8 Hz).

(66-5) Synthesis of 2-amino-2-(2-{4-[3-(2,5-dichlorophenyl)propoxy]-3-trifluoromethylphenyl}ethyl)propane-1,3-diol hydrochloride (Compound 66-5)

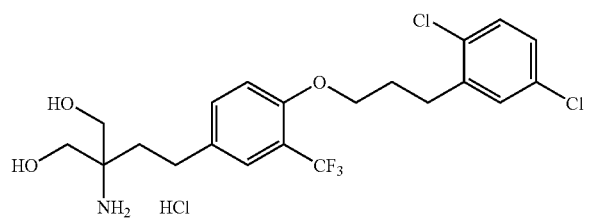

Compound 66-4 (740 mg) was dissolved in ethanol (15 ml), concentrated hydrochloric acid (1.5 ml) was added, and the mixture was stirred at 80° C. for 2 hr. The reaction mixture was concentrated, and the residue was washed with diethyl ether to give the object product (500 mg) as a white powder.

MS(ESI)m/z: 466[M+H]

$^1$H-NMR(DMSO-d$_6$) δ (ppm): 1.74-1.79(2H, m), 1.98-2.06(2H, m), 2.58-2.63(2H, m), 2.87(2H, t, J=7.7 Hz), 3.52 (4H, d, J=5.0 Hz), 4.10(2H, t, J=5.9 Hz), 5.40(2H, t, J=5.1 Hz), 7.19(1H, d, J=8.5 Hz), 7.32(1H, dd, J=8.5, 2.7 Hz), 7.41-7.80(4H, m), 7.83(3H, brs).

Example 67

2-amino-2-(2-{4-[3-(4-chloro-3-methylphenyl)propoxy]-3-trifluoromethylphenyl}ethyl)propane-1,3-diol hydrochloride (67-1) Synthesis of 3-(4-chloro-3-methylphenyl)-2-propyne-1-ol (Compound 67-1)

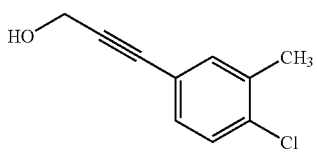

A mixture of 2-chloro-5-iodotoluene (5.00 g), copper(I) iodide (75.4 mg), triphenylphosphine (260 mg), tris(dibenzylideneacetone)dipalladium(0) chloroform adduct (410 mg), propargyl alcohol (1.29 ml), diisopropylethylamine (13.8 ml) and tetrahydrofuran (80 ml) was stirred at room temperature for 8 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=99:1-80:20) to give the object product (3.08 g) as a brown solid.

$^1$H-NMR(CDCl$_3$) δ (ppm): 1.65(1H, t, J=6.1 Hz), 2.34(3H, s), 4.48(2H, d, J=6.1 Hz), 7.19(1H, dd, J=1.5, 8.3 Hz), 7.27 (1H, d, J=8.3 Hz), 7.31(1H, d, J=1.5 Hz).

(67-2) Synthesis of 3-(4-chloro-3-methylphenyl)-1-propanol (Compound 67-2)

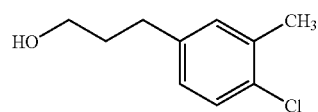

A suspension of Compound 67-1 (3.08 g) and chlorotris (triphenylphosphine)rhodium(I) (3.00 g) in toluene (70 ml) was stirred under a hydrogen atmosphere at 65° C. for 11 hr. The reaction mixture was concentrated, diisopropyl ether was added and the mixture was filtered through celite. The filtrate was concentrated and the obtained residue was purified by silica gel column chromatography (hexane:ethyl acetate=99:1-75:25) to give the object product (2.49 g) as a brown oil.

$^1$H-NMR(CDCl$_3$) δ (ppm): 1.28(1H, brs), 1.83-1.90(2H, m), 2.34(3H, s), 2.65(2H, t, J=7.7 Hz), 3.67(2H, t, J=6.3 Hz), 6.96(1H, dd, J=1.6, 8.2 Hz), 7.06(1H, d, J=1.6 Hz), 7.24(1H, d, J=8.2 Hz).

(67-3) Synthesis of 1-(3-bromopropyl)-4-chloro-3-methylbenzene (Compound 67-3)

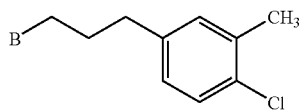

Compound 67-2 (2.49 g) was dissolved in methylene chloride (45 ml), triphenylphosphine (3.90 g) and N-bromosuccinimide (2.64 g) were added under ice-cooling, and the mixture was stirred under ice-cooling for 2.5 hr. Water was added to the reaction mixture, and the mixture was extracted with methylene chloride and washed with saturated brine, and dried over anhydrous sodium sulfate. The solvent was evaporated under reduced pressure. Diethyl ether was added, and the precipitated triphenylphosphine oxide was filtered off. The concentrate of the filtrate was purified by silica gel column chromatography (hexane alone) to give the object product (2.99 g) as a colorless oil.

$^1$H-NMR(DMSO-d$_6$) δ (ppm): 2.05-2.11(2H, m), 2.30(3H, s), 2.66(2H, t, J=7.8 Hz), 3.50(2H, t, J=6.6 Hz), 7.06(1H, dd, J=8.0, 1.8 Hz), 7.20(1H, d, J=1.3 Hz), 7.31(1H, d, J=8.0 Hz).

(67-4) Synthesis of 2-amino-2-(2-{4-[3-(4-chloro-3-methylphenyl)propoxy]-3-trifluoromethylphenyl}ethyl)propane-1,3-diol hydrochloride (Compound 67-4)

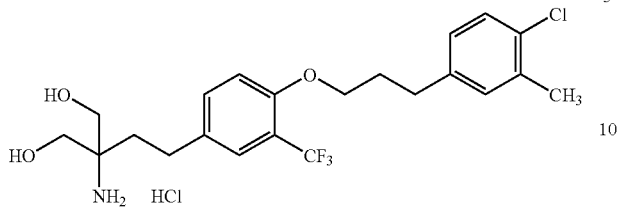

Reference Example compound 2-6 (500 mg) was dissolved in N,N-dimethylformamide (10 ml), potassium carbonate (494 mg) and compound 67-3 (355 mg) were added, and the mixture was stirred at 80° C. for 2 hr. Water was added to the reaction mixture, and the mixture was extracted with ethyl acetate, washed with water and saturated brine, and dried over anhydrous sodium sulfate. The solvent was evaporated under reduced pressure. The obtained pale-white solid was dissolved in ethanol (15 ml), concentrated hydrochloric acid (1.5 ml) was added, and the mixture was stirred at 80° C. for 3 hr. The reaction mixture was concentrated, and the residue was washed with diethyl ether to give the object product (433 mg) as a white powder.

MS(ESI)m/z: 446[M+H]

$^1$H-NMR(DMSO-$d_6$) δ (ppm): 1.74-1.78(2H, m), 1.97-2.04(2H, m), 2.28(3H, s), 2.62-2.58(2H, m), 2.70(2H, t, J=7.6 Hz), 3.52(4H, d, J=5.2 Hz), 4.04(2H, t, J=6.1 Hz), 5.40(2H, t, J=5.2 Hz), 7.03(1H, dd, J=8.3, 1.9 Hz), 7.16(1H, d, J=8.6 Hz), 7.18(1H, s), 7.31(1H, d, J=8.0 Hz), 7.43(1H, d, J=8.5 Hz), 7.47(1H, d, J=1.8 Hz), 7.82(3H, brs).

Example 68

2-amino-2-(2-{4-[3-(3-fluoro-4-trifluoromethylphenyl)propoxy]-3-trifluoromethylphenyl}ethyl)propane-1,3-diol hydrochloride

(68-1) Synthesis of 3-(3-fluoro-4-trifluoromethylphenyl)-2-propyne-1-ol (Compound 68-1)

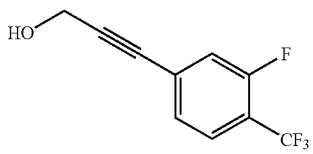

A mixture of 2-fluoro-4-iodobenzotrifluoride (5.00 g), copper(I) iodide (65.5 mg), triphenylphosphine (226 mg), tris(dibenzylideneacetone)dipalladium(0) chloroform adduct (356 mg), propargyl alcohol (1.12 ml), diisopropylethylamine (12.0 ml) and tetrahydrofuran (80 ml) was stirred at room temperature for 11 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=99:1-80:20) to give the object product (3.08 g) as a brown oil.

$^1$H-NMR(CDCl$_3$) δ (ppm): 1.73(1H, t, J=6.2 Hz), 4.52(2H, d, J=6.2 Hz), 7.25(1H, d, J=10.0 Hz), 7.30(1H, d, J=8.2 Hz), 7.55(1H, t, J=7.7 Hz).

(68-2) Synthesis of 3-(3-fluoro-4-trifluoromethylphenyl)-1-propanol (Compound 68-2)

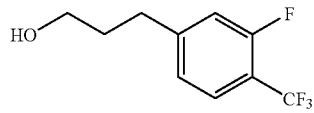

A solution of compound 68-1 (3.08 g) and 10% palladium carbon (1.50 g) in 1,4-dioxane (70 ml) was stirred under a hydrogen atmosphere at room temperature for 8 hr. The reaction mixture was filtered through celite and concentrated to give the object product (2.83 g) as a brown oil.

$^1$H-NMR(CDCl$_3$) δ (ppm): 1.34(1H, brs), 1.86-1.93(2H, m), 2.78(2H, t, J=7.8 Hz), 3.69(2H, t, J=6.2 Hz), 7.03-7.08 (2H, m), 7.51(1H, t, J=7.7 Hz).

(68-3) Synthesis of 1-(3-bromopropyl)-3-fluoro-4-trifluoromethylbenzene (Compound 68-3)

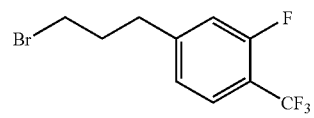

Compound 68-2 (2.83 g) was dissolved in methylene chloride (42 ml), triphenylphosphine (3.67 g) and N-bromosuccinimide (2.56 g) were added under ice-cooling, and the mixture was stirred under ice-cooling for 2 hr. Water was added to the reaction mixture, and the mixture was extracted with methylene chloride and washed with saturated brine, and dried over anhydrous sodium sulfate. The solvent was evaporated under reduced pressure. Diethyl ether was added, and the precipitated triphenylphosphine oxide was filtered off. The concentrate of the filtrate was purified by silica gel column chromatography (hexane alone) to give the object product (2.87 g) as a colorless oil.

$^1$H-NMR(DMSO-$d_6$) δ (ppm): 2.11-2.18(2H, m), 2.82(2H, t, J=7.8 Hz), 3.53(2H, t, J=6.8 Hz), 7.29(1H, d, J=8.0 Hz), 7.41(1H, d, J=12.1 Hz), 7.70(1H, t, J=8.0 Hz).

(68-4) Synthesis of 2-amino-2-(2-{4-[3-(3-fluoro-4-trifluoromethylphenyl)propoxy]-3-trifluoromethylphenyl}ethyl)propane-1,3-diol hydrochloride (Compound 68-4)

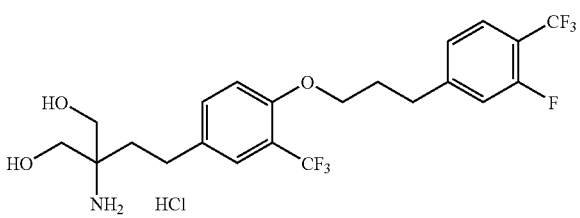

Reference Example compound 2-6 (500 mg) was dissolved in N,N-dimethylformamide (10 ml), potassium carbonate (494 mg) and compound 68-3 (410 mg) were added, and the mixture was stirred at 80° C. for 3.5 hr. Water was added to the reaction mixture, and the mixture was extracted with ethyl acetate, washed with water and saturated brine, and dried over anhydrous sodium sulfate. The solvent was evaporated under reduced pressure. The obtained white solid was dissolved in ethanol (15 ml), concentrated hydrochloric acid (1.5 ml) was added, and the mixture was stirred at 80° C. for 3 hr. The reaction mixture was concentrated, and the residue was washed with diethyl ether to give the object product (458 mg) as a white powder.

MS(ESI)m/z: 484[M+H]

$^1$H-NMR(DMSO-d$_6$) δ (ppm): 1.74-1.78(2H, m), 2.04-2.11(2H, m), 2.58-2.62(2H, m), 2.85(2H, t, J=7.6 Hz), 3.52 (4H, d, J=5.1 Hz), 4.06(2H, t, J=6.1 Hz), 5.40(2H, t, J=5.1 Hz), 7.18(1H, d, J=8.5 Hz), 7.25(1H, d, J=8.0 Hz), 7.38(1H, d, J=12.2 Hz), 7.44(1H, d, J=8.5 Hz), 7.48(1H, s), 7.70(1H, t, J=8.0 Hz), 7.83(3H, brs).

Example 69

2-amino-2-(2-{4-[3-(4-fluoro-3-trifluoromethylphenyl)propoxy]-3-trifluoromethylphenyl}ethyl)propane-1,3-diol hydrochloride (69-1) Synthesis of 3-(4-fluoro-3-trifluoromethylphenyl)-2-propyne-1-ol (Compound 69-1)

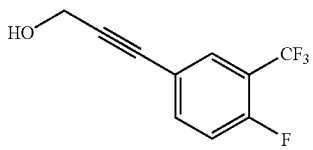

A mixture of 2-fluoro-5-iodobenzotrifluoride (5.00 g), copper(I) iodide (65.5 mg), triphenylphosphine (226 mg), tris(dibenzylideneacetone)dipalladium(0) chloroform adduct (356 mg), propargyl alcohol (1.12 ml), diisopropylethylamine (12.0 ml) and tetrahydrofuran (80 ml) was stirred at room temperature for 11 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=99:1-80:20) to give the object product (3.26 g) as a brown oil.

$^1$H-NMR(CDCl$_3$) δ (ppm): 1.69(1H, t, J=6.2 Hz), 4.50(2H, d, J=6.2 Hz), 7.16(1H, t, J=9.3 Hz), 7.58-7.62(1H, m), 7.69 (1H, dd, J=1.4, 6.8 Hz).

(69-2) Synthesis of 3-(4-fluoro-3-trifluoromethylphenyl)-1-propanol (Compound 69-2)

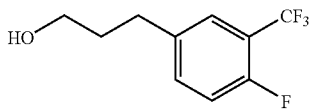

A solution of compound 69-1 (3.26 g) and 10% palladium carbon (1.50 g) in 1,4-dioxane (70 ml) was stirred under a hydrogen atmosphere at room temperature for 8 hr. The reaction mixture was filtered through celite and concentrated to give the object product (3.01 g) as a brown oil.

$^1$H-NMR(CDCl$_3$) δ (ppm): 1.33(1H, brs), 1.85-1.92(2H, m), 2.75(2H, t, J=7.8 Hz), 3.68(2H, t, J=6.2 Hz), 7.09-7.13 (1H, m), 7.34-7.38(1H, m), 7.41-7.43(1H, m).

(69-3) Synthesis of 1-(3-bromopropyl)-4-fluoro-3-trifluoromethylbenzene (Compound 69-3)

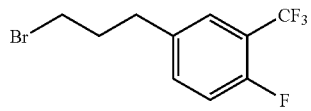

Compound 69-2 (3.05 g) was dissolved in methylene chloride (46 ml), triphenylphosphine (4.00 g) and N-bromosuccinimide (2.69 g) were added under ice-cooling, and the mixture was stirred under ice-cooling for 1.5 hr. Water was added to the reaction mixture, and the mixture was extracted with methylene chloride and washed with saturated brine, and dried over anhydrous sodium sulfate. The solvent was evaporated under reduced pressure. Diethyl ether was added, and the precipitated triphenylphosphine oxide was filtered off. The concentrate of the filtrate was purified by silica gel column chromatography (hexane alone) to give the object product (2.86 g) as a colorless oil.

$^1$H-NMR(DMSO-d$_6$) δ (ppm): 2.08-2.15(2H, m), 2.79(2H, t, J=7.8 Hz), 3.51(2H, t, J=6.5 Hz), 7.43(1H, dd, J=10.5, 8.4 Hz), 7.59-7.64(2H, m).

(69-4) Synthesis of 2-amino-2-(2-{4-[3-(4-fluoro-3-trifluoromethylphenyl)propoxy]-3-trifluoromethylphenyl}ethyl)propane-1,3-diol hydrochloride (Compound 69-4)

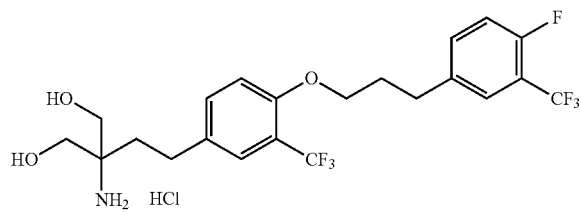

Reference Example compound 2-6 (500 mg) was dissolved in N,N-dimethylformamide (10 ml), potassium carbonate (494 mg) and compound 69-3 (410 mg) were added, and the mixture was stirred at 80° C. for 2 hr. Water was added to the reaction mixture, and the mixture was extracted with ethyl acetate, washed with water and saturated brine, and dried over anhydrous sodium sulfate. The solvent was evaporated under reduced pressure. The obtained white solid was dissolved in ethanol (15 ml), concentrated hydrochloric acid (1.5 ml) was added, and the mixture was stirred at 80° C. for 3 hr. The reaction mixture was concentrated, and the residue was washed with diethyl ether to give the object product (467 mg) as a white powder.

MS(ESI)m/z: 484[M+H]

$^1$H-NMR(DMSO-d$_6$) δ (ppm): 1.74-1.78(2H, m), 2.02-2.08(2H, m), 2.54-2.62(2H, m), 2.82(2H, t, J=7.6 Hz), 3.52 (4H, d, J=5.2 Hz), 4.04(2H, t, J=6.1 Hz), 5.40(2H, t, J=5.2

Hz), 7.17(1H, d, J=8.6 Hz), 7.40-7.45(2H, m), 7.47(1H, d, J=1.8 Hz), 7.56-7.59(2H, m), 7.82(3H, brs).

Example 70

2-amino-2-(2-{4-[3-(2,3,4-trifluorophenyl)propoxy]-3-trifluoromethylphenyl}ethyl)propane-1,3-diol hydrochloride (70-1) Synthesis of 3-(2,3,4-trifluorophenyl)-2-propyne-1-ol (Compound 70-1)

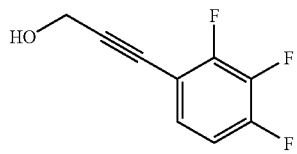

A mixture of 2,3,4-trifluoroiodobenzene (5.00 g), copper (I) iodide (73.9 mg), triphenylphosphine (254 mg), tris(dibenzylideneacetone)dipalladium(0) chloroform adduct (402 mg), propargyl alcohol (1.26 ml), diisopropylethylamine (13.5 ml) and tetrahydrofuran (100 ml) was stirred at room temperature for 17 hr. The reaction mixture was added to brine, and the mixture was extracted with ethyl acetate, washed with saturated brine, and dried over anhydrous magnesium sulfate. The solvent was evaporated under reduced pressure. The residue 5 was purified by silica gel column chromatography (hexane:ethyl acetate=99:1-80:20) to give the object product (3.14 g) as a brown oil.

$^1$H-NMR(CDCl$_3$) δ (ppm): 1.73(1H, t, J=6.3 Hz), 4.53(2H, d, J=6.3 Hz), 6.90-6.97(1H, m), 7.13-7.19(1H, m).

(70-2) Synthesis of 3-(2,3,4-trifluorophenyl)-1-propanol (Compound 70-2)

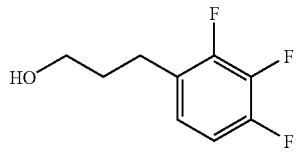

A solution of compound 70-1 (3.14 g) and 10% palladium carbon (1.50 g) in 1.4-dioxane (70 ml) was stirred under a hydrogen atmosphere at room temperature for 9 hr. The reaction mixture was filtered through celite and concentrated to give the object product (2.88 g) as a dark-green oil.

$^1$H-NMR(CDCl$_3$) δ (ppm): 1.34(1H, brs), 1.83-1.90(2H, m), 2.74(2H, t, J=7.6 Hz), 3.68(2H, t, J=6.2 Hz), 6.85-6.94 (2H, m).

(70-3) Synthesis of 1-(3-bromopropyl)-2,3,4-trifluorobenzene (Compound 70-3)

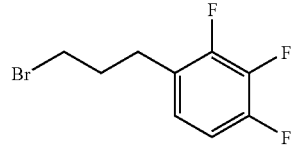

Compound 70-2 (2.90 g) was dissolved in methylene chloride (20 ml), triphenylphosphine (4.40 g) and N-bromosuccinimide (2.99 g) were added under ice-cooling, and the mixture was stirred under ice-cooling for 1 hr, and at room temperature for 1 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (3.14 g) as a colorless oil.

$^1$H-NMR(CDCl$_3$) δ (ppm): 2.11-2.18(2H, m), 2.81(2H, t, J=7.3 Hz), 3.39(2H, t, J=6.4 Hz), 6.88-6.94(2H, m).

(70-4) Synthesis of [5-(2-{4-[3-(2,3,4-trifluorophenyl)propoxy]-3-trifluoromethylphenyl}ethyl)-2,2-dimethyl-1,3-dioxan-5-yl]carbamic acid t-butyl ester (Compound 70-4)

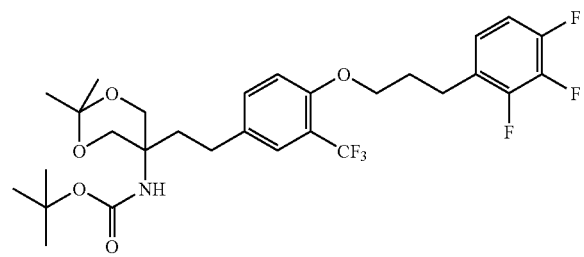

Reference Example compound 2-6 (500 mg) was dissolved in N,N-dimethylformamide (10 ml), potassium carbonate (494 mg) and compound 70-3 (362 mg) were added, and the mixture was stirred at 80° C. for 1.5 hr. Water was added to the reaction mixture, and the mixture was extracted with ethyl acetate, washed with water and saturated brine, and dried over anhydrous magnesium sulfate. The solvent was evaporated under reduced pressure to give the object product (700 mg) as a white solid.

$^1$H-NMR(CDCl$_3$) δ (ppm): 1.43(3H, s), 1.44(3H, s), 1.47 (9H, s), 1.93-1.98(2H, m), 2.07-2.12(2H, m), 2.52-2.56(2H, m), 2.86(2H, t, J=7.4 Hz), 3.69(2H, d, J=11.7 Hz), 3.89(2H, d, J=11.7 Hz), 3.98(2H, t, J=5.8 Hz), 4.99(1H, brs), 6.82-6.89 (3H, m), 7.26-7.28(1H, m), 7.37(1H, d, J=1.8 Hz).

(70-5) Synthesis of 2-amino-2-(2-{4-[3-(2,3,4-trifluorophenyl)propoxy]-3-trifluoromethylphenyl}ethyl)propane-1,3-diol hydrochloride (Compound 70-5)

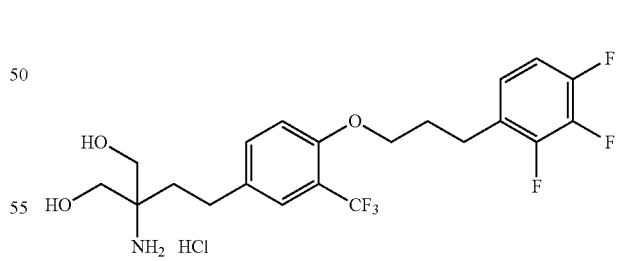

Compound 70-4 (700 mg) was dissolved in ethanol (15 ml), concentrated hydrochloric acid (1.5 ml) was added, and the mixture was stirred at 80° C. for 2 hr. The reaction mixture was concentrated, and the residue was washed with diethyl ether to give the object product (520 mg) as a white powder.

MS(ESI)m/z: 452[M+H]

$^1$H-NMR(DMSO-d$_6$) δ (ppm): 1.74-1.79(2H, m), 1.97-2.05(2H, m), 2.58-2.63(2H, m), 2.80(2H, t, J=7.5 Hz), 3.52 (4H, d, J=5.2 Hz), 4.07(2H, t, J=5.8 Hz), 5.40(2H, t, J=5.1

Hz), 7.12-7.18(2H, m), 7.24-7.26(1H, m), 7.45(1H, d, J=8.6 Hz), 7.47(1H, s), 7.85(3H, brs).

Example 71

2-amino-2-(2-{4-[3-(2-chloro-4-trifluoromethylphenyl)propoxy]-3-trifluoromethylphenyl}ethyl)propane-1,3-diol hydrochloride

(71-1) Synthesis of 3-(2-chloro-4-trifluoromethylphenyl)-2-propyne-1-ol (Compound 71-1)

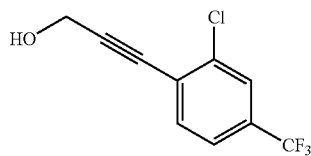

A mixture of 3-chloro-4-iodobenzotrifluoride (5.00 g), copper(I) iodide (62.1 mg), triphenylphosphine (214 mg), tris(dibenzylideneacetone)dipalladium(0) chloroform adduct (337 mg), propargyl alcohol (1.06 ml), diisopropylethylamine (11.4 ml) and tetrahydrofuran (100 ml) was stirred at room temperature for 17 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=99:1-80:20) to give the object product (3.05 g) as a brown solid.

$^1$H-NMR(CDCl$_3$) δ (ppm): 1.74(1H, t, J=6.3 Hz), 4.58(2H, d, J=6.3 Hz), 7.48(1H, d, J=8.5 Hz), 7.59(1H, d, J=8.1 Hz), 7.67(1H, s).

(71-2) Synthesis of 3-(2-chloro-4-trifluoromethylphenyl)-1-propanol (Compound 71-2)

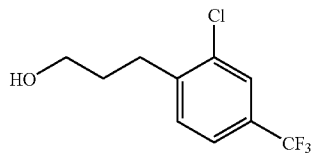

A suspension of Compound 71-1 (3.05 g) and chlorotris(triphenylphosphine)rhodium(I) (3.00 g) in toluene (80 ml) was stirred under a hydrogen atmosphere at 65° C. for 11 hr. The reaction mixture was concentrated, diisopropyl ether was added and the mixture was filtered through celite. The filtrate was concentrated and the obtained residue was purified by silica gel column chromatography (hexane:ethyl acetate=99:1-70:30) to give the object product (2.52 g) as a brown oil.

$^1$H-NMR(CDCl$_3$) δ (ppm): 1.35(1H, t, J=4.8 Hz), 1.87-1.94(2H, m), 2.90(2H, t, J=7.8 Hz), 3.71(2H, q, J=5.6 Hz), 7.37(1H, d, J=8.0 Hz), 7.45(1H, d, J=8.0 Hz), 7.62(1H, s).

(71-3) Synthesis of 1-(3-bromopropyl)-2-chloro-4-trifluoromethylbenzene (Compound 71-3)

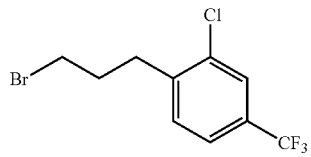

Compound 71-2 (2.48 g) was dissolved in methylene chloride (30 ml), triphenylphosphine (3.00 g) and N-bromosuccinimide (2.03 g) were added under ice-cooling, and the mixture was stirred under ice-cooling for 1 hr, and at room temperature for 16 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (2.79 g) as a colorless oil.

$^1$H-NMR(CDCl$_3$) δ (ppm): 2.16-2.23(2H, m), 2.97(2H, t, J=7.5 Hz), 3.43(2H, t, J=6.4 Hz), 7.39(1H, d, J=8.0 Hz), 7.46(1H, d, J=8.0 Hz), 7.62(1H, s).

(71-4) Synthesis of [5-(2-{4-[3-(2-chloro-4-trifluoromethylphenyl)propoxy]-3-trifluoromethylphenyl}ethyl)-2,2-dimethyl-1,3-dioxan-5-yl]carbamic acid t-butyl ester (Compound 71-4)

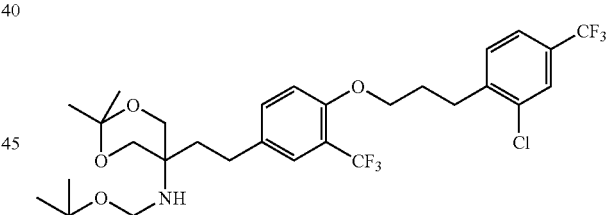

Reference Example compound 2-6 (500 mg) was dissolved in N,N-dimethylformamide (10 ml), potassium carbonate (494 mg) and compound 71-3 (431 mg) were added, and the mixture was stirred at 80° C. for 1 hr. Water was added to the reaction mixture, and the mixture was extracted with ethyl acetate, washed with water and saturated brine, and dried over anhydrous magnesium sulfate. The solvent was evaporated under reduced pressure to give the object product (790 mg) as a white solid.

$^1$H-NMR(CDCl$_3$) δ (ppm): 1.43(3H, s), 1.44(3H, s), 1.48(9H, s), 1.93-1.99(2H, m), 2.12-2.23(2H, m), 2.52-2.57(2H, m), 3.02(2H, brt, J=6.6 Hz), 3.70(2H, d, J=11.6 Hz), 3.89(2H, d, J=11.6 Hz), 4.02(2H, brs), 5.00(1H, brs), 6.85(1H, d, J=8.4 Hz), 7.26-7.28(1H, m), 7.33-7.45(3H, m), 7.64(1H, brs).

(71-5) Synthesis of 2-amino-2-(2-{4-[3-(2-chloro-4-trifluoromethylphenyl)propoxy]-3-trifluoromethylphenyl}ethyl)propane-1,3-diol hydrochloride (Compound 71-5)

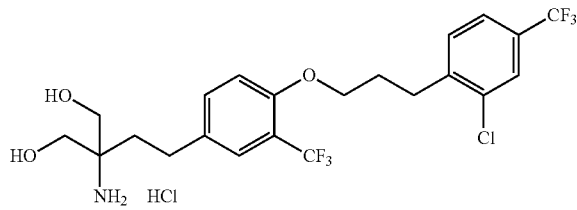

Compound 71-4 (790 mg) was dissolved in ethanol (15 ml), concentrated hydrochloric acid (1.5 ml) was added, and the mixture was stirred at 80° C. for 2 hr. The reaction mixture was concentrated, and the residue was washed with diethyl ether to give the object product (560 mg) as a white powder.

MS(ESI)m/z: 500[M+H]

$^1$H-NMR(DMSO-$d_6$) δ (ppm): 1.74-1.79(2H, m), 2.02-2.08(2H, m), 2.58-2.63(2H, m), 3.06(2H, t, J=7.7 Hz), 3.52 (4H, d, J=5.0 Hz), 4.12(2H, t, J=5.8 Hz), 5.40(2H, t, J=5.1 Hz), 7.19(1H, J=8.5 Hz), 7.45(1H, d, J=8.5 Hz), 7.48(1H, s), 7.57(1H, d, J=8.0 Hz), 7.68(1H, d, J=7.5 Hz), 7.77-7.89(4H, m).

Example 72

2-amino-2-(2-{4-[3-(4-cyanophenyl)propoxy]-3-trifluoromethylphenyl}ethyl)propane-1,3-diol hydrochloride

(72-1) Synthesis of 3-(4-cyanophenyl)-2-propyne-1-ol (Compound 72-1)

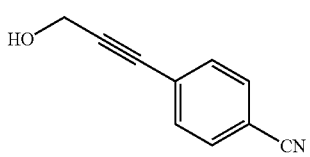

A mixture of 4-iodobenzonitrile (10.0 g), copper(I) iodide (166 mg), triphenylphosphine (572 mg), tris(dibenzylideneacetone)dipalladium(0) chloroform adduct (904 mg), propargyl alcohol (2.83 ml), diisopropylethylamine (30.5 ml) and tetrahydrofuran (170 ml) was stirred at room temperature for 23 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=95:5-67:33) to give the object product (5.79 g) as a brown solid.

$^1$H-NMR(CDCl$_3$) δ (ppm): 1.72(1H, t, J=6.2 Hz), 4.53(2H, d, J=6.2 Hz), 7.52(2H, d, J=8.2 Hz), 7.61(2H, d, J=8.2 Hz).

(72-2) Synthesis of 3-(4-cyanophenyl)-1-propanol (Compound 72-2)

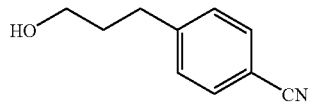

A suspension of Compound 72-1 (5.79 g) and chlorotris (triphenylphosphine)rhodium(I) (5.00 g) in toluene (150 ml) was stirred under a hydrogen atmosphere at 65° C. for 15 hr. The reaction mixture was concentrated, diisopropyl ether was added and the mixture was filtered through celite. The filtrate was concentrated and the obtained residue was purified by silica gel column chromatography (hexane:ethyl acetate=99:1-50:50) to give the object product (4.20 g) as a brown oil.

$^1$H-NMR(CDCl$_3$) δ (ppm): 1.36(1H, brs), 1.86-1.93(2H, m), 2.79(2H, t, J=7.8 Hz), 3.68(2H, t, J=6.2 Hz), 7.31(2H, d, J=8.2 Hz), 7.58(2H, d, J=8.2 Hz).

(72-3) Synthesis of 1-(3-bromopropyl)-4-cyanobenzene (Compound 72-3)

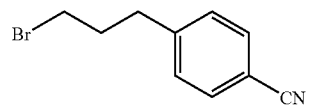

Compound 72-2 (4.22 g) was dissolved in methylene chloride (30 ml), triphenylphosphine (7.58 g) and N-bromosuccinimide (5.14 g) were added under ice-cooling, and the mixture was stirred under ice-cooling for 2 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography to give the object product (5.37 g) as a colorless oil.

$^1$H-NMR(CDCl$_3$) δ (ppm): 2.14-2.21(2H, m), 2.86(2H, t, J=7.5 Hz), 3.39(2H, t, J=6.5 Hz), 7.32(2H, d, J=8.2 Hz), 7.60(2H, d, J=8.2 Hz).

(72-4) Synthesis of [5-(2-{4-[3-(4-cyanophenyl)propoxy]-3-trifluoromethylphenyl}ethyl)-2,2-dimethyl-1,3-dioxan-5-yl]carbamic acid t-butyl ester (Compound 72-4)

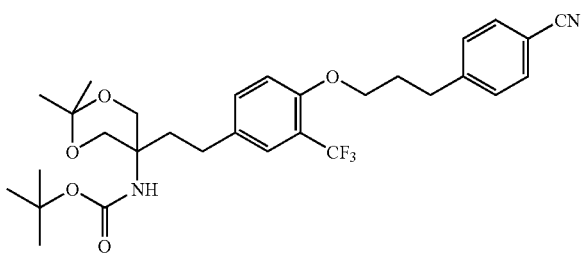

Reference Example compound 2-6 (500 mg) was dissolved in N,N-dimethylformamide (10 ml), potassium carbonate (494 mg) and compound 72-3 (321 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (750 mg) as a white solid.

$^1$H-NMR(CDCl$_3$) δ (ppm): 1.43(3H, s), 1.44(3H, s), 1.47 (9H, s), 1.94-1.98(2H, m), 2.04-2.13(2H, m), 2.52-2.57(2H, m), 2.91(2H, t, J=7.5 Hz), 3.69(2H, d, J=11.7 Hz), 3.89(2H, d, J=11.7 Hz), 3.97(2H, t, J=5.8 Hz), 5.00(1H, brs), 6.86(1H, d, J=8.5 Hz), 7.27-7.32(3H, m), 7.38(1H, d, J=1.8 Hz), 7.56-7.60(2H, m).

(72-5) Synthesis of 2-amino-2-(2-{4-[3-(4-cyanophenyl)propoxy]-3-trifluoromethylphenyl}ethyl) propane-1,3-diol hydrochloride (Compound 72-5)

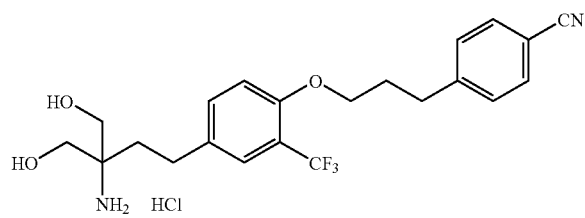

Compound 72-4 (750 mg) was dissolved in a mixed solvent of ethanol (10 ml) and methanol (10 ml), p-toluenesulfonic acid monohydrate (0.041 g) was added, and the mixture was stirred at room temperature for 4.5 hr. To the reaction mixture was added saturated aqueous sodium hydrogen carbonate, and the mixture was extracted with ethyl acetate, washed with saturated brine, and dried over anhydrous magnesium sulfate. The solvent was evaporated under reduced pressure. To a solution of the obtained residue in methylene chloride (15 ml) was added hydrogen chloride containing dioxane (4 mol/l, 5 ml), and the mixture was stirred at room temperature for 4 hr. The reaction mixture was concentrated, and the residue was washed with diethyl ether to give the object product (390 mg) as a white powder.

MS(ESI)m/z: 423[M+H]
$^1$H-NMR(DMSO-d$_6$) δ (ppm): 1.74-1.79(2H, m), 2.02-2.06(2H, m), 2.58-2.63(2H, m), 2.83(2H, t, J=7.5 Hz), 3.52 (4H, d, J=5.2 Hz), 4.03(2H, t, J=6.1 Hz), 5.36(2H, t, J=5.1 Hz), 7.17(1H, d, J=8.6 Hz), 7.40-7.48(4H, m), 7.76(2H, d, J=8.0 Hz), 7.84(3H, brs).

Example 73

2-amino-2-(2-{4-[3-(1-naphthyl)propoxy]-3-trifluoromethylphenyl}ethyl)propane-1,3-diol hydrochloride (73-1) Synthesis of 3-(1-naphthyl)-1-propanol (Compound 73-1)

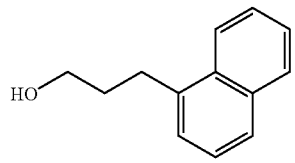

3-(1-Naphthyl) acrylic acid (5.00 g) was dissolved in methanol (30 ml) and tetrahydrofuran (50 ml), 10% palladium carbon (2.40 g) was added, and the mixture was stirred under a hydrogen atmosphere at room temperature for 13 hr. The reaction container was purged with nitrogen, the solution was filtered, and the filtrate was concentrated to give a white solid (5.00 g. The white solid was dissolved in tetrahydrofuran (100 ml), and a tetrahydrofuran-borane.tetrahydrofuran solution (1 mol/l, 27.4 ml) was added dropwise to the mixture under ice-cooling, and the mixture was stirred under ice-cooling for 1 hr, and further at room temperature for 18 hr. To the reaction mixture was added water, and 1M aqueous hydrochloric acid solution was added. The mixture was extracted with ethyl acetate, washed with water, saturated aqueous sodium hydrogen carbonate solution and saturated brine, and dried over anhydrous magnesium sulfate. The solvent was evaporated under reduced pressure. The obtained residue was purified by silica gel column chromatography to give the object product (4.70 g) as a colorless oil.

$^1$H-NMR(CDCl$_3$) δ (ppm): 1.32(1H, brs), 2.00-2.07(2H, m), 3.19(2H, t, J=7.5 Hz), 3.73-3.78(2H, m), 7.34-7.42(2H, m), 7.47-7.52(2H, m), 7.72(1H, d, J=8.2 Hz), 7.84-7.87(1H, m), 8.07(1H, d, J=8.2 Hz).

(73-2) Synthesis of 1-(3-bromopropyl)naphthalene (Compound 73-2)

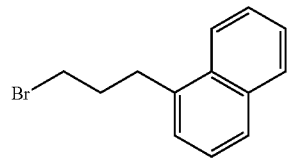

Compound 73-1 (4.70 g) was dissolved in methylene chloride (50 ml), triphenylphosphine (7.13 g) and N-bromosuccinimide (4.84 g) were added under ice-cooling, and the mixture was stirred under ice-cooling for 2 hr, and further at room temperature for 15 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography to give the object product (5.67 g) as a colorless oil.

$^1$H-NMR(CDCl$_3$) δ (ppm): 2.27-2.34(2H, m), 3.26(2H, t, J=7.4 Hz), 3.47(2H, t, J=6.5 Hz), 7.35-7.43(2H, m), 7.46-7.55(2H, m), 7.74(1H, d, J=7.8 Hz), 7.87(1H, d, J=7.8 Hz), 8.05(1H, d, J=8.3 Hz).

(73-3) Synthesis of [2,2-dimethyl-5-(2-{4-[3-(1-naphthyl)propoxy]-3-trifluoromethylphenyl}ethyl)-1,3-dioxan-5-yl]carbamic acid t-butyl ester (Compound 73-3)

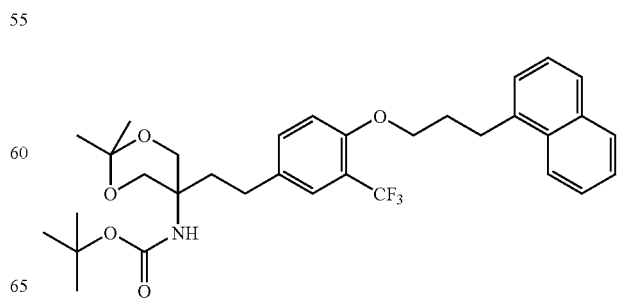

Reference Example compound 2-6 (500 mg) was dissolved in N,N-dimethylformamide (10 ml), potassium carbonate (494 mg) and compound 73-2 (356 mg) were added, and the mixture was stirred at 80° C. for 1.5 hr. Water was added to the reaction mixture, and the mixture was extracted with ethyl acetate, washed with water and saturated brine, and dried over anhydrous magnesium sulfate. The solvent was evaporated under reduced pressure. The obtained residue was purified by silica gel column chromatography to give the object product (620 mg) as a white solid.

$^1$H-NMR(CDCl$_3$) δ (ppm): 1.43(3H, s), 1.44(3H, s), 1.48 (9H, s), 1.94-1.99(2H, m), 2.22-2.28(2H, m), 2.53-2.57(2H, m), 3.31(2H, t, J=7.6 Hz), 3.70(2H, d, J=11.7 Hz), 3.89(2H, d, J=11.7 Hz), 4.06(2H, t, J=5.7 Hz), 5.00(1H, brs), 6.85(1H, d, J=8.5 Hz), 7.25-7.28(1H, m), 7.32-7.40(3H, m), 7.45-7.53 (2H, m), 7.72(1H, d, J=7.9 Hz), 7.84-7.87(1H, m), 8.12(1H, d, J=7.9 Hz).

(73-4) Synthesis of 2-amino-2-(2-{4-[3-(1-naphthyl) propoxy]-3-trifluoromethylphenyl}ethyl)propane-1, 3-diol hydrochloride (Compound 73-4)

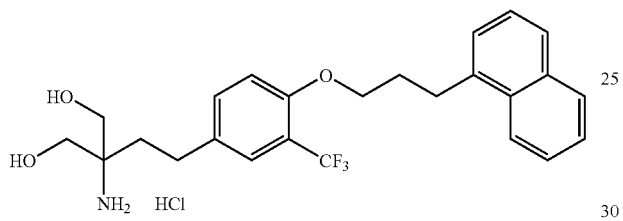

Compound 73-3 (620 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give the object product (490 mg) as a white powder.

MS(ESI)m/z: 448[M+H]

$^1$H-NMR(DMSO-d$_6$) δ (ppm): 1.76-1.80(2H, m), 2.09-2.14(2H, m), 2.60-2.65(2H, m), 3.21-3.25(2H, m), 3.53(4H, d, J=5.1 Hz), 4.15(2H, t, J=5.8 Hz), 5.42(2H, t, J=5.1 Hz), 7.19(1H, d, J=8.6 Hz), 7.36(1H, d, J=6.7 Hz), 7.41-7.47(2H, m), 7.50-7.54(3H, m), 7.79(1H, d, J=8.2 Hz), 7.87(3H, brs), 7.92-7.94(1H, m), 8.10-8.13(1H, m).

Example 74

2-amino-2-(2-{4-[3-(morpholin-4-yl)propoxy]-3-trifluoromethylphenyl}ethyl)propane-1,3-diol dihydrochloride (74-1) Synthesis of 2-amino-2-(2-{4-[3-(morpholin-4-yl)propoxy]-3-trifluoromethylphenyl}ethyl)propane-1,3-diol dihydrochloride (Compound 74-1)

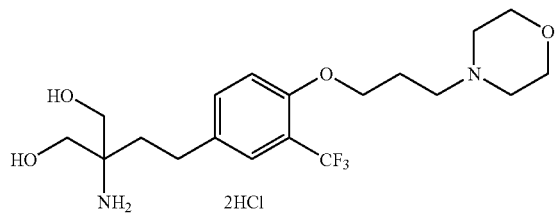

Triphenylphosphine (625 mg) was dissolved in tetrahydrofuran (30 ml), diisopropyl azodicarboxylate (40% toluene solution, 1.27 ml), 4-(3-hydroxypropyl)morpholine (0.347 ml) and Reference Example compound 2-6 (500 mg) were added, and the mixture was stirred at room temperature for 4.5 hr. Water was added to the reaction mixture, and the mixture was extracted with ethyl acetate, washed with saturated brine, and dried over anhydrous magnesium sulfate. The solvent was evaporated under reduced pressure. The obtained residue was dissolved in ethanol (15 ml), concentrated hydrochloric acid (1.5 ml) was added, and the mixture was stirred at 80° C. for 1 hr. The reaction mixture was concentrated and 500 mg of the obtained residue (1 g) was purified by HPLC. The obtained residue was converted to hydrochloride by the addition of hydrogen chloride containing ether (1 mol/l, 5 ml), and the precipitate was collected by filtration and dried to give the object product (80 mg) as a white powder.

MS (ESI)m/z: 407[M+H]

$^1$H-NMR(DMSO-d$_6$) δ (ppm): 1.74-1.79(2H, m), 2.18-2.29(2H, m), 2.60-2.66(2H, m), 3.00-3.11(2H, m), 3.12-3.20 (2H, m), 3.34-3.44(2H, m), 3.52(4H, s), 3.80-3.86(2H, m), 3.97(2H, J=11.3 Hz), 4.18(2H, t, J=6.0 Hz), 5.41(2H, brs), 7.22(1H, J=9.2 Hz), 7.47-7.49(2H, m), 7.90(3H, brs), 11.3 (1H, brs).

Example 75

2-amino-2-(2-{4-[3-(3-cyanophenyl)propoxy]-3-trifluoromethylphenyl}ethyl)propane-1,3-diol hydrochloride (75-1) Synthesis of 3-(3-cyanophenyl)-2-propyne-1-ol (Compound 75-1)

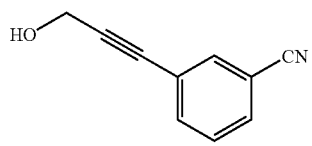

A mixture of 3-iodobenzonitrile (10.0 g), copper(I) iodide (166 mg), triphenylphosphine (572 mg), tris(dibenzylideneacetone)dipalladium(0) chloroform adduct (904 mg), propargyl alcohol (2.83 ml), diisopropylethylamine (30.5 ml) and tetrahydrofuran (170 ml) was stirred at room temperature for 23 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane: ethyl acetate=95:5-67:33) to give the object product (5.59 g) as a brown solid.

$^1$H-NMR(CDCl$_3$) δ (ppm): 1.76(1H, t, J=6.2 Hz), 4.51(2H, d, J=6.2 Hz), 7.44(1H, t, J=7.8 Hz), 7.61(1H, d, J=7.8 Hz), 7.65(1H, d, J=7.8 Hz), 7.71(1H, s).

(75-2) Synthesis of 3-(3-cyanophenyl)-1-propanol (Compound 75-2)

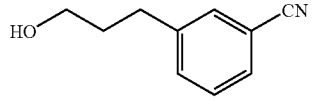

A suspension of compound 75-1 (5.59 g) and chlorotris (triphenylphosphine)rhodium(I) (5.00 g) in toluene (110 ml) was stirred under a hydrogen atmosphere at 65° C. for 15 hr.

The reaction mixture was concentrated, diisopropyl ether was added and the mixture was filtered through celite. The filtrate was concentrated and the obtained residue was purified by silica gel column chromatography (hexane:ethyl acetate=95:5-50:50) to give the object product (4.24 g) as a brown oil.

$^1$H-NMR(CDCl$_3$) δ (ppm): 1.41(1H, brs), 1.86-1.93(2H, m), 2.77(2H, t, J=7.8 Hz), 3.68(2H, t, J=6.3 Hz), 7.37-7.41 (1H, m), 7.44-7.46(1H, m), 7.49-7.50(2H, m).

(75-3) Synthesis of 1-(3-bromopropyl)-3-cyanobenzene (Compound 75-3)

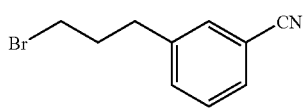

Compound 75-2 (4.45 g) was dissolved in methylene chloride (95 ml), triphenylphosphine (8.13 g) and N-bromosuccinimide (5.51 g) were added under ice-cooling, and the mixture was stirred under ice-cooling for 2 hr. Water was added to the reaction mixture, and the mixture was extracted with methylene chloride and washed with saturated brine, and dried over anhydrous sodium sulfate. The solvent was evaporated under reduced pressure. Diethyl ether was added, and the precipitated triphenylphosphine oxide was filtered off. The concentrate of the filtrate was purified by silica gel column chromatography (hexane:ethyl acetate=10:1) to give the object product (5.44 g) as a colorless oil.

$^1$H-NMR(DMSO-d$_6$) δ (ppm): 2.09-2.16(2H, m), 2.77(2H, t, J=7.8 Hz), 3.51(2H, t, J=6.8 Hz), 7.51(1H, t, J=7.6 Hz), 7.59(1H, d, J=7.8 Hz), 7.68(1H, d, J=7.5 Hz), 7.72(1H, s).

(75-4) Synthesis of [3-{4-[3-(3-cyanophenyl)propoxy]-3-trifluoromethylphenyl}-1,1-bis(hydroxymethyl)propyl]carbamic acid t-butyl ester (Compound 75-4)

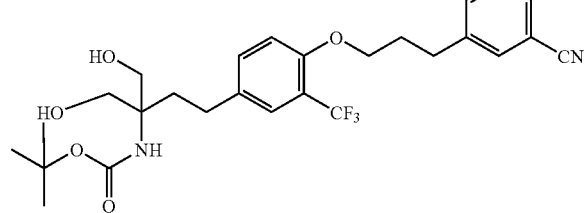

Reference Example compound 2-6 (500 mg) was dissolved in N,N-dimethylformamide (10 ml), potassium carbonate (493 mg) and compound 75-3 (320 mg) were added, and the mixture was stirred at 80° C. for 4 hr. Water was added to the reaction mixture, and the mixture was extracted with ethyl acetate, washed with water and saturated brine, and dried over anhydrous sodium sulfate. The solvent was evaporated under reduced pressure. The obtained white solid was dissolved in a mixed solvent of ethanol (6 ml) and methanol (4 ml), p-toluenesulfonic acid monohydrate (41 mg) was added, and the mixture was stirred at room temperature for 7 hr. Saturated aqueous sodium hydrogen carbonate was added to the reaction mixture, and the mixture was extracted with ethyl acetate, washed with saturated brine, and dried over anhydrous sodium sulfate. The solvent was evaporated, and the residue was purified by silica gel column chromatography (hexane:ethyl acetate) to give the object product (480 mg) as a white solid.

$^1$H-NMR(DMSO-d$_6$) δ (ppm): 1.62(9H, s), 2.01-2.05(2H, m), 2.21-2.30(2H, m), 3.03(2H, t, J=7.8 Hz), 3.65(2H, dd, J=10.6, 5.6 Hz), 3.74(2H, dd, J=10.6, 5.6 Hz), 4.24-4.28(2H, m), 4.84(2H, t, J=5.8 Hz), 6.28(1H, brs), 7.36(1H, d, J=8.5 Hz), 7.60(1H, d, J=8.5 Hz), 7.63(1H, s), 7.72(1H, t, J=7.7 Hz), 7.78(1H, d, J=7.8 Hz), 7.89(1H, d, J=7.3 Hz), 7.92(1H, s).

(75-5) Synthesis of 2-amino-2-(2-{4-[3-(3-cyanophenyl)propoxy]-3-trifluoromethylphenyl}ethyl) propane-1,3-diol hydrochloride (Compound 75-5)

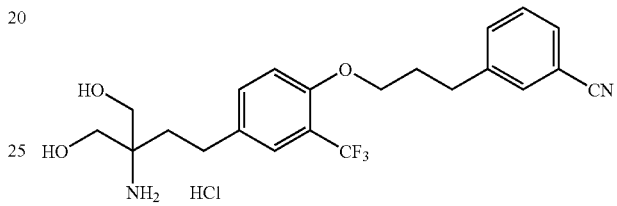

To compound 75-4 (100 mg) was added hydrogen chloride-containing dioxane (4 mol/2 ml), and the mixture was stirred at room temperature for 2 hr. The precipitate was collected by filtration, and dried to give the object product (70 mg) as a white powder.

MS(ESI)m/z: 423[M+H]

$^1$H-NMR(DMSO-d$_6$) δ (ppm): 1.74-1.78(2H, m), 2.02-2.09(2H, m), 2.57-2.62(2H, m), 2.80(2H, t, J=7.8 Hz), 3.51 (4H, d, J=5.0 Hz), 4.05(2H, t, J=6.2 Hz), 5.39(2H, t, J=5.2 Hz), 7.17(1H, d, J=8.5 Hz), 7.44(1H, d, J=8.6 Hz), 7.47-7.49 (1H, m), 7.51(1H, d, J=7.5 Hz), 7.56(1H, d, J=7.8 Hz), 7.67-7.69(2H, m), 7.82(3H, brs).

Example 76

2-amino-2-(2-{4-[3-(2,3-dihydrobenzofuran-5-yl) propoxy]-3-trifluoromethylphenyl}ethyl)propane-1, 3-diol hydrochloride (76-1) Synthesis of 3-(2,3-dihydrobenzofuran-5-yl)-1-propanol (Compound 76-1)

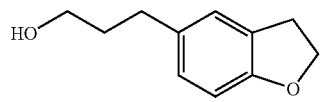

3-(2,3-Dihydrobenzofuran-5-yl)propionic acid (2.00 g) was dissolved in tetrahydrofuran (20 ml), and a tetrahydrofuran-borane.tetrahydrofuran solution (1 mol/l, 11.5 ml) was added dropwise to the mixture under ice-cooling. The mixture was stirred under ice-cooling for 1 hr, and further at room temperature for 16 hr. Water was added to the reaction mixture, and 1M aqueous hydrochloric acid solution was added. The mixture was extracted with ethyl acetate, washed with water, saturated aqueous sodium hydrogen carbonate solution and saturated brine, and dried over anhydrous magnesium sulfate. The solvent was evaporated under reduced pressure. The obtained residue was purified by silica gel column chromatography to give the object product (1.91 g) as a colorless oil.

¹H-NMR(CDCl₃) δ (ppm): 1.21-1.26(1H, m), 1.82-1.89 (2H, m), 2.63(2H, t, J=7.6 Hz), 3.18(2H, t, J=8.6 Hz), 3.65 (2H, q, J=6.2 Hz), 4.54(2H, t, J=8.7 Hz), 6.71(1H, d, J=8.2 Hz), 6.93(1H, d, J=7.7 Hz), 7.03(1H, brs).

(76-2) Synthesis of 5-(3-bromopropyl)-2,3-dihydrobenzofuran (Compound 76-2)

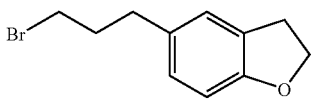

Compound 76-1 (1.91 g) was dissolved in methylene chloride (20 ml), triphenylphosphine (2.97 g) and N-bromosuccinimide (2.01 g) were added under ice-cooling, and the mixture was stirred under ice-cooling for 2 hr, and further at room temperature for 15 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography to give the object product (2.31 g) as a colorless oil.

¹H-NMR(CDCl₃) δ (ppm): 2.08-2.16(2H, m), 2.70(2H, t, J=7.3 Hz), 3.18(2H, t, J=8.7 Hz), 3.39(2H, t, J=6.5 Hz), 4.55(2H, t, J=8.7 Hz), 6.71(1H, d, J=8.0 Hz), 6.92(1H, d, J=8.0 Hz), 7.03(1H, brs).

(76-3) Synthesis of [5-(2-{4-[3-(2,3-dihydrobenzofuran-5-yl)propoxy]-3-trifluoromethylphenyl}ethyl)-2,2-dimethyl-1,3-dioxan-5-yl]carbamic acid t-butyl ester (Compound 76-3)

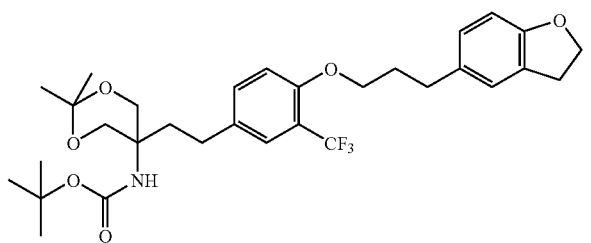

Reference Example compound 2-6 (500 mg) was dissolved in N,N-dimethylformamide (10 ml), potassium carbonate (494 mg) and compound 76-2 (345 mg) were added, and the mixture was stirred at 80° C. for 1.5 hr. Water was added to the reaction mixture, and the mixture was extracted with ethyl acetate, washed with water and saturated brine, and dried over anhydrous magnesium sulfate. The solvent was evaporated under reduced pressure to give the object product (740 mg) as a white solid.

¹H-NMR(CDCl₃) δ (ppm): 1.43(3H, s), 1.44(3H, s), 1.47 (9H, s), 1.93-1.98(2H, m), 2.04-2.14(2H, m), 2.51-2.56(2H, m), 2.75(2H, t, J=7.5 Hz), 3.17(2H, t, J=8.5 Hz), 3.69(2H, d, J=11.7 Hz), 3.89(2H, d, J=11.7 Hz), 3.98(2H, t, J=6.0 Hz), 4.51-4.57(2H, m), 4.99(1H, brs), 6.69(1H, d, J=8.0 Hz), 6.85 (1H, d, J=8.5 Hz), 6.92(1H, d, J=8.0 Hz), 7.03(1H, brs), 7.24-7.27(1H, m), 7.36(1H, brd, J=1.7 Hz).

(76-4) Synthesis of 2-amino-2-(2-{4-[3-(2,3-dihydrobenzofuran-5-yl)propoxy]-3-trifluoromethylphenyl}ethyl)propane-1,3-diol hydrochloride (Compound 76-4)

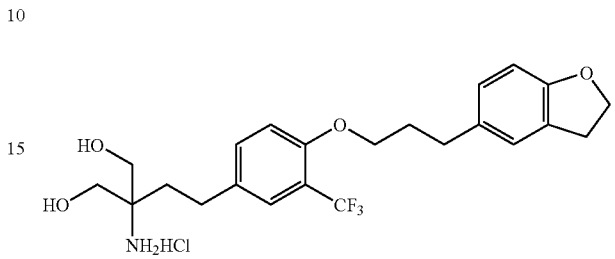

Compound 76-3 (740 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give the object product (500 mg) as a white powder.

MS(ESI)m/z: 440[M+H]

¹H-NMR(DMSO-d₆) δ (ppm): 1.74-1.79(2H, m), 1.92-1.99(2H, m), 2.59-2.67(4H, m), 3.12(2H, t, J=8.6 Hz), 3.52 (4H, brs), 4.03(2H, t, J=5.8 Hz), 4.47(2H, t, J=8.6 Hz), 5.40 (2H, brs), 6.65(1H, d, J=8.2 Hz), 6.87(1H, d, J=8.2 Hz), 7.05(1H, brs), 7.15(1H, d, J=8.6 Hz), 7.44(1H, d, J=8.6 Hz), 7.48(1H, brs), 7.84(3H, brs).

Example 77

2-amino-2-(2-{4-[3-(biphenyl-4-yl)propoxy]-3-trifluoromethylphenyl}ethyl)propane-1,3-diol hydrochloride (77-1) Synthesis of 3-(4-biphenyl)-2-propyne-1-ol (Compound 77-1)

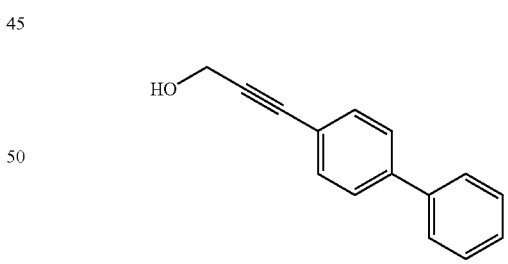

A mixture of 4-iodobiphenyl (5.00 g), copper(I) iodide (68.0 mg), triphenylphosphine (234 mg), tris(dibenzylideneacetone)dipalladium(0) chloroform adduct (370 mg), propargyl alcohol (1.16 ml), diisopropylethylamine (12.4 ml) and tetrahydrofuran (100 ml) was stirred at room temperature for 17 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane: ethyl acetate=99:1-60:40) to give the object product (3.88 g) as a brown solid.

¹H-NMR(CDCl₃) δ (ppm): 1.65(1H, t, J=6.2 Hz), 4.53(2H, d, J=6.2 Hz), 7.34-7.38(1H, m), 7.45(2H, t, J=7.7 Hz), 7.50-7.52(2H, m), 7.55-7.57(2H, m), 7.58-7.60(2H, m).

(77-2) Synthesis of 3-(4-biphenyl)-1-propanol (Compound 77-2)

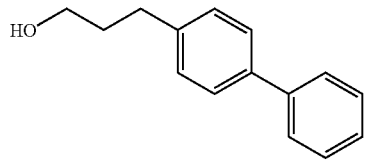

A solution of compound 77-1 (3.88 g) and 10% palladium carbon (1.94 g) in 1,4-dioxane (120 ml) was stirred under a hydrogen atmosphere at room temperature for 9 hr. The reaction mixture was filtered through celite and concentrated, and the obtained residue was purified by silica gel column chromatography (hexane:ethyl acetate=99:1-60:40) to give the object product (2.09 g) as a white powder.

¹H-NMR(CDCl₃) δ (ppm): 1.29(1H, t, J=4.9 Hz), 1.90-1.98(2H, m), 2.76(2H, t, J=7.7 Hz), 3.72(2H, q, J=5.9 Hz), 7.28(2H, d, J=8.0 Hz), 7.31-7.35(1H, m), 7.43(2H, t, J=7.7 Hz), 7.52-7.54(2H, m), 7.57-7.59(2H, m).

(77-3) Synthesis of 4-(3-bromopropyl)biphenyl (Compound 77-3)

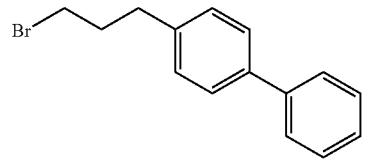

Compound 77-2 (2.02 g) was dissolved in methylene chloride (20 ml), triphenylphosphine (2.75 g) and N-bromosuccinimide (1.87 g) were added under ice-cooling, and the mixture was stirred under ice-cooling for 2 hr, and at room temperature for 20 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (2.40 g) as a colorless oil.

¹H-NMR(CDCl₃) δ (ppm): 2.17-2.24(2H, m), 2.82(2H, t, J=7.4 Hz), 3.43(2H, t, J=6.5 Hz), 7.25-7.29(3H, m), 7.31-7.35(1H, m), 7.43(1H, t, J=7.7 Hz), 7.52-7.54(2H, m), 7.57-7.59(2H, m).

(77-4) Synthesis of [5-(2-{4-[3-(biphenyl-4-yl)propoxy]-3-trifluoromethylphenyl}ethyl)-2,2-dimethyl-1,3-dioxan-5-yl]carbamic acid t-butyl ester (Compound 77-4)

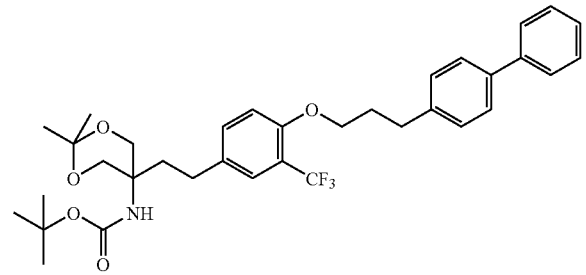

Reference Example compound 2-6 (500 mg) was dissolved in N,N-dimethylformamide (10 ml), potassium carbonate (494 mg) and compound 77-3 (394 mg) were added, and the mixture was stirred at 80° C. for 1 hr. Water was added to the reaction mixture, and the mixture was extracted with ethyl acetate, washed with water and saturated brine, and dried over anhydrous magnesium sulfate. The solvent was evaporated under reduced pressure to give the object product (870 mg) as a white solid.

¹H-NMR(CDCl₃) δ (ppm): 1.43(3H, s), 1.44(3H, s), 1.47(9H, s), 1.93-1.98(2H, m), 2.13-2.16(2H, m), 2.52-2.57(2H, m), 2.88(2H, t, J=7.5 Hz), 3.69(2H, d, J=11.7 Hz), 3.89(2H, d, J=11.7 Hz), 4.02(2H, t, J=5.9 Hz), 5.00(1H, brs), 6.85(1H, d, J=8.5 Hz), 7.24-7.29(3H, m), 7.30-7.40(2H, m), 7.41-7.45(2H, m), 7.50-7.54(2H, m), 7.57-7.59(2H, m).

(77-5) Synthesis of 2-amino-2-(2-{4-[3-(biphenyl-4-yl)propoxy]-3-trifluoromethylphenyl}ethyl)propane-1,3-diol hydrochloride (Compound 77-5)

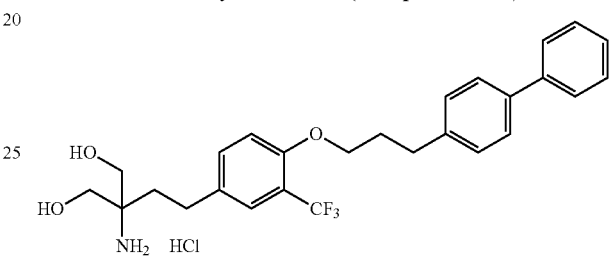

Compound 77-4 (870 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give the object product (530 mg) as a white powder.

MS(ESI)m/z: 474[M+H]

¹H-NMR(DMSO-d₆) δ (ppm): 1.75-1.80(2H, m), 2.02-2.09(2H, m), 2.59-2.64(2H, m), 2.80(2H, t, J=7.5 Hz), 3.52 (4H, d, J=4.7 Hz), 4.08(2H, t, J=5.9 Hz), 5.40(2H, t, J=5.0 Hz), 7.18(1H, d, J=8.6 Hz), 7.30(2H, d, J=8.2 Hz), 7.34(1H, t, J=7.5 Hz), 7.24-7.47(3H, m), 7.49(1H, brs), 7.59(2H, d, J=8.2 Hz), 7.64(2H, d, J=7.5 Hz), 7.85(3H, brs).

Example 78

2-amino-2-(2-{4-[2-(2-naphthyl)ethoxy]-3-trifluoromethylphenyl}ethyl)propane-1,3-diol hydrochloride (78-1) Synthesis of 2-amino-2-(2-{4-[2-(2-naphthyl)ethoxy]-3-trifluoromethylphenyl}ethyl)propane-1,3-diol hydrochloride (Compound 78-1)

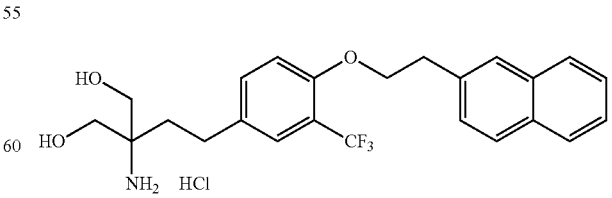

Triphenylphosphine (1.25 g) was dissolved in tetrahydrofuran (20 ml), diisopropyl azodicarboxylate (40% toluene solution, 2.51 ml), 2-naphthaleneethanol (838 mg) and Reference Example compound 2-6 (1.00 g) were added, and the mixture was stirred at room temperature for 20 hr. Water was added to the reaction mixture, and the mixture was extracted with ethyl acetate, washed with saturated brine, and dried over anhydrous magnesium sulfate. The solvent was evaporated under reduced pressure. The obtained residue was dissolved in ethanol (20 ml), concentrated hydrochloric acid (2.0 ml) was added, and the mixture was stirred at 80° C. for 1.5 hr. The reaction mixture was concentrated, and the residue was washed with diethyl ether to give a white powder. The white powder was purified by HPLC, the obtained residue was converted to hydrochloride by adding hydrogen chloride containing ether (1 mol/l, 15 ml), and the precipitate was collected by filtration and dried to give the object product (790 mg) as a white powder.

MS(ESI)m/z: 434[M+H]

$^1$H-NMR(DMSO-d$_6$) δ (ppm): 1.72-1.77(2H, m), 2.57-2.61(2H, m), 3.20(2H, t, J=6.5 Hz), 3.50(4H, d, J=4.5 Hz), 4.37(2H, t, J=6.5 Hz), 5.37(2H, t, J=4.9 Hz), 7.24(1H, d, J=8.4 Hz), 7.43-7.51(5H, m), 7.77(3H, brs), 7.81-7.89(4H, m).

Example 79

2-amino-2-(2-{4-[3-(biphenyl-3-yl)propoxy]-3-trifluoromethylphenyl}ethyl)propane-1,3-diol hydrochloride (79-1) Synthesis of 1-(3-biphenyl)-3-(tetrahydro-2H-pyran-2-yloxy)-1-propyne (Compound 79-1)

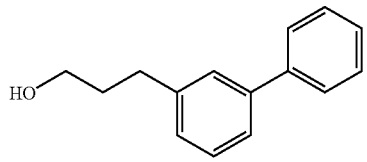

A mixture of 3-bromobiphenyl (5.00 g), cesium carbonate (18.2 g), 2-(2-propynyloxy)tetrahydropyran (4.53 ml), 2-dicyclohexylphosphino-2',4',6'-triisopropylbiphenyl (615 mg), bis(acetonitrile)palladium(II) dichloride (111 mg) and acetonitrile (90 ml) was stirred at 90° C. for 11 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=99:1-80:20) to give the object product (1.90 g) as a brown oil.

$^1$H-NMR(CDCl$_3$) δ (ppm): 1.53-1.72(4H, m), 1.75-1.91 (2H, m), 3.55-3.61(1H, m), 3.88-3.93(1H, m), 4.49(1H, d, J=15.7 Hz), 4.54(1H, d, J=15.7 Hz), 4.92(1H, t, J=3.4 Hz), 7.34-7.40(2H, m), 7.42-7.46(3H, m), 7.53-7.58(3H, m), 7.69-7.70(1H, m).

(79-2) Synthesis of 1-(3-biphenyl)-3-(tetrahydro-2H-pyran-2-yloxy)propane (Compound 79-2)

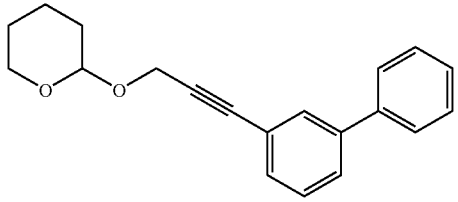

A solution of compound 79-1 (1.90 g) and 10% palladium carbon (0.95 g) in 1,4-dioxane (40 ml) was stirred under a hydrogen atmosphere at room temperature for 15 hr. The reaction mixture was filtered through celite and concentrated to give the object product (1.94 g) as a yellow oil.

$^1$H-NMR(CDCl$_3$) δ (ppm): 1.50-1.64(4H, m), 1.70-1.77 (1H, m), 1.81-1.89(1H, m), 1.98(2H, quint, J=7.2 Hz), 2.72-2.84(2H, m), 3.41-3.53(2H, m), 3.81(1H, dt, J=9.8, 6.5 Hz), 3.85-3.91(1H, m), 4.59(1H, t, J=3.6 Hz), 7.18-7.20(1H, m), 7.31-7.37(2H, m), 7.41-7.45(4H, m), 7.58-7.60(2H, m).

(79-3) Synthesis of 3-(3-biphenyl)-1-propanol (Compound 79-3)

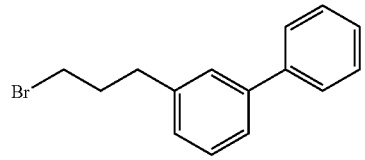

A solution of compound 79-2 (1.94 g) and p-toluenesulfonic acid monohydrate (10.0 mg) in methanol (20 ml) was stirred at room temperature for 17 hr. To the reaction mixture was added triethylamine (0.10 ml), and the solvent was evaporated under reduced pressure. The residue was purified by silica gel column chromatography (hexane:ethyl acetate=99:1-70:30) to give the object product (1.24 g) as a white solid.

$^1$H-NMR(CDCl$_3$) δ (ppm): 1.34(1H, brs), 1.91-1.99(2H, m), 2.78(2H, t, J=7.7 Hz), 3.71(2H, t, J=6.4 Hz), 7.19-7.20 (1H, m), 7.32-7.38(2H, m), 7.42-7.46(4H, m), 7.58-7.60(2H, m).

(79-4) Synthesis of 3-(3-bromopropyl)biphenyl (Compound 79-4)

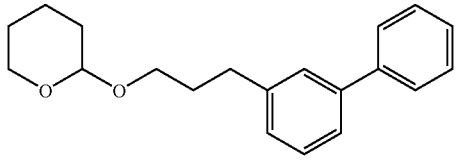

Compound 79-3 (1.23 g) was dissolved in methylene chloride (20 ml), triphenylphosphine (1.67 g) and N-bromosuccinimide (1.13 g) were added under ice-cooling, and the mixture was stirred under ice-cooling for 2 hr, and at room temperature for 15 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (1.49 g) as a colorless oil.

$^1$H-NMR(CDCl$_3$) δ (ppm): 2.18-2.26(2H, m), 2.85(2H, t, J=7.3 Hz), 3.43(2H, t, J=6.5 Hz), 7.19(1H, d, J=7.5 Hz), 7.33-7.39(2H, m), 7.42-7.46(4H, m), 7.57-7.60(2H, m).

(79-5) Synthesis of [5-(2-{4-[3-(biphenyl-3-yl)propoxy]-3-trifluoromethylphenyl}ethyl)-2,2-dimethyl-1,3-dioxan-5-yl]carbamic acid t-butyl ester (Compound 79-5)

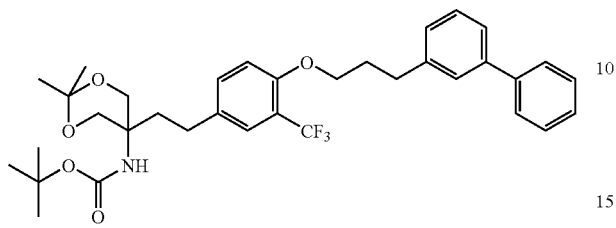

Reference Example compound 2-6 (500 mg) was dissolved in N,N-dimethylformamide (10 ml), potassium carbonate (494 mg) and compound 79-4 (394 mg) were added, and the mixture was stirred at 80° C. for 1 hr. Water was added to the reaction mixture, and the mixture was extracted with ethyl acetate, washed with water and saturated brine, and dried over anhydrous magnesium sulfate. The solvent was evaporated under reduced pressure to give the object product (810 mg) as a white solid.

$^1$H-NMR(CDCl$_3$) δ (ppm): 1.43(3H, s), 1.44(3H, s), 1.47 (9H, s), 1.93-1.98(2H, m), 2.14-2.18(2H, m), 2.51-2.56(2H, m), 2.90(2H, t, J=7.5 Hz), 3.69(2H, d, J=11.7 Hz), 3.89(2H, d, J=11.7 Hz), 4.02(2H, t, J=5.9 Hz), 5.00(1H, brs), 6.85(1H, d, J=8.5 Hz), 7.19(1H, d, J=7.4 Hz), 7.24-7.27(1H, m), 7.33-7.40(2H, m), 7.41-7.46(5H, m), 7.53-7.60(2H, m).

(79-6) Synthesis of 2-amino-2-(2-{4-[3-(biphenyl-3-yl)propoxy]-3-trifluoromethylphenyl}ethyl)propane-1,3-diol hydrochloride (Compound 79-6)

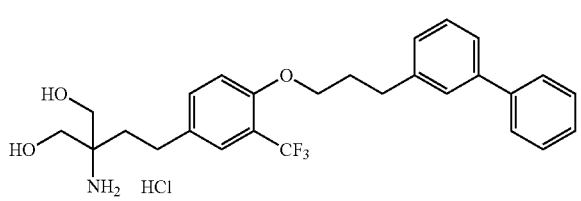

Compound 79-5 (810 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give the object product (530 mg) as a white powder.

MS(ESI)m/z: 474[M+H]

$^1$H-NMR(DMSO-d$_6$) δ (ppm): 1.74-1.79(2H, m), 2.04-2.12(2H, m), 2.59-2.63(2H, m), 2.83(2H, t, J=7.4 Hz), 3.52 (4H, d, J=4.6 Hz), 4.07(2H, t, J=5.9 Hz), 5.40(2H, t, J=4.9 Hz), 7.18(2H, t, J=9.0 Hz), 7.33-7.49(8H, m), 7.58(2H, d, J=7.4 Hz), 7.78(3H, brs).

Example 80

2-amino-2-(2-{4-[3-(benzothiophen-3-yl)propoxy]-3-trifluoromethylphenyl}ethyl)propane-1,3-diol hydrochloride (80-1) Synthesis of 1-(3-benzothienyl)-3-(tetrahydro-2H-pyran-2-yloxy)-1-propyne (Compound 80-1)

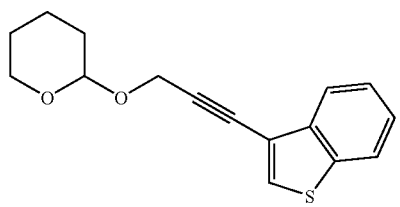

A mixture of 3-bromobenzothiophene(5.00 g), cesium carbonate (20.0 g), 2-(2-propynyloxy)tetrahydropyran (4.96 ml), 2-dicyclohexylphosphino-2',4',6'-triisopropylbiphenyl (672 mg), bis(acetonitrile)palladium(II) dichloride (122 mg) and acetonitrile (100 ml) was stirred at 90° C. for 11 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=99:1-80:20) to give the object product (2.19 g) as a brown oil.

$^1$H-NMR(CDCl$_3$) δ (ppm): 1.52-1.73(4H, m), 1.76-1.92 (2H, m), 3.57-3.62(1H, m), 3.90-3.95(1H, m), 4.57(1H, d, J=15.8 Hz), 4.59(1H, d, J=15.8 Hz), 4.97(1H, t, J=3.4 Hz), 7.39(1H, t, J=7.3 Hz), 7.42-7.46(1H, m), 7.63(1H, s), 7.84 (1H, d, J=7.8 Hz), 7.95(1H, d, J=8.0 Hz).

(80-2) Synthesis of 1-(3-benzothienyl)-3-(tetrahydro-2H-pyran-2-yloxy)propane (Compound 80-2)

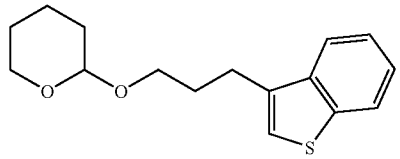

A solution of compound 80-1 (2.19 g) and 10% palladium carbon (1.10 g) in 1,4-dioxane (70 ml) was stirred under a hydrogen atmosphere at room temperature for 9 hr. The reaction mixture was filtered through celite and concentrated to give the object product (2.04 g) as a yellow oil.

$^1$H-NMR(CDCl$_3$) δ (ppm): 1.51-1.65(4H, m), 1.71-1.78 (1H, m), 1.82-1.90(1H, m), 2.06(2H, quint, J=7.0 Hz), 2.89-3.02(2H, m), 3.46-3.54(2H, m), 3.83-3.92(2H, m), 4.59-4.61 (1H, m), 7.11(1H, s), 7.32-7.40(2H, m), 7.76-7.78(1H, m), 7.86(1H, d, J=8.2 Hz).

(80-3) Synthesis of 3-(3-benzothienyl)-1-propanol (Compound 80-3)

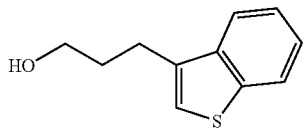

A solution of compound 80-2 (2.04 g) and p-toluenesulfonic acid monohydrate (10.0 mg) in methanol (80 ml) was stirred at room temperature for 20 hr. Saturated aqueous sodium hydrogen carbonate was added to the reaction mixture, and methanol was evaporated under reduced pressure. Water was added to the obtained mixture, and the mixture was extracted with ethyl acetate. The organic layer was washed with saturated brine and dried over anhydrous magnesium sulfate, and the solvent was concentrated under reduced pressure to give the object product (1.48 g) as a brown oil.

$^1$H-NMR(CDCl$_3$) δ (ppm): 1.37(1H, brs), 2.03(2H, quint, J=7.0 Hz), 2.96(2H, t, J=7.6 Hz), 3.75(2H, t, J=5.7 Hz), 7.12(1H, s), 7.32-7.41(2H, m), 7.77(1H, dd, J=1.2, 7.3 Hz), 7.86(1H, dd, J=1.2, 7.3 Hz).

(80-4) Synthesis of 3-(3-bromopropyl)benzothiophene (Compound 80-4)

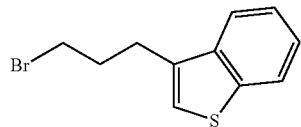

Compound 80-3 (1.46 g) was dissolved in methylene chloride (20 ml), triphenylphosphine (2.19 g) and N-bromosuccinimide (1.49 g) were added under ice-cooling, and the mixture was stirred under ice-cooling for 3 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane alone) to give the object product (1.64 g) as a pale-yellow oil.

$^1$H-NMR(CDCl$_3$) δ (ppm): 2.25-2.33(2H, m), 3.05(2H, t, J=7.3 Hz), 3.47(2H, t, J=6.4 Hz), 7.16(1H, s), 7.33-7.42(2H, m), 7.77(1H, d, J=7.5 Hz), 7.87(1H, dd, J=7.5, 1.0 Hz).

(80-5) Synthesis of [5-(2-{4-[3-(benzothiophen-3-yl)propoxy]-3-trifluoromethylphenyl}ethyl)-2,2-dimethyl-1,3-dioxan-5-yl]carbamic acid t-butyl ester (Compound 80-5)

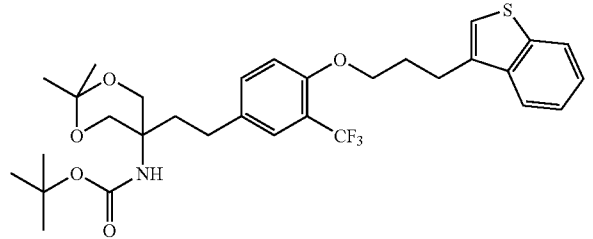

Reference Example compound 2-6 (500 mg) was dissolved in N,N-dimethylformamide (10 ml), potassium carbonate (494 mg) and compound 80-4 (365 mg) were added, and the mixture was stirred at 80° C. for 1.5 hr. Water was added to the reaction mixture, and the mixture was extracted with ethyl acetate, washed with water and saturated brine, and dried over anhydrous magnesium sulfate. The solvent was evaporated under reduced pressure to give the object product (800 mg) as a white solid.

$^1$H-NMR(CDCl$_3$) δ (ppm): 1.43(3H, s), 1.44(3H, s), 1.48 (9H, s), 1.93-1.98(2H, m), 2.21-2.27(2H, m), 2.52-2.57(2H, m), 3.09(2H, t, J=7.5 Hz), 3.69(2H, d, J=11.7 Hz), 3.89(2H, d, J=11.7 Hz), 4.05(2H, t, J=5.8 Hz), 5.00(1H, brs), 6.85(1H, d, J=8.5 Hz), 7.11(1H, brs), 7.24-7.28(1H, m), 7.33-7.40(3H, m), 7.77-7.80(1H, m), 7.84-7.87(1H, m).

(80-6) Synthesis of 2-amino-2-(2-{4-[3-(benzothiophen-3-yl)propoxy]-3-trifluoromethylphenyl}ethyl)propane-1,3-diol hydrochloride (Compound 80-6)

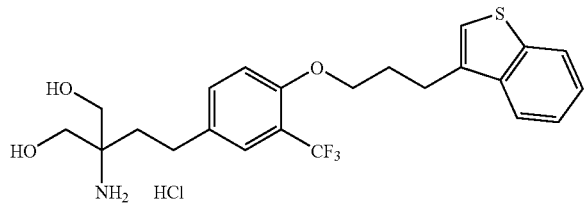

Compound 80-5 (800 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give the object product (510 mg) as a white powder.

MS(ESI)m/z: 454[M+H]

$^1$H-NMR(DMSO-d$_6$) δ (ppm): 1.74-1.79(2H, m), 2.11-2.18(2H, m), 2.59-2.64(2H, m), 3.00(2H, t, J=7.5 Hz), 3.52 (4H, d, J=4.4 Hz), 4.16(2H, t, J=5.9 Hz), 5.40(2H, t, J=4.7 Hz), 7.19(1H, t, J=8.5 Hz), 7.35-7.40(2H, m), 7.41-7.46(2H, m), 7.49(1H, brs), 7.78-7.87(4H, m), 7.97-8.00(1H, m).

Example 81

2-amino-2-(2-{4-[3-(4-cyclopropylphenyl)propoxy]-3-trifluoromethylphenyl}ethyl)propane-1,3-diol hydrochloride

(81-1) Synthesis of [5-(2-{4-[3-(4-cyclopropylphenyl)propoxy]-3-trifluoromethylphenyl}ethyl)-2,2-dimethyl-1,3-dioxan-5-yl]carbamic acid t-butyl ester (Compound 81-1)

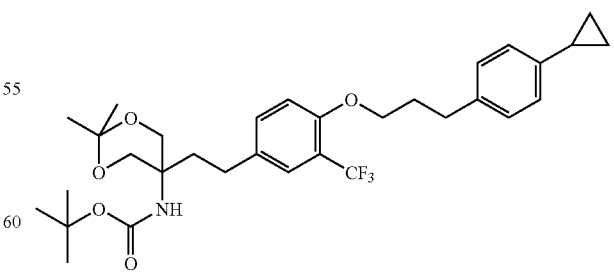

Compound 41-4 (500 mg) was dissolved in tetrahydrofuran (1.6 ml), tripotassium phosphate (430 mg), palladium acetate (9.0 mg), 2-dicyclohexylphosphino-2',6'-dimethoxybiphenyl (17 mg), cyclopropylboronic acid (85 mg) and water (40 μl) were added, and the mixture was stirred at 100° C. for 3 hr. Water was added to the reaction mixture, and the mixture was extracted with ethyl acetate, washed with saturated brine, and dried over anhydrous sodium sulfate. The solvent was evaporated under reduced pressure. The residue was purified by silica gel column chromatography (hexane:ethyl acetate) to give the object product (440 mg) as a colorless oil.

$^{1}$H-NMR(DMSO-d$_{6}$) δ (ppm): 0.57-0.62(2H, m), 0.87-0.92(2H, m), 1.31(3H, s), 1.32(3H, s), 1.40(9H, s), 1.82-1.87 (1H, m), 1.91-1.99(4H, m), 2.44-2.50(2H, m), 2.68(2H, t, J=7.2 Hz), 3.66(2H, d, J=11.5 Hz), 3.88(2H, d, J=11.1 Hz), 4.01(2H, t, J=5.4 Hz), 6.66(1H, brs), 6.98(2H, d, J=7.5 Hz), 7.06(2H, d, J=7.7 Hz), 7.12(1H, d, J=8.1 Hz), 7.36-7.39(2H, m).

(81-2) Synthesis of 2-amino-2-(2-{4-[3-(4-cyclopropylphenyl)propoxy]-3-trifluoromethylphenyl}ethyl)propane-1,3-diol hydrochloride (Compound 81-2)

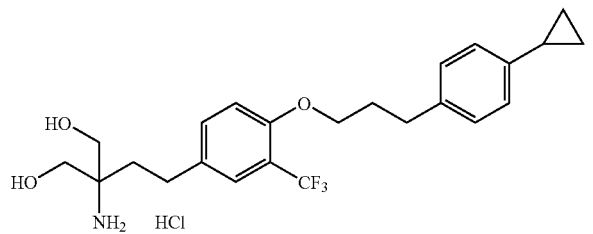

Compound 81-1 (440 mg) was dissolved in ethanol (15 ml), concentrated hydrochloric acid (1.5 ml) was added, and the mixture was stirred at 80° C. for 3 hr. The reaction mixture was concentrated, and the residue was washed with diethyl ether to give the object product (300 mg) as a white powder.

MS(ESI)m/z: 438[M+H]

$^{1}$H-NMR(DMSO-d$_{6}$) δ (ppm): 0.61(2H, dd, J=9.6, 5.4 Hz), 0.90(2H, dd, J=13.1, 5.4 Hz), 1.74-1.78(2H, m), 1.86 (1H, ddd, J=13.4, 9.0, 5.4 Hz), 1.98(2H, quint, J=6.8 Hz), 2.58-2.62(2H, m), 2.68(2H, t, J=7.4 Hz), 3.52(4H, d, J=4.7 Hz), 4.02(2H, t, J=5.8 Hz), 5.40(2H, t, J=4.7 Hz), 6.98(2H, d, J=7.8 Hz), 7.06(2H, d, J=7.8 Hz), 7.15(1H, d, J=8.6 Hz), 7.43(1H, d, J=8.7 Hz), 7.48(1H, s), 7.81(3H, brs).

Example 82

2-amino-2-(2-{4-[3-(indan-5-yl)propoxy]-3-trifluoromethylphenyl}ethyl)propane-1,3-diol hydrochloride (82-1) Synthesis of 3-(indan-5-yl)propanol (Compound 82-1)

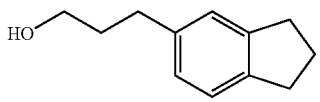

Compound 56-2 (4.20 g) was dissolved in tetrahydrofuran (100 ml), and lithium borohydride (1.33 g) was added under ice-cooling. The mixture was warmed to room temperature and stirred at 80° C. for 5 hr. The reaction mixture was added to (1M hydrogen chloride-containing dioxane:diisopropyl alcohol=1:3, 50 ml), and the mixture was stirred at 50° C. for 10 hr. Water was added to the reaction mixture, and the mixture was extracted with ethyl acetate, washed with saturated brine, and dried over anhydrous magnesium sulfate. The solvent was evaporated under reduced pressure. The obtained residue was dissolved in methanol (10 ml), p-toluenesulfonic acid monohydrate (0.040 g) was added, and the mixture was stirred at 50° C. for 24 hr. Saturated aqueous sodium hydrogen carbonate was added to the reaction mixture, and the mixture was extracted with ethyl acetate, washed with saturated brine, and dried over anhydrous magnesium sulfate. The solvent was evaporated under reduced pressure to give the object product (1.41 g) as a colorless oil. The obtained object product contained 3-(3H-inden-5-yl)propanol in about 40%.

$^{1}$H-NMR(CDCl$_{3}$) δ (ppm): 1.23-1.29(1H, m), 1.85-1.94 (2H, m), 2.02-2.10(2H, m), 2.65-2.70(2H, m), 2.85-2.90(4H, m), 3.66-3.70(2H, m), 6.97(1H, d, J=7.3 Hz), 7.08(1H, brs), 7.32(1H, d, J=7.8 Hz).

(82-2) Synthesis of 5-(3-bromopropyl)indane (Compound 82-2)

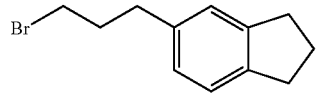

The compound (1.41 g) obtained in Example (82-1) was dissolved in methylene chloride (30 ml), triphenylphosphine (2.31 g) and N-bromosuccinimide (1.57 g) were added under ice-cooling, and the mixture was stirred under ice-cooling for 4 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography to give the object product (700 mg) as a colorless oil. The obtained compound contained 5-(3-bromopropyl)-3H-inden in about 40%.

$^{1}$H-NMR(CDCl$_{3}$) δ (ppm): 2.02-2.08(2H, m), 2.10-2.19 (2H, m), 2.74(2H, t, J=7.3 Hz), 2.81-2.90(4H, m), 3.38-3.42 (2H, m), 6.96(1H, d, J=7.6 Hz), 7.07(1H, brs), 7.15(1H, d, J=7.6 Hz).

(82-3) Synthesis of 2-amino-2-(2-{4-[3-(indan-5-yl)propoxy]-3-trifluoromethylphenyl}ethyl)propane-1,3-diol hydrochloride (Compound 82-3)

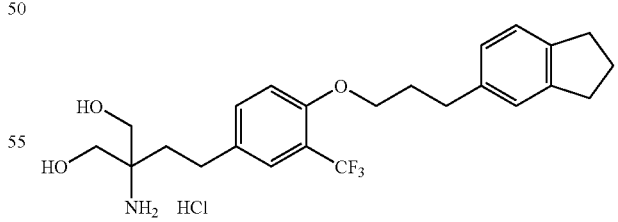

Reference Example compound 2-6 (500 mg) was dissolved in N,N-dimethylfonnamide (10 ml), potassium carbonate (494 mg) and the compound (342 mg) obtained in Example (82-2) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure. The obtained residue was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give a white powder. The white powder was dissolved in methanol (20 ml), 10% palladium carbon (100 mg) was added, and the mixture was stirred under a hydrogen atmosphere at room temperature for 14 hr. The reaction container was purged with nitrogen, and the solution was filtered. The filtrate was concentrated, and the residue was washed with diethyl ether to give the object product (510 mg) as a white powder.

MS(ESI)m/z: 438[M+H]

$^1$H-NMR(DMSO-d$_6$) δ (ppm): 1.74-1.79(2H, m), 1.94-2.01(4H, m), 2.59-2.63(2H, m), 2.69(2H, t, J=7.5 Hz), 2.77-2.82(4H, m), 3.52(4H, d, J=4.9 Hz), 4.03(2H, t, J=6.0 Hz), 5.40(2H, t, J=5.0 Hz), 6.92(1H, d, J=7.6 Hz), 7.05(1H, brs), 7.10-7.17(2H, m), 7.44(1H, d, J=8.6 Hz), 7.48(1H, brs), 7.86 (3H, brs).

Example 83

2-amino-2-(2-{4-[3-(2-methyl-4-thienyl)propoxy]-3-trifluoromethylphenyl}ethyl)propane-1,3-diol hydrochloride (83-1) Synthesis of 1-(2-methylthiophen-4-yl)-3-(tetrahydro-2H-pyran-2-yloxy)-1-propyne (Compound 83-1)

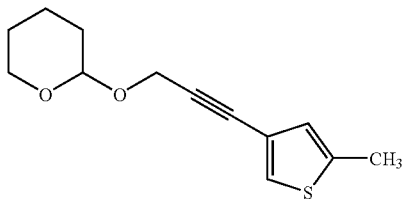

A mixture of 4-bromo-2-methylthiophene(5.00 g), cesium carbonate (23.9 g), 2-(2-propynyloxy)tetrahydropyran (5.96 ml), 2-dicyclohexylphosphino-2',4',6'-triisopropylbiphenyl (806 mg), bis(acetonitrile)palladium(II) dichloride (147 mg) and acetonitrile (90 ml) was stirred at 90° C. for 11 hr. The reaction mixture was added to brine, and the mixture was extracted with ethyl acetate, washed with saturated brine, and dried over anhydrous magnesium sulfate. The solvent was evaporated under reduced pressure. The residue was purified by silica gel column chromatography (hexane:ethyl acetate=99:1-80:20) to give the object product (1.48 g) as a brown oil.

$^1$H-NMR(CDCl$_3$) δ (ppm): 1.53-1.69(4H, m), 1.72-1.89 (2H, m), 2.44(3H, s), 3.53-3.58(1H, m), 3.85-3.91(1H, m), 4.43(1H, d, J=15.8 Hz), 4.47(1H, d, J=15.8 Hz), 4.88(1H, t, J=3.3 Hz), 6.76(1H, s), 7.21(1H, s).

(83-2) Synthesis of 1-(2-methylthiophen-4-yl)-3-(tetrahydro-2H-pyran-2-yloxy)propane (Compound 83-2)

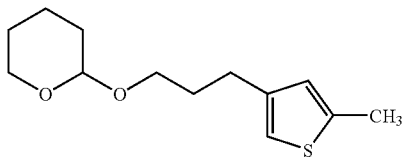

A solution of compound 83-1 (1.48 g) and 10% palladium carbon (0.75 g) in 1,4-dioxane (40 ml) was stirred under a hydrogen atmosphere at room temperature for 15 hr. The reaction mixture was filtered through celite and concentrated to give the object product (1.47 g) as a brown oil.

$^1$H-NMR(CDCl$_3$) δ (ppm): 1.51-1.62(4H, m), 1.69-1.76 (1H, m), 1.80-1.93(3H, m), 2.45(3H, s), 2.61-2.67(2H, m), 3.41(1H, dt, J=9.9, 6.4 Hz), 3.47-3.53(1H, m), 3.77(1H, dt, J=9.8, 6.5 Hz), 3.84-3.90(1H, m), 4.57-4.58(1H, m), 6.61 (1H, s), 6.68(1H, s).

(83-3) Synthesis of 1-(2-methylthiophen-4-yl)-1-propanol (Compound 83-3)

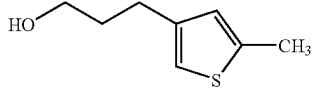

A solution of compound 83-2 (1.47 g) and p-toluenesulfonic acid monohydrate (10.0 mg) in methanol (20 ml) was stirred at room temperature for 17 hr. Triethylamine (0.10 ml) was added to the reaction mixture, and the solvent was evaporated under reduced pressure. The residue was purified by silica gel column chromatography (hexane:ethyl acetate=99:1-70:30) to give the object product (0.73 g) as a brown oil.

$^1$H-NMR(CDCl$_3$) δ (ppm): 1.29(1H, brs), 1.83-1.90(2H, m), 2.45(3H, s), 2.64(2H, t, J=7.6 Hz), 3.68(2H, t, J=6.3 Hz), 6.61(1H, s), 6.69(1H, s).

(83-4) Synthesis of 4-(3-bromopropyl)-2-methylthiophene (Compound 83-4)

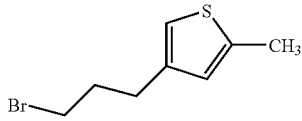

Compound 83-3 (720 mg) was dissolved in methylene chloride (30 ml), triphenylphosphine (1.33 g) and N-bromosuccinimide (0.902 g) were added under ice-cooling, and the mixture was stirred under ice-cooling for 3 hr. The reaction mixture was washed with water and saturated brine, and dried over anhydrous magnesium sulfate. The solvent was evaporated under reduced pressure. Diethyl ether (50 ml) was added, and the precipitated triphenylphosphine oxide was filtered off. The concentrate of the filtrate was purified by silica gel column chromatography (hexane alone) to give the object product (840 mg) as a colorless oil. The obtained object product contained 2-bromo-3-(3-bromopropyl)-5-methylthiophene in about 15%.

$^1$H-NMR(CDCl$_3$) δ (ppm): 2.09-2.16(2H, m), 2.45(3H, s), 2.70(2H, t, J=7.2 Hz), 3.39-3.42(2H, m), 6.60(1H, s), 6.72 (1H, s).

(83-5) Synthesis of 2-amino-2-(2-{4-[3-(2-methyl-4-thienyl)propoxy]-3-trifluoromethylphenyl}ethyl) propane-1,3-diol hydrochloride (Compound 83-5)

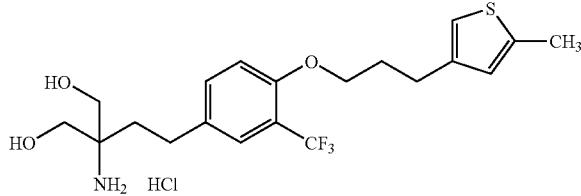

Reference Example compound 2-6 (500 mg) was dissolved in N,N-dimethylformamide (10 ml), potassium carbonate (493 mg) and the compound (313 mg) obtained in Example (83-4) were added, and the mixture was stirred at 80° C. for 1 hr. Water was added to the reaction mixture, and the mixture was extracted with ethyl acetate, washed with water and saturated brine, and dried over anhydrous magnesium sulfate. The solvent was evaporated under reduced pressure. The obtained residue was dissolved in methanol (10 ml), p-toluenesulfonic acid monohydrate (0.041 g) was added, and the mixture was stirred at room temperature for 12.5 hr. Saturated aqueous sodium hydrogen carbonate was added to the reaction mixture, and the mixture was extracted with ethyl acetate, washed with saturated brine, and dried over anhydrous magnesium sulfate. The solvent was evaporated under reduced pressure. To a solution of the obtained residue in methylene chloride (15 ml) was added hydrogen chloride containing dioxane (4 mol/l, 5 ml), and the mixture was stirred at room temperature for 3 hr. The reaction mixture was concentrated, and the residue was washed with diethyl ether to give a white powder. The white powder was separated by HPLC using NOVApack (registered trade mark) HR C18 (0.05% trifluoroacetic acid-water/acetonitrile), a main component peak (primary peak with a shorter retention time) was collected and the obtained residue was converted to hydrochloride by the addition of hydrogen chloride containing ether (1 mol/l, 15 ml), and the precipitate was collected by filtration and dried to give the object product (260 mg) as a white powder.

MS(ESI)m/z: 418[M+H]

$^1$H-NMR(DMSO-$d_6$) δ (ppm): 1.74-1.79(2H, m), 1.96-2.02(2H, m), 2.39(3H, s), 2.59-2.67(4H, m), 3.52(4H, d, J=4.6 Hz), 4.05(2H, t, J=6.1 Hz), 5.40(2H, t, J=4.9 Hz), 6.68(1H, s), 6.85(1H, s), 7.16(1H, d, J=8.5 Hz), 7.46(1H, d, J=8.5 Hz), 7.48(1H, d, J=1.7 Hz), 7.85(3H, brs).

Example 84

2-amino-2-(2-{4-[3-(2-bromo-5-methyl-3-thienyl)propoxy]-3-trifluoromethylphenyl}ethyl)propane-1,3-diol hydrochloride (84-1) Synthesis of 2-amino-2-(2-{4-[3-(2-bromo-5-methyl-3-thienyl)propoxy]-3-trifluoromethylphenyl}ethyl)propane-1,3-diol hydrochloride (Compound 84-1)

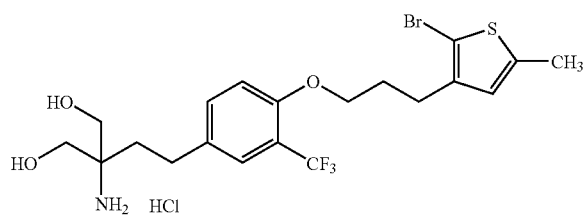

In the purification by HPLC in Example (83-5), a sub-component peak (secondary peak with a longer retention time) was collected and the obtained residue was converted to hydrochloride by the addition of hydrogen chloride containing ether (1 mol/l, 10 ml), and the precipitate was collected by filtration and dried to give the object product (40 mg) as a pale-yellow powder.

MS(ESI)m/z: 496, 498[M+H]

$^1$H-NMR(DMSO-$d_6$) δ (ppm): 1.72-1.77(2H, m), 1.91-1.99(2H, m), 2.45(3H, s), 2.54-2.67(4H, m), 3.50(4H, d, J=4.4 Hz), 4.06(2H, t, J=5.9 Hz), 5.36(2H, brs), 6.67(1H, s), 7.17(1H, d, J=8.6 Hz), 7.44(1H, d, J=8.6 Hz), 7.47(1H, brs), 7.65(3H, brs).

Example 85

2-amino-2-(2-{4-[3-(3-cyclopropylphenyl)propoxy]-3-trifluoromethylphenyl}ethyl)propane-1,3-diol hydrochloride (85-1) Synthesis of [5-(2-{4-[3-(3-cyclopropylphenyl)propoxy]-3-trifluoromethylphenyl}ethyl)-2,2-dimethyl-1,3-dioxan-5-yl]carbamic acid t-butyl ester (Compound 85-1)

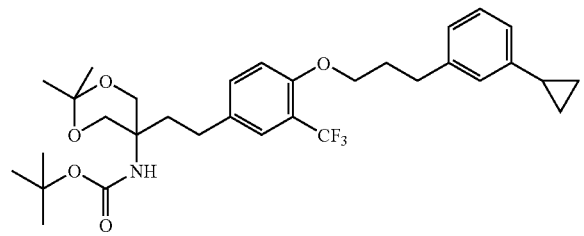

Compound 40-4 (400 mg) was dissolved in tetrahydrofuran (1.3 ml), tripotassium phosphate (350 mg), palladium acetate (7.2 mg), 2-dicyclohexylphosphino-2',6'-dimethoxybiphenyl (13 mg) and cyclopropylboronic acid (80 mg) were added, and the mixture was stirred at 80° C. for 2 hr. Water (30 μl) was added, and the mixture was further stirred for 5.5 hr. Water was added to the reaction mixture, and the mixture was extracted with ethyl acetate, washed with saturated brine, and dried over anhydrous sodium sulfate. The solvent was evaporated under reduced pressure. The residue was purified by silica gel column chromatography (hexane:ethyl acetate) to give the object product (330 mg) as a white solid.

$^1$H-NMR(DMSO-$d_6$) δ (ppm): 0.56(2H, ddd, J=6.1, 4.8, 4.2 Hz), 0.88(2H, ddd, J=8.4, 6.4, 4.1 Hz), 1.31(3H, s), 1.33 (3H, s), 1.40(9H, s), 1.80-1.87(1H, m), 1.91-2.02(4H, m), 2.45-2.50(2H, m), 2.69(2H, t, J=7.5 Hz), 3.66(2H, d, J=11.6 Hz), 3.88(2H, d, J=11.3 Hz), 4.00(2H, t, J=6.1 Hz), 6.66(1H, brs), 6.87(1H, s), 6.87(1H, d, J=7.4 Hz), 6.94(1H, d, J=7.4 Hz), 7.11-7.16(2H, m), 7.37(1H, d, J=8.6 Hz), 7.40(1H, s).

(85-2) Synthesis of 2-amino-2-(2-{4-[3-(3-cyclopropylphenyl)propoxy]-3-trifluoromethylphenyl}ethyl)propane-1,3-diol hydrochloride (Compound 85-2)

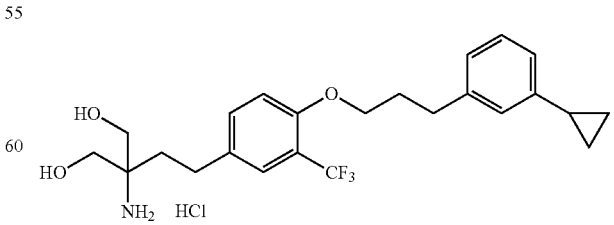

Compound 85-1 (330 mg) was dissolved in ethanol (5 ml), concentrated hydrochloric acid (1 ml) was added, and the mixture was stirred at 80° C. for 2.5 hr. The reaction mixture was concentrated, and the residue was washed with diethyl ether to give the object product (168 mg) as a white powder.

MS(ESI)m/z: 438[M+H]

$^1$H-NMR(DMSO-d$_6$) δ (ppm): 0.57(2H, ddd, J=6.5, 5.2, 4.3 Hz), 0.89(2H, ddd, J=8.4, 6.5, 4.3 Hz), 1.76-1.79(2H, m), 1.81-1.88(1H, m), 1.99(2H, quint, J=6.4 Hz), 2.58-2.63(2H, m), 2.69(2H, t, J=7.4 Hz), 3.52(4H, d, J=5.2 Hz), 4.01(2H, t, J=6.0 Hz), 5.40(2H, t, J=5.2 Hz), 6.87(1H, s), 6.88(1H, d, J=7.8 Hz), 6.94(1H, d, J=7.4 Hz), 7.12-7.16(2H, m), 7.43(1H, d, J=8.6 Hz), 7.48(1H, d, J=1.8 Hz), 7.84(3H, brs).

Example 86

2-amino-2-{2-[4-(3-phenylallyloxy)-3-trifluoromethylphenyl]ethyl}propane-1,3-diol hydrochloride (86-1) Synthesis of 2-amino-2-{2-[4-(3-phenylallyloxy)-3-trifluoromethylphenyl]ethyl}propane-1,3-diol hydrochloride (Compound 86-1)

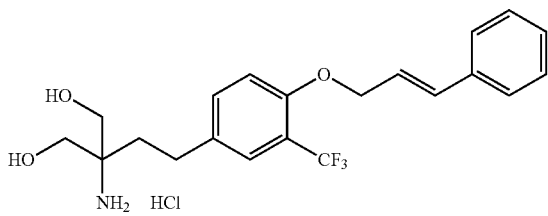

Triphenylphosphine (625 mg) was dissolved in tetrahydrofuran (4 ml), azodicarboxylic acid diisopropyl ester (40% toluene solution, 1.25 ml) and cinnamyl alcohol (320 mg) were added under ice-cooling, and the mixture was stirred at room temperature for 30 min. Reference Example compound 2-6 (500 mg) was added, and the mixture was stirred at room temperature for one day. Water was added to the reaction mixture, and the mixture was extracted with ethyl acetate, washed with saturated brine, and dried over anhydrous sodium sulfate. The solvent was evaporated under reduced pressure. The residue was crudely purified by silica gel column chromatography (hexane:ethyl acetate). The obtained colorless oil was dissolved in ethanol (10 ml), concentrated hydrochloric acid (1 ml) was added, and the mixture was stirred at 80° C. for 2 hr. The reaction mixture was concentrated, and the residue was washed with diethyl ether to give the object product (139 mg) as a white powder.

MS(ESI)m/z: 396[M+H]

$^1$H-NMR(DMSO-d$_6$) δ (ppm): 1.74-1.79(2H, m), 2.59-2.63(2H, m), 3.52(4H, d, J=5.1 Hz), 4.85(2H, d, J=5.4 Hz), 5.40(2H, t, J=5.2 Hz), 6.48(1H, dt, J=16.0, 5.6 Hz), 6.78(1H, d, J=16.1 Hz), 7.27-7.30(2H, m), 7.36(2H, t, J=7.8 Hz), 7.46-7.49(4H, m), 7.82(3H, brs).

Example 87

2-amino-2-(2-{4-[3-(2,2-difluoro-1,3-benzodioxol-5-yl)propoxy]-3-trifluoromethylphenyl}ethyl)propane-1,3-diol hydrochloride (87-1) Synthesis of 1-(2,2-difluoro-1,3-benzodioxol-5-yl)-3-(tetrahydro-2H-pyran-2-yloxy)-1-propyne (Compound 87-1)

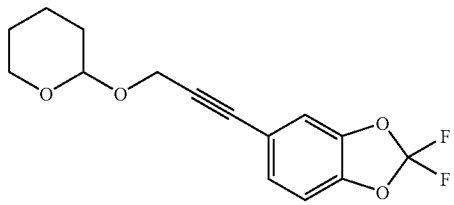

A mixture of 5-bromo-2,2-difluoro-1,3-benzodioxole (10.0 g), cesium carbonate (35.0 g), 2-(2-propynyloxy)tetrahydropyran (8.90 ml), 2-dicyclohexylphosphino-2',4',6'-triisopropylbiphenyl (1.24 g), bis(acetonitrile)palladium(II) dichloride (219 mg) and acetonitrile (100 ml) was stirred at 90° C. for 6 hr. Water was added to the reaction mixture, and the mixture was extracted with ethyl acetate, washed with saturated brine, and dried over anhydrous magnesium sulfate. The solvent was evaporated under reduced pressure. The residue was purified by silica gel column chromatography to give the object product (6.53 g) as a brown oil.

$^1$H-NMR(CDCl$_3$) δ (ppm): 1.54-1.69(4H, m), 1.73-1.90 (2H, m), 3.55-3.59(1H, m), 3.85-3.91(1H, m), 4.43(1H, d, J=15.7 Hz), 4.51(1H, d, J=15.7 Hz), 4.87(1H, t, J=3.3 Hz), 6.99(1H, d, J=8.5 Hz), 7.14(1H, d, J=1.3 Hz), 7.29(1H, dd, J=8.5, 1.3 Hz).

(87-2) Synthesis of 2,2-difluoro-5-(3-hydroxypropyl)-1,3-benzodioxole (Compound 87-2)

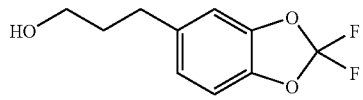

A solution of compound 87-1 (6.53 g) and 10% palladium carbon (3.00 g) in ethyl acetate (30 ml) was stirred under a hydrogen atmosphere at room temperature for 14 hr. The reaction mixture was filtered through celite and concentrated. To a solution of the obtained residue in methanol (30 ml) was added p-toluenesulfonic acid monohydrate (30.0 mg), and the mixture was stirred at room temperature for 24 hr. Saturated aqueous sodium hydrogen carbonate solution was added to the reaction mixture, and the mixture was extracted with ethyl acetate. The organic layer was washed with saturated brine and dried over anhydrous magnesium sulfate. The solvent was evaporated under reduced pressure. The residue was purified by silica gel column chromatography to give the object product (3.54 g) as a yellow oil.

$^1$H-NMR(CDCl$_3$) δ (ppm): 1.24-1.28(1H, m), 1.82-1.90 (2H, m), 2.72(2H, t, J=7.7 Hz), 3.65-3.69(2H, m), 6.87-6.92 (2H, m), 6.96(1H, d, J=8.0 Hz).

(87-3) Synthesis of 5-(3-bromopropyl)-2,2-difluoro-1,3-benzodioxole (Compound 87-3)

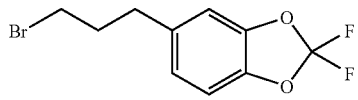

Compound 87-2 (3.54 g) was dissolved in methylene chloride (30 ml), triphenylphosphine (4.73 g) and N-bromosuccinimide (3.21 g) were added under ice-cooling, and the mixture was stirred under ice-cooling for 2.5 hr. The reaction mixture was washed with water and saturated brine, and dried over anhydrous magnesium sulfate. The solvent was evaporated under reduced pressure. Diethyl ether (100 ml) was added, and the precipitated triphenylphosphine oxide was filtered off. The concentrate of the filtrate was purified by silica gel column chromatography to give the object product (4.10 g) as a colorless oil.

$^1$H-NMR(CDCl$_3$) δ (ppm): 2.10-2.17(2H, m), 2.78(2H, t, J=7.3 Hz), 3.38(2H, t, J=6.3 Hz), 6.88-6.92(2H, m), 6.97(1H, d, J=8.0 Hz).

(87-4) Synthesis of [5-(2-{4-[3-(2,2-difluoro-1,3-benzodioxol-5-yl)propoxy]-3-trifluoromethylphenyl}ethyl)-2,2-dimethyl-1,3-dioxan-5-yl]carbamic acid t-butyl ester (Compound 87-4)

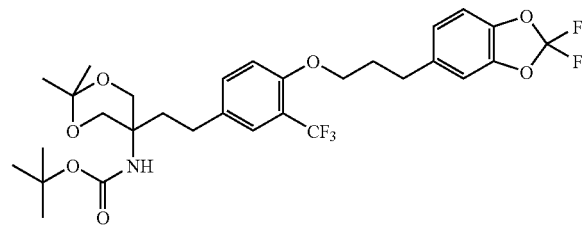

Reference Example compound 2-6 (500 mg) was dissolved in N,N-dimethylformamide (10 ml), potassium carbonate (493 mg) and compound 87-3 (399 mg) were added, and the mixture was stirred at 80° C. for 1 hr. Water was added to the reaction mixture, and the mixture was extracted with ethyl acetate, washed with water and saturated brine, and dried over anhydrous magnesium sulfate. The solvent was evaporated under reduced pressure to give the object product (770 mg) as a white solid.

$^1$H-NMR(CDCl$_3$) δ (ppm): 1.43(3H, s), 1.44(3H, s), 1.47 (9H, s), 1.93-1.98(2H, m), 2.04-2.09(2H, m), 2.52-2.56(2H, m), 2.83(2H, t, J=7.4 Hz), 3.69(2H, d, J=11.7 Hz), 3.89(2H, d, J=11.7 Hz), 3.96(2H, t, J=5.8 Hz), 4.99(1H, brs), 6.82-6.96 (4H, m), 7.26-7.28(1H, m), 7.37(1H, d, J=1.9 Hz).

(87-5) Synthesis of 2-amino-2-(2-{4-[3-(2,2-difluoro-1,3-benzodioxol-5-yl)propoxy]-3-trifluoromethylphenyl}ethyl)propane-1,3-diol hydrochloride (Compound 87-5)

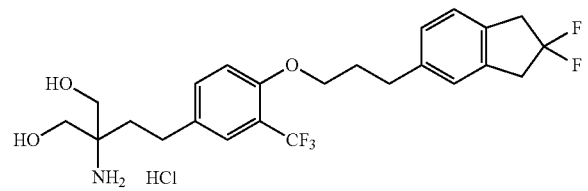

Compound 87-4 (870 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give the object product (510 mg) as a white powder.

MS(ESI)m/z: 478[M+H]

$^1$H-NMR(DMSO-d$_6$) δ (ppm): 1.73-1.78(2H, m), 2.00-2.04(2H, m), 2.58-2.63(2H, m), 2.77(2H, t, J=7.4 Hz), 3.51 (4H, d, J=4.1 Hz), 4.03(2H, t, J=5.8 Hz), 5.39(2H, brs), 7.01 (1H, d, J=8.2 Hz), 7.17(1H, d, J=8.5 Hz), 7.29-7.31(2H, m), 7.44(1H, d, J=8.5 Hz), 7.48(1H, brs), 7.80(3H, brs).

Example 88

2-amino-2-(2-{4-[3-(4-chlorophenyl)allyloxy]-3-trifluoromethylphenyl}ethyl)propane-1,3-diol hydrochloride

(88-1) Synthesis of 3-(4-chlorophenyl)-2-propene-1-ol (Compound 88-1)

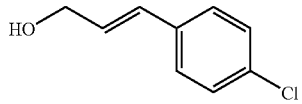

3-(4-Chlorophenyl)methyl acrylate ester (2.00 g) was dissolved in methylene chloride (100 ml), 1M diisobutylaluminum hydride/toluene solution (20 ml) was added dropwise at −78° C., and the mixture was stirred as it was at −78° C. for 1 hr. Saturated aqueous ammonium chloride solution was added to the reaction mixture, and the mixture was stirred at room temperature. Aluminum salt was collected by filtration through celite, extracted with methylene chloride, washed with saturated brine, and dried over anhydrous sodium sulfate. The solvent was evaporated under reduced pressure. The residue was purified by silica gel column chromatography (hexane:ethyl acetate) to give the object product (1.33 g) as a white powder.

$^1$H-NMR(DMSO-d$_6$) δ (ppm): 4.11(2H, td, J=4.7, 1.2 Hz), 4.91(1H, t, J=5.5 Hz), 6.41(1H, dt, J=16.0, 4.7 Hz), 6.55(1H, d, J=16.0 Hz), 7.37(2H, d, J=8.5 Hz), 7.45(2H, d, J=8.5 Hz).

(88-2) Synthesis of 2-amino-2-(2-{4-[3-(4-chlorophenyl)allyloxy]-3-trifluoromethylphenyl}ethyl)propane-1,3-diol hydrochloride (Compound 88-2)

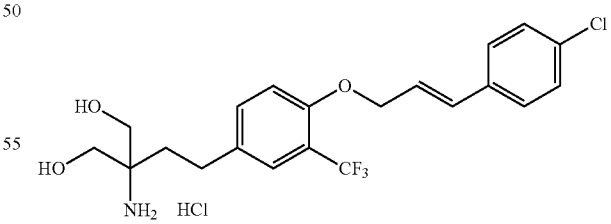

Triphenylphosphine (625 mg) was dissolved in tetrahydrofuran (4 ml), azodicarboxylic acid diisopropyl ester (40% toluene solution, 1.25 ml) and compound 88-1 (400 mg) were added under ice-cooling, and the mixture was stirred at room temperature for 30 min. Reference Example compound 2-6 (500 mg) was added, and the mixture was stirred at room temperature for one day. Water was added to the reaction mixture, and the mixture was extracted with ethyl acetate, washed with saturated brine, and dried over anhydrous sodium sulfate. The solvent was evaporated under reduced pressure, and the residue was crudely purified by silica gel column chromatography (hexane:ethyl acetate). The obtained pale-yellow oil was dissolved in ethanol (10 ml), concentrated hydrochloric acid (1 ml) was added, and the mixture was stirred at 80° C. for 2 hr. The reaction mixture was concentrated, and the residue was washed with diethyl ether to give the object product (94 mg) as a white powder.

MS(ESI)m/z: 430[M+H]

$^1$H-NMR (DMSO-$d_6$) δ (ppm): 1.74-1.78(2H, m), 2.58-2.63(2H, m), 3.51(4H, d, J=5.0 Hz), 4.84(2H, d, J=5.2 Hz), 5.40(2H, t, J=5.2 Hz), 6.52(1H, dt, J=16.2, 5.5 Hz), 6.76(1H, d, J=15.9 Hz), 7.27(1H, d, J=8.5 Hz), 7.41(2H, d, J=8.5 Hz), 7.46-7.51(2H, m), 7.51(2H, d, J=8.5 Hz), 7.81(3H, brs).

Example 89

2-amino-2-(2-{4-[3-(3-chlorophenyl)allyloxy]-3-trifluoromethylphenyl}ethyl)propane-1,3-diol hydrochloride (89-1) Synthesis of 3-(3-chlorophenyl)-2-propene-1-ol (Compound 89-1)

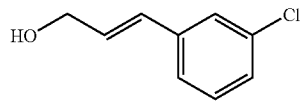

3-(3-Chlorophenyl)acrylic acid (5.0 g) was dissolved in methanol (30 ml), concentrated sulfuric acid (0.5 ml) was added, and the mixture was stirred at 100° C. for 1.5 hr. The reaction mixture was concentrated, and the residue was washed with water. The obtained pale-yellow powder was dissolved in methylene chloride (130 ml), 1M diisobutylaluminum hydride/toluene solution (52 ml) was added dropwise at −78° C., and the mixture was stirred as it was at −78° C. for 2 hr. Saturated aqueous ammonium chloride solution was added to the reaction mixture, and the mixture was stirred at room temperature. Aluminum salt was collected by filtration through celite, extracted with methylene chloride, washed with saturated brine, and dried over anhydrous sodium sulfate. The solvent was evaporated under reduced pressure. The residue was purified by silica gel column chromatography (hexane:ethyl acetate) to give the object product (3.29 g) as a yellow oil.

$^1$H-NMR (DMSO-$d_6$) δ (ppm): 4.11-4.14(2H, m), 4.93 (1H, t, J=5.4 Hz), 6.47(1H, dt, J=16.0, 4.5 Hz), 6.55(1H, d, J=16.0 Hz), 7.27(1H, dt, J=7.8, 1.5 Hz), 7.34(1H, t, J=7.8 Hz), 7.40(1H, dt, J=7.7, 1.5 Hz), 7.50(1H, t, J=1.7 Hz).

(89-2) Synthesis of 2-amino-2-(2-{4-[3-(3-chlorophenyl)allyloxy]-3-trifluoromethylphenyl}ethyl)propane-1,3-diol hydrochloride (Compound 89-2)

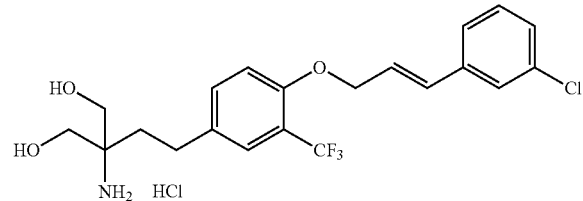

Triphenylphosphine (625 mg) was dissolved in tetrahydrofuran (8 ml), azodicarboxylic acid diisopropyl ester (40% toluene solution, 1.25 ml) and compound 89-1 (400 mg) were added under ice-cooling, and the mixture was stirred at room temperature for 30 min. Reference Example compound 2-6 (500 mg) was added, and the mixture was stirred at room temperature for one day. Water was added to the reaction mixture, and the mixture was extracted with ethyl acetate, washed with saturated brine, and dried over anhydrous sodium sulfate. The solvent was evaporated under reduced pressure, and the residue was crudely purified by silica gel column chromatography (hexane:ethyl acetate). The obtained yellow oil was dissolved in ethanol (25 ml), concentrated hydrochloric acid (3 ml) was added, and the mixture was stirred at 80° C. for 1.5 hr. The reaction mixture was concentrated, and the residue was washed with diethyl ether to give the object product (287 mg) as a white powder.

MS(ESI)m/z: 430[M+H]

$^1$H-NMR(DMSO-$d_6$) δ (ppm): 1.74-1.79(2H, m), 2.59-2.63(2H, m), 3.51(4H, d, J=5.1 Hz), 4.85(2H, d, J=5.3 Hz), 5.40(2H, t, J=5.1 Hz), 6.60(1H, dt, J=16.2, 5.4 Hz), 6.76(1H, d, J=16.0 Hz), 7.27(1H, d, J=8.5 Hz), 7.34(1H, d, J=7.9 Hz), 7.38(1H, t, J=7.8 Hz), 7.43-7.49(3H, m), 7.57(1H, s), 7.82 (3H, brs).

Example 90

2-amino-2-(2-{4-[3-(4-fluorophenyl)allyloxy]-3-trifluoromethylphenyl}ethyl)propane-1,3-diol hydrochloride (90-1) Synthesis of 3-(4-fluorophenyl)-2-propene-1-ol (Compound 90-1)

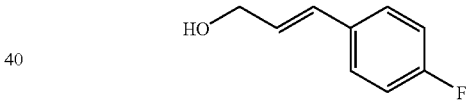

3-(4-Fluorophenyl)acrylic acid (5.0 g) was dissolved in methanol (30 ml), concentrated sulfuric acid (0.5 ml) was added, and the mixture was stirred at 100° C. for 3.5 hr. The reaction mixture was concentrated, and the residue was washed with water. The obtained white powder was dissolved in tetrahydrofuran (110 ml), 1M diisobutylaluminum hydride/toluene solution (55 ml) was added dropwise at −78° C., and the mixture was stirred at it was at −78° C. for 1 Saturated aqueous ammonium chloride solution was added to the reaction mixture, and the mixture was stirred at room temperature. Aluminum salt was collected by filtration through celite, extracted with methylene chloride, washed with saturated brine, and dried over anhydrous sodium sulfate. The solvent was evaporated under reduced pressure. The residue was washed with water and hexane to give the object product (3.82 g) as a white powder.

$^1$H-NMR(DMSO-$d_6$) δ (ppm): 4.10(2H, td, J=5.4, 1.4 Hz), 4.88(1H, t, J=5.4 Hz), 6.33(1H, dt, J=15.8, 5.2 Hz), 6.54(1H, d, J=15.9 Hz), 7.15(2H, d, J=8.7 Hz), 7.47(2H, dd, J=8.6, 5.6 Hz).

(90-2) Synthesis of 2-amino-2-(2-{4-[3-(4-fluorophenyl)allyloxy]-3-trifluoromethylphenyl}ethyl)propane-1,3-diol hydrochloride (Compound 90-2)

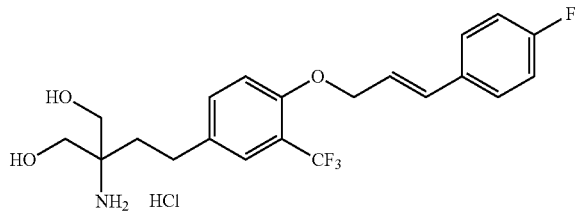

Triphenylphosphine (625 mg) was dissolved in tetrahydrofuran (8 ml), azodicarboxylic acid diisopropyl ester (40% toluene solution, 1.25 ml) and compound 90-1 (360 mg) were added under ice-cooling, and the mixture was stirred at room temperature for 30 min. Reference Example compound 2-6 (500 mg) was added, and the mixture was stirred at room temperature for one day. Water was added to the reaction mixture, and the mixture was extracted with ethyl acetate, washed with saturated brine, and dried over anhydrous sodium sulfate. The solvent was evaporated under reduced pressure, and the residue was crudely purified by silica gel column chromatography (hexane:ethyl acetate). The obtained colorless oil was dissolved in ethanol (25 ml), concentrated hydrochloric acid (2 ml) was added, and the mixture was stirred at 80° C. for 3 hr. The reaction mixture was concentrated, and the residue was washed with diethyl ether to give the object product (203 mg) as a white powder.

MS(ESI)m/z: 414[M+H]

$^1$H-NMR(DMSO-$d_6$) δ (ppm): 1.74-1.78(2H, m), 2.58-2.63(2H, m), 3.51(4H, d, J=5.0 Hz), 4.83(2H, d, J=5.6 Hz), 5.40(2H, t, J=5.0 Hz), 6.44(1H, dt, J=16.0, 5.6 Hz), 6.77(1H, d, J=16.0 Hz), 7.18(2H, t, J=8.7 Hz), 7.28(1H, d, J=8.5 Hz), 7.46(1H, d, J=8.7 Hz), 7.49(1H, s), 7.53(2H, dd, J=8.6, 5.7 Hz), 7.80(3H, brs).

Example 91

2-amino-2-(2-{3-trifluoromethyl-4-[3-(3-trifluoromethylphenyl)allyloxy]phenyl}ethyl)propane-1,3-diol hydrochloride (91-1) Synthesis of 3-(3-trifluoromethylphenyl)-2-propene-1-ol (Compound 91-1)

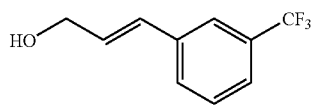

3-(3-Trifluoromethylphenyl)acrylic acid (3.0 g) was dissolved in methanol (30 ml), concentrated sulfuric acid (0.5 ml) was added, and the mixture was stirred at 100° C. for 5.5 hr. The reaction mixture was concentrated, and the residue was washed with water. The obtained white powder was dissolved in tetrahydrofuran (40 ml), 1M diisobutylaluminum hydride/toluene solution (26 ml) was added dropwise at −78° C., and the mixture was stirred as it was at −78° C. for 2 hr. Saturated Rochelle salt water, water and ethyl acetate were added to the reaction mixture, and the mixture was stirred at room temperature, extracted with ethyl acetate, washed with water and saturated brine, and dried over anhydrous sodium sulfate. The solvent was evaporated under reduced pressure. The residue was purified by silica gel column chromatography (hexane:ethyl acetate) to give the object product (2.0 g) as a colorless oil.

$^1$H-NMR(DMSO-$d_6$) δ (ppm): 4.15(2H, td, J=4.9, 0.9 Hz), 4.96(1H, t, J=5.5 Hz), 6.57(1H, dt, J=16.0, 4.6 Hz), 6.67(1H, d, J=15.9 Hz), 7.55-7.67(2H, m), 7.75(2H, s).

(91-2) Synthesis of 2-amino-2-(2-{3-trifluoromethyl-4-[3-(3-trifluoromethylphenyl)allyloxy]phenyl}ethyl)propane-1,3-diol hydrochloride (Compound 91-2)

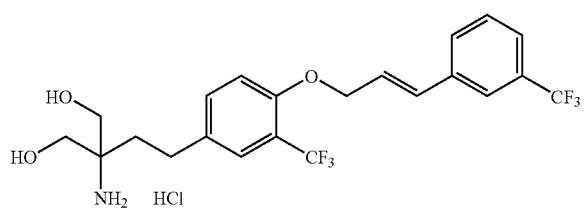

Triphenylphosphine (625 mg) was dissolved in tetrahydrofuran (12 ml), azodicarboxylic acid diisopropyl ester (40% toluene solution, 1.25 ml) and compound 91-1 (480 mg) were added under ice-cooling, and the mixture was stirred at room temperature for 30 min. Reference Example compound 2-6 (500 mg) was added, and the mixture was stirred at room temperature for one day. Water was added to the reaction mixture, and the mixture was extracted with ethyl acetate, washed with saturated brine, and dried over anhydrous sodium sulfate. The solvent was evaporated under reduced pressure, and the residue was crudely purified by silica gel column chromatography (hexane:ethyl acetate). The obtained colorless oil was dissolved in ethanol (10 ml), concentrated hydrochloric acid (3 ml) was added, and the mixture was stirred at 80° C. for 2 hr. The reaction mixture was concentrated, and the residue was washed with diethyl ether to give the object product (76 mg) as a white powder.

MS(ESI)m/z: 464[M+H]

$^1$H-NMR(DMSO-$d_6$) δ (ppm): 1.74-1.79(2H, m), 2.59-2.63(2H, m), 3.52(4H, d, J=5.1 Hz), 4.87(2H, d, J=5.0 Hz), 5.39(2H, t, J=5.1 Hz), 6.69(1H, dt, J=16.1, 5.2 Hz), 6.86(1H, d, J=16.1 Hz), 7.29(1H, d, J=8.5 Hz), 7.47(1H, d, J=8.6 Hz), 7.50(1H, s), 7.57-7.65(2H, m), 7.80(3H, brs), 7.82(2H, brs).

Example 92

2-amino-2-(2-{3-trifluoromethyl-4-[3-(4-trifluoromethylphenyl)allyloxy]phenyl}ethyl)propane-1,3-diol hydrochloride (92-1) Synthesis of 3-(4-trifluoromethylphenyl)-2-propene-1-ol (Compound 92-1)

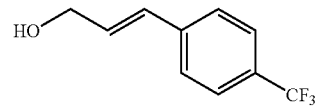

3-(4-Trifluoromethylphenyl)acrylic acid (3.0 g) was dissolved in methanol (30 ml), concentrated sulfuric acid (0.5 ml) was added, and the mixture was stirred at 100° C. for 3.5 hr. The reaction mixture was concentrated, and the residue was washed with water. The obtained white powder was dissolved in tetrahydrofuran (40 ml), 1M diisobutylaluminum hydride/toluene solution (34 ml) was added dropwise at −78° C., and the mixture was stirred as it was at −78° C. for 1 hr. Saturated Rochelle salt water, water and ethyl acetate were added to the reaction mixture, and the mixture was stirred at room temperature. The mixture was extracted with ethyl acetate, and the extract was washed with water and saturated brine, and dried over anhydrous sodium sulfate. The solvent was evaporated under reduced pressure. The residue was purified by silica gel column chromatography (hexane:ethyl acetate) to give the object product (2.64 g) as a white powder.

$^1$H-NMR(DMSO-$d_6$) δ (ppm): 4.17(2H, t, J=4.4 Hz), 4.99 (1H, t, J=5.4 Hz), 6.57(1H, dt, J=16.1, 4.4 Hz), 6.66(1H, d, J=16.2 Hz), 7.64(2H, d, J=8.8 Hz), 7.67(2H, d, J=8.8 Hz).

(92-2) Synthesis of 2-amino-2-(2-{3-trifluoromethyl-4-[3-(4-trifluoromethylphenyl)allyloxy]phenyl}ethyl)propane-1,3-diol hydrochloride (Compound 92-2)

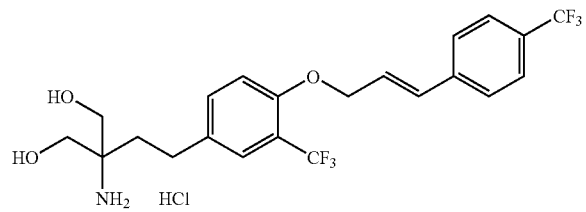

Triphenylphosphine (625 mg) was dissolved in tetrahydrofuran (12 ml), azodicarboxylic acid diisopropyl ester (40% toluene solution, 1.25 ml) and compound 92-1 (480 mg) were added under ice-cooling, and the mixture was stirred at room temperature for 30 min. Reference Example compound 2-6 (500 mg) was added, and the mixture was stirred at room temperature for one day. Water was added to the reaction mixture, and the mixture was extracted with ethyl acetate, washed with saturated brine, and dried over anhydrous sodium sulfate. The solvent was evaporated under reduced pressure, and the residue was crudely purified by silica gel column chromatography (hexane:ethyl acetate). The obtained colorless oil was dissolved in ethanol (15 ml), concentrated hydrochloric acid (3 ml) was added, and the mixture was stirred at 80° C. for 2 hr. The reaction mixture was concentrated, and the residue was washed with diethyl ether to give the object product (423 mg) as a white powder.

MS(ESI)m/z: 464[M+H]

$^1$H-NMR (DMSO-$d_6$) δ (ppm): 1.74-1.78(2H, m), 2.59-2.63(2H, m), 3.51(4H, d, J=4.7 Hz), 4.89(2H, d, J=5.1 Hz), 5.37(2H, t, J=4.8 Hz), 6.67(1H, dt, J=16.1, 5.1 Hz), 6.86(1H, d, J=16.2 Hz), 7.28(1H, d, J=8.5 Hz), 7.47(1H, d, J=8.6 Hz), 7.49(1H, s), 7.68-5 7.72(7H, m).

Example 93

(E)-2-amino-2-(2-{4-[3-(3-methylphenyl)propoxy]-3-trifluoromethylphenyl}vinyl)propane-1,3-diol hydrochloride (93-1) Synthesis of 4-benzyloxy-3-trifluoromethylbenzoic acid (Compound 93-1)

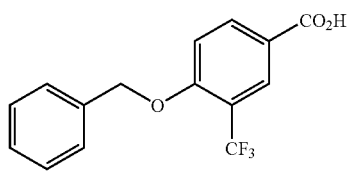

To a solution of potassium t-butoxide (27.5 g) in N,N-dimethylformamide (120 ml) was added dropwise a solution of benzyl alcohol (15.9 ml) in N,N-dimethylformamide (60 ml) over min. The mixture was stirred for 30 min, and a solution of 4-fluoro-3-trifluoromethylbenzoic acid (20.0 g) in N,N-dimethylformamide (90 ml) was added under ice-cooling. The mixture was stirred at room temperature for 1 hr, and further at 50° C. for 1 hr. The reaction mixture was added to ice water, and acidified with 1M hydrochloric acid (300 ml). The precipitated solid was collected by filtration, and washed with water and then hexane to give the object product (28.2 g) as a white powder.

$^1$H-NMR(CDCl$_3$) δ (ppm): 5.29(2H, s), 7.10(1H, d, J=8.7 Hz), 7.33-7.37(1H, m), 7.39-7.45(4H, m), 8.22(1H, dd, J=2.0, 8.7 Hz), 8.36(1H, d, J=2.0 Hz).

(93-2) Synthesis of 4-benzyloxy-3-trifluoromethylbenzyl alcohol (Compound 93-2)

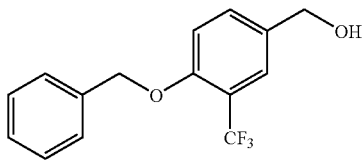

To a solution of compound 93-1 (28.2 g) in toluene (400 ml) was added dropwise a solution of a 70% toluene solution (15.9 ml) of bis(2-methoxyethoxy)aluminum sodium hydride in toluene (80 ml) over 15 min under ice-cooling. Further, under ice-cooling, a solution of a 70% toluene solution (79.3 ml) of bis(2-methoxyethoxy)aluminum sodium hydride in toluene (80 ml) was added dropwise over 15 min. The reaction mixture was stirred at room temperature for 2 hr, at 30° C. for 1 hr and further at 40° C. for 1 hr. The reaction mixture was ice-cooled, a solution of sodium hydroxide (90 g) in water (270 ml) was added dropwise, and the mixture was extracted with toluene. The organic layer was washed with a solution of sodium hydroxide (90 g) in water (270 ml) and saturated brine, and dried over anhydrous magnesium sulfate. The solvent was evaporated under reduced pressure to give the object product (26.6 g) as a white solid.

$^1$H-NMR(CDCl$_3$) δ (ppm): 1.67(1H, t, J=5.9 Hz), 4.66(2H, d, J=5.9 Hz), 5.20(2H, s), 7.02(1H, d, J=8.5 Hz), 7.30-7.34 (1H, m), 7.37-7.40(2H, m), 7.43-7.47(3H, m), 7.61(1H, d, J=1.8 Hz).

(93-3) Synthesis of 4-hydroxy-3-trifluoromethylbenzyl alcohol (Compound 93-3)

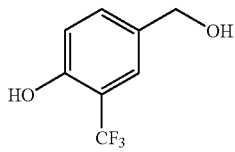

A solution of compound 93-2 (26.6 g) and 10% palladium carbon (5.00 g) in 1,4-dioxane (250 ml) was stirred under a hydrogen atmosphere at room temperature for 5 hr. The reaction mixture was filtered through celite and concentrated to give the object product (18.8 g) as a white solid.

$^1$H-NMR (DMSO-$d_6$) δ (ppm): 4.41(2H, s), 5.16(1H, brs), 6.97(1H, d, J=8.4 Hz), 7.37(1H, dd, J=1.6, 8.4 Hz), 7.44(1H, d, J=1.6 Hz), 10.40(1H, brs).

(93-4) Synthesis of 3-trifluoromethyl-4-[(2-trimethylsilylethoxy)methoxy]benzyl alcohol (Compound 93-4)

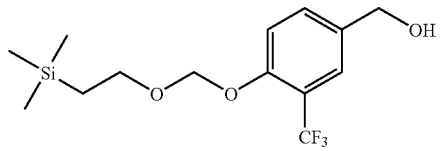

To a solution of compound 93-3 (18.8 g) in N,N-dimethylformamide (120 ml), potassium carbonate (40.6 g) and 2-(trimethylsilyl)ethoxymethyl chloride (19.1 ml) were added under ice-cooling, and the mixture was stirred under ice-cooling for 4 hr and further at room temperature for 4 hr. The reaction mixture was added to water, and the mixture was extracted with ethyl acetate, washed with water and saturated brine, and dried over anhydrous magnesium sulfate. The solvent was evaporated under reduced pressure to give the object product (28.5 g) as a colorless oil.

$^1$H-NMR(CDCl$_3$) δ (ppm): 0.01(9H, s), 0.92-0.99(2H, m), 1.69(1H, brs), 3.74-3.80(2H, m), 4.68(2H, s), 5.32(2H, s), 7.24(1H, d, J=8.5 Hz), 7.48(1H, dd, J=1.6, 8.4 Hz), 7.59(1H, d, J=1.6 Hz).

(93-5) Synthesis of 3-trifluoromethyl-4-[(2-trimethylsilylethoxy)methoxy]benzyl chloride (Compound 93-5)

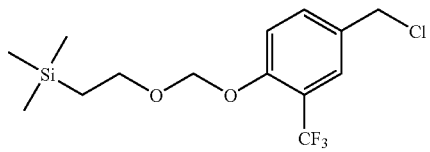

Compound 93-4 (28.5 g) was dissolved in methylene chloride (450 ml), 1-chloro-N,N,2-trimethyl-1-propenylamine (12.9 ml) was added under ice-cooling, and the mixture was stirred under ice-cooling for 1 hr. The reaction mixture was diluted with methylene chloride (200 ml), washed with water and saturated brine, and dried over anhydrous magnesium sulfate. The solvent was evaporated under reduced pressure. The obtained residue was purified by silica gel column chromatography (hexane:ethyl acetate=99:1-90:10) to give the object product (14.5 g) as a colorless oil.

$^1$H-NMR(CDCl$_3$) δ (ppm): 0.01(9H, s), 0.92-0.97(2H, m), 3.75-3.79(2H, m), 4.57(2H, s), 5.32(2H, s), 7.24(1H, d, J=8.6 Hz), 7.50(1H, dd, J=2.1, 8.6 Hz), 7.60(1H, d, J=2.0 Hz).

(93-6) Synthesis of {3-trifluoromethyl-4-[(2-trimethylsilylethoxy)methoxy]benzyl}phosphonic acid dimethyl (Compound 93-6)

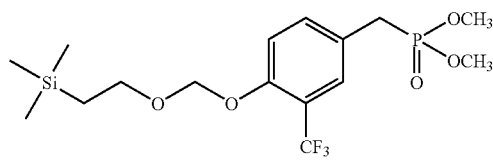

To a mixture of compound 93-5 (14.4 g), tetrabutylammonium iodide (17.2 g), cesium carbonate (15.1 g) and N,N-dimethylformamide (40 ml) was added dimethyl phosphite (4.26 ml) under ice-cooling, and the mixture was stirred at room temperature for 4 hr. The reaction mixture was added to water, and the mixture was extracted with ethyl acetate, washed with water and saturated brine, and dried over anhydrous magnesium sulfate. The solvent was evaporated under reduced pressure. The obtained residue was purified by silica gel column chromatography (hexane:ethyl acetate=98:2-25:75) to give the object product (10.4 g) as a colorless oil.

$^1$H-NMR(CDCl$_3$) δ (ppm): 0.01(9H, s), 0.92-0.96(2H, m), 3.13(2H, d, J=21.4 Hz), 3.70(6H, d, J=10.7 Hz), 3.75-3.79(2H, m), 5.30(2H, s), 7.21(1H, d, J=8.6 Hz), 7.40-7.43(1H, m), 7.46-7.47(1H, m).

(93-7) Synthesis of (E)-[2,2-dimethyl-5-(2-{3-trifluoromethyl-4-[(2-trimethylsilylethoxy)methoxy]phenyl}vinyl)-1,3-dioxan-5-yl]carbamic acid t-butyl ester (Compound 93-7)

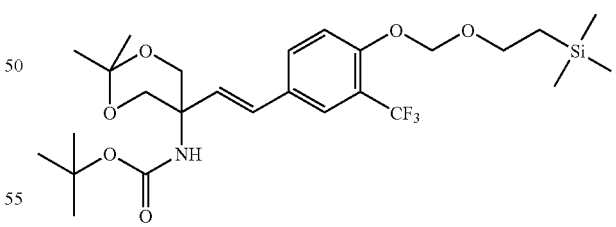

To a solution of t-butoxy potassium (7.88 g) in tetrahydrofuran (170 ml) was added dropwise a solution of compound 93-6 (10.4 g) and Reference Example compound 1-2 (8.45 g) in tetrahydrofuran (150 ml) under ice-cooling, and the mixture was stirred under ice-cooling for 1.5 hr, and further at room temperature for 4 hr. The reaction mixture was added to an aqueous ammonium chloride solution, and extracted with ethyl acetate. The organic layer was washed with water and brine, and dried over anhydrous magnesium sulfate. The solvent was evaporated under reduced pressure. The obtained residue was purified by silica gel column chromatography (hexane:ethyl acetate=99:1-75:25) to give the object product (10.9 g) as a colorless oil.

$^1$H-NMR(CDCl$_3$) δ (ppm): 0.01(9H, s), 0.91-0.95(2H, m), 1.45(9H, s), 1.47(3H, s), 1.49(3H, s), 3.74-3.79(2H, m), 3.90 (2H, d, J=11.5 Hz), 3.97(2H, d, J=11.5 Hz), 5.22(1H, brs), 5.30(2H, s), 6.13(1H, d, J=16.4 Hz), 6.49(1H, d, J=16.4 Hz), 7.18(1H, d, J=8.6 Hz), 7.45(1H, dd, J=1.8, 8.6 Hz), 7.56(1H, d, J=1.6 Hz).

(93-8) Synthesis of (E)-{5-[2-(4-hydroxy-3-trifluoromethylphenyl)vinyl]-2,2-dimethyl-1,3-dioxan-5-yl}carbamic acid t-butyl ester (Compound 93-8)

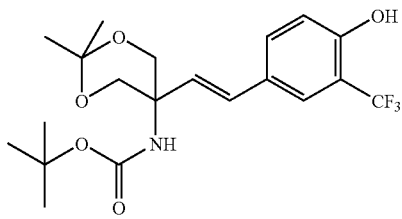

A mixture of compound 93-7 (10.9 g) and a solution (199 ml) of tetrabutylammonium fluoride in 1M tetrahydrofuran was stirred at 50° C. for 19 hr. The reaction mixture was added to brine, and extracted with ethyl acetate. The organic layer was washed with water and brine, and dried over anhydrous magnesium sulfate. The solvent was evaporated under reduced pressure. The obtained residue was suspended in diisopropyl ether (20 ml) and hexane (200 ml), and the solid was collected by filtration, and washed with hexane to give the object product (6.11 g) as a white powder.

$^1$H-NMR(CDCl$_3$) δ (ppm): 1.47(3H, s), 1.49(12H, s), 3.88 (2H, d, J=11.6 Hz), 3.92(2H, d, J=11.6 Hz), 5.44(1H, brs), 5.93(1H, d, J=16.4 Hz), 6.35(1H, d, J=16.4 Hz), 6.64(1H, d, J=7.6 Hz), 6.97(1H, brs), 7.31(1H, s).

(93-9) Synthesis of (E)-[2,2-dimethyl-5-(2-{4-[3-(3-methylphenyl)propoxy]-3-trifluoromethylphenyl}vinyl)-1,3-dioxan-5-yl]carbamic acid t-butyl ester (Compound 93-9)

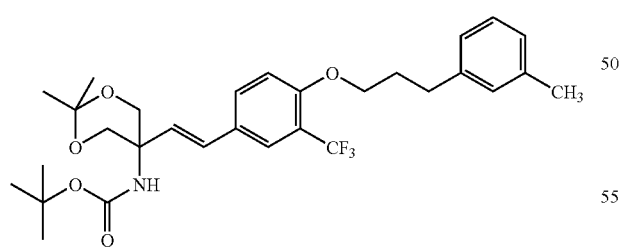

Compound 93-8 (400 mg) was dissolved in N,N-dimethylformamide (10 ml), potassium carbonate (397 mg) and compound 15-2 (246 mg) were added, and the mixture was stirred at 50° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (560 mg) as a white solid.

$^1$H-NMR(CDCl$_3$) δ (ppm): 1.45(9H, s), 1.47(3H, s), 1.49 (3H, s), 2.07-2.14(2H, m), 2.32(3H, s), 2.79(2H, t, J=7.5 Hz), 3.90(2H, d, J=11.4 Hz), 3.96-4.03(4H, m), 5.22(1H, brs), 6.11(1H, d, J=16.4 Hz), 6.48(1H, d, J=16.4 Hz), 6.87(1H, d, J=8.6 Hz), 6.98-7.02(3H, m), 7.17(1H, t, J=7.4 Hz), 7.43(1H, dd, J=8.6, 1.7 Hz), 7.57(1H, d, J=1.7 Hz).

(93-10) Synthesis of (E)-2-amino-2-(2-{4-[3-(3-methylphenyl)propoxy]-3-trifluoromethylphenyl}vinyl) propane-1,3-diol hydrochloride (Compound 93-10)

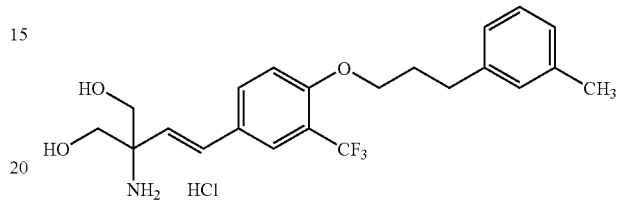

Compound 93-9 (560 mg) was dissolved in ethanol (15 ml), concentrated hydrochloric acid (1.5 ml) was added, and the mixture was stirred at 80° C. for 1 hr. The reaction mixture was concentrated, and the residue was washed with diethyl ether to give the object product (370 mg) as a white powder.

MS(ESI)m/z: 393

$^1$H-NMR(DMSO-d$_6$) δ (ppm): 1.98-2.05(2H, m), 2.26(3H, s), 2.71(2H, t, J=7.5 Hz), 3.59-3.67(4H, m), 4.09 (2H, t, J=6.1 Hz), 5.47(2H, t, J=5.4 Hz), 6.24(1H, d, J=16.6 Hz), 6.70(1H, d, J=16.6 Hz), 6.96-7.01(3H, m), 7.17(1H, t, J=7.4 Hz), 7.24(1H, d, J=8.6 Hz), 7.63(1H, dd, J=8.6, 1.6 Hz), 7.66(1H, brs), 8.05(3H, brs).

Example 94

2-amino-2-(2-{4-[3-(1,2,3,4-tetrahydronaphthalen-1-yl)propoxy]-3-trifluoromethylphenyl}ethyl)propane-1,3-diol hydrochloride (94-1) Synthesis of 1-(3-hydroxypropyl)-1,2,3,4-tetrahydronaphthalene (Compound 94-1)

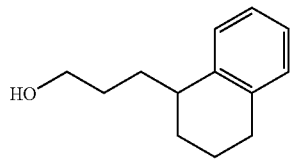

(3-Benzyloxypropyl)triphenylphosphoniumbromide (1.00 g) was dissolved in tetrahydrofuran (10 ml), sodium hydride (162 mg) was added under ice-cooling, and the mixture was stirred at room temperature for 1 hr. α-Tetralone (1.36 ml) was added to the reaction mixture, and the mixture was stirred at 75° C. for 48 hr. Water was added to the reaction mixture, and the mixture was extracted with ethyl acetate, washed with saturated brine, and dried over anhydrous magnesium sulfate. The solvent was evaporated under reduced pressure. To a solution of the obtained residue in ethyl acetate (10 ml) was added 10% palladium carbon (200 mg), and the mixture was stirred under a hydrogen atmosphere at room temperature for 18 hr. The reaction container was purged with nitrogen, the solution was filtered, and the filtrate was concentrated. The obtained residue was purified by silica gel column chromatography to give the object product (140 mg) as a colorless oil.

$^1$H-NMR(CDCl$_3$) δ (ppm): 1.24(1H, brs), 1.60-1.80(6H, m), 1.81-1.89(2H, m), 2.73-2.80(3H, m), 3.68(2H, brs), 7.04-7.10(3H, m), 7.11-7.13(1H, m).

(94-2) Synthesis of 1-(3-bromopropyl)-1,2,3,4-tetrahydronaphthalene (Compound 94-2)

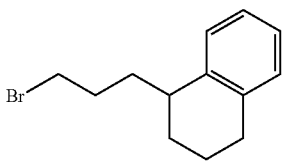

Compound 94-1 (140 mg) was dissolved in methylene chloride (10 ml), triphenylphosphine (212 mg) and N-bromosuccinimide (144 g) were added under ice-cooling, and the mixture was stirred under ice-cooling for 2 hr, and at room temperature 16 hr. The reaction mixture was washed with water and saturated brine, and dried over anhydrous magnesium sulfate. The solvent was evaporated under reduced pressure. Diethyl ether (50 ml) was added, and the precipitated triphenylphosphine oxide was filtered off. The concentrate of the filtrate was purified by silica gel column chromatography to give the object product (190 mg) as a colorless oil.

$^1$H-NMR(CDCl$_3$) δ (ppm): 1.68-1.79(2H, m), 1.80-1.90(4H, m), 1.91-2.02(2H, m), 2.70-2.82(3H, m), 3.40-3.47(2H, m), 7.05-7.18(4H, m).

(94-3) Synthesis of [2,2-dimethyl-5-(2-{4-[3-(1,2,3,4-tetrahydronaphthalen-1-yl)propoxy]-3-trifluoromethylphenyl}ethyl)-1,3-dioxan-5-yl]carbamic acid t-butyl ester (Compound 94-3)

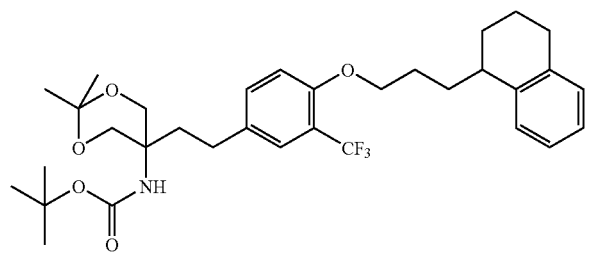

Reference Example compound 2-6 (282 mg) was dissolved in N,N-dimethylformamide (7 ml), potassium carbonate (278 mg) and compound 94-2 (190 mg) were added, and the mixture was stirred at 80° C. for 1.5 hr. Water was added to the reaction mixture, and the mixture was extracted with ethyl acetate, washed with water and saturated brine, and dried over anhydrous magnesium sulfate. The solvent was evaporated under reduced pressure to give the object product (400 mg) as a colorless oil.

$^1$H-NMR(CDCl$_3$) δ (ppm): 1.42(3H, s), 1.44(3H, s), 1.47 (9H, s), 1.69-1.77(3H, m), 1.82-1.97(7H, m), 2.51-2.56(2H, m), 2.74-2.78(2H, m), 2.79-2.88(1H, m), 3.69(2H, d, J=11.7 Hz), 3.89(2H, d, J=11.7 Hz), 4.03(2H, t, J=5.6 Hz), 4.99(1H, brs), 6.87(1H, d, J=8.5 Hz), 7.04-7.14(3H, m), 7.19(1H, brd, J=7.2 Hz), 7.26-7.28(1H, m), 7.35(1H, brd, J=1.8 Hz).

(94-4) Synthesis of 2-amino-2-(2-{4-[3-(1,2,3,4-tetrahydronaphthalen-1-yl)propoxy]-3-trifluoromethylphenyl}ethyl)propane-1,3-diol hydrochloride (Compound 94-4)

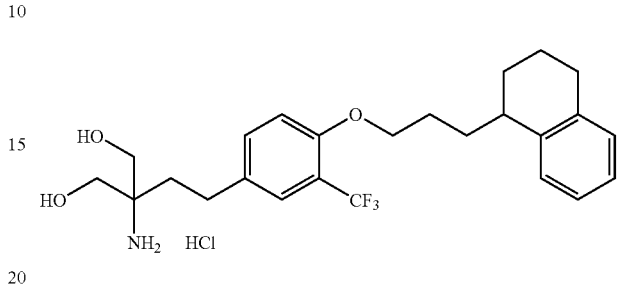

Compound 94-3 (400 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give the object product (270 mg) as a white powder.

MS(ESI)m/z: 452[M+H]

$^1$H-NMR(DMSO-d$_6$) δ (ppm): 1.60-1.71(3H, m), 1.72-1.86(7H, m), 2.58-2.62(2H, m), 2.63-2.72(2H, m), 2.78(1H, brs), 3.51(4H, d, J=4.7 Hz), 4.11(2H, brs), 5.40(2H, t, J=5.0 Hz), 7.02-7.10(3H, m), 7.13-7.20(2H, m), 7.43-7.47(2H, m), 7.82(3H, brs).

Example 95

2-amino-2-(2-{4-[3-(3-nitrophenyl)propoxy]-3-trifluoromethylphenyl}ethyl)propane-1,3-diol hydrochloride (95-1) Synthesis of 3-(3-nitrophenyl)-1-propanol (Compound 95-1)

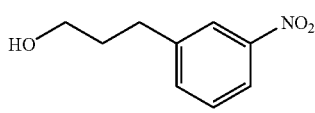

3-(3-Nitrophenyl)propionic acid (1.00 g) was dissolved in tetrahydrofuran (20 ml), and a tetrahydrofuran-borane.tetrahydrofuran solution (1 mol/l, 7.25 ml) was added dropwise to the mixture under ice-cooling. The mixture was stirred under ice-cooling for 30 min, and further at room temperature for 2.5 hr. Water was added to the reaction mixture, and 1 mol/l aqueous hydrochloric acid solution was added. The mixture was extracted with ethyl acetate, washed with water, saturated aqueous sodium hydrogen carbonate solution and saturated brine, and dried over anhydrous magnesium sulfate. The solvent was evaporated under reduced pressure. The residue was purified by silica gel chromatography to give the object product (220 mg) as a yellow oil.

$^1$H-NMR(CDCl$_3$) δ (ppm): 1.31(1H, t, J=5.0 Hz), 1.90-1.97(2H, m), 2.85(2H, t, J=7.8 Hz), 3.71(2H, q, J=6.1 Hz), 7.46(1H, t, J=7.8 Hz), 7.55(1H, d, J=7.5 Hz), 8.05-8.08(2H, m).

(95-2) Synthesis of 1-(3-bromopropyl)-3-nitrobenzene (Compound 95-2)

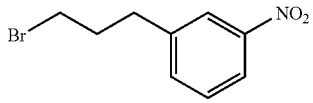

Compound 95-1 (220 mg) was dissolved in methylene chloride (10 ml), triphenylphosphine (350 mg) and N-bromosuccinimide (238 mg) were added under ice-cooling, and the mixture was stirred under ice-cooling for 1 hr, and at room temperature for 12 hr. The reaction mixture was washed with water and saturated brine, and dried over anhydrous magnesium sulfate. The solvent was evaporated under reduced pressure. Diethyl ether (30 ml) was added, and the precipitated triphenylphosphine oxide was filtered off. The concentrate of the filtrate was purified by silica gel column chromatography to give the object product (280 mg) as a colorless oil.

$^1$H-NMR(CDCl$_3$) δ (ppm): 2.18-2.25(2H, m), 2.92(2H, t, J=7.5 Hz), 3.41(2H, t, J=6.4 Hz), 7.45-7.50(1H, m), 7.55(1H, d, J=7.7 Hz), 8.08-8.10(2H, m).

(95-3) Synthesis of [2,2-dimethyl-5-(2-{4-[3-(3-nitrophenyl)propoxy]-3-trifluoromethylphenyl}ethyl)-1,3-dioxan-5-yl]carbamic acid t-butyl ester (Compound 95-3)

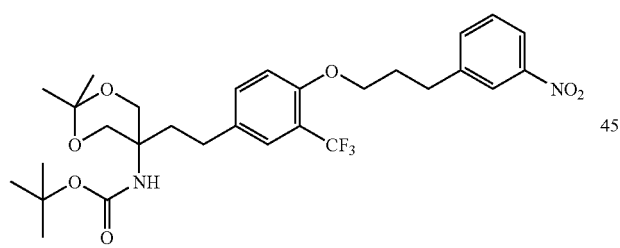

Reference Example compound 2-6 (437 mg) was dissolved in N,N-dimethylformamide (10 ml), potassium carbonate (431 mg) and compound 95-2 (280 mg) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (587 mg) as a white solid.

$^1$H-NMR(CDCl$_3$) δ (ppm): 1.43(3H. s), 1.44(3H, s), 1.48 (9H, s), 1.94-1.98(2H, m), 2.08-2.19(2H, m), 2.52-2.57(2H, m), 2.96(2H, t, J=7.5 Hz), 3.69(2H, d, J=11.7 Hz), 3.89(2H, d, J=11.7 Hz), 4.00(2H, t, J=5.9 Hz), 5.00(1H, brs), 6.84(1H, d, J=8.4 Hz), 7.26-7.28(1H, m), 7.38(1H, brd, J=1.5 Hz), 7.45 (1H, t, J=7.8 Hz), 7.54(1H, d, J=7.3 Hz), 8.05-8.08(2H, m).

(95-4) Synthesis of 2-amino-2-(2-{4-[3-(3-nitrophenyl)propoxy]-3-trifluoromethylphenyl}ethyl)propane-1,3-diol hydrochloride (Compound 95-4)

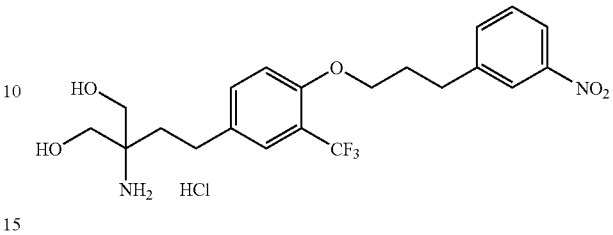

Compound 95-3 (587 mg) was dissolved in ethanol (15 ml), concentrated hydrochloric acid (1.5 ml) was added, and the mixture was stirred at 80° C. for 1 hr. The reaction mixture was concentrated, and the residue was washed with diethyl ether to give the object product (430 mg) as a white powder.

MS(ESI)m/z: 443[M+H]

$^1$H-NMR(DMSO-d$_6$) δ (ppm): 1.74-1.79(2H, m), 2.06-2.12(2H, m), 2.58-2.63(2H, m), 2.89(2H, t, J=7.5 Hz), 3.52 (4H, d, J=4.9 Hz), 4.07(2H, t, J=6.0 Hz), 5.40(2H, t, J=5.0 Hz), 7.18(1H, d, J=8.6 Hz), 7.44(1H, d, J=8.6 Hz), 7.48(1H, brd, J=1.8 Hz), 7.60(1H, t, J=8.3 Hz), 7.69(1H, d, J=7.6 Hz), 7.82(3H, brs), 8.06-8.08(2H, m).

Example 96

2-amino-2-(2-{4-[3-(4-methylthiophenyl)propoxy]-3-trifluoromethylphenyl}ethyl)propane-1,3-diol hydrochloride (96-1) Synthesis of 3-(4-methylthiophenyl)-1-propanol (Compound 96-1)

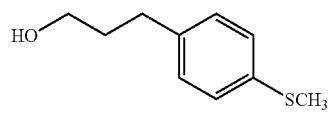

3-(4-Methylsulfanylphenyl)propionic acid (1.00 g) was dissolved in tetrahydrofuran (20 ml), and a tetrahydrofuran.borane.tetrahydrofuran solution (1 mol/l, 6.42 ml) was added dropwise to the mixture under ice-cooling. The mixture was stirred under ice-cooling for 30 min, and further at room temperature for 1 hr. Water was added to the reaction mixture, and 1 mol/l aqueous hydrochloric acid solution was added. The mixture was extracted with ethyl acetate, washed with water, saturated aqueous sodium hydrogen carbonate solution and saturated brine, and dried over anhydrous magnesium sulfate. The solvent was evaporated under reduced pressure. The residue was purified by silica gel chromatography to give the object product (940 mg) as a colorless oil.

$^1$H-NMR(CDCl$_3$) δ (ppm): 1.28(1H, brs), 1.85-1.89(2H, m), 2.47(3H, s), 2.68(2H, t, J=7.7 Hz), 3.67(2H, brt, J=6.0 Hz), 7.13(2H, d, J=8.2 Hz), 7.19-7.22(2H, m).

(96-2) Synthesis of 1-(3-bromopropyl)-4-methylthiobenzene (Compound 96-2)

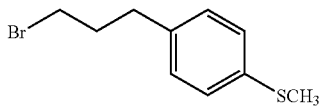

Compound 96-1 (940 mg) was dissolved in methylene chloride (20 ml), triphenylphosphine (1.43 g) and N-bromosuccinimide (966 mg) were added under ice-cooling, and the mixture was stirred under ice-cooling for 1 hr, and at room temperature for 18 hr. The reaction mixture was washed with water and saturated brine, and dried over anhydrous magnesium sulfate. The solvent was evaporated under reduced pressure. Diethyl ether (50 ml) was added, and the precipitated triphenylphosphine oxide was filtered off. The concentrate of the filtrate was purified by silica gel column chromatography to give the object product (1.13 g) as a colorless oil.

$^1$H-NMR(CDCl$_3$) δ (ppm): 2.10-2.18(2H, m), 2.47(3H, s), 2.74(2H, t, J=7.3 Hz), 3.38(2H, t, J=6.6 Hz), 7.13(2H, d, J=8.2 Hz), 7.19-7.22(2H, m).

(96-3) Synthesis of [2,2-dimethyl-5-(2-{4-[3-(4-methylthiophenyl)propoxy]-3-trifluoromethylphenyl}ethyl)-1,3-dioxan-5-yl]carbamic acid t-butyl ester (Compound 96-3)

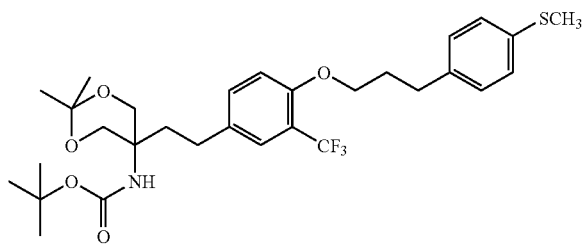

Reference Example compound 2-6 (500 mg) was dissolved in N,N-dimethylformamide (10 ml), potassium carbonate (494 mg) and compound 96-2 (351 mg) were added, and the mixture was stirred at 80° C. for 3 hr. Water was added to the reaction mixture, and the mixture was extracted with ethyl acetate, washed with water and saturated brine, and dried over anhydrous magnesium sulfate. The solvent was evaporated under reduced pressure to give the object product (740 mg) as a white solid.

$^1$H-NMR(CDCl$_3$) δ (ppm): 1.43(3H, s), 1.44(3H, s), 1.47 (9H, s), 1.93-1.98(2H, m), 2.04-2.12(2H, m), 2.52(3H, s), 2.53-2.56(2H, m), 2.79(2H, t, J=7.5 Hz), 3.69(2H, d, J=11.7 Hz), 3.89(2H, d, J=11.7 Hz), 3.97(2H, t, J=6.0 Hz), 4.99(1H, brs), 6.83(1H, d, J=8.5 Hz), 7.12(2H, d, J=8.3 Hz), 7.18-7.22 (2H, m), 7.25-7.26(1H, m), 7.36(1H, s).

(96-4) Synthesis of 2-amino-2-(2-{4-[3-(4-methylthiophenyl)propoxy]-3-trifluoromethylphenyl}ethyl)propane-1,3-diol hydrochloride (Compound 96-4)

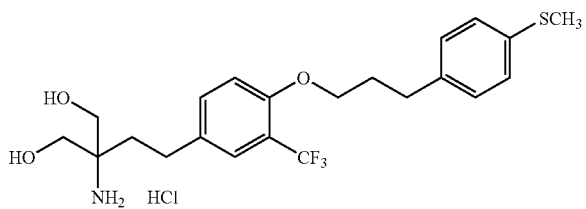

Compound 96-3 (587 mg) was dissolved in ethanol (15 ml), concentrated hydrochloric acid (1.5 ml) was added, and the mixture was stirred at 80° C. for 1 hr. The reaction mixture was concentrated, and the residue was washed with diethyl ether to give the object product (490 mg) as a white powder.

MS(ESI)m/z: 444[M+H]

$^1$H-NMR(DMSO-d$_6$) δ (ppm): 1.74-1.79(2H, m), 1.97-2.02(2H, m), 2.44(3H, s), 2.58-2.63(2H, m), 2.71(2H, t, J=7.4 Hz), 3.52(4H, d, J=4.6 Hz), 4.03(2H, t, J=6.0 Hz), 5.40(2H, t, J=4.9 Hz), 7.13-7.20(5H, m), 7.44(1H, d, J=8.5 Hz), 7.48(1H, brs), 7.82(3H, brs).

Example 97

2-amino-2-(2-{4-[3-(4-methanesulfinylphenyl)propoxy]-3-trifluoromethylphenyl}ethyl)propane-1,3-diol hydrochloride

(97-1) Synthesis of 2-amino-2-(2-{4-[3-(4-methanesulfinylphenyl)propoxy]-3-trifluoromethylphenyl}ethyl)propane-1,3-diol hydrochloride (Compound 97-1)

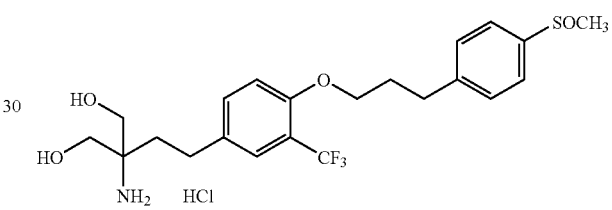

Compound 96-3 (720 mg) was dissolved in methylene chloride (20 ml), m-chloroperbenzoic acid (containing 25% water, 293 mg) was added under ice-cooling, and the mixture was stirred at room temperature for 20 hr. m-Chloroperbenzoic acid (containing 25% water, 234 mg) was further added to the reaction mixture under ice-cooling, and the mixture was stirred at room temperature for 2 hr. Saturated aqueous sodium hydrogen carbonate solution was added to the reaction mixture, and the mixture was extracted with chloroform, washed with water, saturated aqueous sodium hydrogen carbonate solution and saturated brine, and dried over anhydrous magnesium sulfate. The solvent was evaporated under reduced pressure. The obtained residue was dissolved in ethanol (15 ml), concentrated hydrochloric acid (1.5 ml) was added, and the mixture was stirred at 80° C. for 1 hr. The reaction mixture was concentrated, and the residue was washed with diethyl ether to give a white powder. The white powder was separated by HPLC using capcellpac (registered trade mark) UG80 (0.05% trifluoroacetic acid-water/0.05% trifluoroacetic acid-acetonitrile), and the residue obtained by collecting a peak with a shorter retention time (primary peak) was converted to hydrochloride by the addition of hydrogen chloride containing ether (1 mol/l, 10 ml), and the precipitate was collected by filtration and dried to give the object product (75 mg) as a white powder.

MS (ESI)m/z: 460[M+H]

$^1$H-NMR(DMSO-d$_6$) δ (ppm): 1.74-1.79(2H, m), 2.02-2.10(2H, m), 2.59-2.64(2H, m), 2.72(3H, s), 2.82(2H, t, J=7.5 Hz), 3.52(4H, d, J=5.2 Hz), 4.07(2H, t, J=6.0 Hz), 5.41(2H, t, J=5.2 Hz), 7.13-7.20(1H, m), 7.40-7.48(4H, m), 7.61(2H, d, J=8.0 Hz), 7.86(3H, brs).

Example 98

2-amino-2-(2-{4-[3-(4-methanesulfonylphenyl)propoxy]-3-trifluoromethylphenyl}ethyl)propane-1,3-diol hydrochloride (98-1) Synthesis of 2-amino-2-(2-{4-[3-(4-methanesulfonylphenyl)propoxy]-3-trifluoromethylphenyl}ethyl)propane-1,3-diol hydrochloride (Compound 98-1)

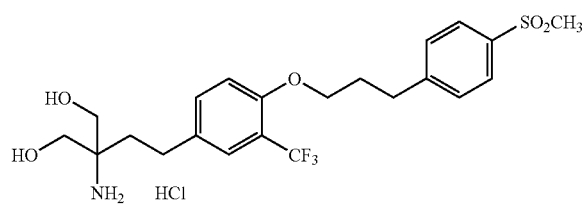

In the purification by HPLC in Example (97-1), the residue obtained by collecting a peak with a longer retention time (secondary peak) was converted to hydrochloride by the addition of hydrogen chloride containing ether (1 mol/l, 10 ml), and the precipitate was collected by filtration and dried to give the object product (95 mg) as a pale-yellow powder.

MS(ESI)m/z: 476[M+H]
$^1$H-NMR(DMSO-$d_6$) δ (ppm): 1.74-1.79(2H, m), 2.03-2.10(2H, m), 2.59-2.64(2H, m), 2.86(2H, t, J=7.5 Hz), 3.19 (3H, s), 3.52(4H, d, J=5.0 Hz), 4.07(2H, t, J=6.0 Hz), 5.41 (2H, t, J=5.0 Hz), 7.18(1H, d, J=8.5 Hz), 7.43-7.50(4H, m), 7.85(2H, d, J=8.3 Hz), 7.87(3H, brs).

Example 99

2-amino-2-(2-{4-[3-(piperidin-1-yl)propoxy]-3-trifluoromethylphenyl}ethyl)propane-1,3-diol dihydrochloride (99-1) Synthesis of 2-amino-2-(2-{4-[3-(piperidin-1-yl)propoxy]-3-trifluoromethylphenyl}ethyl)propane-1,3-diol dihydrochloride (Compound 99-1)

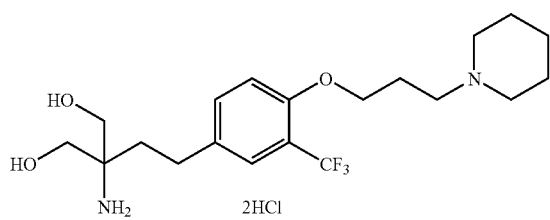

Triphenylphosphine (750 mg) was dissolved in tetrahydrofuran (30 ml), diisopropyl azodicarboxylate (40% toluene solution, 1.51 ml), 1-piperidinepropanol (0.447 ml) and Reference Example compound 2-6 (600 mg) were added, and the mixture was stirred at room temperature for 4 hr. Water was added to the reaction mixture, and the mixture was extracted with ethyl acetate, washed with saturated brine, and dried over anhydrous magnesium sulfate. The solvent was evaporated under reduced pressure. The obtained residue was dissolved in ethanol (15 ml), concentrated hydrochloric acid (1.5 ml) was added, and the mixture was stirred at 80° C. for 1 hr. The reaction mixture was concentrated and the obtained oil was purified by HPLC, the obtained residue was converted to hydrochloride by adding hydrogen chloride containing ether (1 mol/l, 15 ml), and the precipitate was collected by filtration and dried to give the object product (580 mg) as a white powder.

MS(ESI)m/z: 405[M+H]
$^1$H-NMR(DMSO-$d_6$) δ (ppm): 1.32-1.48(1H, m), 1.74-1.82(7H, m), 2.17-2.24(2H, m), 2.60-2.65(2H, m), 2.82-2.92 (2H, m), 3.08-3.14(2H, m), 3.35-3.42(2H, m), 3.52(4H, s), 4.17(2H, t, J=6.0 Hz), 5.42(2H, brs), 7.22(1H, d, J=9.1 Hz), 7.47-7.49(2H, m), 7.91(3H, brs), 10.5(1H, brs).

Example 100

(E)-2-amino-2-{2-[4-(3-phenylpropoxy)-3-trifluoromethylphenyl]vinyl}propane-1,3-diol hydrochloride (100-1) Synthesis of (E)-(2,2-dimethyl-5-{2-[4-(3-phenylpropoxy)-3-trifluoromethylphenyl]vinyl}-1,3-dioxan-5-yl)carbamic acid t-butyl ester (Compound 100-1)

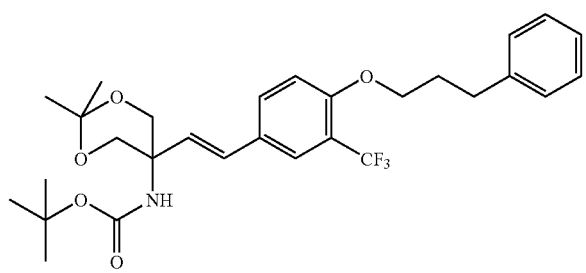

Compound 93-8 (400 mg) was dissolved in N,N-dimethylformamide (10 ml), potassium carbonate (397 mg) and 3-phenylpropylbromide (0.175 ml) were added, and the mixture was stirred at 50° C. for 2 hr, and at 70° C. for 1 hr. Water was added to the reaction mixture, and the mixture was extracted with ethyl acetate, washed with water and saturated brine, and dried over anhydrous magnesium sulfate. The solvent was evaporated under reduced pressure to give the object product (560 mg) as a colorless oil.

$^1$H-NMR(CDCl$_3$) δ (ppm): 1.45(9H, s), 1.47(3H, s), 1.49 (3H, s), 2.09-2.15(2H, m), 2.83(2H, t, J=7.5 Hz), 3.90(2H, d, J=11.4 Hz), 3.96-4.03(4H, m), 5.22(1H, brs), 6.11(1H, d, J=16.4 Hz), 6.48(1H, d, J=16.4 Hz), 6.86(1H, d, J=8.6 Hz), 7.17-7.21(3H, m), 7.27-7.30(2H, m), 7.43(1H, dd, J=8.6, 1.6 Hz), 7.57(1H, d, J=1.6 Hz).

(100-2) Synthesis of (E)-2-amino-2-{2-[4-(3-phenylpropoxy)-3-trifluoromethylphenyl]vinyl}propane-1,3-diol hydrochloride (Compound 100-2)

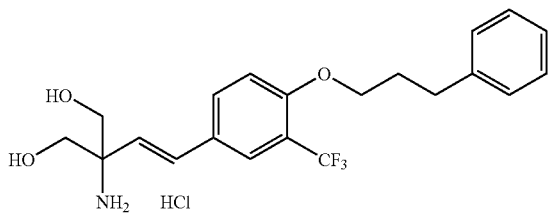

Compound 100-1 (560 mg) was dissolved in ethanol (15 ml), concentrated hydrochloric acid (1.5 ml) was added, and the mixture was stirred at 80° C. for 1 hr. The reaction mixture was concentrated, and the residue was washed with diethyl ether to give the object product (380 mg) as a white powder.

MS(ESI)m/z: 379

$^1$H-NMR(DMSO-$d_6$) δ (ppm): 2.00-2.06(2H, m), 2.75(2H, t, J=7.5 Hz), 3.57-3.67(4H, m), 4.09(2H, t, J=6.1 Hz), 5.47(2H, t, J=5.4 Hz), 6.24(1H, d, J=16.8 Hz), 6.69(1H, d, J=16.8 Hz), 7.16-7.25(4H, m), 7.26-7.31(2H, m), 7.63(1H, dd, J=8.7, 1.5 Hz), 7.66(1H, brs), 8.06(3H, brs).

Example 101

(E)-2-amino-2-(2-{4-[3-(2-fluorophenyl)propoxy]-3-trifluoromethylphenyl}vinyl)propane-1,3-diol hydrochloride (101-1) Synthesis of (E)-[5-(2-{4-[3-(2-fluorophenyl)propoxy]-3-trifluoromethylphenyl}vinyl)-2,2-dimethyl-1,3-dioxan-5-yl]carbamic acid t-butyl ester (Compound 101-1)

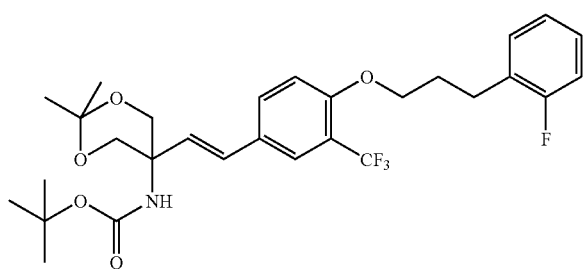

Compound 93-8 (400 mg) was dissolved in N,N-dimethylformamide (10 ml), potassium carbonate (397 mg) and compound 22-2 (397 mg) were added, and the mixture was stirred at 70° C. for 1 hr. Water was added to the reaction mixture, and the mixture was extracted with ethyl acetate, washed with water and saturated brine, and dried over anhydrous magnesium sulfate. The solvent was evaporated under reduced pressure to give the object product (600 mg) as a yellow oil.

$^1$H-NMR(CDCl$_3$) δ (ppm): 1.45(9H, s), 1.47(3H, s), 1.49 (3H, s), 2.09-2.14(2H, m), 2.87(2H, t, J=7.4 Hz), 3.90(2H, d, J=11.4 Hz), 3.96-4.04(4H, m), 5.21(1H, brs), 6.11(1H, d, J=16.4 Hz), 6.49(1H, d, J=16.4 Hz), 6.87(1H, d, J=8.6 Hz), 6.98-6.07(2H, m), 7.15-7.22(2H, m), 7.44(1H, dd, J=8.6, 1.9 Hz), 7.57(1H, brd, J=1.9 Hz).

(101-2) Synthesis of (E)-2-amino-2-(2-{4-[3-(2-fluorophenyl)propoxy]-3-trifluoromethylphenyl}vinyl)propane-1,3-diol hydrochloride (Compound 101-2)

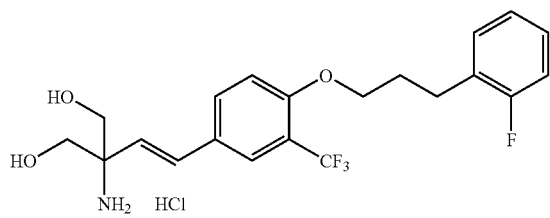

Compound 101-1 (600 mg) was dissolved in ethanol (15 ml), concentrated hydrochloric acid (1.5 ml) was added, and the mixture was stirred at 80° C. for 1 hr. The reaction mixture was concentrated, and the residue was washed with diethyl ether to give the object product (370 mg) as a white powder.

MS(ESI)m/z: 397

$^1$H-NMR(DMSO-$d_6$) δ (ppm): 1.99-2.05(2H, m), 2.80(2H, t, J=7.5 Hz), 3.58-3.67(4H, m), 4.13(2H, t, J=5.9 Hz), 5.47(2H, t, J=5.2 Hz), 6.24(1H, d, J=16.7 Hz), 6.70(1H, d, J=16.7 Hz), 7.11-7.17(2H, m), 7.24-7.29(3H, m), 7.62-7.66(2H, m), 8.05(3H, brs).

Example 102

2-amino-2-(2-{4-[3-(4-methylphenyl)allyloxy]-3-trifluoromethylphenyl}ethyl)propane-1,3-diol hydrochloride (102-1) Synthesis of 3-(4-methylphenyl)-2-propene-1-ol (Compound 102-1)

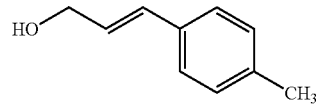

3-(4-Methylphenyl)acrylic acid (5.0 g) was dissolved in methanol (30 ml), concentrated sulfuric acid (0.5 ml) was added, and the mixture was stirred at 100° C. for 2.5 hr. The reaction mixture was concentrated, and the residue was washed with water. The obtained white solid was dissolved in tetrahydrofuran (120 ml), 1M diisobutylaluminum hydride/toluene solution (67 ml) was added dropwise at −78° C., and the mixture was stirred as it was at −78° C. for 2 hr. Saturated aqueous ammonium chloride solution was added to the reaction mixture, and the mixture was stirred at room temperature. Aluminum salt was collected by filtration through celite, extracted with methylene chloride, washed with saturated brine, and dried over anhydrous sodium sulfate. The solvent was evaporated under reduced pressure. The residue was purified by silica gel column chromatography (hexane:ethyl acetate) to give the object product (3.84 g) as a white powder.

$^1$H-NMR(DMSO-$d_6$) δ (ppm): 2.28(3H, s), 4.10(2H, td, J=5.5, 1.2 Hz), 4.84(1H, t, J=5.5 Hz), 6.30(1H, dt, J=15.9, 5.2 Hz), 6.50(1H, d, J=16.1 Hz), 7.13(2H, d, J=7.9 Hz), 7.30(2H, d, J=8.1 Hz).

(102-2) Synthesis of 1-(3-chloro-1-propenyl)-4-methylbenzene (Compound 102-2)

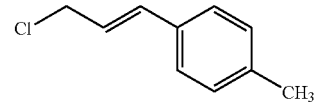

Compound 102-1 (2.50 g) was dissolved in methylene chloride (60 ml), triphenylphosphine (4.86 g) and N-chlorosuccinimide (2.84 g) were added under ice-cooling, and the mixture was stirred under ice-cooling for 1 hr. Triphenylphosphine (4.86 g) and N-chlorosuccinimide (2.84 g) were further added, and the mixture was stirred for 1 hr. Water was added to the reaction mixture, and the mixture was extracted with methylene chloride and washed with saturated brine, and dried over anhydrous sodium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane:ethyl acetate) to give the object product (1.20 g) as a colorless oil.

$^1$H-NMR(DMSO-$d_6$) δ (ppm): 2.29(3H, s), 4.38(2H, d, J=7.0 Hz), 6.38(1H, dt, J=15.6, 7.2 Hz), 6.71(1H, d, J=15.6 Hz), 7.16(2H, d, J=7.9 Hz), 7.37(2H, d, J=8.0 Hz).

(102-3) Synthesis of [2,2-dimethyl-5-(2-{4-[3-(4-methylphenyl)allyloxy]-3-trifluoromethylphenyl}ethyl)-1,3-dioxan-5-yl]carbamic acid t-butyl ester (Compound 102-3)

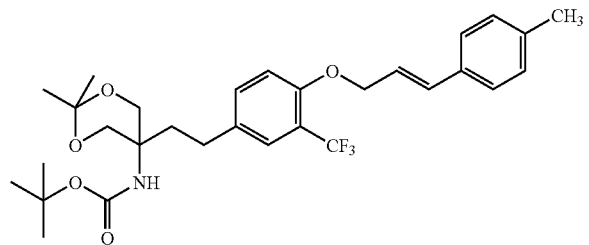

Reference Example compound 2-6 (500 mg) was dissolved in N,N-dimethylformamide (10 ml), potassium carbonate (494 mg) and compound 102-2 (400 mg) were added, and the mixture was stirred at room temperature for one day. Water was added to the reaction mixture, and the mixture was extracted with ethyl acetate, washed with water and saturated brine, and dried over anhydrous sodium sulfate. The solvent was evaporated under reduced pressure to give the object product (565 mg) as a white solid.

$^1$H-NMR(DMSO-$d_6$) δ (ppm): 1.31(3H, s), 1.33(3H, s), 1.40(9H, s), 1.91-1.95(2H, m), 2.29(3H,$), 2.45-2.48(2H, m), 3.66(2H, d, J=11.7 Hz), 3.87(2H, d, J=11.4 Hz), 4.82(2H, d, J=5.5 Hz), 6.40(1H, dt, J=16.1, 5.6 Hz), 6.65(1H, brs), 6.73(1H, d, J=16.1 Hz), 7.16(2H, d, J=8.0 Hz), 7.24(1H, d, J=9.1 Hz), 7.36(2H, d, J=8.1 Hz), 7.39-7.40(2H, m).

(102-4) Synthesis of 2-amino-2-(2-{4-[3-(4-methylphenyl)allyloxy]-3-trifluoromethylphenyl}ethyl)propane-1,3-diol hydrochloride (Compound 102-4)

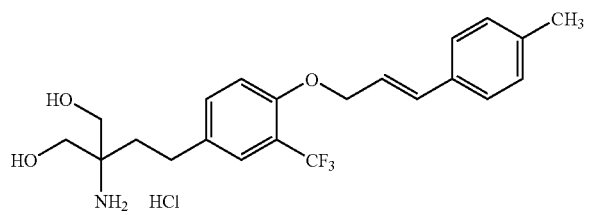

Compound 102-3 (550 mg) was dissolved in ethanol (18 ml), concentrated hydrochloric acid (3.5 ml) was added, and the mixture was stirred at 50° C. for 4 hr. The reaction mixture was concentrated, and the residue was washed with diethyl ether and methanol to give the object product (180 mg) as a white powder.

MS(ESI)m/z: 410[M+H]

$^1$H-NMR (DMSO-$d_6$) δ (ppm): 1.74-1.78(2H, m), 2.29 (3H, s), 2.59-2.63(2H, m), 3.52(4H, d, J=5.0 Hz), 4.83(2H, d, J=5.7 Hz), 5.39(2H, t, J=5.0 Hz), 6.40(1H, dt, J=15.9, 5.7 Hz), 6.73(1H, d, J=15.9 Hz), 7.16(2H, d, J=8.0 Hz), 7.27(1H, d, J=8.4 Hz), 7.36(2H, d, J=8.0 Hz), 7.46(1H, d, J=8.8 Hz), 7.48(1H, s), 7.82(3H, brs).

Example 103

2-amino-2-(2-{4-[3-(3-methylphenyl)allyloxy]-3-trifluoromethylphenyl}ethyl)propane-1,3-diol hydrochloride (103-1) Synthesis of 3-(3-methylphenyl)-2-propene-1-ol (Compound 103-1)

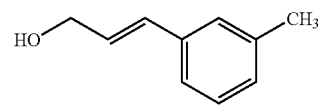

3-(3-Methylphenyl)acrylic acid (3.0 g) was dissolved in methanol (30 ml), concentrated sulfuric acid (0.5 ml) was added, and the mixture was stirred at 100° C. for 2.5 hr. The reaction mixture was concentrated, and the residue was washed with water. The obtained colorless oil was dissolved in tetrahydrofuran (60 ml), 1M diisobutylaluminum hydride/toluene solution (38 ml) was added dropwise at −78° C., and the mixture was stirred as it was at −78° C. for 2 hr. Saturated Rochelle salt water, water and ethyl acetate were added to the reaction mixture, and the mixture was stirred at room temperature. The mixture was extracted with ethyl acetate, washed with saturated brine, and dried over anhydrous sodium sulfate. The solvent was evaporated under reduced pressure. The residue was purified by silica gel column chromatography (hexane:ethyl acetate) to give the object product (2.45 g) as a colorless oil.

$^1$H-NMR(DMSO-$d_6$) δ (ppm): 2.19(3H, s), 4.12(2H, t, J=5.4 Hz), 4.89(1H, t, J=5.5 Hz), 6.35(1H, dt, J=15.8, 5.2 Hz), 6.51(1H, d, J=15.8 Hz), 7.03(1H, t, J=4.1 Hz), 7.20-7.22 (3H, m).

(103-2) Synthesis of 1-(3-chloro-1-propenyl)-3-methylbenzene (Compound 103-2)

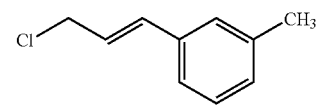

Compound 103-1 (2.00 g) was dissolved in methylene chloride (45 ml), triphenylphosphine (3.89 g) and N-chlorosuccinimide (1.98 g) were added under ice-cooling, and the mixture was stirred under ice-cooling for 2 hr. Water was added to the reaction mixture, and the mixture was extracted with methylene chloride and washed with saturated brine, and dried over anhydrous sodium sulfate. The solvent was evaporated under reduced pressure. Diethyl ether (100 ml) was added, and the precipitated triphenylphosphine oxide was filtered off. The concentrate of the filtrate was purified by silica gel column chromatography (hexane:ethyl acetate=100:0-95:5) to give the object product (1.30 g) as a colorless oil.

¹H-NMR(DMSO-d₆) δ (ppm): 2.30(3H, s), 4.39(2H, d, J=7.6 Hz), 6.42(1H, dt, J=15.6, 7.4 Hz), 6.71(1H, d, J=15.8 Hz), 7.10(1H, d, J=6.9 Hz), 7.22-7.30(3H, m).

(103-3) Synthesis of [2,2-dimethyl-5-(2-{4-[3-(3-methylphenyl)allyloxy]-3-trifluoromethylphenyl}ethyl)-1,3-dioxan-5-yl]carbamic acid t-butyl ester (Compound 103-3)

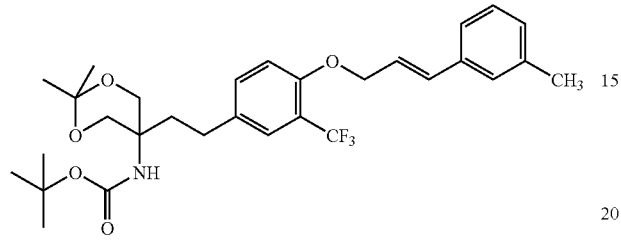

Reference Example compound 2-6 (500 mg) was dissolved in N,N-dimethylformamide (10 ml), potassium carbonate (495 mg) and compound 103-2 (400 mg) were added, and the mixture was stirred at room temperature for 4 hr. Water was added to the reaction mixture, and the mixture was extracted with ethyl acetate, washed with water and saturated brine, and dried over anhydrous sodium sulfate, and the solvent was evaporated under reduced pressure to give the object product (415 mg) as a white solid.

¹H-NMR(DMSO-d₆) δ (ppm): 1.31(3H, s), 1.33(3H, s), 1.40(9H, s), 1.91-1.95(2H, m), 2.30(3H, s), 2.45-2.48(2H, m), 3.66(2H, d, J=11.7 Hz), 3.88(2H, d, J=11.5 Hz), 4.83(2H, d, J=5.1 Hz), 6.44(1H, dt, J=15.9 Hz), 6.65(1H, brs), 6.73(1H, d, 16.0 Hz), 7.09(1H, d, J=6.6 Hz), 7.20-7.28(4H, m), 7.39-7.40(2H, m).

(103-4) Synthesis of 2-amino-2-(2-{4-[3-(3-methylphenyl)allyloxy]-3-trifluoromethylphenyl}ethyl)propane-1,3-diol hydrochloride (Compound 103-4)

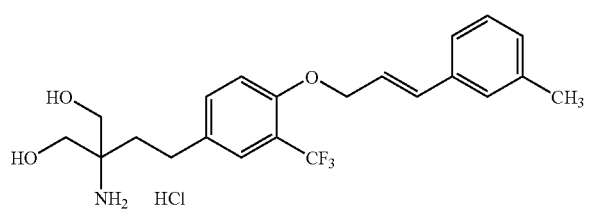

Compound 103-3 (410 mg) was dissolved in ethanol (25 ml), concentrated hydrochloric acid (3.0 ml) was added, and the mixture was stirred at 50° C. for 4 hr. The reaction mixture was concentrated, and the residue was washed with diethyl ether to give the object product (135 mg) as a white powder.

MS(ESI)m/z: 410[M+H]

¹H-NMR(DMSO-d₆) δ (ppm): 1.74-1.79(2H, m), 2.30(3H, s), 2.59-2.63(2H, m), 3.52(4H, d, J=5.0 Hz), 4.84 (2H, d, J=5.4 Hz), 5.40(2H, t, J=5.2 Hz), 6.45(1H, dt, J=16.0, 5.5 Hz), 6.74(1H, d, J=16.0 Hz), 7.09(1H, d, J=6.4 Hz), 7.21-7.28(4H, d, J=8.5 Hz), 7.47(1H, d, J=8.7 Hz), 7.49(1H, s), 7.82(3H, brs).

Example 104

2-amino-2-methyl-4-{4-[3-(3-methylphenyl)propoxy]-3trifluoromethylphenyl}butanol hydrochloride (104-1) Synthesis of (1-(methoxymethoxy)methyl-1-methyl-3-{4-[3-(3-methylphenyl)propoxy]-3-trifluoromethylphenyl}propyl)carbamic acid t-butyl ester (Compound 104-1)

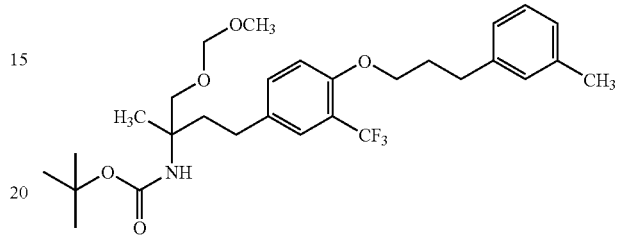

To a solution of compound 27-4 (400 mg) in N,N-dimethylformamide (1 ml) were added potassium carbonate (406 mg) and compound 15-2 (251 mg), and the mixture was stirred at 70° C. for 1 hr. The reaction mixture was added to water, and the mixture was extracted with ethyl acetate. The organic layer was washed with saturated brine and dried over anhydrous magnesium sulfate. The solvent was evaporated under reduced pressure to give the object product (580 mg) as a pale-yellow oil.

¹H-NMR(CDCl₃) δ (ppm): 1.34(3H, s), 1.45(9H, s), 1.88-1.99(1H, m), 2.00-2.20(3H, m), 2.32(3H, s), 2.57(2H, t, J=8.5 Hz), 2.79(2H, t, J=7.5 Hz), 3.38(3H, s), 3.48(1H, d, J=9.5 Hz), 3.65(1H, d, J=9.5 Hz), 3.99(2H, t, J=6.0 Hz), 4.65(2H, s), 4.72(1H, brs), 6.83(1H, d, J=8.5 Hz), 6.99-7.02(3H, m), 7.17(1H, t, J=7.4 Hz), 7.25-7.27(1H, m), 7.37(1H, d, J=1.9 Hz).

(104-2) Synthesis of 2-amino-2-methyl-4-{4-[3-(3-methylphenyl)propoxy]-3-trifluoromethylphenyl}butanol hydrochloride (Compound 104-2)

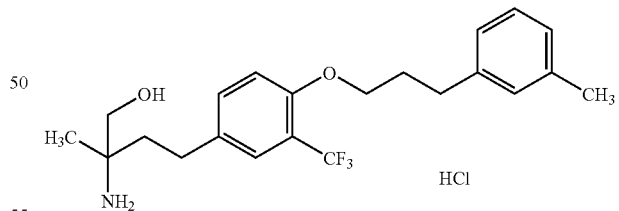

To a solution of compound 104-1 (580 mg) in ethanol (15 ml) was added concentrated hydrochloric acid (1.5 ml), and the mixture was stirred at 80° C. for 1.5 hr. The reaction mixture was concentrated, and the residue was washed with diisopropyl ether to give the object product (370 mg) as a pale-red powder.

MS(ESI)m/z: 396[M+H]

¹H-NMR(DMSO-d₆) δ (ppm): 1.21(311, s), 1.70-1.85(2H, m), 1.96-2.04(2H, m), 2.26(3H, s), 2.62(2H, t, J=8.7 Hz), 2.70(2H, t, J=7.6 Hz), 3.41(1H, dd, J=4.8, 11.2 Hz), 3.47(1H, dd, J=4.8, 11.2 Hz), 4.04(2H, t, J=6.0 Hz), 5.51(1H, brt, J=4.7

Hz), 6.96-7.01(3H, m), 7.14-7.18(2H, m), 7.45(1H, d, J=8.5 Hz), 7.48(1H, brs), 7.90(3H, brs).

Example 105

2-amino-2-ethyl-4-{4-[3-(3-methylphenyl)propoxy]-3-trifluoromethylphenyl}butanol hydrochloride (105-1) Synthesis of [1-ethyl-1-(methoxymethoxy)methyl-3-{4-[3-(3-methylphenyl)propoxy]-3-trifluoromethylphenyl}propyl]carbamic acid t-butyl ester (Compound 105-1)

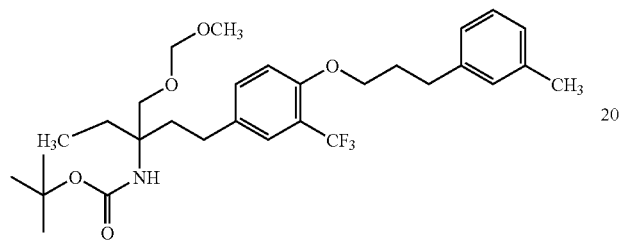

To a solution of compound 30-4 (400 mg) in N,N-dimethylformamide (10 ml), potassium carbonate (394 mg) and compound 15-2 (243 mg) were added, and the mixture was stirred at 70° C. for 1 hr. The reaction mixture was added to water, and the mixture was extracted with ethyl acetate. The organic layer was washed with saturated brine and dried over anhydrous magnesium sulfate. The solvent was evaporated under reduced pressure to give the object product (570 mg) as a colorless oil.

$^1$H-NMR(CDCl$_3$) δ (ppm): 0.89(3H, t, J=7.4 Hz), 1.45(9H, s), 1.68-1.82(2H, m), 1.92-1.99(2H, m), 2.06-2.16(2H, m), 2.32(3H, s), 2.52-2.57(2H, m), 2.79(2H, t, J=7.5 Hz), 3.38 (3H, s), 3.57(1H, d, J=9.7 Hz), 3.63(1H, d, J=9.7 Hz), 3.99 (2H, t, J=6.1 Hz), 4.61(1H, brs), 4.64(2H, s), 6.84(1H, d, J=8.5 Hz), 6.99-7.01(3H, m), 7.17(1H, t, J=7.4 Hz), 7.25-7.16(1H, m), 7.37(1H, d, J=1.5 Hz).

(105-2) Synthesis of 2-amino-2-ethyl-4-{4-[3-(3-methylphenyl)propoxy]-3-trifluoromethylphenyl}butanol hydrochloride (Compound 105-2)

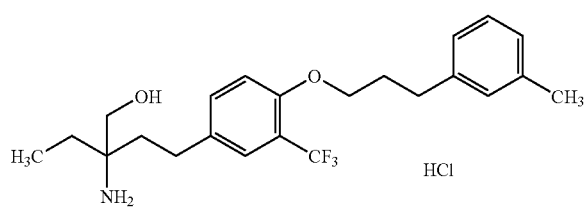

To a solution of compound 105-1 (570 mg) in ethanol (15 ml), concentrated hydrochloric acid (1.5 ml) was added, and the mixture was stirred at 80° C. for 1 hr. The reaction mixture was concentrated, and the residue was washed with diethyl ether to give the object product (400 mg) as a white powder.

MS(ESI)m/z: 410[M+H]

$^1$H-NMR (DMSO-d$_6$) δ (ppm): 0.89(3H, t, J=7.5 Hz), 1.58-1.69(2H, m), 1.70-1.79(2H, m), 1.98-2.02(2H, m), 2.26 (3H, s), 2.56-2.61(2H, m), 2.70(2H, t, J=7.6 Hz), 3.46(2H, brs), 4.04(2H, t, J=6.0 Hz), 5.46(1H, brs), 6.96-7.01(3H, m), 7.14-7.18(2H, m), 7.45(1H, J=8.6 Hz), 7.48(1H, brs), 7.75 (3H, brs).

Example 106

2-amino-2-(2-{4-[3-(3-methylphenyl)propoxy]-3-trifluoromethylphenyl}ethyl)butane-1,4-diol hydrochloride (106-1) Synthesis of 2-[(t-butyloxycarbonyl)amino]-2-[2-(tetrahydro-2H-pyran-2-yloxy)ethyl]malonic acid diethyl (Compound 106-1)

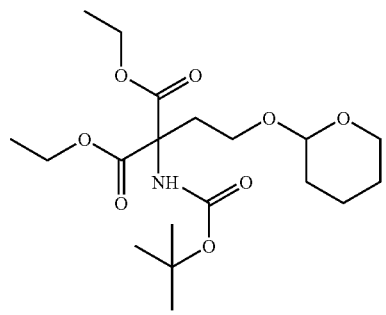

Diethyl(t-butyloxycarbonyl)aminomalonate (52.3 g) was dissolved in tetrahydrofuran (400 ml), and sodium t-butoxide (19.2 g) was added. A solution of 2-(2-bromoethoxy)tetrahydro-2H-pyran (40.4 g) in tetrahydrofuran (100 ml) was added to the reaction mixture at 70° C., and the mixture was heated with stirring for 10 hr. The reaction mixture was cooled, and poured into saturated brine. After partitioning by extraction by ethyl acetate, the organic layer was washed with saturated brine and dried over anhydrous magnesium sulfate. The solvent was evaporated under reduced pressure, and the obtained residue was purified by silica gel column chromatography to give the object product (50.0 g) as a colorless oil.

$^1$H-NMR(CDCl$_3$) δ (ppm): 1.30(6H, t, J=7.1 Hz), 1.45(9H, s), 1.45-1.55(4H, m), 1.58-1.78(2H, m), 2.60-2.64(2H, m), 3.35-3.41(1H, m), 3.46-3.50(1H, m), 3.77-3.84(2H, m), 4.12-4.28(4H, m), 4.49-4.51(1H, m), 6.08(1H, brs).

(106-2) Synthesis of 1,1-bis(hydroxymethyl)-3-(tetrahydro-2H-pyran-2-yloxy)propylcarbamic acid t-butyl ester (Compound 106-2)

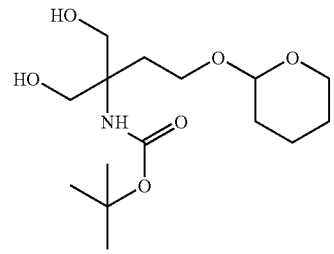

Compound 106-1 (50.0 g) was dissolved in a mixture of ethanol (530 ml), tetrahydrofuran (130 ml) and water (260 ml). Calcium chloride (27.5 g) was added thereto at 0° C., then sodium borohydride (18.8 g) was added by portions, and the mixture was stirred at the same temperature for 2 hr, and further at room temperature for 18 hr. The reaction mixture was concentrated under reduced pressure, added to saturated aqueous ammonium chloride solution (31), and partitioned by extraction by ethyl acetate. The organic layer was washed with saturated brine and dried over anhydrous magnesium sulfate. The solvent was evaporated under reduced pressure and the obtained residue was purified by silica gel chromatography to give the object product (21.6 g) as a colorless oil.

$^1$H-NMR(CDCl$_3$) δ (ppm): 1.43(9H, s), 1.53-1.62(4H, m), 1.71-1.83(2H, m), 1.95(1H, ddd, J=15.3, 8.0, 2.8 Hz), 2.02 (1H, ddd, J=15.3, 7.4, 2.8 Hz), 3.46-3.59(4H, m), 3.69-3.73 (2H, m), 3.82-3.88(1H, m), 3.91-3.96(1H, m), 4.13(2H, brs), 4.60-4.62(1H, m), 5.79(1H, brs).

(106-3) Synthesis of 1-hydroxymethyl-1-(methoxymethoxy)methyl-3-(tetrahydro-2H-pyran-2-yloxy)propylcarbamic acid t-butyl ester (Compound 106-3)

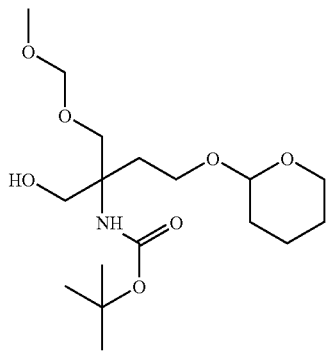

To a solution of compound 106-2 (21.6 g) in methylene chloride (250 ml) were added N,N-diisopropylethylamine (14.7 ml) and methoxymethyl chloride (6.37 ml) under ice-cooling, and the mixture was stirred under ice-cooling for 1.5 hr, and further at room temperature for 17 hr. Water was added to the reaction mixture, and the mixture was extracted with methylene chloride. The organic layer was washed with saturated brine and dried over anhydrous magnesium sulfate. The solvent was evaporated under reduced pressure. The obtained residue was purified by silica gel chromatography to give the object product (9.61 g) as a colorless oil.

$^1$H-NMR(CDCl$_3$) δ (ppm): 1.42(9H, s), 1.51-1.63(4H, m), 1.68-1.93(3H, m), 2.03-2.10(1H, m), 3.37(3H, s), 3.51-3.60 (3H, m), 3.69-4.00(5H, m), 4.26, 4.35(1H, 2×brs), 4.61-4.66 (3H, m), 5.61, 5.75(1H, 2×brs).

(106-4) Synthesis of 1-formyl-1-(methoxymethoxy)methyl-3-(tetrahydro-2H-pyran-2-yloxy)propylcarbamic acid t-butyl ester (Compound 106-4)

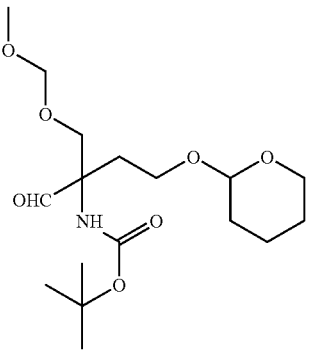

To a solution of compound 106-3 (9.59 g) and sodium bromide (2.72 g) in a mixture of toluene (50 ml), ethyl acetate (50 ml) and water (9 ml) was added 2,2,6,6-tetramethylpiperidine 1-oxyl, free radical (82.5 mg) under ice-cooling, and then 10% aqueous sodium hypochlorite solution (21.7 g) and a solution of sodium hydrogen carbonate (3.19 g) in water (75 ml) were added dropwise over 2 hr. The mixture was further stirred for 2 hr under ice-cooling, 10% aqueous sodium hypochlorite solution (10.9 g) and a solution of sodium hydrogen carbonate (3.19 g) in water (35 ml) were added dropwise over 20 min, and the mixture was further stirred for min. The organic layer was partitioned, and diluted with is ethyl acetate (200 ml). The organic layer was washed with saturated brine and dried over anhydrous magnesium sulfate. The solvent was evaporated under reduced pressure to give the object product (8.54 g) as a brown oil.

$^1$H-NMR(CDCl$_3$) δ (ppm): 1.44(9H, s), 1.45-1.78(6H, m), 2.10-2.18(1H, m), 2.35-2.46(1H, m), 3.31, 3.32(3H, 2×s), 3.33-3.41(1H, m), 3.47-3.51(1H, m), 3.67-3.74(1H, m), 3.77-3.84(2H, m), 4.05-4.13(1H, m), 4.43-4.45, 4.56-4.58(1H, 2×m), 4.58, 4.58(2H, 2×s), 5.72, 5.74(1H, 2×brs), 9.40, 9.44 (1H, 2×s).

(106-5) Synthesis of 3-(4-benzyloxy-3-trifluoromethylphenyl)-1-(methoxymethoxy)methyl-1-[2-(tetrahydro-2H-pyran-2-yloxy)ethyl]propylcarbamic acid t-butyl ester (Compound 106-5)

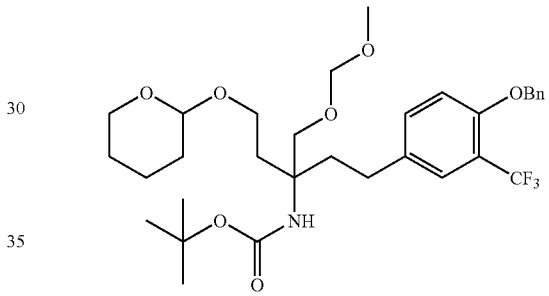

Reference Example compound 2-5 (10.9 g) was suspended in tetrahydrofuran (80 ml), potassium t-butoxide (2.17 g) was added under ice-cooling, and the mixture was stirred for 30 min. To the mixed solution was added a solution of compound 106-4 (3.50 g) in tetrahydrofuran (25 ml), and the mixture was stirred under ice-cooling for 20 min, and further at room temperature for 5 hr. The reaction mixture was added to brine, and the mixture was extracted with ethyl acetate. The organic layer was washed with saturated brine and dried over anhydrous magnesium sulfate. The solvent was evaporated under reduced pressure. The obtained residue was purified by silica gel column chromatography to give 3-(4-benzyloxy-3-trifluoromethylphenyl)-1-(methoxymethoxy)methyl-1-[2-(tetrahydro-2H-pyran-2-yloxy)ethyl]allylcarbamic acid t-butyl ester 4.95 g as a pale-yellow oil. The geometric isomer ratio of the obtained compound was (E:Z=1:3). To a solution of the oil in toluene (200 ml) was added chlorotris(triphenylphosphine)rhodium(I) (5.0 g), and the mixture was stirred under a hydrogen atmosphere at 60° C. for 19 hr. Chlorotris(triphenylphosphine)rhodium(I) (2.5 g) was added, and the mixture was stirred under a hydrogen atmosphere at 60° C. for 10 hr. The reaction mixture was filtered through celite and concentrated. The obtained residue was purified by silica gel column chromatography to give the object product (4.95 g) as a yellow oil.

$^1$H-NMR(CDCl$_3$) δ (ppm): 1.43(9H, s), 1.51-1.64(4H, m), 1.67-1.75(1H, m), 1.79-1.88(1H, m), 1.92-2.28(4H, m), 2.54-2.62(2H, m), 3.36, 3.37(3H, 2×s), 3.46-3.59(2H, m), 3.71-

3.78(2H, m), 3.82-4.03(2H, m), 4.60-4.64(3H, m), 5.15(2H, s), 5.41, 5.55(1H, 2×brs), 6.93(1H, d, J=8.5 Hz), 7.26-7.32 (2H, m), 7.36-7.44(5H, m).

(106-6) Synthesis of 3-(4-hydroxy-3-trifluoromethylphenyl)-1-(methoxymethoxy)methyl-1-[2-(tetrahydro-2H-pyran-2-yloxy)ethyl]propylcarbamic acid t-butyl ester (Compound 106-6)

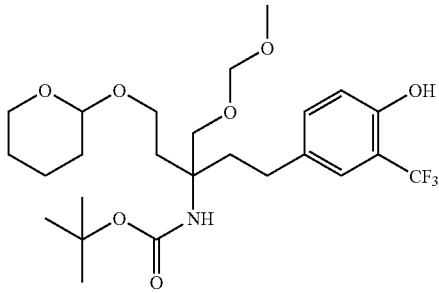

To a solution of compound 106-5 (4.94 g) in 1,4-dioxane (150 ml) was added 10% palladium carbon (containing water about 50%, 2 g), and the mixture was stirred under a hydrogen atmosphere for 22 hr. The reaction mixture was filtered through celite and concentrated to give the object product (4.07 g) as a colorless oil.

$^1$H-NMR(CDCl$_3$) δ (ppm): 1.43(9H, s), 1.52-1.64(4H, m), 1.68-1.75(1H, m), 1.79-1.88(1H, m), 1.92-2.27(4H, m), 2.55-2.61(2H, m), 3.36, 3.37(3H, 2×s), 3.46-3.60(2H, m), 3.71-4.03(4H, m), 4.61-4.63(3H, m), 5.45, 5.59(1H, 2×brs), 5.54 (1H, brs), 6.85(1H, d, J=8.4 Hz), 7.21-7.23(1H, m), 7.30(1H, brs).

(106-7) Synthesis of 2-amino-2-(2-{4-[3-(3-methylphenyl)propoxy]-3-trifluoromethylphenyl}ethyl)butane-1,4-diol hydrochloride (Compound 106-7)

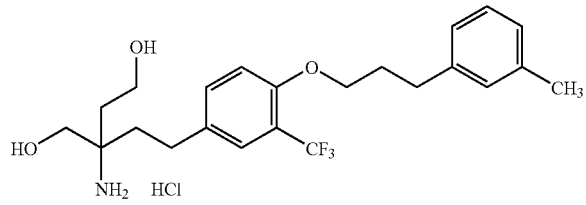

Compound 106-6 (1.17 g) was dissolved in N,N-dimethylformamide (25 ml), potassium carbonate (930 mg) and compound 15-2 (573 mg) were added, and the mixture was stirred at 80° C. for 1.5 hr. Water was added to the reaction mixture, and the mixture was extracted with ethyl acetate, washed with water and saturated brine, and dried over anhydrous magnesium sulfate. The solvent was evaporated under reduced pressure to give a colorless oil (1.52 g). The colorless oil was dissolved in ethanol (30 ml), concentrated hydrochloric acid (3 ml) was added, and the mixture was stirred at 80° C. for 1.5 hr. The m reaction mixture was concentrated, and the residue was washed with diethyl ether to give the object product (930 mg) as a white powder.

MS(ESI)m/z: 426[M+H]

$^1$H-NMR(DMSO-d$_6$) δ (ppm): 1.78-1.85(4H, m), 1.96-2.04(2H, m), 2.26(3H, s), 2.61-2.65(2H, m), 2.70(2H, t, J=7.5 Hz), 3.51(2H, d, J=4.6 Hz), 3.60(2H, t, J=6.5 Hz), 4.04(2H, t, J=6.1 Hz), 5.48(1H, t, J=4.8 Hz), 6.96-7.01(3H, m), 7.14-7.18(2H, m), 7.44(1H, dd, J=8.5, 1.6 Hz), 7.48(1H, brs), 7.85(3H, brs).

Example 107

2-amino-4-fluoro-2-(2-{4-[3-(3-methylphenyl)propoxy]-3-trifluoromethylphenyl}ethyl)butanol hydrochloride (107-1) Synthesis of 4-(2-fluoroethyl)-4-(2-{4-[3-(3-methylphenyl)propoxy]-3-trifluoromethylphenyl}ethyl)-2-methyl-2-oxazoline (Compound 107-1)

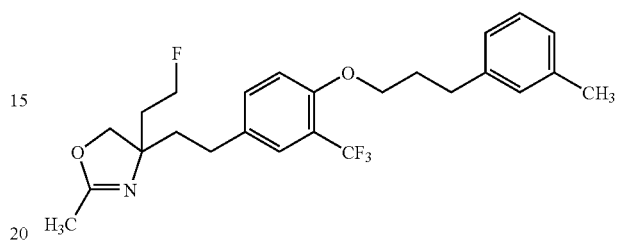

To a solution of compound 106-7 (820 mg) in N,N-dimethylformamide (20 ml) were added N,N-diisopropylethylamine (0.956 ml) and trimethyl orthoacetate (0.450 ml), and the mixture was stirred at 120° C. for 3 hr. Water was added to the reaction mixture, and the mixture was extracted with ethyl acetate, washed with water and saturated brine, and dried over anhydrous magnesium sulfate. The solvent was evaporated under reduced pressure to give a brown oil (920 mg). To a solution of the brown oil in tetrahydrofuran (30 ml) were added molecular sieves 4Å(8.0 g), p-toluenesulfonyl fluoride (638 mg) and 1M-tetrabutylammonium fluoride/tetrahydrofuran solution (5.34 ml), and the mixture was heated under reflux for one day. The reaction mixture was filtered, and 1M hydrochloric acid was added to the filtrate. The mixture was extracted with ethyl acetate, washed with saturated aqueous sodium hydrogen carbonate solution and saturated brine, and dried over anhydrous sodium sulfate. The solvent was evaporated under reduced pressure. The obtained residue was purified by silica gel column chromatography (hexane:ethyl acetate=1:2-1:3) to give the object product (230 mg) as a brown oil.

$^1$H-NMR(DMSO-d$_6$) δ (ppm): 1.75-1.95(2H, m), 1.97-2.05(1H, m), 2.02(3H, s), 2.05-2.13(3H, m), 2.32(3H, s), 2.48-2.65(2H, m), 2.79(2H, t, J=7.5 Hz), 3.99(2H, t, J=6.0 Hz), 4.07(1H, d, J=8.8 Hz), 4.14(1H, d, J=8.8 Hz), 4.50-4.58 (1H, m), 4.61-4.68(1H, m), 6.85(1H, d, J=8.5 Hz), 6.98-7.02 (3H, m), 7.17(1H, t, J=7.4 Hz), 7.24-7.26(1H, m), 7.38(1H, d, J=1.5 Hz).

(107-2) Synthesis of 2-amino-4-fluoro-2-(2-{4-[3-(3-methylphenyl)propoxy]-3-trifluoromethylphenyl}ethyl)butanol hydrochloride (Compound 107-2)

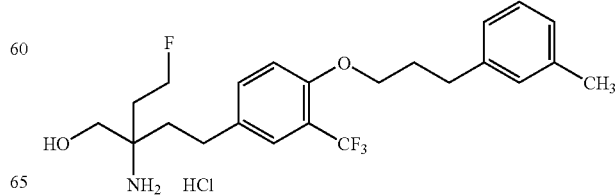

Compound 107-1 (230 mg) was dissolved in ethanol (15 ml), concentrated hydrochloric acid (2 ml) was added, and the mixture was stirred at 80° C. for 1 hr. The reaction mixture was concentrated, and the residue was washed with diisopropyl ether to give the object product (230 mg) as a white powder.

MS(ESI)m/z: 428[M+H]

$^1$H-NMR(DMSO-$d_6$) δ (ppm): 1.78-1.85(2H, m), 1.97-2.05(3H, m), 2.10(1H, t, J=5.9 Hz), 2.26(3H, s), 2.60-2.65 (2H, m), 2.70(2H, t, J=7.5 Hz), 3.53(2H, d, J=4.9 Hz), 4.04 (2H, t, J=5.9 Hz), 4.61(1H, dt, J=47.0, 5.9 Hz), 4.73(1H, dt, J=47.0, 5.9 Hz), 5.58(1H, t, J=4.9 Hz), 6.96-7.01(3H, m), 7.14-7.18(2H, m), 7.44(1H, d, J=8.6 Hz), 7.48(1H, brs), 8.03 (3H, brs).

Example 108

2-amino-4-[4-(5-phenylpentyloxy)-3-trifluoromethylphenyl]-2-(phosphoryloxymethyl)butanol (108-1) Synthesis of 4-di(t-butyl)phosphoryloxymethyl-2-methyl-4-{2-[4-(5-phenylpentyloxy)-3-trifluoromethylphenyl]ethyl}-2-oxazoline (Compound 108-1)

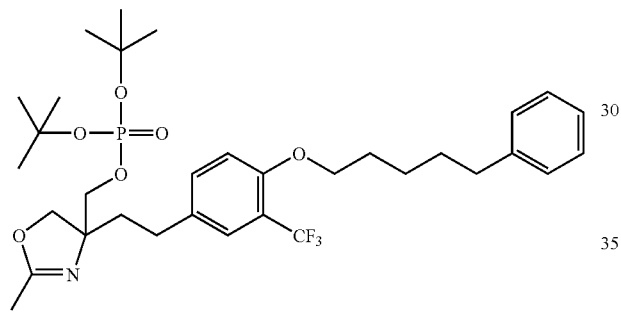

To a solution of compound 5-2 (350 mg) in N,N-dimethylformamide (10 ml) were added N,N-diisopropylethylamine (0.408 ml) and trimethyl orthoacetate (0.146 ml), and the mixture was stirred at 120° C. for 5.5 hr. Water was added to the reaction mixture, and the mixture was extracted with ethyl acetate, washed with water and saturated brine, and dried over anhydrous magnesium sulfate. The solvent was evaporated under reduced pressure to give a brown oil (320 mg). To a solution of the brown oil (320 mg) in methylene chloride (5 ml) and acetonitrile (2 ml) were added 1H-tetrazole (100 mg) and di-t-butyl diethylphosphoramidite (0.425 ml), and the mixture was stirred at room temperature for 1.5 hr. The reaction solution was ice-cooled, m-chloroperbenzoic acid (containing 25% water, 377 mg) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:3—ethyl acetate alone) to give the object product (230 mg) as a pale-brown oil.

$^1$H-NMR(CD$_3$OD) δ (ppm): 1.47(9H, s), 1.48(9H, s), 1.48-1.59(2H, m), 1.65-1.74(2H, m), 1.79-1.90(4H, m), 2.00 (3H, s), 2.52-2.71(4H, m), 3.89-3.92(2H, m), 4.03(2H, t, J=6.2 Hz), 4.17(1H, d, J=9.2 Hz), 4.32(1H, d, J=9.2 Hz), 7.04(1H, d, J=8.4 Hz), 7.10-7.20(3H, m), 7.21-7.27(2H, m), 7.36-7.41(2H, m).

(108-2) Synthesis of 2-amino-4-[4-(5-phenylpentyloxy)-3-trifluoromethylphenyl]-2-(phosphoryloxymethyl)butanol (Compound 108-2)

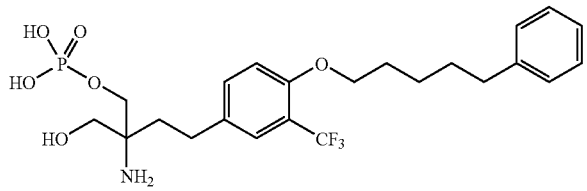

Compound 108-1 (230 mg) was dissolved in ethanol (5 ml), concentrated hydrochloric acid (1 ml) was added, and the mixture was stirred at 50° C. for 3 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (139 mg) as a white solid.

MS(ESI)m/z: 506[M+H]

$^1$H-NMR(CD$_3$OD) δ (ppm): 1.48-1.59(2H, m), 1.64-1.73 (2H, m), 1.77-1.88(2H, m), 1.92-2.00(2H, m), 2.60-2.73(4H, m), 3.70(2H, brs), 3.95-4.03(2H, m), 4.04(2H, t, J=6.2 Hz), 7.06(1H, d, J=8.4 Hz), 7.10-7.19(3H, m), 7.21-7.26(2H, m), 7.41-7.44(2H, m).

Example 109

2-amino-4-[4-(3-benzyloxybenzyloxy)-3-trifluoromethylphenyl]-2-(phosphoryloxymethyl)butanol (109-1) Synthesis of 4-{2-[4-(3-benzyloxybenzyloxy)-3-trifluoromethylphenyl]ethyl}-4-di(t-butyl)phosphoryloxymethyl-2-methyl-2-oxazoline (Compound 109-1)

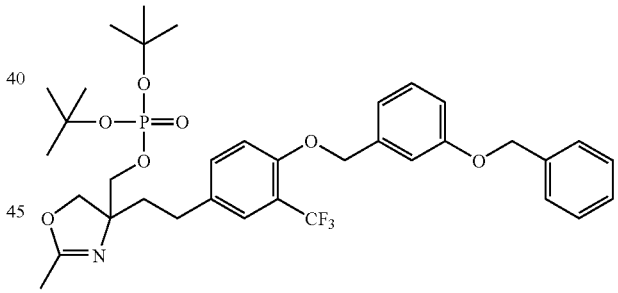

To a solution of compound 6-3 (480 mg) in N,N-dimethylformamide (10 ml) were added N,N-diisopropylethylamine (0.505 ml) and trimethyl orthoacetate (0.178 ml), and the mixture was stirred at 120° C. for 6 hr. Water was added to the reaction mixture, and the mixture was extracted with ethyl acetate, washed with water and saturated brine, and dried over anhydrous magnesium sulfate. The solvent was evaporated under reduced pressure to give a brown oil (470 mg). To a solution of the brown oil (470 mg) in methylene chloride (5 ml) and acetonitrile (2 ml) were added 1H-tetrazole (132 mg) and di-t-butyl diethylphosphoramidite (0.563 ml), and the mixture was stirred at room temperature for 2 hr. The reaction solution was ice-cooled, m-chloroperbenzoic acid (containing 25% water, 499 mg) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (360 mg) as a yellow oil.

$^1$H-NMR(CD$_3$OD) δ (ppm): 1.47(9H, s), 1.49(9H, s), 1.81-1.90(2H, m), 2.00(3H, s), 2.51-2.70(2H, m), 3.88-3.91 (2H, m), 4.17(1H, d, J=8.9 Hz), 4.32(1H, d, J=8.9 Hz), 5.07 (2H, s), 5.16(2H, s), 6.92(1H, dd, J=8.2, 2.3 Hz), 7.01(1H, d, J=7.6 Hz), 7.08-7.11(2H, m), 7.24-7.46(8H, m).

(109-2) Synthesis of 2-amino-4-[4-(3-benzyloxybenzyloxy)-3-trifluoromethylphenyl]-2-(phosphoryloxymethyl)butanol (Compound 109-2)

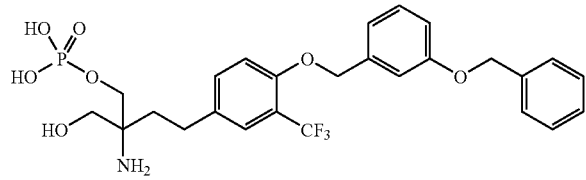

Compound 109-1 (360 mg) was dissolved in ethanol (5 ml), concentrated hydrochloric acid (1 ml) was added, and the mixture was stirred at 50° C. for 3 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (220 mg) as a white solid.

MS(ESI)m/z: 556[M+H]

$^1$H-NMR(CD$_3$OD) δ (ppm): 1.92-1.99(2H, m), 2.63-2.72 (2H, m), 3.70(2H, brs), 3.95-4.01(2H, m), 5.07(2H, s), 5.18 (2H, s), 6.93(1H, dd, J=8.2, 2.4 Hz), 7.02(1H, d, J=7.7 Hz), 7.09-7.12(2H, m), 7.25-7.49(8H, m).

Example 110

2-amino-4-[4-(3-phenoxybenzyloxy)-3-trifluoromethylphenyl]-2-(phosphoryloxymethyl)butanol (110-1) Synthesis of 4-di(t-butyl)phosphoryloxymethyl-2-methyl-4-{2-[4-(3-phenoxybenzyloxy)-3-trifluoromethylphenyl]ethyl}-2-oxazoline (Compound 110-1)

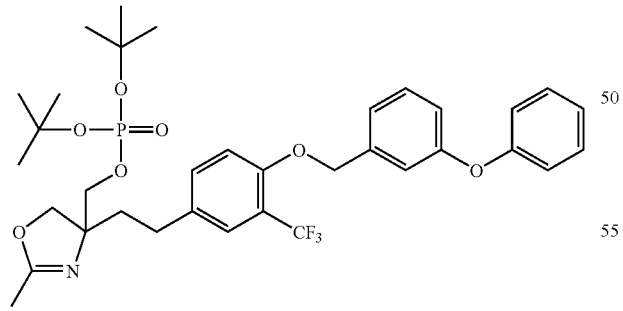

To a solution of compound 7-2 (490 mg) in N,N-dimethylformamide (10 ml) were added N,N-diisopropylethylamine (0.528 ml) and trimethyl orthoacetate (0.186 ml), and the mixture was stirred at 120° C. for 6 hr. Water was added to the reaction mixture, and the mixture was extracted with ethyl acetate, washed with water and saturated brine, and dried over anhydrous magnesium sulfate. The solvent was evaporated under reduced pressure to give a brown oil (460 mg). To a solution of the brown oil (460 mg) in methylene chloride (5 ml) and acetonitrile (2 ml) were added 1H-tetrazole (133 mg) and di-t-butyl diethylphosphoramidite (0.569 ml), and the mixture was stirred at room temperature for 3 hr. The reaction solution was ice-cooled, m-chloroperbenzoic acid (containing 25% water, 504 mg) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (340 mg) as a yellow oil.

$^1$H-NMR(CD$_3$OD) δ (ppm): 1.47(9H, s), 1.48(9H, s), 1.81-1.90(2H, m), 2.00(3H, s), 2.55-2.70(2H, m), 3.88-3.91 (2H, m), 4.17(1H, d, J=9.1 Hz), 4.32(1H, d, J=9.1 Hz), 5.17 (2H, s), 6.91(1H, dd, J=8.1, 2.2 Hz), 6.97(2H, d, J=7.7 Hz), 7.07-7.19(4H, m), 7.31-7.46(5H, m).

(110-2) Synthesis of 2-amino-4-[4-(3-phenoxybenzyloxy)-3-trifluoromethylphenyl]-2-(phosphoryloxymethyl)butanol (Compound 110-2)

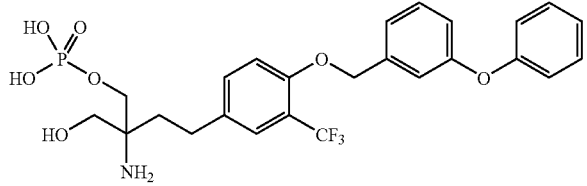

Compound 110-1 (340 mg) was dissolved in ethanol (5 ml), concentrated hydrochloric acid (1 ml) was added, and the mixture was stirred at 50° C. for 3 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (225 mg) as a white solid.

MS(ESI)m/z: 542[M+H]

$^1$H-NMR(CD$_3$OD) δ (ppm): 1.92-1.98(2H, m), 2.60-2.72 (2H, m), 3.70(2H, brs), 3.95-4.02(2H, m), 5.18(2H, s), 6.92 (1H, dd, J=8.2, 2.2 Hz), 6.97(2H, d, J=8.2 Hz), 7.07-7.19(4H, m), 7.30-7.49(5H, m).

Example 111

2-amino-4-[4-(3-phenylpropoxy)-3-trifluoromethylphenyl]-2-(phosphoryloxymethyl)butanol (111-1) Synthesis of N-{1-di(t-butyl)phosphoryloxymethyl-1-hydroxymethyl-3-[4-(3-phenylpropoxy)-3-trifluoromethylphenyl]propyl}acetamide (Compound 111-1)

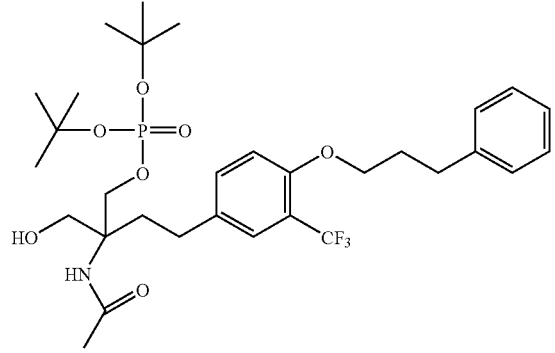

249

To a solution of compound 8-2 (460 mg) in N,N-dimethylformamide (10 ml) were added N,N-diisopropylethylamine (0.571 ml) and trimethyl orthoacetate (0.201 ml), and the mixture was stirred at 120° C. for 7 hr. Water was added to the reaction mixture, and the mixture was extracted with ethyl acetate, washed with water and saturated brine, and dried over anhydrous magnesium sulfate. The solvent was evaporated under reduced pressure to give a brown oil (430 mg). To a solution of the brown oil (430 mg) in methylene chloride (5 ml) and acetonitrile (2 ml) were added 1H-tetrazole (143 mg) and di-t-butyl diethylphosphoramidite (0.610 ml), and the mixture was stirred at room temperature for 3 hr. The reaction solution was ice-cooled, m-chloroperbenzoic acid (containing 25% water, 542 mg) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (ethyl acetate alone) to give the object product (180 mg) as a pale-yellow oil. The obtained compound was an acetamide compound formed by ring opening of oxazoline.

$^1$H-NMR(CD$_3$OD) δ (ppm): 1.47-1.51(2H, m), 1.49(18H, s), 1.96(3H, s), 2.02-2.10(2H, m), 2.59-2.65(2H, m), 2.81 (2H, t, J=7.5 Hz), 3.71(1H, d, J=11.1 Hz), 3.79(1H, d, J=11.1 Hz), 4.00(2H, t, J=5.9 Hz), 4.16-4.25(2H, m), 6.99(1H, d, J=8.5 Hz), 7.13-7.26(5H, m), 7.37(1H, dd, J=8.5, 1.5 Hz), 7.44(1H, d, J=1.5 Hz).

(111-2) Synthesis of 2-amino-4-[4-(3-phenylpropoxy)-3-trifluoromethylphenyl]-2-(phosphoryloxymethyl)butanol (Compound 111-2)

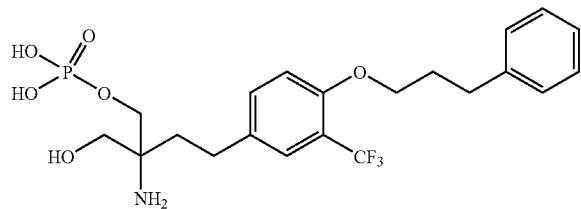

Compound 111-1 (180 mg) was dissolved in ethanol (5 ml), concentrated hydrochloric acid (1 ml) was added, and the mixture was stirred at 50° C. for 3 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (76 mg) as a white solid.

MS(ESI)m/z: 478[M+H]

$^1$H-NMR(CD$_3$OD) δ (ppm): 1.93-1.98(2H, m), 2.05-2.11 (2H, m), 2.60-2.76(2H, m), 2.81(2H, t, J=7.5 Hz), 3.70(2H, brs), 3.94-4.05(4H, m), 7.02(1H, d, J=8.5 Hz), 7.15-7.28(5H, m), 7.42(1H, d, J=8.7 Hz), 7.48(1H, brs).

250

Example 112

2-amino-4-[4-(3-cyclohexylpropoxy)-3-trifluoromethylphenyl]-2-(phosphoryloxymethyl)butanol (112-1) Synthesis of 4-di(t-butyl)phosphoryloxymethyl-4-{2-[4-(3-cyclohexylpropoxy)-3-trifluoromethylphenyl]ethyl}-2-methyl-2-oxazoline (Compound 112-1)

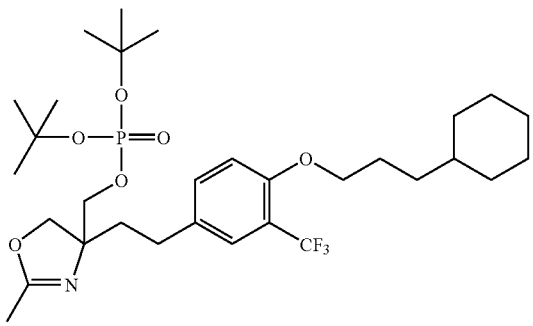

To a solution of compound 9-3 (420 mg) in N,N-dimethylformamide (10 ml) were added N,N-diisopropylethylamine (0.512 ml) and trimethyl orthoacetate (0.180 ml), and the mixture was stirred at 120° C. for 6 hr. Water was added to the reaction mixture, and the mixture was extracted with ethyl acetate, washed with water and saturated brine, and dried over anhydrous magnesium sulfate. The solvent was evaporated under reduced pressure to give a brown oil (400 mg). To a solution of the brown oil (400 mg) in methylene chloride (5 ml) and acetonitrile (2 ml) were added 1H-tetrazole (132 mg) and di-t-butyl diethylphosphoramidite (0.563 ml), and the mixture was stirred at room temperature for 2 hr. The reaction solution was ice-cooled, m-chloroperbenzoic acid (containing 25% water, 499 mg) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (180 mg) as a yellow oil.

$^1$H-NMR(CD$_3$OD) δ (ppm): 0.88-0.99(2H, m), 1.12-1.40 (7H, m), 1.47(9H, s), 1.48(9H, s), 1.64-1.90(8H, m), 2.01(3H, s), 2.51-2.70(2H, m), 3.89-3.91(2H, m), 4.02(2H, t, J=6.2 Hz), 4.18(1H, d, J=9.2 Hz), 4.32(1H, d, J=9.2 Hz), 7.05(1H, d, J=8.4 Hz), 7.37-7.40(2H, m).

(112-2) Synthesis of 2-amino-4-[4-(3-cyclohexylpropoxy)-3-trifluoromethylphenyl]-2-(phosphoryloxymethyl)butanol (Compound 112-2)

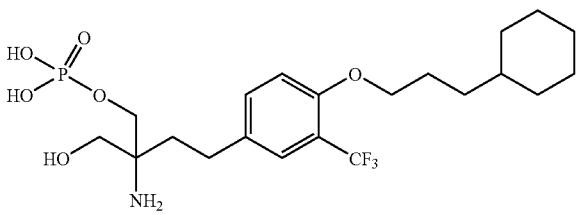

Compound 112-1 (180 mg) was dissolved in ethanol (5 ml), concentrated hydrochloric acid (1 ml) was added, and the mixture was stirred at 50° C. for 3 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (112 mg) as a white solid.

MS(ESI)m/z: 484[M+H]

$^1$H-NMR(CD$_3$OD) δ (ppm): 0.85-0.96(2H, m), 1.15-1.40 (6H, m), 1.62-1.85(7H, m), 1.92-1.98(2H, m), 2.63-2.75(2H, m), 3.70(2H, brs), 3.95-4.05(4H, m), 7.06(1H, d, J=8.2 Hz), 7.42-7.45(2H, m).

Example 113

2-amino-4-{4-[3-(4-methoxyphenyl)propoxy]-3-trifluoromethylphenyl}-2-(phosphoryloxymethyl) butanol (113-1) Synthesis of N-[1-di(t-butyl)phosphoryloxymethyl-1-hydroxymethyl-3-{4-[3-(4-methoxyphenyl)propoxy]-3-trifluoromethylphenyl}propyl] acetamide (Compound 113-1)

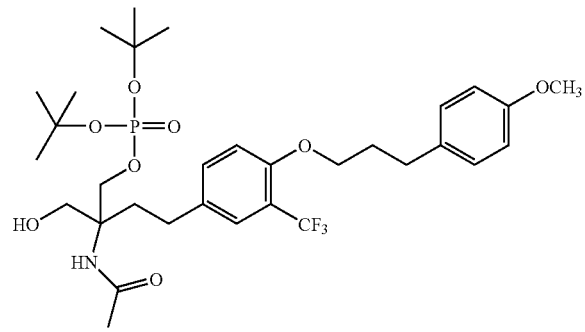

To a solution of compound 10-3 (440 mg) in N,N-dimethylformamide (10 ml) were added N,N-diisopropylethylamine (0.512 ml) and trimethyl orthoacetate (0.180 ml), and the mixture was stirred at 120° C. for 6 hr. Water was added to the reaction mixture, and the mixture was extracted with ethyl acetate, washed with water and saturated brine, and dried over anhydrous magnesium sulfate. The solvent was evaporated under reduced pressure to give a brown oil (430 mg). To a solution of the brown oil (430 mg) in methylene chloride (5 ml) and acetonitrile (2 ml) were added 1H-tetrazole (131 mg) and di-t-butyl diethylphosphoramidite (0.560 ml), and the mixture was stirred at room temperature for 2 hr. The reaction solution was ice-cooled, m-chloroperbenzoic acid (containing 25% water, 281 mg) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (280 mg) as a yellow oil. The obtained compound was an acetamide compound formed by ring opening of oxazoline.

$^1$H-NMR(CD$_3$OD) δ (ppm): 1.49(18H, s), 1.96(3H, s), 2.02-2.10(4H, m), 2.59-2.65(2H, m), 2.81(2H, t, J=7.5 Hz), 3.71(1H, d, J=11.1 Hz), 3.75(3H, s), 3.79(1H, d, J=11.1 Hz), 4.00(2H, t, J=5.9 Hz), 4.16-4.25(2H, m), 6.99(1H, d, J=8.5 Hz), 7.13-7.26(5H, m), 7.37 (1H, dd, J=8.5, 1.5 Hz), 7.44(1H, d, J=1.5 Hz).

(113-2) Synthesis of 2-amino-4-{4-[3-(4-methoxyphenyl)propoxy]-3-trifluoromethylphenyl}-2-(phosphoryloxymethyl)butanol (Compound 113-2)

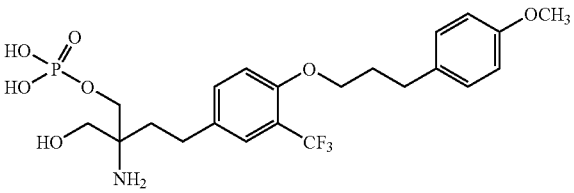

Compound 113-1 (280 mg) was dissolved in ethanol (5 ml), concentrated hydrochloric acid (1 ml) was added, and the mixture was stirred at 50° C. for 2.5 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (180 mg) as a white solid.

MS (ESI)m/z: 508[M+H]

$^1$H-NMR(CD$_3$OD) δ (ppm): 1.95-2.00(2H, m), 2.01-2.09 (2H, m), 2.65-2.72(2H, m), 2.75(2H, t, J=7.4 Hz), 3.70(2H, brs), 3.75(3H, s), 3.96-4.05(4H, m), 6.81(2H, d, J=8.6 Hz), 7.01(1H, d, J=8.5 Hz), 7.09(2H, d, J=8.5 Hz), 7.42(1H, d, J=8.6 Hz), 7.47(1H, brs).

Example 114

2-amino-2-(phosphoryloxymethyl)-4-{3-trifluoromethyl-4-[3-(4-trifluoromethylphenyl)propoxy] phenyl}butanol (114-1) Synthesis of 4-di(t-butyl)phosphoryloxymethyl-2-methyl-4-(2-{3-trifluoromethyl-4-[3-(4-trifluoromethylphenyl)propoxy]phenyl}ethyl)-2-oxazoline (Compound 114-1)

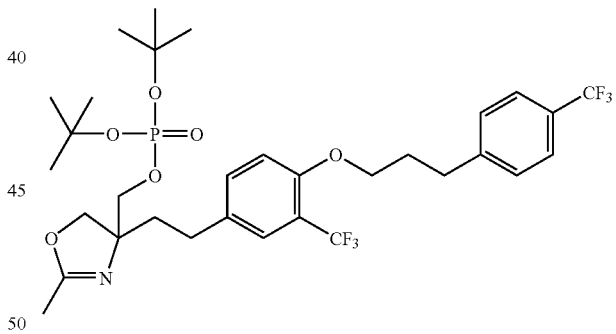

To a solution of compound 11-4 (470 mg) in N,N-dimethylformamide (10 ml) were added N,N-diisopropylethylamine (0.504 ml) and trimethyl orthoacetate (0.178 ml), and the mixture was stirred at 120° C. for 4.5 hr. Water was added to the reaction mixture, and the mixture was extracted with ethyl acetate, washed with water and saturated brine, and dried over anhydrous magnesium sulfate. The solvent was evaporated under reduced pressure to give a brown oil (450 mg). To a solution of the brown oil (450 mg) in methylene chloride (5 ml) and acetonitrile (2 ml) were added 1H-tetrazole (129 mg) and di-t-butyl diethylphosphoramidite (0.551 ml), and the mixture was stirred at room temperature for 1.5 hr. The reaction solution was ice-cooled, m-chloroperbenzoic acid (containing 25% water, 272 mg) was added, and the mixture was stirred at room temperature for 30 min. Saturated aqueous sodium hydrogen carbonate solution was added to the reaction mixture, and the mixture was extracted with chloroform.

The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (270 mg) as a yellow oil. The obtained compound was a 1:1 mixture of compound 54-1 and N-[1-di(t-butyl)phosphoryloxymethyl-1-hydroxymethyl-3-{3-trifluoromethyl-4-[3-(4-trifluoromethylphenyl)propoxy]phenyl}propyl]acetamide compound formed by ring opening of oxazoline thereof.

(114-2) Synthesis of 2-amino-2-(phosphoryloxymethyl)-4-{3-trifluoromethyl-4-[3-(4-trifluoromethylphenyl)propoxy]phenyl}butanol (Compound 114-2)

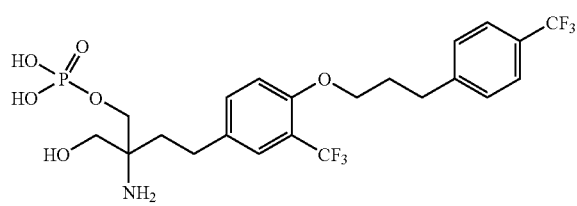

Compound 114-1 (270 mg) was dissolved in ethanol (5 ml), concentrated hydrochloric acid (1 ml) was added, and the mixture was stirred at 50° C. for 3 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (173 mg) as a white solid.

MS(ESI)m/z: 546[M+H]
$^1$H-NMR(CD$_3$OD) δ (ppm): 1.92-2.00(2H, m), 2.09-2.16 (2H, m), 2.61-2.75(2H, m), 2.91(2H, t, J=7.5 Hz), 3.70(2H, brs), 3.94-4.00(2H, m), 4.04(2H, t, J=7.5 Hz), 7.04(1H, d, J=8.5 Hz), 7.38-7.45(3H, m), 7.48(1H, brs), 7.56(2H, d, J=8.1 Hz).

Example 115

2-amino-2-(phosphoryloxymethyl)-4-{3-trifluoromethyl-4-[3-(3-trifluoromethylphenyl)propoxy]phenyl}butanol (115-1) Synthesis of 4-di(t-butyl)phosphoryloxymethyl-2-methyl-4-(2-{3-trifluoromethyl-4-[3-(3-trifluoromethylphenyl)propoxy]phenyl}ethyl)-2-oxazoline (Compound 115-1)

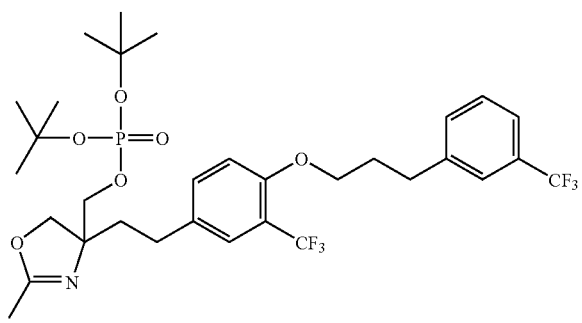

To a solution of compound 12-4 (450 mg) in N,N-dimethylformamide (10 ml) were added N,N-diisopropylethylamine (0.485 ml) and trimethyl orthoacetate (0.171 ml), and the mixture was stirred at 120° C. for 7 hr. Water was added to the reaction mixture, and the mixture was extracted with ethyl acetate, washed with water and saturated brine, and dried over anhydrous magnesium sulfate. The solvent was evaporated under reduced pressure to give a brown oil (450 mg). To a solution of the brown oil (450 mg) in methylene chloride (5 ml) and acetonitrile (2 ml) were added 1H-tetrazole (126 mg) and di-t-butyl diethylphosphoramidite (0.539 ml), and the mixture was stirred at room temperature for 1.5 hr. The reaction solution was ice-cooled, m-chloroperbenzoic acid (containing 25% water, 266 mg) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (330 mg) as a yellow oil.

$^1$H-NMR(CD$_3$OD) δ (ppm): 1.49(18H, s), 1.80-1.90(2H, m), 2.01(3H, s), 2.07-2.15(2H, m), 2.55-2.71(2H, m), 2.92 (2H, t, J=7.5 Hz), 3.88-3.92(2H, m), 4.02(2H, t, J=5.9 Hz), 4.18(1H, d, J=9.0 Hz), 4.32(1H, d, J=9.0 Hz), 7.02(1H, d, J=8.5 Hz), 7.39(1H, d, J=8.5 Hz), 7.43-7.49(5H, m).

(115-2) Synthesis of 2-amino-2-(phosphoryloxymethyl)-4-{3-trifluoromethyl-4-[3-(3-trifluoromethylphenyl)propoxy]phenyl}butanol (Compound 115-2)

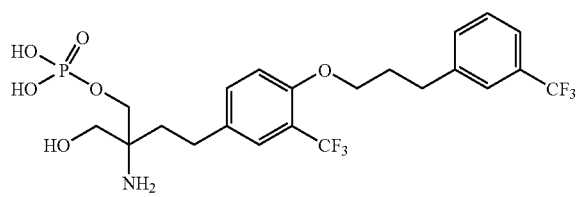

Compound 115-1 (330 mg) was dissolved in ethanol (5 ml), concentrated hydrochloric acid (1 ml) was added, and the mixture was stirred at 50° C. for 3 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (227 mg) as a white solid.

MS(ESI)m/z: 546[M+H]
$^1$H-NMR(CD$_3$OD) δ (ppm): 1.92-2.02(2H, m), 2.06-2.15 (2H, m), 2.64-2.76(2H, m), 2.92(2H, t, J=7.4 Hz), 3.71(2H, brs), 3.96-4.07(4H, m), 7.04(1H, d, J=8.4 Hz), 7.40-7.52(6H, m).

Example 116

2-amino-4-{4-[3-(4-methylphenyl)propoxy]-3-trifluoromethylphenyl}-2-(phosphoryloxymethyl)butanol (116-1) Synthesis of 4-di(t-butyl)phosphoryloxymethyl-2-methyl-4-(2-{4-[3-(4-methylphenyl)propoxy]-3-trifluoromethylphenyl}ethyl)-2-oxazoline (Compound 116-1)

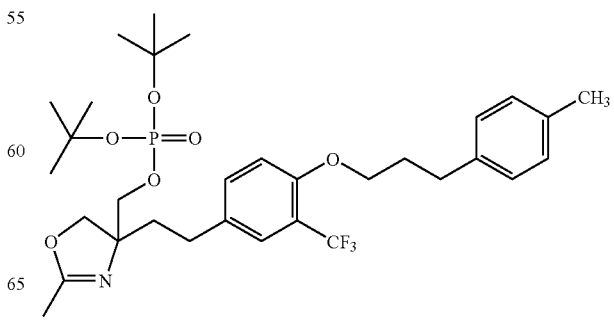

To a solution of compound 13-4 (410 mg) in N,N-dimethylformamide (10 ml) were added N,N-diisopropylethylamine (0.493 ml) and trimethyl orthoacetate (0.174 ml), and the mixture was stirred at 120° C. for 3 hr. Water was added to the reaction mixture, and the mixture was extracted with ethyl acetate, washed with water and saturated brine, and dried over anhydrous magnesium sulfate. The solvent was evaporated under reduced pressure to give a brown oil (410 mg). To a solution of the brown oil (410 mg) in methylene chloride (5 ml) and acetonitrile (2 ml) were added 1H-tetrazole (129 mg) and di-t-butyl diethylphosphoramidite (0.551 ml), and the mixture was stirred at room temperature for 1.5 hr. The reaction solution was ice-cooled, t-butyl hydroperoxide containing decane solution (5-6M, 0.552 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (390 mg) as a yellow oil.

$^1$H-NMR(CD$_3$OD) δ (ppm): 1.49(18H, s), 1.80-1.90(2H, m), 2.00(3H, s), 2.01-2.10(2H, m), 2.27(3H, s), 2.53-2.69 (2H, m), 2.76(2H, t, J=7.5 Hz), 3.89-3.92(2H, m), 3.99(2H, t, J=6.0 Hz), 4.17(1H, d, J=9.1 Hz), 4.32(1H, d, J=9.1 Hz), 6.99(1H, d, J=8.4 Hz), 7.06(4H, s), 7.37(1H, d, J=9.6 Hz), 7.42(1H, brs).

(116-2) Synthesis of 2-amino-4-{4-[3-(4-methylphenyl)propoxy]-3-trifluoromethylphenyl}-2-(phosphoryloxymethyl)butanol (Compound 116-2)

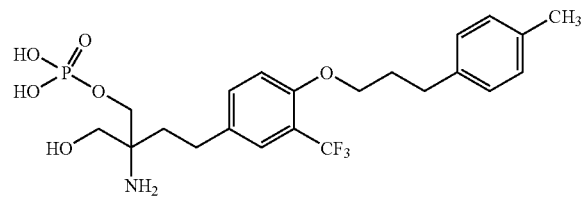

Compound 116-1 (390 mg) was dissolved in ethanol (5 ml), concentrated hydrochloric acid (1 ml) was added, and the mixture was stirred at 50° C. for 3 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (260 mg) as a white solid.

MS (ESI)m/z: 492[M+H]

$^1$H-NMR(CD$_3$OD) δ (ppm): 1.93-2.00(2H, m), 2.01-2.10 (2H, m), 2.28(3H, s), 2.64-2.75(2H, m), 2.76(2H, t, J=7.4 Hz), 3.70(2H, brs), 3.94-4.03(4H, m), 7.01(1H, d, J=8.5 Hz), 7.06(4H, s), 7.42(1H, dd, J=8.5, 1.5 Hz), 7.47(1H, brs).

Example 117

2-amino-4-{4-[3-(2-methylphenyl)propoxy]-3-trifluoromethylphenyl}-2-(phosphoryloxymethyl)butanol (117-1) Synthesis of 4-di(t-butyl)phosphoryloxymethyl-2-methyl-4-(2-{4-[3-(2-methylphenyl)propoxy]-3-trifluoromethylphenyl}ethyl)-2-oxazoline (Compound 117-1)

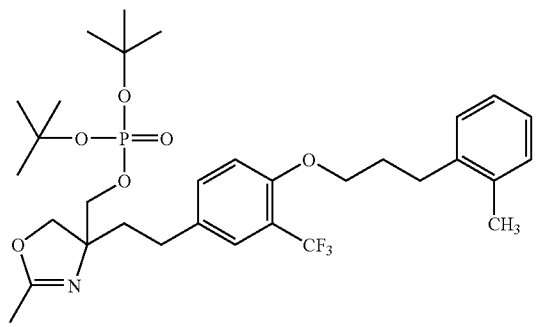

To a solution of compound 14-4 (390 mg) in N,N-dimethylformamide (10 ml) were added N,N-diisopropylethylamine (0.469 ml) and trimethyl orthoacetate (0.165 ml), and the mixture was stirred at 120° C. for 5 hr. Water was added to the reaction mixture, and the mixture was extracted with ethyl acetate, washed with water and saturated brine, and dried over anhydrous magnesium sulfate. The solvent was evaporated under reduced pressure to give a brown oil (380 mg). To a solution of the brown oil (380 mg) in methylene chloride (5 ml) and acetonitrile (2 ml) were added 1H-tetrazole (122 mg) and di-t-butyl diethylphosphoramidite (0.521 ml), and the mixture was stirred at room temperature for 1.5 hr. The reaction solution was ice-cooled, t-butyl hydroperoxide-containing decane solution (5-6M, 0.522 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (320 mg) as a yellow oil.

$^1$H-NMR(CD$_3$OD) δ (ppm): 1.49(18H, s), 1.82-1.91(2H, m), 2.00(3H, s), 2.00-2.08(2H, m), 2.30(3H, s), 2.53-2.71 (2H, m), 2.83(2H, t, J=7.6 Hz), 3.89-3.92(2H, m), 4.06(2H, t, J=5.8 Hz), 4.18(1H, d, J=9.0 Hz), 4.32(1H, d, J=9.0 Hz), 7.02-7.08(3H, m), 7.10-7.13(2H, m), 7.39(1H, dd, J=8.5, 1.5 Hz), 7.43(1H, d, J=1.5 Hz).

(117-2) Synthesis of 2-amino-4-{4-[3-(2-methylphenyl)propoxy]-3-trifluoromethylphenyl}-2-(phosphoryloxymethyl)butanol (Compound 117-2)

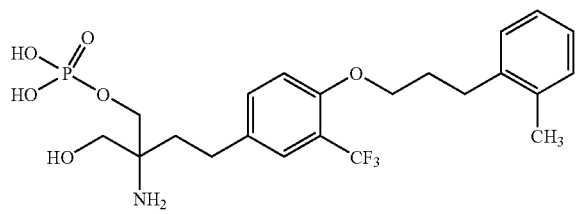

Compound 117-1 (320 mg) was dissolved in ethanol (5 ml), concentrated hydrochloric acid (1 ml) was added, and the mixture was stirred at 50° C. for 3 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (172 mg) as a white solid.

MS(ESI)m/z: 492[M+H]

$^1$H-NMR(CD$_3$OD) δ (ppm): 1.94-2.08(4H, m), 2.30(3H, s), 2.64-2.76(2H, m), 2.83(2H, t, J=7.6 Hz), 3.71(2H, brs), 3.95-4.03(2H, m), 4.06(2H, t, J=5.7 Hz), 7.01-7.08(3H, m), 7.10-7.13(2H, m), 7.44(1H, d, J=8.6 Hz), 7.48(1H, brs).

Example 118

2-amino-4-{4-[3-(3-methylphenyl)propoxy]-3-trifluoromethylphenyl}-2-(phosphoryloxymethyl)butanol

(118-1) Synthesis of 4-di(t-butyl)phosphoryloxymethyl-2-methyl-4-(2-{4-[3-(3-methylphenyl)propoxy]-3-trifluoromethylphenyl}ethyl)-2-oxazoline (Compound 118-1)

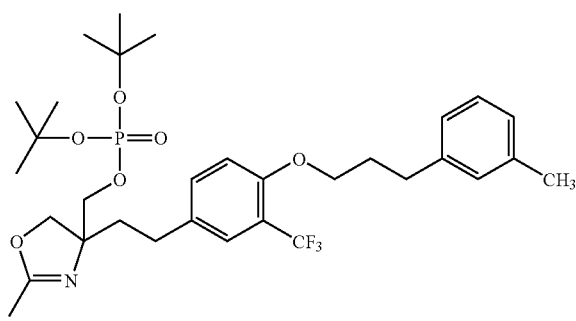

To a solution of compound 15-4 (390 mg) in N,N-dimethylformamide (10 ml) were added N,N-diisopropylethylamine (0.469 ml) and trimethyl orthoacetate (0.165 ml), and the mixture was stirred at 120° C. for 5 hr. Water was added to the reaction mixture, and the mixture was extracted with ethyl acetate, washed with water and saturated brine, and dried over anhydrous magnesium sulfate. The solvent was evaporated under reduced pressure to give a brown oil (390 mg). To a solution of the brown oil (390 mg) in methylene chloride (5 ml) and acetonitrile (2 ml) were added 1H-tetrazole (122 mg) and di-t-butyl diethylphosphoramidite (0.521 ml), and the mixture was stirred at room temperature for 1 hr. The reaction solution was ice-cooled, t-butyl hydroperoxide-containing decane solution (5-6M, 0.522 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (360 mg) as a yellow oil.

$^1$H-NMR(CD$_3$OD) δ (ppm): 1.49(18H, s), 1.80-1.91(2H, m), 2.01(3H, s), 2.01-2.09(2H, m), 2.28(3H, s), 2.52-2.71(2H, m), 2.77(2H, t, J=7.5 Hz), 3.89-3.91(2H, m), 4.00(2H, t, J=5.9 Hz), 4.17(1H, d, J=9.2 Hz), 4.32(1H, d, J=9.2 Hz), 6.95-7.00(4H, m), 7.12(1H, t, J=7.6 Hz), 7.37(1H, d, J=9.8 Hz), 7.43(1H, d, J=2.0 Hz).

(118-2) Synthesis of 2-amino-4-{4-[3-(3-methylphenyl)propoxy]-3-trifluoromethylphenyl}-2-(phosphoryloxymethyl)butanol (Compound 118-2)

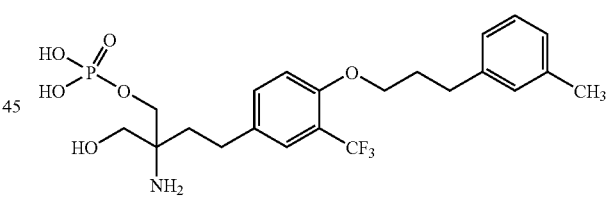

Compound 118-1 (360 mg) was dissolved in ethanol (5 ml), concentrated hydrochloric acid (1 ml) was added, and the mixture was stirred at 50° C. for 3 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (165 mg) as a pale-yellow solid.

MS(ESI)m/z: 492[M+H]

$^1$H-NMR(CD$_3$OD) δ (ppm): 1.92-2.00(2H, m), 2.01-2.09 (2H, m), 2.28(3H, s), 2.62-2.74(2H, m), 2.77(2H, t, J=7.4 Hz), 3.71(2H, brs), 3.96-4.03(4H, m), 6.95-7.03(4H, m), 7.11 (1H, d, J=7.6 Hz), 7.42(1H, d, J=8.6 Hz), 7.47(1H, brs).

Example 119

2-amino-4-{4-[3-(3-methoxyphenyl)propoxy]-3-trifluoromethylphenyl}-2-(phosphoryloxymethyl)butanol (119-1) Synthesis of 4-di(t-butyl)phosphoryloxymethyl-4-(2-{4-[3-(3-methoxyphenyl)propoxy]-3-trifluoromethylphenyl}ethyl)-2-methyl-2-oxazoline (Compound 119-1)

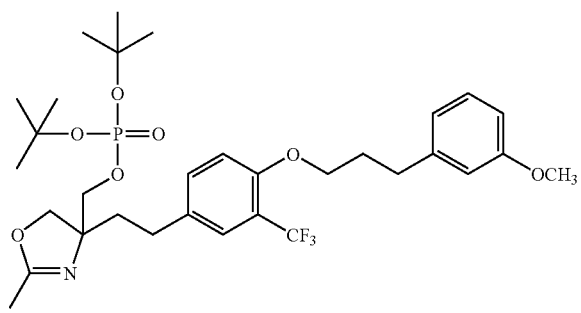

To a solution of compound 16-4 (420 mg) in N,N-dimethylformamide (10 ml) were added N,N-diisopropylethylamine (0.488 ml) and trimethyl orthoacetate (0.173 ml), and the mixture was stirred at 120° C. for 3 hr. Water was added to the reaction mixture, and the mixture was extracted with ethyl acetate, washed with water and saturated brine, and dried over anhydrous magnesium sulfate. The solvent was evaporated under reduced pressure to give a brown oil (440 mg). To a solution of the brown oil (440 mg) in methylene chloride (5 ml) and acetonitrile (2 ml) were added 1H-tetrazole (127 mg) and di-t-butyl diethylphosphoramidite (0.545 ml), and the mixture was stirred at room temperature for 2 hr. The reaction solution was ice-cooled, t-butyl hydroperoxide-containing decane solution (5-6M, 0.546 ml) was added, and the mixture was stirred at room temperature for 30 min. Saturated aqueous sodium hydrogen carbonate solution was added to the reaction mixture, and extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (370 mg) as a yellow oil.

$^1$H-NMR(CD$_3$OD) δ (ppm): 1.49(18H, s), 1.80-1.90(2H, m), 2.01(3H, s), 2.02-2.10(2H, m), 2.55-2.70(2H, m), 2.79 (2H, t, J=7.4 Hz), 3.71(3H, s), 3.89-3.92(2H, m), 4.00(2H, t, J=5.9 Hz), 4.17(1H, d, J=9.2 Hz), 4.32(1H, d, J=9.2 Hz), 6.70-6.78(3H, m), 7.00(1H, d, J=8.5 Hz), 7.16(1H, t, J=7.7 Hz), 7.37(1H, dd, J=8.5, 1.6 Hz), 7.43(1H, d, J=1.6 Hz).

(119-2) Synthesis of 2-amino-4-{4-[3-(3-methoxyphenyl)propoxy]-3-trifluoromethylphenyl}-2-(phosphoryloxymethyl)butanol (Compound 119-2)

Compound 119-1 (370 mg) was dissolved in ethanol (5 ml), concentrated hydrochloric acid (1 ml) was added, and the mixture was stirred at 50° C. for 2.5 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (255 mg) as a white solid.

MS(ESI)m/z: 508[M+H]

$^1$H-NMR(CD$_3$OD) δ (ppm): 1.94-2.01(2H, m), 2.04-2.10 (2H, m), 2.65-2.72(2H, m), 2.79(2H, t, J=7.4 Hz), 3.71(5H, brs), 3.96-4.04(4H, m), 6.70-6.78(3H, m), 7.02(1H, d, J=8.5 Hz), 7.16(1H, t, J=7.7 Hz), 7.42(1H, d, J=8.5 Hz), 7.48(1H, d, J=1.8 Hz).

Example 120

2-amino-4-{4-[3-(2-methoxyphenyl)propoxy]-3-trifluoromethylphenyl}-2-(phosphoryloxymethyl)butanol (120-1) Synthesis of 4-di(t-butyl)phosphoryloxymethyl-4-(2-{4-[3-(2-methoxyphenyl)propoxy]-3-trifluoromethylphenyl}ethyl)-2-methyl-2-oxazoline (Compound 120-1)

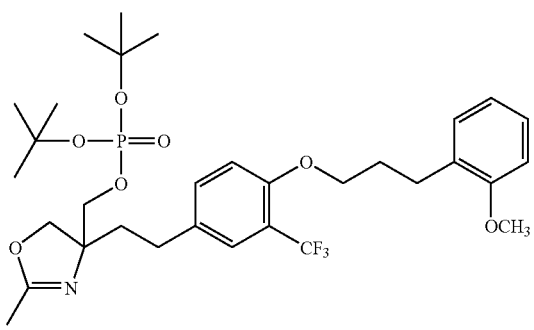

To a solution of compound 17-4 (440 mg) in N,N-dimethylformamide (10 ml) were added N,N-diisopropylethylamine (0.511 ml) and trimethyl orthoacetate (0.180 ml), and the mixture was stirred at 120° C. for 5 hr. Water was added to the reaction mixture, and the mixture was extracted with ethyl acetate, washed with water and saturated brine, and dried over anhydrous magnesium sulfate. The solvent was evaporated under reduced pressure to give a brown oil (440 mg). To a solution of the brown oil (440 mg) in methylene chloride (5 ml) and acetonitrile (2 ml) were added 1H-tetrazole (131 mg) and di-t-butyl diethylphosphoramidite (0.569 ml), and the mixture was stirred at room temperature for 1 hr. The reaction solution was ice-cooled, t-butyl hydroperoxide containing decane solution (5-6M, 0.570 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (390 mg) as a brown oil.

$^1$H-NMR(CD$_3$OD) δ (ppm): 1.49(18H, s), 1.82-1.90(2H, m), 2.01(3H, s), 2.01-2.09(2H, m), 2.52-2.70(2H, m), 2.80 (2H, t, J=7.4 Hz), 3.78(3H, s), 3.89-3.92(2H, m), 3.99(2H, t, J=6.0 Hz), 4.17(1H, d, J=9.2 Hz), 4.32(1H, d, J=9.2 Hz), 6.79-6.83(1H, m), 6.90(1H, d, J=8.2 Hz), 6.99(1H, d, J=8.5

Hz), 7.08(1H, dd, J=7.1, 1.3 Hz), 7.14(1H, d, J=8.8 Hz), 7.37(1H, d, J=8.5 Hz), 7.43(1H, d, J=1.3 Hz).

(120-2) Synthesis of 2-amino-4-{4-[3-(2-methoxyphenyl)propoxy]-3-trifluoromethylphenyl}-2-(phosphoryloxymethyl)butanol (Compound 120-2)

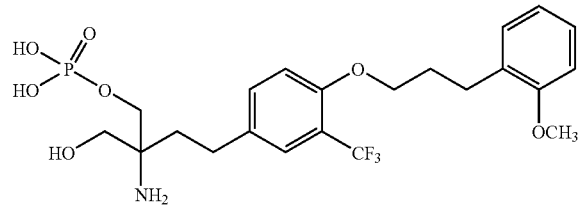

Compound 120-1 (390 mg) was dissolved in ethanol (5 ml), concentrated hydrochloric acid (1 ml) was added, and the mixture was stirred at 50° C. for 3 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (265 mg) as a white solid.

MS(ESI)m/z: 508[M+H]

$^1$H-NMR(CD$_3$OD) δ (ppm): 1.92-2.00(2H, m), 2.01-2.09 (2H, m), 2.65-2.74(2H, m), 2.80(2H, t, J=7.4 Hz), 3.71(2H, brs), 3.78(3H, s), 4.00(4H, brs), 6.81(1H, t, J=7.4 Hz), 6.90 (1H, d, J=8.2 Hz), 7.01(1H, d, J=8.4 Hz), 7.08(2H, t, J=7.1 Hz), 7.15(1H, t, J=7.4 Hz), 7.47(1H, brs).

Example 121

2-amino-4-{4-[3-(3,4-dimethoxyphenyl)propoxy]-3-trifluoromethylphenyl}-2-(phosphoryloxymethyl)butanol (121-1) Synthesis of 4-di(t-butyl)phosphoryloxymethyl-4-(2-{4-[3-(3,4-dimethoxyphenyl)propoxy]-3-trifluoromethylphenyl}ethyl)-2-methyl-2-oxazoline (Compound 121-1)

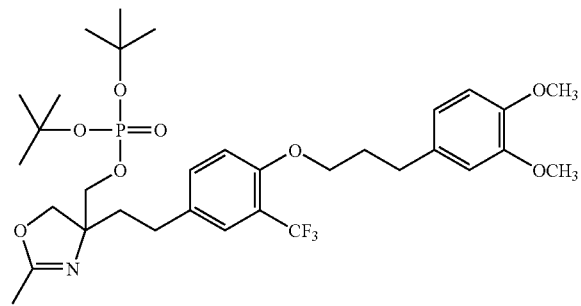

To a solution of compound 18-4 (470 mg) in N,N-dimethylformamide (10 ml) were added N,N-diisopropylethylamine (0.512 ml) and trimethyl orthoacetate (0.180 ml), and the mixture was stirred at 120° C. for 5.5 hr. Water was added to the reaction mixture, and the mixture was extracted with ethyl acetate, washed with water and saturated brine, and dried over anhydrous magnesium sulfate. The solvent was evaporated under reduced pressure to give a brown oil (460 mg). To a solution of the brown oil (460 mg) in methylene chloride (5 ml) and acetonitrile (2 ml) were added 1H-tetrazole (131 mg) and di-t-butyl diethylphosphoramidite (0.569 ml), and the mixture was stirred at room temperature for 2 hr. The reaction solution was ice-cooled, t-butyl hydroperoxide-containing decane solution (5-6M, 0.570 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (530 mg) as a brown oil.

$^1$H-NMR(CD$_3$OD) δ (ppm): 1.49(18H, s), 1.80-1.89(2H, m), 2.01(3H, s), 2.02-2.09(2H, m), 2.52-2.70(2H, m), 2.76 (2H, t, J=7.3 Hz), 3.71(3H, s), 3.78(3H, s), 3.88-3.94(2H, m), 3.99(2H, t, J=5.9 Hz), 4.17(1H, d, J=9.0 Hz), 4.32(1H, d, J=9.0 Hz), 6.73(1H, dd, J=8.1, 1.8 Hz), 6.78(1H, d, J=1.8 Hz), 6.84(1H, d, J=8.1 Hz), 7.00(1H, t, J=8.5 Hz), 7.37(1H, dd, J=8.5, 1.8 Hz), 7.43(1H, d, J=1.8 Hz).

(121-2) Synthesis of 2-amino-4-{4-[3-(3,4-dimethoxyphenyl)propoxy]-3-trifluoromethylphenyl}-2-(phosphoryloxymethyl)butanol (Compound 121-2)

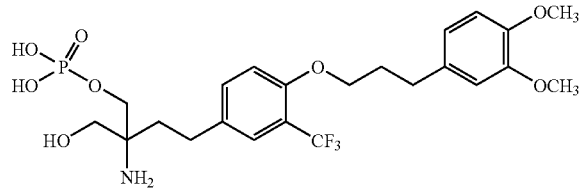

Compound 121-1 (530 mg) was dissolved in ethanol (5 ml), concentrated hydrochloric acid (1 ml) was added, and the mixture was stirred at 50° C. for 2.5 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (365 mg) as a white solid.

MS(ESI)m/z: 538[M+H]

$^1$H-NMR(CD$_3$OD) δ (ppm): 1.93-1.99(2H, m), 2.01-2.09 (2H, m), 2.63-2.73(2H, m), 2.76(2H, t, J=7.3 Hz), 3.71(5H, brs), 3.78(3H, s) 3.94-4.04(4H, m), 6.71-6.78(2H, m), 6.84 (1H, d, J=8.3 Hz), 7.02(1H, d, J=8.5 Hz), 7.42(1H, d, J=8.5 Hz), 7.48(1H, brs).

Example 122

2-amino-4-{4-[3-(2,4-dimethoxyphenyl)propoxy]-3-trifluoromethylphenyl}-2-(phosphoryloxymethyl)butanol (122-1) Synthesis of 4-di(t-butyl)phosphoryloxymethyl-4-(2-{4-[3-(2,4-dimethoxyphenyl)propoxy]-3-trifluoromethylphenyl}ethyl)-2-methyl-2-oxazoline (Compound 122-1)

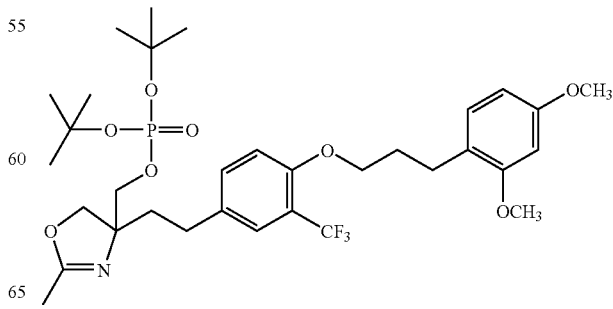

To a solution of compound 19-4 (390 mg) in N,N-dimethylformamide (10 ml) were added N,N-diisopropylethylamine (0.327 ml) and trimethyl orthoacetate (0.150 ml), and the mixture was stirred at 120° C. for 3 hr. Water was added to the reaction mixture, and the mixture was extracted with ethyl acetate, washed with water and saturated brine, and dried over anhydrous magnesium sulfate. The solvent was evaporated under reduced pressure to give a brown oil (370 mg). To a solution of the brown oil (370 mg) in methylene chloride (5 ml) and acetonitrile (2 ml) were added 1H-tetrazole (108 mg) and di-t-butyl diethylphosphoramidite (0.461 ml), and the mixture was stirred at room temperature for 2 hr. The reaction solution was ice-cooled, t-butyl hydroperoxide-containing decane solution (5-6M, 0.462 ml) was added, and the mixture was stirred at room temperature for 30 min. Saturated aqueous sodium hydrogen carbonate solution was added to the reaction mixture, and extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (440 mg) as a brown oil.

$^1$H-NMR(CD$_3$OD) δ (ppm): 1.48(18H, s), 1.81-1.89(2H, m), 1.95-2.02(2H, m), 2.01(3H, s), 2.52-2.69(2H, m), 2.72 (2H, t, J=7.3 Hz), 3.75(3H, s), 3.76(3H, s), 3.89-3.93(2H, m), 3.97(2H, t, J=6.1 Hz), 4.17(1H, d, J=9.0 Hz), 4.32(1H, d, J=9.0 Hz), 6.39(1H, dd, J=8.0, 2.4 Hz), 6.48(1H, d, J=2.4 Hz), 6.98(2H, t, J=7.8 Hz), 7.37(1H, d, J=8.5 Hz), 7.42(1H, d, J=1.8 Hz).

(122-2) Synthesis of 2-amino-4-{4-[3-(2,4-dimethoxyphenyl)propoxy]-3-trifluoromethylphenyl}-2-(phosphoryloxymethyl)butanol (Compound 122-2)

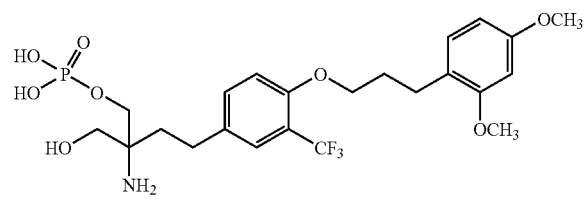

Compound 122-1 (440 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (305 mg) as a white solid.

MS (ESI)m/z: 538[M+H]

$^1$H-NMR(CD$_3$OD) δ (ppm): 1.94-2.02(4H, m), 2.64-2.78 (4H, m), 3.70(2H, brs), 3.75(3H, s), 3.76(3H, s), 3.95-4.03 (4H, m), 6.39(1H, dd, J=8.0, 2.3 Hz), 6.48(1H, d, J=2.3 Hz), 6.97(1H, J=8.0 Hz), 7.00(1H, d, J=8.5 Hz), 7.41(1H, d, J=8.5 Hz), 7.47(1H, brs).

Example 123

2-amino-4-{4-[3-(4-fluorophenyl)propoxy]-3-trifluoromethylphenyl}-2-(phosphoryloxymethyl)butanol (123-1) Synthesis of 4-di(t-butyl)phosphoryloxymethyl-4-(2-{4-[3-(4-fluorophenyl)propoxy]-3-trifluoromethylphenyl}ethyl)-2-methyl-2-oxazoline (Compound 123-1)

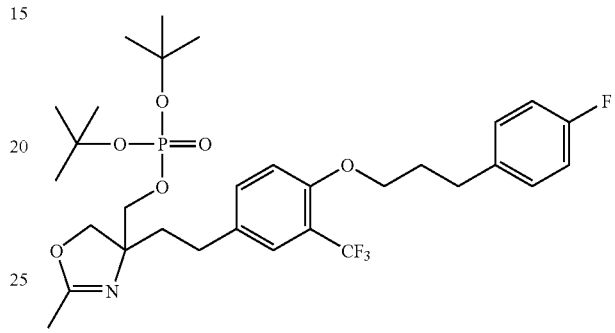

To a solution of compound 20-4 (400 mg) in N,N-dimethylformamide (10 ml) were added N,N-diisopropylethylamine (0.477 ml) and trimethyl orthoacetate (0.169 ml), and the mixture was stirred at 120° C. for 2 hr. Water was added to the reaction mixture, and the mixture was extracted with ethyl acetate, washed with water and saturated brine, and dried over anhydrous magnesium sulfate. The solvent was evaporated under reduced pressure to give a brown oil (400 mg). To a solution of the brown oil (400 mg) in methylene chloride (5 ml) and acetonitrile (2 ml) were added 1H-tetrazole (125 mg) and di-t-butyl diethylphosphoramidite (0.533 ml), and the mixture was stirred at room temperature for 1.5 hr. The reaction solution was ice-cooled, t-butyl hydroperoxide containing decane solution (5-6M, 0.534 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (440 mg) as a yellow oil.

$^1$H-NMR(CD$_3$OD) δ (ppm): 1.49(18H, s), 1.80-1.90(2H, m), 2.01(3H, s), 2.01-2.10(2H, m), 2.53-2.69(2H, m), 2.80 (2H, t, J=7.5 Hz), 3.89-3.92(2H, m), 4.01(2H, t, J=6.0 Hz), 4.17(1H, d, J=9.0 Hz), 4.32(1H, d, J=9.0 Hz), 6.95-7.02(3H, m), 7.16-7.22(2H, m), 7.38(1H, dd, J=8.5, 1.5 Hz), 7.43(1H, d, J=1.9 Hz).

(123-2) Synthesis of 2-amino-4-{4-[3-(4-fluorophenyl)propoxy]-3-trifluoromethylphenyl}-2-(phosphoryloxymethyl)butanol (Compound 123-2)

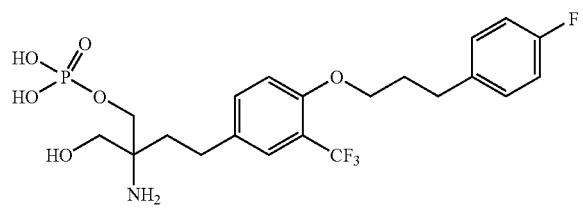

Compound 123-1 (440 mg) was dissolved in ethanol (6 ml), concentrated hydrochloric acid (1.5 ml) was added, and the mixture was stirred at 50° C. for 3 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (285 mg) as a pale-yellow solid.

MS(ESI)m/z: 496[M+H]

$^1$H-NMR(CD$_3$OD) δ (ppm): 1.93-1.99(2H, m), 2.00-2.12 (2H, m), 2.64-2.74(2H, m), 2.81(2H, t, J=7.5 Hz), 3.71(2H, brs), 3.95-4.03(4H, m), 6.94-7.04(3H, m), 7.16-7.21(2H, m), 7.43(1H, d, J=8.5 Hz), 7.47(1H, brs).

Example 124

2-amino-4-{4-[3-(3,4-methylenedioxyphenyl)propoxy]-3-trifluoromethylphenyl}-2-(phosphoryloxymethyl)butanol

(124-1) Synthesis of 4-di(t-butyl)phosphoryloxymethyl-2-methyl-4-(2-{4-[3-(3,4-methylenedioxyphenyl)propoxy]-3-trifluoromethylphenyl}ethyl)-2-oxazoline (Compound 124-1)

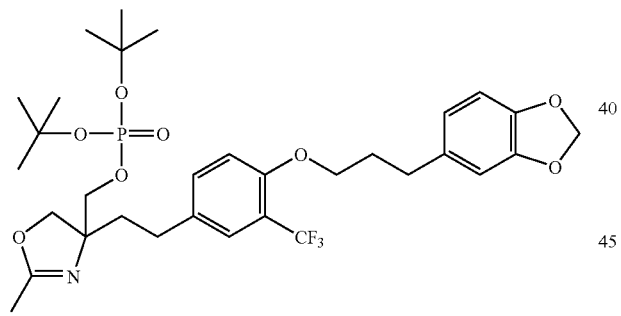

To a solution of compound 21-4 (450 mg) in N,N-dimethylformamide (10 ml) were added N,N-diisopropylethylamine (0.549 ml) and trimethyl orthoacetate (0.193 ml), and the mixture was stirred at 120° C. for 2 hr. Water was added to the reaction mixture, and the mixture was extracted with ethyl acetate, washed with water and saturated brine, and dried over anhydrous magnesium sulfate. The solvent was evaporated under reduced pressure to give a brown oil (470 mg). To a solution of the brown oil (470 mg) in methylene chloride (5 ml) and acetonitrile (2 ml) were added 1H-tetrazole (141 mg) and di-t-butyl diethylphosphoramidite (0.604 ml), and the mixture was stirred at room temperature for 1.5 hr. The reaction solution was ice-cooled, t-butyl hydroperoxide-containing decane solution (5-6M, 0.606 ml) was added, and the mixture was stirred at room temperature for 30 min. Saturated aqueous sodium hydrogen carbonate solution was added to the reaction mixture, and extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (520 mg) as a yellow oil.

$^1$H-NMR(CD$_3$OD) δ (ppm): 1.49(18H, s), 1.80-1.90(2H, m), 2.00(3H, s), 2.00-2.07(2H, m), 2.53-2.69(2H, m), 2.73 (2H, t, J=7.4 Hz), 3.89-3.92(2H, m), 3.99(2H, t, J=5.9 Hz), 4.17(1H, d, J=9.1 Hz), 4.32(1H, d, J=9.1 Hz), 5.87(2H, s), 6.62(1H, d, J=7.8 Hz), 6.64-6.70(2H, m), 7.01(1H, d, J=8.5 Hz), 7.37(1H, dd, J=8.5, 1.8 Hz), 7.43(1H, d, J=1.8 Hz).

(124-2) Synthesis of 2-amino-4-{4-[3-(3,4-methylenedioxyphenyl)propoxy]-3-trifluoromethylphenyl}-2-(phosphoryloxymethyl)butanol (Compound 124-2)

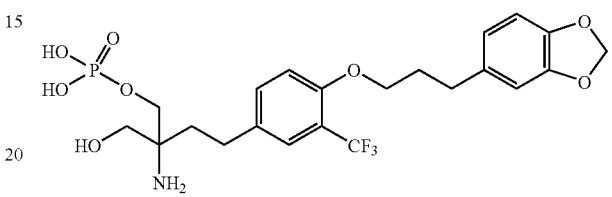

Compound 124-1 (520 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (7 ml) and propylene oxide (7 ml) were added to the residue. The precipitated powder was collected by filtration, and washed with ethyl acetate and diethyl ether to give the object product (365 mg) as a white solid.

MS (ESI)m/z: 522[M+H]

$^1$H-NMR(CD$_3$OD) δ (ppm): 1.94-2.07(4H, m), 2.60-2.76 (4H, m), 3.71(2H, brs), 3.96-4.04(4H, m), 5.87(2H, s), 6.62-6.71(3H, m), 7.02(1H, d, J=8.5 Hz), 7.42(1H, dd, J=8.3, 1.5 Hz), 7.47(1H, brs).

Example 125

2-amino-4-{4-[3-(2-fluorophenyl)propoxy]-3-trifluoromethylphenyl}-2-(phosphoryloxymethyl)butanol

(125-1) Synthesis of 4-di(t-butyl)phosphoryloxymethyl-4-(2-{4-[3-(2-fluorophenyl)propoxy]-3-trifluoromethylphenyl}ethyl)-2-methyl-2-oxazoline (Compound 125-1)

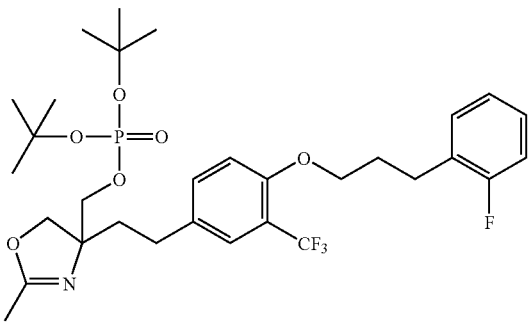

To a solution of compound 22-4 (420 mg) in N,N-dimethylformamide (10 ml) were added N,N-diisopropylethylamine (0.501 ml) and trimethyl orthoacetate (0.176 ml), and the mixture was stirred at 120° C. for 2.5 hr. Water was added to the reaction mixture, and the mixture was extracted with ethyl acetate, washed with water and saturated brine, and dried over anhydrous magnesium sulfate. The solvent was evaporated under reduced pressure to give a brown oil (410 mg). To a solution of the brown oil (410 mg) in methylene chloride (5 ml) and acetonitrile (2 ml) were added 1H-tetrazole (130 mg)

and di-t-butyl diethylphosphoramidite (0.557 ml), and the mixture was stirred at room temperature for 2 hr. The reaction solution was ice-cooled, t-butyl hydroperoxide containing decane solution (5-6M, 0.558 ml) was added, and the mixture was stirred at room temperature for 30 min. Saturated aqueous sodium hydrogen carbonate solution was added to the reaction mixture, and extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (460 mg) as a yellow oil.

$^1$H-NMR(CD$_3$OD) δ (ppm): 1.49(18H, s), 1.82-1.90(2H, m), 2.01(3H, s), 2.01-2.11(2H, m), 2.52-2.69(2H, m), 2.86 (2H, t, J=7.5 Hz), 3.89-3.92(2H, m), 4.03(2H, t, J=5.9 Hz), 4.18(1H, d, J=9.0 Hz), 4.32(1H, d, J=9.0 Hz), 7.00-7.08(3H, m), 7.17-7.22(2H, m), 7.38(1H, d, J=8.5 Hz), 7.43(1H, d, J=1.5 Hz).

(125-2) Synthesis of 2-amino-4-{4-[3-(2-fluorophenyl)propoxy]-3-trifluoromethylphenyl}-2-(phosphoryloxymethyl)butanol (Compound 125-2)

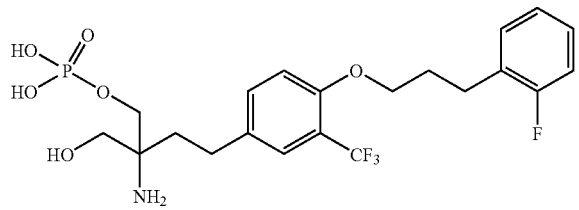

Compound 125-1 (460 mg) was dissolved in ethanol (5 ml), concentrated hydrochloric acid (1 ml) was added, and the mixture was stirred at 50° C. for 3.5 hr. The solvent was concentrated under reduced pressure, and methanol (5 ml), diethyl ether (7 ml) and propylene oxide (7 ml) were added to the residue. The precipitated powder was collected by filtration, and washed with ethyl acetate and diethyl ether to give the object product (335 mg) as a white solid.

MS(ESI)m/z: 496[M+H]

$^1$H-NMR(CD$_3$OD) δ (ppm): 1.94-1.99(2H, m), 2.01-2.12 (2H, m), 2.64-2.74(2H, m), 2.86(2H, t, J=7.5 Hz), 3.71(2H, brs), 3.97-4.06(4H, m), 6.98-7.08(3H, m), 7.17-7.23(2H, m), 7.42(1H, d, J=8.3 Hz), 7.47(1H, brs).

Example 126

2-amino-4-{4-[3-(3-fluorophenyl)propoxy]-3-trifluoromethylphenyl}-2-(phosphoryloxymethyl)butanol (126-1) Synthesis of 4-di(t-butyl)phosphoryloxymethyl-4-(2-{4-[3-(3-fluorophenyl)propoxy]-3-trifluoromethylphenyl}ethyl)-2-methyl-2-oxazoline (Compound 126-1)

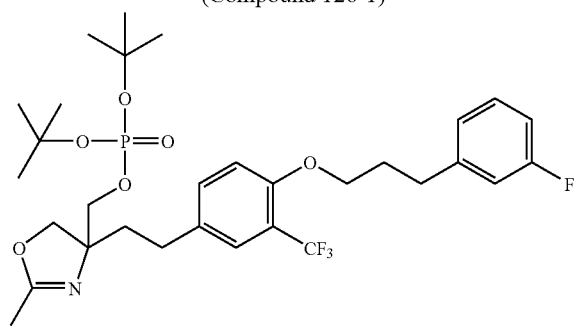

To a solution of compound 23-4 (390 mg) in N,N-dimethylformamide (10 ml) were added N,N-diisopropylethylamine (0.465 ml) and trimethyl orthoacetate (0.163 ml), and the mixture was stirred at 120° C. for 2 hr. Water was added to the reaction mixture, and the mixture was extracted with ethyl acetate, washed with water and saturated brine, and dried over anhydrous magnesium sulfate. The solvent was evaporated under reduced pressure to give a brown oil (410 mg). To a solution of the brown oil (410 mg) in methylene chloride (5 ml) and acetonitrile (2 ml) were added 1H-tetrazole (120 mg) and di-t-butyl diethylphosphoramidite (0.515 ml), and the mixture was stirred at room temperature for 2 hr. The reaction solution was ice-cooled, t-butyl hydroperoxide-containing decane solution (5-6M, 0.516 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (480 mg) as a yellow oil.

$^1$H-NMR(CD$_3$OD) δ (ppm): 1.49(18H, s), 1.80-1.89(2H, m), 2.00(3H, s), 2.01-2.12(2H, m), 2.52-2.69(2H, m), 2.83 (2H, t, J=7.5 Hz), 3.89-3.92(2H, m), 4.02(2H, t, J=5.9 Hz), 4.18(1H, d, J=9.0 Hz), 4.32(1H, d, J=9.0 Hz), 6.85-6.95(2H, m), 6.99-7.02(2H, m), 7.24-7.29(1H, m), 7.38(1H, d, J=8.5 Hz), 7.43(1H, d, J=1.9 Hz).

(126-2) Synthesis of 2-amino-4-{4-[3-(3-fluorophenyl)propoxy]-3-trifluoromethylphenyl}-2-(phosphoryloxymethyl)butanol (Compound 126-2)

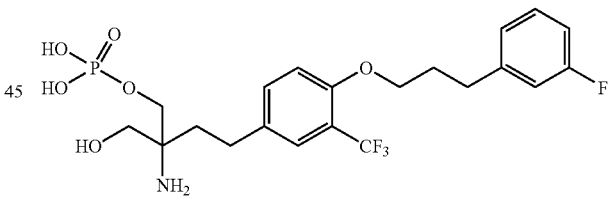

Compound 126-1 (480 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (7 ml) and propylene oxide (7 ml) were added to the residue. The precipitated powder was collected by filtration, and washed with ethyl acetate and diethyl ether to give the object product (185 mg) as a white solid.

MS(ESI)m/z: 496[M+H]

$^1$H-NMR(CD$_3$OD) δ (ppm): 1.93-2.01(2H, m), 2.02-2.14 (2H, m), 2.64-2.76(2H, m), 2.83(2H, brs), 3.71(2H, brs), 3.94-4.05(4H, m), 6.85-6.96(2H, m), 6.98-7.07(2H, m), 7.24 (1H, brs), 7.43(1H, d, J=7.8 Hz), 7.48(1H, brs).

Example 127

2-amino-2-(phosphoryloxymethyl)-4-{3-trifluoromethyl-4-[3-(2-trifluoromethylphenyl)propoxy]phenyl}butanol (127-1) Synthesis of 4-di(t-butyl)phosphoryloxymethyl-2-methyl-4-(2-{3-trifluoromethyl-4-[3-(2-trifluoromethylphenyl)propoxy]phenyl}ethyl)-2-oxazoline (Compound 127-1)

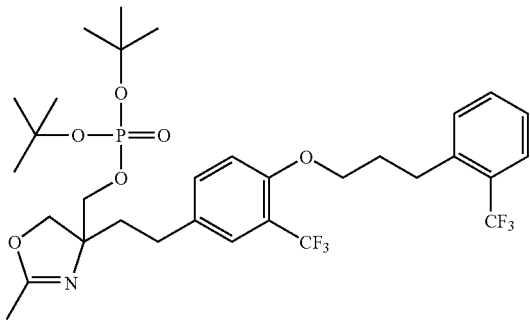

To a solution of compound 24-4 (480 mg) in N,N-dimethylformamide (10 ml) were added N,N-diisopropylethylamine (0.517 ml) and trimethyl orthoacetate (0.182 ml), and the mixture was stirred at 120° C. for 2 hr. Water was added to the reaction mixture, and the mixture was extracted with ethyl acetate, washed with water and saturated brine, and dried over anhydrous magnesium sulfate. The solvent was evaporated under reduced pressure to give a brown oil (470 mg). To a solution of the brown oil (470 mg) in methylene chloride (5 ml) and acetonitrile (2 ml) were added 1H-tetrazole (134 mg) and di-t-butyl diethylphosphoramidite (0.576 ml), and the mixture was stirred at room temperature for 1.5 hr. The reaction solution was ice-cooled, t-butyl hydroperoxide-containing decane solution (5-6M, 0.576 ml) was added, and the mixture was stirred at room temperature for 30 min. Saturated aqueous sodium hydrogen carbonate solution was added to the reaction mixture, and extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (550 mg) as a yellow oil.

$^1$H-NMR(CD$_3$OD) δ (ppm): 1.49(18H, s), 1.80-1.90(2H, m), 2.01(3H, s), 2.07-2.14(2H, m), 2.52-2.71(2H, m), 3.01 (2H, t, J=7.9 Hz), 3.90-3.92(2H, m), 4.10(2H, t, J=5.9 Hz), 4.18(1H, d, J=9.1 Hz), 4.32(1H, d, J=9.1 Hz), 7.06(1H, d, J=8.4 Hz), 7.32-7.46(4H, m), 7.52(1H, t, J=7.5 Hz), 7.64(1H, d, J=7.8 Hz).

(127-2) Synthesis of 2-amino-2-(phosphoryloxymethyl)-4-{3-trifluoromethyl-4-[3-(2-trifluoromethylphenyl)propoxy]phenyl}butanol (Compound 127-2)

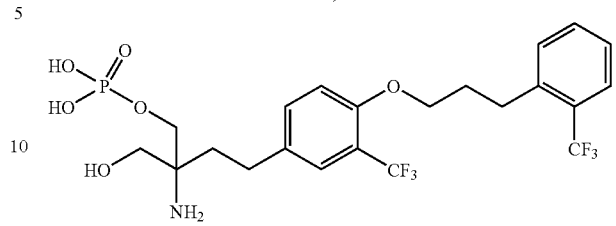

Compound 127-1 (550 mg) was dissolved in ethanol (6 ml), concentrated hydrochloric acid (1.2 ml) was added, and the mixture was stirred at 50° C. for 4 hr. The solvent was concentrated under reduced pressure, and methanol (5 ml), diethyl ether (7 ml) and propylene oxide (7 ml) were added to the residue. The precipitated powder was collected by filtration, and washed with ethyl acetate and diethyl ether to give the object product (377 mg) as a white solid.

MS(ESI)m/z: 546[M+H]

$^1$H-NMR(CD$_3$OD) δ (ppm): 1.94-2.02(2H, m), 2.03-2.15 (2H, m), 2.64-2.76(2H, m), 3.01(2H, t, J=7.5 Hz), 3.71(2H, brs), 3.96-4.07(2H, m), 4.11(2H, t, J=5.7 Hz), 7.08(1H, d, J=8.4 Hz), 7.35(1H, t, J=7.5 Hz), 7.41-7.56(4H, m), 7.64(1H, d, J=7.9 Hz).

Example 128

2-amino-4-{4-[3-(3-chlorophenyl)propoxy]-3-trifluoromethylphenyl}-2-(phosphoryloxymethyl)butanol (128-1) Synthesis of 4-di(t-butyl)phosphoryloxymethyl-4-(2-{4-[3-(3-chlorophenyl)propoxy]-3-trifluoromethylphenyl}ethyl)-2-methyl-2-oxazoline (Compound 128-1)

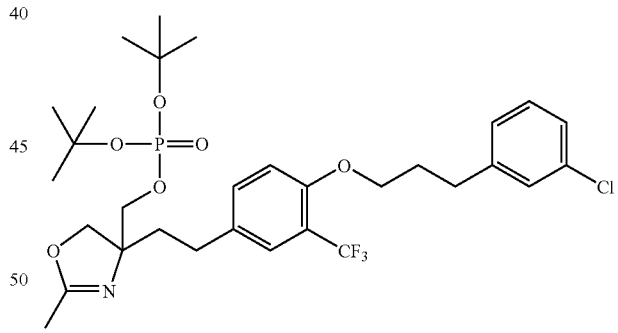

To a solution of compound 25-4 (390 mg) in N,N-dimethylformamide (10 ml) were added N,N-diisopropylethylamine (0.448 ml) and trimethyl orthoacetate (0.157 ml), and the mixture was stirred at 120° C. for 3 hr. Water was added to the reaction mixture, and the mixture was extracted with ethyl acetate, washed with water and saturated brine, and dried over anhydrous magnesium sulfate. The solvent was evaporated under reduced pressure to give a brown oil (360 mg). To a solution of the brown oil (360 mg) in methylene chloride (5 ml) and acetonitrile (2 ml) were added 1H-tetrazole (111 mg) and di-t-butyl diethylphosphoramidite (0.473 ml), and the mixture was stirred at room temperature for 2 hr. The reaction solution was ice-cooled, t-butyl hydroperoxide-containing decane solution (5-6M, 0.474 ml) was added, and the mixture was stirred at room temperature for 30 min. Saturated aqueous sodium hydrogen carbonate solution was added to the reaction mixture, and extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (370 mg) as a brown oil.

$^1$H-NMR(CD$_3$OD) δ (ppm): 1.49(18H, s), 1.80-1.90(2H, m), 2.01(3H, s), 2.02-2.11(2H, m), 2.51-2.71(2H, m), 2.82 (2H, t, J=7.5 Hz), 3.89-3.92(2H, m), 4.01(2H, t, J=5.9 Hz), 4.18(1H, d, J=9.0 Hz), 4.32(1H, d, J=9.0 Hz), 6.99-7.03(1H, m), 7.10-7.25(4H, m), 7.38(1H, t, J=8.3 Hz), 7.43(1H, brs).

(128-2) Synthesis of 2-amino-4-{4-[3-(3-chlorophenyl)propoxy]-3-trifluoromethylphenyl}-2-(phosphoryloxymethyl)butanol (Compound 128-2)

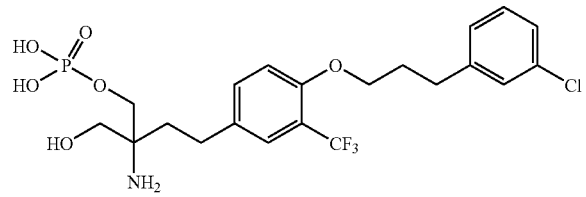

Compound 128-1 (370 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (7 ml) and propylene oxide (7 ml) were added to the residue. The precipitated powder was collected by filtration, and washed with ethyl acetate and diethyl ether to give the object product (263 mg) as a pale-brown solid.

MS (ESI)m/z: 512[M+H]

$^1$H-NMR(CD$_3$OD) δ (ppm): 1.92-2.01(2H, m), 2.02-2.12 (2H, m), 2.64-2.76(2H, m), 2.82(2H, t, J=7.5 Hz), 3.70(2H, brs), 3.96-4.03(4H, m), 7.04(1H, d, J=8.5 Hz), 7.10-7.26(4H, m), 7.43(1H, d, J=8.5 Hz), 7.48(1H, brs).

Example 129

2-amino-4-{4-[3-(4-chlorophenyl)propoxy]-3-trifluoromethylphenyl}-2-(phosphoryloxymethyl)butanol (129-1) Synthesis of 4-di(t-butyl)phosphoryloxymethyl-4-(2-{4-[3-(4-chlorophenyl)propoxy]-3-trifluoromethylphenyl}ethyl)-2-methyl-2-oxazoline (Compound 129-1)

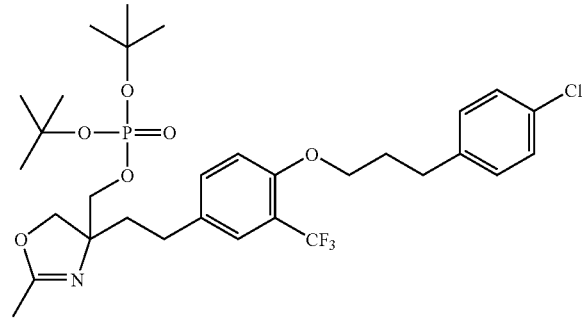

To a solution of compound 26-2 (83 mg) in N,N-dimethylformamide (7 ml) were added N,N-diisopropylethylamine (0.095 ml) and trimethyl orthoacetate (0.034 ml), and the mixture was stirred at 120° C. for 5 hr. N,N-diisopropylethylamine (0.095 ml) and trimethyl orthoacetate (0.034 ml) were further added to the reaction mixture, and the mixture was stirred at 120° C. for 3 hr. Water was added to the reaction mixture, and the mixture was extracted with ethyl acetate, washed with water and saturated brine, and dried over anhydrous magnesium sulfate. The solvent was evaporated under reduced pressure to give a brown oil (90 mg). To a solution of the brown oil (90 mg) in methylene chloride (3 ml) and acetonitrile (1 ml) were added 1H-tetrazole (25 mg) and di-t-butyl diethylphosphoramidite (0.108 ml), and the mixture was stirred at room temperature for 2 hr. The reaction solution was ice-cooled, t-butyl hydroperoxide-containing decane solution (5-6M, 0.108 ml) was added, and the mixture was stirred at room temperature for 30 min. Saturated aqueous sodium hydrogen carbonate solution was added to the reaction mixture, and extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (70 mg) as a yellow oil.

$^1$H-NMR (CD$_3$OD) δ (ppm): 1.49(18H, s), 1.80-1.90(2H, m), 2.01(3H, s), 2.02-2.11(2H, m), 2.51-2.71(2H, m), 2.81 (2H, t, J=7.5 Hz), 3.89-3.92(2H, m), 4.01(2H, t, J=5.9 Hz), 4.18(1H, d, J=9.1 Hz), 4.32(1H, d, J=9.1 Hz), 7.01(1H, d, J=8.5 Hz), 7.18(2H, d, J=8.2 Hz), 7.25(2H, d, J=8.5 Hz), 7.38(1H, dd, J=8.2, 1.5 Hz), 7.43(1H, brs).

(129-2) Synthesis of 2-amino-4-{4-[3-(4-chlorophenyl)propoxy]-3-trifluoromethylphenyl}-2-(phosphoryloxymethyl)butanol (Compound 129-2)

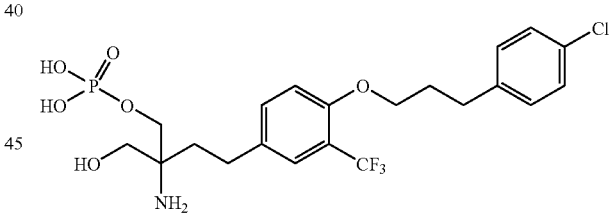

Compound 129-1 (70 mg) was dissolved in ethanol (4 ml), concentrated hydrochloric acid (0.8 ml) was added, and the mixture was stirred at 50° C. for 3 hr. The solvent was concentrated under reduced pressure, and methanol (2 ml), diethyl ether (5 ml) and propylene oxide (5 ml) were added to the residue. The precipitated powder was collected by filtration, and washed with ethyl acetate and diethyl ether to give the object product (35 mg) as a pale-yellow solid.

MS (ESI)m/z: 512[M+H]

$^1$H-NMR(CD$_3$OD) δ (ppm): 1.92-2.01(2H, m), 2.02-2.11 (2H, m), 2.64-2.76(2H, m), 2.81(2H, t, J=7.5 Hz), 3.70(2H, brs), 3.96-4.03(4H, m), 7.03(1H, d, J=8.5 Hz), 7.18(2H, d, J=8.3 Hz), 7.25(2H, d, J=8.3 Hz), 7.43(1H, d, J=8.3 Hz), 7.48(1H, brs).

Example 130 phosphoric acid mono(2-amino-2-methyl-4-{3-trifluoromethyl-4-[3-(4-trifluoromethylphenyl)propoxy]phenyl}butyl)ester (130-1) Synthesis of [1-di(t-butyl)phosphoryloxymethyl-1-methyl-3-{3-trifluoromethyl-4-[3-(4-trifluoromethylphenyl)propoxy]phenyl}propyl]carbamic acid t-butyl ester (Compound 130-1)

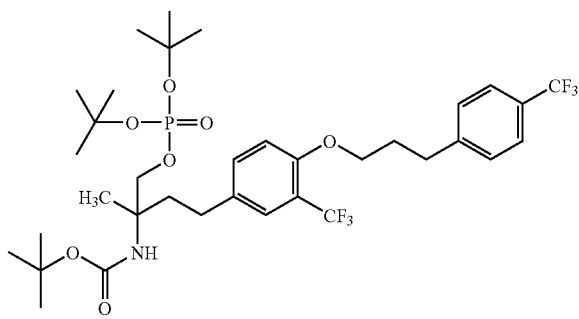

To a solution of compound 27-6 (360 mg) in methanol (10 ml) were added triethylamine (0.312 ml) and di-t-butyl-dicarbonate (242 mg), and the mixture was stirred at room temperature for 22 hr. Di-t-butyl-dicarbonate (242 mg) was further added to the reaction mixture, and the mixture was stirred at room temperature for 6 hr. Water was added to the reaction mixture, and the mixture was extracted with ethyl acetate. The organic layer was washed with saturated brine and dried over anhydrous magnesium sulfate. The solvent was evaporated under reduced pressure. The obtained residue was purified by silica gel column chromatography (hexane:ethyl acetate=1:1-1:2) to give an amine-protected compound as a colorless oil (420 mg). To a solution of the colorless oil (420 mg) in methylene chloride (5 ml) and acetonitrile (2 ml) were added 1H-tetrazole (104 mg) and di-t-butyl diethylphosphoramidite (0.443 ml), and the mixture was stirred at room temperature for 2 hr. The reaction solution was ice-cooled, t-butyl hydroperoxide containing decane solution (5-6M, 0.444 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:1-1:2) to give the object product (580 mg) as a colorless oil.

$^1$H-NMR(CD$_3$OD) δ (ppm): 1.30(3H, s), 1.45(9H, s), 1.49 (18H, s), 1.71-1.79(1H, m), 2.09-2.16(3H, m), 2.58-2.66(2H, m), 2.91(1H, t, J=7.5 Hz), 3.94(1H, dd, J=9.6, 4.6 Hz), 4.03 (2H, t, J=5.9 Hz), 4.11(1H, dd, J=9.6, 4.6 Hz), 7.01(1H, d, J=8.5 Hz), 7.35-7.44(4H, m), 7.56(2H, d, J=8.1 Hz).

(130-2) Synthesis of phosphoric acid mono(2-amino-2-methyl-4-{3-trifluoromethyl-4-[3-(4-trifluoromethylphenyl)propoxy]phenyl}butyl)ester (Compound 130-2)

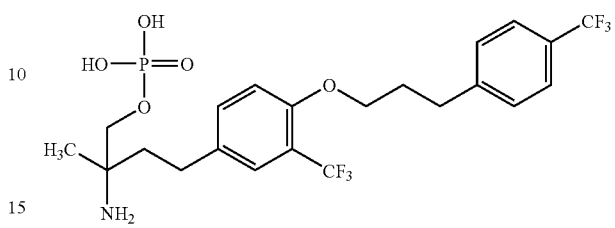

Compound 130-1 (580 mg) was dissolved in methylene chloride (6 ml), hydrogen chloride containing dioxane (4 mol/l, 3 ml) was added, and the mixture was stirred at room temperature for 4.5 hr. The solvent was concentrated under reduced pressure, and methanol (3 ml), diethyl ether (7 ml) and propylene oxide (7 ml) were added to the residue. The precipitated powder was collected by filtration, and washed with ethyl acetate and diethyl ether to give the object product (110 mg) as a white solid.

MS (ESI)m/z: 530[M+H]

$^1$H-NMR(CD$_3$OD) δ (ppm): 1.38(3H, s), 1.80-1.91(1H, m), 1.96-2.08(1H, m), 2.10-2.18(2H, m), 2.60-2.69(2H, m), 2.92(2H, t, J=7.6 Hz), 3.85(1H, dd, J=5.4, 11.4 Hz), 3.94(1H, dd, J=5.9, 11.4 Hz), 4.04(2H, t, J=5.9 Hz), 7.05(1H, d, J=8.4 Hz), 7.38-7.48(4H, m), 7.56(2H, d, J=8.1 Hz).

Example 131

(S)-phosphoric acid mono(2-amino-2-methyl-4-{3-trifluoromethyl-4-[3-(4-trifluoromethylphenyl)propoxy]phenyl}butyl)ester (131-1) Synthesis of (S)-[1-di(t-butyl)phosphoryloxymethyl-1-methyl-3-{3-trifluoromethyl-4-[3-(4-trifluoromethylphenyl)propoxy]phenyl}propyl]carbamic acid t-butyl ester (Compound 131-1)

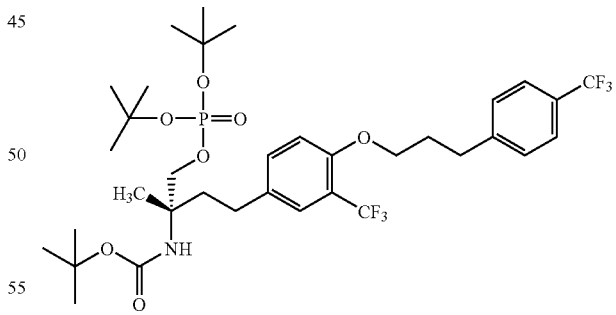

To a solution of compound 28-2 (125 mg) in methanol (5 ml) were added triethylamine (0.108 ml) and di-t-butyl-dicarbonate (114 mg), and the mixture was stirred at room temperature for 18 hr. Water was added to the reaction mixture, and the mixture was extracted with ethyl acetate. The organic layer was washed with saturated brine and dried over anhydrous magnesium sulfate. The solvent was evaporated under reduced pressure. The obtained residue was purified by silica gel column chromatography to give an amine-protected compound as a colorless oil (120 mg). To a solution of the colorless oil (120 mg) in methylene chloride (3 ml) and acetonitrile (2 ml) were added 1H-tetrazole (31 mg) and di-t-butyl diethylphosphoramidite (0.132 ml), and the mixture was stirred at room temperature for 2 hr. The reaction solution was ice-cooled, t-butyl hydroperoxide containing decane solution (5-6M, 0.132 ml) was added, and the mixture was stirred at room temperature for 30 min. Saturated aqueous sodium hydrogen carbonate solution was added to the reaction mixture, and extracted with chloroform. The organic layer was dried over anhydrous magnesium sulfate and the solvent was evaporated under reduced pressure. The obtained residue was purified by silica gel column chromatography to give the object product (140 mg) as a colorless oil.

$^1$H-NMR(CD$_3$OD) δ (ppm): 1.30(3H, s), 1.45(9H, s), 1.49 (18H, s), 1.71-1.79(1H, m), 2.09-2.16(3H, m), 2.58-2.66(2H, m), 2.91(2H, t, J=7.5 Hz), 3.94(1H, dd, J=9.6, 4.6 Hz), 4.03 (2H, t, J=5.9 Hz), 4.11(1H, dd, J=9.6, 4.6 Hz), 7.01(1H, d, J=8.5 Hz), 7.35-7.42(4H, m), 7.56(2H, d, J=8.1 Hz).

(131-2) Synthesis of (S)-phosphoric acid mono(2-amino-2-methyl-4-{3-trifluoromethyl-4-[3-(4-trifluoromethylphenyl)propoxy]phenyl}butyl)ester (Compound 131-2)

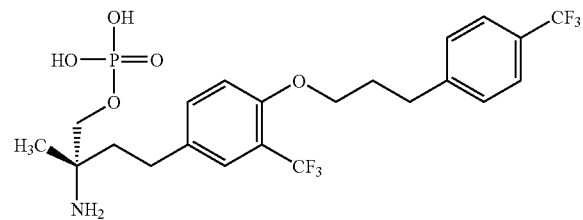

Compound 131-1 (140 mg) was dissolved in methylene chloride (3 ml), hydrogen chloride containing dioxane (4 mol/l, 2 ml) was added, and the mixture was stirred at room temperature for 3.5 hr. The solvent was concentrated under reduced pressure, and isopropyl alcohol (5 ml) and propylene oxide (5 ml) were added to the residue. The precipitated powder was collected by filtration, and washed with isopropyl alcohol to give the object product (90 mg) as a white solid.

MS(ESI)m/z: 530[M+H]

$^1$H-NMR(CD$_3$OD) δ (ppm): 1.38(3H, s), 1.80-1.91(1H, m), 1.96-2.05(1H, m), 2.09-2.16(2H, m), 2.60-2.77(2H, m), 2.92(2H, t, J=7.6 Hz), 3.85(1H, dd, J=11.4, 5.3 Hz), 3.94(1H, dd, J=11.4, 5.9 Hz), 4.04(2H, t, J=5.9 Hz), 7.05(1H, d, J=8.6 Hz), 7.38-7.48(4H, m), 7.56(2H, d, J=8.1 Hz).

Example 132

(R)-phosphoric acid mono(2-amino-2-methyl-4-{3-trifluoromethyl-4-[3-(4-trifluoromethylphenyl)propoxy]phenyl}butyl)ester (132-1) Synthesis of (R)-[1-di(t-butyl)phosphoryloxymethyl-1-methyl-3-{3-trifluoromethyl-4-[3-(4-trifluoromethylphenyl)propoxy]phenyl}propyl]carbamic acid t-butyl ester (Compound 132-1)

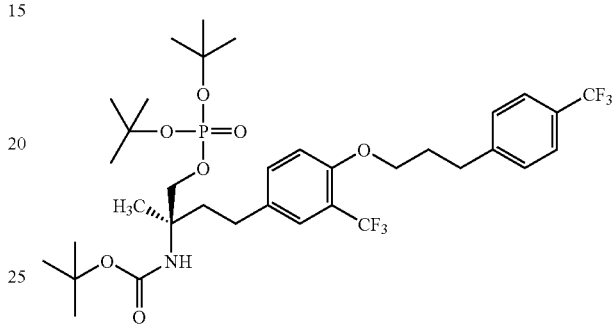

To a solution of compound 29-1 (117 mg) in methanol (5 ml) were added triethylamine (0.102 ml) and di-t-butyl-dicarbonate (105 mg), and the mixture was stirred at room temperature for 18 hr. Di-t-butyl-dicarbonate (50 mg) was further added, and the mixture was stirred at room temperature for 3 hr. Water was added to the reaction mixture, and the mixture was extracted with ethyl acetate. The organic layer was washed with saturated brine and dried over anhydrous magnesium sulfate. The solvent was evaporated under reduced pressure. The obtained residue was purified by silica gel column chromatography to give an amine-protected compound as a colorless oil (140 mg). To a solution of the colorless oil (140 mg) in methylene chloride (5 ml) and acetonitrile (1 ml) were added 1H-tetrazole (34 mg) and di-t-butyl diethylphosphoramidite (0.144 ml), and the mixture was stirred at room temperature for 2 hr. The reaction solution was ice-cooled, t-butyl hydroperoxide-containing decane solution (5-6M, 0.144 ml) was added, and the mixture was stirred at room temperature for 30 min. Saturated aqueous sodium hydrogen carbonate solution was added to the reaction mixture, and extracted with chloroform. The organic layer was dried over anhydrous magnesium sulfate and the solvent was evaporated under reduced pressure. The obtained residue was purified by silica gel column chromatography to give the object product (150 mg) as a colorless oil.

$^1$H-NMR(CD$_3$OD) δ (ppm): 1.30(3H, s), 1.45(9H, s), 1.49 (18H, s), 1.71-1.79(1H, m), 2.08-2.15(3H, m), 2.58-2.65(2H, m), 2.91(2H, t, J=7.6 Hz), 3.97(1H, dd, J=9.7, 4.6 Hz), 4.03 (2H, t, J=5.9 Hz), 4.11(1H, dd, J=9.7, 4.6 Hz), 7.01(1H, d, J=8.5 Hz), 7.35-7.42(4H, m), 7.56(2H, d, J=8.1 Hz).

(132-2) Synthesis of (R)-phosphoric acid mono(2-amino-2-methyl-4-{3-trifluoromethyl-4-[3-(4-trifluoromethylphenyl)propoxy]phenyl}butyl)ester (Compound 132-2)

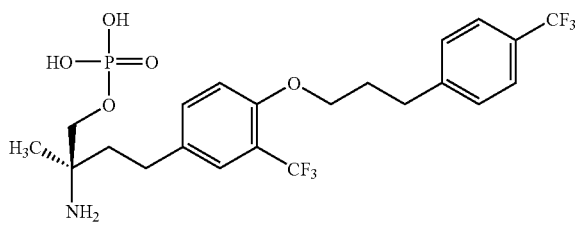

Compound 132-1 (150 mg) was dissolved in methylene chloride (3 ml), hydrogen chloride-containing dioxane (4 mol/l, 2 ml) was added, and the mixture was stirred at room temperature for 3.5 hr. The solvent was concentrated under reduced pressure, and isopropyl alcohol (5 ml) and propylene oxide (5 ml) were added to the residue. The precipitated powder was collected by filtration, and washed with isopropyl alcohol to give the object product (74 mg) as a white solid.

MS(ESI)m/z: 530[M+H]

$^1$H-NMR(CD$_3$OD) δ (ppm): 1.38(3H, s), 1.82-1.91(1H, m), 1.97-2.05(1H, m), 2.08-2.16(2H, m), 2.60-2.77(2H, m), 2.92(2H, t, J=7.6 Hz), 3.85(1H, dd, J=11.4, 5.3 Hz), 3.94(1H, dd, J=11.4, 5.9 Hz), 4.04(2H, t, J=5.9 Hz), 7.05(1H, d, J=8.5 Hz), 7.38-7.48(4H, m), 7.56(2H, d, J=8.0 Hz).

Example 133 phosphoric acid mono(2-amino-2-ethyl-4-{3-trifluoromethyl-4-[3-(4-trifluoromethylphenyl)propoxy]phenyl}butyl)ester (133-1) Synthesis of [1-di(t-butyl)phosphoryloxymethyl-1-ethyl-3-{3-trifluoromethyl-4-[3-(4-trifluoromethylphenyl)propoxy]phenyl}propyl]carbamic acid t-butyl ester (Compound 133-1)

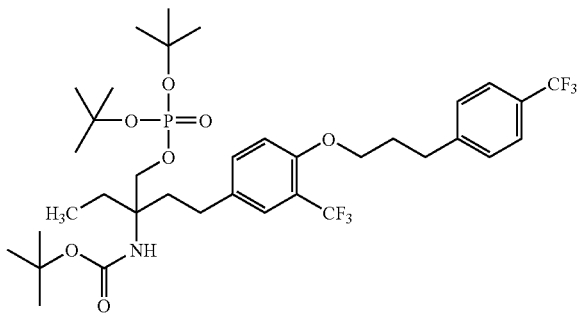

To a solution of compound 30-6 (430 mg) in methanol (10 ml) were added triethylamine (0.363 ml) and di-t-butyl-dicarbonate (282 mg), and the mixture was stirred at room temperature for 23 hr. Di-t-butyl-dicarbonate (200 mg) was further added to the reaction mixture, and the mixture was stirred at room temperature for 24 hr. Water was added to the reaction mixture, and the mixture was extracted with ethyl acetate. The organic layer was washed with saturated brine and dried over anhydrous magnesium sulfate. The solvent was evaporated under reduced pressure. The obtained residue was purified by silica gel column chromatography (hexane:ethyl acetate=1:1-1:2) to give an amine-protected compound as a colorless oil (410 mg). To a solution of the colorless oil (410 mg) in methylene chloride (5 ml) and acetonitrile (2 ml) were added 1H-tetrazole (102 mg) and di-t-butyl diethylphosphoramidite (0.437 ml), and the mixture was stirred at room temperature for 1.5 hr. The reaction solution was ice-cooled, t-butyl hydroperoxide-containing decane solution (5-6M, 0.438 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:1-1:2) to give the object product (640 mg) as a colorless oil.

$^1$H-NMR(CD$_3$OD) δ (ppm): 0.91(3H, t, J=7.3 Hz), 1.45 (9H, s), 1.50(18H, s), 1.65-1.90(3H, m), 1.91-2.14(1H, m), 2.15-2.19(2H, m), 2.58(2H, t, J=8.5 Hz), 2.91(2H, t, J=7.4 Hz), 4.03(2H, t, J=5.6 Hz), 4.09(2H, brd, J=10.9 Hz), 7.02 (1H, d, J=8.3 Hz), 7.35-7.41(4H, m), 7.56(2H, d, J=7.8 Hz).

(133-2) Synthesis of phosphoric acid mono(2-amino-2-ethyl-4-{3-trifluoromethyl-4-[3-(4-trifluoromethylphenyl)propoxy]phenyl}butyl)ester (Compound 133-2)

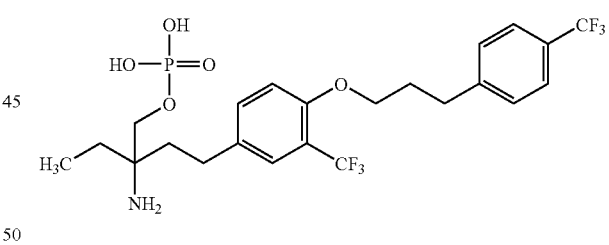

Compound 133-1 (640 mg) was dissolved in methylene chloride (5 ml), hydrogen chloride containing dioxane (4 mol/l, 2 ml) was added, and the mixture was stirred at room temperature for 4 hr. The solvent was concentrated under reduced pressure, and methanol (3 ml), diethyl ether (7 ml) and propylene oxide (7 ml) were added to the residue. The precipitated powder was collected by filtration, and washed with ethyl acetate and diethyl ether to give the object product (115 mg) as a white solid.

MS(ESI)m/z: 544[M+H]

$^1$H-NMR(CD$_3$OD) δ (ppm): 1.03(3H, t, J=7.5 Hz), 1.70-2.01(4H, m), 2.07-2.18(2H, m), 2.56-2.75(2H, m), 2.91(2H, t, J=7.5 Hz), 3.89-3.97(2H, m), 4.04(2H, t, J=5.9 Hz), 7.05 (1H, d, J=8.5 Hz), 7.38-7.47(4H, m), 7.56(2H, d, J=8.0 Hz).

Example 134

(S)-phosphoric acid mono(2-amino-2-ethyl-4-{3-trifluoromethyl-4-[3-(4-trifluoromethylphenyl)propoxy]phenyl}butyl)ester (134-1) Synthesis of (S)-[1-di(t-butyl)phosphoryloxymethyl-1-ethyl-3-{3-trifluoromethyl-4-[3-(4-trifluoromethylphenyl)propoxy]phenyl}propyl]carbamic acid t-butyl ester (Compound 134-1)

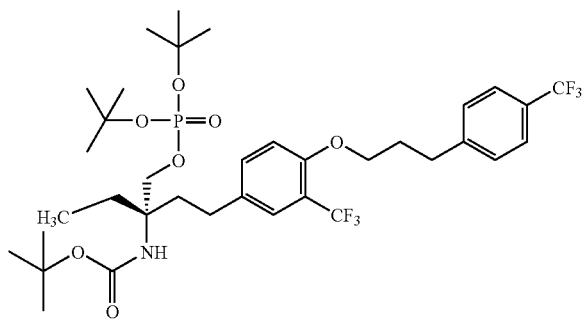

To a solution of compound 31-2 (110 mg) in methanol (5 ml) were added triethylamine (0.093 ml) and di-t-butyl-dicarbonate (72.0 mg), and the mixture was stirred at room temperature for 22 hr. Di-t-butyl-dicarbonate (72.0 mg) was further added to the reaction mixture, and the mixture was stirred at room temperature for 3 hr. Water was added to the reaction mixture, and the mixture was extracted with ethyl acetate. The organic layer was washed with saturated brine and dried over anhydrous magnesium sulfate. The solvent was evaporated under reduced pressure. The obtained residue was purified by silica gel column chromatography (hexane:ethyl acetate=1:1-1:2) to give an amine-protected compound as a colorless oil (90 mg). To a solution of the colorless oil (90 mg) in methylene chloride (3 ml) and acetonitrile (2 ml) were added 1H-tetrazole (23.0 mg) and di-t-butyl diethylphosphoramidite (0.096 ml), and the mixture was stirred at room temperature for 1.5 hr. The reaction solution was ice-cooled, t-butyl hydroperoxide containing decane solution (5-6M, 0.096 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was m evaporated under reduced pressure. The obtained residue was purified by silica gel column chromatography (hexane:ethyl acetate=1:1-1:2) to give the object product (90 mg) as a colorless oil.

$^1$H-NMR(CD$_3$OD) δ (ppm): 0.89-0.94(3H, m), 1.45(9H, s), 1.50(18H, s), 1.67-1.89(3H, m), 1.91-2.05(1H, m), 2.08-2.14(2H, m), 2.57(2H, t, J=8.5 Hz), 2.91(2H, t, J=7.5 Hz), 4.03(2H, t, J=5.9 Hz), 4.04-4.20(2H, brm), 7.02(1H, d, J=8.4 Hz), 7.35-7.40(4H, m), 7.56(2H, d, J=8.0 Hz).

(134-2) Synthesis of (S)-phosphoric acid mono(2-amino-2-ethyl-4-{3-trifluoromethyl-4-[3-(4-trifluoromethylphenyl)propoxy]phenyl}butyl)ester (Compound 134-2)

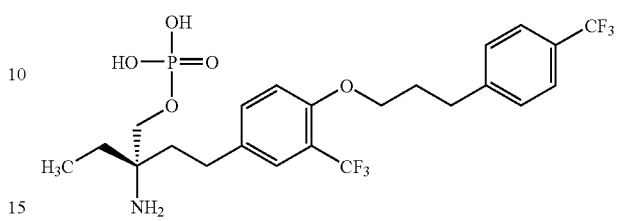

Compound 134-1 (90 mg) was dissolved in methylene chloride (3 ml), hydrogen chloride containing dioxane (4 mol/l, 2 ml) was added, and the mixture was stirred at room temperature for 3 hr. The solvent was concentrated under reduced pressure, and isopropyl alcohol (5 ml) was added to the residue. The precipitated powder was collected by filtration, and washed with isopropyl alcohol to give the object product (10 mg) as a white solid.

MS(ESI)m/z: 544[M+H]

$^1$H-NMR(CD$_3$OD) δ (ppm): 1.03(3H, t, J=7.5 Hz), 1.72-2.00(4H, m), 2.08-2.17(2H, m), 2.56-2.75(2H, m), 2.92(2H, t, J=7.5 Hz), 3.90-3.95(2H, m), 4.04(2H, t, J=5.8 Hz), 7.05 (1H, d, J=8.5 Hz), 7.38-7.47(4H, m), 7.56(2H, d, J=8.0 Hz).

Example 135

(R)-phosphoric acid mono(2-amino-2-ethyl-4-{3-trifluoromethyl-4-[3-(4-trifluoromethylphenyl)propoxy]phenyl}butyl)ester (135-1) Synthesis of (R)-[1-di(t-butyl)phosphoryloxymethyl-1-ethyl-3-{3-trifluoromethyl-4-[3-(4-trifluoromethylphenyl)propoxy]phenyl}propyl]carbamic acid t-butyl ester (Compound 135-1)

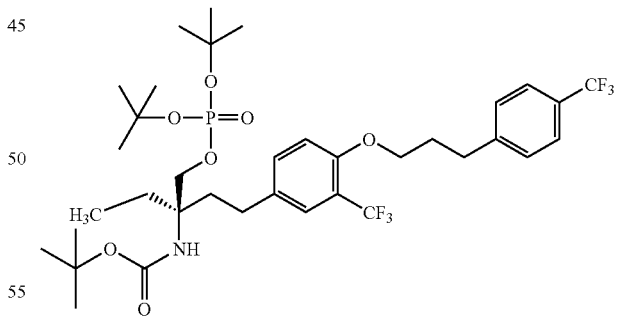

To a solution of compound 32-1 (110 mg) in methanol (5 ml) were added triethylamine (0.093 ml) and di-t-butyl-dicarbonate (0.072 mg), and the mixture was stirred at room temperature for 26 hr. Di-t-butyl-dicarbonate (0.072 mg) was further added to the reaction mixture, and the mixture was stirred at room temperature for 3 hr. Water was added to the reaction mixture, and the mixture was extracted with ethyl acetate. The organic layer was washed with saturated brine and dried over anhydrous magnesium sulfate. The solvent was evaporated under reduced pressure. The obtained residue was purified by silica gel column chromatography (hexane: ethyl acetate=1:1-1:2) to give an amine-protected compound as a colorless oil (110 mg). To a solution of the colorless oil (110 mg) in methylene chloride (5 ml) and acetonitrile (2 ml) were added 1H-tetrazole (27.0 mg) and di-t-butyl diethylphosphoramidite (0.117 ml), and the mixture was stirred at room temperature for 1.5 hr. The reaction solution was ice-cooled, t-butyl hydroperoxide-containing decane solution (5-6M, 0.117 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:1-1:2) to give the object product (160 mg) as a colorless oil.

$^1$H-NMR(CD$_3$OD) δ (ppm): 0.91(3H, t, J=7.4 Hz), 1.45 (9H, s), 1.50(18H, s), 1.65-1.89(3H, m), 1.91-2.02(1H, m), 2.07-2.15(2H, m), 2.57(2H, t, J=8.5 Hz), 2.91(2H, t, J=7.6 Hz), 4.03(2H, t, J=5.9 Hz), 4.09(2H, dd, J=11.5, 3.8 Hz), 7.02(1H, d, J=8.5 Hz), 7.35-7.41(4H, m), 7.56(2H, d, J=8.0 Hz).

(135-2) Synthesis of (R)-phosphoric acid mono(2-amino-2-ethyl-4-{3-trifluoromethyl-4-[3-(4-trifluoromethylphenyl)propoxy]phenyl}butyl)ester (Compound 135-2)

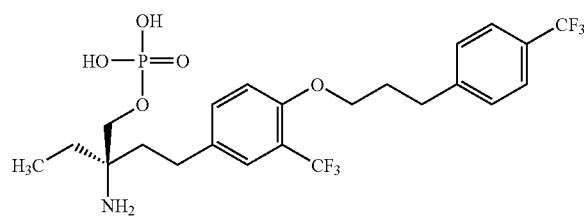

Compound 135-1 (160 mg) was dissolved in methylene chloride (3 ml), hydrogen chloride containing dioxane (4 mol/l, 2 ml) was added, and the mixture was stirred at room temperature for 4 hr. The solvent was concentrated under reduced pressure, and isopropyl alcohol (5 ml) was added to the residue. The precipitated powder was collected by filtration, and washed with isopropyl alcohol to give the object product (10 mg) as a white solid.

MS (ESI)m/z: 544[M+H]

$^1$H-NMR(CD$_3$OD) δ (ppm): 1.03(3H, t, J=7.5 Hz), 1.70-2.01(4H, m), 2.05-2.12(2H, m), 2.56-2.75(2H, m), 2.92(2H, t, J=7.5 Hz), 3.89-3.97(2H, m), 4.04(2H, t, J=5.9 Hz), 7.06 (1H, d, J=8.5 Hz), 7.38-7.47(4H, m), 7.56(2H, d, J=8.1 Hz).

Example 136

4-{4-[2-(4-acetylphenyl)ethoxy]-3-trifluoromethylphenyl}-2-amino-2-(phosphoryloxymethyl)butanol (136-1) Synthesis of 4-(2-{4-[2-(4-acetylphenyl)ethoxy]-3-trifluoromethylphenyl}ethyl)-4-di(t-butyl)phosphoryloxymethyl-2-methyl-2-oxazoline (Compound 136-1)

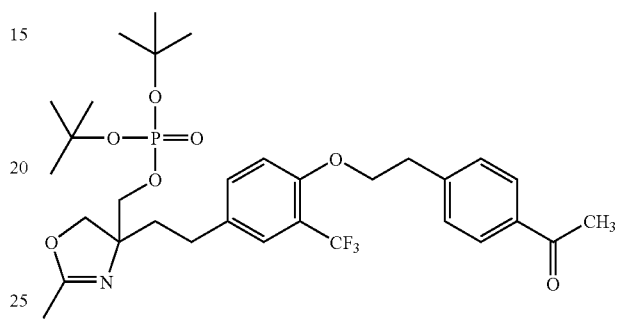

To a solution of compound 34-3 (139 mg) in N,N-dimethylformamide (10 ml) were added N,N-diisopropylethylamine (0.162 ml) and trimethyl orthoacetate (0.057 ml), and the mixture was stirred at 120° C. for 4 hr. N,N-Diisopropylethylamine (0.162 ml) and trimethyl orthoacetate (0.057 ml) were further added, and the mixture was stirred at 120° C. for 6 hr. Water was added to the reaction mixture, and the mixture was extracted with ethyl acetate, washed with water and saturated brine, and dried over anhydrous magnesium sulfate. The solvent was evaporated under reduced pressure to give a brown oil (120 mg). To a solution of the brown oil (120 mg) in methylene chloride (5 ml) and acetonitrile (2 ml) were added 1H-tetrazole (38 mg) and di-t-butyl diethylphosphoramidite (0.162 ml), and the mixture was stirred at room temperature for 2 hr. 1H-tetrazole (38 mg) and di-t-butyl diethylphosphoramidite (0.162 ml) were further added, and the mixture was stirred at room temperature for 1 hr. The reaction solution was ice-cooled, t-butyl hydroperoxide-containing decane solution (5-6M, 0.162 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (110 mg) as a yellow oil.

$^1$H-NMR(CD$_3$OD) δ (ppm): 1.48(18H, s), 1.80-1.89(2H, m), 2.00(3H, s), 2.58(3H, s), 2.58-2.68(2H, m), 3.16(2H, t, J=6.2 Hz), 3.89(2H, brd, J=3.9 Hz), 4.17(1H, d, J=9.2 Hz), 4.27-4.32(3H, m), 7.06(1H, d, J=8.4 Hz), 7.36-7.40(2H, m), 7.42-7.47(2H, m), 7.93(2H, d, J=8.1 Hz).

(136-2) Synthesis of 4-{4-[2-(4-acetylphenyl)ethoxy]-3-trifluoromethylphenyl}-2-amino-2-(phosphoryloxymethyl)butanol (Compound 136-2)

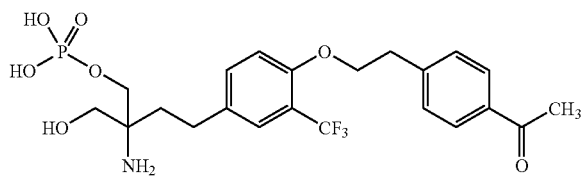

Compound 136-1 (110 mg) was dissolved in ethanol (5 ml), concentrated hydrochloric acid (1 ml) was added, and the mixture was stirred at 50° C. for 3.5 hr. The solvent was concentrated under reduced pressure, and methanol (2 ml), diethyl ether (2 ml) and propylene oxide (3 ml) were added to the residue. The precipitated powder' was collected by filtration, and washed with methanol, ethyl acetate and diethyl ether to give the object product (51 mg) as a pale-yellow solid.

MS(ESI)m/z: 506[M+H]

$^1$H-NMR(CD$_3$OD) δ (ppm): 1.91-1.98(2H, m), 2.58(3H, s), 2.63-2.72(2H, m), 3.17(2H, t, J=6.2 Hz), 3.69(2H, s), 3.93-4.02(2H, m), 4.29(2H, t, J=6.2 Hz), 7.08(1H, d, J=8.4 Hz), 7.41-7.47(4H, m), 7.93(2H, d, J=8.3 Hz).

Example 137

2-amino-4-{4-[3-(3,5-dichlorophenyl)propoxy]-3-trifluoromethylphenyl}-2-(phosphoryloxymethyl)butanol (137-1) Synthesis of 4-di(t-butyl)phosphoryloxymethyl-4-(2-{4-[3-(3,5-dichlorophenyl)propoxy]-3-trifluoromethylphenyl}ethyl)-2-methyl-2-oxazoline (Compound 137-1)

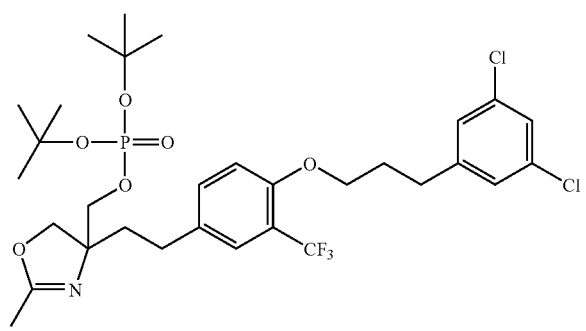

To a solution of compound 35-5 (440 mg) in N,N-dimethylformamide (10 ml) were added N,N-diisopropylethylamine (0.471 ml) and trimethyl orthoacetate (0.167 ml), and the mixture was stirred at 120° C. for 4 hr. Water was added to the reaction mixture, and the mixture was extracted with ethyl acetate, washed with water and saturated brine, and dried over anhydrous magnesium sulfate. The solvent was evaporated under reduced pressure to give a brown oil (460 mg). To a solution of the brown oil (460 mg) in methylene chloride (5 ml) and acetonitrile (2 ml) were added 1H-tetrazole (123 mg) and di-t-butyl diethylphosphoramidite (0.527 ml), and the mixture was stirred at room temperature for 2 hr. The reaction solution was ice-cooled, t-butyl hydroperoxide-containing decane solution (5-6M, 0.528 ml) was added, and the mixture was stirred at room temperature for 30 min. Saturated aqueous sodium hydrogen carbonate solution was added to the reaction mixture, and extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (430 mg) as a yellow oil.

$^1$H-NMR(CD$_3$OD) δ (ppm): 1.49(18H, s), 1.83-1.90(2H, m), 2.01(3H, s), 2.02-2.11(2H, m), 2.55-2.70(2H, m), 2.82 (2H, t, J=7.5 Hz), 3.89-3.91(2H, m), 4.02(2H, t, J=5.8 Hz), 4.18(1H, d, J=9.0 Hz), 4.32(1H, d, J=9.0 Hz), 7.03(1H, d, J=8.5 Hz), 7.16-7.17(2H, m), 7.24-7.25(1H, m), 7.39(1H, t, J=8.5 Hz), 7.44(1H, brs).

(137-2) Synthesis of 2-amino-4-{4-[3-(3,5-dichlorophenyl)propoxy]-3-trifluoromethylphenyl}-2-(phosphoryloxymethyl)butanol (Compound 137-2)

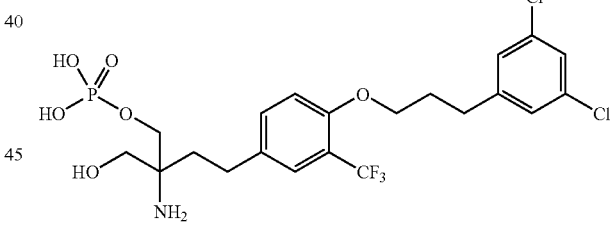

Compound 137-1 (430 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (285 mg) as a white solid.

MS(ESI)m/z: 546[M+H]

$^1$H-NMR(CD$_3$OD) δ (ppm): 1.92-2.01(2H, m), 2.04-2.15 (2H, m), 2.65-2.72(2H, m), 2.82(2H, t, J=7.5 Hz), 3.70(2H, brs), 3.96-4.04(4H, m), 7.05(1H, d, J=8.6 Hz), 7.17(2H, d, J=1.9 Hz), 7.25(1H, d, J=1.5 Hz), 7.44(1H, d, J=7.9 Hz), 7.49(1H, brs).

Example 138

2-amino-4-{4-[3-(3,5-dimethylphenyl)propoxy]-3-trifluoromethylphenyl}-2-(phosphoryloxymethyl)butanol (138-1) Synthesis of 4-di(t-butyl)phosphoryloxymethyl-4-(2-{4-[3-(3,5-dimethylphenyl)propoxy]-3-trifluoromethylphenyl}ethyl)-2-methyl-2-oxazoline (Compound 138-1)

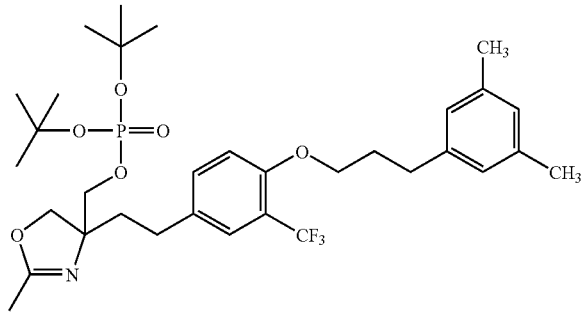

To a solution of compound 36-5 (420 mg) in N,N-dimethylformamide (10 ml) were added N,N-diisopropylethylamine (0.490 ml) and trimethyl orthoacetate (0.173 ml), and the mixture was stirred at 120° C. for 5 hr. Water was added to the reaction mixture, and the mixture was extracted with ethyl acetate, washed with water and saturated brine, and dried over anhydrous magnesium sulfate. The solvent was evaporated under reduced pressure to give a brown oil (410 mg). To a solution of the brown oil (410 mg) in methylene chloride (5 ml) and acetonitrile (2 ml) were added 1H-tetrazole (127 mg) and di-t-butyl diethylphosphoramidite (0.545 ml), and the mixture was stirred at room temperature for 2 hr. The reaction solution was ice-cooled, t-butyl hydroperoxide-containing decane solution (5-6M, 0.546 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (350 mg) as a pale-brown oil.

$^1$H-NMR(CD$_3$OD) δ (ppm): 1.48(18H, s), 1.83-1.90(2H, m), 1.99-2.07(5H, m), 2.22(6H, s), 2.52-2.71(2H, m), 2.72 (2H, brt, J=7.3 Hz), 3.89(2H, brs), 4.18(2H, brt, J=4.6 Hz), 4.16-4.19(1H, m), 4.29-4.33(1H, m), 6.79(3H, brs), 7.00(1H, brd, J=8.4 Hz), 7.37(1H, brd, J=8.4 Hz), 7.43(1H, brs).

(138-2) Synthesis of 2-amino-4-{4-[3-(3,5-dimethylphenyl)propoxy]-3-trifluoromethylphenyl}-2-(phosphoryloxymethyl)butanol (Compound 138-2)

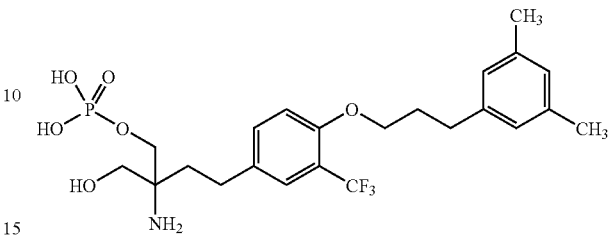

Compound 138-1 (350 mg) was dissolved in ethanol (5 ml), concentrated hydrochloric acid (1 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (270 mg) as a white solid.

MS(ESI)m/z: 506[M+H]

$^1$H-NMR(CD$_3$OD) δ (ppm): 1.93-1.99(2H, m), 2.03-2.06 (2H, m), 2.23(6H, s), 2.66-2.74(4H, m), 3.70(2H, brs), 3.96-4.04(4H, m), 6.79(3H, brs), 7.01(1H, d, J=8.5 Hz), 7.42(1H, d, J=8.5 Hz), 7.48(1H, brs).

Example 139

2-amino-4-{4-[3-(3,4-dimethylphenyl)propoxy]-3-trifluoromethylphenyl}-2-(phosphoryloxymethyl)butanol (139-1) Synthesis of 4-di(t-butyl)phosphoryloxymethyl-4-(2-{4-[3-(3,4-dimethylphenyl)propoxy]-3-trifluoromethylphenyl}ethyl)-2-methyl-2-oxazoline (Compound 139-1)

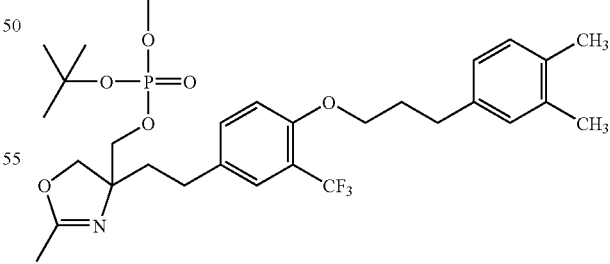

To a solution of compound 37-5 (330 mg) in N,N-dimethylformamide (10 ml) were added N,N-diisopropylethylamine (0.382 ml) and trimethyl orthoacetate (0.135 ml), and the mixture was stirred at 120° C. for 6 hr. Water was added to the reaction mixture, and the mixture was extracted with ethyl acetate, washed with water and saturated brine, and dried over anhydrous magnesium sulfate. The solvent was evaporated under reduced pressure to give a brown oil (340 mg). To a solution of the brown oil (340 mg) in methylene chloride (5 ml) and acetonitrile (2 ml) were added 1H-tetrazole (99 mg) and di-t-butyl diethylphosphoramidite (0.425 ml), and the mixture was stirred at room temperature for 2 hr. The reaction solution was ice-cooled, t-butyl hydroperoxide containing decane solution (5-6M, 0.426 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (320 mg) as a yellow oil.

$^1$H-NMR(CD$_3$OD) δ (ppm): 1.48(18H, s), 1.79-1.90(2H, m), 1.99-2.07(5H, m), 2.20(6H, s), 2.53-2.71(2H, m), 2.73 (2H, brt, J=7.4 Hz), 3.89(2H, brs), 3.99(2H, t, J=5.9 Hz), 4.18(1H, d, J=9.2 Hz), 4.32(1H, d, J=9.2 Hz), 6.88(1H, d, J=7.1 Hz), 6.94(1H, s), 6.99(2H, d, J=7.9 Hz), 7.37(1H, brd, J=8.5 Hz), 7.43(1H, brs).

(139-2) Synthesis of 2-amino-4-{4-[3-(3,4-dimethylphenyl)propoxy]-3-trifluoromethylphenyl}-2-(phosphoryloxymethyl)butanol (Compound 139-2)

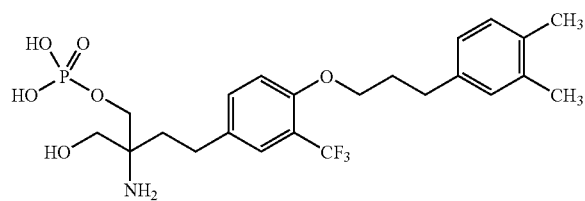

Compound 139-1 (320 mg) was dissolved in ethanol (5 ml), concentrated hydrochloric acid (1 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (205 mg) as a white solid.

MS(ESI)m/z: 506[M+H]

$^1$H-NMR(CD$_3$OD) δ (ppm): 1.94-1.99(2H, m), 2.02-2.06 (2H, m), 2.20(6H, s), 2.66-2.75(4H, m), 3.70(2H, brs), 3.96-4.02(4H, m), 6.88(1H, d, J=7.6 Hz), 6.94(1H, brs), 6.98-7.02 (2H, m), 7.42(1H, d, J=8.6 Hz), 7.48(1H, brd, J=1.6 Hz).

Example 140

2-amino-4-{4-[3-(3,4-dichlorophenyl)propoxy]-3-trifluoromethylphenyl}-2-(phosphoryloxymethyl)butanol (140-1) Synthesis of 4-di(t-butyl)phosphoryloxymethyl-4-(2-{4-[3-(3,4-dichlorophenyl)propoxy]-3-trifluoromethylphenyl}ethyl)-2-methyl-2-oxazoline (Compound 140-1)

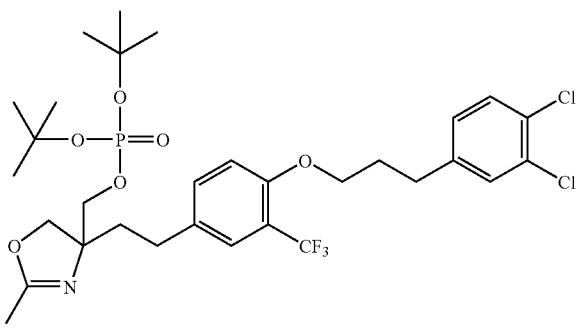

To a solution of compound 38-5 (460 mg) in N,N-dimethylformamide (10 ml) were added N,N-diisopropylethylamine (0.490 ml) and trimethyl orthoacetate (0.173 ml), and the mixture was stirred at 120° C. for 12 hr. Water was added to the reaction mixture, and the mixture was extracted with ethyl acetate, washed with water and saturated brine, and dried over anhydrous magnesium sulfate. The solvent was evaporated under reduced pressure to give a brown oil (470 mg). To a solution of the brown oil (470 mg) in methylene chloride (5 ml) and acetonitrile (2 ml) were added 1H-tetrazole (127 mg) and di-t-butyl diethylphosphoramidite (0.545 ml), and the mixture was stirred at room temperature for 2 hr. The reaction solution was ice-cooled, t-butyl hydroperoxide-containing decane solution (5-6M, 0.546 ml) was added, and the mixture was stirred at room temperature for 15 min. Saturated aqueous sodium hydrogen carbonate solution was added to the reaction mixture, and extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (470 mg) as a yellow oil.

$^1$H-NMR(CD$_3$OD) δ (ppm): 1.48(18H, s), 1.82-1.89(2H, m), 2.01(3H, s), 2.04-2.11(2H, m), 2.56-2.70(2H, m), 2.81 (2H, t, J=7.5 Hz), 3.89-3.91(2H, m), 4.02(2H, t, J=5.8 Hz), 4.18(1H, d, J=9.1 Hz), 4.32(1H, d, J=9.1 Hz), 7.03(1H, d, J=8.4 Hz), 7.14(1H, dd, J=8.4, 1, 7 Hz), 7.35-7.44(4H, m).

(140-2) Synthesis of 2-amino-4-{4-[3-(3,4-dichlorophenyl)propoxy]-3-trifluoromethylphenyl}-2-(phosphoryloxymethyl)butanol (Compound 140-2)

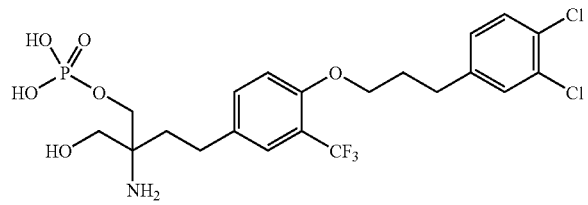

Compound 140-1 (470 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (285 mg) as a white solid.

MS(ESI)m/z: 546[M+H]
$^1$H-NMR(CD$_3$OD) δ (ppm): 1.94-1.99(2H, m), 2.05-2.10 (2H, m), 2.66-2.74(2H, m), 2.82(2H, t, J=7.5 Hz), 3.70(2H, brs), 3.96-4.04(4H, m), 7.04(1H, d, J=8.5 Hz), 7.13(1H, dd, J=8.2, 1.6 Hz), 7.36(1H, d, J=1.6 Hz), 7.40(1H, d, J=8.2 Hz), 7.43(1H, brd, J=8.5 Hz), 7.48(1H, brs).

Example 141

2-amino-4-{4-[3-(4-ethylphenyl)propoxy]-3-trifluoromethylphenyl}-2-(phosphoryloxymethyl)butanol

(141-1) Synthesis of 4-di(t-butyl)phosphoryloxymethyl-4-(2-{4-[3-(4-ethylphenyl)propoxy]-3-trifluoromethylphenyl}ethyl)-2-methyl-2-oxazoline (Compound 141-1)

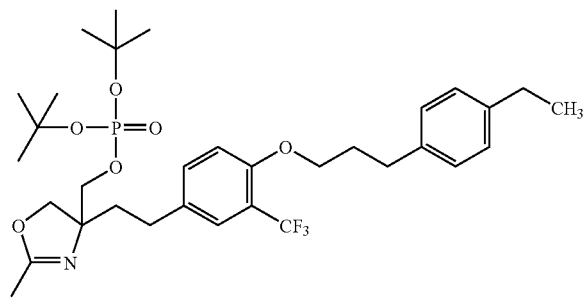

To a solution of compound 39-5 (410 mg) in N,N-dimethylformamide (10 ml) were added N,N-diisopropylethylamine (0.478 ml) and trimethyl orthoacetate (0.169 ml), and the mixture was stirred at 120° C. for 9 hr. Water was added to the reaction mixture, and the mixture was extracted with ethyl acetate, washed with water and saturated brine, and dried over anhydrous magnesium sulfate. The solvent was evaporated under reduced pressure to give a brown oil (420 mg). To a solution of the brown oil (420 mg) in methylene chloride (5 ml) and acetonitrile (2 ml) were added 1H-tetrazole (125 mg) and di-t-butyl diethylphosphoramidite (0.533 ml), and the mixture was stirred at room temperature for 2 hr. The reaction solution was ice-cooled, t-butyl hydroperoxide-containing decane solution (5-6M, 0.534 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (460 mg) as a yellow oil.

$^1$H-NMR(CD$_3$OD) δ (ppm): 1.19(3H, t, J=7.6 Hz), 1.48 (18H, s), 1.82-1.88(2H, m), 2.01(3H, s), 2.02-2.08(2H, m), 2.53-2.71(4H, m), 2.77(2H, t, J=7.5 Hz), 3.89-3.91(2H, m), 4.00(2H, t, J=6.0 Hz), 4.18(1H, d, J=9.0 Hz), 4.32(1H, d, J=9.0 Hz), 7.00(1H, d, J=8.5 Hz), 7.08(4H, s), 7.35-7.38(1H, m), 7.43(1H, d, J=1.5 Hz).

(141-2) Synthesis of 2-amino-4-{4-[3-(4-ethylphenyl)propoxy]-3-trifluoromethylphenyl}-2-(phosphoryloxymethyl)butanol (Compound 141-2)

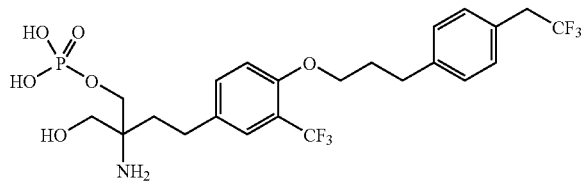

Compound 141-1 (460 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (310 mg) as a pale-yellow solid.

MS(ESI)m/z: 506[M+H]
$^1$H-NMR(CD$_3$OD) δ (ppm): 1.20(3H, t, J=7.6 Hz), 1.93-2.00(2H, m), 2.01-2.10(2H, m), 2.54-2.62(2H, m), 2.63-2.74 (2H, m), 2.77(2H, t, J=7.4 Hz), 3.70(2H, brs), 3.96-4.04(4H, m), 7.02(1H, d, J=8.5 Hz), 7.09(4H, brs), 7.42(1H, d, J=8.5 Hz), 7.47(1H, brs).

Example 142

2-amino-4-{4-[3-(3-bromophenyl)propoxy]-3-trifluoromethylphenyl}-2-(phosphoryloxymethyl)butanol

(142-1) Synthesis of 4-(2-{4-[3-(3-bromophenyl)propoxy]-3-trifluoromethylphenyl}ethyl)-4-di(t-butyl)phosphoryloxymethyl-2-methyl-2-oxazoline (Compound 142-1)

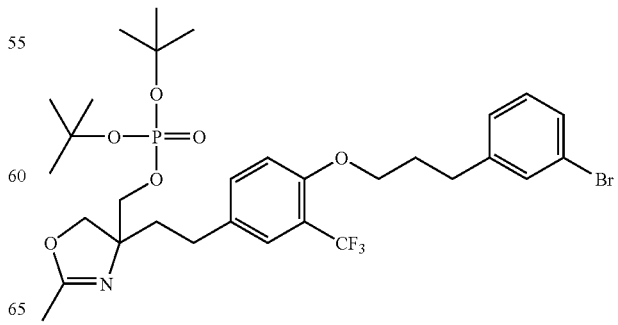

To a solution of compound 40-5 (480 mg) in N,N-dimethylformamide (10 ml) were added N,N-diisopropylethylamine (0.504 ml) and trimethyl orthoacetate (0.178 ml), and the mixture was stirred at 120° C. for 7 hr. Water was added to the reaction mixture, and the mixture was extracted with ethyl acetate, washed with water and saturated brine, and dried over anhydrous magnesium sulfate. The solvent was evaporated under reduced pressure to give a brown oil (500 mg). To a solution of the brown oil (500 mg) in methylene chloride (5 ml) and acetonitrile (2 ml) were added 1H-tetrazole (132 mg) and di-t-butyl diethylphosphoramidite (0.563 ml), and the mixture was stirred at room temperature for 2 hr. The reaction solution was ice-cooled, t-butyl hydroperoxide containing decane solution (5-6M, 0.564 ml) was added, and the mixture was stirred at room temperature for 15 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (460 mg) as a yellow oil.

$^1$H-NMR(CD$_3$OD) δ (ppm): 1.48(18H, s), 1.82-1.89(2H, m), 2.01(3H, s), 2.03-2.10(2H, m), 2.56-2.72(2H, m), 2.81 (2H, t, J=7.5 Hz), 3.88-3.91(2H, m), 4.01(2H, t, J=5.9 Hz), 4.18(1H, d, J=9.1 Hz), 4.32(1H, d, J=9.1 Hz), 7.02(1H, d, J=8.4 Hz), 7.16-7.18(2H, m), 7.31-7.37(3H, m), 7.39(1H, brs).

(142-2) Synthesis of 2-amino-4-{4-[3-(3-bromophenyl)propoxy]-3-trifluoromethylphenyl}-2-(phosphoryloxymethyl)butanol (Compound 142-2)

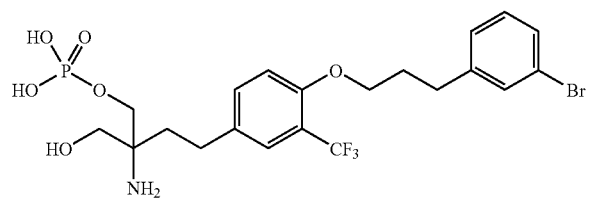

Compound 142-1 (460 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (310 mg) as a white solid.

MS(ESI)m/z: 556, 558[M+H]

$^1$H-NMR(CD$_3$OD) δ (ppm): 1.93-1.99(2H, m), 2.04-2.12 (2H, m), 2.65-2.76(2H, m), 2.81(2H, t, J=7.5 Hz), 3.70(2H, brs), 3.97-4.03(4H, m), 7.03(1H, d, J=8.5 Hz), 7.14-7.21(2H, m), 7.31-7.33(1H, m), 7.36(1H, brs), 7.43(1H, d, J=8.5 Hz), 7.48(1H, brs).

Example 143

2-amino-4-{4-[3-(4-bromophenyl)propoxy]-3-trifluoromethylphenyl}-2-(phosphoryloxymethyl)butanol (143-1) Synthesis of 4-(2-{4-[3-(4-bromophenyl)propoxy]-3-trifluoromethylphenyl}ethyl)-4-di(t-butyl)phosphoryloxymethyl-2-methyl-2-oxazoline (Compound 143-1)

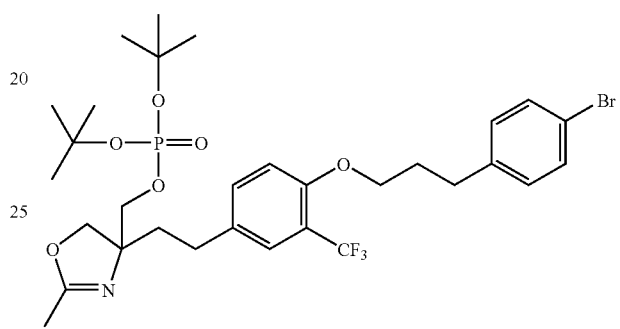

To a solution of compound 41-5 (460 mg) in N,N-dimethylformamide (10 ml) were added N,N-diisopropylethylamine (0.483 ml) and trimethyl orthoacetate (0.171 ml), and the mixture was stirred at 120° C. for 5 hr. Water was added to the reaction mixture, and the mixture was extracted with ethyl acetate, washed with water and saturated brine, and dried over anhydrous magnesium sulfate. The solvent was evaporated under reduced pressure to give a brown oil (470 mg). To a solution of the brown oil (470 mg) in methylene chloride (5 ml) and acetonitrile (2 ml) were added 1H-tetrazole (126 mg) and di-t-butyl diethylphosphoramidite (0.539 ml), and the mixture was stirred at room temperature for 2 hr. The reaction solution was ice-cooled, t-butyl hydroperoxide-containing decane solution (5-6M, 0.540 ml) was added, and the mixture was stirred at room temperature for 15 min. Saturated aqueous sodium hydrogen carbonate solution was added to the reaction mixture, and extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (450 mg) as a pale-brown oil.

$^1$H-NMR(CD$_3$OD) δ (ppm): 1.48(18H, s), 1.82-1.89(2H, m), 2.01(3H, s), 2.03-2.10(2H, m), 2.52-2.71(2H, m), 2.79 (2H, t, J=7.5 Hz), 3.88-3.91(2H, m), 4.01(2H, t, J=5.8 Hz), 4.18(1H, d, J=9.0 Hz), 4.32(1H, d, J=9.0 Hz), 7.01(1H, d, J=8.5 Hz), 7.08-7.13(2H, m), 7.37-7.43(4H, m).

(143-2) Synthesis of 2-amino-4-{4-[3-(4-bromophenyl)propoxy]-3-trifluoromethylphenyl}-2-(phosphoryloxymethyl)butanol (Compound 143-2)

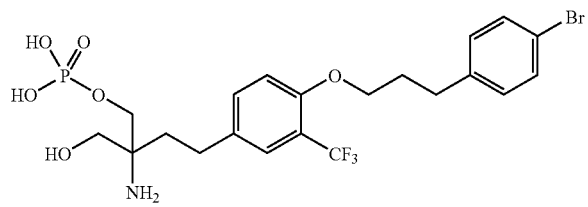

Compound 143-1 (450 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to in the residue. The precipitated powder was collected by filtration, and washed with methanol, ethyl acetate and diethyl ether to give the object product (316 mg) as a white solid.

MS(ESI)m/z: 556, 558[M+H]

$^1$H-NMR(CD$_3$OD) δ (ppm): 1.93-2.01(2H, m), 2.02-2.10 (2H, m), 2.64-2.75(2H, m), 2.79(2H, t, J=7.5 Hz), 3.70(2H, brs), 3.96-4.03(4H, m), 7.03(1H, d, J=8.4 Hz), 7.12(2H, d, J=8.4 Hz), 7.40(2H, d, J=8.4 Hz), 7.44(1H, brs), 7.48(1H, brs).

Example 144

2-amino-4-{4-[3-(4-methoxy-3-methylphenyl)propoxy]-3-trifluoromethylphenyl}-2-(phosphoryloxymethyl)butanol (144-1) Synthesis of 4-di(t-butyl)phosphoryloxymethyl-4-(2-{4-[3-(4-methoxy-3-methylphenyl)propoxy]-3-trifluoromethylphenyl}ethyl)-2-methyl-2-oxazoline (Compound 144-1)

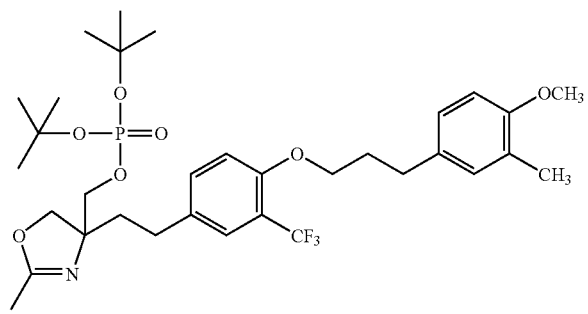

To a solution of compound 42-6 (440 mg) in N,N-dimethylformamide (10 ml) were added N,N-diisopropylethylamine (0.495 ml) and trimethyl orthoacetate (0.174 ml), and the mixture was stirred at 120° C. for 10 hr. Water was added to the reaction mixture, and the mixture was extracted with ethyl acetate, washed with water and saturated brine, and dried over anhydrous magnesium sulfate. The solvent was evaporated under reduced pressure to give a brown oil (460 mg). To a solution of the brown oil (460 mg) in methylene chloride (5 ml) and acetonitrile (2 ml) were added 1H-tetrazole (129 mg) and di-t-butyl diethylphosphoramidite (0.551 ml), and the mixture was stirred at room temperature for 2 hr. The reaction solution was ice-cooled, t-butyl hydroperoxide-containing decane solution (5-6M, 0.552 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (420 mg) as a yellow oil.

$^1$H-NMR(CD$_3$OD) δ (ppm): 1.48(18H, s), 1.80-1.90(2H, m), 1.99-2.06(5H, m), 2.12(3H, s), 2.52-2.70(2H, m), 2.71 (2H, t, J=7.4 Hz), 3.77(3H, s), 3.89-3.91(2H, m), 3.98(2H, t, J=5.9 Hz), 4.18(1H, d, J=9.0 Hz), 4.32(1H, d, J=9.0 Hz), 6.77(1H, d, J=7.9 Hz), 6.94-7.00(3H, m), 7.37(1H, d, J=8.6 Hz), 7.43(1H, brs).

(144-2) Synthesis of 2-amino-4-{4-[3-(4-methoxy-3-methylphenyl)propoxy]-3-trifluoromethylphenyl}-2-(phosphoryloxymethyl)butanol (Compound 144-2)

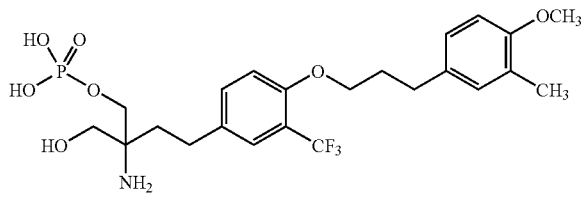

Compound 144-1 (420 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml), propylene oxide (5 ml) were added to the residue. The precipitated powder was collected by filtration, and washed with methanol, ethyl acetate and diethyl ether to give the object product (290 mg) as a pale-brown solid.

MS(ESI)m/z: 522[M+H]

$^1$H-NMR(CD$_3$OD) δ (ppm): 1.94-2.06(4H, m), 2.12(3H, s), 2.64-2.72(4H, m), 3.70(2H, brs), 3.77(3H, s), 3.94-4.02 (4H, m), 6.77(1H, d, J=7.9 Hz), 6.93-6.96(2H, m), 7.01(1H, d, J=8.5 Hz), 7.42(1H, d, J=8.5 Hz), 7.47(1H, brs).

Example 145

2-amino-4-{4-[2-(4-ethylphenyl)ethoxy]-3-trifluoromethylphenyl}-2-(phosphoryloxymethyl)butanol (145-1) Synthesis of 4-di(t-butyl)phosphoryloxymethyl-4-(2-{4-[2-(4-ethylphenyl)ethoxy]-3-trifluoromethylphenyl}ethyl)-2-methyl-2-oxazoline (Compound 145-1)

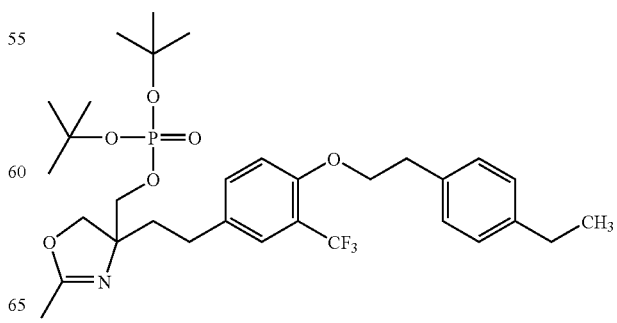

To a solution of compound 43-3 (300 mg) in N,N-dimethylformamide (10 ml) were added N,N-diisopropylethylamine (0.361 ml) and trimethyl orthoacetate (0.127 ml), and the mixture was stirred at 120° C. for 5 hr. Water was added to the reaction mixture, and the mixture was extracted with ethyl acetate, washed with water and saturated brine, and dried over anhydrous magnesium sulfate. The solvent was evaporated under reduced pressure to give a brown oil (290 mg). To a solution of the brown oil (290 mg) in methylene chloride (5 ml) and acetonitrile (2 ml) were added 1H-tetrazole (93 mg) and di-t-butyl diethylphosphoramidite (0.398 ml), and the mixture was stirred at room temperature for 2 hr. The reaction solution was ice-cooled, t-butyl hydroperoxide-containing decane solution (5-6M, 0.402 ml) was added, and the mixture was stirred at room temperature for 15 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (290 mg) as a yellow oil.

$^1$H-NMR(CD$_3$OD) δ (ppm): 1.18-1.21(3H, m), 1.47(18H, s), 1.81-1.89(2H, m), 2.00(3H, s), 2.52-2.70(4H, m), 3.03 (2H, t, J=6.0 Hz), 3.89(2H, brd, J=4.1 Hz), 4.15-4.22(3H, m), 4.31(1H, brd, J=9.2 Hz), 7.04(1H, d, J=8.3 Hz), 7.11(2H, d, J=7.9 Hz), 7.15-7.22(2H, m), 7.37(1H, d, J=8.3 Hz), 7.40(1H, brs).

(145-2) Synthesis of 2-amino-4-{4-[2-(4-ethylphenyl)ethoxy]-3-trifluoromethylphenyl}-2-(phosphoryloxymethyl)butanol (Compound 145-2)

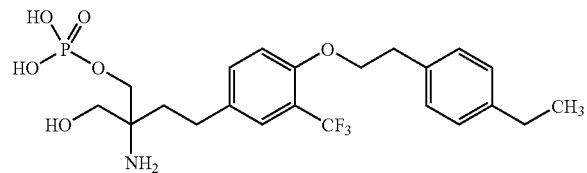

Compound 145-1 (290 mg) was dissolved in ethanol (5 ml), concentrated hydrochloric acid (1 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (187 mg) as a pale-brown solid.

MS(ESI)m/z: 492[M+H]

$^1$H-NMR(CD$_3$OD) δ (ppm): 1.18-1.22(3H, m), 1.91-1.98 (2H, m), 2.57-2.71(4H, m), 3.04(2H, t, J=6.6 Hz), 3.69(2H, brs), 3.92-4.01(2H, m), 4.21(2H, t, J=6.7 Hz), 7.06(1H, d, J=8.4 Hz), 7.12(2H, d, J=8.0 Hz), 7.19-7.21(2H, m), 7.40-7.45(2H, m).

Example 146

2-amino-4-{4-[3-(4-fluoro-3-methylphenyl)propoxy]-3-trifluoromethylphenyl}-2-(phosphoryloxymethyl)butanol (146-1) Synthesis of 4-di(t-butyl)phosphoryloxymethyl-4-(2-{4-[3-(4-fluoro-3-methylphenyl)propoxy]-3-trifluoromethylphenyl}ethyl)-2-methyl-2-oxazoline (Compound 146-1)

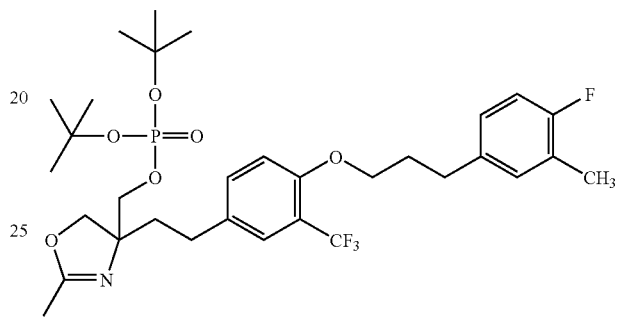

To a solution of compound 44-6 (440 mg) in N,N-dimethylformamide (10 ml) were added N,N-diisopropylethylamine (0.509 ml) and trimethyl orthoacetate (0.178 ml), and the mixture was stirred at 120° C. for 6 hr. Water was added to the reaction mixture, and the mixture was extracted with ethyl acetate, washed with water and saturated brine, and dried over anhydrous magnesium sulfate. The solvent was evaporated under reduced pressure to give a brown oil (430 mg). To a solution of the brown oil (430 mg) in methylene chloride (5 ml) and acetonitrile (2 ml) were added 1H-tetrazole (132 mg) and di-t-butyl diethylphosphoramidite (0.563 ml), and the mixture was stirred at room temperature for 1.5 hr. The reaction solution was ice-cooled, t-butyl hydroperoxide-containing decane solution (5-6M, 0.564 ml) was added, and the mixture was stirred at room temperature for 15 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (430 mg) as a yellow oil.

$^1$H-NMR(CD$_3$OD) δ (ppm): 1.48(18H, s), 1.82-1.89(2H, m), 1.99-2.08(2H, m), 2.01(3H, s), 2.20(3H, s), 2.52-2.71 (2H, m), 2.76(2H, t, J=7.4 Hz), 3.89-3.91(2H, m), 4.00(2H, brt, J=5.9 Hz), 4.18(1H, d, J=9.1 Hz), 4.32(1H, d, J=9.1 Hz), 6.86-6.91(1H, m), 6.97-7.05(3H, m), 7.38(1H, dd, J=8.4, 1.6 Hz), 7.43(1H, brs).

(146-2) Synthesis of 2-amino-4-{4-[3-(4-fluoro-3-methylphenyl)propoxy]-3-trifluoromethylphenyl}-2-(phosphoryloxymethyl)butanol (Compound 146-2)

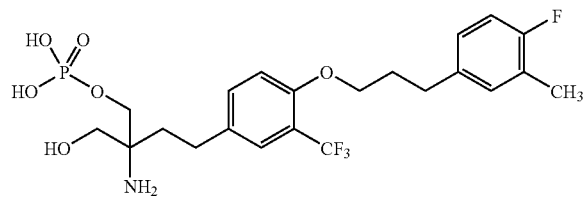

Compound 146-1 (430 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (278 mg) as a pale-brown solid.

MS(ESI)m/z: 510[M+H]
$^1$H-NMR(CD$_3$OD) δ (ppm): 1.93-1.99(2H, m), 2.03-2.07 (2H, m), 2.20(3H, s), 2.66-2.74(2H, m), 2.76(2H, t, J=7.5 Hz), 3.71(2H, brs), 3.97-4.03(4H, m), 6.88-6.92(1H, m), 6.95-7.05(3H, m), 7.43(1H, d, J=8.6 Hz), 7.48(1H, brs).

Example 147

2-amino-4-{4-[3-(2-fluoro-5-methylphenyl)propoxy]-3-trifluoromethylphenyl}-2-(phosphoryloxymethyl)butanol (147-1) Synthesis of 4-di(t-butyl)phosphoryloxymethyl-4-(2-{4-[3-(2-fluoro-5-methylphenyl)propoxy]-3-trifluoromethylphenyl}ethyl)-2-methyl-2-oxazoline (Compound 147-1)

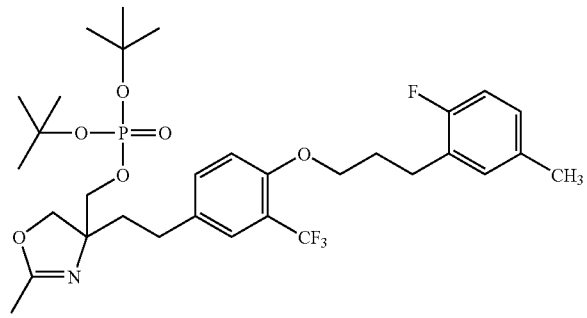

To a solution of compound 45-6 (360 mg) in N,N-dimethylformamide (10 ml) were added N,N-diisopropylethylamine (0.416 ml), trimethyl orthoacetate (0.146 ml), and the mixture was stirred at 120° C. for 5 hr. Water was added to the reaction mixture, and the mixture was extracted with ethyl acetate, washed with water and saturated brine, and dried over anhydrous magnesium sulfate. The solvent was evaporated under reduced pressure to give a brown oil (360 mg). To a solution of the brown oil (360 mg) in methylene chloride (5 ml) and acetonitrile (2 ml) were added 1H-tetrazole (108 mg) and di-t-butyl diethylphosphoramidite (0.461 ml), and the mixture was stirred at room temperature for 1.5 hr. The reaction solution was ice-cooled, t-butyl hydroperoxide-containing decane solution (5-6M, 0.462 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (380 mg) as a yellow oil.

$^1$H-NMR(CD$_3$OD) δ (ppm): 1.48(18H, s), 1.82-1.89(2H, m), 2.01(3H, s), 2.02-2.09(2H, m), 2.24(3H, s), 2.55-2.68 (2H, m), 2.81(2H, t, J=7.5 Hz), 3.89-3.91(2H, m), 4.03(2H, t, J=5.9 Hz), 4.18(1H, d, J=9.2 Hz), 4.32(1H, d, J=9.2 Hz), 6.86-6.91(1H, m), 6.97-7.03(3H, m), 7.38(1H, dd, J=8.4, 1.4 Hz), 7.43(1H, brs).

(147-2) Synthesis of 2-amino-4-{4-[3-(2-fluoro-5-methylphenyl)propoxy]-3-trifluoromethylphenyl}-2-(phosphoryloxymethyl)butanol (Compound 147-2)

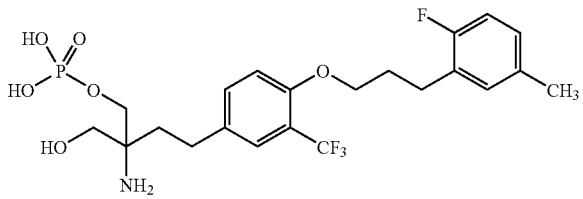

Compound 147-1 (380 mg) was dissolved in ethanol (5 ml), concentrated hydrochloric acid (1 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (225 mg) as a white solid.

MS(ESI)m/z: 510[M+H]
$^1$H-NMR(CD$_3$OD) δ (ppm): 1.92-1.99(2H, m), 2.00-2.08 (2H, m), 2.24(3H, s), 2.62-2.74(2H, m), 2.81(2H, brt, J=7.4 Hz), 3.70(2H, brs), 3.97-4.05(4H, m), 6.85-6.91(1H, m), 6.95-7.05(3H, m), 7.43(1H, brd, J=7.1 Hz), 7.48(1H, brs).

Example 148

2-amino-2-(phosphoryloxymethyl)-4-{4-[3-(2-thienyl)propoxy]-3-trifluoromethylphenyl}butanol (148-1) Synthesis of 4-di(t-butyl)phosphoryloxymethyl-2-methyl-4-(2-{4-[3-(2-thienyl)propoxy]-3-trifluoromethylphenyl}ethyl)-2-oxazoline (Compound 148-1)

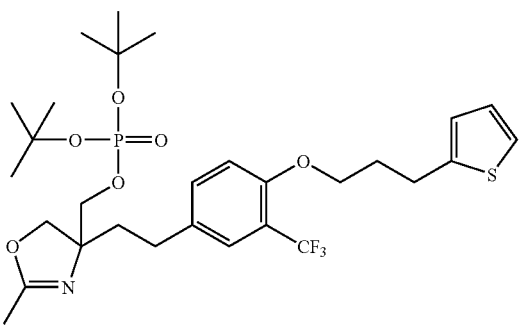

To a solution of compound 46-5 (290 mg) in N,N-dimethylformamide (10 ml) were added N,N-diisopropylethylamine (0.355 ml) and trimethyl orthoacetate (0.125 ml), and the mixture was stirred at 120° C. for 6 hr. Water was added to the reaction mixture, and the mixture was extracted with ethyl acetate, washed with water and saturated brine, and dried over anhydrous magnesium sulfate. The solvent was evaporated under reduced pressure to give a brown oil (300 mg). To a solution of the brown oil (300 mg) in methylene chloride (5 ml) and acetonitrile (2 ml) were added 1H-tetrazole (92 mg) and di-t-butyl diethylphosphoramidite (0.395 ml), and the mixture was stirred at room temperature for 2 hr. The reaction solution was ice-cooled, t-butyl hydroperoxide-containing decane solution (5-6M, 0.396 ml) was added, and the mixture was stirred under ice-cooling for 10 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (360 mg) as a yellow oil.

$^1$H-NMR(CD$_3$OD) δ (ppm): 1.48(18H, s), 1.82-1.89(2H, m), 2.01(3H, s) 2.07-2.15(2H, m), 2.52-2.71(2H, m), 3.04 (2H, t, J=7.3 Hz), 3.89-3.92(2H, m), 4.05(2H, t, J=5.8 Hz), 4.18(1H, d, J=9.1 Hz), 4.32(1H, d, J=9.1 Hz), 6.80(1H, brd, J=2.8 Hz), 6.89(1H, dd, J=5.3, 3.8 Hz), 7.02(1H, d, J=8.4 Hz), 7.17(1H, d, J=5.9 Hz), 7.38(1H, d, J=8.4 Hz), 7.42(1H, brs).

(148-2) Synthesis of 2-amino-2-(phosphoryloxymethyl)-4-{4-[3-(2-thienyl)propoxy]-3-trifluoromethylphenyl}butanol (Compound 148-2)

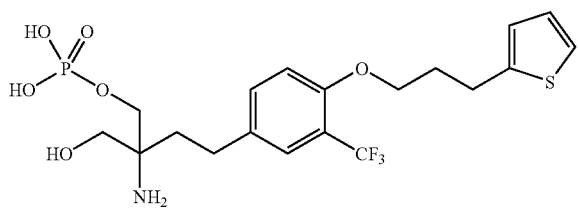

Compound 148-1 (360 mg) was dissolved in ethanol (5 ml), concentrated hydrochloric acid (1 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (197 mg) as a pale-brown solid.

MS(ESI)m/z: 484[M+H]

$^1$H-NMR(CD$_3$OD) δ (ppm): 1.93-1.98(2H, m), 2.09-2.16 (2H, m), 2.64-2.75(2H, m), 3.04(2H, t, J=7.3 Hz), 3.70(2H, brs), 3.96-4.02(2H, m), 4.05(2H, t, J=5.8 Hz), 6.80(1H, brd, J=3.4 Hz), 6.89(1H, dd, J=4.7, 3.4 Hz), 7.04(1H, d, J=8.6 Hz), 7.17(1H, d, J=4.7 Hz), 7.43(1H, d, J=8.6 Hz), 7.48(1H, brs).

Example 149

2-amino-4-{4-[3-(3-ethylphenyl)propoxy]-3-trifluoromethylphenyl}-2-(phosphoryloxymethyl)butanol (149-1) Synthesis of 4-di(t-butyl)phosphoryloxymethyl-4-(2-{4-[3-(3-ethylphenyl)propoxy]-3-trifluoromethylphenyl}ethyl)-2-methyl-2-oxazoline (Compound 149-1)

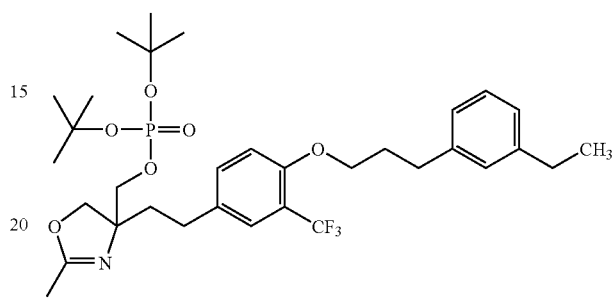

To a solution of compound 47-6 (440 mg) in N,N-dimethylformamide (10 ml) were added N,N-diisopropylethylamine (0.512 ml) and trimethyl orthoacetate (0.180 ml), and the mixture was stirred at 120° C. for 5.5 hr. Water was added to the reaction mixture, and the mixture was extracted with ethyl acetate, washed with water and saturated brine, and dried over anhydrous magnesium sulfate. The solvent was evaporated under reduced pressure to give a brown oil (430 mg). To a solution of the brown oil (430 mg) in methylene chloride (5 ml) and acetonitrile (2 ml) were added 1H-tetrazole (133 mg) and di-t-butyl diethylphosphoramidite (0.569 ml), and the mixture was stirred at room temperature for 2 hr. The reaction solution was ice-cooled, t-butyl hydroperoxide-containing decane solution (5-6M, 0.570 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (470 mg) as a yellow oil.

$^1$H-NMR(CD$_3$OD) δ (ppm): 1.12-1.17(3H, m), 1.48(18H, s), 1.81-1.88(2H, m), 1.99-2.11(5H, m), 2.51-2.71(4H, m), 2.78(2H, brs), 3.89(2H, brs), 3.98(2H, brs), 4.17-4.20(1H, m), 4.29-4.35(1H, m), 7.00(4H, brs), 7.10-7.20(1H, m), 7.36 (1H, brs), 7.43(1H, brs).

(149-2) Synthesis of 2-amino-4-{4-[3-(3-ethylphenyl)propoxy]-3-trifluoromethylphenyl}-2-(phosphoryloxymethyl)butanol (Compound 149-2)

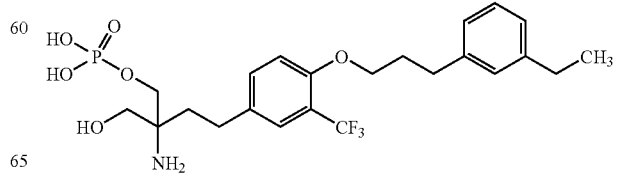

Compound 149-1 (470 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (297 mg) as a pale-brown solid.

MS(ESI)m/z: 506[M+H]

$^1$H-NMR(CD$_3$OD) δ (ppm): 1.16(3H, t, J=7.4 Hz), 1.92-2.00(2H, m), 2.01-2.10(2H, m), 2.54-2.60(2H, m), 2.61-2.72(2H, m), 2.78(2H, t, J=7.4 Hz), 3.70(2H, brs), 3.94-4.01(4H, m), 6.96-7.10(4H, m), 7.15(1H, t, J=7.4 Hz), 7.42(1H, d, J=8.4 Hz), 7.48(1H, brs).

Example 150

2-amino-4-{4-[3-(5-methyl-2-thienyl)propoxy]-3-trifluoromethylphenyl}-2-(phosphoryloxymethyl) butanol (150-1) Synthesis of 4-di(t-butyl)phosphoryloxymethyl-2-methyl-4-(2-{4-[3-(5-methyl-2-thienyl)propoxy]-3-trifluoromethylphenyl}ethyl)-2-oxazoline (Compound 150-1)

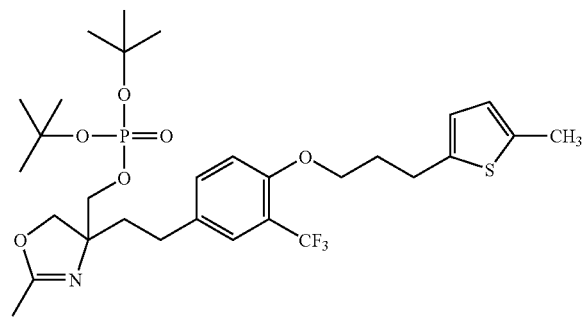

To a solution of compound 48-5 (400 mg) in N,N-dimethylformamide (10 ml) were added N,N-diisopropylethylamine (0.474 ml) and trimethyl orthoacetate (0.167 ml), and the mixture was stirred at 120° C. for 12 hr. Water was added to the reaction mixture, and the mixture was extracted with ethyl acetate, washed with water and saturated brine, and dried over anhydrous magnesium sulfate. The solvent was evaporated under reduced pressure to give a brown oil (390 mg). To a solution of the brown oil (390 mg) in methylene chloride (5 ml) and acetonitrile (2 ml) were added 1H-tetrazole (123 mg) and di-t-butyl diethylphosphoramidite (0.527 ml), and the mixture was stirred at room temperature for 2 hr. The reaction solution was ice-cooled, t-butyl hydroperoxide-containing decane solution (5-6M, 0.528 ml) was added, and the mixture was stirred under ice-cooling for 10 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (420 mg) as a yellow oil.

$^1$H-NMR(CD$_3$OD) δ (ppm): 1.48(18H, s), 1.82-1.89(2H, m), 2.01(3H, s), 2.04-2.11(2H, m), 2.38(3H, s), 2.52-2.70 (2H, m), 2.93(2H, t, J=7.2 Hz), 3.89-3.91(2H, m), 4.05(2H, t, J=5.8 Hz), 4.18(1H, d, J=9.0 Hz), 4.32(1H, d, J=9.0 Hz), 6.51-6.54(2H, m), 7.02(1H, d, J=8.4 Hz), 7.36(1H, brd, J=8.4 Hz), 7.42(1H, brs).

(150-2) Synthesis of 2-amino-4-{4-[3-(5-methyl-2-thienyl)propoxy]-3-trifluoromethylphenyl}-2-(phosphoryloxymethyl)butanol (Compound 150-2)

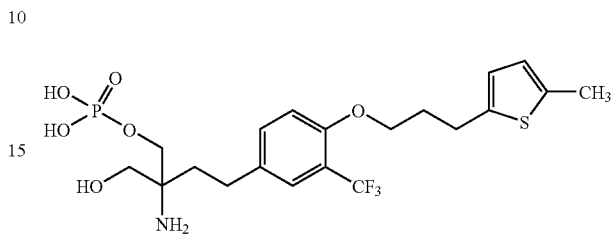

Compound 150-1 (420 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (265 mg) as a pale-brown solid.

MS(ESI)m/z: 498[M+H]

$^1$H-NMR(CD$_3$OD) δ (ppm): 1.93-1.99(2H, m), 2.04-2.14(2H, m), 2.39(3H, s), 2.64-2.73(2H, m), 2.94(2H, t, J=7.3 Hz), 3.70(2H, brs), 3.95-4.02(2H, m), 4.05(2H, t, J=5.9 Hz), 6.52-6.54(2H, m), 7.03(1H, d, J=8.5 Hz), 7.43(1H, d, J=8.5 Hz), 7.47(1H, brs).

Example 151

2-amino-4-{4-[3-(2,3-dimethylphenyl)propoxy]-3-trifluoromethylphenyl}-2-(phosphoryloxymethyl) butanol (151-1) Synthesis of 4-di(t-butyl)phosphoryloxymethyl-4-(2-{4-[3-(2,3-dimethylphenyl)propoxy]-3-trifluoromethyl}ethyl)-2-methyl-2-oxazoline (Compound 151-1)

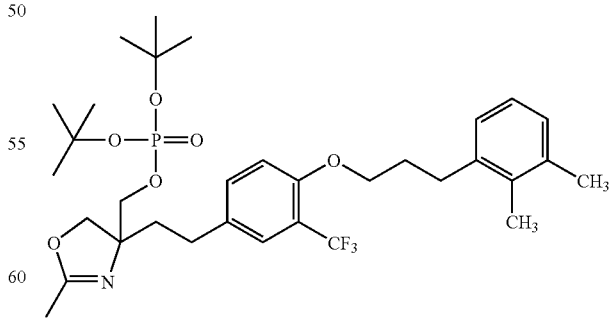

To a solution of compound 49-5 (350 mg) in N,N-dimethylformamide (7.5 ml) were added N,N-diisopropylethylamine (0.39 ml) and trimethyl orthoacetate (0.21 ml), and the mixture was stirred at 120° C. for 3.5 hr. Water was added to the reaction mixture, and the mixture was extracted with ethyl acetate, washed with water and saturated brine, and dried over anhydrous sodium sulfate. The solvent was evaporated under reduced pressure. To a solution of the obtained brown oil in methylene chloride (5 ml) and acetonitrile (3.5 ml) were added 1H-tetrazole (107 mg) and di-t-butyl diethylphosphoramidite (0.42 ml), and the mixture was stirred at room temperature for 3 hr. The reaction solution was ice-cooled, t-butyl hydroperoxide-containing decane solution (5-6M, 0.45 ml) was added and the mixture was stirred for 30 min. Saturated aqueous sodium hydrogen carbonate solution was added to the reaction mixture, and the mixture was extracted with methylene chloride. The organic layer was dried over anhydrous sodium sulfate and the solvent was evaporated under reduced pressure. The obtained residue was purified by silica gel column chromatography (hexane:ethyl acetate) to give the object product (350 mg) as a yellow oil.

$^1$H-NMR(DMSO-$d_6$) δ (ppm): 1.39(18H, d, J=1.2 Hz), 1.69-1.82(2H, m), 1.88-1.93(2H, m), 1.90(3H, s), 2.15(3H, s), 2.22(3H, s), 2.46-2.53(1H, m), 2.58(1H, td, J=11.2, 5.8 Hz), 2.76(2H, t, J=7.6 Hz), 3.75-3.82(2H, m), 4.05-4.08(3H, m), 4.12(1H, d, J=8.7 Hz), 6.95-6.98(3H, m), 7.13(1H, d, J=8.4 Hz), 7.43-7.46(2H, m).

(151-2) Synthesis of 2-amino-4-{4-[3-(2,3-dimethylphenyl)propoxy]-3-trifluoromethylphenyl}-2-(phosphoryloxymethyl)butanol (Compound 151-2)

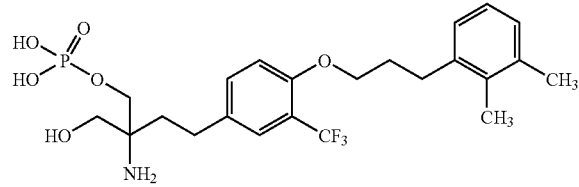

Compound 151-1 (350 mg) was dissolved in ethanol (5 ml), concentrated hydrochloric acid (1 ml) was added, and the mixture was stirred at 50° C. for 3 hr. The solvent was concentrated under reduced pressure, and methanol (2 ml), diethyl ether (5 ml) and propylene oxide (5 ml) were added to the residue. The precipitated powder was collected by filtration and washed with methanol and diethyl ether to give the object product (215 mg) as a white powder.

MS(ESI)m/z: 506[M+H]

$^1$H-NMR(CD$_3$OD) δ (ppm): 1.93-2.04(4H, m), 2.22(3H, s), 2.26(3H, s), 2.66-2.72(2H, m), 2.85(2H, t, J=7.4 Hz), 3.70(2H, s), 3.97-4.06(4H, m), 6.95(3H, brs), 7.04(1H, d, J=8.6 Hz), 7.43(1H, d, J=8.6 Hz), 7.48(1H, s).

Example 152

2-amino-2-(phosphoryloxymethyl)-4-(3-trifluoromethyl-4-{3-[3,5-bis(trifluoromethyl)phenyl] propoxy}phenyl)butanol (152-1) Synthesis of 4-di(t-butyl)phosphoryloxymethyl-2-methyl-4-[2-(3-trifluoromethyl-4-{3-[3,5-bis(trifluoromethyl)phenyl]propoxy}phenyl)ethyl]-2-oxazoline (Compound 152-1)

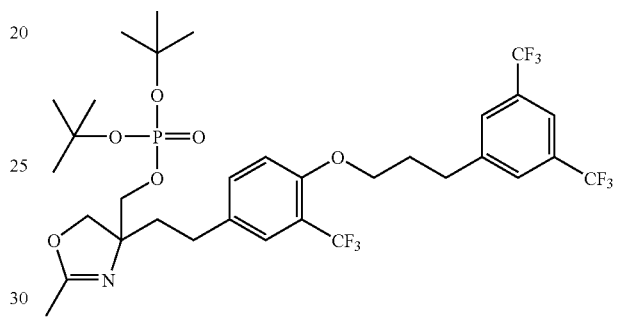

To a solution of compound 50-4 (500 mg) in N,N-dimethylformamide (8.8 ml) were added N,N-diisopropylethylamine (0.45 ml) and trimethyl orthoacetate (0.24 ml), and the mixture was stirred at 120° C. for 3.5 hr. Water was added to the reaction mixture, and the mixture was extracted with ethyl acetate, washed with water and saturated brine, and dried over anhydrous sodium sulfate. The solvent was evaporated under reduced pressure. To a solution of the obtained brown oil in methylene chloride (5.8 ml) and acetonitrile (4.0 ml) were added 1H-tetrazole (123 mg) and di-t-butyl diethylphosphoramidite (0.49 ml), and the mixture was stirred at room temperature for 2 hr. The reaction solution was ice-cooled, t-butyl hydroperoxide-containing decane solution (5-6M, 0.53 ml) was added, and the mixture was stirred for 5 hr. Saturated aqueous sodium hydrogen carbonate solution was added to the reaction mixture, and the mixture was extracted with methylene chloride. The organic layer was dried over anhydrous sodium sulfate, and the solvent was evaporated under reduced pressure. The obtained residue was purified by silica gel column chromatography (hexane:ethyl acetate) to give the object product (490 mg) as a yellow oil.

$^1$H-NMR(DMSO-$d_6$) δ (ppm): 1.39(18H, d, J=1.2 Hz), 1.72-1.78(2H, m), 1.90(3H, s), 2.07-2.14(2H, m), 2.46-2.53 (1H, m), 2.61(1H, td, J=11.6, 5.4 Hz), 2.95(2H, t, J=7.4 Hz), 3.75-3.82(2H, m), 4.00-4.13(4H, m), 7.14(1H, d, J=8.4 Hz), 7.42-7.45(2H, m), 7.92(3H, brs).

(152-2) Synthesis of 2-amino-2-(phosphoryloxymethyl)-4-(3-trifluoromethyl-4-{3-[3,5-bis(trifluoromethyl)phenyl]propoxy}phenyl)butanol (Compound 152-2)

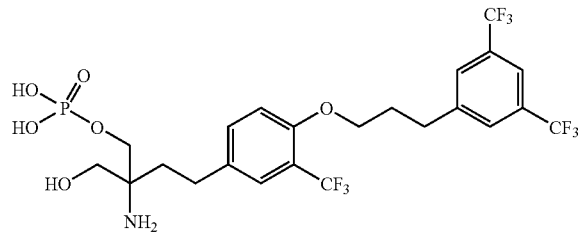

Compound 152-1 (490 mg) was dissolved in ethanol (5 ml), concentrated hydrochloric acid (1 ml) was added, and the mixture was stirred at 50° C. for 2 hr. The solvent was concentrated under reduced pressure, and methanol (2 ml), diethyl ether (5 ml) and propylene oxide (5 ml) were added to the residue. The precipitated powder was collected by filtration and washed with methanol and diethyl ether to give the object product (255 mg) as a white powder.

MS(ESI)m/z: 614[M+H]
$^1$H-NMR(DMSO-$d_6$) δ (ppm): 1.73-1.83(2H, m), 2.07-2.15(2H, s), 2.58-2.64(2H, m), 2.94(2H, t, J=7.3 Hz), 3.52 (2H, brs), 3.80-3.86(2H, m), 4.06(2H, t, J=5.4 Hz), 7.17(1H, d, J=8.2 Hz), 7.43(1H, d, J=9.2 Hz), 7.46(1H, s), 7.92(3H, brs).

Example 153

2-amino-2-(phosphoryloxymethyl)-4-{4-[3-(4-trifluoromethoxyphenyl)propoxy]-3-trifluoromethylphenyl}butanol (153-1) Synthesis of 4-di(t-butyl)phosphoryloxymethyl-2-methyl-4-(2-{4-[3-(4-trifluoromethoxyphenyl)propoxy]-3-trifluoromethylphenyl}ethyl)-2-oxazoline (Compound 153-1)

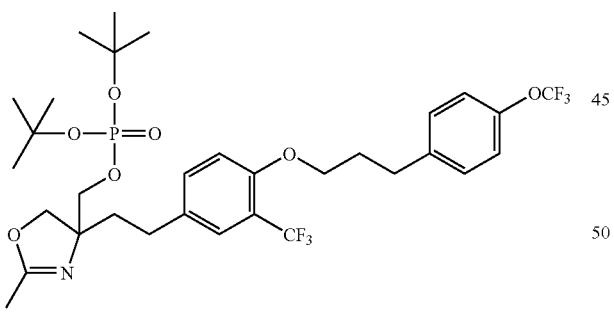

To a solution of compound 52-5 (510 mg) in N,N-dimethylformamide (10 ml) were added N,N-diisopropylethylamine (0.530 ml) and trimethyl orthoacetate (0.186 ml), and the mixture was stirred at 120° C. for 5.5 hr. Water was added to the reaction mixture, and the mixture was extracted with ethyl acetate, washed with water and saturated brine, and dried over anhydrous magnesium sulfate. The solvent was evaporated under reduced pressure to give a brown oil (510 mg). To a solution of the brown oil (510 mg) in methylene chloride (5 ml) and acetonitrile (2 ml) were added 1H-tetrazole (137 mg) and di-t-butyl diethylphosphoramidite (0.586 ml), and the mixture was stirred at room temperature for 2 hr. The reaction solution was ice-cooled, t-butyl hydroperoxide-containing decane solution (5-6M, 0.588 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (590 mg) as a yellow oil.

$^1$H-NMR(CD$_3$OD) δ (ppm): 1.49(18H, s), 1.82-1.89(2H, m), 2.01(3H, s), 2.05-2.12(2H, m), 2.52-2.70(2H, m), 2.85 (2H, t, J=7.5 Hz), 3.88-3.92(2H, m), 4.02(2H, t, J=5.9 Hz), 4.18(1H, d, J=9.0 Hz), 4.32(1H, d, J=9.0 Hz), 7.02(1H, d, J=8.5 Hz), 7.16(2H, d, J=8.2 Hz), 7.29(2H, d, J=8.5 Hz), 7.39(1H, d, J=8.5 Hz), 7.44(1H, d, J=1.8 Hz).

(153-2) Synthesis of 2-amino-2-(phosphoryloxymethyl)-4-{4-[3-(4-trifluoromethoxyphenyl)propoxy]-3-trifluoromethylphenyl}butanol (Compound 153-2)

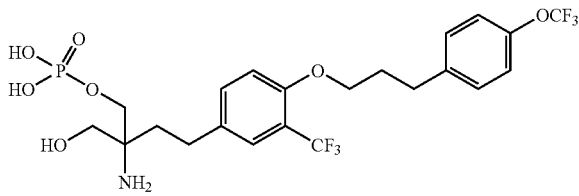

Compound 153-1 (590 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (400 mg) as a pale-brown solid.

MS(ESI)m/z: 562[M+H]
$^1$H-NMR(CD$_3$OD) δ (ppm): 1.92-2.00(2H, m), 2.09-2.16 (2H, m), 2.61-2.75(2H, m), 2.81-2.90(2H, m), 3.70(2H, brs), 3.94-4.08(4H, m), 7.01-7.10(1H, m), 7.17(2H, brs), 7.29(2H, brd, J=7.3 Hz), 7.40-7.47(1H, m), 7.48(1H, brs).

Example 154

2-amino-4-{4-[3-(3,4-difluorophenyl)propoxy]-3-trifluoromethylphenyl}-2-(phosphoryloxymethyl)butanol (154-1) Synthesis of 4-di(t-butyl)phosphoryloxymethyl-4-(2-{4-[3-(3,4-difluorophenyl)propoxy]-3-trifluoromethyl}ethyl)-2-methyl-2-oxazoline (Compound 154-1)

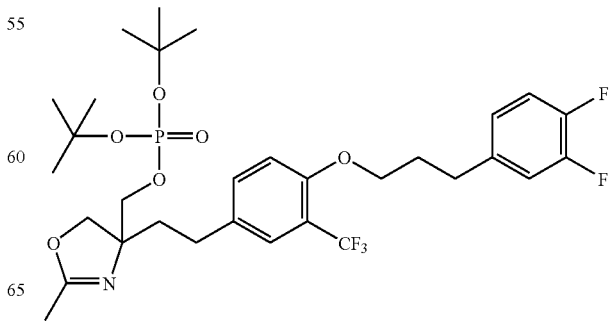

To a solution of compound 53-4 (360 mg) in N,N-dimethylformamide (7.7 ml) were added N,N-diisopropylethylamine (0.39 ml) and trimethyl orthoacetate (0.21 ml), and the mixture was stirred at 120° C. for 6 hr. Water was added to the reaction mixture, and the mixture was extracted with ethyl acetate, washed with water and saturated brine, and dried over anhydrous sodium sulfate. The solvent was evaporated under reduced pressure. To a solution of the obtained brown oil in methylene chloride (5 ml) and acetonitrile (3.75 ml) were added 1H-tetrazole (110 mg) and di-t-butyl diethylphosphoramidite (0.43 ml), and the mixture was stirred at room temperature for 5 hr. The reaction solution was ice-cooled, t-butyl hydroperoxide-containing decane solution (5-6M, 0.46 ml) was added and the mixture was stirred for 1 hr. Saturated aqueous sodium hydrogen carbonate solution was added to the reaction mixture, and the mixture was extracted with methylene chloride. The organic layer was dried over anhydrous sodium sulfate and the solvent was evaporated under reduced pressure. The obtained residue was purified by silica gel column chromatography (hexane:ethyl acetate) to give the object product (190 mg) as a yellow oil.

$^1$H-NMR(DMSO-$d_6$) δ (ppm): 1.39(18H, d, J=1.2 Hz), 1.68-1.81(2H, m), 1.90(3H, s), 1.98-2.04(2H, m), 2.45-2.54 (1H, m), 2.61(1H, td, J=12.3, 5.2 Hz), 2.73(2H, t, J=7.5 Hz), 3.74-3.82(2H, m), 4.02(2H, t, J=5.4 Hz), 4.07(1H, d, J=9.0 Hz), 4.11(1H, d, J=8.8 Hz), 7.01-7.04(1H, m), 7.13(1H, d, J=8.4 Hz), 7.25-7.36(2H, m), 7.42-7.45(2H, m).

(154-2) Synthesis of 2-amino-4-{4-[3-(3,4-difluorophenyl)propoxy]-3-trifluoromethylphenyl}-2-(phosphoryloxymethyl)butanol (Compound 154-2)

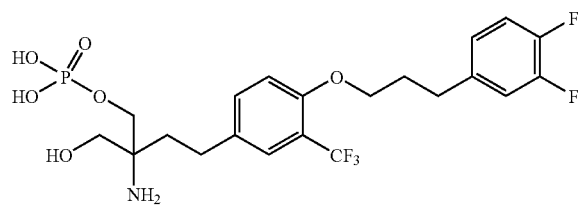

Compound 154-1 (190 mg) was dissolved in ethanol (5 ml), concentrated hydrochloric acid (1 ml) was added, and the mixture was stirred at 50° C. for 3 hr. The solvent was concentrated under reduced pressure, and methanol (2 ml), diethyl ether (5 ml) and propylene oxide (5 ml) were added to the residue. The precipitated powder was collected by filtration and washed with diethyl ether to give the object product (100 mg) as a white powder.

MS(ESI)m/z: 514[M+H]

$^1$H-NMR(CD$_3$OD) δ (ppm): 1.95-1.98(2H, m), 2.04-2.11 (2H, m), 2.65-2.72(2H, m), 2.81(2H, t, J=7.6 Hz), 3.71(2H, s), 4.00-4.03(4H, m), 6.97-7.00(1H, m), 7.04(1H, d, J=8.6 Hz), 7.06-7.17(2H, m), 7.43(1H, d, J=8.6 Hz), 7.48(1H, s).

Example 155

2-amino-4-{4-[3-(3-chloro-4-methylphenyl)propoxy]-3-trifluoromethylphenyl}-2-(phosphoryloxymethyl)butanol (155-1) Synthesis of 4-di(t-butyl)phosphoryloxymethyl-4-(2-{4-[3-(3-chloro-4-methylphenyl)propoxy]-3-trifluoromethyl}ethyl)-2-methyl-2-oxazoline (Compound 155-1)

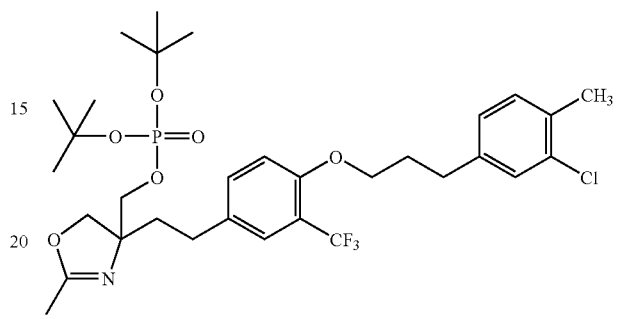

To a solution of compound 55-4 (350 mg) in N,N-dimethylformamide (7.2 ml) were added N,N-diisopropylethylamine (0.37 ml) and trimethyl orthoacetate (0.20 ml), and the mixture was stirred at 120° C. for 4.5 hr. Water was added to the reaction mixture, and the mixture was extracted with ethyl acetate, washed with water and saturated brine, and dried over anhydrous sodium sulfate. The solvent was evaporated under reduced pressure. To a solution of the obtained brown oil in methylene chloride (5.8 ml) and acetonitrile (4.5 ml) were added 1H-tetrazole (120 mg) and di-t-butyl diethylphosphoramidite (0.48 ml), and the mixture was stirred at room temperature for 1.5 hr. The reaction solution was ice-cooled, t-butyl hydroperoxide-containing decane solution (5-6M, 0.52 ml) was added and the mixture was stirred for 30 min. Saturated aqueous sodium hydrogen carbonate solution was added to the reaction mixture, and the mixture was extracted with methylene chloride. The organic layer was dried over anhydrous sodium sulfate and the solvent was evaporated under reduced pressure. The obtained residue was purified by silica gel column chromatography (hexane:ethyl acetate) to give the object product (352 mg) as a pale-yellow oil.

$^1$H-NMR(DMSO-$d_6$) δ (ppm): 1.39(18H, d, J=1.1 Hz), 1.68-1.80(2H, m), 1.90(3H, s), 1.95-2.03(2H, m), 2.27(3H, s), 2.45-2.53(1H, m), 2.61(1H, td, J=11.4, 5.2 Hz), 2.70(2H, t, J=7.4 Hz), 3.74-3.82(2H, m), 4.00-4.12(4H, m), 7.06(1H, dd, J=7.8, 1.1 Hz), 7.12(1H, d, J=8.5 Hz), 7.24(1H, s), 7.25 (1H, d, 7.8 Hz), 7.43(1H, d, J=8.6 Hz), 7.45(1H, s).

(155-2) Synthesis of 2-amino-4-{4-[3-(3-chloro-4-methylphenyl)propoxy]-3-trifluoromethylphenyl}-2-(phosphoryloxymethyl)butanol (Compound 155-2)

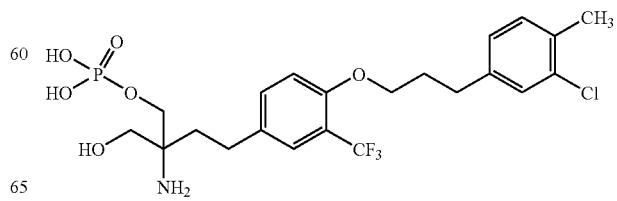

Compound 155-1 (332 mg) was dissolved in ethanol (5 ml), concentrated hydrochloric acid (1 ml) was added, and the mixture was stirred at 50° C. for 4.5 hr. The solvent was concentrated under reduced pressure, and methanol (2 ml), diethyl ether (5 ml) and propylene oxide (5 ml) were added to the residue. The precipitated powder was collected by filtration and washed with diethyl ether to give the object product (185 mg) as a white powder.

MS(ESI)m/z: 526[M+H]

$^1$H-NMR(CD$_3$OD) δ (ppm): 1.92-1.98(2H, m), 2.02-2.09 (2H, m), 2.30(3H, s), 2.65-2.72(2H, m), 2.77(2H, t, J=7.6 Hz), 3.70(2H, s), 3.97-4.02(4H, m), 7.01-7.03(2H, m), 7.16 (1H, d, J=7.8 Hz), 7.18(1H, s), 7.43(1H, d, J=8.7 Hz), 7.48 (1H, s).

Example 156

2-amino-4-{4-[3-(1-indanon-5-yl)propoxy]-3-trifluoromethylphenyl}-2-(phosphoryloxymethyl)butanol (156-1) Synthesis of 4-di(t-butyl)phosphoryloxymethyl-4-(2-{4-[3-(1-indanon-5-yl)propoxy]-3-trifluoromethylphenyl}ethyl)-2-methyl-2-oxazoline (Compound 156-1)

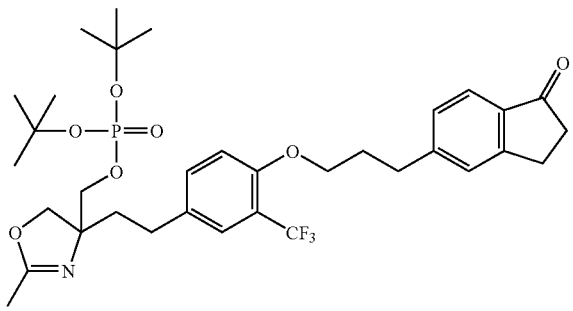

To a solution of compound 56-5 (360 mg) in N,N-dimethylformamide (10 ml) were added N,N-diisopropylethylamine (0.397 ml) and trimethyl orthoacetate (0.140 ml), and the mixture was stirred at 120° C. for 6.5 hr. Water was added to the reaction mixture, and the mixture was extracted with ethyl acetate, washed with water and saturated brine, and dried over anhydrous magnesium sulfate. The solvent was evaporated under reduced pressure to give a brown oil (320 mg). To a solution of the brown oil (320 mg) in methylene chloride (5 ml) and acetonitrile (2 ml) were added 1H-tetrazole (94 mg) and di-t-butyl diethylphosphoramidite (0.404 ml), and the mixture was stirred at room temperature for 1 hr. The reaction solution was ice-cooled, t-butyl hydroperoxide-containing decane solution (5-6M, 0.402 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (260 mg) as a yellow oil.

$^1$H-NMR(CD$_3$OD) δ (ppm): 1.49(18H, s), 1.82-1.90(2H, m), 2.01(3H, s), 2.08-2.15(2H, m), 2.53-2.65(1H, m), 2.66-2.68(3H, m), 2.93(2H, t, J=7.5 Hz), 3.10-3.13(2H, m), 3.90-3.92(2H, m), 4.04(2H, t, J=5.9 Hz), 4.18(1H, d, J=9.0 Hz), 4.32(1H, d, J=9.0 Hz), 7.03(1H, d, J=8.5 Hz), 7.27(1H, d, J=7.9 Hz), 7.37-7.40(2H, m), 7.44(1H, brs), 7.62(1H, d, J=7.9 Hz).

(156-2) Synthesis of 2-amino-4-{4-[3-(1-indanon-5-yl)propoxy]-3-trifluoromethylphenyl}-2-(phosphoryloxymethyl)butanol (Compound 156-2)

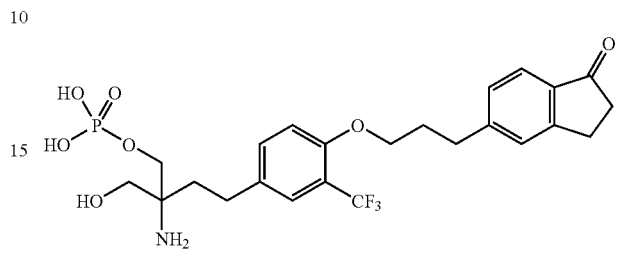

Compound 156-1 (260 mg) was dissolved in ethanol (5 ml), concentrated hydrochloric acid (1 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (185 mg) as a white solid.

MS (ESI)m/z: 532[M+H]

$^1$H-NMR(CD$_3$OD) δ (ppm): 1.93-1.99(2H, m), 2.12-2.17 (2H, m), 2.65-2.76(4H, m), 2.94(2H, t, J=7.5 Hz), 3.10-3.17 (2H, m), 3.70(2H, brs), 3.97-4.02(2H, m), 4.05(2H, t, J=5.9 Hz), 7.04(1H, d, J=8.4 Hz), 7.27(1H, d, J=7.9 Hz), 7.40(1H, brs), 7.44(1H, d, J=8.4 Hz), 7.49(1H, brs), 7.62(1H, d, J=7.9 Hz).

Example 157

2-amino-4-{4-[3-(2-chloro-5-trifluoromethylphenyl)propoxy]-3-trifluoromethylphenyl}-2-(phosphoryloxymethyl)butanol (157-1) Synthesis of 4-di(t-butyl)phosphoryloxymethyl-4-(2-{4-[3-(2-chloro-5-trifluoromethylphenyl)propoxy]-3-trifluoromethylphenyl}ethyl)-2-methyl-2-oxazoline (Compound 157-1)

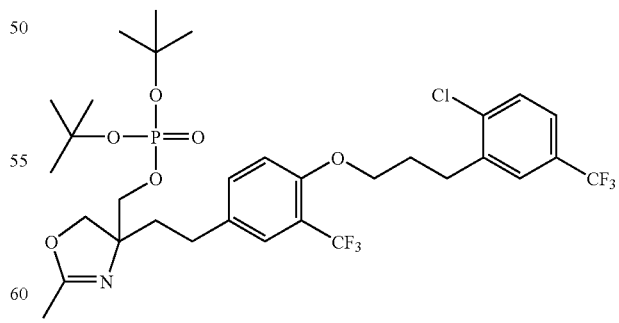

To a solution of compound 57-5 (490 mg) in N,N-dimethylformamide (10 ml) were added N,N-diisopropylethylamine (0.492 ml) and trimethyl orthoacetate (0.173 ml), and the mixture was stirred at 120° C. for 10 hr. Water was added to the reaction mixture, and the mixture was extracted with ethyl acetate, washed with water and saturated brine, and dried over anhydrous magnesium sulfate. The solvent was evaporated under reduced pressure to give a brown oil (490 mg). To a solution of the brown oil (490 mg) in methylene chloride (5 ml) and acetonitrile (2 ml) were added 1H-tetrazole (127 mg) and di-t-butyl diethylphosphoramidite (0.545 ml), and the mixture was stirred at room temperature for 2 hr. The reaction solution was ice-cooled, t-butyl hydroperoxide-containing decane solution (5-6M, 0.546 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (550 mg) as a yellow oil.

$^1$H-NMR(CD$_3$OD) δ (ppm): 1.49(18H, s), 1.83-1.90(2H, m), 2.01(3H, s), 2.08-2.16(2H, m), 2.53-2.71(2H, m), 3.05 (2H, t, J=7.6 Hz), 3.89-3.92(2H, m), 4.06(2H, t, J=5.7 Hz), 4.18(1H, d, J=9.0 Hz), 4.32(1H, d, J=9.0 Hz), 7.04(1H, d, J=8.5 Hz), 7.40(1H, d, J=8.5 Hz), 7.45(1H, d, J=1.8 Hz), 7.49(1H, dd, J=8.5, 1.8 Hz), 7.56-7.59(2H, m).

(157-2) Synthesis of 2-amino-4-{4-[3-(2-chloro-5-trifluoromethylphenyl)propoxy]-3-trifluoromethylphenyl}-2-(phosphoryloxymethyl)butanol (Compound 157-2)

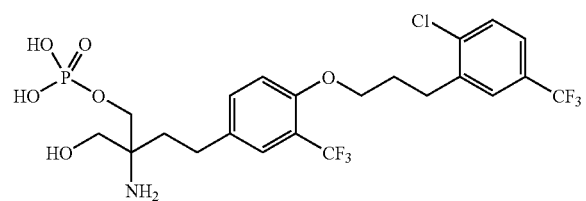

Compound 157-1 (550 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (177 mg) as a pale-brown solid.

MS(ESI)m/z: 580[M+H]

$^1$H-NMR(CD$_3$OD) δ (ppm): 1.92-2.01(2H, m), 2.07-2.17 (2H, m), 2.62-2.72(2H, m), 3.05(2H, t, J=7.5 Hz), 3.70(2H, brs), 3.96-4.02(2H, m), 4.06(2H, t, J=5.7 Hz), 7.06(1H, d, J=8.5 Hz), 7.43(1H, d, J=8.5 Hz), 7.49(2H, brs), 7.56-7.59 (2H, m).

Example 158

2-amino-2-(phosphoryloxymethyl)-4-{4-[3-(3-trifluoromethoxyphenyl)propoxy]-3-trifluoromethylphenyl}butanol (158-1) Synthesis of 4-di(t-butyl)phosphoryloxymethyl-2-methyl-4-(2-{4-[3-(3-trifluoromethoxyphenyl)propoxy]-3-trifluoromethylphenyl}ethyl)-2-oxazoline (Compound 158-1)

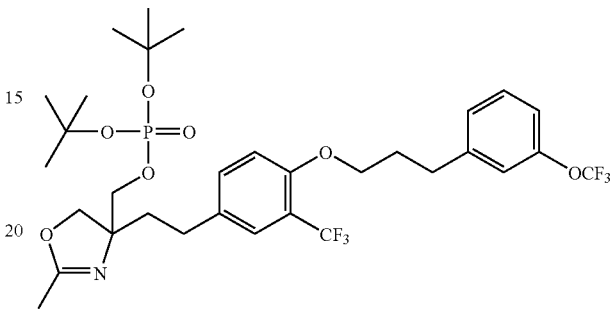

To a solution of compound 58-5 (460 mg) in N,N-dimethylformamide (10 ml) were added N,N-diisopropylethylamine (0.479 ml) and trimethyl orthoacetate (0.168 ml), and the mixture was stirred at 120° C. for 4 hr. Water was added to the reaction mixture, and the mixture was extracted with ethyl acetate, washed with water and saturated brine, and dried over anhydrous magnesium sulfate. The solvent was evaporated under reduced pressure to give a brown oil (450 mg). To a solution of the brown oil (450 mg) in methylene chloride (5 ml) and acetonitrile (2 ml) were added 1H-tetrazole (125 mg) and di-t-butyl diethylphosphoramidite (0.533 ml), and the mixture was stirred at room temperature for 2 hr. The reaction solution was ice-cooled, t-butyl hydroperoxide-containing decane solution (5-6M, 0.534 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (510 mg) as a yellow oil.

$^1$H-NMR(CD$_3$OD) δ (ppm): 1.48(18H, s), 1.82-1.89(2H, m), 2.01(3H, s), 2.05-2.13(2H, m), 2.52-2.70(2H, m), 2.87 (2H, t, J=7.5 Hz), 3.89-3.92(2H, m), 4.01(2H, t, J=5.9 Hz), 4.18(1H, d, J=9.1 Hz), 4.32(1H, d, J=9.1 Hz), 7.01(1H, d, J=8.5 Hz), 7.05-7.11(2H, m), 7.20(1H, d, J=7.6 Hz), 7.33-7.40(2H, m), 7.44(1H, d, J=1.5 Hz).

(158-2) Synthesis of 2-amino-2-(phosphoryloxymethyl)-4-{4-[3-(3-trifluoromethoxyphenyl)propoxy]-3-trifluoromethylphenyl}butanol (Compound 158-2)

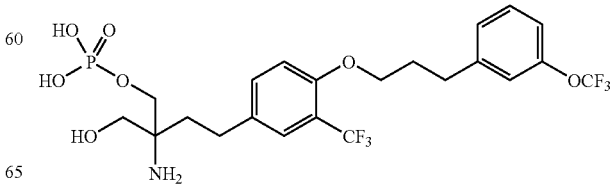

Compound 158-1 (510 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (333 mg) as a white solid.

MS(ESI)m/z: 562[M+H]

$^1$H-NMR(CD$_3$OD) δ (ppm): 1.93-1.98(2H, m), 2.06-2.13 (2H, m), 2.61-2.76(2H, m), 2.87(2H, t, J=7.5 Hz), 3.70(2H, brs), 3.94-4.03(4H, m), 7.03(1H, d, J=8.5 Hz), 7.05-7.11(2H, m), 7.20(1H, d, J=7.8 Hz), 7.36(1H, t, J=7.8 Hz), 7.43(1H, dd, J=8.5, 1.4 Hz), 7.49(1H, d, J=1.4 Hz).

Example 159

2-amino-4-{4-[3-(2-naphthyl)propoxy]-3-trifluoromethylphenyl}-2-(phosphoryloxymethyl)butanol (159-1) Synthesis of 4-di(t-butyl)phosphoryloxymethyl-2-methyl-4-(2-{4-[3-(2-naphthyl)propoxy]-3-trifluoromethylphenyl}ethyl)-2-oxazoline (Compound 159-1)

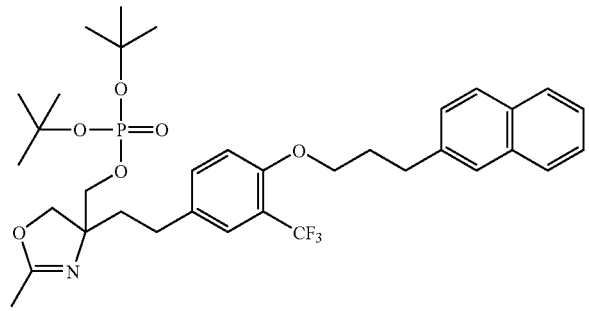

To a solution of compound 59-4 (310 mg) in N,N-dimethylformamide (10 ml) were added N,N-diisopropylethylamine (0.345 ml) and trimethyl orthoacetate (0.121 ml), and the mixture was stirred at 120° C. for 3 hr. Furthermore, N,N-diisopropylethylamine (0.345 ml) and trimethyl orthoacetate (0.121 ml) was added, and the mixture was stirred at 120° C. for 3 hr. Water was added to the reaction mixture, and the mixture was extracted with ethyl acetate, washed with water and saturated brine, and dried over anhydrous magnesium sulfate. The solvent was evaporated under reduced pressure to give a brown oil (330 mg). To a solution of the brown oil (330 mg) in methylene chloride (5 ml) and acetonitrile (2 ml) were added 1H-tetrazole (90 mg) and di-t-butyl diethylphosphoramidite (0.383 ml), and the mixture was stirred at room temperature for 2 hr. The reaction solution was ice-cooled, t-butyl hydroperoxide-containing decane solution (5-6M, 0.384 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (270 mg) as a yellow oil.

$^1$H-NMR(CD$_3$OD) δ (ppm): 1.48(18H, s), 1.82-1.89(2H, m), 2.01(3H, s), 2.16-2.22(2H, m), 2.52-2.69(2H, m), 2.99 (2H, t, J=7.5 Hz), 3.89-3.92(2H, m), 4.05(2H, t, J=6.0 Hz), 4.18(1H, d, J=9.0 Hz), 4.32(1H, d, J=9.0 Hz), 7.00(1H, d, J=8.6 Hz), 7.34-7.48(5H, m), 7.63(1H, s), 7.72-7.80(3H, m).

(159-2) Synthesis of 2-amino-4-{4-[3-(2-naphthyl)propoxy]-3-trifluoromethylphenyl}-2-(phosphoryloxymethyl)butanol (Compound 159-2)

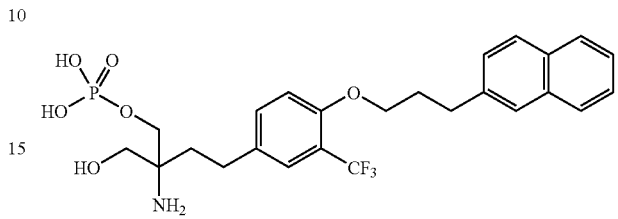

Compound 159-1 (270 mg) was dissolved in ethanol (5 ml), concentrated hydrochloric acid (1 ml) was added, and the mixture was stirred at 50° C. for 3 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (180 mg) as a white solid.

MS(ESI)m/z: 528[M+H]

$^1$H-NMR(CD$_3$OD) δ (ppm): 1.93-1.99(2H, m), 2.16-2.22 (2H, m), 2.62-2.72(2H, m), 2.99(2H, t, J=7.4 Hz), 3.70(2H, brs), 3.95-4.05(2H, m), 4.05(2H, t, J=5.9 Hz), 7.00(1H, d, J=8.6 Hz), 7.34-7.45(4H, m), 7.49(1H, brs), 7.63(1H, s), 7.72-7.80(3H, m).

Example 160

2-amino-4-{4-[3-(2,3-dichlorophenyl)propoxy]-3-trifluoromethylphenyl}-2-(phosphoryloxymethyl)butanol (160-1) Synthesis of 4-di(t-butyl)phosphoryloxymethyl-4-(2-{4-[3-(2,3-dichlorophenyl)propoxy]-3-trifluoromethylphenyl}ethyl)-2-methyl-2-oxazoline (Compound 160-1)

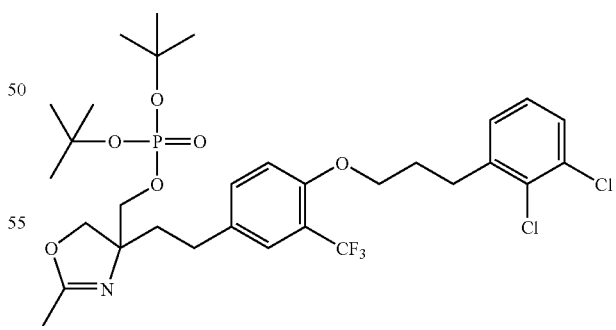

To a solution of compound 60-5 (420 mg) in N,N-dimethylformamide (10 ml) were added N,N-diisopropylethylamine (0.451 ml) and trimethyl orthoacetate (0.159 ml), and the mixture was stirred at 120° C. for 4 hr. Furthermore, N,N-diisopropylethylamine (0.451 ml) and trimethyl orthoacetate (0.159 ml) were added, and the mixture was stirred at 120° C. for 3 hr. Water was added to the reaction mixture, and the mixture was extracted with ethyl acetate, washed with water and saturated brine, and dried over anhydrous magnesium sulfate. The solvent was evaporated under reduced pressure to give a brown oil (420 mg). To a solution of the brown oil (420 mg) in methylene chloride (5 ml) and acetonitrile (2 ml) were added 1H-tetrazole (118 mg) and di-t-butyl diethylphosphoramidite (0.503 ml), and the mixture was stirred at room temperature for 2 hr. The reaction solution was ice-cooled, t-butyl hydroperoxide-containing decane solution (5-6M, 0.504 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane: ethyl acetate=1:4-ethyl acetate alone) to give the object product (330 mg) as a yellow oil.

$^1$H-NMR(CD$_3$OD) δ (ppm): 1.48(18H, s), 1.83-1.90(2H, m), 2.01(3H, s) 2.02-2.14(2H, m), 2.53-2.71(2H, m), 3.01 (2H, t, J=7.6 Hz), 3.89-3.92(2H, m), 4.06(2H, t, J=5.8 Hz), 4.18(1H, d, J=9.1 Hz), 4.32(1H, d, J=9.1 Hz), 7.04(1H, d, J=8.5 Hz), 7.16-7.23(2H, m), 7.36-7.42(2H, m), 7.44(1H, brd, J=1.4 Hz).

(160-2) Synthesis of 2-amino-4-{4-[3-(2,3-dichlorophenyl)propoxy]-3-trifluoromethylphenyl}-2-(phosphoryloxymethyl)butanol (Compound 160-2)

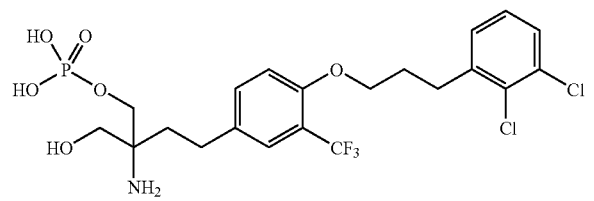

Compound 160-1 (330 mg) was dissolved in ethanol (5 ml), concentrated hydrochloric acid (1 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (240 mg) as a white solid.

MS(ESI)m/z: 546[M+H]

$^1$H-NMR(CD$_3$OD) δ (ppm): 1.92-2.00(2H, m), 2.05-2.16 (2H, m), 2.65-2.77(2H, m), 3.02(2H, t, J=7.5 Hz), 3.70(2H, brs), 3.96-4.02(2H, m), 4.07(2H, t, J=5.8 Hz), 7.06(1H, d, J=8.6 Hz), 7.16-7.24(2H, m), 7.38(1H, dd, J=7.5, 1.6 Hz), 7.44(1H, d, J=8.6 Hz), 7.49(1H, brs).

Example 161

2-amino-4-{4-[3-(3-chloro-4-fluorophenyl)propoxy]-3-trifluoromethylphenyl}-2-(phosphoryloxymethyl)butanol (161-1) Synthesis of 4-di(t-butyl)phosphoryloxymethyl-4-(2-{4-[3-(3-chloro-4-fluorophenyl)propoxy]-3-trifluoromethylphenyl}ethyl)-2-methyl-2-oxazoline (Compound 161-1)

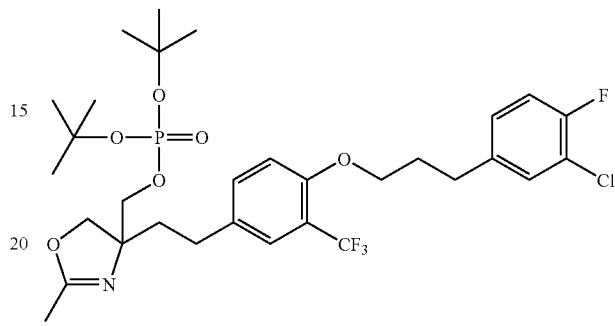

To a solution of compound 61-5 (400 mg) in N,N-dimethylformamide (10 ml) were added N,N-diisopropylethylamine (0.443 ml) and trimethyl orthoacetate (0.207 ml), and the mixture was stirred at 120° C. for 7 hr. Water was added to the reaction mixture, and the mixture was extracted with ethyl acetate, washed with water and saturated brine, and dried over anhydrous magnesium sulfate. The solvent was evaporated under reduced pressure to give a brown oil (420 mg). To a solution of the brown oil (420 mg) in methylene chloride (5 ml) and acetonitrile (2 ml) were added 1H-tetrazole (115 mg) and di-t-butyl diethylphosphoramidite (0.491 ml), and the mixture was stirred at room temperature for 2 hr. The reaction solution was ice-cooled, t-butyl hydroperoxide-containing decane solution (5-6M, 0.492 ml) was added, and the mixture was stirred at room temperature for 15 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (450 mg) as a yellow oil.

$^1$H-NMR(CD$_3$OD) δ (ppm): 1.48(18H, s), 1.82-1.89(2H, m), 2.01(3H, s), 2.02-2.10(2H, m), 2.52-2.70(2H, m), 2.81 (2H, t, J=7.5 Hz), 3.89-3.91(2H, m), 4.02(2H, t, J=5.9 Hz), 4.18(1H, d, J=9.0 Hz), 4.32(1H, d, J=9.0 Hz), 7.02(1H, d, J=8.5 Hz), 7.09-7.16(2H, m), 7.30(1H, dd, J=7.4, 1, 7 Hz), 7.39(1H, dd, J=8.5, 1, 7 Hz), 7.44(1H, brs).

(161-2) Synthesis of 2-amino-4-{4-[3-(3-chloro-4-fluorophenyl)propoxy]-3-trifluoromethylphenyl}-2-(phosphoryloxymethyl)butanol (Compound 161-2)

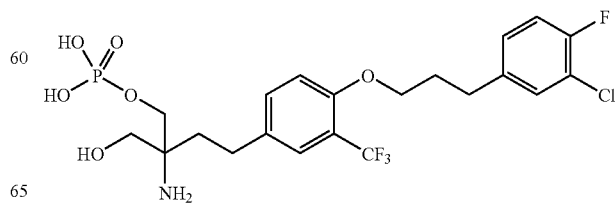

Compound 161-1 (450 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (270 mg) as a white solid.

MS(ESI)m/z: 530[M+H]

$^1$H-NMR(CD$_3$OD) δ (ppm): 1.93-1.99(2H, m), 2.02-2.12 (2H, m), 2.65-2.74(2H, m), 2.81(2H, t, J=7.5 Hz), 3.70(2H, brs), 3.97-4.03(4H, m), 7.04(1H, d, J=8.6 Hz), 7.11-7.15(2H, m), 7.29(1H, d, J=7.3 Hz), 7.44(1H, d, J=8.6 Hz), 7.48(1H, brs).

Example 162

2-amino-4-{4-[3-(2,5-dimethylphenyl)propoxy]-3-trifluoromethylphenyl}-2-(phosphoryloxymethyl) butanol (162-1) Synthesis of 4-di(t-butyl)phosphoryloxymethyl-2-methyl-4-(2-{4-[3-(2,5-dimethylphenyl)propoxy]-3-trifluoromethyl}ethyl)-2-oxazoline (Compound 162-1)

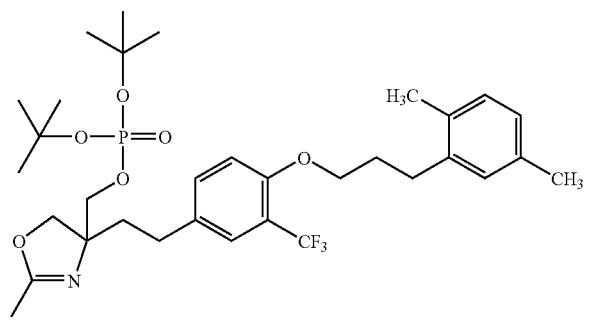

To a solution of compound 62-4 (330 mg) in N,N-dimethylformamide (7.0 ml) were added N,N-diisopropylethylamine (0.36 ml) and trimethyl orthoacetate (0.20 ml), and the mixture was stirred at 120° C. for 2.5 hr. Water was added to the reaction mixture, and the mixture was extracted with ethyl acetate, washed with water and saturated brine, and dried over anhydrous sodium sulfate. The solvent was evaporated under reduced pressure. To a solution of the obtained brown oil in methylene chloride (4.75 ml) and acetonitrile (3.5 ml) were added 1H-tetrazole (100 mg) and di-t-butyl diethylphosphoramidite (0.40 ml), and the mixture was stirred at room temperature for 3 hr. The reaction solution was ice-cooled, t-butyl hydroperoxide-containing decane solution (5-6M, 0.43 ml) was added and the mixture was stirred for 30 min. Saturated aqueous sodium hydrogen carbonate solution was added to the reaction mixture, and the mixture was extracted with methylene chloride. The organic layer was dried over anhydrous sodium sulfate and the solvent was evaporated under reduced pressure. The obtained residue was purified by silica gel column chromatography (hexane:ethyl acetate) to give the object product (290 mg) as a yellow oil.

$^1$H-NMR(DMSO-D6) δ (ppm): 1.39(18H, s), 1.73-1.82 (2H, m), 1.90(3H, s), 1.90-1.95(2H, m), 2.19(3H, s), 2.21(3H, s), 2.46-2.43(1H, m), 2.62(1H, td, J=11.5, 5.8 Hz), 2.69(2H, t, J=7.6 Hz), 3.75-3.82(2H, m), 4.06-4.12(4H, m), 6.89(1H, d, J=7.7 Hz), 6.93(1H, s), 7.01(1H, d, J=7.6 Hz), 7.14(1H, d, J=8.4 Hz), 7.43-7.46(2H, m).

(162-2) Synthesis of 2-amino-4-{4-[3-(2,5-dimethylphenyl)propoxy]-3-trifluoromethylphenyl}-2-(phosphoryloxymethyl)butanol (Compound 162-2)

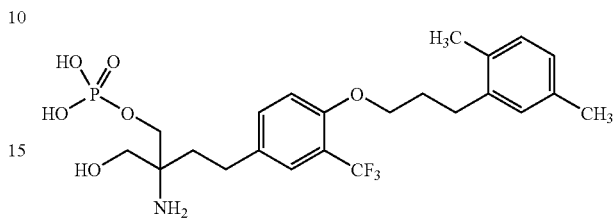

Compound 162-1 (290 mg) was dissolved in ethanol (5 ml), concentrated hydrochloric acid (1 ml) was added, and the mixture was stirred at 50° C. for 3 hr. The solvent was concentrated under reduced pressure, to the residue were added methanol (2 ml), diethyl ether (5 ml) and propylene oxide (5 ml) and the mixture was stood still in a refrigerator. The precipitated powder was collected by filtration and washed with diethyl ether to give the object product (185 mg) as a white powder.

MS(ESI)m/z: 506[M+H]

$^1$H-NMR(CD$_3$OD) δ (ppm): 1.93-2.04(4H, m), 2.22(3H, s), 2.24(3H, s), 2.66-2.72(2H, m), 2.78(2H, t, J=7.6 Hz), 3.70(2H, s), 3.98(2H, t, J=5.6 Hz), 4.05(2H, t, J=5.7 Hz), 6.87(1H, d, J=8.8 Hz), 6.92(1H, s), 6.99(1H, d, J=7.7 Hz), 7.05(1H, d, J=8.5 Hz), 7.43(1H, d, J=8.5 Hz), 7.48(1H, s).

Example 163

2-amino-4-{4-[3-(3-chloro-2-fluorophenyl)propoxy]-3-trifluoromethylphenyl}-2-(phosphoryloxymethyl)butanol (163-1) Synthesis of 4-di(t-butyl)phosphoryloxymethyl-4-(2-{4-[3-(3-chloro-2-fluorophenyl)propoxy]-3-trifluoromethyl}ethyl)-2-methyl-2-oxazoline (Compound 163-1)

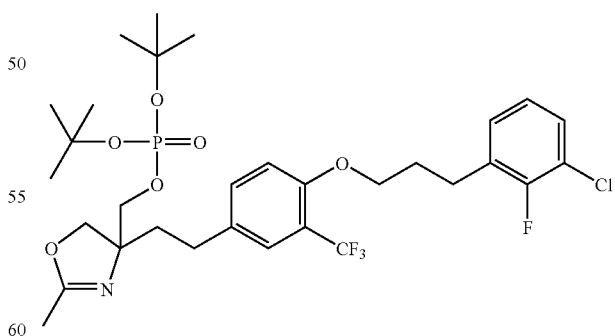

To a solution of compound 63-4 (340 mg) in N,N-dimethylformamide (7.0 ml) were added N,N-diisopropylethylamine (0.37 ml) and trimethyl orthoacetate (0.19 ml), and the mixture was stirred at 120° C. for 2.5 hr. Water was added to the reaction mixture, and the mixture was extracted with ethyl acetate, washed with water and saturated brine, and dried over anhydrous sodium sulfate. The solvent was evaporated under reduced pressure. To a solution of the obtained brown oil in methylene chloride (4.5 ml) and acetonitrile (3.5 ml) were added 1H-tetrazole (93 mg) and di-t-butyl diethylphosphoramidite (0.37 ml), and the mixture was stirred at room temperature for 1.5 hr. The reaction solution was ice-cooled, t-butyl hydroperoxide-containing decane solution (5-6M, 0.40 ml) was added and the mixture was stirred for 1.5 hr. Saturated aqueous sodium hydrogen carbonate solution was added to the reaction mixture, and the mixture was extracted with methylene chloride. The organic layer was dried over anhydrous sodium sulfate and the solvent was evaporated under reduced pressure. The obtained residue was purified by silica gel column chromatography (hexane:ethyl acetate) to give the object product (260 mg) as a yellow oil.

$^1$H-NMR(DMSO-$d_6$) δ (ppm): 1.39(18H, s), 1.68-1.83 (2H, m). 1.90(3H, s), 1.98-2.04(2H, m), 2.46-2.53(1H, m), 2.61(1H, td, J=11.2, 5.5 Hz), 2.82(2H, t, J=7.4 Hz), 3.74-3.82 (2H, m), 4.00-4.08(3H, m), 4.11(1H, d, J=8.8 Hz), 7.12-7.18 (2H, m), 7.25(1H, t, J=7.7 Hz), 7.41-7.45(3H, m).

(163-2) Synthesis of 2-amino-4-{4-[3-(3-chloro-2-fluorophenyl)propoxy]-3-trifluoromethylphenyl}-2-(phosphoryloxymethyl)butanol (Compound 163-2)

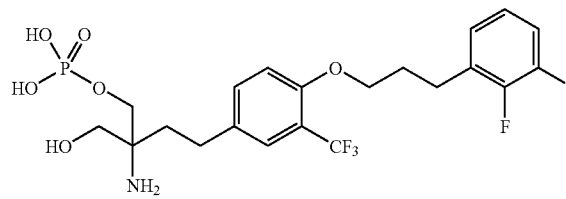

Compound 163-1 (260 mg) was dissolved in ethanol (5 ml), concentrated hydrochloric acid (1 ml) was added, and the mixture was stirred at 50° C. for 3 hr. The solvent was concentrated under reduced pressure, and methanol (2 ml), diethyl ether (5 ml) and propylene oxide (5 ml) were added to the residue. The precipitated powder was collected by filtration and washed with diethyl ether to give the object product (145 mg) as a white powder.

MS(ESI)m/z: 530[M+H]

$^1$H-NMR(CD$_3$OD) δ (ppm): 1.93-1.99(2H, m), 2.06-2.13 (2H, m), 2.65-2.72(2H, m), 2.90(2H, t, J=7.5 Hz), 3.70(2H, brs), 3.99(2H, t, J=5.7 Hz), 4.05(2H, t, J=5.7 Hz), 7.06(2H, dd, J=7.7, 5.6 Hz), 7.17(1H, t, J=7.8 Hz), 7.30(1H, dd, J=7.9, 1.4 Hz), 7.44(1H, d, J=8.4 Hz), 7.48(1H, s).

Example 164

2-amino-4-{4-[3-(5-chloro-2-fluorophenyl)propoxy]-3-trifluoromethylphenyl}-2-(phosphoryloxymethyl)butanol (164-1) Synthesis of 4-di(t-butyl)phosphoryloxymethyl-4-(2-{4-[3-(5-chloro-2-fluorophenyl)propoxy]-3-trifluoromethyl}ethyl)-2-methyl-2-oxazoline (Compound 164-1)

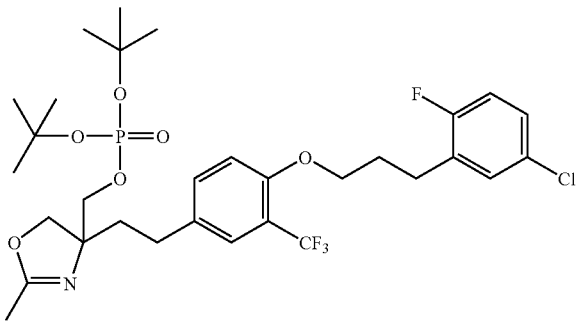

To a solution of compound 64-4 (360 mg) in N,N-dimethylformamide (7.5 ml) were added N,N-diisopropylethylamine (0.38 ml) and trimethyl orthoacetate (0.20 ml), and the mixture was stirred at 120° C. for 3.5 hr. Water was added to the reaction mixture, and the mixture was extracted with ethyl acetate, washed with water and saturated brine, and dried over anhydrous sodium sulfate. The solvent was evaporated under reduced pressure. To a solution of the obtained brown oil in methylene chloride (5 ml) and acetonitrile (3.75 ml) were added 1H-tetrazole (105 mg) and di-t-butyl diethylphosphoramidite (0.42 ml), and the mixture was stirred at room temperature for 7 hr. The reaction solution was ice-cooled, t-butyl hydroperoxide-containing decane solution (5-6M, 0.45 ml) was added and the mixture was stirred for 1 hr. Saturated aqueous sodium hydrogen carbonate solution was added to the reaction mixture, and the mixture was extracted with methylene chloride. The organic layer was dried over anhydrous sodium sulfate and the solvent was evaporated under reduced pressure. The obtained residue was purified by silica gel column chromatography (hexane:ethyl acetate) to give the object product (234 mg) as a yellow oil.

$^1$H-NMR(DMSO-$d_6$) δ (ppm): 1.39(18H, d, J=1.2 Hz), 1.68-1.82(2H, m), 1.90(3H, s), 1.97-2.04(2H, m), 2.45-2.53 (1H, m), 2.61(1H, td, J=11.7, 5.2 Hz), 2.77(2H, t, J=7.4 Hz), 3.74-3.82(2H, m), 4.05-4.08(3H, m), 4.11(1H, d, J=8.8 Hz), 7.14(1H, d, J=8.2 Hz), 7.21(1H, t, J=9.3 Hz), 7.32(1H, ddd, J=8.6, 4.4, 2.8 Hz), 7.36(1H, dd, J=6.5, 2.7 Hz), 7.43-7.45 (1H, m), 7.45(1H, s).

(164-2) Synthesis of 2-amino-4-{4-[3-(5-chloro-2-fluorophenyl)propoxy]-3-trifluoromethylphenyl}-2-(phosphoryloxymethyl)butanol (Compound 164-2)

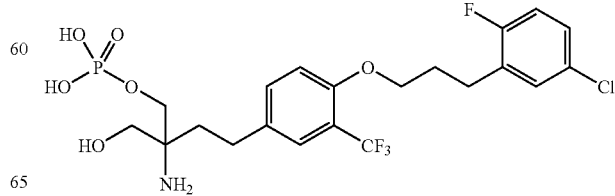

Compound 164-1 (234 mg) was dissolved in ethanol (5 ml), concentrated hydrochloric acid (1 ml) was added, and the mixture was stirred at 50° C. for 3 hr. The solvent was concentrated under reduced pressure, and methanol (2 ml), diethyl ether (5 ml) and propylene oxide (5 ml) were added to the residue. The precipitated powder was collected by filtration and washed with diethyl ether to give the object product (154 mg) as a white powder.

MS(ESI)m/z: 530[M+H]

$^1$H-NMR(CD$_3$OD) δ (ppm): 1.93-1.98(2H, m), 2.04-2.11 (2H, m), 2.67-2.72(2H, m), 2.85(2H, t, J=7.7 Hz), 3.70(2H, s), 3.94-4.01(2H, m), 4.05(2H, t, J=5.8 Hz), 7.02-7.07(2H, m), 7.18-7.24(2H, m), 7.44(1H, d, J=8.6 Hz), 7.48(1H, d, J=1.5 Hz).

Example 165

2-amino-4-{4-[3-(2,4-difluorophenyl)propoxy]-3-trifluoromethylphenyl}-2-(phosphoryloxymethyl)butanol (165-1) Synthesis of 4-di(t-butyl)phosphoryloxymethyl-4-(2-{4-[3-(2,4-difluorophenyl)propoxy]-3-trifluoromethylphenyl}ethyl)-2-methyl-2-oxazoline (Compound 165-1)

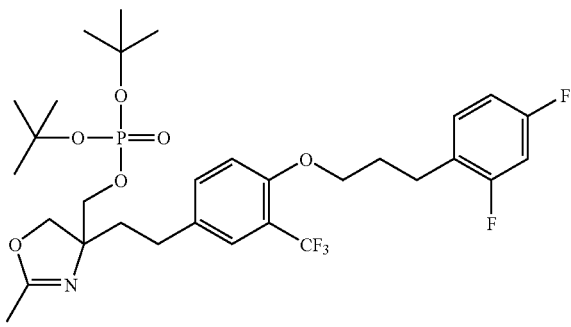

To a solution of compound 65-5 (370 mg) in N,N-dimethylformamide (10 ml) were added N,N-diisopropylethylamine (0.424 ml) and trimethyl orthoacetate (0.200 ml), and the mixture was stirred at 120° C. for 3.5 hr. Water was added to the reaction mixture, and the mixture was extracted with ethyl acetate, washed with water and saturated brine, and dried over anhydrous magnesium sulfate. The solvent was evaporated under reduced pressure to give a brown oil (380 mg). To a solution of the brown oil (380 mg) in methylene chloride (5 ml) and acetonitrile (2 ml) were added 1H-tetrazole (111 mg) and di-t-butyl diethylphosphoramidite (0.473 ml), and the mixture was stirred at room temperature for 1.5 hr. The reaction solution was ice-cooled, t-butyl hydroperoxide-containing decane solution (5-6M, 0.474 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (430 mg) as a yellow oil.

$^1$H-NMR(CD$_3$OD) δ (ppm): 1.48(18H, s), 1.82-1.89(2H, m), 2.02(3H, s), 2.03-2.10(2H, m), 2.52-2.70(2H, m), 2.84 (2H, t, J=7.5 Hz), 3.90-3.92(2H, m), 4.03(2H, t, J=5.9 Hz), 4.20(1H, d, J=9.0 Hz), 4.33(1H, d, J=9.0 Hz), 6.83-6.91(2H, m), 7.03(1H, d, J=8.5 Hz), 7.20-7.26(1H, m), 7.39(1H, d, J=8.5 Hz), 7.43(1H, brd, J=1.6 Hz).

(165-2) Synthesis of 2-amino-4-{4-[3-(2,4-difluorophenyl)propoxy]-3-trifluoromethylphenyl}-2-(phosphoryloxymethyl)butanol (Compound 165-2)

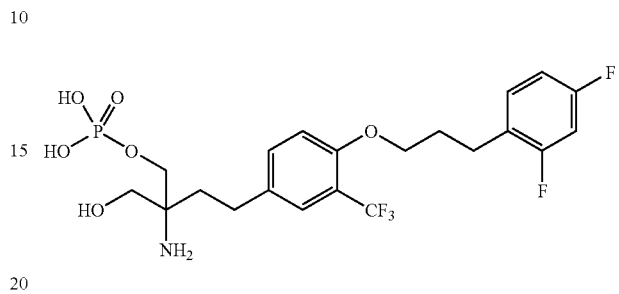

Compound 165-1 (430 mg) was dissolved in ethanol (5 ml), concentrated hydrochloric acid (1 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (290 mg) as a pale-brown solid.

MS(ESI)m/z: 514[M+H]

$^1$H-NMR(CD$_3$OD) δ (ppm): 1.92-1.99(2H, m), 2.00-2.11 (2H, m), 2.65-2.74(2H, m), 2.84(2H, t, J=7.4 Hz), 3.70(2H, brs), 3.94-4.06(4H, m), 6.83-6.91(2H, m), 7.04(1H, d, J=8.4 Hz), 7.20-7.25(1H, m), 7.44(1H, d, J=8.4 Hz), 7.48(1H, brs).

Example 166

2-amino-4-{4-[3-(2,5-dichlorophenyl)propoxy]-3-trifluoromethylphenyl}-2-(phosphoryloxymethyl)butanol (166-1) Synthesis of 4-di(t-butyl)phosphoryloxymethyl-4-(2-{4-[3-(2,5-dichlorophenyl)propoxy]-3-trifluoromethylphenyl}ethyl)-2-methyl-2-oxazoline (Compound 166-1)

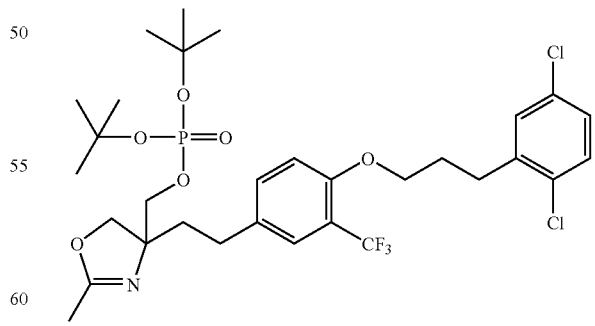

To a solution of compound 66-5 (380 mg) in N,N-dimethylformamide (10 ml) were added N,N-diisopropylethylamine (0.407 ml) and trimethyl orthoacetate (0.192 ml), and the mixture was stirred at 120° C. for 3 hr. Water was added to the reaction mixture, and the mixture was extracted with ethyl acetate, washed with water and saturated brine, and dried over anhydrous magnesium sulfate. The solvent was evaporated under reduced pressure to give a brown oil (380 mg). To a solution of the brown oil (380 mg) in methylene chloride (5 ml) and acetonitrile (2 ml) were added 1H-tetrazole (106 mg) and di-t-butyl diethylphosphoramidite (0.455 ml), and the mixture was stirred at room temperature for 2 hr. The reaction solution was ice-cooled, t-butyl hydroperoxide-containing decane solution (5-6M, 0.456 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (410 mg) as a yellow oil.

$^1$H-NMR(CD$_3$OD) δ (ppm): 1.48(18H, s), 1.82-1.89(2H, m), 2.01(3H, s), 2.05-2.12(2H, m), 2.52-2.70(2H, m), 2.94 (2H, t, J=7.6 Hz), 3.89-3.92(2H, m), 4.06(2H, t, J=5.8 Hz), 4.18(1H, d, J=9.0 Hz), 4.32(1H, d, J=9.0 Hz), 7.05(1H, d, J=8.5 Hz), 7.20(1H, dd, J=8.5, 2.5 Hz), 7.29(1H, d, J=2.5 Hz), 7.35(1H, d, J=8.5 Hz), 7.40(1H, d, J=8.5 Hz), 7.44(1H, brd, J=1.4 Hz).

(166-2) Synthesis of 2-amino-4-{4-[3-(2,5-dichlorophenyl)propoxy]-3-trifluoromethylphenyl}-2-(phosphoryloxymethyl)butanol (Compound 166-2)

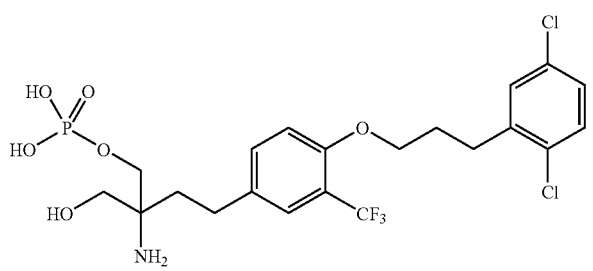

Compound 166-1 (410 mg) was dissolved in ethanol (5 ml), concentrated hydrochloric acid (1 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (287 mg) as a white solid.

MS(ESI)m/z: 546[M+H]

$^1$H-NMR(CD$_3$OD) δ (ppm): 1.94-1.99(2H, m), 2.05-2.10 (2H, m), 2.66-2.74(2H, m), 2.95(2H, t, J=7.5 Hz), 3.70(2H, brs), 3.96-4.08(4H, m), 7.07(1H, brd, J=7.4 Hz), 7.18-7.22 (1H, m), 7.29(1H, brs), 7.35(1H, brd, J=8.5 Hz), 7.45(1H, brd, J=8.5 Hz), 7.49(1H, brs).

Example 167

2-amino-4-{4-[3-(4-chloro-3-methylphenyl)propoxy]-3-trifluoromethylphenyl}-2-(phosphoryloxymethyl)butanol (167-1) Synthesis of 4-di(t-butyl)phosphoryloxymethyl-4-(2-{4-[3-(4-chloro-3-methylphenyl)propoxy]-3-trifluoromethyl}ethyl)-2-methyl-2-oxazoline (Compound 167-1)

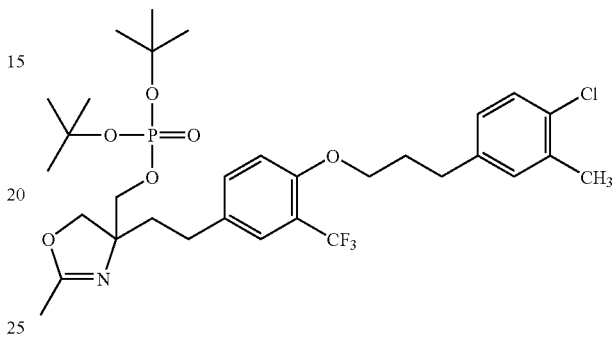

To a solution of compound 67-4 (320 mg) in N,N-dimethylformamide (6.6 ml) were added N,N-diisopropylethylamine (0.34 ml) and trimethyl orthoacetate (0.18 ml), and the mixture was stirred at 120° C. for 3.5 hr. Water was added to the reaction mixture, and the mixture was extracted with ethyl acetate, washed with water and saturated brine, and dried over anhydrous sodium sulfate. The solvent was evaporated under reduced pressure. To a solution of the obtained brown oil in methylene chloride (4.5 ml) and acetonitrile (3.75 ml) were added 1H-tetrazole (93 mg) and di-t-butyl diethylphosphoramidite (0.37 ml) was added, and the mixture was stirred at room temperature for 3 hr. The reaction solution was ice-cooled, t-butyl hydroperoxide-containing decane solution (5-6M, 0.40 ml) was added and the mixture was stirred for 2 hr. Saturated aqueous sodium hydrogen carbonate solution was added to the reaction mixture, and the mixture was extracted with methylene chloride. The organic layer was dried over anhydrous sodium sulfate and the solvent was evaporated under reduced pressure. The obtained residue was purified by silica gel column chromatography (hexane:ethyl acetate) to give the object product (259 mg) as a yellow oil.

$^1$H-NMR(DMSO-d$_6$) δ (ppm): 1.39(18H, d, J=1.3 Hz), 1.71-1.78(2H, m), 1.90(3H, s), 1.96-2.02(2H, m), 2.28(3H, s), 2.46-2.53(1H, m), 2.61(1H, td, J=11.7, 5.4 Hz), 2.70(2H, t, J=7.4 Hz), 3.74-3.82(2H, m), 4.00-4.04(2H, m), 4.07(1H, d, J=8.8 Hz), 4.11(1H, d, J=8.7 Hz), 7.03(1H, dd, J=8.5, 1.8 Hz), 7.12(1H, d, J=8.4 Hz), 7.18(1H, s), 7.30(1H, d, J=8.1 Hz), 7.43(1H, d, J=8.6 Hz), 7.45(1H, s).

(167-2) Synthesis of 2-amino-4-{4-[3-(4-chloro-3-methylphenyl)propoxy]-3-trifluoromethylphenyl}-2-(phosphoryloxymethyl)butanol (Compound 167-2)

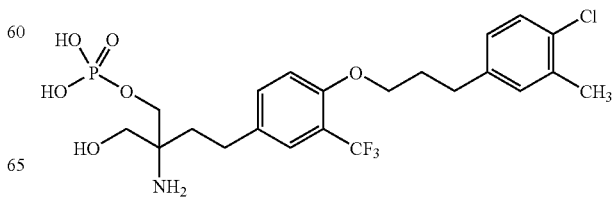

Compound 167-1 (259 mg) was dissolved in ethanol (5 ml), concentrated hydrochloric acid (1 ml) was added, and the mixture was stirred at 50° C. for 3 hr. The solvent was concentrated under reduced pressure, and methanol (2 ml), diethyl ether (5 ml) and propylene oxide (5 ml) were added to the residue. The precipitated powder was collected by filtration and washed with diethyl ether to give the object product (178 mg) as a white powder.

MS(ESI)m/z: 526[M+H]

$^1$H-NMR(CD$_3$OD) δ (ppm): 1.95(2H, ddd, J=11.2, 9.7, 3.5 Hz), 2.03-2.09(2H, m), 2.30(3H, s), 2.65-2.72(2H, m), 2.77 (2H, t, J=7.4 Hz), 3.70(2H, s), 3.94-4.02(4H, m), 6.99(1H, dd, J=8.3, 1.9 Hz), 7.03(1H, d, J=8.5 Hz), 7.11(1H, s), 7.22(1H, d, J=8.2 Hz), 7.43(1H, d, J=8.7 Hz), 7.48(1H, s).

Example 168

2-amino-4-{4-[3-(3-fluoro-4-trifluoromethylphenyl) propoxy]-3-trifluoromethylphenyl}-2-(phosphoryloxymethyl)butanol (168-1) Synthesis of 4-di(t-butyl)phosphoryloxymethyl-4-(2-{4-[3-(3-fluoro-4-trifluoromethylphenyl) propoxy]-3-trifluoromethyl}ethyl)-2-methyl-2-oxazoline (Compound 168-1)

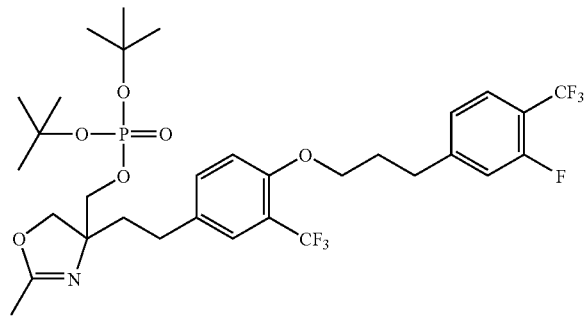

To a solution of compound 68-4 (340 mg) in N,N-dimethylformamide (6.6 ml) were added N,N-diisopropylethylamine (0.33 ml) and trimethyl orthoacetate (0.18 ml), and the mixture was stirred at 120° C. for 4 hr. Water was added to the reaction mixture, and the mixture was extracted with ethyl acetate, washed with water and saturated brine, and dried over anhydrous sodium sulfate. The solvent was evaporated under reduced pressure. To a solution of the obtained brown oil in methylene chloride (4.4 ml) and acetonitrile (3.75 ml) were added 1H-tetrazole (92 mg) and di-t-butyl diethylphosphoramidite (0.36 ml), and the mixture was stirred at room temperature for 2 hr. The reaction solution was ice-cooled, t-butyl hydroperoxide-containing decane solution (5-6M, 0.39 ml) was added and the mixture was stirred for 1 hr. Saturated aqueous sodium hydrogen carbonate solution was added to the reaction mixture, and the mixture was extracted with methylene chloride. The organic layer was dried over anhydrous sodium sulfate and the solvent was evaporated under reduced pressure. The obtained residue was purified by silica gel column chromatography (hexane:ethyl acetate) to give the object product (200 mg) as a yellow oil.

$^1$H-NMR(DMSO-d$_6$) δ (ppm): 1.39(18H, s), 1.71-1.82 (2H, m), 1.90(3H, s), 2.03-2.10(2H, m), 2.45-2.53(1H, m), 2.61(1H, td, J=11.3, 5.8 Hz), 2.85(2H, t, J=7.6 Hz), 3.74-3.82 (2H, m), 4.00-4.07(3H, m), 4.09(1H, d, J=8.9 Hz), 7.14(1H, d, J=8.4 Hz), 7.24(1H, d, J=8.0 Hz), 7.38(1H, d, J=12.1 Hz), 7.43-7.45(2H, m), 7.69(1H, t, J=7.9 Hz).

(168-2) Synthesis of 2-amino-4-{4-[3-(3-fluoro-4-trifluoromethylphenyl)propoxy]-3-trifluoromethylphenyl}-2-(phosphoryloxymethyl)butanol (Compound 168-2)

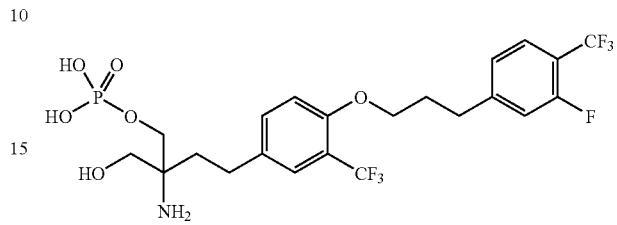

Compound 168-1 (200 mg) was dissolved in ethanol (5 ml), concentrated hydrochloric acid (1 ml) was added, and the mixture was stirred at 50° C. for 3 hr. The solvent was concentrated under reduced pressure, and methanol (2 ml), diethyl ether (5 ml) and propylene oxide (5 ml) were added to the residue. The precipitated powder was collected by filtration and washed with diethyl ether to give the object product (130 mg) as a white powder.

MS(ESI)m/z: 564[M+H]

$^1$H-NMR(CD$_3$OD) δ (ppm): 1.92-1.98(2H, m), 2.10-2.18 (2H, m), 2.65-2.72(2H, m), 2.92(2H, t, J=7.5 Hz), 3.70(2H, s), 3.93-4.01(2H, m), 4.04(2H, t, J=5.9 Hz), 7.05(1H, d, J=8.3 Hz), 7.16-7.19(2H, m), 7.44(1H, d, J=8.6 Hz), 7.48(1H, s), 7.58(1H, t, J=8.3 Hz).

Example 169

2-amino-4-{4-[3-(4-fluoro-3-trifluoromethylphenyl) propoxy]-3-trifluoromethylphenyl}-2-(phosphoryloxymethyl)butanol (169-1) Synthesis of 4-di(t-butyl)phosphoryloxymethyl-4-(2-{4-[3-(4-fluoro-3-trifluorophenyl)propoxy]-3-trifluoromethyl}ethyl)-2-methyl-2-oxazoline (Compound 169-1)

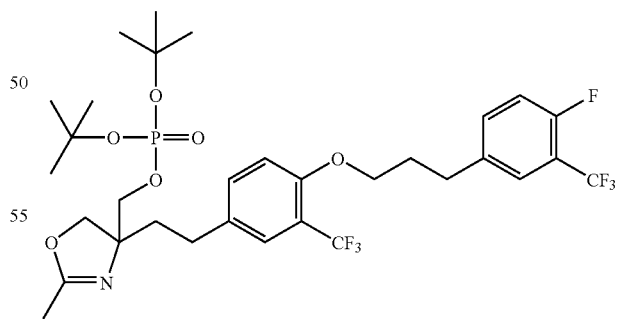

To a solution of compound 69-4 (350 mg) in N,N-dimethylformamide (6.7 ml) were added N,N-diisopropylethylamine (0.34 ml) and trimethyl orthoacetate (0.18 ml), and the mixture was stirred at 120° C. for 4 hr. Water was added to the reaction mixture, and the mixture was extracted with ethyl acetate, washed with water and saturated brine, and dried over anhydrous sodium sulfate. The solvent was evaporated under reduced pressure. To a solution of the obtained brown oil in methylene chloride (4.5 ml) and acetonitrile (3.75 ml) were added 1H-tetrazole (95 mg) and di-t-butyl diethylphosphoramidite (0.38 ml), and the mixture was stirred at room temperature for 3 hr. The reaction solution was ice-cooled, t-butyl hydroperoxide-containing decane solution (5-6M, 0.40 ml) was added and the mixture was stirred for 1 hr. Saturated aqueous sodium hydrogen carbonate solution was added to the reaction mixture, and the mixture was extracted with methylene chloride. The organic layer was dried over anhydrous sodium sulfate and the solvent was evaporated under reduced pressure. The obtained residue was purified by silica gel column chromatography (hexane:ethyl acetate) to give the object product (200 mg) as a yellow oil.

$^{1}$H-NMR(DMSO-$d_6$) δ (ppm): 1.39(18H, d, J=1.2 Hz), 1.69-1.78(2H, m), 1.90(3H, s), 2.00-2.07(2H, m), 2.45-2.53 (1H, m), 2.61(1H, td, J=11.4, 6.0 Hz), 2.81(2H, t, J=7.6 Hz), 3.74-3.82(2H, m), 4.00-4.04(2H, m), 4.07(1H, d, J=9.3 Hz), 4.11(1H, d, J=8.9 Hz), 7.13(1H, d, J=8.4 Hz), 7.40-7.45(3H, m), 7.56-7.59(1H, m), 7.58(1H, d, J=6.0 Hz).

(169-2) Synthesis of 2-amino-4-{4-[3-(4-fluoro-3-trifluoromethylphenyl)propoxy]-3-trifluoromethylphenyl}-2-(phosphoryloxymethyl)butanol (Compound 169-2)

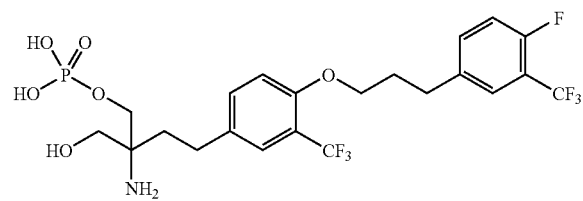

Compound 169-1 (200 mg) was dissolved in ethanol (5 ml), concentrated hydrochloric acid (1 ml) was added, and the mixture was stirred at 50° C. for 3 hr. The solvent was concentrated under reduced pressure, and methanol (2 ml), diethyl ether (5 ml) and propylene oxide (5 ml) were added to the residue. The precipitated powder was collected by filtration, and washed with methanol to give the object product (99 mg) as a white powder.

MS(ESI)m/z: 564[M+H]

$^{1}$H-NMR(CD$_3$OD) δ (ppm): 1.93-1.98(2H, m), 2.07-2.13 (2H, m), 2.65-2.72(2H, m), 2.89(2H, t, J=7.4 Hz), 3.70(2H, s), 3.94-4.00(2H, m), 4.02(2H, t, J=5.8 Hz), 7.43(1H, d, J=8.5 Hz), 7.22(1H, t, J=9.5 Hz), 7.44(1H, d, J=8.6 Hz), 7.48-7.51 (3H, m).

Example 170

2-amino-4-{4-[3-(2,3,4-trifluorophenyl)propoxy-3-trifluoromethyl]phenyl}-2-(phosphoryloxymethyl)butanol (170-1) Synthesis of 4-di(t-butyl)phosphoryloxymethyl-4-(2-{4-[3-(2,3,4-trifluorophenyl)propoxy]-3-trifluoromethylphenyl}ethyl)-2-methyl-2-oxazoline (Compound 170-1)

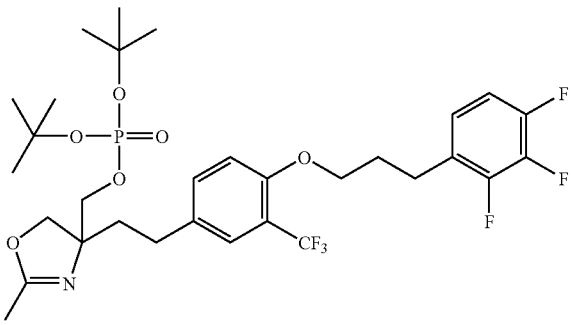

To a solution of compound 70-5 (400 mg) in N,N-dimethylformamide (10 ml) were added N,N-diisopropylethylamine (0.443 ml) and trimethyl orthoacetate (0.207 ml), and the mixture was stirred at 120° C. for 4 hr. Water was added to the reaction mixture, and the mixture was extracted with ethyl acetate, washed with water and saturated brine, and dried over anhydrous magnesium sulfate. The solvent was evaporated under reduced pressure to give a brown oil (390 mg). To a solution of the brown oil (390 mg) in methylene chloride (5 ml) and acetonitrile (2 ml) were added 1H-tetrazole (11 mg) and di-t-butyl diethylphosphoramidite (0.491 ml), and the mixture was stirred at room temperature for 1.5 hr. The reaction solution was ice-cooled, t-butyl hydroperoxide-containing decane solution (5-6M, 0.492 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (400 mg) as a yellow oil.

$^{1}$H-NMR(CD$_3$OD) δ (ppm): 1.48(18H, s), 1.82-1.89(2H, m), 2.01(3H, s), 2.04-2.11(2H, m), 2.52-2.70(2H, m), 2.88 (2H, t, J=7.5 Hz), 3.89-3.91(2H, m), 4.04(2H, t, J=5.9 Hz), 4.18(1H, d, J=9.0 Hz), 4.32(1H, d, J=9.0 Hz), 6.99-7.05(3H, m), 7.39(1H, d, J=8.5 Hz), 7.44(1H, d, J=1, 9 Hz).

(170-2) Synthesis of 2-amino-4-{4-[3-(2,3,4-trifluorophenyl)propoxy-3-trifluoromethyl]phenyl}-2-(phosphoryloxymethyl)butanol (Compound 170-2)

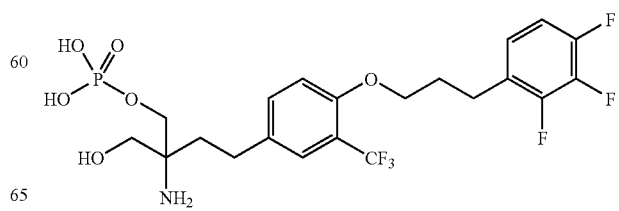

Compound 170-1 (400 mg) was dissolved in ethanol (5 ml), concentrated hydrochloric acid (1 ml) was added, and the mixture was stirred at 50° C. for 3.5 hr. The solvent was concentrated under reduced pressure, and methanol (5 ml), ethyl acetate (5 ml) were added to the residue. The precipitated powder was collected by filtration, and washed with methanol, ethyl acetate and diethyl ether to give the object product (60 mg) as a pale-brown solid.

MS(ESI)m/z: 532[M+H]

$^1$H-NMR(CD$_3$OD) δ (ppm): 1.94-1.99(2H, m), 2.02-2.10 (2H, m), 2.66-2.74(2H, m), 2.88(2H, t, J=7.5 Hz), 3.70(2H, brs), 3.96-4.00(2H, m), 4.05(2H, t, J=5.7 Hz), 7.00-7.07(3H, m), 7.44(1H, brd, J=8.7 Hz), 7.48(1H, brs).

Example 171

2-amino-4-{4-[3-(2-chloro-4-trifluoromethylphenyl)propoxy]-3-trifluoromethylphenyl}-2-(phosphoryloxymethyl)butanol (171-1) Synthesis of 4-di(t-butyl)phosphoryloxymethyl-4-(2-{4-[3-(2-chloro-4-trifluoromethylphenyl)propoxy]-3-trifluoromethylphenyl}ethyl)-2-methyl-2-oxazoline (Compound 171-1)

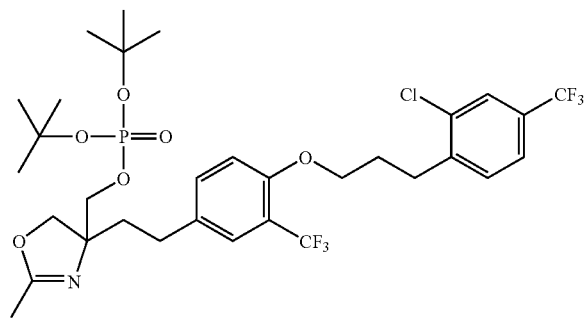

To a solution of compound 71-5 (430 mg) in N,N-dimethylformamide (10 ml) were added N,N-diisopropylethylamine (0.432 ml) and trimethyl orthoacetate (0.203 ml), and the mixture was stirred at 120° C. for 3 hr. Water was added to the reaction mixture, and the mixture was extracted with ethyl acetate, washed with water and saturated brine, and dried over anhydrous magnesium sulfate. The solvent was evaporated under reduced pressure to give a brown oil (460 mg). To a solution of the brown oil (460 mg) in methylene chloride (5 ml) and acetonitrile (2 ml) were added 1H-tetrazole (112 mg) and di-t-butyl diethylphosphoramidite (0.479 ml), and the mixture was stirred at room temperature for 2 hr. The reaction solution was ice-cooled, t-butyl hydroperoxide-containing decane solution (5-6M, 0.480 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (450 mg) as a yellow oil.

$^1$H-NMR(CD$_3$OD) δ (ppm): 1.48(18H, s), 1.82-1.89(2H, m), 2.01(3H, s), 2.08-2.17(2H, m), 2.53-2.70(2H, m), 3.05 (2H, t, J=7.6 Hz), 3.89-3.92(2H, m), 4.08(2H, t, J=5.7 Hz), 4.18(1H, d, J=9.1 Hz), 4.32(1H, d, J=9.1 Hz), 7.06(1H, d, J=8.5 Hz), 7.40(1H, d, J=8.5 Hz), 7.44(1H, s), 7.47-7.54(2H, m), 7.68(1H, brs).

(171-2) Synthesis of 2-amino-4-{4-[3-(2-chloro-4-trifluoromethylphenyl)propoxy]-3-trifluoromethylphenyl}-2-(phosphoryloxymethyl)butanol (Compound 171-2)

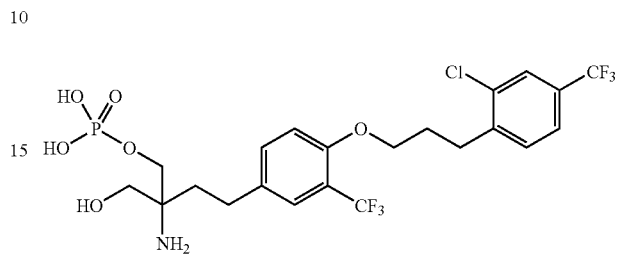

Compound 171-1 (450 mg) was dissolved in ethanol (5 ml), concentrated hydrochloric acid (1 ml) was added, and the mixture was stirred at 50° C. for 3 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (353 mg) as a white solid.

MS(ESI)m/z: 580[M+H]

$^1$H-NMR(CD$_3$OD) δ (ppm): 1.94-1.99(2H, m), 2.09-2.17 (2H, m), 2.65-2.74(2H, m), 3.05(2H, t, J=7.6 Hz), 3.71(2H, brs), 3.97-4.02(2H, m), 4.09(2H, t, J=5.8 Hz), 7.07(1H, d, J=8.5 Hz), 7.43-7.55(4H, m), 7.68(1H, brs).

Example 172

2-amino-4-{4-[3-(4-cyanophenyl)propoxy]-3-trifluoromethylphenyl}-2-(phosphoryloxymethyl)butanol (172-1) Synthesis of 1-(dibenzyl)phosphoryloxymethyl-[3-{4-[3-(4-cyanophenyl)propoxy]-3-trifluoromethylphenyl}-1-(hydroxymethyl)propyl]carbamic acid benzyl ester (Compound 172-1)

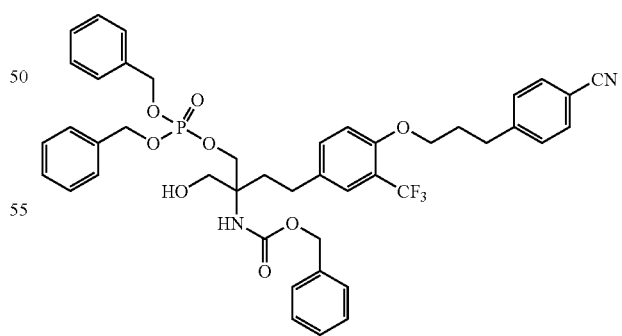

Compound 72-5 (310 mg), ethyl acetate (10 ml), saturated aqueous sodium hydrogen carbonate solution (10 ml) and benzyloxycarbonyl chloride (0.125 ml) were stirred in an nonuniform state at room temperature for 15 hr. The ethyl acetate layer was separated, and the aqueous layer was extracted with ethyl acetate. The separated ethyl acetate layer and the ethyl acetate layer obtained by extraction were combined, washed with saturated brine, dried over anhydrous magnesium sulfate The solvent was evaporated under reduced pressure to give an amine-protected compound as a colorless oil (380 mg). The colorless oil (380 mg), pyrophosphoric acid tetrabenzyl ester (740 mg), silver oxide (315 mg) and tetra-n-hexylammonium iodide (655 mg) were added to a mixed solvent of toluene (4 ml), methylene chloride (4 ml) and perfluorohexane (4 ml), and the mixture was stirred at room temperature for 14 hr. Insoluble material was filtered off and the solvent was evaporated under reduced pressure. The residue was purified by HPLC to give the object product (230 mg) as a colorless oil.

$^1$H-NMR(CD$_3$OD) δ (ppm): 1.75-1.87(1H, m), 1.89-2.00 (1H, m), 2.09-2.13(2H, m), 2.49-2.57(2H, m), 2.91(2H, t, J=7.6 Hz), 3.59(1H, d, J=10.7 Hz), 3.69(1H, d, J=10.7 Hz), 4.01(2H, t, J=5.7 Hz), 4.15-4.21(1H, m), 4.25-4.32(1H, m), 4.99-5.03(6H, m), 6.96(1H, d, J=8.3 Hz), 7.24-7.41(19H, m), 7.63(2H, d, J=8.0 Hz).

(172-2) Synthesis of 2-amino-4-{4-[3-(4-cyanophenyl)propoxy]-3-trifluoromethylphenyl}-2-(phosphoryloxymethyl)butanol (Compound 172-2)

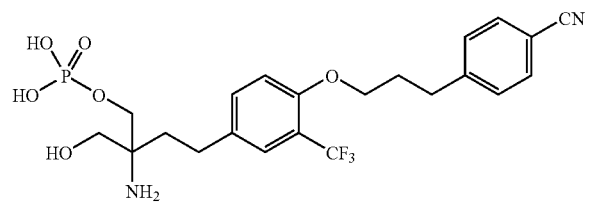

Compound 172-1 (230 mg) was dissolved in acetonitrile (4 ml), trimethylsilyl iodide (0.200 ml) was added, and the mixture was stirred under ice-cooling for 2 hr. The reaction mixture was concentrated under reduced pressure, isopropyl alcohol (5 ml) was added, and the resulting solid was collected by filtration. The solid was washed with isopropyl alcohol and methanol to give the object product (57 mg) as a pale-yellow powder.

MS(ESI)m/z: 503[M+H]

$^1$H-NMR(CD$_3$OD) δ (ppm): 1.92-2.01(2H, m), 2.09-2.16 (2H, m), 2.61-2.75(2H, m), 2.92(2H, t, J=7.6 Hz), 3.70(2H, brs), 3.97-4.05(4H, m), 7.04(1H, d, J=8.4 Hz), 7.38-7.46(3H, m), 7.48(1H, brs), 7.61-7.65(2H, m).

Example 173

2-amino-4-{4-[3-(1-naphthyl)propoxy]-3-trifluoromethylphenyl}-2-(phosphoryloxymethyl)butanol (173-1) Synthesis of 4-di(t-butyl)phosphoryloxymethyl-2-methyl-4-(2-{4-[3-(1-naphthyl)propoxy]-3-trifluoromethylphenyl}ethyl)-2-oxazoline (Compound 173-1)

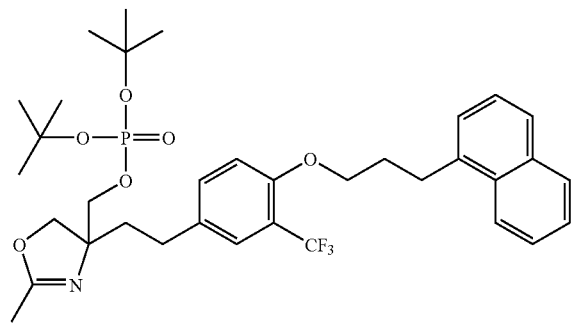

To a solution of compound 73-4 (360 mg) in N,N-dimethylformamide (10 ml) were added N,N-diisopropylethylamine (0.401 ml) and trimethyl orthoacetate (0.187 ml), and the mixture was stirred at 120° C. for 3 hr. Water was added to the reaction mixture, and the mixture was extracted with ethyl acetate, washed with water and saturated brine, and dried over anhydrous magnesium sulfate. The solvent was evaporated under reduced pressure to give a brown oil (390 mg). To a solution of the brown oil (390 mg) in methylene chloride (5 ml) and acetonitrile (2 ml) were added 1H-tetrazole (104 mg) and di-t-butyl diethylphosphoramidite (0.443 ml), and the mixture was stirred at room temperature for 2 hr. The reaction solution was ice-cooled, t-butyl hydroperoxide-containing decane solution (5-6M, 0.444 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (430 mg) as a yellow oil.

$^1$H-NMR(CD$_3$OD) δ (ppm): 1.48(18H, s), 1.82-1.89(2H, m), 2.01(3H, s), 2.16-2.22(2H, m), 2.52-2.69(2H, m), 3.28-3.40(2H, m), 3.89-3.92(2H, m), 4.09(2H, t, J=5.5 Hz), 4.19 (1H, d, J=8.9 Hz), 4.33(1H, d, J=8.9 Hz), 7.03(1H, d, J=8.5 Hz), 7.34-7.40(3H, m), 7.41-7.47(3H, m), 7.71(1H, d, J=7.6 Hz), 7.82-7.86(1H, m), 8.12-8.15(1H, m).

(173-2) Synthesis of 2-amino-4-{4-[3-(1-naphthyl) propoxy]-3-trifluoromethylphenyl}-2-(phosphoryloxymethyl)butanol (Compound 173-2)

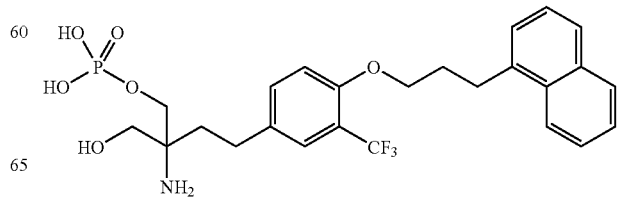

Compound 173-1 (430 mg) was dissolved in ethanol (5 ml), concentrated hydrochloric acid (1 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (305 mg) as a white solid.

MS(ESI)m/z: 528[M+H]

$^1$H-NMR(CD$_3$OD) δ (ppm): 1.93-2.00(2H, m), 2.16-2.22 (2H, m), 2.62-2.78(2H, m), 3.30-3.35(2H, m), 3.71(2H, brs), 3.97-4.05(2H, m), 4.10(2H, t, J=5.6 Hz), 7.05(1H, d, J=8.6 Hz), 7.32-7.39(2H, m), 7.42-7.47(3H, m), 7.51(1H, brs), 7.71 (1H, d, J=7.3 Hz), 7.83-7.86(1H, m), 8.12-8.15(1H, m).

Example 174

2-amino-4-{4-[3-(2,3-dihydrobenzofuran-5-yl)propoxy]-3-trifluoromethylphenyl}-2-(phosphoryloxymethyl)butanol (174-1) Synthesis of 4-di(t-butyl)phosphoryloxymethyl-4-(2-{4-[3-(2,3-dihydrobenzofuran-5-yl)propoxy]-3-trifluoromethylphenyl}ethyl)-2-methyl-2-oxazoline (Compound 174-1)

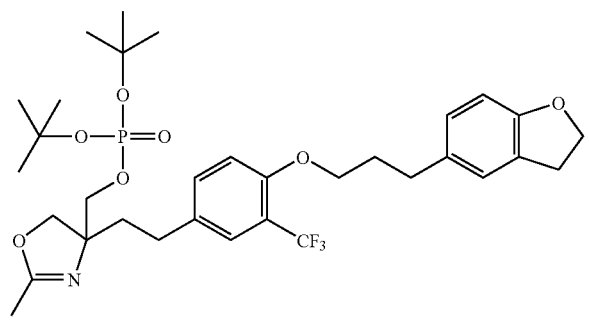

To a solution of compound 76-4 (370 mg) in N,N-dimethylformamide (10 ml) were added N,N-diisopropylethylamine (0.420 ml) and trimethyl orthoacetate (0.197 ml), and the mixture was stirred at 120° C. for 5 hr. Water was added to the reaction mixture, and the mixture was extracted with ethyl acetate, washed with water and saturated brine, and dried over anhydrous magnesium sulfate. The solvent was evaporated under reduced pressure to give a brown oil (370 mg). To a solution of the brown oil (370 mg) in methylene chloride (5 ml) and acetonitrile (2 ml) were added 1H-tetrazole (109 mg) and di-t-butyl diethylphosphoramidite (0.467 ml), and the mixture was stirred at room temperature for 2 hr. The reaction solution was ice-cooled, t-butyl hydroperoxide-containing decane solution (5-6M, 0.468 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (450 mg) as a yellow oil.

$^1$H-NMR(CD$_3$OD) δ (ppm): 1.48(18H, s), 1.82-1.90(2H, m), 2.01(3H, s), 2.02-2.10(2H, m), 2.52-2.70(2H, m), 2.73 (2H, t, J=7.4 Hz), 3.13(2H, t, J=8.6 Hz), 3.89-3.91(2H, m), 3.99(2H, t, J=5.9 Hz), 4.18(1H, d, J=9.0 Hz), 4.32(1H, d, J=9.0 Hz), 4.48(2H, t, J=8.6 Hz), 6.60(1H, d, J=8.0 Hz), 6.88(1H, d, J=8.0 Hz), 7.00(1H, d, J=8.5 Hz), 7.03(1H, brs), 7.37(1H, d, J=8.5 Hz), 7.43(1H, brs).

(174-2) Synthesis of 2-amino-4-{4-[3-(2,3-dihydrobenzofuran-5-yl)propoxy]-3-trifluoromethylphenyl}-2-(phosphoryloxymethyl)butanol (Compound 174-2)

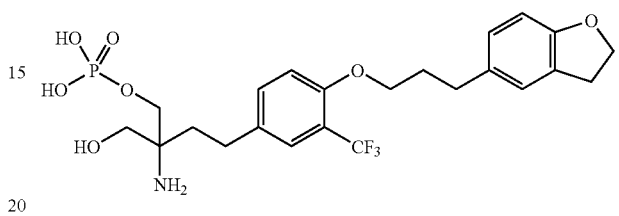

Compound 174-1 (450 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (315 mg) as a pale-brown solid.

MS(ESI)m/z: 520[M+H]

$^1$H-NMR(CD$_3$OD) δ (ppm): 1.93-2.07(4H, m), 2.65-2.76 (4H, m), 3.14(2H, t, J=8.6 Hz), 3.70(2H, brs), 3.97-4.04(4H, m), 4.48(2H, t, J=8.6 Hz), 6.60(1H, d, J=8.1 Hz), 6.88(1H, d, J=8.1 Hz), 7.00-7.05(2H, m), 7.42(1H, d, J=8.5 Hz), 7.47(1H, brs).

Example 175

2-amino-4-{4-[3-(biphenyl-4-yl)propoxy]-3-trifluoromethylphenyl}-2-(phosphoryloxymethyl)butanol (175-1) Synthesis of 4-(2-{4-[3-(biphenyl-4-yl)propoxy]-3-trifluoromethylphenyl}ethyl)-4-di(t-butyl)phosphoryloxymethyl-2-methyl-2-oxazoline (Compound 175-1)

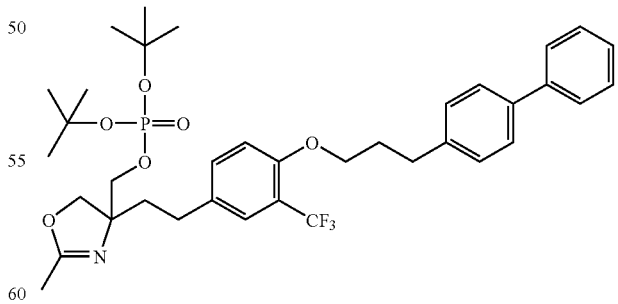

To a solution of compound 77-5 (400 mg) in N,N-dimethylformamide (10 ml) were added N,N-diisopropylethylamine (0.422 ml) and trimethyl orthoacetate (0.197 ml), and the mixture was stirred at 120° C. for 3 hr. Water was added to the reaction mixture, and the mixture was extracted with ethyl acetate, washed with water and saturated brine, and dried over anhydrous magnesium sulfate. The solvent was evaporated under reduced pressure to give a brown oil (430 mg). To a solution of the brown oil (430 mg) in methylene chloride (5 ml) and acetonitrile (2 ml) were added 1H-tetrazole (110 mg) and di-t-butyl diethylphosphoramidite (0.467 ml), and the mixture was stirred at room temperature for 2 hr. The reaction solution was ice-cooled, t-butyl hydroperoxide-containing decane solution (5-6M, 0.468 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (490 mg) as a yellow oil.

$^1$H-NMR(CD$_3$OD) δ (ppm): 1.48(18H, s), 1.82-1.89(2H, m), 2.01(3H, s), 2.08-2.19(2H, m), 2.52-2.70(2H, m), 2.86 (2H, t, J=7.4 Hz), 3.89-3.92(2H, m), 4.04(2H, t, J=5.9 Hz), 4.19(1H, d, J=9.0 Hz), 4.33(1H, d, J=9.0 Hz), 7.03(1H, d, J=8.5 Hz), 7.26-7.31(3H, m), 7.37-7.44(4H, m), 7.52(2H, d, J=8.0 Hz), 7.58(2H, d, J=7.4 Hz).

(175-2) Synthesis of 2-amino-4-{4-[3-(biphenyl-4-yl)propoxy]-3-trifluoromethylphenyl}-2-(phosphoryloxymethyl)butanol (Compound 175-2)

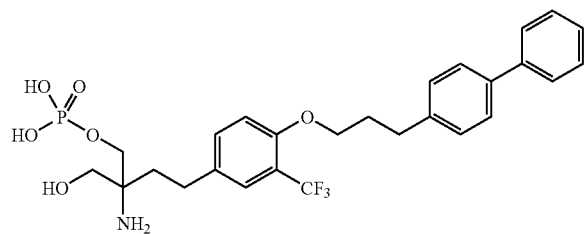

Compound 175-1 (490 mg) was dissolved in ethanol (5 ml), concentrated hydrochloric acid (1 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (365 mg) as a white solid.

MS(ESI)m/z: 554[M+H]

$^1$H-NMR(CD$_3$OD) δ (ppm): 1.93-2.00(2H, m), 2.10-2.19 (2H, m), 2.61-2.72(2H, m), 2.87(2H, t, J=7.4 Hz), 3.71(2H, brs), 3.97-4.01(2H, m), 4.05(2H, t, J=5.9 Hz), 7.04(1H, d, J=8.5 Hz), 7.26-7.32(3H, m), 7.38-7.45(3H, m), 7.48-7.55 (3H, m), 7.58(2H, d, J=7.6 Hz).

Example 176

2-amino-4-{4-[2-(2-naphthyl)ethoxy]-3-trifluoromethylphenyl}-2-(phosphoryloxymethyl)butanol

(176-1) Synthesis of 4-di(t-butyl)phosphoryloxymethyl-2-methyl-4-(2-{4-[2-(2-naphthyl)ethoxy]-3-trifluoromethylphenyl}ethyl)-2-oxazoline (Compound 176-1)

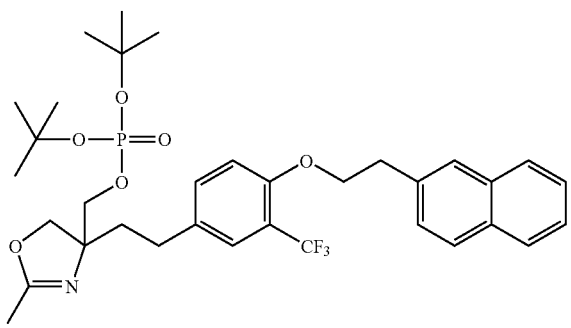

To a solution of compound 78-1 (560 mg) in N,N-dimethylformamide (10 ml) were added N,N-diisopropylethylamine (0.643 ml) and trimethyl orthoacetate (0.301 ml), and the mixture was stirred at 120° C. for 3 hr. Water was added to the reaction mixture, and the mixture was extracted with ethyl acetate, washed with water and saturated brine, and dried over anhydrous magnesium sulfate. The solvent was evaporated under reduced pressure to give a brown oil (580 mg). To a solution of the brown oil (580 mg) in methylene chloride (5 ml) and acetonitrile (2 ml) were added 1H-tetrazole (168 mg) and di-t-butyl diethylphosphoramidite (0.712 ml), and the mixture was stirred at room temperature for 2 hr. The reaction solution was ice-cooled, t-butyl hydroperoxide-containing decane solution (5-6M, 0.714 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (700 mg) as a yellow oil.

$^1$H-NMR(CD$_3$OD) δ (ppm): 1.45(9H, s), 1.46(9H, s), 1.81-1.88(2H, m), 1.99(3H, s), 2.52-2.69(2H, m), 3.25(2H, t, J=6.4 Hz), 3.87(2H, d, J=4.8 Hz), 4.16(1H, d, J=8.9 Hz), 4.29-4.35(3H, m), 7.08(1H, d, J=8.5 Hz), 7.35-7.48(5H, m), 7.77-7.82(4H, m).

(176-2) Synthesis of 2-amino-4-{4-[2-(2-naphthyl)ethoxy]-3-trifluoromethylphenyl}-2-(phosphoryloxymethyl)butanol (Compound 176-2)

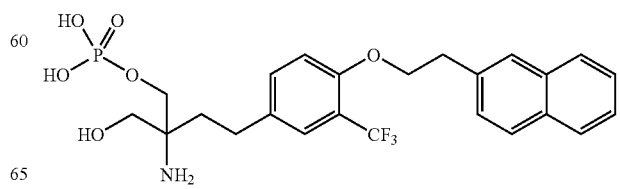

Compound 176-1 (700 mg) was dissolved in ethanol (6 ml), concentrated hydrochloric acid (1.2 ml) was added, and the mixture was stirred at 50° C. for 2.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (420 mg) as a pale-brown solid.

MS(ESI)m/z: 514[M+H]

$^1$H-NMR(CD$_3$OD) δ (ppm): 1.89-1.98(2H, m), 2.60-2.72 (2H, m), 3.25(2H, t, J=6.5 Hz), 3.69(2H, brs), 3.95-4.02(2H, m), 4.33(2H, t, J=6.5 Hz), 7.09(1H, d, J=8.4 Hz), 7.40-7.48 (5H, m), 7.78-7.81(4H, m).

Example 177

2-amino-4-{4-[3-(biphenyl-3-yl)propoxy]-3-trifluoromethylphenyl}-2-(phosphoryloxymethyl)butanol (177-1) Synthesis of 4-(2-{4-[3-(biphenyl-3-yl)propoxy]-3-trifluoromethylphenyl}ethyl)-4-di(t-butyl)phosphoryloxymethyl-2-methyl-2-oxazoline (Compound 177-1)

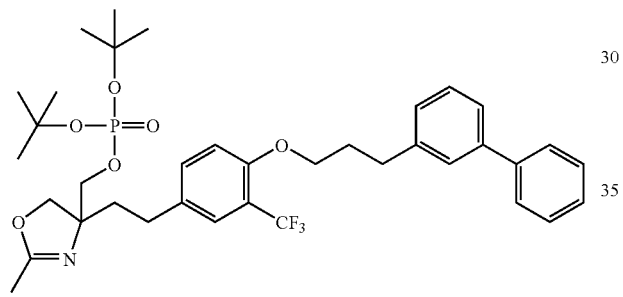

To a solution of compound 79-6 (420 mg) in N,N-dimethylformamide (10 ml) were added N,N-diisopropylethylamine (0.443 ml) and trimethyl orthoacetate (0.207 ml), and the mixture was stirred at 120° C. for 2 hr. Water was added to the reaction mixture, and the mixture was extracted with ethyl acetate, washed with water and saturated brine, and dried over anhydrous magnesium sulfate. The solvent was evaporated under reduced pressure to give a brown oil (440 mg). To a solution of the brown oil (440 mg) in methylene chloride (5 ml) and acetonitrile (2 ml) were added 1H-tetrazole (115 mg) and di-t-butyl diethylphosphoramidite (0.491 ml), and the mixture was stirred at room temperature for 2 hr. The reaction solution was ice-cooled, t-butyl hydroperoxide-containing decane solution (5-6M, 0.492 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (480 mg) as a yellow oil.

$^1$H-NMR(CD$_3$OD) δ (ppm): 1.48(18H, s), 1.82-1.89(2H, m), 2.01(3H, s), 2.10-2.19(2H, m), 2.52-2.70(2H, m), 2.90 (2H, t, J=7.4 Hz), 3.89-3.92(2H, m), 4.03(2H, t, J=5.9 Hz), 4.19(1H, d, J=9.0 Hz), 4.33(1H, d, J=9.0 Hz), 7.01(1H, d, J=8.5 Hz), 7.18(1H, d, J=7.3 Hz), 7.27-7.42(7H, m), 7.45(1H, d, J=1.5 Hz), 7.49-7.52(2H, m).

(177-2) Synthesis of 2-amino-4-{4-[3-(biphenyl-3-yl)propoxy]-3-trifluoromethylphenyl}-2-(phosphoryloxymethyl)butanol (Compound 177-2)

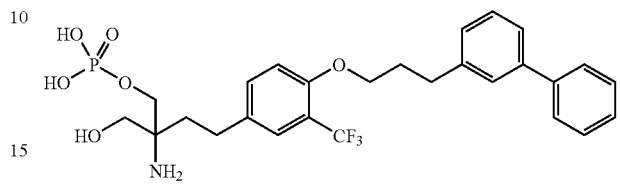

Compound 177-1 (480 mg) was dissolved in ethanol (5 ml), concentrated hydrochloric acid (1 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (345 mg) as a white solid.

MS(ESI)m/z: 554[M+H]

$^1$H-NMR(CD$_3$OD) δ (ppm): 1.93-2.00(2H, m), 2.10-2.19 (2H, m), 2.61-2.72(2H, m), 2.90(2H, t, J=7.4 Hz), 3.71(2H, brs), 3.97-4.01(2H, m), 4.04(2H, t, J=5.9 Hz), 7.03(1H, d, J=8.5 Hz), 7.19(1H, d, J=7.3 Hz), 7.28-7.43(7H, m), 7.48-7.52(3H, m).

Example 178

2-amino-4-{4-[3-(benzothiophen-3-yl)propoxy]-3-trifluoromethylphenyl}-2-(phosphoryloxymethyl)butanol (178-1) Synthesis of 4-(2-{4-[3-(benzothiophen-3-yl)propoxy]-3-trifluoromethylphenyl}ethyl)-4-di(t-butyl)phosphoryloxymethyl-2-methyl-2-oxazoline (Compound 178-1)

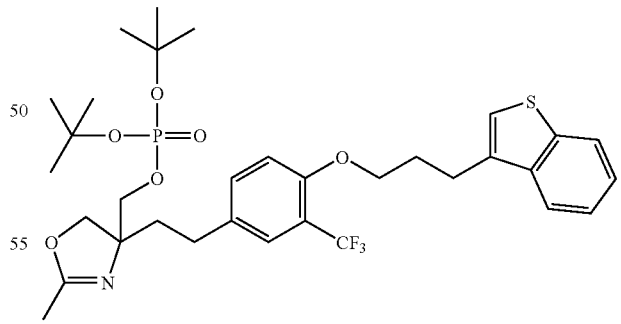

To a solution of compound 80-6 (390 mg) in N,N-dimethylformamide (10 ml) were added N,N-diisopropylethylamine (0.429 ml) and trimethyl orthoacetate (0.202 ml), and the mixture was stirred at 120° C. for 2 hr. Water was added to the reaction mixture, and the mixture was extracted with ethyl acetate, washed with water and saturated brine, and dried over anhydrous magnesium sulfate. The solvent was evaporated under reduced pressure to give a brown oil (400 mg). To a solution of the brown oil (400 mg) in methylene chloride (5 ml) and acetonitrile (2 ml) were added 1H-tetrazole (112 mg) and di-t-butyl diethylphosphoramidite (0.479 ml), and the mixture was stirred at room temperature for 2 hr. The reaction solution was ice-cooled, t-butyl hydroperoxide-containing decane solution (5-6M, 0.480 ml) was added, and the mixture was stirred under ice-cooling for 15 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (460 mg) as a yellow oil.

$^1$H-NMR(CD$_3$OD) δ (ppm): 1.48(18H, s), 1.83-1.89(2H, m), 2.01(3H, s), 2.17-2.24(2H, m), 2.53-2.70(2H, m), 3.09 (2H, t, J=7.5 Hz), 3.89-3.92(2H, m), 4.10(2H, t, J=5.7 Hz), 4.19(1H, d, J=9.0 Hz), 4.33(1H, d, J=9.0 Hz), 7.03(1H, d, J=8.5 Hz), 7.22(1H, brs), 7.30-7.40(3H, m), 7.45(1H, d, J=1.9 Hz), 7.79-7.81(1H, m), 7.84-7.86(1H, m).

(178-2) Synthesis of 2-amino-4-{4-[3-(benzothiophen-3-yl)propoxy]-3-trifluoromethylphenyl}-2-(phosphoryloxymethyl)butanol (Compound 178-2)

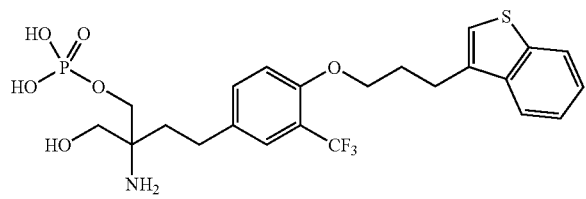

Compound 178-1 (460 mg) was dissolved in ethanol (5 ml), concentrated hydrochloric acid (1 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (335 mg) as a white solid.

MS (ESI)m/z: 534[M+H]

$^1$H-NMR(CD$_3$OD) δ (ppm): 1.93-2.00(2H, m), 2.16-2.25 (2H, m), 2.62-2.78(2H, m), 3.09(2H, t, J=7.5 Hz), 3.71(2H, brs), 3.97-4.05(2H, m), 4.10(2H, t, J=5.8 Hz), 7.05(1H, d, J=8.5 Hz), 7.22(1H, brs), 7.31-7.38(2H, m), 7.43(1H, d, J=8.5 Hz), 7.49(1H, brs), 7.79-7.81(1H, m), 7.84-7.86(1H, m).

Example 179

2-amino-4-{4-[3-(4-cyclopropylphenyl)propoxy]-3-trifluoromethylphenyl}-2-(phosphoryloxymethyl)butanol (179-1) Synthesis of 4-di(t-butyl)phosphoryloxymethyl-4-(2-{4-[3-(4-cyclopropylphenyl)propoxy]-3-trifluoromethyl}ethyl)-2-methyl-2-oxazoline (Compound 179-1)

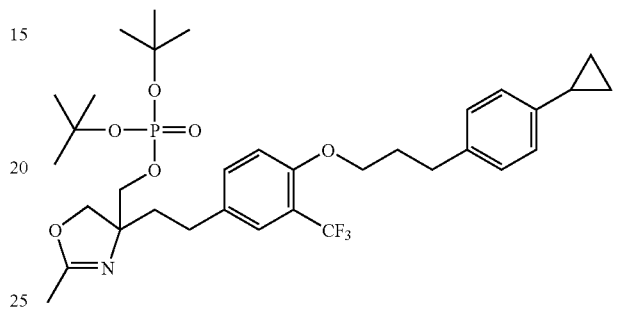

To a solution of compound 81-2 (220 mg) in N,N-dimethylformamide (5.0 ml) were added N,N-diisopropylethylamine (0.26 ml) and trimethyl orthoacetate (0.14 ml), and the mixture was stirred at 120° C. for 3.5 hr. Water was added to the reaction mixture, and the mixture was extracted with ethyl acetate, washed with water and saturated brine, and dried over anhydrous sodium sulfate. The solvent was evaporated under reduced pressure. To a solution of the obtained brown oil in methylene chloride (3.5 ml) and acetonitrile (2.75 ml) were added 1H-tetrazole (70 mg) and di-t-butyl diethylphosphoramidite (0.28 ml) was added, and the mixture was stirred at room temperature for 2 hr. To the reaction mixture were further added 1H-tetrazole (35 mg) and di-t-butyl diethylphosphoramidite (0.14 ml) and acetonitrile (1 ml), and the mixture was stirred at 120° C. for 1.5 hr. The reaction solution was ice-cooled, t-butyl hydroperoxide-containing decane solution (5-6M, 0.30 ml) was added and the mixture was stirred for 1 hr. Saturated aqueous sodium hydrogen carbonate solution was added to the reaction mixture, and the mixture was extracted with methylene chloride. The organic layer was dried over anhydrous sodium sulfate and the solvent was evaporated under reduced pressure. The obtained residue was purified by silica gel column chromatography (hexane:ethyl acetate) to give the object product (75 mg) as a pale-yellow oil.

$^1$H-NMR(DMSO-d$_6$) δ (ppm): 0.60(2H, ddd, J=6.2, 4.9, 4.6 Hz), 0.89(2H, ddd, J=8.5, 6.2, 4.4 Hz), 1.39(18H, s), 1.68-1.80(2H, m), 1.82-1.87(1H, m), 1.90(3H, s), 1.93-2.00 (2H, m), 2.45-2.52(1H, m), 2.57-2.63(1H, m), 2.68(2H, t, J=7.4 Hz), 3.74-3.82(2H, m), 4.01(2H, t, J=5.9 Hz), 4.07(1H, d, J=8.8 Hz), 4.11(1H, d, J=8.8 Hz), 6.97(2H, d, J=8.0 Hz), 7.05(2H, d, J=8.1 Hz), 7.11(1H, d, J=8.5 Hz), 7.42(1H, d, J=8.4 Hz), 7.45(1H, s).

(179-2) Synthesis of 2-amino-4-{4-[3-(4-cyclopropylphenyl)propoxy]-3-trifluoromethylphenyl}-2-(phosphoryloxymethyl)butanol (Compound 179-2)

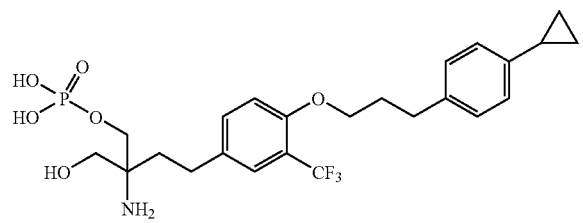

Compound 179-1 (75 mg) was dissolved in ethanol (5 ml), concentrated hydrochloric acid (1 ml) was added, and the mixture was stirred at 50° C. for 3 hr. The solvent was concentrated under reduced pressure, and methanol (2 ml), diethyl ether (5 ml) and propylene oxide (5 ml) were added to the residue. The precipitated powder was collected by filtration and washed with diethyl ether to give the object product (45 mg) as a white powder.

MS(ESI)m/z: 518[M+H]

$^1$H-NMR(CD$_3$OD) δ (ppm): 0.61(2H, ddd, J=6.2, 5.2, 4.3 Hz). 0.90(2H, ddd, J=8.4, 6.2, 4.2 Hz), 1.81-1.87(1H, m), 1.94-1.98(2H, m), 2.01-2.08(2H, m), 2.65-2.72(2H, m), 2.76 (2H, t, J=7.4 Hz), 3.70(2H, s), 3.97-4.03(4H, m), 6.96(2H, d, J=8.5 Hz), 7.00-7.07(1H, m), 7.05(2H, d, J=8.0 Hz), 7.42(1H, d, J=7.7 Hz), 7.47(1H, s).

Example 180

2-amino-4-{4-[3-(indan-5-yl)propoxy]-3-trifluoromethylphenyl}-2-(phosphoryloxymethyl)butanol (180-1) Synthesis of 4-di(t-butyl)phosphoryloxymethyl-4-(2-{4-[3-(indan-5-yl)propoxy]-3-trifluoromethylphenyl}ethyl)-2-methyl-2-oxazoline (Compound 180-1)

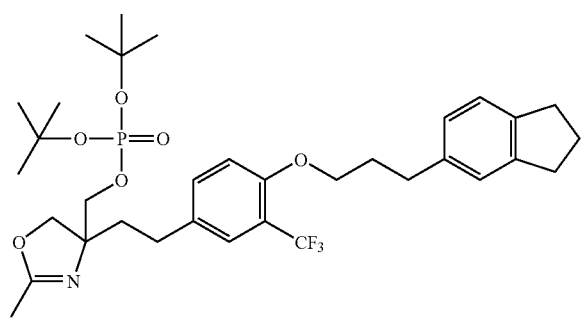

To a solution of compound 82-3 (390 mg) in N,N-dimethylformamide (10 ml) were added N,N-diisopropylethylamine (0.443 ml) and trimethyl orthoacetate (0.207 ml), and the mixture was stirred at 120° C. for 6 hr. Water was added to the reaction mixture, and the mixture was extracted with ethyl acetate, washed with water and saturated brine, and dried over anhydrous magnesium sulfate. The solvent was evaporated under reduced pressure to give a brown oil (410 mg). To a solution of the brown oil (410 mg) in methylene chloride (5 ml) and acetonitrile (2 ml) were added 1H-tetrazole (115 mg) and di-t-butyl diethylphosphoramidite (0.491 ml), and the mixture was stirred at room temperature for 2 hr. The reaction solution was ice-cooled, t-butyl hydroperoxide-containing decane solution (5-6M, 0.492 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4-ethyl acetate alone) to give the object product (480 mg) as a yellow oil.

$^1$H-NMR(CD$_3$OD) δ (ppm): 1.48(18H, s), 1.82-1.90(2H, m), 2.02(3H, s), 2.02-2.10(4H, m), 2.52-2.70(2H, m), 2.76 (2H, t, J=7.4 Hz), 2.83(4H, t, J=7.4 Hz), 3.89-3.91(2H, m), 3.99(2H, t, J=6.0 Hz), 4.18(1H, d, J=9.0 Hz), 4.32(1H, d, J=9.0 Hz), 6.92(1H, d, J=7.7 Hz), 7.00(1H, d, J=8.4 Hz), 7.03(1H, brs), 7.08(1H, d, J=7.7 Hz), 7.37(1H, d, J=8.4 Hz), 7.43(1H, brs).

(180-2) Synthesis of 2-amino-4-{4-[3-(indan-5-yl)propoxy]-3-trifluoromethylphenyl}-2-(phosphoryloxymethyl)butanol (Compound 180-2)

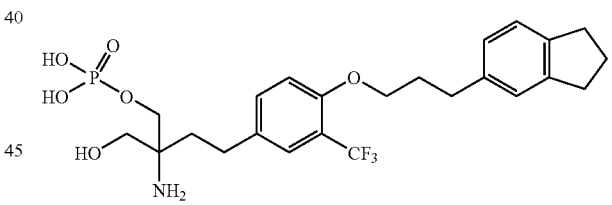

Compound 180-1 (480 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (310 mg) as a white solid.

MS(ESI)m/z: 518[M+H]

$^1$H-NMR(CD$_3$OD) δ (ppm): 1.93-2.00(2H, m), 2.01-2.09 (4H, m), 2.60-2.72(2H, m), 2.76(2H, t, J=7.4 Hz), 2.84(4H, t, J=7.4 Hz), 3.70(2H, brs), 3.97-4.03(4H, m), 6.92(1H, d, J=8.1 Hz), 7.00-7.04(2H, m), 7.08(1H, d, J=7.6 Hz), 7.42(1H, d, J=8.5 Hz), 7.47(1H, brs).

Example 181

2-amino-4-{4-[3-(2-methyl-4-thienyl)propoxy]-3-trifluoromethylphenyl}-2-(phosphoryloxymethyl)butanol (181-1) Synthesis of (1-(dibenzyl)phosphoryloxymethyl-1-hydroxymethyl-3-{4-[3-(2-methyl-4-thienyl)propoxy]-3-trifluoromethylphenyl}propyl)carbamic acid benzyl ester (Compound 181-1)

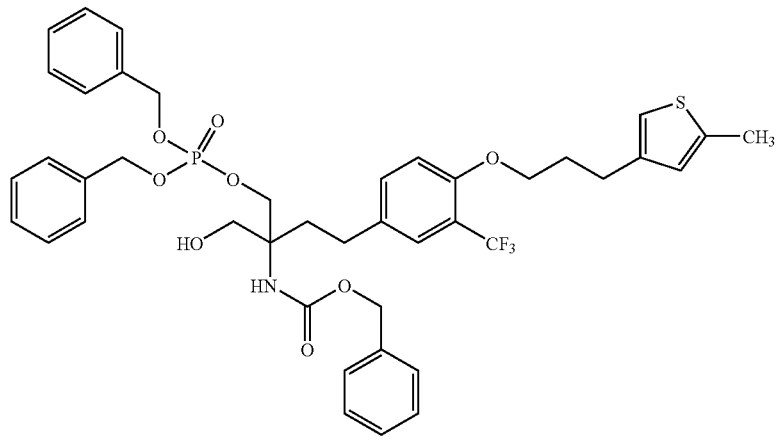

Compound 83-5 (220 mg), ethyl acetate (10 ml), saturated aqueous sodium hydrogen carbonate solution (10 ml) and benzyloxycarbonyl chloride (0.090 ml) were stirred in an nonuniform state at room temperature for 15 hr. The ethyl acetate layer was separated, and the aqueous layer was extracted with ethyl acetate. The separated ethyl acetate layer and the ethyl acetate layer obtained by extraction were combined, washed with saturated brine and dried over anhydrous magnesium sulfate. The solvent was evaporated under reduced pressure to give an amine-protected compound as a colorless oil (250 mg). The colorless oil (250 mg), pyrophosphoric acid tetrabenzyl ester (495 mg), silver oxide (210 mg) and tetra-n-hexylammonium iodide (438 mg) were added to a mixed solvent of toluene (4 ml), methylene chloride (4 ml) and perfluorohexane (4 ml), and the mixture was stirred at room temperature for 14 hr. Insoluble material was filtered off and the solvent was evaporated under reduced pressure. The residue was purified by HPLC to give the object product (200 mg) as a colorless oil.

$^1$H-NMR(CD$_3$OD) δ (ppm): 1.75-1.87(1H, m), 1.90-2.00 (1H, m). 2.01-2.10(2H, m), 2.41(3H, s), 2.49-2.58(2H, m), 2.73(2H, t, J=7.4 Hz), 3.59(1H, d, J=11.1 Hz), 3.69(1H, d, J=11.1 Hz), 4.00(2H, t, J=6.0 Hz), 4.15-4.21(1H, m), 4.25-4.32(1H, m), 4.99-5.03(6H, m), 6.62(1H, s), 6.71(1H, s), 6.94(1H, d, J=8.5 Hz), 7.24-7.38(17H, m).

(181-2) Synthesis of 2-amino-4-{4-[3-(2-methyl-4-thienyl)propoxy]-3-trifluoromethylphenyl}-2-(phosphoryloxymethyl)butanol (Compound 181-2)

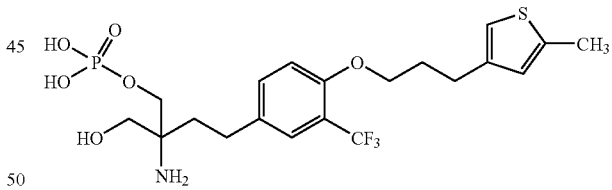

Compound 181-1 (200 mg) was dissolved in acetonitrile (4 ml), trimethylsilyl iodide (0.175 ml) was added, and the mixture was stirred under ice-cooling for 2.5 hr. The reaction mixture was concentrated under reduced pressure, isopropyl alcohol (5 ml) was added, and the resulting solid was collected by filtration. The solid was washed with methanol to give the object product (15 mg) as a pale-yellow powder.

MS(ESI)m/z: 498[M+H]

$^1$H-NMR(CD$_3$OD) δ (ppm): 1.93-1.99(2H, m), 2.00-2.10 (2H, m), 2.41(3H, s), 2.62-2.75(4H, m), 3.70(2H, brs), 3.97-4.03(4H, m), 6.62(1H, s), 6.71(1H, s), 7.03(1H, d, J=8.5 Hz), 7.43(1H, d, J=8.5 Hz), 7.46(1H, brs).

Example 182

2-amino-4-{4-[3-(3-cyclopropylphenyl)propoxy]-3-trifluoromethylphenyl}-2-(phosphoryloxymethyl)butanol (182-1) Synthesis of 2-amino-4-{4-[3-(3-cyclopropylphenyl)propoxy]-3-trifluoromethylphenyl}-2-(phosphoryloxymethyl)butanol (Compound 182-1)

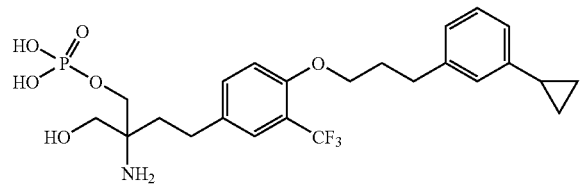

To a solution of compound 85-2 (100 mg) in N,N-dimethylformamide (2.1 ml) were added N,N-diisopropylethylamine (0.11 ml) and trimethyl orthoacetate (0.06 ml), and the mixture was stirred at 120° C. for 4 hr. Water was added to the reaction mixture, and the mixture was extracted with ethyl acetate, washed with water and saturated brine, and dried over anhydrous sodium sulfate. The solvent was evaporated under reduced pressure. To a solution of the obtained brown oil in methylene chloride (1.5 ml) and acetonitrile (1.0 ml) were added 1H-tetrazole (30 mg) and di-t-butyl diethylphosphoramidite (0.12 ml) was added, and the mixture was stirred at room temperature for 1.5 hr. The reaction solution was ice-cooled, t-butyl hydroperoxide-containing decane solution (5-6M, 0.12 ml) was added and the mixture was stirred for 1.5 hr. Saturated aqueous sodium hydrogen carbonate solution was added to the reaction mixture, and the mixture was extracted with methylene chloride. The organic layer was dried over anhydrous sodium sulfate and the solvent was evaporated under reduced pressure. The obtained residue was purified by silica gel column chromatography (hexane:ethyl acetate) to give 4-di(t-butyl)phosphoryloxymethyl-4-(2-{4-[3-(3-cyclopropylphenyl)propoxy]-3-trifluoromethyllethyl)-2-methyl-2-oxazoline as a yellow oil. The obtained yellow oil (95 mg) was dissolved in ethanol (5 ml), concentrated hydrochloric acid (1 ml) was added, and the mixture was stirred at 50° C. for 3 hr. The solvent was concentrated under reduced pressure, and methanol (2 ml), diethyl ether (5 ml) and propylene oxide (5 ml) were added to the residue. The precipitated powder was collected by filtration and washed with diethyl ether to give the object product (60 mg) as a white powder.

MS(ESI)m/z: 518[M+H]

$^1$H-NMR(CD$_3$OD) δ (ppm): 0.55(2H, ddd, J=6.2, 4.8, 4.2 Hz), 0.88(2H, ddd, J=8.4, 6.0, 3.9 Hz), 1.80-1.84(1H, m), 1.93-1.98(2H, m), 2.01-2.08(2H, m), 2.65-2.72(2H, m), 2.76 (2H, t, J=7.4 Hz), 3.70(2H, brs), 3.96-4.00(4H, m), 6.86-6.88 (2H, m), 6.94(1H, d, J=7.7 Hz), 7.00(1H, d, J=8.4 Hz), 7.11 (1H, t, J=7.5 Hz), 7.42(1H, d, J=8.6 Hz), 7.48(1H, s).

Example 183

2-amino-4-{4-[3-(2,2-difluoro-1,3-benzodioxol-5-yl)propoxy]-3-trifluoromethylphenyl}-2-(phosphoryloxymethyl)butanol (183-1) Synthesis of 4-di(t-butyl)phosphoryloxymethyl-4-(2-{4-[3-(2,2-difluoro-1,3-benzodioxol-5-yl)propoxy]-3-trifluoromethylphenyl}ethyl)-2-methyl-2-oxazoline (Compound 183-1)

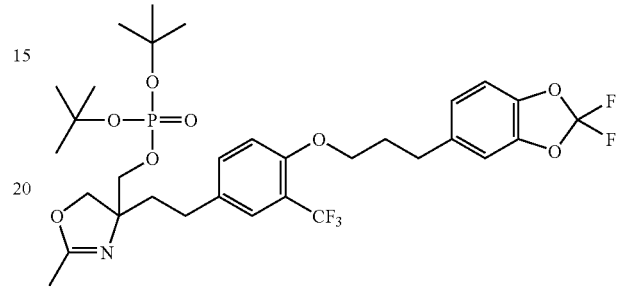

To a solution of compound 87-5 (400 mg) in N,N-dimethylformamide (10 ml) were added N,N-diisopropylethylamine (0.420 ml) and trimethyl orthoacetate (0.197 ml), and the mixture was stirred at 120° C. for 4 hr. Water was added to the reaction mixture, and the mixture was extracted with ethyl acetate, washed with water and saturated brine, and dried over anhydrous magnesium sulfate. The solvent was evaporated under reduced pressure to give a brown oil (440 mg). To a solution of the brown oil (440 mg) in methylene chloride (5 ml) and acetonitrile (2 ml) were added 1H-tetrazole (109 mg) and di-t-butyl diethylphosphoramidite (0.467 ml), and the mixture was stirred at room temperature for 2 hr. The reaction solution was ice-cooled, t-butyl hydroperoxide-containing decane solution (5-6M, 0.468 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The m obtained residue was purified by silica gel column chromatography (hexane:ethyl acetate=1:4—ethyl acetate alone) to give the object product (560 mg) as a yellow oil.

$^1$H-NMR(CD$_3$OD) δ (ppm): 1.48(18H, s), 1.82-1.89(2H, m), 2.01(3H, s), 2.03-2.12(2H, m), 2.52-2.70(2H, m), 2.85 (2H, t, J=7.5 Hz), 3.89-3.91(2H, m), 4.01(2H, t, J=5.9 Hz), 4.18(1H, d, J=9.0 Hz), 4.32(1H, d, J=9.0 Hz), 6.96-7.08(4H, m), 7.39(1H, d, J=8.5 Hz), 7.44(1H, brs).

(183-2) Synthesis of 2-amino-4-{4-[3-(2,2-difluoro-1,3-benzodioxol-5-yl)propoxy]-3-trifluoromethylphenyl}-2-(phosphoryloxymethyl)butanol (Compound 183-2)

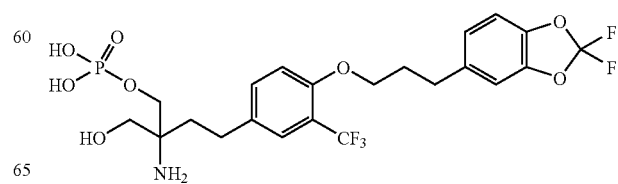

Compound 183-1 (560 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (350 mg) as a pale-brown solid.

MS(ESI)m/z: 558[M+H]

$^1$H-NMR(CD$_3$OD) δ (ppm): 1.93-1.99(2H, m), 2.00-2.09 (2H, m), 2.65-2.80(2H, m), 2.85(2H, brs), 3.71(2H, brs), 3.92-4.10(4H, m), 6.90-7.12(4H, m), 7.39-7.50(2H, m).

Example 184

2-amino-4-{4-[3-(3-chlorophenyl)allyloxy]-3-trifluoromethylphenyl}-2-(phosphoryloxymethyl)butanol (184-1) Synthesis of 2-amino-4-{4-[3-(3-chlorophenyl)allyloxy]-3-trifluoromethylphenyl}-2-(phosphoryloxymethyl)butanol (Compound 184-1)

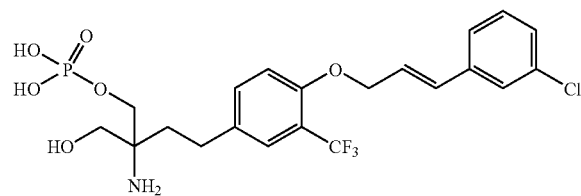

To a solution of compound 89-2 (200 mg) in N,N-dimethylformamide (5.0 ml) were added N,N-diisopropylethylamine (0.22 ml) and trimethyl orthoacetate (0.12 ml), and the mixture was stirred at 120° C. for 6.5 hr. Water was added to the reaction mixture, and the mixture was extracted with ethyl acetate, washed with water and saturated brine, and dried over anhydrous sodium sulfate. The solvent was evaporated under reduced pressure. To a solution of the obtained brown oil in methylene chloride (2.8 ml) and acetonitrile (2.25 ml) were added 1H-tetrazole (60 mg) and di-t-butyl diethylphosphoramidite (0.24 ml), and the mixture was stirred at room temperature for 1.5 hr. The reaction solution was ice-cooled, t-butyl hydroperoxide-containing decane solution (5-6M, 0.26 ml) was added and the mixture was stirred for 30 min. Saturated aqueous sodium hydrogen carbonate solution was added to the reaction mixture, and the mixture was extracted with methylene chloride. The organic layer was dried over anhydrous sodium sulfate and the solvent was evaporated under reduced pressure. The obtained residue was purified by silica gel column chromatography (hexane:ethyl acetate) to give 4-di(t-butyl)phosphoryloxymethyl-4-(2-{4-[3-(3-chlorophenyl)allyloxy]-3-trifluoromethylphenyl}ethyl)-2-methyl-2-oxazoline as a yellow oil. The obtained yellow oil was dissolved in ethanol (15 ml), concentrated hydrochloric acid (3 ml) was added, and the mixture was stirred at 50° C. for 4 hr. The solvent was concentrated under reduced pressure, and methanol (2 ml), diethyl ether (5 ml) and propylene oxide (5 ml) were added to the residue. The precipitated powder was collected by filtration and washed with methanol and diethyl ether to give the object product (105 mg) as a white powder.

MS (ESI)m/z: 510 [M+H]

$^1$H-NMR(CD$_3$OD) δ (ppm): 1.94-2.01(2H, m), 2.63-2.73 (2H, m), 3.70(2H, s), 3.96-4.04(2H, at), 4.82(2H, dd, J=5.3, 1.2 Hz), 6.48(1H, dt, 15.8, 5.3 Hz), 6.75(1H, d, J=15.8 Hz), 7.16(1H, d, J=8.4 Hz), 7.24(1H, d, J=7.8 Hz), 7.30(1H, t, J=7.8 Hz), 7.35(1H, d, J=7.8 Hz), 7.43(1H, s), 7.46(1H, d, J=8.6 Hz), 7.50(1H, s).

Example 185

2-amino-2-(phosphoryloxymethyl)-4-{3-trifluoromethyl-4-[3-(4-trifluoromethylphenyl)allyloxy]phenyl}butanol (185-1) Synthesis of 2-amino-2-(phosphoryloxymethyl)-4-{3-trifluoromethyl-4-[3-(4-trifluoromethylphenyl)allyloxy]phenyl}butanol (Compound 185-1)

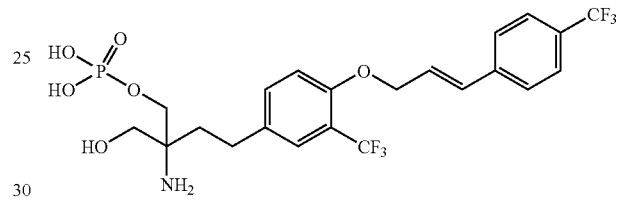

To a solution of compound 92-2 (290 mg) in N,N-dimethylformamide (5.8 ml) were added N,N-diisopropylethylamine (0.30 ml) and trimethyl orthoacetate (0.16 ml), and the mixture was stirred at 120° C. for 2.5 hr. Water was added to the reaction mixture, and the mixture was extracted with ethyl acetate, washed with water and saturated brine, and dried over anhydrous sodium sulfate. The solvent was evaporated under reduced pressure. To a solution of the obtained brown solid in methylene chloride (3.8 ml) and acetonitrile (3.2 ml) were added 1H-tetrazole (81 mg) and di-t-butyl diethylphosphoramidite (0.32 ml), and the mixture was stirred at room temperature for 1.5 hr. The reaction solution was ice-cooled, t-butyl hydroperoxide-containing decane solution (5-6M, 0.35 ml) was added and the mixture was stirred for 30 min. Saturated aqueous sodium hydrogen carbonate solution was added to the reaction mixture, and the mixture was extracted with methylene chloride. The organic layer was dried over anhydrous sodium sulfate and the solvent was evaporated under reduced pressure. The obtained residue was purified by silica gel column chromatography (hexane:ethyl acetate) to give 4-di(t-butyl)phosphoryloxymethyl-2-methyl-4-(2-{3-trifluoromethyl-4-[3-(4-trifluoromethylphenyl)allyloxy]}ethyl)-2-oxazoline as a yellow oil. The obtained yellow oil was dissolved in ethanol (5 ml), concentrated hydrochloric acid (1 ml) was added, and the mixture was stirred at 50° C. for 3.5 hr. The solvent was concentrated under reduced pressure, and methanol (2 ml), diethyl ether (5 ml) and propylene oxide (5 ml) were added to the residue. The precipitated powder was collected by filtration and washed with methanol and diethyl ether to give the object product (170 mg) as a white powder.

MS(ESI)m/z: 544[M+H]

$^1$H-NMR(CD$_3$OD) δ (ppm): 1.92-1.99(2H, m), 2.66-2.75 (2H, m), 3.70(2H, s), 3.94-4.02(2H, m), 4.84-4.85(2H, m), 6.60(1H, dt, 16.2, 5.2 Hz), 6.86(1H, d, J=16.1 Hz), 7.16(1H, d, J=8.5 Hz), 7.47(1H, dd, J=8.5, 1.8 Hz), 7.50(1H, d, J=2.2 Hz), 7.61(4H, s).

Example 186

(E)-2-amino-4-{4-[3-(3-methylphenyl)propoxy]-3-trifluoromethylphenyl}-2-(phosphoryloxymethyl)-3-butenol (186-1) Synthesis of (E)-4-di(t-butyl)phosphoryloxymethyl-2-methyl-4-(2-{4-[3-(3-methylphenyl)propoxy]-3-trifluoromethylphenyl}vinyl)-2-oxazoline (Compound 186-1)

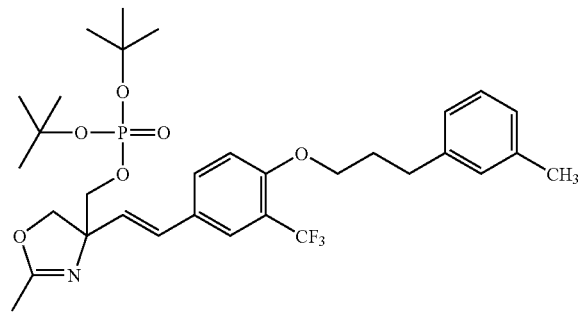

To a solution of compound 93-10(280 mg) in N,N-dimethylformamide (10 ml) were added N,N-diisopropylethylamine (0.338 ml) and trimethyl orthoacetate (0.159 ml), and the mixture was stirred at 120° C. for 4 hr. Water was added to the reaction mixture, and the mixture was extracted with ethyl acetate, washed with water and saturated brine, and dried over anhydrous magnesium sulfate. The solvent was evaporated under reduced pressure to give a brown oil (320 mg). To a solution of the brown oil (320 mg) in methylene chloride (5 ml) and acetonitrile (2 ml) were added 1H-tetrazole (88 mg) and di-t-butyl diethylphosphoramidite (0.377 ml), and the mixture was stirred at room temperature for 1 hr. The reaction solution was ice-cooled, t-butyl hydroperoxide-containing decane solution (5-6M, 0.378 ml) was added, and the mixture was stirred under ice-cooling for 10 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (370 mg) as a yellow oil.

$^1$H-NMR(CD$_3$OD) δ (ppm): 1.48(18H, s), 2.05(3H, s), 2.05-2.10(2H, m), 2.28(3H, s), 2.77(2H, t, J=7.5 Hz), 3.94-4.05(4H, m), 4.23(1H, d, J=8.9 Hz), 4.50(1H, d, J=8.9 Hz), 6.31(1H, d, J=16.2 Hz), 6.42(1H, d, J=16.2 Hz), 6.96-6.98 (2H, m), 7.01(1H, s), 7.06(1H, d, J=8.7 Hz), 7.12(1H, t, J=7.6 Hz), 7.60(1H, d, J=8.7 Hz), 7.65(1H, brs).

(186-2) Synthesis of (E)-2-amino-4-{4-[3-(3-methylphenyl)propoxy]-3-trifluoromethylphenyl}-2-(phosphoryloxymethyl)-3-butenol (Compound 186-2)

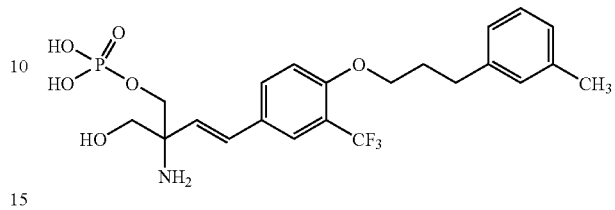

Compound 186-1 (370 mg) was dissolved in ethanol (5 ml), concentrated hydrochloric acid (1 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (180 mg) as a pale-yellow solid.

MS(ESI)m/z: 490[M+H]

$^1$H-NMR(CD$_3$OD) δ (ppm): 2.04-2.11(2H, m), 2.27(3H, s), 2.77(2H, t, J=7.4 Hz), 3.75(1H, d, J=11.7 Hz), 3.84(1H, d, J=11.7 Hz), 3.99-4.06(3H, m), 4.09-4.14(1H, m), 6.23(1H, d, J=16.6 Hz), 6.76(1H, d, J=16.6 Hz), 6.95-6.99(2H, m), 7.01 (1H, s), 7.07-7.15(2H, m), 7.65(1H, t, J=8.6 Hz), 7.69(1H, d, J=1.4 Hz).

Example 187

2-amino-2-(phosphoryloxymethyl)-4-{4-[3-(1,2,3,4-tetrahydronaphthalen-1-yl)propoxy]-3-trifluoromethylphenyl}butanol (187-1) Synthesis of 4-di(t-butyl)phosphoryloxymethyl-2-methyl-4-(2-{4-[3-(1,2,3,4-tetrahydronaphthalen-1-yl)propoxy]-3-trifluoromethylphenyl}ethyl)-2-oxazoline (Compound 187-1)

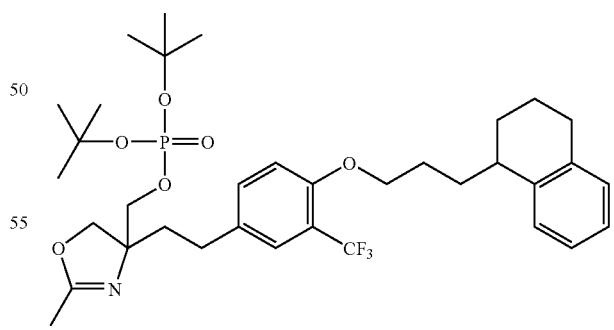

To a solution of compound 94-4 (230 mg) in N,N-dimethylformamide (10 ml) were added N,N-diisopropylethylamine (0.235 ml) and trimethyl orthoacetate (0.119 ml), and the mixture was stirred at 120° C. for 1 hr. Water was added to the reaction mixture, and the mixture was extracted with ethyl acetate, washed with water and saturated brine, and dried over anhydrous magnesium sulfate. The solvent was evaporated under reduced pressure to give a brown oil (220 mg). To a solution of the brown oil (220 mg) in methylene chloride (5 ml) and acetonitrile (2 ml) were added 1H-tetrazole (64 mg) and di-t-butyl diethylphosphoramidite (0.275 ml), and the mixture was stirred at room temperature for 2 hr. The reaction solution was ice-cooled, t-butyl hydroperoxide-containing decane solution (5-6M, 0.276 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (280 mg) as a yellow oil.

$^1$H-NMR(CD$_3$OD) δ (ppm): 1.48(18H, s), 1.70-1.92(10H, m), 2.01(3H, s), 2.52-2.70(2H, m), 2.71-2.79(2H, m), 2.83 (1H, brs), 3.86-3.90(2H, m), 4.03-4.08(2H, m), 4.18(1H, d, J=8.8 Hz), 4.32(1H, d, J=8.8 Hz), 6.98-7.06(4H, m), 7.15(1H, d, J=7.0 Hz), 7.37(1H, d, J=8.8 Hz), 7.41(1H, brs).

(187-2) Synthesis of 2-amino-2-(phosphoryloxymethyl)-4-{4-[3-(1,2,3,4-tetrahydronaphthalen-1-yl)propoxy]-3-trifluoromethylphenyl}butanol (Compound 187-2)

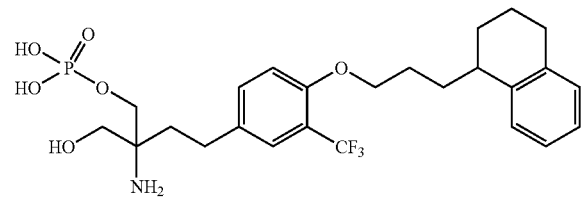

Compound 187-1 (280 mg) was dissolved in ethanol (5 ml), concentrated hydrochloric acid (1 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (190 mg) as a white solid.

MS(ESI)m/z: 532[M+H]

$^1$H-NMR(CD$_3$OD) δ (ppm): 1.70-1.89(4H, m), 1.90-2.00 (6H, m), 2.60-2.78(4H, m), 2.82(1H, brs), 3.70(2H, brs), 3.96-4.02(2H, m), 4.08(2H, brs), 7.01-7.08(4H, m), 7.15(1H, d, J=6.9 Hz), 7.43(1H, d, J=8.4 Hz), 7.46(1H, brs).

Example 188

2-amino-4-{4-[3-(3-nitrophenyl)propoxy]-3-trifluoromethylphenyl}-2-(phosphoryloxymethyl)butanol (188-1) Synthesis of 4-di(t-butyl)phosphoryloxymethyl-2-methyl-4-(2-{4-[3-(3-nitrophenyl)propoxy]-3-trifluoromethylphenyl}ethyl)-2-oxazoline (Compound 188-1)

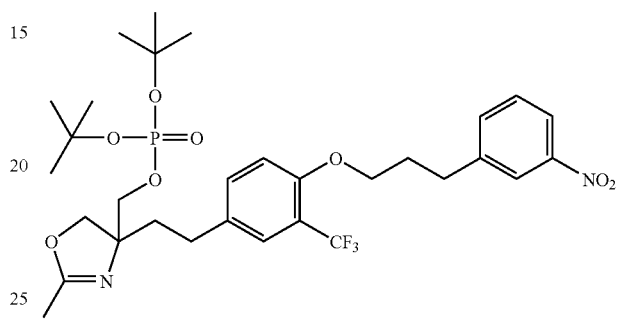

To a solution of compound 95-4 (310 mg) in N,N-dimethylformamide (10 ml) were added N,N-diisopropylethylamine (0.349 ml) and trimethyl orthoacetate (0.164 ml), and the mixture was stirred at 120° C. for 2 hr. Water was added to the reaction mixture, and the mixture was extracted with ethyl acetate, washed with water and saturated brine, and dried over anhydrous magnesium sulfate. The solvent was evaporated under reduced pressure to give a brown oil (330 mg). To a solution of the brown oil (330 mg) in methylene chloride (5 ml) and acetonitrile (2 ml) were added 1H-tetrazole (91 mg) and di-t-butyl diethylphosphoramidite (0.389 ml), and the mixture was stirred at room temperature for 2 hr. The reaction solution was ice-cooled, t-butyl hydroperoxide-containing decane solution (5-6M, 0.390 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (390 mg) as a yellow oil.

$^1$H-NMR(CD$_3$OD) δ (ppm): 1.48(18H, s), 1.82-1.89(2H, m), 2.01(3H, s), 2.10-2.19(2H, m), 2.52-2.70(2H, m), 2.97 (2H, t, J=7.5 Hz), 3.89-3.92(2H, m), 4.05(2H, t, J=5.9 Hz), 4.18(1H, d, J=9.0 Hz), 4.32(1H, d, J=9.0 Hz), 7.03(1H, d, J=8.5 Hz), 7.38(1H, dd, J=8.5, 1.6 Hz), 7.44(1H, d, J=1.6 Hz), 7.52(1H, t, J=7.8 Hz), 7.63(1H, d, J=7.8 Hz), 8.07(1H, d, J=8.5 Hz), 8.09(1H, brs).

(188-2) Synthesis of 2-amino-4-{4-[3-(3-nitrophenyl)propoxy]-3-trifluoromethylphenyl)-2-(phosphoryloxymethyl)butanol (Compound 188-2)

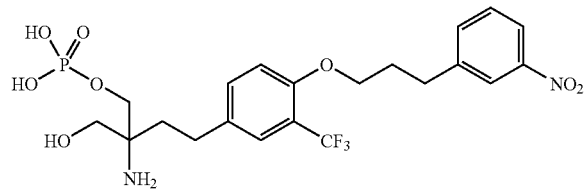

Compound 188-1 (390 mg) was dissolved in ethanol (6 ml), concentrated hydrochloric acid (1.2 ml) was added, and the mixture was stirred at 50° C. for 3.5 hr. The solvent was to concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (260 mg) as a pale-brown solid.

MS(ESI)m/z: 523[M+H]
$^1$H-NMR(CD$_3$OD) δ (ppm): 1.93-1.99(2H, m), 2.10-2.13 (2H, m), 2.64-2.72(2H, m), 2.97(2H, t, J=7.5 Hz), 3.71(2H, brs), 3.99-4.07(4H, m), 7.05(1H, d, J=8.6 Hz), 7.43(1H, d, J=8.6 Hz), 7.49(1H, brs), 7.52(1H, t, J=7.6 Hz), 7.63(1H, d, J=7.6 Hz), 8.07(1H, d, J=8.6 Hz), 8.09(1H, brs).

Example 189

2-amino-4-{4-[3-(3-chloro-2-methylphenyl)propoxy]-3-trifluoromethylphenyl}-2-(phosphoryloxymethyl)butanol

(189-1) Synthesis of 4-di(t-butyl)phosphoryloxymethyl-4-(2-{4-[3-(3-chloro-2-methylphenyl)propoxy]-3-trifluoromethylphenyl}ethyl)-2-methyl-2-oxazoline (Compound 189-1)

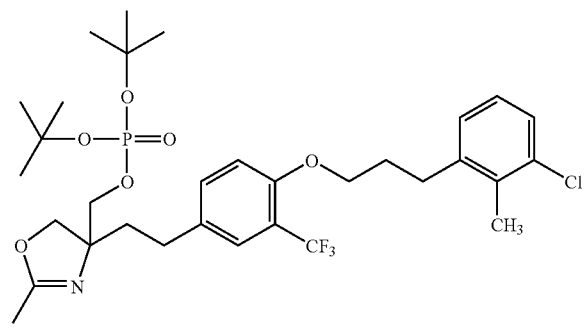

To a solution of compound 54-4 (420 mg) in N,N-dimethylformamide (8.7 ml) were added N,N-diisopropylethylamine (0.45 ml) and trimethyl orthoacetate (0.24 ml), and the mixture was stirred at 120° C. for 4 hr. Water was added to the reaction mixture, and the mixture was extracted with ethyl acetate, washed with water and saturated brine, and dried over anhydrous sodium sulfate. The solvent was evaporated under reduced pressure. To a solution of the obtained brown oil in methylene chloride (5.8 ml) and acetonitrile (4.5 ml) were added 1H-tetrazole (120 mg) and di-t-butyl diethylphosphoramidite (0.48 ml), and the mixture was stirred at room temperature for 3 hr. The reaction solution was ice-cooled, t-butyl hydroperoxide-containing decane solution (5-6M, 0.52 ml) was added and the mixture was stirred for 1 hr. Saturated aqueous sodium hydrogen carbonate solution was added to the reaction mixture, and the mixture was extracted with methylene chloride. The organic layer was dried over anhydrous sodium sulfate and the solvent was evaporated under reduced pressure. The obtained residue was purified by silica gel column chromatography (hexane:ethyl acetate) to give the object product (352 mg) as a pale-yellow oil.

$^1$H-NMR(DMSO-d$_6$) δ (ppm): 1.40(18H, s), 1.68-1.82 (2H, m), 1.90(3H, s), 1.93(2H, dd, J=9.6, 3.4 Hz), 2.30(3H, s), 2.46-2.54(1H, m), 2.62(1H, td, J=11.3, 5.4 Hz), 2.81(2H, t, J=7.6 Hz), 3.75-3.82(2H, m), 4.06-4.09(3H, m), 4.12(1H, d, J=8.8 Hz), 7.11-7.16(3H, m), 7.27(1H, dd, J=6.2, 3.2 Hz), 7.44-7.46(1H, m), 7.46(1H, s).

(189-2) Synthesis of 2-amino-4-{4-[3-(3-chloro-2-methylphenyl)propoxy]-3-trifluoromethylphenyl}-2-(phosphoryloxymethyl)butanol (Compound 189-2)

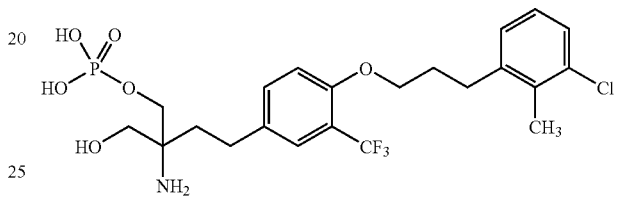

Compound 189-1 (352 mg) was dissolved in ethanol (5 ml), concentrated hydrochloric acid (1 ml) was added, and the mixture was stirred at 50° C. for 3 hr. The solvent was concentrated under reduced pressure, and methanol (2 ml), diethyl ether (5 ml) and propylene oxide (5 ml) were added to the residue. The precipitated powder was collected by filtration and washed with diethyl ether to give the object product (216 mg) as a white powder.

MS(ESI)m/z: 526[M+H]
$^1$H-NMR(CD$_3$OD) δ (ppm): 1.93-2.06(4H, m), 2.64-2.71 (2H, m), 2.90(2H, t, J=7.9 Hz), 3.70(2H, s), 3.97(2H, t, J=5.8 Hz), 4.06(2H, t, J=5.7 Hz), 7.04(1H, d, J=7.8 Hz), 7.07-7.10 (2H, m), 7.20(1H, d, J=4.0 Hz), 7.44(1H, d, J=8.8 Hz), 7.49 (1H, s).

Example 190

2-amino-4-[4-(4-cyclohexylbutoxy)-3-trifluoromethylphenyl]-2-(phosphoryloxymethyl)butanol

(190-1) Synthesis of {1-(dibenzyl)phosphoryloxymethyl-3-[4-(4-cyclohexylbutoxy)-3-trifluoromethylphenyl]-1-hydroxymethylpropyl}carbamic acid benzyl ester (Compound 190-1)

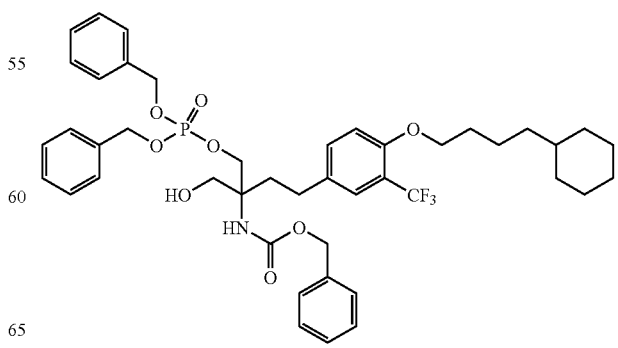

Compound 3-9 (330 mg), ethyl acetate (5 ml), saturated aqueous sodium hydrogen carbonate solution (5 ml) and benzyloxycarbonyl chloride (0.134 ml) were stirred in an nonuniform state at room temperature 6 hr. Furthermore, to the reaction mixture was added benzyloxycarbonyl chloride (0.074 ml), and the mixture was stirred in an nonuniform state at room temperature 2 hr. The ethyl acetate layer was separated, and the aqueous layer was extracted with ethyl acetate. The separated ethyl acetate layer and the ethyl acetate layer obtained by extraction were combined, washed with saturated brine, and dried over anhydrous magnesium sulfate. The solvent was evaporated under reduced pressure. The residue was purified by silica gel column chromatography (hexane:ethyl acetate=1:3-1:4) to give an amine-protected compound as a colorless oil (120 mg). The colorless oil (120 mg), pyrophosphoric acid tetrabenzyl ester (237 mg), silver oxide (102 mg) and tetra-n-hexylammonium iodide (212 mg) were added to a mixed solvent of toluene (4 ml), methylene chloride (4 ml) and perfluorohexane (4 ml), and the mixture was stirred at room temperature for 15 hr. Insoluble material was filtered off and the solvent was evaporated under reduced pressure. The residue was purified by HPLC to give the object product (90 mg) as a colorless oil.

$^1$H-NMR(CD$_3$OD) δ (ppm): 0.85-0.96(2H, m), 1.28-1.31 (6H, m), 1.47-1.55(2H, m), 1.66-1.89(8H, m), 1.90-2.01(1H, m), 2.49-2.59(2H, m), 3.59(1H, d, J=11.2 Hz), 3.69(1H, d, J=11.2 Hz), 4.02(2H, t, J=6.2 Hz), 4.15-4.21(1H, m), 4.25-4.34(1H, m), 4.99-5.03(6H, m), 6.98(1H, d, J=8.6 Hz), 7.22-7.34(17H, m).

(190-2) Synthesis of 2-amino-4-[4-(4-cyclohexylbutoxy)-3-trifluoromethylphenyl]-2-(phosphoryloxymethyl)butanol (Compound 190-2)

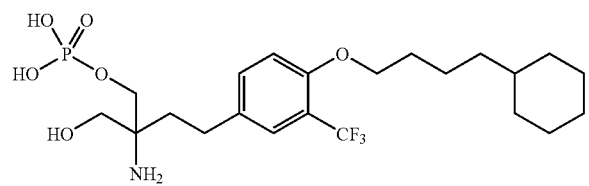

Compound 190-1 (90 mg) was dissolved in methanol (5 ml), 10% palladium carbon (45 mg) was added, and the reaction vessel was purged with hydrogen. The mixture was stirred at room temperature for 4 hr, the reaction vessel was purged with nitrogen, and the reaction mixture was filtered. The filtrate was concentrated to give the object product (15.0 mg) as a white powder.

MS(ESI)m/z: 498[M+H]

$^1$H-NMR(CD$_3$OD) δ (ppm): 0.85-0.96(2H, m), 1.15-1.32 (6H, m), 1.46-1.58(2H, m), 1.63-1.80(7H, m), 1.81-1.94(2H, m), 2.65-2.72(2H, m), 3.64(1H, d, J=11.7 Hz), 3.68(1H, d, J=11.7 Hz), 3.85-3.98(2H, m), 4.04(2H, t, J=6.2 Hz), 7.05 (1H, d, J=8.3 Hz), 7.39-7.44(2H, m).

Example 191

2-amino-4-[4-(4-phenylbutoxy)-3-trifluoromethylphenyl]-2-(phosphoryloxymethyl)butanol (191-1) Synthesis of 4-di(t-butyl)phosphoryloxymethyl-2-methyl-4-{2-[4-(4-phenylbutoxy)-3-trifluoromethylphenyl]ethyl}-2-oxazoline (Compound 191-1)

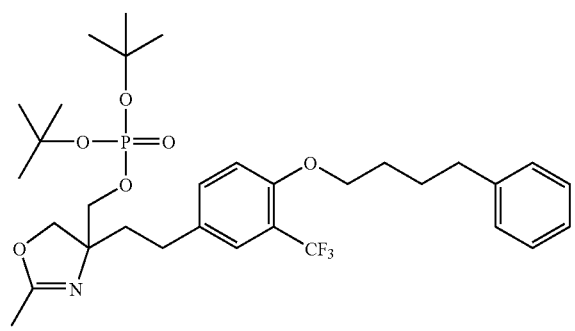

To a solution of compound 4-2 (290 mg) in N,N-dimethylformamide (10 ml) were added N,N-diisopropylethylamine (0.349 ml) and trimethyl orthoacetate (0.125 ml), and the mixture was stirred at 120° C. for 6.5 hr. Water was added to the reaction mixture, and the mixture was extracted with ethyl acetate, washed with water and saturated brine, and dried over anhydrous magnesium sulfate. The solvent was evaporated under reduced pressure to give a brown oil (270 mg). To a solution of the brown oil (270 mg) in methylene chloride (5 ml) and acetonitrile (2 ml) were added 1H-tetrazole (87 mg) and di-t-butyl diethylphosphoramidite (0.371 ml), and the mixture was stirred at room temperature for 2 hr. The reaction solution was ice-cooled, m-chloroperbenzoic acid (containing 25% water, 329 mg) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (260 mg) as a yellow oil.

$^1$H-NMR(CD$_3$OD) δ (ppm): 1.48(18H, s), 1.81(6H, brs), 2.00(3H, s), 2.51-2.71(4H, m), 3.90(2H, brs), 4.05(2H, brs), 4.17(1H, d, J=9.0 Hz), 4.32(1H, d, J=9.0 Hz), 7.04(1H, d, J=8.2 Hz), 7.10-7.20(3H, m), 7.21-7.27(2H, m), 7.36-7.41 (2H, m).

(191-2) Synthesis of 2-amino-4-[4-(4-phenylbutoxy)-3-trifluoromethylphenyl]-2-(phosphoryloxymethyl)butanol (Compound 191-2)

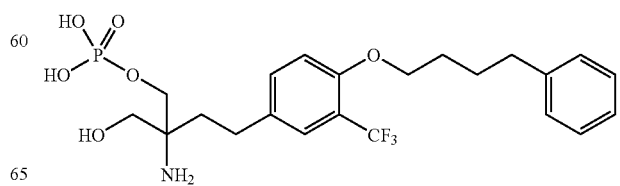

Compound 191-1 (260 mg) was dissolved in ethanol (5 ml), concentrated hydrochloric acid (1 ml) was added, and the mixture was stirred at 50° C. for 3 hr. The solvent was concentrated under reduced pressure, and methanol (5 ml), diethyl ether (5 ml) and propylene oxide (5 ml) were added to the residue. The precipitated powder was collected by filtration, and washed with ethyl acetate and diethyl ether to give the object product (92.2 mg) as a pale-yellow solid.

MS (ESI)m/z: 492 [M+H]
$^1$H-NMR(CD$_3$OD) δ (ppm): 1.79-1.84(4H, m), 1.92-1.99 (2H, m), 2.64-2.72(4H, m), 3.70(2H, brs), 3.95-4.02(2H, m), 4.06(2H, brs), 7.05(1H, d, J=8.4 Hz), 7.11-7.19(3H, m), 7.21-7.27(2H, m), 7.41-7.44(2H, m).

Example 192

(E)-2-amino-4-[4-(3-phenylpropoxy)-3-trifluoromethylphenyl]-2-(phosphoryloxymethyl)-3-butenol (192-1) Synthesis of (E)-4-di(t-butyl)phosphoryloxymethyl-2-methyl-4-{2-[4-(3-phenylpropoxy)-3-trifluoromethylphenyl]vinyl}-2-oxazoline (Compound 192-1)

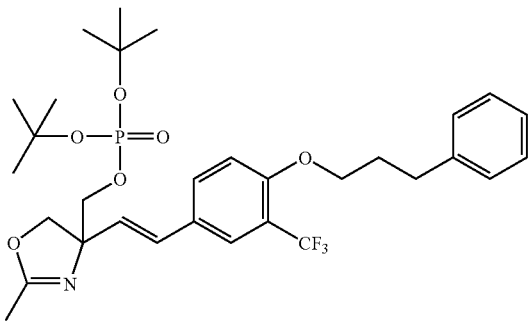

To a solution of compound 100-2 (300 mg) in N,N-dimethylformamide (10 ml) were added N,N-diisopropylethylamine (0.374 ml) and trimethyl orthoacetate (0.174 ml), and the mixture was stirred at 120° C. for 2.5 hr. Water was added to the reaction mixture, and the mixture was extracted with ethyl acetate, washed with water and saturated brine, and dried over anhydrous magnesium sulfate. The solvent was evaporated under reduced pressure to give a brown oil (300 mg). To a solution of the brown oil (300 mg) in methylene chloride (5 ml) and acetonitrile (2 ml) were added 1H-tetrazole (97 mg) and di-t-butyl diethylphosphoramidite (0.413 ml), and the mixture was stirred at room temperature for 2 hr. The reaction solution was ice-cooled, t-butyl hydroperoxide-containing decane solution (5-6M, 0.414 ml) was added, and the mixture was stirred under ice-cooling for 10 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (400 mg) as a yellow oil.

$^1$H-NMR(CD$_3$OD) δ (ppm): 1.48(18H, s), 2.05(3H, s), 2.05-2.12(2H, m), 2.82(2H, t, J=7.5 Hz), 3.94-4.06(4H, m), 4.23(1H, d, J=8.9 Hz), 4.50(1H, d, J=8.9 Hz), 6.31(1H, d, J=16.2 Hz), 6.42(1H, d, J=16.2 Hz), 7.06(1H, d, J=8.6 Hz), 7.15-7.20(3H, m), 7.23-7.27(2H, m), 7.60(1H, d, J=8.6 Hz), 7.65(1H, brs).

(192-2) Synthesis of (E)-2-amino-4-[4-(3-phenylpropoxy)-3-trifluoromethylphenyl]-2-(phosphoryloxymethyl)-3-butenol (Compound 192-2)

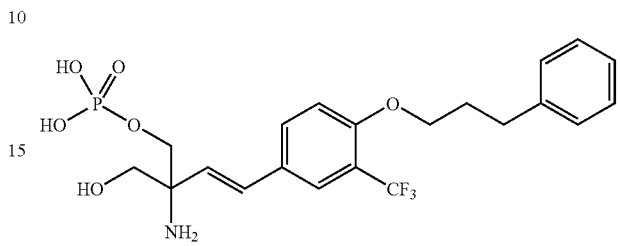

Compound 192-1 (400 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (230 mg) as a pale-brown solid.

MS(ESI)m/z: 476[M+H]
$^1$H-NMR(CD$_3$OD) δ (ppm): 2.04-2.12(2H, m), 2.82(2H, t, J=7.5 Hz), 3.76(1H, d, J=11.7 Hz), 3.84(1H, d, J=11.7 Hz), 4.00-4.07(3H, m), 4.10-4.14(1H, m), 6.23(1H, d, J=16.7 Hz), 6.76(1H, d, J=16.7 Hz), 7.08(1H, d, J=8.7 Hz), 7.13-7.20(3H, m), 7.23-7.27(2H, m), 7.65(1H, dd, J=8.7, 1.5 Hz), 7.69(1H, brs).

Example 193

(E)-2-amino-4-{4-[3-(2-fluorophenyl)propoxy]-3-trifluoromethylphenyl}-2-(phosphoryloxymethyl)-3-butenol (193-1) Synthesis of (E)-4-di(t-butyl)phosphoryloxymethyl-4-(2-{4-[3-(2-fluorophenyl)propoxy]-3-trifluoromethylphenyl}vinyl)-2-methyl-2-oxazoline (Compound 193-1)

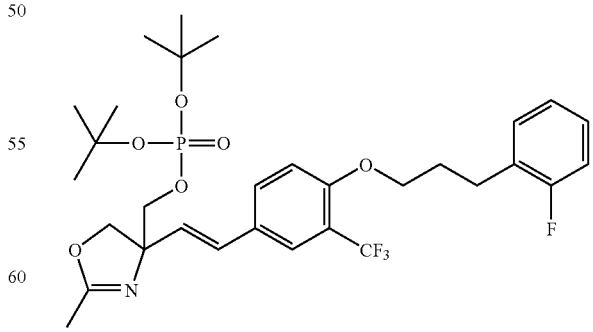

To a solution of compound 101-2 (290 mg) in N,N-dimethylformamide (10 ml) were added N,N-diisopropylethylamine (0.347 ml) and trimethyl orthoacetate (0.162 ml), and the mixture was stirred at 120° C. for 1.5 hr. Water was added to the reaction mixture, and the mixture was extracted with ethyl acetate, washed with water and saturated brine, and dried over anhydrous magnesium sulfate. The solvent was evaporated under reduced pressure to give a brown oil (300 mg). To a solution of the brown oil (300 mg) in methylene chloride (5 ml) and acetonitrile (2 ml) were added 1H-tetrazole (90 mg) and di-t-butyl diethylphosphoramidite (0.383 ml), and the mixture was stirred at room temperature for 2 hr. The reaction solution was ice-cooled, t-butyl hydroperoxide-containing decane solution (5-6M, 0.384 ml) was added, and the mixture was stirred under ice-cooling for 10 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:4—ethyl acetate alone) to give the object product (370 mg) as a yellow oil.

$^1$H-NMR(CD$_3$OD) δ (ppm): 1.49(18H, s), 2.05(3H, s), 2.05-2.11(2H, m), 2.87(2H, t, J=7.5 Hz), 3.94-4.09(4H, m), 4.23(1H, J=8.8 Hz), 4.50(1H, d, J=8.8 Hz), 6.32(1H, d, J=16.2 Hz), 6.64(1H, d, J=16.2 Hz), 7.00-7.10(3H, m), 7.17-7.23(2H, m), 7.61(1H, d, J=8.7 Hz), 7.65(1H, brs).

(193-2) Synthesis of (E)-2-amino-4-{4-[3-(2-fluorophenyl)propoxy]-3-trifluoromethylphenyl}-2-(phosphoryloxymethyl)-3-butenol (Compound 193-2)

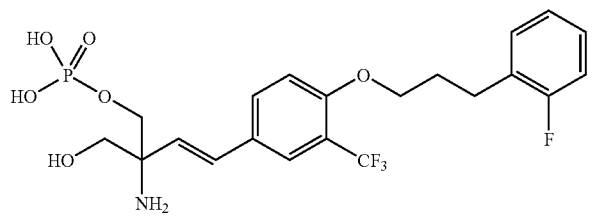

Compound 193-1 (370 mg) was dissolved in ethanol (6 ml), concentrated hydrochloric acid (1.2 ml) was added, and the mixture was stirred at 50° C. for 3.5 hr. The solvent was concentrated under reduced pressure, and methanol (5 ml), diethyl ether (5 ml) and propylene oxide (5 ml) were added to the residue. The precipitated powder was collected by filtration, and washed with methanol, ethyl acetate and diethyl ether to give the object product (150 mg) as a pale-brown solid.

MS(ESI)m/z: 494[M+H]

$^1$H-NMR(CD$_3$OD) δ (ppm): 2.04-2.12(2H, m), 2.87(2H, t, J=7.5 Hz), 3.76(1H, d, J=11.7 Hz), 3.84(1H, d, J=11.7 Hz), 4.00-4.16(4H, m). 6.23(1H, d, J=16.6 Hz), 6.76(1H, d, J=16.6 Hz), 7.00-7.12(3H, m), 7.17-7.23(2H, m), 7.66(1H, d, J=8.6 Hz), 7.69(1H, brs).

Example 194 phosphoric acid mono(2-amino-2-methyl-4-{4-[3-(3-methylphenyl)propoxy]-3-trifluoromethylphenyl}butyl)ester (194-1) Synthesis of (1-di(t-butyl)phosphoryloxymethyl-1-methyl-3-{4-[3-(3-methylphenyl)propoxy]-3-trifluoromethylphenyl}propyl)carbamic acid t-butyl ester (Compound 194-1)

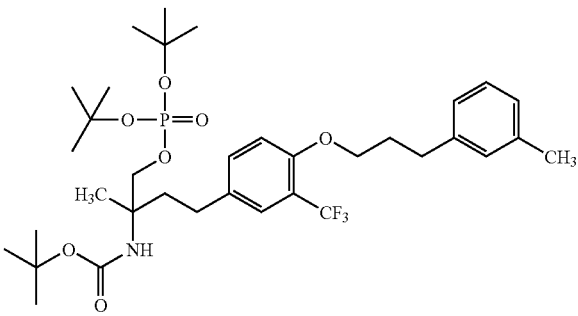

To a solution of compound 104-2 (300 mg) in methanol (10 ml) were added triethylamine (0.291 ml) and di-t-butyl-dicarbonate (301 mg) was added, and the mixture was stirred at room temperature for 22 hr. Furthermore, to the reaction mixture was added di-t-butyl-dicarbonate (100 mg), and the mixture was stirred at room temperature for 4 hr. Water was added to the reaction mixture, and the mixture was extracted with ethyl acetate. The organic layer was washed with saturated brine and dried over anhydrous magnesium sulfate. The solvent was evaporated under reduced pressure. To a solution of the obtained residue in methylene chloride (5 ml) and acetonitrile (2 ml) were added 1H-tetrazole (97 mg) and di-t-butyl diethylphosphoramidite (0.413 ml), and the mixture was stirred at room temperature for 2 hr. The reaction solution was ice-cooled, t-butyl hydroperoxide-containing decane solution (5-6M, 0.414 ml) was added, and the mixture was stirred at room temperature for 15 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:1-1:2) to give the object product (460 mg) as a colorless oil.

$^1$H-NMR(CD$_3$OD) δ (ppm): 1.36(3H, s), 1.45(9H, s), 1.49 (18H, s), 1.70-1.78(1H, m), 2.00-2.16(3H, m), 2.28(3H, s), 2.58-2.66(2H, m), 2.77(2H, t, J=7.5 Hz), 3.95-3.99(1H, m), 4.00(2H, t, J=5.9 Hz), 4.09-4.12(1H, m), 6.95-7.00(4H, m), 7.12(1H, t, J=7.5 Hz), 7.36(1H, dd, J=8.5, 1.8 Hz), 7.41(1H, d, J=1.8 Hz).

(194-2) Synthesis of phosphoric acid mono(2-amino-2-methyl-4-{4-[3-(3-methylphenyl)propoxy]-3-trifluoromethylphenyl)butyl)ester (Compound 194-2)

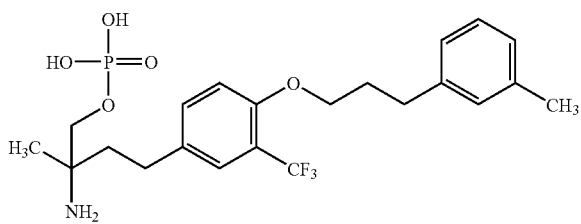

Compound 194-1 (460 mg) was dissolved in methylene chloride (6 ml), hydrogen chloride containing dioxane (4 mol/l, 3 ml) was added, and the mixture was stirred at room temperature for 3 hr. The solvent was concentrated under reduced pressure, and methanol (3 ml), diethyl ether (3 ml) and propylene oxide (7 ml) were added to the residue. The precipitated powder was collected by filtration, and washed with isopropyl alcohol to give the object product (210 mg) as a white solid.

MS(ESI)m/z: 476[M+H]

$^1$H-NMR(CD$_3$OD) δ (ppm): 1.38(3H, s), 1.82-1.90(1H, m), 1.96-2.09(3H, m), 2.28(3H, s), 2.60-2.69(2H, m), 2.77 (2H, t, J=7.6 Hz), 3.85(1H, dd, J=5.3, 11.5 Hz), 3.94(1H, dd, J=5.8, 11.5 Hz), 4.01(2H, t, J=5.8 Hz), 6.95-6.98(2H, m), 7.00-7.04(2H, m), 7.12(1H, t, J=7.5 Hz), 7.22(1H, dd, J=8.5, 1.8 Hz), 7.41(1H, d, J=1.8 Hz).

Example 195 phosphoric acid mono(2-amino-2-ethyl-4-{4-[3-(3-methylphenyl)propoxy]-3-trifluoromethylphenyl}butyl)ester (195-1) Synthesis of (1-di(t-butyl)phosphoryloxymethyl-1-ethyl-3-{4-[3-(3-methylphenyl)propoxy]-3-trifluoromethylphenyl}propyl)carbamic acid t-butyl ester (Compound 195-1)

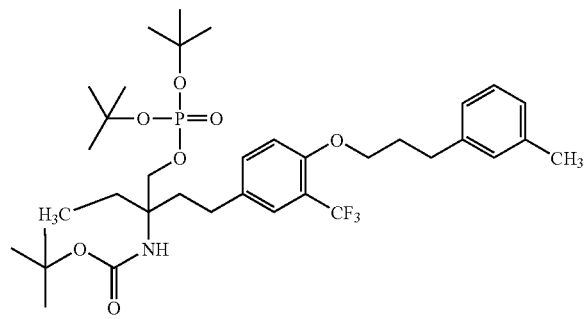

To a solution of compound 105-2 (310 mg) in methanol (10 ml) were added triethylamine (0.294 ml) and di-t-butyl-dicarbonate (306 mg) was added, and the mixture was stirred at room temperature for 23 hr. Furthermore, to the reaction mixture was added di-t-butyl-dicarbonate (200 mg), and the mixture was stirred at room temperature for 4 hr. Water was added to the reaction mixture, and the mixture was extracted with ethyl acetate. The organic layer was washed with saturated brine and dried over anhydrous magnesium sulfate. The solvent was evaporated under reduced pressure. To a solution of the obtained residue in methylene chloride (5 ml) and acetonitrile (2 ml) were added 1H-tetrazole (98 mg) and di-t-butyl diethylphosphoramidite (0.419 ml), and the mixture was stirred at room temperature for 1.5 hr. The reaction solution was ice-cooled, t-butyl hydroperoxide-containing decane solution (5-6M, 0.420 ml) was added, and the mixture was stirred at room temperature for 15 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography (hexane:ethyl acetate=1:1-1:2) to give the object product (520 mg) as a colorless oil.

$^1$H-NMR(CD$_3$OD) δ (ppm): 0.91(3H, t, J=7.4 Hz), 1.45 (9H, s), 1.50(18H, s), 1.65-1.90(3H, m), 1.91-2.15(3H, m), 2.27(3H, s), 2.57(2H, t, J=8.6 Hz), 2.77(2H, t, J=7.5 Hz), 4.00(2H, t, J=5.9 Hz), 4.05-4.10(2H, m), 6.95-7.00(4H, m), 7.12(1H, t, J=7.5 Hz), 7.35(1H, d, J=8.5 Hz), 7.40(1H, d, J=1.8 Hz).

(195-2) Synthesis of phosphoric acid mono(2-amino-2-ethyl-4-{4-[3-(3-methylphenyl)propoxy]-3-trifluoromethylphenyl}butyl)ester (Compound 195-2)

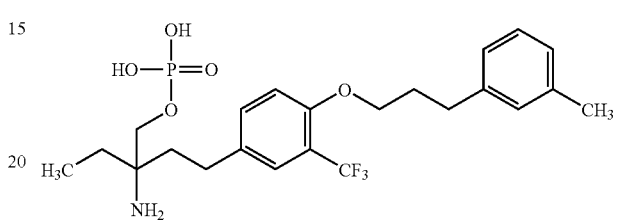

Compound 195-1 (520 mg) was dissolved in methylene chloride (6 ml), hydrogen chloride containing dioxane (4 mol/l, 3 ml) was added, and the mixture was stirred at room temperature for 2.5 hr. The solvent was concentrated under reduced pressure, and methanol (3 ml), diethyl ether (3 ml) and propylene oxide (7 ml) were added to the residue. The precipitated powder was collected by filtration, and washed with isopropyl alcohol to give the object product (80 mg) as a white solid.

MS(ESI)m/z: 490[M+H]

$^1$H-NMR(CD$_3$OD) δ (ppm): 1.03(3H, t, J=7.5 Hz), 1.70-2.01(4H, m), 2.07-2.19(2H, m), 2.56-2.75(2H, m), 2.77(2H, t, J=7.5 Hz), 3.89-3.97(2H, m), 4.01(2H, t, J=6.0 Hz), 6.95-6.98(2H, m), 7.00-7.03(2H, m), 7.12(1H, t, J=7.5 Hz), 7.42 (1H, dd, J=8.6, 1.8 Hz), 7.46(1H, brs).

Example 196

2-amino-4-[3-cyano-4-(4-phenylbutoxy)phenyl]-2-(phosphoryloxymethyl)butanol (196-1) Synthesis of {1-(dibenzyl)phosphoryloxymethyl-3-[3-cyano-4-(4-phenylbutoxy)phenyl]-1-(hydroxymethyl)propyl}carbamic acid t-butyl ester (Compound 196-1)

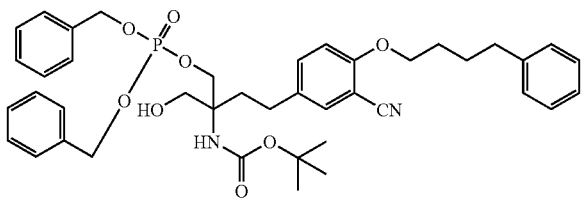

Compound 2-3 (103 mg) was dissolved in ethanol (2 ml), p-toluenesulfonic acid monohydrate (35.0 mg) was added, and the mixture was stirred at room temperature for 15 hr. Water was added to the reaction mixture, and the mixture was neutralized with saturated aqueous sodium hydrogen carbonate, extracted with ethyl acetate, washed with saturated brine, and dried over anhydrous sodium sulfate. The solvent was evaporated, and the obtained residue was dissolved in a mixed solvent of methylene chloride (2 ml) and toluene (2 ml). Perfluorohexane (2 ml), silver oxide (94.0 mg) and pyrophosphoric acid tetrabenzyl ester (218 mg) were added, and the mixture was stirred at room temperature for stirred. Five minutes later, tetra-n-hexylammonium iodide (195 mg) was added, and the mixture was further stirred at 19 hr. Insoluble material was filtered off, and the solvent was evaporated. The residue was purified by silica gel chromatography and HPLC to give the object product (84.0 mg) as a colorless oil.

$^1$H-NMR(CDCl$_3$) δ (ppm): 1.43(9H, s), 1.84-1.86(4H, m), 1.92-2.06(2H, m), 2.39-2.53(2H, m), 2.70(2H, t, J=6.8 Hz), 3.47-3.58(2H, m), 3.97-4.09(4H, m), 4.79(1H, s), 5.00-5.06 (4H, m), 6.80(1H, d, J=8.4 Hz), 7.17-7.21(4H, m), 7.25-7.28 (3H, m), 7.30-7.31(10H, m).

(196-2) Synthesis of 2-amino-4-[3-cyano-4-(4-phenylbutoxy)phenyl]-2-(phosphoryloxymethyl)butanol (Compound 196-2)

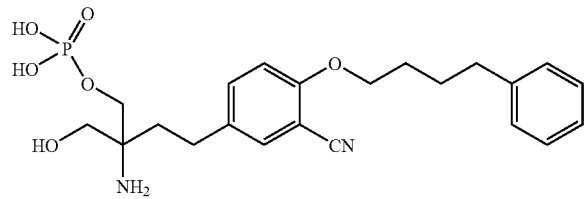

Compound 196-1 (83.0 mg) was dissolved in acetonitrile (2 ml), sodium iodide (85.0 mg) and chlorotrimethylsilane (62.0 mg) were added, and the mixture was stirred at room temperature for 3 hr. Water and ethyl acetate were added, and the mixture was ultrasonicated. The resulting solid was collected by filtration. The solid was washed with water and ethyl acetate, and further with methanol to give the object product (29.0 mg) as a white powder.

MS(ESI)m/z: 449[M+H]

$^1$H-NMR(CD$_3$OD) δ (ppm): 1.46-1.50(2H, m), 1.82-1.85 (6H, m), 2.63-2.65(2H, m), 3.67-3.71(2H, m), 3.96-3.98(2H, m), 4.10-4.12(2H, m), 7.05-7.09(1H, m), 7.14-7.15(1H, m), 7.19-7.26(4H, m), 7.45-7.50(2H, m).

Example 197

(E)-2-amino-2-(2-{4-[3-(3-bromophenyl)propoxy]-3-trifluoromethylphenyl}vinyl)propane-1,3-diol hydrochloride (197-1) Synthesis of (E)-[5-(2-{4-[3-(3-bromophenyl)propoxy]-3-trifluoromethylphenyl}vinyl)-2,2-dimethyl-1,3-dioxan-5-yl]carbamic acid t-butyl ester (Compound 197-1)

Compound 93-8 (205 mg) was dissolved in N,N-dimethylformamide (5 ml), potassium carbonate (207 mg), compound 40-3 (165 mg) was added, and the mixture was stirred at 70° C. for 1.5 hr. Water was added to the reaction mixture, and the mixture was extracted with ethyl acetate, washed with water and saturated brine, and dried over anhydrous magnesium sulfate. The solvent was evaporated under reduced pressure. The obtained residue was purified by silica gel chromatography to give the object product (290 mg) as a colorless oil.

$^1$H-NMR(CDCl$_3$) δ (ppm): 1.45(9H, s), 1.47(3H, s), 1.49 (3H, s), 2.07-2.14(2H, m), 2.81(2H, t, J=7.6 Hz), 3.90(2H, d, J=11.4 Hz), 3.96-4.02(4H, m), 5.22(1H, brs), 6.12(1H, d, J=16.4 Hz), 6.49(1H, d, J=16.4 Hz), 6.87(1H, d, J=8.6 Hz), 7.10-7.16(2H, m), 7.31-7.36(2H, m), 7.44(1H, dd, J=8.6, 1.8 Hz), 7.57(1H, brd, J=1.6 Hz).

(197-2) Synthesis of (E)-2-amino-2-(2-{4-[3-(3-bromophenyl)propoxy]-3-trifluoromethylphenyl}vinyl) propane-1,3-diol hydrochloride (Compound 197-2)

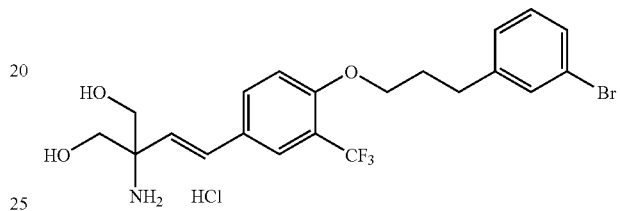

Compound 197-1 (290 mg) was dissolved in ethanol (15 ml), concentrated hydrochloric acid (1.5 ml) was added, and the mixture was stirred at 80° C. for 1 hr. The reaction mixture was concentrated, and the residue was washed with diethyl ether to give the object product (200 mg) as a white powder.

MS(ESI)m/z: 459

$^1$H-NMR(DMSO-d$_6$) δ (ppm): 2.00-2.08(2H, m), 2.75(2H, t, J=7.5 Hz), 3.58-3.66(4H, m), 4.09(2H, t, J=6.0 Hz), 5.44(2H, t, J=5.2 Hz), 6.24(1H, d, J=16.6 Hz), 6.69(1H, d, J=16.6 Hz), 7.19-7.28(2H, m), 7.38-7.42(3H, m), 7.62-7.66(2H, m), 7.98(3H, brs).

Example 198

(E)-2-amino-2-(2-{4-[3-(4-bromophenyl)propoxy]-3-trifluoromethylphenyl}vinyl)propane-1,3-diol hydrochloride (198-1) Synthesis of (E)-[5-(2-{4-[3-(4-bromophenyl)propoxy]-3-trifluoromethylphenyl}vinyl)-2,2-dimethyl-1,3-dioxan-5-yl]carbamic acid t-butyl ester (Compound 198-1)

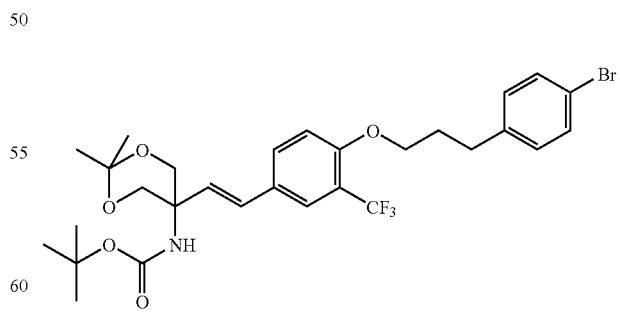

Compound 93-8 (400 mg) was dissolved in N,N-dimethylformamide (10 ml), potassium carbonate (397 mg) and compound 41-3 (359 mg) were added, and the mixture was stirred at 70° C. for 1 hr. Water was added to the reaction mixture, and the mixture was extracted with ethyl acetate, washed with water and saturated brine, and dried over anhydrous magnesium sulfate. The solvent was evaporated under reduced pressure to give the object product (700 mg) as a colorless oil.

$^1$H-NMR(CDCl$_3$) δ (ppm): 1.45(9H, s), 1.47(3H, s), 1.49 (3H, s), 2.07-2.15(2H, m), 2.77-2.81(2H, m), 3.90(2H, d, J=11.4 Hz), 3.96-4.00(4H, m), 5.21(1H, brs), 6.12(1H, d, J=16.4 Hz), 6.49(1H, d, J=16.4 Hz), 6.85(1H, d, J=8.6 Hz), 7.05-7.09(2H, m), 7.38-7.45(3H, m), 7.57(1H, brd, J=1.6 Hz).

(198-2) Synthesis of (E)-2-amino-2-(2-{4-(3-(4-bromophenyl)propoxy]-3-trifluoromethylphenyl}vinyl) propane-1,3-diol hydrochloride (Compound 198-2)

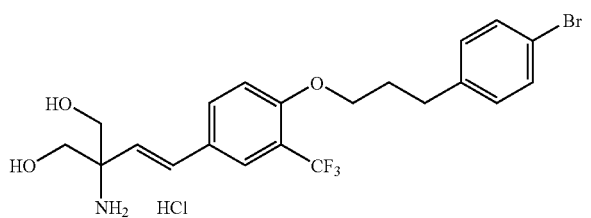

Compound 198-1 (700 mg) was dissolved in ethanol (15 ml), concentrated hydrochloric acid (1.5 ml) was added, and the mixture was stirred at 80° C. for 1 hr. The reaction mixture was concentrated, and the residue was washed with diethyl ether to give the object product (470 mg) as a pale-yellow powder.

MS(ESI)m/z: 459

$^1$H-NMR(DMSO-d$_6$) δ (ppm): 1.98-2.05(2H, m), 2.72(2H, t, J=7.5 Hz), 3.58-3.67(4H, m), 4.08(2H, t, J=6.1 Hz), 5.46(2H, t, J=5.3 Hz), 6.24(1H, d, J=16.8 Hz), 6.70(1H, d, J=16.8 Hz), 7.17(2H,d, J=8.4 Hz), 7.26(1H,d, J=8.6 Hz), 7.45-7.48(2H, m), 7.61-7.65(2H, m), 8.07(3H, brs).

Example 199 phosphoric acid mono(2-amino-2-(2-fluoroethyl)-4-{4-[3-(3-methylphenyl)propoxy]-3-trifluoromethylphenyl}butyl)ester (199-1) Synthesis of (1-di(t-butyl)phosphoryloxymethyl-1-(2-fluoroethyl)-3-{4-[3-(3-methylphenyl) propoxy]-3-trifluoromethylphenyl}propyl)carbamic acid t-butyl ester (Compound 199-1)

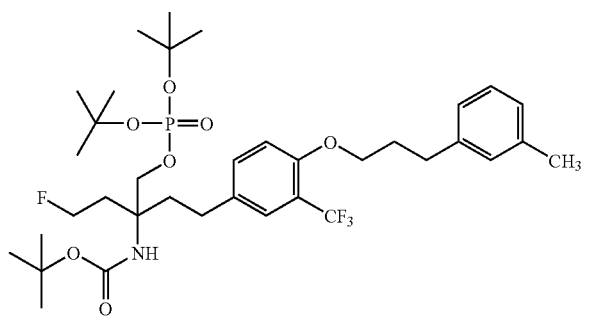

To a solution of compound 107-2 (170 mg) in methanol (10 ml) were added triethylamine (0.154 ml) and di-t-butyl-dicarbonate (161 mg), and the mixture was stirred at room temperature for 23 hr. Furthermore, to the reaction mixture was added di-t-butyl-dicarbonate (240 mg), and the mixture was stirred at room temperature for 3 hr. Water was added to the reaction mixture, and the mixture was extracted with ethyl acetate. The organic layer was washed with saturated brine and dried over anhydrous magnesium sulfate. The solvent was lo evaporated under reduced pressure. The obtained residue was dissolved in a mixed solvent of methylene chloride (5 ml) and acetonitrile (2 ml). To this solution were added 1H-tetrazole (40 mg) and di-t-butyl diethylphosphoramidite (0.171 ml), and the mixture was stirred at room temperature for 2 hr. The reaction solution was ice-cooled, t-butyl hydroperoxide-containing decane solution (5-6M, 0.168 ml) was added, and the mixture was stirred at room temperature for 15 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography to give the object product (230 mg) as a colorless oil.

$^1$H-NMR(CD$_3$OD) δ (ppm): 1.45(9H, s), 1.50(18H, s), 1.90-2.10(4H, m), 2.11-2.22(2H, m), 2.28(3H, s), 2.58-2.64 (2H, m), 2.72-2.78(2H, m), 4.00(2H, t, J=5.9 Hz), 4.10-4.28 (2H, m), 4.55(1H, dt, J=47.5, 5.6 Hz), 4.67(1H, dt, J=47.5, 5.6 Hz), 6.95-7.00(4H, m), 7.09-7.14(1H, m), 7.35(1H, d, J=8.6 Hz), 7.40(1H, brs).

(199-2) Synthesis of phosphoric acid mono(2-amino-2-(2-fluoroethyl)-4-{4-[3-(3-methylphenyl)propoxy]-3-trifluoromethylphenyl}butyl)ester (Compound 199-2)

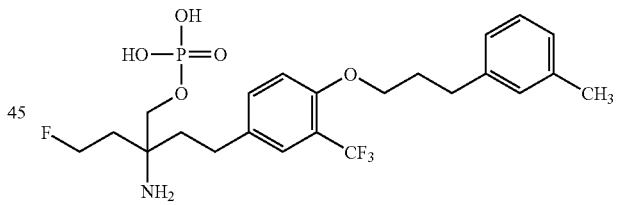

Compound 199-1 (230 mg) was dissolved in methylene chloride (4 ml), hydrogen chloride containing dioxane (4 mol/l, 2 ml) was added, and the mixture was stirred at room temperature for 3 hr. The solvent was concentrated under reduced pressure, and methanol (2 ml), diethyl ether (3 ml) and propylene oxide (3 ml) were added to the residue. The precipitated powder was collected by filtration, and washed with methanol to give the object product (50 mg) as a white solid.

MS(ESI)m/z: 507

$^1$H-NMR(DMSO-d$_6$) δ (ppm): 1.95-2.09(4H, m), 2.15-2.19(1H, m), 2.21-2.26(1H, m), 2.78(3H, s), 2.63-2.78(2H, m), 2.76(2H, t, J=7.5 Hz), 3.09-4.02(4H, m), 4.68(1H, dt, J=47.1, 5.4 Hz), 4.80(1H, dt, J=47.1, 5.4 Hz), 6.95-7.03(4H, m), 7.12(1H, t, J=7.5 Hz), 7.42(1H, d, J=8.3 Hz), 7.47(1H, brs).

Example 200

(E)-2-amino-4-{4-[3-(3-bromophenyl)propoxy]-3-trifluoromethylphenyl}-2-(phosphoryloxymethyl)-3-butenol (200-1) Synthesis of (E)-4-(2-(4-[3-(3-bromophenyl)propoxy]-3-trifluoromethylphenyl}vinyl)-4-di(t-butyl)phosphoryloxymethyl-2-methyl-2-oxazoline (Compound 200-1)

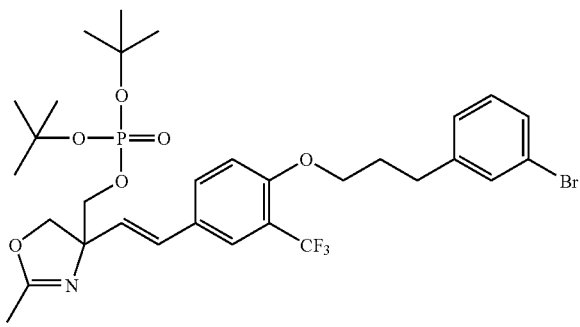

To a solution of compound 197-2 (150 mg) in N,N-dimethylformamide (10 ml) were added N,N-diisopropylethylamine (0.147 ml) and trimethyl orthoacetate (0.073 ml), and the mixture was stirred at 120° C. for 3 hr. Water was added to the reaction mixture, and the mixture was extracted with ethyl acetate, washed with water and saturated brine, and dried over anhydrous magnesium sulfate. The solvent was evaporated under reduced pressure to give a brown oil (145 mg). The brown oil (145 mg) was dissolved in a mixed solvent of methylene chloride (3 ml) and acetonitrile (1 ml). To this solution were added 1H-tetrazole (41 mg) and di-t-butyl diethylphosphoramidite (0.174 ml), and the mixture was stirred at room temperature for 2 hr. The reaction solution was ice-cooled, t-butyl hydroperoxide-containing decane solution (5-6M, 0.174 ml) was added, and the mixture was stirred under ice-cooling for 15 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography to give the object product (150 mg) as a yellow oil.

$^1$H-NMR(CD$_3$OD) δ (ppm): 1.48(9H, s), 1.49(9H, s), 2.05 (3H, s), 2.05-2.11(2H, m), 2.82(2H, t, J=7.5 Hz), 3.94-4.06 (2H, m), 25 4.05(2H, t, J=5.9 Hz), 4.24(1H, d, J=8.7 Hz), 4.50(1H, d, J=8.7 Hz), 6.32(1H, d, J=16.2 Hz), 6.65(1H, d, J=16.2 Hz), 7.08(1H, d, J=8.6 Hz), 7.17-7.21(2H, m), 7.31-7.34(1H, m), 7.37(1H, brs), 7.61(1H, d, J=8.7 Hz), 7.65(1H, brs).

(200-2) Synthesis of (E)-2-amino-4-{4-[3-(3-bromophenyl)propoxy]-3-trifluoromethylphenyl}-2-(phosphoryloxymethyl)-3-butenol (Compound 200-2)

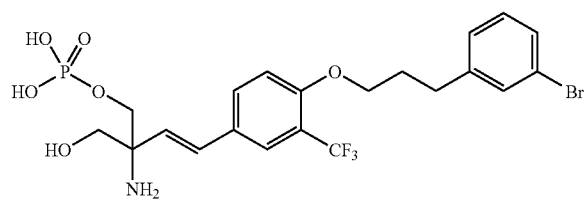

Compound 200-1 (150 mg) was dissolved in ethanol (5 ml), concentrated hydrochloric acid (1 ml) was added, and the mixture was stirred at 50° C. for 3.5 hr. The solvent was concentrated under reduced pressure, and methanol (3 ml), diethyl ether (3 ml) and propylene oxide (3 ml) were added to the residue. The precipitated powder was collected by filtration, and washed with methanol, ethyl acetate and diethyl ether to give the object product (50 mg) as a white solid.

MS(ESI)m/z: 554, 556[M+H]

$^1$H-NMR(CD$_3$OD) δ (ppm): 2.05-2.13(2H, m), 2.82(2H, t, J=7.5 Hz), 3.75(1H, d, J=11.7 Hz), 3.84(1H, d, J=11.7 Hz), 4.00-4.14(4H, m), 6.23(1H, d, J=16.5 Hz), 6.76(1H, d, J=16.5 Hz), 7.11(1H, d, J=8.7 Hz), 7.17-7.20(2H, m), 7.31-7.34(1H, m), 7.37(1H, brs), 7.66(1H, dd, J=8.6, 1.6 Hz), 7.70(1H, d, J=1.6 Hz).

Example 201

(E)-2-amino-4-{4-[3-(4-bromophenyl)propoxy]-3-trifluoromethylphenyl}-2-(phosphoryloxymethyl)-3-butenol (201-1) Synthesis of (E)-4-(2-{4-[3-(4-bromophenyl)propoxy]-3-trifluoromethylphenyl)vinyl)-4-di(t-butyl)phosphoryloxymethyl-2-methyl-2-oxazoline (Compound 201-1)

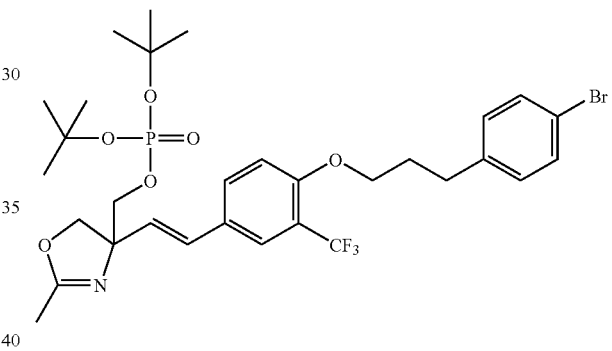

To a solution of compound 198-2 (330 mg) in N,N-dimethylformamide (10 ml) were added N,N-diisopropylethylamine (0.348 ml) and trimethyl orthoacetate (0.164 ml), and the mixture was stirred at 120° C. for 2 hr. Water was added to the reaction mixture, and the mixture was extracted with ethyl acetate, washed with water and saturated brine, and dried over anhydrous magnesium sulfate. The solvent was evaporated under reduced pressure to give a brown oil (340 mg). The brown oil (340 mg) was dissolved in a mixed solvent of methylene chloride (5 ml) and acetonitrile (2 ml). To this solution were added 1H-tetrazole (91 mg) and di-t-butyl diethylphosphoramidite (0.389 ml), and the mixture was stirred at room temperature for 2 hr. The reaction solution was ice-cooled, t-butyl hydroperoxide-containing decane solution (5-6M, 0.390 ml) was added, and the mixture was stirred under ice-cooling for 10 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography to give the object product (350 mg) as a yellow oil.

$^1$H-NMR(CD$_3$OD) δ (ppm): 1.48(9H, s), 1.49(9H, s), 2.05 (3H, s), 2.05-2.10(2H, m), 2.80(2H, t, J=7.5 Hz), 3.94-4.06 (2H, m), 4.05(2H, t, J=6.0 Hz), 4.23(1H, d, J=8.8 Hz), 4.50 (1H, d, J=8.8 Hz), 6.31(1H, d, J=16.1 Hz), 6.43(1H, d, J=16.1

Hz), 7.08(1H, d, J=8.7 Hz), 7.13(2H, d, J=8.3 Hz), 7.40(2H, d, J=8.3 Hz), 7.61(1H, d, J=8.7 Hz), 7.65(1H, brs).

(201-2) Synthesis of (E)-2-amino-4-{4-[3-(4-bromophenyl)propoxy]-3-trifluoromethylphenyl}-2-(phosphoryloxymethyl)-3-butenol (Compound 201-2)

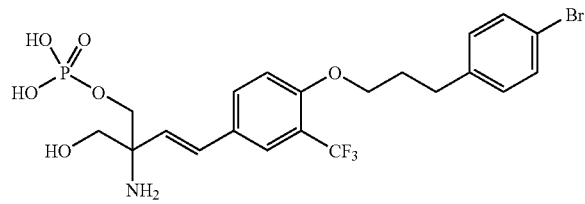

Compound 201-1 (350 mg) was dissolved in ethanol (6 ml), concentrated hydrochloric acid (1.2 ml) was added, and the mixture was stirred at 50° C. for 3.5 hr. The solvent was concentrated under reduced pressure, and methanol (3 ml), diethyl ether (5 ml) and propylene oxide (5 ml) were added to the residue. The precipitated powder was collected by filtration, and washed with methanol, ethyl acetate and diethyl ether to give the object product (65 mg) as a white solid.

MS(ESI)m/z: 554, 556[M+H]

$^1$H-NMR(CD$_3$OD) δ (ppm): 2.06-2.12(2H, m), 2.80(2H, t, J=7.5 Hz), 3.76(1H, d, J=11.7 Hz), 3.84(1H, d, J=11.7 Hz), 4.00-4.14(4H, m), 6.23(1H, d, J=16.8 Hz), 6.76(1H, d, J=16.8 Hz), 7.09-7.14(3H, m), 7.39-7.41(2H, m), 7.66(1H, dd, J=8.6, 1.7 Hz), 7.69(1H, brs).

Example 202

2-amino-4-{4-[3-(3,4-dichlorophenyl)propoxy]-3-trifluoromethylphenyl}-2-methylbutanol hydrochloride (202-1) Synthesis of (3-{4-[3-(3,4-dichlorophenyl)propoxy]-3-trifluoromethylphenyl}-1-(methoxymethoxy)methyl-1-methyl)propylcarbamic acid t-butyl ester (Compound 202-1)

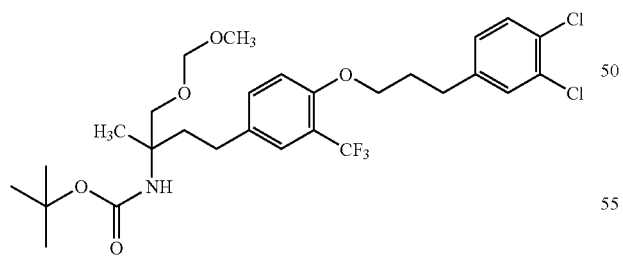

To a solution of compound 27-4 (460 mg) in N,N-dimethylformamide (10 ml) were added potassium carbonate (352 mg) and compound 38-3 (273 mg), and the mixture was stirred at 70° C. for 2 hr. The reaction mixture was added to water, and the mixture was extracted with ethyl acetate. The organic layer was washed with saturated brine and dried over anhydrous magnesium sulfate. The solvent was evaporated under reduced pressure to give the object product (650 mg) as a pale-yellow oil.

$^1$H-NMR(CDCl$_3$) δ (ppm): 1.34(3H, s), 1.45(9H, s), 1.88-1.96(1H, m), 2.01-2.16(3H, m), 2.58(2H, t, J=8.5 Hz), 2.75-2.82(2H, m), 3.38(3H, s), 3.48(1H, d, J=9.5 Hz), 3.65(1H, d, J=9.5 Hz), 3.97(2H, t, J=5.8 Hz), 4.65(2H, s), 4.72(1H, brs), 6.83(1H, d, J=8.5 Hz), 7.03(1H, dd, J=8.4, 2.0 Hz), 7.27-7.34 (3H, m), 7.38(1H, d, J=1.6 Hz).

(202-2) Synthesis of 2-amino-4-{4-[3-(3,4-dichlorophenyl)propoxy]-3-trifluoromethylphenyl}-2-methylbutanol hydrochloride (Compound 202-2)

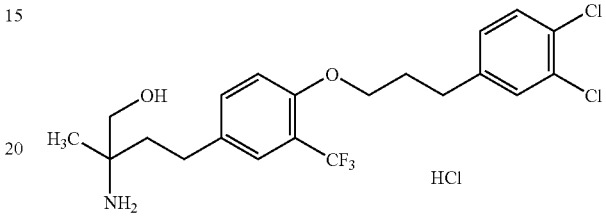

To a solution of compound 202-1 (650 mg) in ethanol (15 ml) was added concentrated hydrochloric acid (1.5 ml), and the mixture was stirred at 80° C. for 1.5 hr. The reaction mixture was concentrated, and the residue was washed with diisopropyl ether to give the object product (470 mg) as a white powder.

MS(ESI)m/z: 450[M+H]

$^1$H-NMR(DMSO-d$_6$) δ (ppm): 1.21(3H, s), 1.70-1.82(2H, m), 1.99-2.07(2H, m), 2.62(2H, t, J=8.7 Hz), 2.75(2H, t, J=7.5 Hz), 3.38-3.42(1H, m), 3.45-3.49(1H, m), 4.04(2H, t, J=6.1 Hz), 5.52(1H, t, J=4.8 Hz), 7.15-7.21(2H, m), 7.45(1H, d, J=8.5 Hz), 7.47-7.49(2H, m), 7.54(1H, d, J=8.5 Hz), 7.86 (3H, brs).

Example 203

(S)-2-amino-4-{4-[3-(3,4-dichlorophenyl)propoxy]-3-trifluoromethylphenyl}-2-methylbutanol hydrochloride (203-1) Synthesis of (S)-2-amino-4-{4-[3-(3,4-dichlorophenyl)propoxy]-3-trifluoromethylphenyl}-2-methylbutanol (Compound 203-1-1) and (R)-2-amino-4-{4-[3-(3,4-dichlorophenyl)propoxy]-3-trifluoromethylphenyl}-2-methylbutanol (Compound 203-1-2)

compound 203-1-1

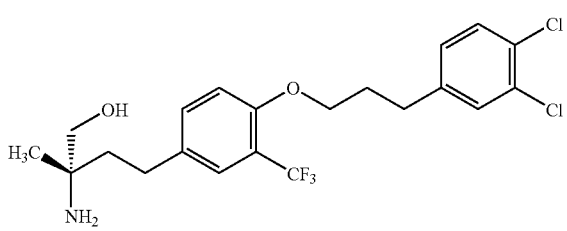

-continued compound 203-1-2

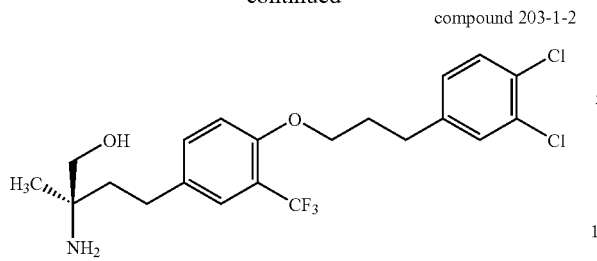

To a solution of compound 202-1 (1.97 g) in ethanol (30 ml) was added concentrated hydrochloric acid (3 ml) and the mixture was stirred at 80° C. for 1 hr. The reaction mixture was concentrated, ethyl acetate (70 ml) and 1M aqueous sodium hydroxide solution (70 ml) were added, and the mixture was stirred at room temperature for 30 min. The mixture was extracted with ethyl acetate. The organic layer was washed with saturated brine and dried over anhydrous sodium sulfate, and the solvent was evaporated under reduced pressure to give a mixture of (1.50 g) of compound 203-1-1 and compound 203-1-2. The mixture (1.50 g) was separated by supercritical fluid chromatography (SFC) using CHIRAL-PAK (registered trade mark) AD-H (carbon dioxide/ethanol/diethylamine) to give both enantiomers as colorless oil. The primary peak with a shorter retention time was S-configuration (0.63 g, compound 203-1-1), and the secondary peak with a longer retention time was R-configuration (0.65 g, compound 203-1-2).

(203-2) Synthesis of (S)-2-amino-4-{4-[3-(3,4-dichlorophenyl)propoxy]-3-trifluoromethylphenyl}-2-methylbutanol hydrochloride (Compound 203-2)

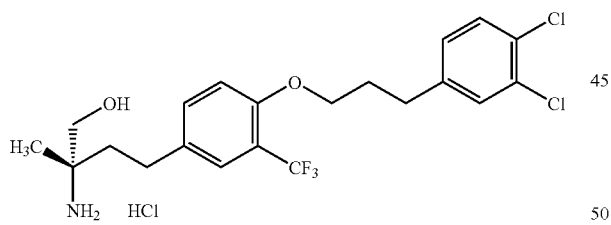

Compound 203-1-1 (0.63 g) was dissolved in methanol (5 ml) and methylene chloride (10 ml), hydrogen chloride containing ether (1 mol/l, 15 ml) was added and the mixture was stirred at room temperature for 15 min, and the precipitate was collected by filtration and dried to give the object product (665 mg) as a white powder.

MS(ESI)m/z: 450[M+H]

$^1$H-NMR(DMSO-$d_6$) δ (ppm): 1.21(3H, s), 1.73-1.83(2H, m), 1.99-2.06(2H, m), 2.62(2H, t, J=8.7 Hz), 2.75(2H, t, J=7.5 Hz), 3.39-3.43(1H, m), 3.45-3.50(1H, m), 4.04(2H, t, J=6.1 Hz), 5.53(1H, t, J=5.1 Hz), 7.16-7.21(2H, m), 7.45(1H, d, J=8.5 Hz), 7.47-7.49(2H, m), 7.54(1H, d, J=8.5 Hz), 7.95 (3H, brs).

Example 204

(R)-2-amino-4-{4-[3-(3,4-dichlorophenyl)propoxy]-3-trifluoromethylphenyl}-2-methylbutanol hydrochloride (204-1) Synthesis of (R)-2-amino-4-{4-[3-(3,4-dichlorophenyl)propoxy]-3-trifluoromethylphenyl}-2-methylbutanol hydrochloride (Compound 204-1)

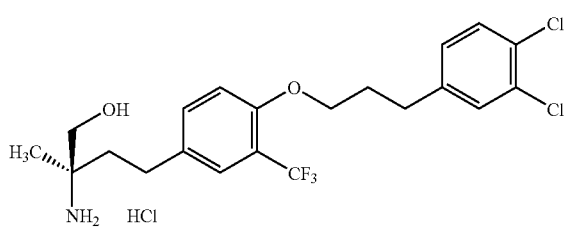

Compound 203-1-2 (0.65 g) was dissolved in methanol (5 ml) and methylene chloride (10 ml), hydrogen chloride containing ether (1 mol/l, 15 ml) was added and the mixture was stirred at room temperature 30 min was stirred. The precipitate was collected by filtration and dried to give the object product (695 mg) as a white powder.

MS(ESI)m/z: 450[M+H]

$^1$H-NMR(DMSO-$d_6$) δ (ppm): 1.21(3H, s), 1.70-1.84(2H, m), 1.99-2.06(2H, m), 2.62(2H, t, J=8.7 Hz), 2.75(2H, t, J=7.5 Hz), 3.38-3.43(1H, m), 3.45-3.50(1H, m), 4.04(2H, t, J=6.1 Hz), 5.52(1H, t, J=5.1 Hz), 7.15-7.21(2H, m), 7.45(1H, d, J=8.3 Hz), 7.48-7.49(2H, m), 7.54(1H, d, J=8.3 Hz), 7.92 (3H, brs).

Example 205

2-amino-4-{4-[3-(3,4-dichlorophenyl)propoxy]-3-trifluoromethylphenyl}-2-ethylbutanol hydrochloride (205-1) Synthesis of (3-{4-[3-(3,4-dichlorophenyl)propoxy]-3-trifluoromethylphenyl}-1-ethyl-1-(methoxymethoxy)methyl)propylcarbamic acid t-butyl ester (Compound 205-1)

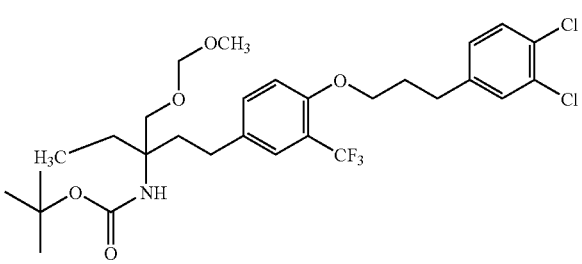

To a solution of compound 30-4 (400 mg) in N,N-dimethylformamide (10 ml) were added potassium carbonate (394 mg) and compound 38-3 (305 mg), and the mixture was stirred at 70° C. for 2 hr. The reaction mixture was added to water, and the mixture was extracted with ethyl acetate. The organic layer was washed with saturated brine and dried over anhydrous magnesium sulfate. The solvent was evaporated under reduced pressure to give the object product (660 mg) as a pale-yellow oil.

$^1$H-NMR(CDCl$_3$) δ (ppm): 0.89(3H, t, J=7.5 Hz), 1.45(9H, s), 1.69-1.75(1H, m), 1.76-1.83(1H, m), 1.93-1.98(2H, m), 2.04-2.12(2H, m), 2.53-2.58(2H, m), 2.80(2H, t, J=7.5 Hz), 3.38(3H, s), 3.57(1H, d, J=9.7 Hz), 3.63(1H, d, J=9.7 Hz), 3.97(2H, t, J=5.8 Hz), 4.61(1H, brs), 4.64(2H, s), 6.83(1H, d, J=8.5 Hz), 7.03(1H, dd, J=8.2, 1.9 Hz), 7.26-7.29(2H, m), 7.33(1H, J=8.0 Hz), 7.38(1H, d, J=1.9 Hz).

(205-2) Synthesis of 2-amino-4-{4-[3-(3,4-dichlorophenyl)propoxy]-3-trifluoromethylphenyl}-2-ethylbutanol hydrochloride (Compound 205-2)

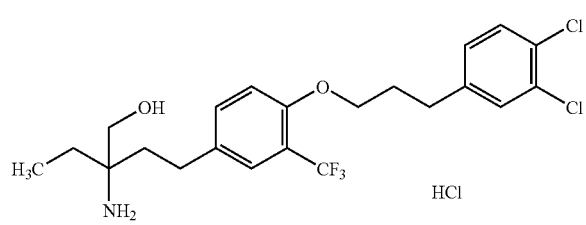

To a solution of compound 205-1 (660 mg) in ethanol (15 ml) was added concentrated hydrochloric acid (1.5 ml), and the mixture was stirred at 80° C. for 1 hr. The reaction mixture was concentrated, and the residue was washed with diethyl ether to give the object product (480 mg) as a white powder.

MS (ESI)m/z: 464 [M+H]

$^1$H-NMR(DMSO-d$_6$) δ (ppm): 0.90(3H, t, J=7.5 Hz), 1.58-1.68(2H, m), 1.72-1.78(2H, m), 1.99-2.06(2H, m), 2.56-2.62 (2H, m), 2.75(2H, t, J=7.5 Hz), 3.47(2H, brs), 4.04(2H, t, J=6.1 Hz), 5.48(1H, brs), 7.15-7.21(2H, m), 7.45-7.49(3H, m), 7.54(1H, d, J=8.3 Hz), 7.91(3H, brs).

Example 206

(R)-2-amino-4-{4-[3-(3,4-dichlorophenyl)propoxy]-3-trifluoromethylphenyl}-2-ethylbutanol hydrochloride (206-1) Synthesis of (R)-[1-ethyl-3-(4-hydroxy-3-trifluoromethylphenyl)-1-(methoxymethoxy)methyl]propylcarbamic acid t-butyl ester and (S)-[1-ethyl-3-(4-hydroxy-3-trifluoromethylphenyl)-1-(methoxymethoxy)methyl]propylcarbamic acid t-butyl ester compound 206-1-1

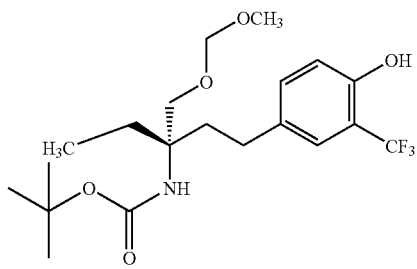

compound 206-1-2

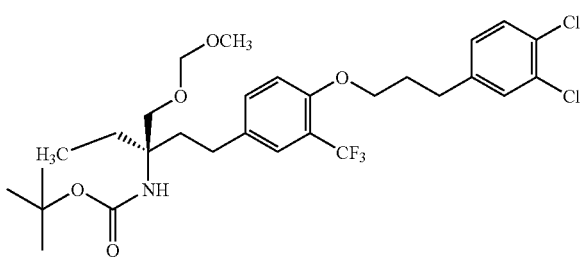

Compound 30-4 (10 g) was separated by HPLC using CHIRALPAK (registered trade mark) AD-H (hexane/isopropyl alcohol) to give both enantiomers each as a white powder. The primary peak with a shorter retention time was R-configuration (4.5 g, compound 206-1-1), and the secondary peak with a longer retention time was S-configuration (4.4 g, compound 206-1-2).

(206-2) Synthesis of (R)-(3-{4-[3-(3,4-dichlorophenyl)propoxy]-3-trifluoromethylphenyl}-1-ethyl-1-(methoxymethoxy)methyl)propylcarbamic acid t-butyl ester (Compound 206-2)

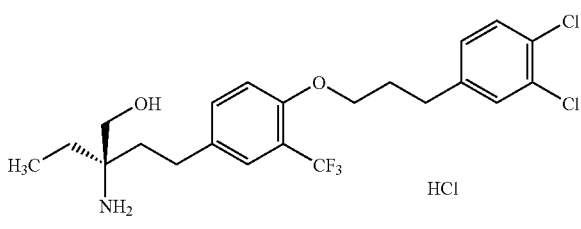

To a solution of compound 206-1-1 (400 mg) in N,N-dimethylformamide (10 ml) were added potassium carbonate (394 mg) and compound 38-3 (305 mg), and the mixture was stirred at 80° C. for 1.5 hr. The reaction mixture was added to water, and the mixture was extracted with ethyl acetate. The organic layer was washed with saturated brine and dried over anhydrous magnesium sulfate. The solvent was evaporated under reduced pressure to give the object product (640 mg) as a pale-yellow oil.

$^1$H-NMR(CDCl$_3$) δ (ppm): 0.89(3H, t, J=7.5 Hz), 1.45(9H, s), 1.68-1.75(1H, m), 1.76-1.83(1H, m), 1.94-1.98(2H, m), 2.04-2.11(2H, m), 2.53-2.58(2H, m), 2.80(2H, t, J=7.5 Hz), 3.39(3H, s), 3.57(1H, d, J=9.8 Hz), 3.64(1H, d, J=9.8 Hz), 3.97(2H, t, J=5.8 Hz), 4.62(1H, brs), 4.64(2H, s), 6.84(1H, d, J=8.5 Hz), 7.01-7.05(1H, m), 7.26-7.29(2H, m), 7.33(1H, d, J=8.1 Hz), 7.38(1H, d, J=1.9 Hz).

(206-3) Synthesis of (R)-2-amino-4-{4-[3-(3,4-dichlorophenyl)propoxy]-3-trifluoromethylphenyl}-2-ethylbutanol hydrochloride (Compound 206-3)

To a solution of compound 206-2 (640 mg) in ethanol (15 ml) was added concentrated hydrochloric acid (1.5 ml), and the mixture was stirred at 80° C. for 1 hr. The reaction mixture was concentrated, and the residue was washed with diethyl ether to give the object product (480 mg) as a white powder.

MS(ESI)m/z: 464[M+H]

$^1$H-NMR(DMSO-d$_6$) δ (ppm): 0.90(3H, t, J=7.5 Hz), 1.58-1.68(2H, m), 1.72-1.78(2H, m), 1.99-2.06(2H, m), 2.56-2.62 (2H, m), 2.75(2H, t, J=7.5 Hz), 3.47(2H, brs), 4.04(2H, t, J=6.1 Hz), 5.50(1H, brs), 7.16-7.22(2H, m), 7.45-7.49(3H, m), 7.54(1H, d, J=8.0 Hz), 7.95(3H, brs).

Example 207

(S)-2-amino-4-{4-[3-(3,4-dichlorophenyl)propoxy]-3-trifluoromethylphenyl}-2-ethylbutanol hydrochloride (207-1) Synthesis of (S)-(3-{4-[3-(3,4-dichlorophenyl)propoxy]-3-trifluoromethylphenyl}-1-ethyl-1-(methoxymethoxy)methyl)propylcarbamic acid t-butyl ester (Compound 207-1)

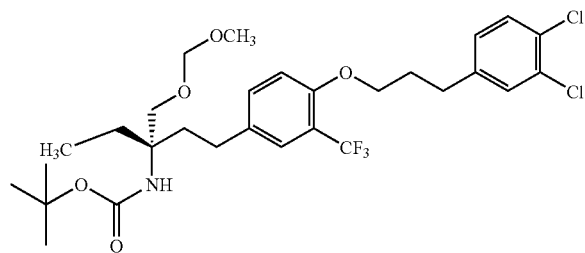

To a solution of compound 206-1-2 (400 mg) in N,N-dimethylformamide (10 ml) were added potassium carbonate (394 mg) and compound 38-3 (305 mg), and the mixture was stirred at 80° C. for 1 hr. The reaction mixture was added to water, and the mixture was extracted with ethyl acetate. The organic layer was washed with saturated brine and dried over anhydrous magnesium sulfate. The solvent was evaporated under reduced pressure to give the object product (710 mg) as a pale-yellow oil.

$^1$H-NMR(CDCl$_3$) δ (ppm): 0.90(3H, t, J=7.5 Hz), 1.45(9H, s), 1.68-1.75(1H, m), 1.76-1.83(1H, m), 1.93-1.98(2H, m), 2.04-2.12(2H, m), 2.53-2.58(2H, m), 2.80(2H, t, J=7.5 Hz), 3.39(3H, s), 3.57(1H, d, J=9.8 Hz), 3.64(1H, d, J=9.8 Hz), 3.97(2H, t, J=5.8 Hz), 4.62(1H, brs), 4.64(2H, s), 6.84(1H, d, J=8.4 Hz), 7.01-7.05(1H, m), 7.26-7.29(2H, m), 7.33(1H, d, J=8.0 Hz), 7.38(1H, d, J=1.9 Hz).

(207-2) Synthesis of (S)-2-amino-4-{4-[3-(3,4-dichlorophenyl)propoxy]-3-trifluoromethylphenyl}-2-ethylbutanol hydrochloride (Compound 207-2)

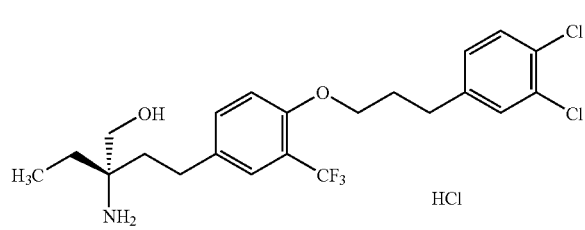

To a solution of compound 207-1 (710 mg) in ethanol (15 ml) was added concentrated hydrochloric acid (1.5 ml), and the mixture was stirred at 80° C. for 1 hr. The reaction mixture was concentrated, and the residue was washed with diethyl ether to give the object product (460 mg) as a white powder.

MS(ESI)m/z: 464[M+H]

$^1$H-NMR (DMSO-d$_6$) δ (ppm): 0.90(3H, t, J=7.5 Hz), 1.58-1.67(2H, m), 1.71-1.78(2H, m), 1.99-2.06(2H, m), 2.57-2.62(2H, m), 2.75(2H, t, J=7.5 Hz), 3.47(2H, brs), 4.04(2H, t, J=6.0 Hz), 5.50(1H, brs), 7.16-7.21(2H, m), 7.45-7.49(3H, m), 7.54(1H, d, J=8.0 Hz), 7.91(3H, brs).

Example 208

2-amino-2-(2-{3-cyano-4-[3-(3-methylphenyl)propoxy]phenyl}ethyl)propane-1,3-diol hydrochloride (208-1) Synthesis of 5-bromo-2-[3-(3-methylphenyl)propoxy]benzonitrile (Compound 208-1)

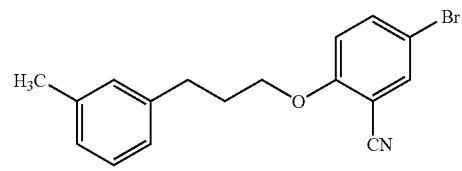

Compound 15-1 (1.30 g) was dissolved in N,N-dimethylformamide (30 ml) and sodium hydride (60%, 1.04 g) was added at room temperature. After stirring for 30 min, 5-bromo-2-fluorobenzonitrile (1.00 g) was added, and the mixture was stirred at 50° C. for 4 hr. The reaction mixture was added to water, and the mixture was extracted with ethyl acetate, washed with water and saturated brine, and dried over anhydrous magnesium sulfate. The solvent was evaporated under reduced pressure. The residue was purified by silica gel column chromatography to give the object product (1.04 g) as a yellow oil.

$^1$H-NMR(CDCl$_3$) δ (ppm): 2.12-2.20(2H, m), 2.32(3H, s), 2.79-2.85(2H, m), 4.01-4.07(2H, m), 6.79(1H, d, J=9.1 Hz), 6.96-7.04(3H, m), 7.15-7.20(1H, m), 7.46-7.49(1H, m), 7.56 (1H, brs).

(208-2) Synthesis of [5-(2-{3-cyano-4-[3-(3-methylphenyl)propoxy]phenyl}ethyl)-2,2-dimethyl-1,3-dioxan-5-yl]carbamic acid t-butyl ester (Compound 208-2)

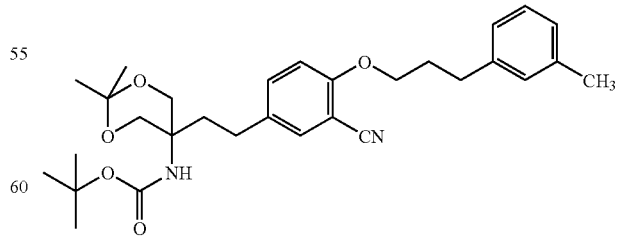

Compound 208-1 (1.04 g), (5-ethynyl-2,2-dimethyl-1,3-dioxan-5-yl)carbamic acid t-butyl ester (0.885 g), 2-dicyclohexylphosphino-2',4',6'-triisopropylbiphenyl (0.093 g), bis(acetonitrile)palladium(II) dichloride (0.017 g), cesium carbonate (2.67 g) were stirred in acetonitrile (30 ml) at 90° C. for 7 hr. Water was added to the reaction mixture, and the mixture was extracted with ethyl acetate, washed with saturated brine, and dried over anhydrous sodium sulfate. The solvent was evaporated under reduced pressure. The residue was purified by silica gel column chromatography to give [5-(2-{3-cyano-4-[3-(3-methylphenyl)propoxy]phenyl}ethynyl)-2,2-dimethyl-1,3-dioxan-5-yl]carbamic acid t-butyl ester as a pale-brown solid. The solid was dissolved in ethyl acetate (10 ml), 10% palladium carbon (containing about 50% water, 0.140 g) was added and the mixture was stirred under a hydrogen atmosphere at room temperature for 3 hr. The solution was filtered, and the filtrate was concentrated to give the object product (0.360 g) as a yellow oil.

$^1$H-NMR(CDCl$_3$) δ (ppm): 1.43(3H, s), 1.44(3H, s), 1.47 (9H, s), 1.92-1.96(2H, m), 2.11-2.17(2H, m), 2.32(3H, s), 2.48-2.54(2H, m), 2.81(2H, t, J=7.5 Hz), 3.63-3.70(2H, m), 3.85-3.91(2H, m), 4.13(2H, t, J=7.1 Hz), 5.00(1H, brs), 6.81 (1H, d, J=8.6 Hz), 7.00-7.03(3H, m), 7.17(1H, t, J=7.5 Hz), 7.30(1H, dd, J=8.6, 2.2 Hz), 7.36(1H, d, J=2.2 Hz).

(208-3) Synthesis of 2-amino-2-(2-{3-cyano-4-[3-(3-methylphenyl)propoxy]phenyl}ethyl)propane-1,3-diol hydrochloride (Compound 208-3)

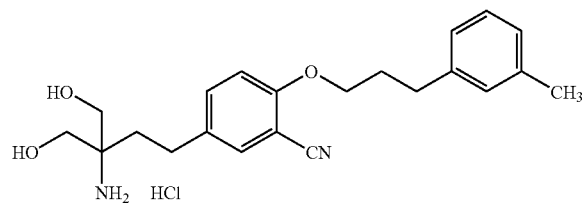

Compound 208-2 (0.360 g) was dissolved in a mixed solvent of tetrahydrofuran (4 ml) and water (1 ml), trifluoroacetic acid (1 ml) was added, and the mixture was stirred at room temperature for 4 hr. To the reaction mixture was added 1M aqueous sodium hydroxide solution, and the mixture was extracted with ethyl acetate, washed with saturated brine, and dried over anhydrous magnesium sulfate. The solvent was evaporated under reduced pressure to give a yellow oil. To a solution of the yellow oil in methylene chloride (5 ml) was added hydrogen chloride containing dioxane (4 mol/l, 5 ml), and the mixture was stirred at room temperature for 3 hr. The reaction mixture was concentrated, and the residue was washed with diethyl ether to give a white powder. The white powder was purified by HPLC, the obtained residue was converted to hydrochloride by adding hydrogen chloride containing ether (1 mol/l, 15 ml), and the precipitate was collected by filtration and dried to give the object product (110 mg) as a pale-brown powder.

MS(ESI)m/z: 369[M+H]

$^1$H-NMR(DMSO-d$_6$) δ (ppm): 1.73-1.78(2H, m), 1.99-2.06(2H, m), 2.26(3H, s), 2.55-2.60(2H, m), 2.72(2H, t, J=7.5 Hz), 3.51(4H, d, J=4.6 Hz), 4.08(2H, t, J=6.2 Hz), 5.41(2H, t, J=4.8 Hz), 6.99-7.04(3H, m), 7.14-7.19(2H, m), 7.49(1H, dd, J=8.6, 1.7 Hz), 7.57(1H, d, J=1.7 Hz), 7.81(3H, brs).

Example 209 phosphoric acid mono(2-amino-4-{4-[3-(3,4-dichlorophenyl)propoxy]-3-trifluoromethylphenyl}-2-methylbutyl)ester (209-1) Synthesis of [1-di(t-butyl)phosphoryloxymethyl-3-{4-[3-(3,4-dichlorophenyl)propoxy]-3-trifluoromethylphenyl}-1-methylpropyl]carbamic acid t-butyl ester (Compound 209-1)

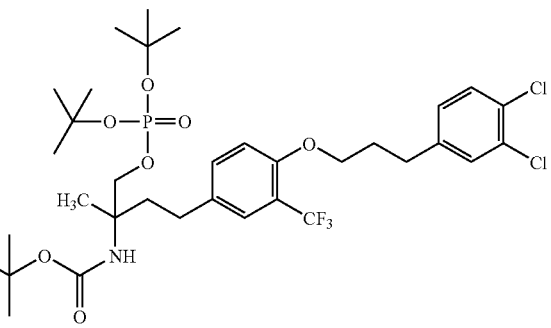

To a solution of compound 202-2 (350 mg) in methanol (20 ml) were added triethylamine (0.303 ml) and di-t-butyl-dicarbonate (314 mg), and the mixture was stirred at room temperature for 25 hr. Furthermore, to the reaction mixture was added di-t-butyl-dicarbonate (150 mg), and the mixture was stirred at room temperature for 3 hr. Water was added to the reaction mixture, and the mixture was extracted with ethyl acetate. The organic layer was washed with saturated brine and dried over anhydrous magnesium sulfate. The solvent was evaporated under reduced pressure. The obtained residue was purified by silica gel column chromatography to give an amine-protected compound as a colorless oil (520 mg). The colorless oil was dissolved in a mixed solution of methylene chloride (5 ml) and acetonitrile (2 ml), 1H-tetrazole (101 mg) and di-t-butyl diethylphosphoramidite (0.431 ml) was further added, and the mixture was stirred at room temperature for 1.5 hr. The reaction solution was ice-cooled, t-butyl hydroperoxide-containing decane solution (5-6M, 0.432 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography to give the object product (610 mg) as a colorless oil.

$^1$H-NMR(CD$_3$OD) δ (ppm): 1.30(3H, s), 1.45(9H, s), 1.49 (9H, s), 1.51(9H, s), 1.71-1.74(1H, m), 2.01-2.11(3H, m), 2.59-2.64(2H, m), 2.82(2H, t, J=7.5 Hz), 3.95-4.00(1H, m), 4.01(2H, t, J=5.9 Hz), 4.08-4.12(1H, m), 7.01(1H, d, J=8.5 Hz), 7.13(1H, dd, J=8.5, 2.0 Hz), 7.36-7.41(4H, m).

(209-2) Synthesis of phosphoric acid mono(2-amino-4-{4-[3-(3,4-dichlorophenyl)propoxy]-3-trifluoromethylphenyl}-2-methylbutyl)ester (Compound 209-2)

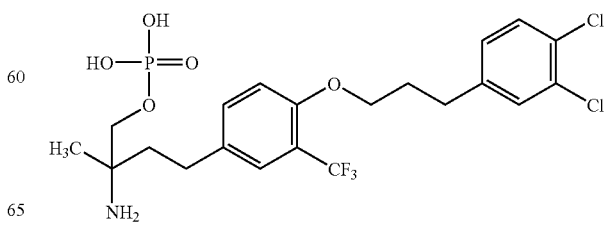

Compound 209-1 (610 mg) was dissolved in methylene chloride (6 ml), hydrogen chloride containing dioxane (4 mol/l, 3 ml) was added, and the mixture was stirred at room temperature for 3 hr. The solvent was concentrated under reduced pressure, and methanol (3 ml), diethyl ether (3 ml) and propylene oxide (5 ml) were added to the residue. The precipitated powder was collected by filtration, and washed with ethyl acetate and diethyl ether to give the object product (55 mg) as a white solid.

MS(ESI)m/z: 530[M+H]

$^1$H-NMR(CD$_3$OD) δ (ppm): 1.34(3H, s), 1.82-1.91(1H, m), 1.96-2.01(1H, m), 2.03-2.12(2H, m), 2.63-2.75(2H, m), 2.82(2H, t, J=7.5 Hz), 3.85(1H, dd, J=5.3, 11.4 Hz), 3.94(1H, dd, J=5.9, 11.4 Hz), 4.02(2H, t, J=5.8 Hz), 7.05(1H, d, J=8.4 Hz), 7.13(1H, dd, J=8.4, 1.9 Hz), 7.36(1H, d, J=1.9 Hz), 7.39-7.45(2H, m), 7.48(1H, d, J=1.6 Hz).

Example 210 phosphoric acid mono(2-amino-4-{4-[3-(3,4-dichlorophenyl)propoxy]-3-trifluoromethylphenyl}-2-ethylbutyl)ester (210-1) Synthesis of [1-di(t-butyl)phosphoryloxymethyl-3-{4-[3-(3,4-dichlorophenyl)propoxy]-3-trifluoromethylphenyl}-1-ethylpropyl]carbamic acid t-butyl ester (Compound 210-1)

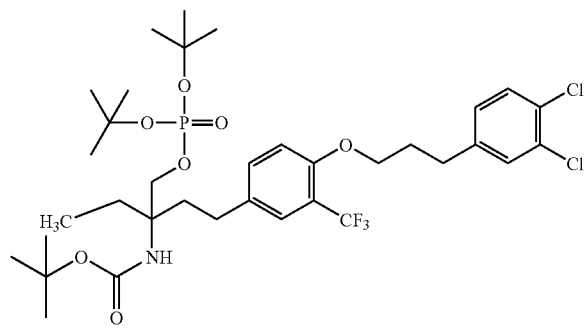

To a solution of compound 205-2 (340 mg) in methanol (20 ml) were added triethylamine (0.287 ml) and di-t-butyl-dicarbonate (297 mg) was added, and the mixture was stirred at room temperature for 24 hr. Furthermore, to the reaction mixture was added di-t-butyl-dicarbonate (150 mg), and the mixture was stirred at room temperature for 5 hr. Water was added to the reaction mixture, and the mixture was extracted with ethyl acetate. The organic layer was washed with saturated brine and dried over anhydrous magnesium sulfate. The solvent was evaporated under reduced pressure. The obtained residue was purified by silica gel column chromatography to give an amine-protected compound as a colorless oil (450 mg). The colorless oil was dissolved in a mixed solvent of methylene chloride (5 ml) and acetonitrile (2 ml). To this solution were added 1H-tetrazole (95 mg) and di-t-butyl diethylphosphoramidite (0.407 ml), and the mixture was stirred at room temperature for 2 hr. The reaction solution was ice-cooled, t-butyl hydroperoxide-containing decane solution (5-6M, 0.408 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography to give the object product (560 mg) as a colorless oil.

$^1$H-NMR(CD$_3$OD) δ (ppm): 0.91(3H, t, J=7.4 Hz), 1.45 (9H, s), 1.50(9H, s), 1.51(9H, s), 1.65-1.83(3H, m), 1.90-2.00 (1H, m), 2.04-2.11(2H, m), 2.57(2H, t, J=8.5 Hz), 2.82(2H, t, J=7.5 Hz), 4.02(2H, t, J=5.9 Hz), 4.05-4.14(2H, m), 7.02(1H, d, J=8.4 Hz), 7.13(1H, dd, J=8.4, 1.9 Hz), 7.36-7.38(2H, m), 7.39-7.41(2H, m).

(210-2) Synthesis of phosphoric acid mono(2-amino-4-{4-[3-(3,4-dichlorophenyl)propoxy]-3-trifluoromethylphenyl}-2-ethylbutyl)ester (Compound 210-2)

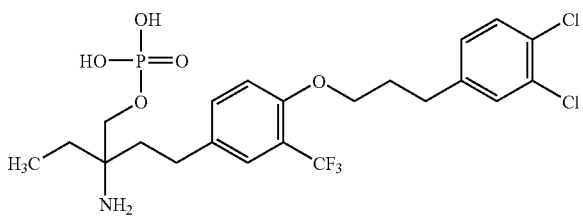

Compound 210-1 (560 mg) was dissolved in methylene chloride (6 ml), hydrogen chloride containing dioxane (4 mol/l, 3 ml) was added, and the mixture was stirred at room temperature for 3 hr. The solvent was concentrated under reduced pressure, and methanol (3 ml), diethyl ether (3 ml) and propylene oxide (5 ml) were added to the residue. The precipitated powder was collected by filtration, and washed with ethyl acetate and diethyl ether to give the object product (15 mg) as a white solid.

MS(ESI)m/z: 544[M+H]

$^1$H-NMR(CD$_3$OD) δ (ppm): 1.03(3H, t, J=7.5 Hz), 1.72-2.01(4H, m), 2.02-2.12(2H, m), 2.57-2.74(2H, m), 2.82(2H, t, J=7.5 Hz), 3.88-3.96(2H, m), 4.02(2H, t, J=5.9 Hz), 7.05 (1H, d, J=8.5 Hz), 7.13(1H, dd, J=8.0, 1.7 Hz), 7.36(1H, d, J=1.7 Hz), 7.40(1H, d, J=8.0 Hz), 7.44(1H, d, J=8.5 Hz), 7.47(1H, brs).

Example 211

(R)-phosphoric acid mono(2-amino-4-{4-[3-(3,4-dichlorophenyl)propoxy]-3-trifluoromethylphenyl}-2-ethylbutyl)ester (211-1) Synthesis of (R)-[1-di(t-butyl)phosphoryloxymethyl-3-{4-[3-(3,4-dichlorophenyl)propoxy]-3-trifluoromethylphenyl}-1-ethylpropyl]carbamic acid t-butyl ester (Compound 211-1)

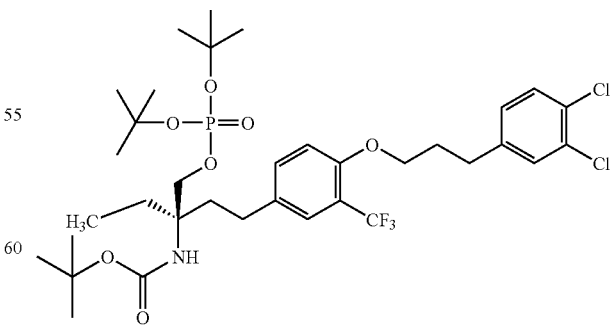

To a solution of compound 206-3 (360 mg) in methanol (10 ml) were added triethylamine (0.303 ml) and di-t-butyl-dicarbonate (314 mg), and the mixture was stirred at room temperature for 20 hr. Water was added to the reaction mixture, and the mixture was extracted with ethyl acetate. The organic layer was washed with saturated brine and dried over anhydrous magnesium sulfate. The solvent was evaporated under reduced pressure. The obtained residue was purified by silica gel column chromatography to give an amine-protected compound as a colorless oil (290 mg). The colorless oil was dissolved in a mixed solvent of methylene chloride (5 ml) and acetonitrile (2 ml). To this solution were added 1H-tetrazole (72 mg) and di-t-butyl diethylphosphoramidite (0.308 ml), and the mixture was stirred at room temperature for 2 hr. The reaction solution was ice-cooled, t-butyl hydroperoxide-containing decane solution (5-6M, 0.306 ml) was added, and the mixture was stirred at room temperature for 20 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography to give the object product (420 mg) as a colorless oil.

$^1$H-NMR(CD$_3$OD) δ (ppm): 0.91(3H, t, J=7.4 Hz), 1.45 (9H, s), 1.51(9H, s), 1.52(9H, s), 1.65-1.83(3H, m), 1.90-2.00 (1H, m), 2.04-2.11(2H, m), 2.57(2H, t, J=8.6 Hz), 2.81(2H, t, J=7.5 Hz), 4.02(2H, t, J=5.8 Hz), 4.05-4.13(2H, m), 7.02(1H, d, J=8.4 Hz), 7.13(1H, dd, J=8.4, 1.9 Hz), 7.35-7.38(2H, m), 7.39-7.41(2H, m).

(211-2) Synthesis of (R)-phosphoric acid mono(2-amino-4-{4-[3-(3,4-dichlorophenyl)propoxy]-3-trifluoromethylphenyl}-2-ethylbutyl)ester (Compound 211-2)

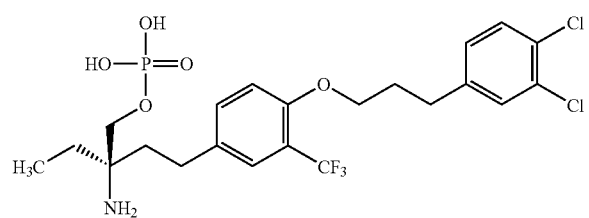

Compound 211-1 (420 mg) was dissolved in methylene chloride (6 ml), hydrogen chloride containing dioxane (4 mol/l, 3 ml) was added, and the mixture was stirred at room temperature for 3 hr. The solvent was concentrated under reduced pressure, and isopropyl alcohol (3 ml) and water (2 ml) were added to the residue. The precipitated powder was collected by filtration, and washed with water to give the object product (12 mg) as a white solid.

MS(ESI)m/z: 543[M+H]

$^1$H-NMR(CD$_3$OD) δ (ppm): 1.03(3H, t, J=7.5 Hz), 1.72-2.01(4H, m), 2.02-2.12(2H, m), 2.57-2.74(2H, m), 2.82(2H, t, J=7.5 Hz), 3.89-3.96(2H, m), 4.02(2H, t, J=5.9 Hz), 7.05 (1H, d, J=8.5 Hz), 7.13(1H, dd, J=8.1, 1.7 Hz), 7.36(1H, d, J=1.7 Hz), 7.40(1H, d, J=8.1 Hz), 7.44(1H, d, J=8.5 Hz), 7.47(1H, brs).

Example 212

(S)-phosphoric acid mono(2-amino-4-{4-[3-(3,4-dichlorophenyl)propoxy]-3-trifluoromethylphenyl}-2-ethylbutyl)ester (212-1) Synthesis of (S)-[1-di(t-butyl)phosphoryloxymethyl-3-{4-[3-(3,4-dichlorophenyl)propoxy]-3-trifluoromethylphenyl}-1-ethylpropyl]carbamic acid t-butyl ester (Compound 212-1)

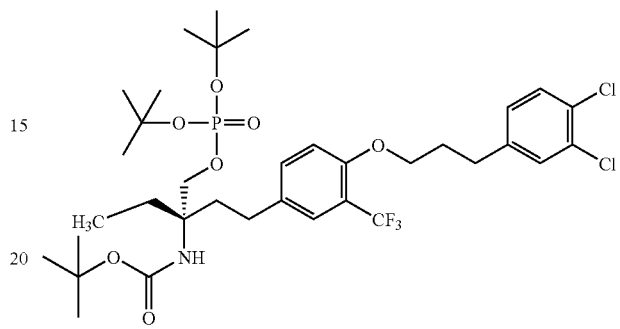

To a solution of compound 207-2 (330 mg) in methanol (10 ml) were added triethylamine (0.278 ml) and di-t-butyl-dicarbonate (288 mg), and the mixture was stirred at room temperature for 28 hr. Water was added to the reaction mixture, and the mixture was extracted with ethyl acetate. The organic layer was washed with saturated brine and dried over anhydrous magnesium sulfate. The solvent was evaporated under reduced pressure. The obtained residue was purified by silica gel column chromatography to give an amine-protected compound as a colorless oil (110 mg). The colorless oil was dissolved in a mixed solution of methylene chloride (3 ml) and acetonitrile (2 ml). To this solution were added 1H-tetrazole (27 mg) and di-t-butyl diethylphosphoramidite (0.114 ml), and the mixture was stirred at room temperature for 2 hr. The reaction solution was ice-cooled, t-butyl hydroperoxide-containing decane solution (5-6M, 0.114 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography to give the object product (240 mg) as a colorless oil.

$^1$H-NMR(CD$_3$OD) δ (ppm): 0.91(3H, t, J=7.3 Hz), 1.45 (9H, s), 1.50(9H, s), 1.51(9H, s), 1.65-1.83(3H, m), 1.92-2.00 (1H, m), 2.04-2.11(2H, m), 2.57(2H, t, J=8.5 Hz), 2.81(2H, t, J=7.5 Hz), 4.01(2H, t, J=5.8 Hz), 4.05-4.14(2H, m), 7.02(1H, d, J=8.4 Hz), 7.13(1H, dd, J=8.4, 1.9 Hz), 7.35-7.38(2H, m), 7.39-7.41(2H, m).

(212-2) Synthesis of (S)-phosphoric acid mono(2-amino-4-{4-[3-(3,4-dichlorophenyl)propoxy]-3-trifluoromethylphenyl}-2-ethylbutyl)ester (Compound 212-2)

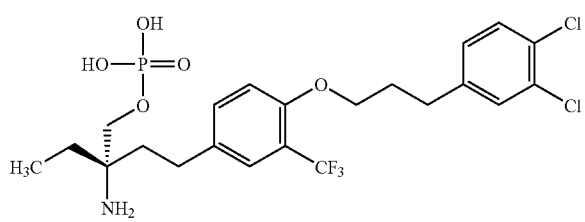

Compound 212-1 (240 mg) was dissolved in methylene chloride (4 ml), hydrogen chloride containing dioxane (4 mol/l, 2 ml) was added, and the mixture was stirred at room temperature for 3 hr. The solvent was concentrated under reduced pressure, and methanol (3 ml) and isopropyl alcohol (3 ml) were added to the residue. The precipitated powder was collected by filtration, and washed with isopropyl alcohol to give the object product (75 mg) as a white solid.

MS(ESI)m/z: 543[M+H]

$^1$H-NMR(CD$_3$OD) δ (ppm): 1.03(3H, t, J=7.4 Hz), 1.71-2.01(4H, m), 2.02-2.12(2H, m), 2.57-2.74(2H, m), 2.82(2H, t, J=7.5 Hz), 3.88-3.97(2H, m), 4.02(2H, t, J=5.8 Hz), 7.05 (1H, d, J=8.5 Hz), 7.13(1H, dd, J=8.0, 1.3 Hz), 7.36(1H, d, J=1.3 Hz), 7.40(1H, d, J=8.0 Hz), 7.44(1H, d, J=8.5 Hz), 7.47(1H, brs).

Example 213

2-amino-2-methyl-4-{4-[3-(4-trifluoromethoxyphenyl)propoxy]-3-trifluoromethylphenyl}butanol hydrochloride (213-1) Synthesis of (1-(methoxymethoxy)methyl-1-methyl-3-{4-[3-(4-trifluoromethoxyphenyl)propoxy]-3-trifluoromethylphenyl}propyl)carbamic acid t-butyl ester (Compound 213-1)

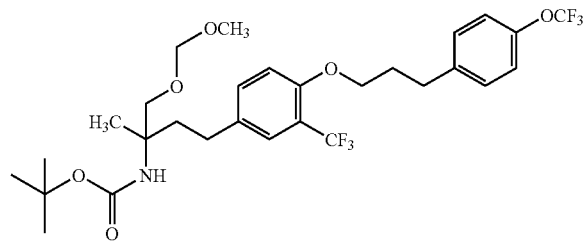

To a solution of compound 27-4 (400 mg) in N,N-dimethylformamide (10 ml) were added potassium carbonate (406 mg) and compound 52-3 (334 mg), and the mixture was stirred at 80° C. for 1 hr. The reaction mixture was added to water, and the mixture was extracted with ethyl acetate. The organic layer was washed with saturated brine and dried over anhydrous magnesium sulfate. The solvent was evaporated under reduced pressure to give the object product (640 mg) as a yellow oil.

$^1$H-NMR(CDCl$_3$) δ (ppm): 1.34(3H, s), 1.45(9H, s), 1.88-1.96(1H, m), 2.02-2.20(3H, m), 2.58(2H, t, J=8.5 Hz), 2.84 (2H, t, J=7.5 Hz), 3.38(3H, s), 3.48(1H, d, J=9.5 Hz), 3.65 (1H, d, J=9.5 Hz), 3.98(2H, t, J=5.9 Hz), 4.65(2H, s), 4.73 (1H, brs), 6.84(1H, d, J=8.5 Hz), 7.11-7.15(2H, m), 7.20-7.23 (2H, m), 7.26-7.28(1H, m), 7.38(1H, d, J=1.8 Hz).

(213-2) Synthesis of 2-amino-2-methyl-4-{4-[3-(4-trifluoromethoxyphenyl)propoxy]-3-trifluoromethylphenyl}butanol hydrochloride (Compound 213-2)

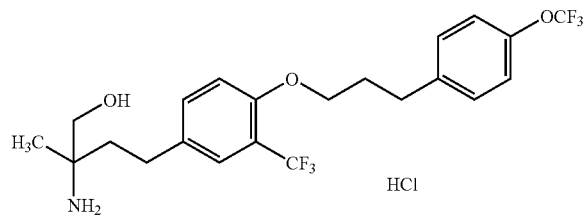

To a solution of compound 213-1 (640 mg) in ethanol (15 ml) was added concentrated hydrochloric acid (1.5 ml), and the mixture was stirred at 80° C. for 1 hr. The reaction mixture was concentrated, and the residue was washed with diisopropyl ether to give the object product (440 mg) as a pale-red powder.

MS(ESI)m/z: 466[M+H]

$^1$H-NMR(DMSO-d$_6$) δ (ppm): 1.21(3H, s), 1.70-1.84(2H, m), 1.98-2.07(2H, m), 2.62(2H, t, J=8.6 Hz), 2.78(2H, t, J=7.5 Hz), 3.37-3.50(2H, m), 4.05(2H, t, J=6.0 Hz), 5.54(1H, t, J=5.0 Hz), 7.17(1H, d, J=8.5 Hz), 7.27-7.34(4H, m), 7.45 (1H, d, J=8.5 Hz), 7.48(1H, brs), 7.88(3H, brs).

Example 214

2-amino-2-methyl-4-{4-[3-(3-trifluoromethoxyphenyl)propoxy]-3-trifluoromethylphenyl}butanol hydrochloride (214-1) Synthesis of (1-(methoxymethoxy)methyl-1-methyl-3-{4-[3-(3-trifluoromethoxyphenyl)propoxy]-3-trifluoromethylphenyl}propyl)carbamic acid t-butyl ester (Compound 214-1)

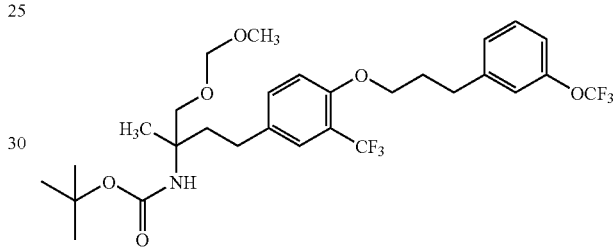

To a solution of compound 27-4 (400 mg) in N,N-dimethylformamide (10 ml) were added potassium carbonate (406 mg) and compound 58-3 (334 mg), and the mixture was stirred at 80° C. for 1 hr. The reaction mixture was added to water, and the mixture was extracted with ethyl acetate. The organic layer was washed with saturated brine and dried over anhydrous magnesium sulfate. The solvent was evaporated under reduced pressure to give the object product (670 mg) as a pale-yellow oil.

$^1$H-NMR(CDCl$_3$) δ (ppm): 1.34(3H, s), 1.45(9H, s), 1.88-1.95(1H, m), 2.03-2.19(3H, m), 2.58(2H, t, J=8.6 Hz), 2.86 (2H, t, J=7.5 Hz), 3.38(3H, s), 3.47(1H, d, J=9.5 Hz), 3.65 (1H, d, J=9.5 Hz), 3.98(2H, t, J=5.9 Hz), 4.65(2H, s), 4.73 (1H, brs), 6.84(1H, d, J=8.5 Hz), 7.03-7.06(2H, m), 7.13(1H, d, J=7.7 Hz), 7.26-7.32(2H, m), 7.38(1H, d, J=1.6 Hz).

(214-2) Synthesis of 2-amino-2-methyl-4-{4-[3-(3-trifluoromethoxyphenyl)propoxy]-3-trifluoromethylphenyl}butanol hydrochloride (Compound 214-2)

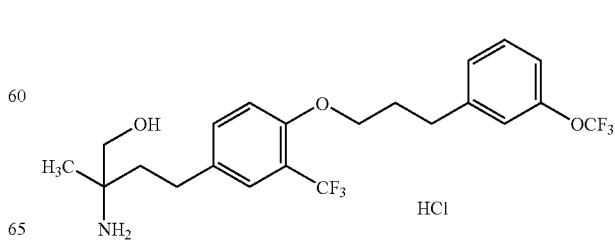

To a solution of compound 214-1 (670 mg) in ethanol (15 ml) was added concentrated hydrochloric acid (1.5 ml), and the mixture was stirred at 80° C. for 1 hr. The reaction mixture was concentrated, and the residue was washed with diisopropyl ether to give the object product (430 mg) as a pale-red powder.

MS(ESI)m/z: 466[M+H]

$^1$H-NMR(DMSO-$d_6$) δ (ppm): 1.21(3H, s), 1.70-1.84(2H, m), 2.00-2.08(2H, m), 2.62(2H, t, J=8.7 Hz), 2.80(2H, t, J=7.5 Hz), 3.41(1H, dd, J=5.2, 11.4 Hz), 3.48(1H, dd, J=4.8, 11.4 Hz), 4.04(2H, t, J=6.0 Hz), 5.54(1H, t, J=5.1 Hz), 7.15-7.20(3H, m), 7.25(1H, d, J=7.6 Hz), 7.40-7.46(2H, m), 7.49 (1H, d, J=1.5 Hz).

Example 215 phosphoric acid mono(2-amino-2-methyl-4-{4-[3-(4-trifluoromethoxyphenyl)propoxy]-3-trifluoromethylphenyl}butyl)ester (215-1) Synthesis of [1-di(t-butyl)phosphoryloxymethyl-1-methyl-3-{4-[3-(4-trifluoromethoxyphenyl)propoxy]-3-trifluoromethylphenyl}propyl]carbamic acid t-butyl ester (Compound 215-1)

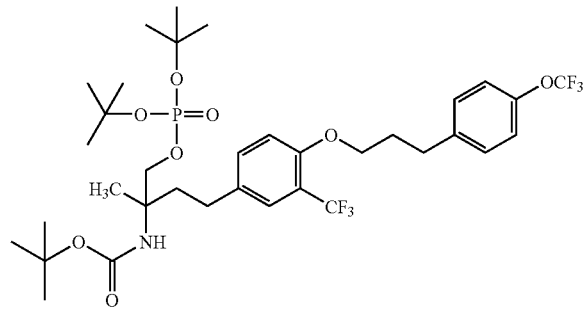

To a solution of compound 213-2 (320 mg) in methanol (10 ml) were added triethylamine (0.269 ml) and di-t-butyl-dicarbonate (279 mg), and the mixture was stirred at room temperature for 22 hr. Furthermore, to the reaction mixture was added di-t-butyl-dicarbonate (242 mg), and the mixture was stirred at room temperature for 16 hr. Water was added to the reaction mixture, and the mixture was extracted with ethyl acetate. The organic layer was washed with saturated brine and dried over anhydrous magnesium sulfate. The solvent was evaporated under reduced pressure. The obtained residue was purified by silica gel column chromatography to give an amine-protected compound as a pale-yellow oil (320 mg). The pale-yellow oil (320 mg) was dissolved in a mixed solvent of methylene chloride (5 ml) and acetonitrile (2 ml). To this solution were added 1H-tetrazole (79 mg) and di-t-butyl diethylphosphoramidite (0.338 ml), and the mixture was stirred at room temperature for 2 hr. The reaction solution was ice-cooled, t-butyl hydroperoxide-containing decane solution (5-6M, 0.342 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography to give the object product (440 mg) as a colorless oil.

$^1$H-NMR(CD$_3$OD) δ (ppm): 1.30(3H, s), 1.45(9H, s), 1.49 (9H, s), 1.51(9H, s), 1.62-1.78(1H, m), 2.07-2.12(3H, m), 2.58-2.62(2H, m), 2.85(2H, t, J=7.5 Hz), 3.97(1H, dd, J=9.8, 4.6 Hz), 4.02(2H, t, J=5.9 Hz), 4.11(1H, dd, J=9.8, 4.6 Hz), 7.01(1H, d, J=8.5 Hz), 7.17(2H, d, J=8.2 Hz), 7.27-7.31(2H, m), 7.37(1H, d, J=8.5 Hz), 7.42(1H, d, J=1.6 Hz).

(215-2) Synthesis of phosphoric acid mono(2-amino-2-methyl-4-{4-[3-(4-trifluoromethoxyphenyl)propoxy]-3-trifluoromethylphenyl}butyl)ester (Compound 215-2)

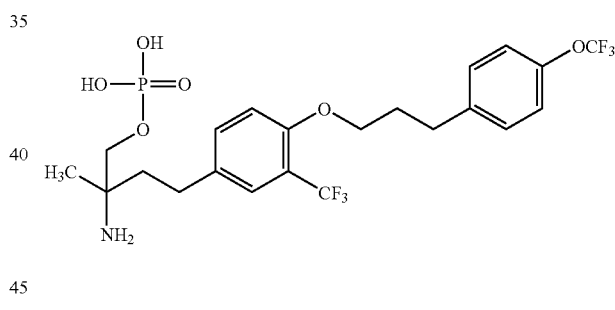

Compound 215-1 (440 mg) was dissolved in methylene chloride (6 ml), hydrogen chloride containing dioxane (4 mol/l, 3 ml) was added, and the mixture was stirred at room temperature for 3.5 hr. The solvent was concentrated under reduced pressure, and isopropyl alcohol (10 ml) was added to the residue. The precipitated powder was collected by filtration, and washed with isopropyl alcohol to give the object product (55 mg) as a white solid.

MS(ESI)m/z: 546[M+H]

$^1$H-NMR(CD$_3$OD) δ (ppm): 1.38(3H, s), 1.82-1.91(1H, m), 1.96-2.07(1H, m), 2.08-2.13(2H, m), 2.60-2.78(2H, m), 2.86(2H, t, J=7.5 Hz), 3.85(1H, dd, J=5.2, 11.3 Hz), 3.94(1H, dd, J=5.8, 11.3 Hz), 4.03(2H, t, J=5.9 Hz), 7.05(1H, d, J=8.5 Hz), 7.12(2H, d, J=8.2 Hz), 7.29(2H, d, J=8.5 Hz), 7.43(1H, dd, J=8.5, 1.7 Hz), 7.48(1H, d, J=1.7 Hz).

Example 216 phosphoric acid mono(2-amino-2-methyl-4-{4-[3-(3-trifluoromethoxyphenyl)propoxy]-3-trifluoromethylphenyl}butyl)ester

(216-1) Synthesis of (1-(dibenzyl)phosphoryloxymethyl-1-methyl-3-{4-[3-(3-trifluoromethoxyphenyl)propoxy]-3-trifluoromethylphenyl}propyl)carbamic acid benzyl ester (Compound 216-1)

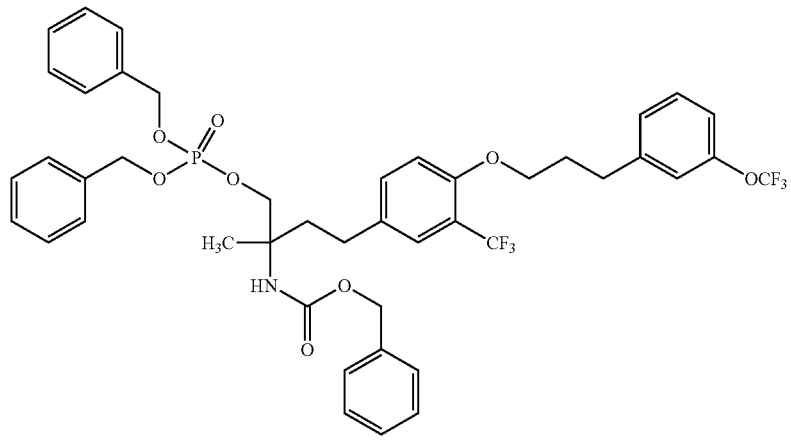

A mixture of compound 214-2 (470 mg), ethyl acetate (15 ml), saturated aqueous sodium hydrogen carbonate solution (15 ml) and benzyloxycarbonyl chloride (0.182 ml) was stirred in a two-layer state at room temperature for 16 hr. Furthermore, benzyloxycarbonyl chloride (0.182 ml) was added to the reaction mixture, and the mixture was stirred at room temperature for 3 hr. The ethyl acetate layer was separated, and the aqueous layer was extracted with ethyl acetate. The separated ethyl acetate layer and the ethyl acetate layer obtained by extraction were combined, washed with saturated brine, and dried over anhydrous magnesium sulfate. The solvent was evaporated under reduced pressure. The residue was purified by silica gel column chromatography to give an amine-protected compound as a colorless oil (350 mg). The colorless oil (350 mg) was dissolved in a mixed solvent of methylene chloride (5 ml) and acetonitrile (2 ml). To this solution were added 1H-tetrazole (82 mg) and dibenzyl diisopropylphosphoramidite (0.393 ml), and the mixture was stirred at room temperature for 3 hr. The reaction solution was ice-cooled, m-chloroperbenzoic acid (containing 25% water, 288 mg) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography to give the object product (400 mg) as a colorless oil.

$^1$H-NMR(CD$_3$OD) δ (ppm): 1.26(3H, s), 1.58-1.65(1H, m), 2.04-2.12(3H, m), 2.48-2.59(2H, m), 2.87(2H, t, J=7.5 Hz), 4.00(2H, t, J=5.9 Hz), 4.01-4.05(1H, m), 4.19-4.24(1H, m), 5.00-5.05(6H, m), 6.96(1H, d, J=8.5 Hz), 7.07-7.10(2H, m), 7.19-7.39(19H, m).

(216-2) Synthesis of phosphoric acid mono(2-amino-2-methyl-4-{4-[3-(3-trifluoromethoxyphenyl)propoxy]-3-trifluoromethylphenyl}butyl)ester (Compound 216-2)

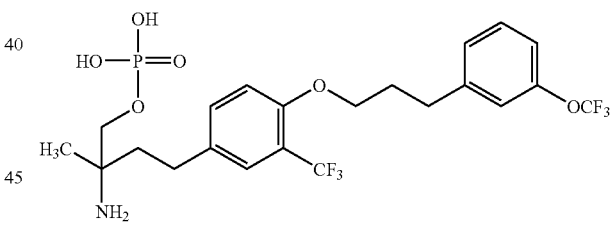

Compound 216-1 (400 mg) was dissolved in methanol (10 ml), 10% palladium carbon (200 mg) was added, and the reaction vessel was purged with hydrogen. After stirring at room temperature for 3.5 hr, the reaction vessel was purged with nitrogen, and the reaction mixture was filtered. The filtrate was concentrated, and isopropyl alcohol (5 ml) and water (10 ml) were added to the residue. The precipitated powder was collected by filtration, and washed with water to give the object product (303 mg) as a white solid.

MS(ESI)m/z: 546[M+H]

$^1$H-NMR(CD$_3$OD) δ (ppm): 1.38(3H, s), 1.82-1.91(1H, m), 1.97-2.05(1H, m), 2.06-2.13(2H, m), 2.60-2.78(2H, m), 2.87(2H, t, J=7.5 Hz), 3.88(1H, dd, J=5.2, 11.2 Hz), 3.94(1H, dd, J=5.8, 11.2 Hz), 4.02(2H, t, J=5.9 Hz), 7.02(1H, d, J=8.6 Hz), 7.05-7.11(2H, m), 7.20(1H, d, J=7.8 Hz), 7.36(1H, t, J=7.8 Hz), 7.43(1H, dd, J=8.6, 1.5 Hz), 7.48(1H, brs).

Example 217

2-amino-2-ethyl-4-{4-[3-(4-trifluoromethoxyphenyl)propoxy]-3-trifluoromethylphenyl}butanol hydrochloride (217-1) Synthesis of (1-ethyl-1-(methoxymethoxy)methyl-3-{4-[3-(4-trifluoromethoxyphenyl)propoxy]-3-trifluoromethylphenyl}propyl)carbamic acid t-butyl ester (Compound 217-1)

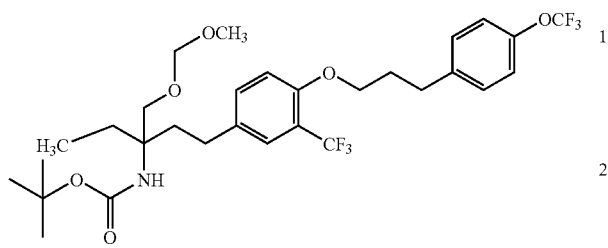

To a solution of compound 30-4 (400 mg) in N,N-dimethylformamide (10 ml) were added potassium carbonate (358 mg) and compound 52-3 (292 mg), and the mixture was stirred at 80° C. for 1 hr. The reaction mixture was added to water, and the mixture was extracted with ethyl acetate. The organic layer was washed with saturated brine and dried over anhydrous magnesium sulfate. The solvent was evaporated under reduced pressure to give the object product (640 mg) as a yellow oil.

$^1$H-NMR(CDCl$_3$) δ (ppm): 0.90(3H, t, J=7.5 Hz), 1.45(9H, s), 1.68-1.84(2H, m), 1.92-1.98(2H, m), 2.06-2.13(2H, m), 2.53-2.58(2H, m), 2.84(2H, t, J=7.5 Hz), 3.39(3H, s), 3.57 (1H, d, J=9.8 Hz), 3.64(1H, d, J=9.8 Hz), 3.98(2H, t, J=5.9 Hz), 4.62(1H, brs). 4.64(2H, s), 6.84(1H, d, J=8.6 Hz), 7.11-7.15(2H, m), 7.21(2H, d, J=8.6 Hz), 7.26-7.28(1H, m), 7.38 (1H, d, J=1.5 Hz).

(217-2) Synthesis of 2-amino-2-ethyl-4-{4-[3-(4-trifluoromethoxyphenyl)propoxy]-3-trifluoromethylphenyl}butanol hydrochloride (Compound 217-2)

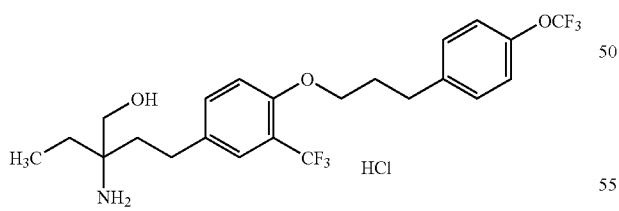

To a solution of compound 217-1 (640 mg) in ethanol (15 ml) was added concentrated hydrochloric acid (1.5 ml), and the mixture was stirred at 80° C. for 1 hr. The reaction mixture was concentrated, and the residue was washed with diisopropyl ether to give a white powder. The white powder was purified by HPLC, the obtained residue was converted to hydrochloride by adding hydrogen chloride containing ether (1 mol/l, 15 ml), and the precipitate was collected by filtration and dried to give the object product (370 mg) as a white powder.

MS(ESI)m/z: 480[M+H]

$^1$H-NMR(DMSO-d$_6$) δ (ppm): 0.90(3H, t, J=7.5 Hz), 1.60-1.68(2H, m), 1.71-1.78(2H, m), 1.99-2.06(2H, m), 2.60(2H, t, J=8.6 Hz), 2.78(2H, t, J=7.5 Hz), 3.48(2H, brs), 4.05(2H, t, J=6.0 Hz), 5.50(1H, t, J=4.7 Hz), 7.17(1H, d, J=8.6 Hz), 7.27-7.34(4H, m), 7.47(1H, d, J=8.6 Hz), 7.49(1H, brs), 7.94 (3H, brs).

Example 218

(R)-2-amino-2-ethyl-4-{4-[3-(4-trifluoromethoxyphenyl)propoxy]-3-trifluoromethylphenyl}butanol hydrochloride (218-1) Synthesis of (R)-(1-ethyl-1-(methoxymethoxy)methyl-3-{4-[3-(4-trifluoromethoxyphenyl)propoxy]-3-trifluoromethylphenyl}propyl)carbamic acid t-butyl ester (Compound 218-1)

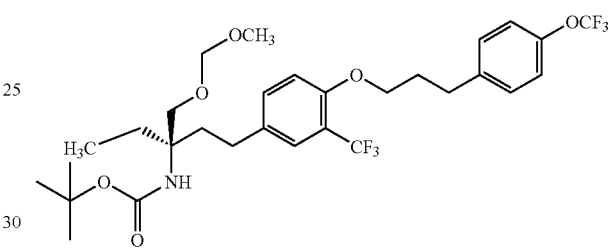

To a solution of compound 206-1-1 (300 mg) in N,N-dimethylformamide (10 ml) were added potassium carbonate (268 mg) and compound 52-3 (221 mg), and the mixture was stirred at 80° C. for 1 hr. The reaction mixture was added to water, and the mixture was extracted with ethyl acetate. The organic layer was washed with saturated brine and dried over anhydrous magnesium sulfate. The solvent was evaporated under reduced pressure to give the object product (450 mg) as a pale-yellow oil.

$^1$H-NMR(CDCl$_3$) δ (ppm): 0.90(3H, t, J=7.5 Hz), 1.45(9H, s), 1.69-1.84(2H, m), 1.92-1.98(2H, m), 2.06-2.13(2H, m), 2.53-2.58(2H, m), 2.84(2H, t, J=7.5 Hz), 3.39(3H, s), 3.57 (1H, d, J=9.8 Hz), 3.64(1H, d, J=9.8 Hz), 3.98(2H, t, J=5.8 Hz), 4.62(1H, brs), 4.64(2H, s), 6.84(1H, d, J=8.5 Hz), 7.11-7.15(2H, m), 7.21(2H, d, J=8.5 Hz), 7.26-7.28(1H, m), 7.38 (1H, d, J=1.8 Hz).

(218-2) Synthesis of (R)-2-amino-2-ethyl-4-{4-[3-(4-trifluoromethoxyphenyl)propoxy]-3-trifluoromethylphenyl}butanol hydrochloride (Compound 218-2)

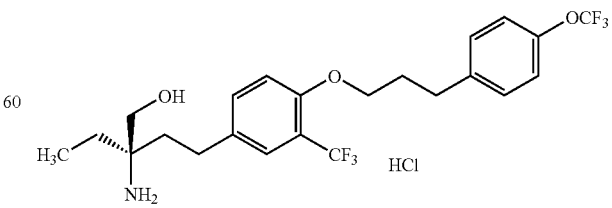

To a solution of compound 218-1 (450 mg) in ethanol (15 ml) was added concentrated hydrochloric acid (1.5 ml), and the mixture was stirred at 80° C. for 1 hr. The reaction mixture was concentrated, and the residue was washed with diisopropyl ether to give the object product (310 mg) as a white powder.

MS(ESI)m/z: 480[M+H]

$^1$H-NMR (DMSO-d$_6$) δ (ppm): 0.90(3H, t, J=7.4 Hz), 1.58-1.68(2H, m). 1.70-1.78(2H, m), 1.99-2.06(2H, m), 2.57-2.62(2H, m), 2.78(2H, t, J=7.5 Hz), 3.46(2H, brs), 4.05(2H, t, J=6.0 Hz), 5.50(1H, t, J=4.9 Hz), 7.17(1H, d, J=8.6 Hz), 7.27-7.34(4H, m), 7.46(1H, d, J=8.6 Hz), 7.49 (1H, brs), 7.90 (3H, brs).

Example 219

2-amino-2-ethyl-4-{4-[3-(3-trifluoromethoxyphenyl)propoxy]-3-trifluoromethylphenyl}butanol hydrochloride (219-1) Synthesis of (1-ethyl-1-(methoxymethoxy)methyl-3-{4-[3-(3-trifluoromethoxyphenyl)propoxy]-3-trifluoromethylphenyl}propyl)carbamic acid t-butyl ester (Compound 219-1)

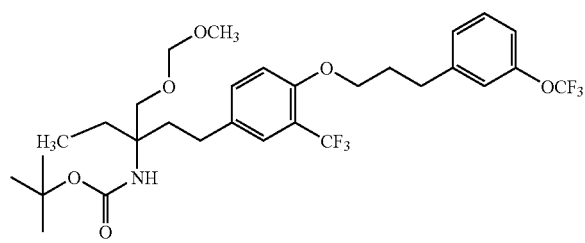

To a solution of compound 30-4 (400 mg) in N,N-dimethylformamide (10 ml) were added potassium carbonate (358 mg) and compound 58-3 (292 mg), and the mixture was stirred at 80° C. for 1 hr. The reaction mixture was added to water, and the mixture was extracted with ethyl acetate. The organic layer was washed with saturated brine and dried over anhydrous magnesium sulfate. The solvent was evaporated under reduced pressure to give the object product (640 mg) as a yellow oil.

$^1$H-NMR(CDCl$_3$) δ (ppm): 0.90(3H, t, J=7.5 Hz), 1.45(9H, s), 1.68-1.82(2H, m), 1.92-1.98(2H, m), 2.07-2.15(2H, m), 2.53-2.58(2H, m), 2.86(2H, t, J=7.5 Hz), 3.39(3H, s), 3.58 (1H, d, J=9.7 Hz), 3.64(1H, d, J=9.7 Hz), 3.98(2H, t, J=5.9 Hz), 4.61(1H, brs), 4.64(2H, s), 6.84(1H, d, J=8.5 Hz), 7.02-7.05(2H, m), 7.13(1H, d, J=7.7 Hz), 7.26-7.31(2H, m), 7.38 (1H, d, J=1.8 Hz).

(219-2) Synthesis of 2-amino-2-ethyl-4-(4-[3-(3-trifluoromethoxyphenyl)propoxy]-3-trifluoromethylphenyl}butanol hydrochloride (Compound 219-2)

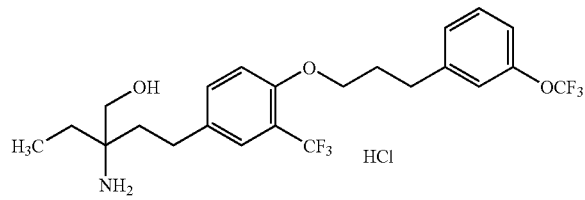

To a solution of compound 219-1 (640 mg) in ethanol (15 ml) was added concentrated hydrochloric acid (1.5 ml), and the mixture was stirred at 80° C. for 1 hr. The reaction mixture was concentrated, and the residue was washed with diethyl ether to give the object product (430 mg) as a white powder.

MS(ESI)m/z: 480[M+H]

$^1$H-NMR (DMSO-d$_6$) δ (ppm): 0.90(3H, t, J=7.5 Hz), 1.58-1.68(2H, m). 1.71-1.79(2H, m), 2.01-2.08(2H, m), 2.58-2.62(2H, m), 2.80(2H, t, J=7.5 Hz), 3.47(2H, brs), 4.04(2H, t, J=6.0 Hz), 5.50(1H, brs), 7.15-7.18(3H, m), 7.25(1H, d, J=7.6 Hz), 7.40-7.50(3H, m), 7.93(3H, brs).

Example 220

(R)-2-amino-2-ethyl-4-(4-[3-(3-trifluoromethoxyphenyl)propoxy]-3-trifluoromethylphenyl}butanol hydrochloride (220-1) Synthesis of (R)-(1-ethyl-1-(methoxymethoxy)methyl-3-(4-[3-(3-trifluoromethoxyphenyl)propoxy]-3-trifluoromethylphenyl}propyl)carbamic acid t-butyl ester (Compound 220-1)

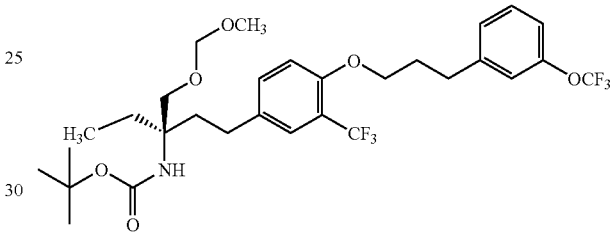

To a solution of compound 206-1-1 (300 mg) in N,N-dimethylformamide (10 ml) were added potassium carbonate (268 mg) and compound 58-3 (221 mg), and the mixture was stirred at 80° C. for 1 hr. The reaction mixture was added to water, and the mixture was extracted with ethyl acetate. The organic layer was washed with saturated brine and dried over anhydrous magnesium sulfate. The solvent was evaporated under reduced pressure to give the object product (450 mg) as a colorless to oil.

$^1$H-NMR(CDCl$_3$) δ (ppm): 0.90(3H, t, J=7.5 Hz), 1.45(9H, s), 1.68-1.83(2H, m), 1.92-1.98(2H, m), 2.07-2.15(2H, m), 2.53-2.58(2H, m), 2.86(2H, t, J=7.5 Hz), 3.40(3H, s), 3.58 (1H, d, J=9.7 Hz), 3.64(1H, d, J=9.7 Hz), 3.98(2H, t, J=5.9 Hz), 4.61(1H, brs), 4.64(2H, s), 6.84(1H, d, J=8.5 Hz), 7.02-7.05(2H, m), 7.13(1H, d, J=7.8 Hz), 7.26-7.30(2H, m), 7.38 (1H, d, J=1.8 Hz).

(220-2) Synthesis of (R)-2-amino-2-ethyl-4-{4-[3-(3-trifluoromethoxyphenyl)propoxy]-3-trifluoromethylphenyl}butanol hydrochloride (Compound 220-2)

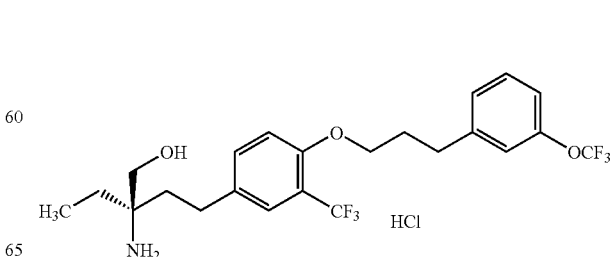

To a solution of compound 220-1 (450 mg) in ethanol (15 ml) was added concentrated hydrochloric acid (1.5 ml), and the mixture was stirred at 80° C. for 1 hr. The reaction mixture was concentrated, and the residue was washed with diethyl ether to give the object product (350 mg) as a white powder.

MS(ESI)m/z: 480[M+H]

$^1$H-NMR (DMSO-$d_6$) δ (ppm): 0.90(3H, t, J=7.5 Hz), 1.58-1.68(2H, m). 1.71-1.79(2H, m), 2.01-2.08(2H, m), 2.57-2.62(2H, m), 2.80(2H, t, J=7.5 Hz), 3.47(2H, brs), 4.04(2H, t, J=6.0 Hz), 5.49(1H, t, J=4.8 Hz), 7.15-7.18(3H, m), 7.25(1H, d, J=7.6 Hz), 7.40-7.49(3H, m), 7.91(3H, brs).

Example 221 phosphoric acid mono(2-amino-2-ethyl-4-{4-[3-(4-trifluoromethoxyphenyl)propoxy]-3-trifluoromethylphenyl}butyl)ester (221-1) Synthesis of (1-di(t-butyl)phosphoryloxymethyl-1-ethyl-3-{4-[3-(4-trifluoromethoxyphenyl)propoxy]-3-trifluoromethylphenyl}propyl)carbamic acid t-butyl ester (Compound 221-1)

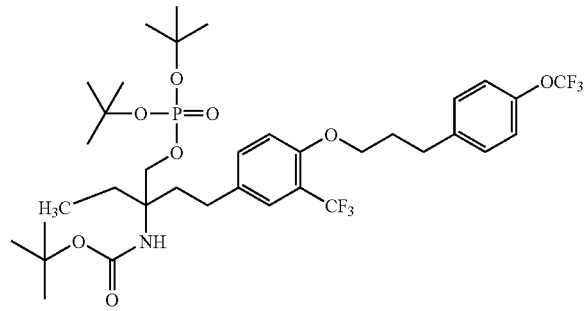

To a solution of compound 217-2 (290 mg) in methanol (10 ml) were added triethylamine (0.237 ml) and di-t-butyl-dicarbonate (244 mg), and the mixture was stirred at room temperature for 21 hr. Furthermore, to the reaction mixture was added di-t-butyl-dicarbonate (122 mg), and the mixture was stirred at room temperature for 18 hr. Water was added to the reaction mixture, and the mixture was extracted with ethyl acetate. The organic layer was washed with saturated brine and dried over anhydrous magnesium sulfate. The solvent was evaporated under reduced pressure. The obtained residue was purified by silica gel column chromatography to give an amine-protected compound as a colorless oil (290 mg). The colorless oil (290 mg) was dissolved in a mixed solvent of methylene chloride (5 ml) and acetonitrile (2 ml). To this solution were added 1H-tetrazole (70 mg) and di-t-butyl diethylphosphoramidite (0.299 ml), and the mixture was stirred at room temperature for 2 hr. The reaction solution was ice-cooled, t-butyl hydroperoxide-containing decane solution (5-6M, 0.300 ml) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography to give the object product (370 mg) as a colorless oil.

$^1$H-NMR(CD$_3$OD) δ (ppm): 0.91(3H, t, J=7.4 Hz), 1.45 (9H, s), 1.50(9H, s), 1.51(9H, s), 1.65-1.83(3H, m), 1.87-2.01 (1H, m), 2.07-2.12(2H, m), 2.60(2H, t, J=8.5 Hz), 2.85(2H, t, J=7.5 Hz), 4.02(2H, t, J=5.9 Hz), 4.05-4.15(2H, m), 7.01(1H, d, J=8.6 Hz), 7.17(2H, d, J=8.2 Hz), 7.29(2H, d, J=8.6 Hz), 7.36(1H, J=8.6 Hz), 7.40(1H, brs).

(221-2) Synthesis of phosphoric acid mono(2-amino-2-ethyl-4-{4-[3-(4-trifluoromethoxyphenyl)propoxy]-3-trifluoromethylphenyl)butyl)ester (Compound 221-2)

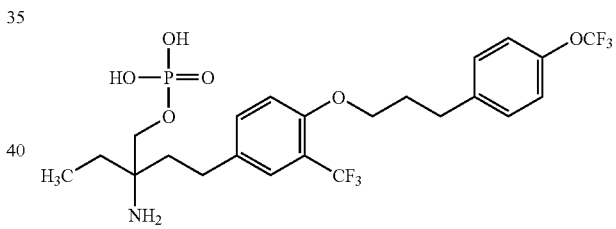

Compound 221-1 (370 mg) was dissolved in methylene chloride (6 ml), hydrogen chloride containing dioxane (4 mol/l, 3 ml) was added, and the mixture was stirred at room temperature for 3.5 hr. The solvent was concentrated under reduced pressure, and methanol (3 ml), diethyl ether (3 ml) and propylene oxide (5 ml) were added to the residue. The precipitated powder was collected by filtration, and washed with ethyl acetate and diethyl ether to give the object product (47 mg) as a white solid.

MS(ESI)m/z: 560[M+H]

$^1$H-NMR(CD$_3$OD) δ (ppm): 1.03(3H, t, J=7.5 Hz), 1.72-2.01(4H, m), 2.06-2.13(2H, m), 2.57-2.75(2H, m), 2.86(2H, t, J=7.5 Hz), 3.89-3.97(2H, m), 4.03(2H, t, J=5.8 Hz), 7.05 (1H, d, J=8.5 Hz), 7.17(2H, d, J=8.2 Hz), 7.29(2H, d, J=8.5 Hz), 7.44(1H, d, J=8.5 Hz), 7.47(1H, brs).

Example 222

(R)-phosphoric acid mono(2-amino-2-ethyl-4-{4-[3-(4-trifluoromethoxyphenyl)propoxy]-3-trifluoromethylphenyl}butyl)ester (222-1) Synthesis of (R)-(1-(dibenzyl)phosphoryloxymethyl-1-ethyl-3-{4-[3-(4-trifluoromethoxyphenyl)propoxy]-3-trifluoromethylphenyl}propyl)carbamic acid benzyl ester (Compound 222-1)

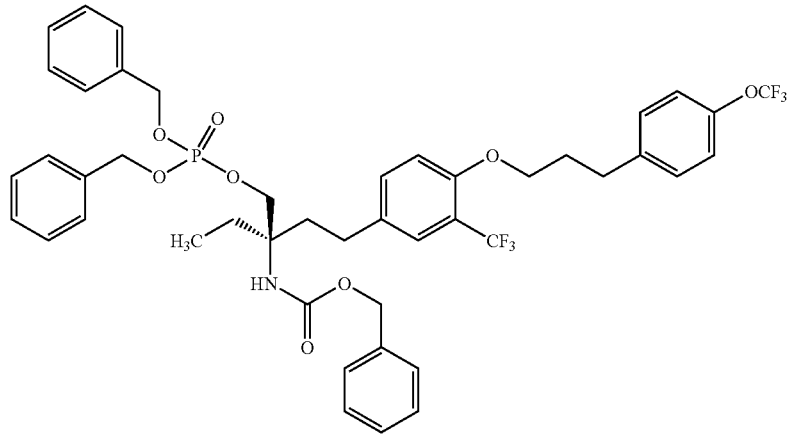

A mixture of compound 218-2 (260 mg), ethyl acetate (15 ml), saturated aqueous sodium hydrogen carbonate solution (15 ml) and benzyloxycarbonyl chloride (0.098 ml) was stirred in a two-layer state at room temperature for 16 hr. Furthermore, benzyloxycarbonyl chloride (0.182 ml) was added to the reaction mixture, and the mixture was stirred at room temperature for 20 hr. The ethyl acetate layer was separated, and the aqueous layer was extracted with ethyl acetate. The separated ethyl acetate layer and the ethyl acetate layer obtained by extraction were combined, washed with saturated brine, and dried over anhydrous magnesium sulfate. The solvent was evaporated under reduced pressure. The residue was purified by silica gel column chromatography to give an amine-protected compound as a colorless oil (160 mg). The colorless oil (160 mg) was dissolved in a mixed solvent of methylene chloride (5 ml) and acetonitrile (2 ml). To this solution were added 1H-tetrazole (37 mg) and dibenzyl diisopropylphosphoramidite (0.194 ml), and the mixture was stirred at room temperature for 3 hr. The reaction solution was ice-cooled, m-chloroperbenzoic acid (containing 25% water, 96 mg) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography to give the object product (270 mg) as a colorless oil.

$^1$H-NMR(CD$_3$OD) δ (ppm): 0.85(3H, t, J=7.5 Hz), 1.58-1.78(3H, m), 1.85-1.98(1H, m), 2.05-2.12(2H, m), 2.44-2.51(2H, m), 2.85(2H, t, J=7.5 Hz), 4.00(2H, t, J=5.9 Hz), 4.15-4.24(2H, m), 5.02-5.05(6H, m), 6.95(1H, d, J=8.5 Hz), 7.16(2H, d, J=8.3 Hz), 7.23-7.41(19H, m).

(222-2) Synthesis of (R)-phosphoric acid mono(2-amino-2-ethyl-4-{4-[3-(4-trifluoromethoxyphenyl)propoxy]-3-trifluoromethylphenyl}butyl)ester (Compound 222-2)

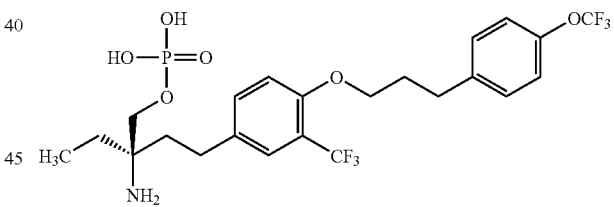

Compound 222-1 (270 mg) was dissolved in methanol (10 ml), 10% palladium carbon (150 mg) was added, and the reaction vessel was purged with hydrogen. After stirring at room temperature for 6.5 hr, the reaction vessel was purged with nitrogen, and the reaction mixture was filtered. The filtrate was concentrated, and ethanol (3 ml) and water (10 ml) were added to the residue. The precipitated powder was collected by filtration, and washed with water to give the object product (110 mg) as a white solid.

MS(ESI)m/z: 560[M+H]

$^1$H-NMR(CD$_3$OD) δ (ppm): 1.03(3H, t, J=7.3 Hz), 1.72-2.01(4H, m), 2.02-2.13(2H, m), 2.57-2.75(2H, m), 2.86(2H, t, J=7.3 Hz), 3.92(2H, brs), 4.03(2H, t, J=5.5 Hz), 7.05(1H, d, J=8.5 Hz), 7.16(2H, d, J=8.5 Hz), 7.29(2H, d, J=8.2 Hz), 7.43(1H, d, J=8.2 Hz), 7.47(1H, brs).

Example 223 phosphoric acid mono(2-amino-2-ethyl-4-{4-[3-(3-trifluoromethoxyphenyl)propoxy]-3-trifluoromethylphenyl}butyl)ester (223-1) Synthesis of (1-(dibenzyl)phosphoryloxymethyl-1-ethyl-3-{4-[3-(3-trifluoromethoxyphenyl)propoxy]-3-trifluoromethylphenyl}propyl)carbamic acid benzyl ester (Compound 223-1)

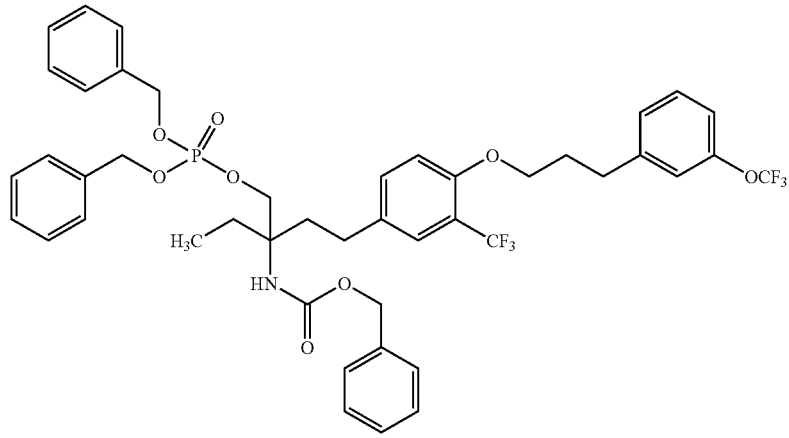

A mixture of compound 219-2 (450 mg), ethyl acetate (15 ml), saturated aqueous sodium hydrogen carbonate solution (15 ml) and benzyloxycarbonyl chloride (0.168 ml) was stirred in a two-layer state at room temperature for 16 hr. Furthermore, benzyloxycarbonyl chloride (0.182 ml) was added to the reaction mixture, and the mixture was stirred at room temperature for 23 hr. The ethyl acetate layer was separated, and the aqueous layer was extracted with ethyl acetate. The separated ethyl acetate layer and the ethyl acetate layer obtained by extraction were combined, washed with saturated brine, and dried over anhydrous magnesium sulfate. The solvent was evaporated under reduced pressure. The residue was purified by silica gel column chromatography to give an amine-protected compound as a colorless oil (360 mg). The colorless oil (360 mg) was dissolved in a mixed solvent of methylene chloride (5 ml) and acetonitrile (2 ml). To this solution were added 1H-tetrazole (63 mg) and dibenzyl diisopropylphosphoramidite (0.397 ml), and the mixture was stirred at room temperature for 3 hr. The reaction solution was ice-cooled, m-chloroperbenzoic acid (containing 25% water, 217 mg) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography to give the object product (640 mg) as a colorless oil.

$^1$H-NMR(CD$_3$OD) δ (ppm): 0.85(3H, t, J=7.5 Hz), 1.58-1.75(3H, m), 1.87-1.96(1H, m), 2.05-2.12(2H, m), 2.45-2.50 (2H, m), 2.87(2H, t, J=7.5 Hz), 3.99(2H, t, J=5.8 Hz), 4.14-4.26(2H, m), 4.99-5.02(6H, m), 6.95(1H, d, J=8.6 Hz), 7.07-7.12(2H, m), 7.19-7.38(19H, m).

(223-2) Synthesis of phosphoric acid mono(2-amino-2-ethyl-4-{4-[3-(3-trifluoromethoxyphenyl)propoxy]-3-trifluoromethylphenyl}butyl)ester (Compound 223-2)

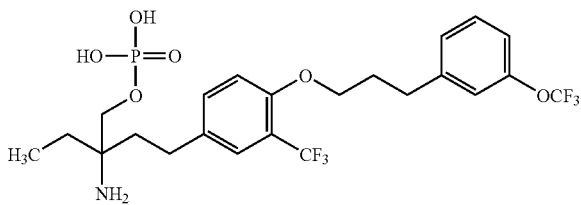

Compound 223-1 (640 mg) was dissolved in methanol (10 ml), 10% palladium carbon (300 mg) was added, and the reaction vessel was purged with hydrogen. After stirring at room temperature for 5 hr, the reaction vessel was purged with nitrogen, and the reaction mixture was filtered. The filtrate was concentrated, and ethanol (5 ml) and water (10 ml) were added to the residue. The precipitated powder was collected by filtration, and washed with water to give the object product (310 mg) as a white solid.

MS(ESI)m/z: 560[M+H]

$^1$H-NMR(CD$_3$OD) δ (ppm): 1.03(3H, t, J=7.5 Hz), 1.72-2.02(4H, m), 2.06-2.13(2H, m), 2.57-2.75(2H, m), 2.87(2H, t, J=7.5 Hz), 3.88-3.97(2H, m), 4.02(2H, t, J=5.8 Hz), 7.04 (1H, d, J=8.6 Hz), 7.05-7.11(2H, m), 7.21(1H, d, J=7.8 Hz), 7.36(1H, t, J=7.8 Hz), 7.43(1H, d, J=8.6 Hz), 7.47(1H, brs).

Example 224

(R)-phosphoric acid mono(2-amino-2-ethyl-4-{4-[3-(3-trifluoromethoxyphenyl)propoxy]-3-trifluoromethylphenyl}butyl)ester (224-1) Synthesis of (R)-(1-(dibenzyl)phosphoryloxymethyl-1-ethyl-3-{4-[3-(3-trifluoromethoxyphenyl)propoxy]-3-trifluoromethylphenyl}propyl)carbamic acid benzyl ester (Compound 224-1)

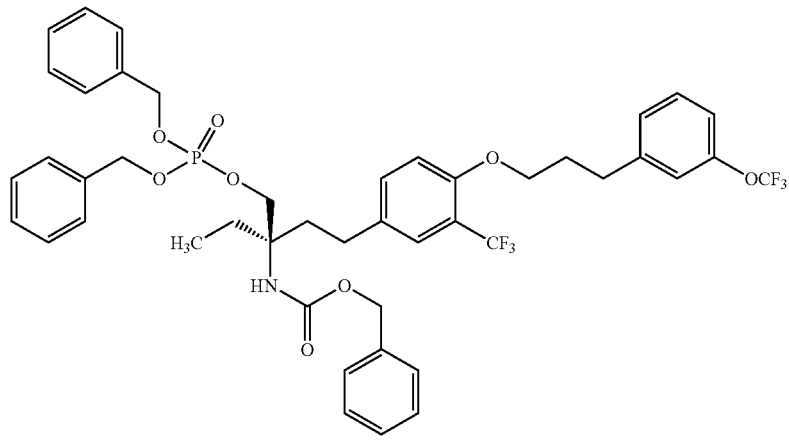

A mixture of compound 220-2 (280 mg), ethyl acetate (15 ml), saturated aqueous sodium hydrogen carbonate solution (15 ml) and benzyloxycarbonyl chloride (0.106 ml) was stirred in a two-layer state at room temperature for 18 hr. Furthermore, benzyloxycarbonyl chloride (0.050 ml) was added to the reaction mixture, and the mixture was stirred at room temperature for 2 hr. The ethyl acetate layer was separated, and the aqueous layer was extracted with ethyl acetate. The separated ethyl acetate layer and the ethyl acetate layer obtained by extraction were combined, washed with saturated brine, and dried over anhydrous magnesium sulfate. The solvent io was evaporated under reduced pressure. The residue was purified by silica gel column chromatography to give an amine-protected compound as a colorless oil (340 mg). The colorless oil (340 mg) was dissolved in a mixed solvent of methylene chloride (5 ml) and acetonitrile (2 ml). To this solution were added 1H-tetrazole (76 mg) and dibenzyl diisopropylphosphoramidite (0.403 ml), and the mixture was stirred at room temperature for 2.5 hr. The reaction solution was ice-cooled, m-chloroperbenzoic acid (containing 25% water, 200 mg) was added, and the mixture was stirred at room temperature for 30 min. Saturated aqueous sodium hydrogen carbonate solution was added to the reaction mixture, and the mixture was extracted with chloroform. The organic layer was dried over anhydrous magnesium sulfate and the solvent was evaporated under reduced pressure. The obtained residue was purified by silica gel column chromatography to give the object product (390 mg) as a colorless oil.

$^1$H-NMR(CD$_3$OD) δ (ppm): 0.85(3H, t, J=7.5 Hz), 1.58-1.75(3H, m), 1.87-1.96(1H, m), 2.05-2.12(2H, m), 2.45-2.50 (2H, m), 2.87(2H, t, J=7.5 Hz), 3.99(2H, t, J=5.9 Hz), 4.14-4.26(2H, m), 4.99-5.02(6H, m), 6.94(1H, d, J=8.5 Hz), 7.07-7.12(2H, m), 7.19-7.38(19H, m).

(224-2) Synthesis of (R)-phosphoric acid mono(2-amino-2-ethyl-4-{4-[3-(3-trifluoromethoxyphenyl)propoxy]-3-trifluoromethylphenyl}butyl)ester (Compound 224-2)

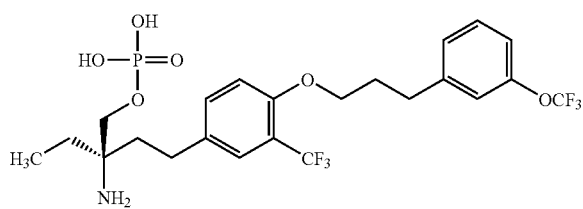

Compound 224-1 (390 mg) was dissolved in methanol (10 ml), 10% palladium carbon (200 mg) was added, and the reaction vessel was purged with hydrogen. After stirring at room temperature for 18 hr, the reaction vessel was purged with nitrogen, and the reaction mixture was filtered. The filtrate was concentrated, and ethanol (3 ml) and water (10 ml) were added to the residue. The precipitated powder was collected by filtration, and washed with water to give the object product (205 mg) as a white solid.

MS(ESI)m/z: 560[M+H]

$^1$H-NMR(CD$_3$OD) δ (ppm): 1.03(3H, t, J=7.5HZ), 1.72-2.02(4H, m), 2.06-2.13(2H, m), 2.57-2.75(2H, m), 2.87(2H, t, J=7.5 Hz), 3.88-3.97(2H, m), 4.02(2H, t, J=5.8 Hz), 7.04 (1H, d, J=8.5 Hz), 7.05-7.11(2H, m), 7.20(1H, d, J=7.8 Hz), 7.36(1H, t, J=7.8 Hz), 7.43(1H, d, J=8.5 Hz), 7.47(1H, brs).

Example 225

2-amino-2-(2-{4-[3-(3,4-dichlorophenyl)-2-propynyloxy]-3-trifluoromethylphenyl}ethyl)propane-1,3-diol hydrochloride (225-1) Synthesis of 2-amino-2-(2-{4-[3-(3,4-dichlorophenyl)-2-propynyloxy]-3-trifluoromethylphenyl}ethyl)propane-1,3-diol hydrochloride (Compound 225-1)

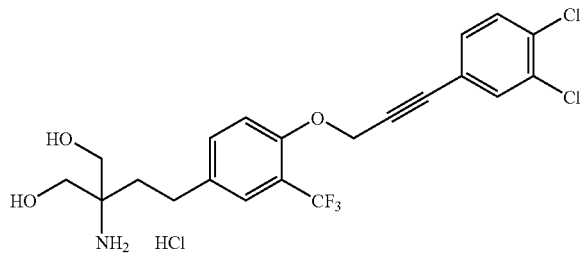

Triphenylphosphine (525 mg) was dissolved in THF (3.5 ml), azodicarboxylic acid diisopropyl ester (40% toluene solution, 1.05 ml) and compound 38-1 (402 mg) were added under ice-cooling and the mixture was stirred at room temperature for 1.5 hr. Reference Example compound 2-6 (420 mg) was added, and the mixture was stirred at room temperature for one day. Water was added to the reaction mixture, and the mixture was extracted with ethyl acetate, washed with saturated brine, and dried over anhydrous sodium sulfate. The solvent was evaporated under reduced pressure, and the residue was crudely purified by silica gel column chromatography (hexane:ethyl acetate). The obtained colorless oil was dissolved in 2M hydrochloric acid-ethanol solution (5 ml), and the mixture was stirred at 50° C. for 3.5 hr. The reaction mixture was concentrated, the residue was purified by HPLC, the obtained residue was converted to hydrochloride by the addition of hydrogen chloride containing ethyl acetate (4 mol/l, 2 ml), and the precipitate was collected by filtration and dried to give the object product (15 mg) as a white powder.

MS (ESI)m/z: 462 [M+H]

$^1$H-NMR (DMSO-$d_6$) δ (ppm): 1.74-1.79(2H, m), 2.59-2.64(2H, m), 3.51(4H, d, J=5.0 Hz), 5.21(2H, s), 5.39(2H, t, J=5.0 Hz), 7.37(1H, d, J=9.2 Hz), 7.43(1H, dd, J=8.1, 1.6 Hz), 7.50-7.51(2H, m), 7.67(1H, d, J=8.3 Hz), 7.74(1H, d, J=1.6 Hz), 7.67(3H, brs).

Example 226

2-amino-2-{2-[4-(3-phenylbutoxy)-3-trifluoromethylphenyl]ethyl}propane-1,3-diol hydrochloride (226-1) Synthesis of (2,2-dimethyl-5-{2-[4-(3-phenylbutoxy)-3-trifluoromethylphenyl]ethyl}-1,3-dioxan-5-yl)carbamic acid t-butyl ester (Compound 226-1)

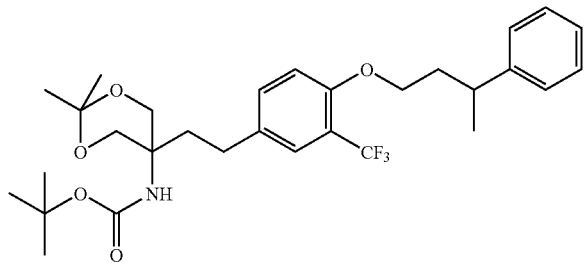

Triphenylphosphine (525 mg) was dissolved in THF (3.5 ml), azodicarboxylic acid diisopropyl ester (40% toluene solution, 1.05 ml) and 3-phenyl-1-butanol (0.24 ml) were added under ice-cooling and the mixture was stirred at room temperature for 30 min. Reference Example compound 2-6 (420 mg) was added, and the mixture was stirred at room temperature for one day. Water was added to the reaction mixture, and the mixture was extracted with ethyl acetate, washed with saturated brine, and dried over anhydrous sodium sulfate. The solvent was evaporated under reduced pressure, and the residue was purified by silica gel column chromatography (hexane:ethyl acetate) to give the object product (425 mg) as a white powder.

$^1$H-NMR(DMSO-$d_6$) δ (ppm): 1.25(3H, d, J=7.0 Hz), 1.31 (3H, s), 1.32(3H, s), 1.39(9H, s), 1.89-2.06(4H, m), 2.43-2.47 (2H, m), 2.94-2.99(1H, m), 3.65(2H, d, J=11.7 Hz), 3.79-3.88 (3H, m), 3.96-4.01(1H, m), 6.64(1H, brs), 7.04(1H, d, J=8.5 Hz), 7.16-7.22(3H, m), 7.28(2H, t, J=7.4 Hz), 7.33(1H, d, J=8.6 Hz), 7.37(1H, s).

(226-2) Synthesis of 2-amino-2-12-[4-(3-phenylbutoxy)-3-trifluoromethylphenyl]ethyl}propane-1,3-diol hydrochloride (Compound 226-2)

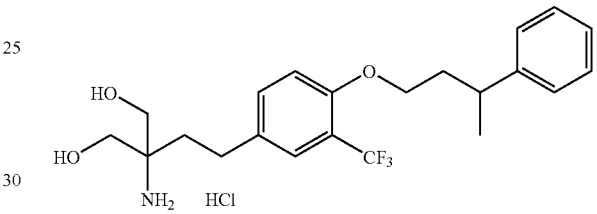

Compound 226-1 (425 mg) was dissolved in 2M hydrochloric acid-ethanol solution (5 ml) and the mixture was stirred at 50° C. for 4 hr. The reaction mixture was concentrated, and the residue was washed with diethyl ether to give the object product (120 mg) as a white powder.

MS (ESI)m/z: 412 [M+H]

$^1$H-NMR(DMSO-$d_6$) δ (ppm): 1.25(3H, d, J=7.0 Hz), 1.73-1.77(2H, m), 1.91-2.07(2H, m), 2.57-2.62(2H, m), 2.92-3.01(1H, m), 3.51(4H, d, J=5.2 Hz), 3.80-3.85(1H, m), 3.97-4.02(1H, m), 5.40(2H, t, J=5.2 Hz), 7.07(1H, d, J=8.6 Hz), 7.16-7.22(3H, m), 7.27-7.31(2H, m), 7.40(1H, dd, J=8.6, 1.6 Hz), 7.46(1H, d, J=1.8 Hz), 7.85(3H, brs).

Example 227

2-amino-2-(2-[4-(3-phenylpropylthio)-3-trifluoromethylphenyl]ethyl}propane-1,3-diol hydrochloride (227-1) Synthesis of {2,2-dimethyl-5-[2-(4-trifluoromethanesulfonyloxy-3-trifluoromethylphenyl)ethyl]-1,3-dioxan-5-yl}carbamic acid t-butyl ester (Compound 227-1)

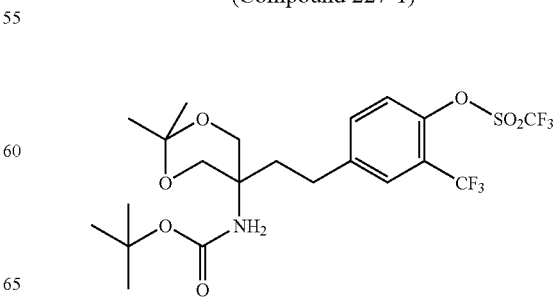

To a solution of Reference Example compound 2-6 (2.00 g) in methylene chloride (30 ml) was added pyridine(1.85 ml), a solution of trifluoromethanesulfonic anhydride (0.963 ml) in methylene chloride (5 ml) was added dropwise under ice-cooling, and the mixture was stirred under ice-cooling for 5 hr. Furthermore, a solution of trifluoromethanesulfonic anhydride (0.482 ml) in methylene chloride (3 ml) was added dropwise under ice-cooling, and the mixture was stirred under ice-cooling for 2 hr. To the reaction mixture was added saturated aqueous sodium hydrogen carbonate solution, and the mixture was extracted with methylene chloride, washed with saturated brine, and dried over anhydrous sodium sulfate. The solvent was evaporated under reduced pressure. The obtained residue was purified by silica gel column chromatography to give the object product (2.46 g) as a pale-yellow solid.

$^1$H-NMR(CDCl$_3$) δ (ppm): 1.44(3H, s), 1.45(3H, s), 1.47 (9H, s), 1.91-2.04(2H, m), 2.62-2.67(2H, m), 3.72(2H, d, J=11.7 Hz), 3.89(2H, d, J=11.7 Hz), 5.04(1H, brs), 7.39(1H, d, J=8.6 Hz), 7.47(1H, dd, J=8.6, 1.7 Hz), 7.55(1H, d, J=1.7 Hz).

(227-2) Synthesis of 2-amino-2-{2-[4-(3-phenylpropylthio)-3-trifluoromethylphenyl]ethyl}propane-1,3-diol hydrochloride (Compound 227-2)

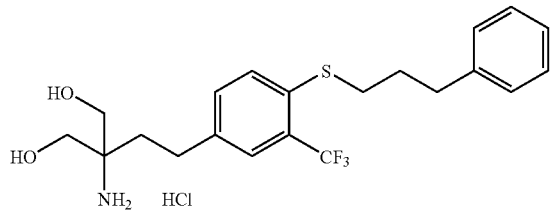

To a solution of 3-phenylpropylbromide (1.08 g) in ethanol (8 ml) was added sodium hydrosulfide (0.871 g), and the mixture was stirred at room temperature for 20 hr. Water was added to the reaction mixture, extracted with diethyl ether, washed with saturated brine, and dried over anhydrous magnesium sulfate. The solvent was evaporated under reduced pressure to give 3-phenylpropanethiol. To a solution of the obtained 3-phenylpropanethiol in dioxane (15 ml) were added compound 227-1 (500 mg), diisopropylamine (0.327 ml), 4,5-bis(diphenylphosphino)-9,9-dimethylxanthene (Xantphos) (27 mg) And tris(dibenzylideneacetone)palladium(0)-chloroform adduct (24 mg), and the mixture was stirred at 120° C. for 2 days. Water was added to the reaction mixture, and the mixture was extracted with ethyl acetate, washed with saturated brine, and dried over anhydrous magnesium sulfate. The solvent was evaporated under reduced pressure. The obtained residue was purified by silica gel column chromatography to give a mixture of (2,2-dimethyl-5-{2-[4-(3-phenylpropylthio)-3-trifluoromethylphenyl]ethyl}-1,3-dioxan-5-yl)carbamic acid t-butyl ester and a starting material (Compound 227-1). Again, 3-phenylpropanethiol in the same amount as the above was prepared, and the above-mentioned operation was repeated using the mixture of (2,2-dimethyl-5-{2-[4-(3-phenylpropylthio)-3-trifluoromethylphenyl]ethyl}-1,3-dioxan-5-yl)carbamic acid t-butyl ester and the starting material obtained above instead of compound 227-1 to give (2,2-dimethyl-5-{2-[4-(3-phenylpropylthio)-3-trifluoromethylphenyl]ethyl}-1,3-dioxan-5-yl)carbamic acid t-butyl ester as a pale-yellow oil. The pale-yellow oil was dissolved in ethanol (15 ml), concentrated hydrochloric acid (1.5 ml) was added, and the mixture was stirred at 80° C. for 1 hr. The reaction mixture was concentrated, the residue was washed with diethyl ether to give a pale-yellow solid. The pale-yellow solid was purified by HPLC, the obtained residue was converted to hydrochloride by adding hydrogen chloride containing ether (1 mol/l, 15 ml), and the precipitate was collected by filtration and dried to give the object product (90 mg) as a white powder.

MS(ESI)m/z: 414[M+H]

$^1$H-NMR(DMSO-d$_6$) δ (ppm): 1.75-1.80(2H, m), 1.82-1.88(2H, m), 2.63-2.72(4H, m), 3.03(2H, t, J=7.2 Hz), 3.52 (4H, d, J=5.0 Hz), 5.41(2H, t, J=5.2 Hz), 7.16-7.20(3H, m), 7.25-7.31(2H, m), 7.46(1H, d, J=8.1 Hz), 7.54(1H, d, J=8.1 Hz), 7.59(1H, d, J=0.9 Hz), 7.87(3H, brs).

Example 228

2-amino-2-(2-{4-[3-(3-methylphenyl)-2-propynyloxy]-3-trifluoromethylphenyl}ethyl)propane-1,3-diol hydrochloride (228-1) Synthesis of 3-(3-methylphenyl)-2-propyne-1-ol (Compound 228-1)

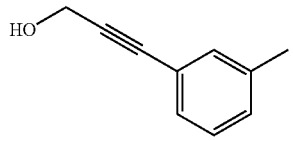

A mixture of 3-methyliodobenzene (25.1 g), copper(I) iodide (440 mg), triphenylphosphine (1.50 g), tris(dibenzylideneacetone)dipalladium(0) chloroform adduct (2.39 g), propargyl alcohol (7.50 ml), diisopropylethylamine (80.0 ml) and tetrahydrofuran (230 ml) was stirred at room temperature for 10 hr. The reaction mixture was added to water, and the mixture was extracted with ethyl acetate, washed with saturated brine, and dried over anhydrous sodium sulfate. The solvent was evaporated under reduced pressure. The residue was purified by silica gel column chromatography (hexane: ethyl acetate) to give the object product (8.6 g) as a brown oil.

$^1$H-NMR(DMSO-d$_6$) δ (ppm): 2.29(3H, s), 4.29(2H, d, J=6.1 Hz), 5.32(1H, t, J=6.1 Hz), 7.17-7.28(4H, m).

(228-2) Synthesis of 2-amino-2-(2-{4-[3-(3-methylphenyl)-2-propynyloxy]-3-trifluoromethylphenyl}ethyl)propane-1,3-diol hydrochloride (Compound 228-2)

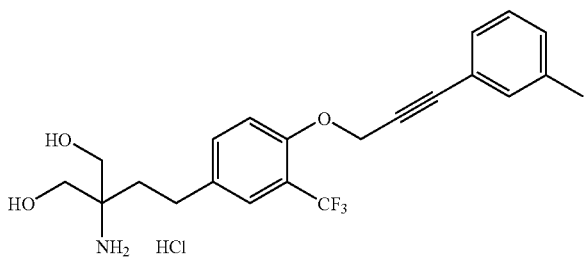

triphenylphosphine (525 mg) was dissolved in THF (3.5 ml), azodicarboxylic acid diisopropyl ester (40% toluene solution, 1.05 ml) and compound 228-1 (293 mg) were added under ice-cooling and the mixture was stirred at room temperature for 20 min. Reference Example compound 2-6 (420 mg) was added, and the mixture was stirred at room temperature for 4 hr. Water was added to the reaction mixture, and the mixture was extracted with ethyl acetate, washed with saturated brine, and dried over anhydrous sodium sulfate. The solvent was evaporated under reduced pressure, and the residue was crudely purified by silica gel columnchromatography (hexane:ethyl acetate). The obtained yellow oil was dissolved in 2M hydrochloric acid-ethanol solution (10 ml), and the mixture was stirred at 50° C. for 3 hr. The reaction mixture was concentrated, and the residue was washed with diethyl ether to give the object product (230 mg) as a white powder.

MS(ESI)m/z: 408[M+H]

$^1$H-NMR(DMSO-$d_6$) δ (ppm): 1.74-1.79(2H, m), 2.28(3H, s), 2.59-2.63(2H, m), 3.51(4H, d, J=5.1 Hz), 5.18 (2H, s), 5.40(2H, t, J=5.2 Hz), 7.21-7.30(4H, m), 7.37(1H, d, J=9.1 Hz), 7.50-7.52(2H, m), 7.78(3H, brs).

Example 229

2-amino-4-{4-[3-(3-methylphenyl)-2-propynyloxy]-3-trifluoromethylphenyl}-2-(phosphoryloxymethyl)butanol (229-1) Synthesis of 4-di(t-butyl)phosphoryloxymethyl-2-methyl-4-(2-{4-[3-(3-methylphenyl)-2-propynyloxy]-3-trifluoromethylphenyl}ethyl)-2-oxazoline (Compound 229-1)

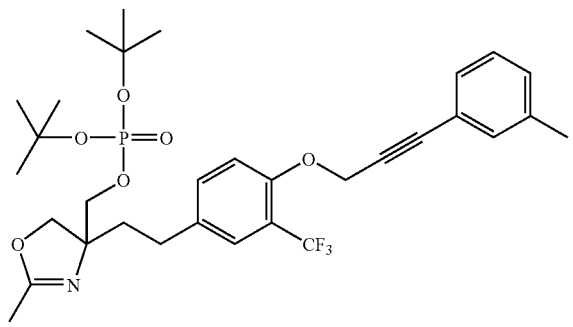

To a solution of compound 228-2 (170 mg) in N,N-dimethylformamide (3.8 ml) were added N,N-diisopropylethylamine (0.20 ml) and trimethyl orthoacetate (0.10 ml), and the mixture was stirred at 120° C. for 6.5 hr. Water was added to the reaction mixture, and the mixture was extracted with ethyl acetate, washed with water and saturated brine, and dried over anhydrous sodium sulfate. The solvent was evaporated under reduced pressure. The obtained brown oil was dissolved in a mixed solvent of methylene chloride (3.8 ml) and acetonitrile (3.5 ml). To this solution were added 1H-tetrazole (67 mg) and di-t-butyl diethylphosphoramidite (0.27 ml), and the mixture was stirred at room temperature for 3 hr. 1H-Tetrazole (38 mg) and di-t-butyl diethylphosphoramidite (0.13 ml) were further added, and the mixture was stirred at room temperature for 1.5 hr. The reaction solution was ice-cooled, t-butyl hydroperoxide containing decane solution (5-6M, 0.38 ml) was added and the mixture was stirred for 30 min. Saturated aqueous sodium hydrogen carbonate solution was added to the reaction mixture, and the mixture was extracted with dichloromethane. The organic layer was dried over anhydrous sodium sulfate and the solvent was evaporated under reduced pressure. The obtained residue was purified by silica gel column chromatography (hexane:ethyl acetate) to give the object product (122 mg) as a pale-yellow oil.

$^1$H-NMR(DMSO-$d_6$) δ (ppm): 1.38(9H, s), 1.39(9H, s), 1.69-1.83(2H, m), 1.89(3H, s), 2.28(3H, s), 2.47-2.54(1H, m), 2.59-2.67(1H, m), 3.75-3.82(2H, m), 4.06-4.12(2H, m), 5.17(2H, s), 7.20-7.29(4H, m), 7.33(1H, d, J=8.5 Hz), 7.49-7.52(2H, m).

(229-2) Synthesis of 2-amino-4-{4-[3-(3-methylphenyl)-2-propynyloxy]-3-trifluoromethylphenyl}-2-(phosphoryloxymethyl)butanol (Compound 229-2)

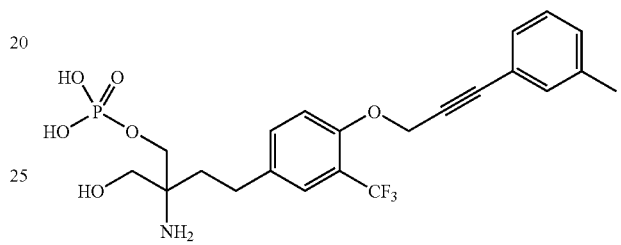

Compound 229-1 (122 mg) was dissolved in ethanol (5 ml), concentrated hydrochloric acid (1 ml) was added, and the mixture was stirred at 50° C. for 4 hr. The solvent was concentrated under reduced pressure, and methanol (1 ml) and water (3 ml) were added to the residue. The precipitated powder was collected by filtration, and washed with methanol to give the object product (50 mg) as a white powder.

MS(ESI)m/z: 488[M+H]

$^1$H-NMR(CD$_3$OD) δ (ppm): 1.94-2.00(2H, m), 2.30(3H, s), 2.64-2.77(2H, m), 3.70(2H, s), 3.97-4.05(2H, m), 5.05 (2H, s), 7.17(1H, d, J=8.2 Hz), 7.17-7.22(4H, m), 7.31(1H, d, J=9.1 Hz), 7.49-7.51(2H, m).

Example 230

2-amino-2-(2-{4-[3-(3-methylphenyl)propylthio]-3-trifluoromethylphenyl}ethyl)propane-1,3-diol hydrochloride (230-1) Synthesis of 2-amino-2-(2-{4-[3-(3-methylphenyl)propylthio]-3-trifluoromethylphenyl}ethyl)propane-1,3-diol hydrochloride (Compound 230-1)

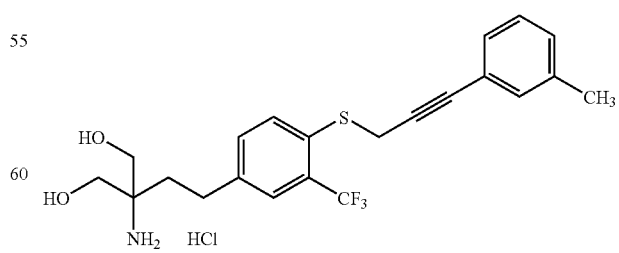

To a solution of compound 15-2 (0.967 g) in ethanol (10 ml) were added sodium hydrosulfide (0.729 g), and the mixture was stirred at room temperature for 20 hr. Water was added to the reaction mixture, and the mixture was extracted with diethyl ether, washed with saturated brine, and dried over anhydrous magnesium sulfate. The solvent was evaporated under reduced pressure to give 3-(3-methylphenyl)propanethiol. To a solution of the obtained 3-(3-methylphenyl)propanethiol in dioxane (15 ml) were added compound 227-1 (500 mg), diisopropylamine (0.327 ml), 4,5-bis(diphenylphosphino)-9,9-dimethylxanthene (Xantphos) (27 mg) and tris(dibenzylideneacetone)palladium(0)-chloroform adduct (24 mg), and the mixture was stirred at 120° C. for 2 days. Water was added to the reaction mixture, and the mixture was extracted with ethyl acetate, washed with saturated brine, and dried over anhydrous magnesium sulfate. The solvent was evaporated under reduced pressure. The obtained residue was purified by silica gel column chromatography to give a mixture of [2,2-dimethyl-5-(2-{4-[3-(3-methylphenyl)propylthio]-3-trifluoromethylphenyl}ethyl)-1,3-dioxan-5-yl]carbamic acid t-butyl ester and a starting material (compound 227-1). Again, 3-(3-methylphenyl)propanethiol in the same amount as the above was prepared, and the above-mentioned operation was repeated using the mixture of [2,2-dimethyl-5-(2-{4-[3-(3-methylphenyl)propylthio]-3-trifluoromethylphenyliethyl)-1,3-dioxan-5-yl]carbamic acid t-butyl ester and the starting material obtained above instead of compound 227-1 to give [2,2-dimethyl-5-(2-{4-[3-(3-methylphenyl)propylthio]-3-trifluoromethylphenyl}ethyl)-1,3-dioxan-5-yl]carbamic acid t-butyl ester as a pale-yellow oil. The pale-yellow oil was dissolved in ethanol (15 ml), concentrated hydrochloric acid (1.5 ml) was added, and the mixture was stirred at 80° C. for 1 hr. The reaction mixture was concentrated, the residue was washed with diethyl ether to give a pale-yellow solid. The pale-yellow solid was purified by HPLC, the obtained residue was converted to hydrochloride by adding hydrogen chloride containing ether (1 mol/l, 15 ml), and the precipitate was collected by filtration and dried to give the object product (115 mg) as a white powder.

MS(ESI)m/z: 428[M+H]0

$^1$H-NMR(DMSO-d$_6$) δ (ppm): 1.75-1.86(4H, m), 2.26(3H, s), 2.62-2.68(4H, m), 3.02(2H, t, J=7.1 Hz), 3.51 (4H, d, J=5.1 Hz), 5.39(2H, t, J=5.1 Hz), 6.94-7.01(3H, m), 7.16(1H, t, J=7.8 Hz), 7.45(1H, d, J=8.1 Hz), 7.54(1H, d, J=8.1 Hz), 7.58(1H, brs), 7.78(3H, brs).

Example 231

2-dimethylamino-2-(2-{4-[3-(3-methylphenyl)propoxy]-3-trifluoromethylphenyl}ethyl)propane-1,3-diol (231-1) Synthesis of 2-dimethylamino-2-(2-{4-[3-(3-methylphenyl)propoxy]-3-trifluoromethylphenyl}ethyl)propane-1,3-diol (Compound 231-1)

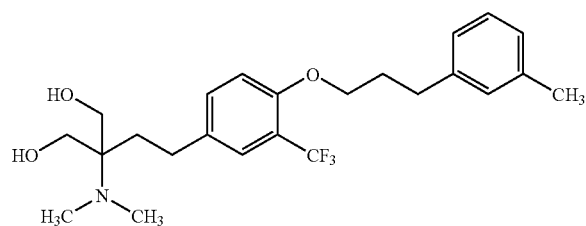

To a solution of compound 15-4 (0.470 g), 37% formaldehyde (10 ml), 30% aqueous acetic acid solution (1.5 ml) in acetonitrile (15 ml) was added sodium cyanoborohydride (0.301 g) under ice-cooling, and the mixture was stirred for 1.5 hr. To the reaction mixture was added saturated aqueous sodium hydrogen carbonate solution (30 ml), and acetonitrile was evaporated under reduced pressure. To the obtained concentrate was added saturated aqueous sodium hydrogen carbonate solution, and the mixture was extracted with ethyl acetate, washed with saturated brine, and dried over anhydrous magnesium sulfate. The solvent was evaporated under reduced pressure to give a colorless oil. The colorless oil was purified by HPLC to give the object product (210 mg) as a colorless oil.

MS(ESI)m/z: 440[M+H]

$^1$H-NMR(DMSO-d$_6$) δ (ppm): 1.58-1.63(2H, m), 1.95-2.03(2H, m), 2.26(3H, s), 2.33(6H, s), 2.52-2.57(2H, m), 2.70(2H, t, J=7.5 Hz), 3.44(2H, d, J=11.0 Hz), 3.52(2H, d, J=11.0 Hz). 4.03(2H, t, J=6.0 Hz), 4.37(2H, brs), 6.96-7.01 (3H, m), 7.11(1H, d, J=9.0 Hz), 7.16(1H, d, J=7.4 Hz), 7.39-7.41(2H, m).

Example 232

2-amino-2-(2-{4-[3-(3,4-dichlorophenyl)propylthio]-3-trifluoromethylphenyl}ethyl)propane-1,3-diol hydrochloride (232-1) Synthesis of 2-amino-2-(2-{4-[3-(3,4-dichlorophenyl)propylthio]-3-trifluoromethylphenyl}ethyl)propane-1,3-diol hydrochloride (Compound 232-1)

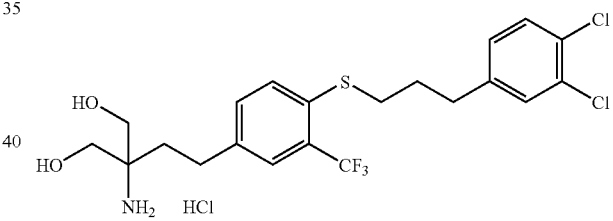

To a solution of compound 38-3 (0.500 g) in ethanol (8 ml) was added sodium hydrosulfide (0.300 g), and the mixture was stirred at room temperature for 20 hr. Water was added to the reaction mixture, and the mixture was extracted with diethyl ether, washed with saturated brine, and dried over anhydrous magnesium sulfate. The solvent was evaporated under reduced pressure to give 3-(3,4-dichlorophenyl)propanethiol. To a solution of the obtained 3-(3,4-dichlorophenyl)propanethiol in dioxane (15 ml) were added compound 227-1 (500 mg), diisopropylamine (0.327 ml), 4,5-bis(diphenylphosphino)-9,9-dimethylxanthene (Xantphos) (27 mg) and tris(dibenzylideneacetone)palladium(0)-chloroform adduct (24 mg), and the mixture was stirred at 120° C. for 2 days. Water was added to the reaction mixture, and the mixture was extracted with ethyl acetate, washed with saturated brine, and dried over anhydrous magnesium sulfate. The solvent was evaporated under reduced pressure. The obtained residue was purified by silica gel column chromatography to give a mixture of [5-(2-{4-[3-(3,4-dichlorophenyl)propylthio]-3-trifluoromethylphenyl}ethyl)-2,2-dimethyl-1,3-dioxan-5-yl]carbamic acid t-butyl ester and a starting material (compound 227-1). Again, 3-(3,4-dichlorophenyl)propanethiol in the same amount as the above was prepared, and the above-mentioned operation was repeated using the mixture of [5-(2-{4-[3-(3,4-dichlorophenyl)propylthio]-3-trifluoromethylphenyl}ethyl)-2,2-dimethyl-1,3-dioxan-5-yl]carbamic acid t-butyl ester and the starting material obtained above instead of compound 227-1 to give [5-(2-{4-[3-(3,4-dichlorophenyl)propylthio]-3-trifluoromethylphenyl}ethyl)-2,2-dimethyl-1,3-dioxan-5-yl]carbamic acid t-butyl ester as a pale-yellow solid. The pale-yellow solid was dissolved in ethanol (15 ml), concentrated hydrochloric acid (1.5 ml) was added, and the mixture was stirred at 80° C. for 1 hr. The reaction mixture was concentrated, the residue was washed with diethyl ether to give a pale-yellow solid. The pale-yellow solid was purified by HPLC, the obtained residue was converted to hydrochloride by adding hydrogen chloride containing ether (1 mol/l, 15 ml), and the precipitate was collected by filtration and dried to give the object product (65 mg) as a white powder.

MS(ESI)m/z: 482[M+H]

$^1$H-NMR(DMSO-$d_6$) δ (ppm): 1.75-1.79(2H, m), 1.80-1.89(2H, m), 2.63-2.68(2H, m), 2.71(2H, t, J=7.5 Hz), 3.02 (2H, t, J=7.2 Hz), 3.52(4H, d, J=5.0 Hz), 5.39(2H, t, J=5.0 Hz), 7.19(1H, dd, J=8.2, 1.9 Hz), 7.44-7.47(2H, m), 7.52-7.59(3H, m), 7.79(3H, brs).

Example 233

2-amino-2-(2-{4-[3-(4-trifluoromethoxyphenyl)propylthio]-3-trifluoromethylphenyl}ethyl)propane-1,3-diol hydrochloride (233-1) Synthesis of 2-amino-2-(2-(4-[3-(4-trifluoromethoxyphenyl)propylthio]-3-trifluoromethylphenyl}ethyl)propane-1,3-diol hydrochloride (Compound 233-1)

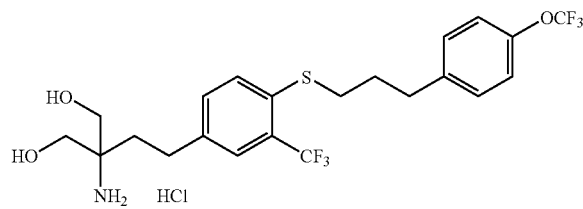

To a solution of compound 52-3 (0.500 g) in ethanol (8 ml) was added sodium hydrosulfide (0.284 g), and the mixture was stirred at room temperature for 20 hr. Water was added to the reaction mixture, extracted with diethyl ether washed with saturated brine, and dried over anhydrous magnesium sulfate. The solvent was evaporated under reduced pressure to give 3-(4-trifluoromethoxyphenyl)propanethiol. To a solution of the obtained 3-(4-trifluoromethoxyphenyl)propanethiol in dioxane (15 ml) were added compound 227-1 (500 mg), diisopropylamine (0.327 ml), 4,5-bis(diphenylphosphino)-9,9-dimethylxanthene (Xantphos) (27 mg) and tris(dibenzylideneacetone)palladium(0)-chloroform adduct (24 mg), and the mixture was stirred at 120° C. for 2 days. Water was added to the reaction mixture, and the mixture was extracted with ethyl acetate, washed with saturated brine, and dried over anhydrous magnesium sulfate. The solvent was evaporated under reduced pressure. The obtained residue was purified by silica gel column chromatography to give a mixture of [2,2-dimethyl-5-(2-{4-[3-(4-trifluoromethoxyphenyl)propylthio]-3-trifluoromethylphenyl}ethyl)-1,3-dioxan-5-yl]carbamic acid t-butyl ester and a starting material (compound 227-1). Again, 3-(4-trifluoromethoxyphenyl)propanethiol in the same amount as the above was prepared, and the above-mentioned operation was repeated using the mixture of [2,2-dimethyl-5-(2-{4-[3-(4-trifluoromethoxyphenyl)propylthio]-3-trifluoromethylphenyl}ethyl)-1,3-dioxan-5-yl]carbamic acid t-butyl ester and the starting material obtained above instead of compound 227-1 to give [2,2-dimethyl-5-(2-{4-[3-(4-trifluoromethoxyphenyl)propylthio]-3-trifluoromethylphenyl}ethyl)-1,3-dioxan-5-yl]carbamic acid t-butyl ester as a yellow oil. The yellow oil was dissolved in ethanol (15 ml), concentrated hydrochloric acid (1.5 ml) was added, and the mixture was stirred at 80° C. for 1 hr. The reaction mixture was concentrated, the residue was washed with diethyl ether to give a pale-yellow solid. The pale-yellow solid was purified by HPLC, the obtained residue was converted to hydrochloride by adding hydrogen chloride containing ether (1 mol/l, 15 ml), and the precipitate was collected by filtration and dried to give the object product (100 mg) as a white powder.

MS(ESI)m/z: 498[M+H]

$^1$H-NMR(DMSO-$d_6$) δ (ppm): 1.76-1.81(2H, m), 1.82-1.89(2H, m), 2.65-2.69(2H, m), 2.74(2H, t, J=7.5 Hz), 3.04 (2H, t, J=7.1 Hz), 3.52(4H, d, J=5.2 Hz), 5.41(2H, t, J=5.2 Hz), 7.25-7.32(4H, m), 7.47(1H, d, J=8.4 Hz), 7.56(1H, d, J=8.2 Hz), 7.59(1H, d, J=1.2 Hz), 7.86(3H, brs).

Experimental Example 1

Evaluation of Peripheral Blood Lymphocyte Number Decreasing Action in Mouse

The compound of the present invention was dissolved or suspended in 20% cyclodextrin (manufactured by Nihon Shokuhin Kako Co., Ltd.), and intraperitoneally administered to 7- to 10-week-old male BALB/cAnNCrj mice (Charles River Laboratories Japan, Inc.) at a dose of 0.001-10 mg/kg body weight. After 24 hr from the administration of the compound of the present invention, peripheral blood (about 0.3 ml) was drawn from the postcava of the mice using a tuberculin syringe (manufactured by TERUMO CORPORATION) treated with heparin sodium (manufactured by Novo Nordisk Pharma Led.) under ether anesthesia. 0.1 ml of the blood was hemolyzed using an automatic hemolysis treatment apparatus (TQ-Prep, manufactured by Beckman Coulter Inc.), and the lymphocyte number was counted using a flow cytometer (CYTOMICS FC 500, manufactured by Beckman Coulter Inc.) and according to a gating method using Flow-Count™ Fluorospheres (manufactured by Beckman Coulter Inc.), which are standard particles in known numbers, as an internal standard and forward and side scattering of laser beam as an index. The dose necessary for reducing the lymphocyte count of the vehicle group (100%) by 50% was calculated and used as $ED_{50}$ value (mg/kg body weight). The results are shown below.

TABLE 1

| Test compound | $ED_{50}$ (mg/kg body weight) |
|---|---|
| Compound 11-4 | 0.06 |
| Compound 12-4 | 0.04 |
| Compound 15-4 | 0.03 |
| Compound 38-5 | 0.07 |
| Compound 52-5 | 0.08 |
| Compound 58-5 | 0.06 |
| Compound 68-4 | 0.04 |
| Compound 89-2 | 0.04 |
| Compound 100-2 | 0.07 |

TABLE 1-continued

| Test compound | $ED_{50}$ (mg/kg body weight) |
| --- | --- |
| Compound 101-2 | 0.10 |
| Compound 204-1 | 0.005 |
| Compound 206-3 | 0.02 |

Experimental Example 2

Evaluation of Peripheral Blood Lymphocyte Number Decreasing Action in Rat

The compound of the present invention was dissolved or suspended in 0.5% hydroxypropylmethylcellulose solution (manufactured by Shin-Etsu Chemical Co., Ltd.), and orally administered to 6- to 10-week-old male F344 rats (Charles River Laboratories Japan, Inc.) at a dose of 0.001-10 mg/kg body weight. After 24 hr from the administration of the compound of the present invention, peripheral blood (about 0.5 ml) was drawn from the postcava of the rats using a tuberculin syringe (manufactured by TERUMO CORPORATION) treated with heparin sodium (manufactured by Novo Nordisk Pharma Led.) under ether anesthesia. 0.1 ml of the blood was hemolyzed using an automatic hemolysis treatment apparatus (TQ-Prep, manufactured by Beckman Coulter Inc.), and the lymphocyte number was counted using a flow cytometer (CYTOMICS FC 500, manufactured by Beckman Coulter Inc.) and according to a gating method using Flow-Count™ Fluorospheres (manufactured by Beckman Coulter Inc.), which are standard particles in known numbers, as an internal standard and forward and side scattering of laser beam as an index. The dose necessary for reducing the lymphocyte count of the vehicle group (100%) by 50% was calculated and used as $ED_{50}$ value (mg/kg body weight). The results are shown below.

TABLE 2

| Test compound | $ED_{50}$ (mg/kg body weight) |
| --- | --- |
| Compound 11-4 | 0.09 |
| Compound 12-4 | 0.11 |
| Compound 15-4 | 0.05 |
| Compound 29-1 | 0.03 |
| Compound 32-1 | 0.02 |
| Compound 38-5 | 0.07 |
| Compound 52-5 | 0.05 |
| Compound 58-5 | 0.07 |
| Compound 68-4 | 0.09 |
| Compound 89-2 | 0.06 |
| Compound 100-2 | 0.07 |
| Compound 204-1 | 0.03 |
| Compound 206-3 | 0.05 |
| Compound 218-2 | 0.03 |
| Compound 220-2 | 0.03 |

Experimental Example 3

Action on Heart Rate in Rat

Male Crl:CD(SD) rats were anesthetized by intraperitoneal administration of Nembutal (manufactured by Dainippon Sumitomo Pharma Co., Ltd.), and a pressure sensor connected to a telemetry transmitter (TL11M2-C50-PTX, manufactured by Data Sciences International) was inserted into the abdominal aorta and a transmitter was subcutaneously placed in the abdomen. The blood pressure and heart rate data were recorded by an analysis software (Dataquest A.R.T., manufactured by Data Sciences International) via a receiver (RPC-1, manufactured by Data Sciences International). After confirmation of recovery of circadian rhythm of the heart rate, the rats were subjected to the experiment. The compound of the present invention was suspended in 0.5% hydroxypropylmethylcellulose (manufactured by Shin-Etsu Chemical Co., Ltd.) and orally administered. The heart rate was measured from 72 hr before the administration to 24 hr after the administration. Compound 11-4, compound 12-4, compound 15-4, compound 38-5 and compound 52-5 did not reduce the heart rate of the rats up to the dose of 30 mg/kg to body weight. Compound 204-1 did not reduce the heart rate of the rats up to the dose of 10 mg/kg body weight.

Experimental Example 4

Action on Heart Rate in Rat Under Anesthesia

Male Sprague-Dawley (IGS) rats were anesthetized by intraperitoneal administration of Nembutal (manufactured by Dainippon Sumitomo Pharma Co., Ltd.), and fixed at the dorsal position. Electrodes were mounted on four limbs, and the electrocardiogram was measured according to Standard Limb Lead II using an electrocardiogram amplifier (AC-601G, manufactured by NIHON KOHDEN CORPORATION). With the electrocardiographic wave as a trigger, the heart rate was measured with an instantaneous heart rate unit (AT-601G, manufactured by NIHON KOHDEN CORPORATION). The test compound was dissolved in 20% cyclodextrin (manufactured by Nihon Shokuhin Kako Co., Ltd.) and intravenously administered at a dose of 0.001-10 mg/kg body weight over 30 sec. The heart rate was measured before administration, and 1, 2, 3, 4, 5, 10 and 15 minutes after the administration. Compound 132-2, compound 153-2, compound 158-2, compound 168-2, compound 192-2, compound 193-2, compound 209-2, compound 221-2 and compound 223-2 did not reduce the heart rate of the rat by 20% or more up to the dose of 0.03 mg/kg body weight as compared to the value before administration.

From the results of the above-mentioned Experimental Examples 1 and 2, since the compound of the present invention has a superior peripheral blood lymphocyte decrease action, it is expected to be superior in the immunosuppressive action, rejection suppressive action or allergy suppressive action, and effective for the treatment or prophylaxis of autoimmune diseases; prophylaxis or suppression of resistance or acute rejection or chronic rejection in transplantation of an organ or tissue; treatment or prophylaxis of graft vs host (GvH) disease caused by bone marrow transplantation; or treatment or prophylaxis of an allergic disease. From the results of the above-mentioned Experimental Example 3 and Experimental Example 4, moreover, the compound of the present invention is considered to show reduced side effects such as bradycardia and the like.

This application is based on a patent application No. 2007-157128 filed in Japan, the contents of which are incorporated in full herein by this reference.

The invention claimed is:
1. An amine compound represented by the following formula (I)

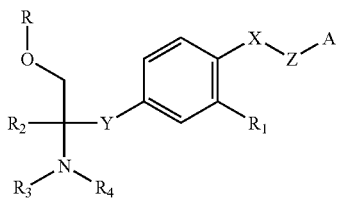

wherein R is a hydrogen atom or $P(=O)(OH)_2$,
X is an oxygen atom or a sulfur atom,
Y is —$CH_2CH_2$— or —CH=CH—,
Z is alkylene having 1 to 5 carbon atoms, alkenylene having 2 to 5 carbon atoms or alkynylene having 2 to 5 carbon atoms,
$R_1$ is cyano or alkyl having 1 to 4 carbon atoms, which is substituted by a halogen atom,
$R_2$ is alkyl having 1 to 4 carbon atoms, which is optionally substituted by a hydroxyl group or halogen atom,
$R_3$ and $R_4$ are optionally the same or different and each is a hydrogen atom or alkyl having 1 to 4 carbon atoms, and
A is optionally substituted aryl having 6 to 10 carbon atoms, optionally substituted heteroaryl having 5 to 10 ring-constituting atoms, which contains, as ring-constituting atom(s), 1 or 2 atoms from nitrogen atom, oxygen atom and sulfur atom, optionally substituted cycloalkyl having 3 to 7 carbon atoms, which is optionally condensed with optionally substituted benzene, or heterocycloalkyl having 5 to 7 ring-constituting atoms, which contains, as ring-constituting atom(s), optionally substituted 1 or 2 atoms from nitrogen atom and oxygen atom, or a pharmaceutically acceptable acid addition salt thereof.

2. The amine compound according to claim 1, wherein X is an oxygen atom, $R_3$ is a hydrogen atom and $R_4$ is a hydrogen atom, or a pharmaceutically acceptable acid addition salt thereof.

3. The amine compound according to claim 1, wherein A is optionally substituted aryl having 6 to 10 carbon atoms, or optionally substituted heteroaryl having 5 to 9 ring-constituting atoms, which contains, as ring-constituting atom(s), 1 or 2 atoms from sulfur atom and oxygen atom, or a pharmaceutically acceptable acid addition salt thereof.

4. The amine compound according to claim 1, wherein A is unsubstituted or when it has substituents, the number of the substituents is 1 to 3, the substituents are the same or different and each is alkyl having 1 to 4 carbon atoms, which is optionally substituted by a halogen atom; alkoxy having 1 to 4 carbon atoms, which is optionally substituted by a halogen atom; alkylthio having 1 to 4 carbon atoms; alkylsulfinyl having 1 to 4 carbon atoms; alkylsulfonyl having 1 to 4 carbon atoms; alkylcarbonyl having 2 to 5 carbon atoms; a halogen atom; cyano; nitro; cycloalkyl having 3 to 7 carbon atoms; aryl having 6 to 10 carbon atoms; aralkyloxy having 7 to 14 carbon atoms; or aryloxy having 6 to 10 carbon atoms; or alkylene having 3 or 4 carbon atoms, which is optionally substituted by oxo or a halogen atom, alkyleneoxy having 2 or 3 carbon atoms, which is optionally substituted by oxo or a halogen atom, or alkylenedioxy having 1 or 2 carbon atoms, which is optionally substituted by oxo or a halogen atom, each of which is formed by two substituents from the above in combination, or a pharmaceutically acceptable acid addition salt thereof.

5. The amine compound according to claim 1, wherein A is represented by

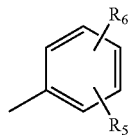

wherein $R_5$ and $R_6$ may be the same or different and each is a hydrogen atom, alkyl having 1 to 4 carbon atoms, which is optionally substituted by a halogen atom, alkoxy having 1 to 4 carbon atoms, which is optionally substituted by a halogen atom or a halogen atom, or a pharmaceutically acceptable acid addition salt thereof.

6. The amine compound according to claim 1, wherein Z is trimethylene, or a pharmaceutically acceptable acid addition salt thereof.

7. The amine compound according to claim 1, wherein $R_1$ is trifluoromethyl, or a pharmaceutically acceptable acid addition salt thereof.

8. The amine compound according to claim 1, wherein $R_2$ is hydroxymethyl, or a pharmaceutically acceptable acid addition salt thereof.

9. The amine compound according to claim 1, wherein R is a hydrogen atom, or a pharmaceutically acceptable acid addition salt thereof.

10. The amine compound according to claim 1, wherein the compound of the formula (I) is any of the following a-z and aa-ff, or a pharmaceutically acceptable acid addition salt thereof:

a. 2-amino-2-(2-{3-trifluoromethyl-4-[3-(4-trifluoromethylphenyl)propoxy]phenyl}ethyl)propane-1,3-diol, or a pharmaceutically acceptable acid addition salt thereof, b. 2-amino-2-(phosphoryloxymethyl)-4-{3-trifluoromethyl-4-[3-(4-trifluoromethylphenyl)propoxy]phenyl}butanol, or a pharmaceutically acceptable acid addition salt thereof, c. 2-amino-2-(2-{3-trifluoromethyl-4-[3-(3-trifluoromethylphenyl)propoxy]phenyl}elethyl)propane-1,3-diol, or a pharmaceutically acceptable acid addition salt thereof, d. 2-amino-2-(phosphoryloxymethyl)-4-{3-trifluoromethyl-4-[3-(3-trifluoromethylphenyl)propoxy]phenyl}butanol, or a pharmaceutically acceptable acid addition salt thereof, e. 2-amino-2-(2-{4-[3-(3-methylphenyl)propoxy]-3-trifluoromethylphenyl}ethyl)propane-1,3-diol or a pharmaceutically acceptable acid addition salt thereof, f. 2-amino-4-{4-[3-(3-methylphenyl)propoxy]-3-trifluoromethylphenyl}-2-(phosphoryloxymethy)butanol or a pharmaceutically acceptable acid addition salt thereof, g. 2-amino-2-(2-{4-[3-(3,4-dichlorophenyl)propoxy]-3-trifluoromethylphenyl}ethyl)propane-1,3-diol, or a pharmaceutically acceptable acid addition salt thereof, h. 2-amino-4-{4-[3-(3,4-dichlorophenyl)propoxy]-3-trifluoromethylphenyl}-2-(phosphoryloxymethyl)butanol, or a pharmaceutically acceptable acid addition salt thereof, i. 2-amino-2-(2-{4-[3-(4-trifluoromethoxyphenyl)propoxy-3-trifluoromethyl]phenyl}ethyl)propane-1,3-diol, or a pharmaceutically acceptable acid addition salt thereof,
j. 2-amino-2-(phosphoryloxymethyl)-4-{4-[3-(4-trifluoromethoxyphenyl)propoxy]-3-trifluoromethylphenyl}butanol, or a pharmaceutically acceptable acid addition salt thereof,
k. 2-amino-2-(2-{4-[3-(3-trifluoromethoxypheny)propoxy-3-trifluoromethyl]phenyl}ethyl)propane-1,3-diol, or a pharmaceutically acceptable acid addition salt thereof,
l. 2-amino-2-(phosphoryloxymethyl)-4-{4-[3-(3-trifluoromethoxyphenyl)propoxy]-3-trifluoromethylphenyl}butanol, or a pharmaceutically acceptable acid addition salt thereof,
m. 2-amino-2-(2-{4-[3-(3-fluoro-4-trifluoromethylphenyl)propoxy]-3-trifluoromethylphenyl}ethyl)propane-1,3-diol, or a pharmaceutically acceptable acid addition salt thereof,
n. 2-amino-4-{4-[3-(3-fluoro-4-trifluoromethylphenyl)propoxy]-3-trifluoromethylphenyl}-2-(phosphoryloxymethyl)butanol, or a pharmaceutically acceptable acid addition salt thereof,
o. (R)-2-amino-2-methyl-4-{3-trifluoromethyl-4-[3-(4-trifluoromethylphenyl)propoxy]phenyl}butanol, or a pharmaceutically acceptable acid addition salt thereof,
p. (R)-phosphoric acid mono(2-amino-2-methyl-4-{3-trifluoromethyl-4-[3-(4-trifluoromethylphenyl)propoxy]phenyl}butyl) ester, or a pharmaceutically acceptable acid addition salt thereof,
q. (R)-2-amino-2-ethyl-4-{3-trifluoromethyl-4-[3-(4-trifluoromethylphenyl)propoxy]phenyl}butanol, or a pharmaceutically acceptable acid addition salt thereof,
r. (R)-phosphoric acid mono(2-amino-2-ethyl-4-{3-trifluoromethyl-4-[3-(4-trifluoromethylphenyl)propoxy]phenyl}butyl) ester, or a pharmaceutically acceptable acid addition salt thereof,
s. 2-amino -2-(2-{4-[3-(3-chlorophenyl)allyloxy]-3-trifluoromethylphenyl}ethyl)propane-1,3 -diol, or a pharmaceutically acceptable acid addition salt thereof,
t. 2-amino-4-{4-[3-(3-chlorophenyl)allyloxy]-3-trifluoromethylphenyl}-2-(phosphoryloxymethyl)butanol, or a pharmaceutically acceptable acid addition salt thereof,
u. (E)-2-amino-2-{2-[4-(3-phenylpropoxy)-3-trifluoromethylphenyl]vinyl}propane-1,3 -diol, or a pharmaceutically acceptable acid addition salt thereof,
v. (E)-2-amino-4-[4-3-phenylpropoxy)-3-trifluoromethylphenyl]-2-(phosphoryloxymethyl)-3-butenol, or a pharmaceutically acceptable acid addition salt thereof,
w. (E)-2-amino-2-(2-{4-[3-(2-fluorophenyl)propoxy]-3-trifluoromethylphenyl}vinyl)propane-1,3-diol, or a pharmaceutically acceptable acid addition salt thereof,
x. (E)-2-amino-4-{4-[3-(2-fluorophenyl)propoxy]-3-trifluoromethylphenyl}-2-(phosphoryloxymethyl)-3-butenol, or a pharmaceutically acceptable acid addition salt thereof,
y. (R)-2-amino-4-{4-[3-(3,4-dichlorophenyl)propoxy]-3-trifluoromethylphenyl}-2-methylbutanol, or a pharmaceutically acceptable acid addition salt thereof,
z. phosphoric acid mono(2-amino-4-{4-[3-3,4-dichlorophenyl)propoxy]-3-trifluoromethylphenyl}-2-methylbutyl) ester, or a pharmaceutically acceptable acid addition salt thereof,
aa. (R)-2-amino-4-{4-[3-(3,4-dichlorophenyl)propoxy]-3-trifluoromethylphenyl}-2-ethylbutanol, or a pharmaceutically acceptable acid addition salt thereof,
bb. (R)-phosphoric acid mono(2-amino-4-{4-[3-(3,4-dichlorophenyl)propoxy]-3-trifluoromethylphenyl}-2-ethylbutyl) ester, or a pharmaceutically acceptable acid addition salt thereof,
cc. (R)-2-amino-2-ethyl-4-{4-[3-(4-trifluoromethoxyphenyl)propoxy]-3-trifluoromethylphenyl}butanol, or a pharmaceutically acceptable acid addition salt thereof,
dd. (R)-phosphoric acid mono(2-amino-2-ethyl-4-{4-[3-(4-trifluoromethoxyphenyl)propoxy]-3-trifluoromethylphenyl}butyl) ester, or a pharmaceutically acceptable acid addition salt thereof,
ee. (R)-2-amino-2-ethyl-4-{4-[3-(3-trifluoromethoxyphenyl)propoxy]-3-trifluoromethylphenyl}butanol, or a pharmaceutically acceptable acid addition salt thereof, and
ff. (R)-phosphoric acid mono(2-amino-2-ethyl-4-{4-[3-(3-trifluoromethoxyphenyl)propoxy]-3-trifluoromethylphenyl}butyl) ester, or a pharmaceutically acceptable acid addition salt thereof.

11. A pharmaceutical composition comprising a compound according to claim 1 or a pharmaceutically acceptable acid addition salt thereof and a pharmaceutically acceptable carrier.

12. A method for the treatment of an autoimmune disease selected from the group consisting of rheumatoid arthritis, multiple sclerosis, encephalomyelitis, systemic lupus erythematosus, lupus nephritis, nephrosis syndrome, psoriasis and Type I diabetes mellitus; suppression of resistance in transplantation of an organ or tissue, suppression of acute rejection in transplantation of an organ or tissue, or suppression of chronic rejection in transplantation of an organ or tissue; treatment of graft vs host (GvH) disease caused by bone marrow transplantation; or treatment of an allergic disease selected from the group consisting of atopic dermatitis, allergic rhinitis and asthma, comprising administering an effective amount of a compound according to claim 1 or a pharmaceutically acceptable acid addition salt thereof to a subject.

* * * * *